(12) United States Patent
Sugioka et al.

(10) Patent No.: US 9,388,249 B2
(45) Date of Patent: Jul. 12, 2016

(54) METHOD OF CLASSIFYING ANTIBODY, METHOD OF IDENTIFYING ANTIGEN, METHOD OF OBTAINING ANTIBODY OR ANTIBODY SET, METHOD OF CONSTRUCTING ANTIBODY PANEL AND ANTIBODY OR ANTIBODY SET AND USE OF THE SAME

(71) Applicant: Fujita Health University, Toyoake-shi (JP)

(72) Inventors: Atsushi Sugioka, Nagoya (JP); Gene Kurosawa, Nagoya (JP); Mariko Sumitomo, Nagoya (JP); Yoshikazu Kurosawa, Nagoya (JP)

(73) Assignee: AMANO ENZYME INC., Nagoya-Shi (JP)

(*) Notice: Subject to any disclaimer, the term of this patent is extended or adjusted under 35 U.S.C. 154(b) by 0 days.

(21) Appl. No.: 14/265,416

(22) Filed: Apr. 30, 2014

(65) Prior Publication Data
US 2014/0235833 A1    Aug. 21, 2014

Related U.S. Application Data

(60) Division of application No. 12/318,829, filed on Jan. 9, 2009, which is a continuation-in-part of application No. PCT/JP2007/063689, filed on Jul. 9, 2007.

(30) Foreign Application Priority Data

Jul. 10, 2006 (JP) ................. 2006-189872
Mar. 8, 2007 (JP) ................. 2007-058458

(51) Int. Cl.
| | | |
|---|---|---|
| A61K 39/395 | (2006.01) | |
| C07K 16/30 | (2006.01) | |
| C07K 16/00 | (2006.01) | |
| C07K 16/28 | (2006.01) | |
| C07K 16/32 | (2006.01) | |
| C07K 16/40 | (2006.01) | |
| C12N 15/113 | (2010.01) | |
| G01N 33/574 | (2006.01) | |
| G01N 33/68 | (2006.01) | |

(52) U.S. Cl.
CPC ............ *C07K 16/30* (2013.01); *C07K 16/005* (2013.01); *C07K 16/28* (2013.01); *C07K 16/2803* (2013.01); *C07K 16/2863* (2013.01); *C07K 16/2896* (2013.01); *C07K 16/303* (2013.01); *C07K 16/32* (2013.01); *C07K 16/40* (2013.01); *C12N 15/1138* (2013.01); *G01N 33/57492* (2013.01); *G01N 33/6854* (2013.01); *C07K 2317/56* (2013.01); *C07K 2317/565* (2013.01); *C07K 2317/73* (2013.01); *C07K 2317/732* (2013.01); *C12N 2310/14* (2013.01)

(58) Field of Classification Search
None
See application file for complete search history.

(56) References Cited

U.S. PATENT DOCUMENTS

| 5,844,093 A | 12/1998 | Kettleborough et al. |
|---|---|---|
| 7,498,142 B2 | 3/2009 | Yarden et al. |
| 2002/0012665 A1* | 1/2002 | Hanna .............. A61K 39/39541 424/145.1 |

FOREIGN PATENT DOCUMENTS

| EP | 0965594 | 12/1999 |
|---|---|---|
| EP | 1264885 A1 | 12/2002 |
| EP | 1314740 | 5/2003 |
| EP | 1429143 A1 | 6/2004 |
| JP | 2000-000097 | 1/2000 |
| JP | 2005-185281 A | 7/2005 |
| JP | 2006-025749 A | 2/2006 |
| JP | 2006-509828 A | 3/2006 |
| WO | WO-01/62907 | 8/2001 |
| WO | WO-01/96401 | 12/2001 |
| WO | WO0202641 * | 1/2002 |
| WO | WO-2004/005890 A2 | 1/2004 |
| WO | WO-2004/056847 A2 | 7/2004 |

OTHER PUBLICATIONS

Mass et al., "The Concordance Between the Clinical Trials Assay(CTA) and Fluorescence in Situ Hybridization(FISH) in the Herceptin Pivotal Trials," *Proc Am Soci Clin Oncol*, vol. 19, 75a, 2000, 1 page.

Berinstein et al., "Association of serum Rituximab (IDEC-C2B8) concentration and anti-tumor response in the treatment of recurrent low-grade or follicular non-Hodgkin's lymphoma," *Annals of Oncology*, vol. 9, 1998, pp. 995-1001.

Brüggemann et al., "Comparison of the effector functions of human immunoglobulins using a matched set of chimeric antibodies," *J. Exp. Med.*, vol. 166, 1987, pp. 1351-1361.

Loos, "The classical complement pathway: mechanism of activation of the first component by antigen-antibody complexes," *Prog. Allergy*, vol. 30, 1982, pp. 135-192.

Imai et al., "YMC Library no Screening," *Protein Nucleic Acid and Enzyme*, 1993, vol. 38, No. 3, pp. 591-599, 720.

Kurosawa et al., "Comprehensive screening for antigens overexpressed on carcinomas via isolation of human mAbs that may be therapeutic," *PNAS*, May 20, 2008, vol. 105, No. 20, pp. 7287-7292.

(Continued)

*Primary Examiner* — Laura B Goddard
(74) *Attorney, Agent, or Firm* — Locke Lord LLP; James E. Armstrong, IV; Nicholas R. Herrel

(57) ABSTRACT

The present invention relates to an isolated antibody against HER1, an isolated antibody against CD147, an isolated antibody against CD73, and an isolated antibody against EpCAM; reagents and compositions including said antibodies; and uses of said reagents, compositions, and antibodies. The present invention also relates to nucleic acids and vectors expressing said antibodies. The invention further relates to transformants comprising said nucleic acids or vectors.

6 Claims, 91 Drawing Sheets

(56) References Cited

OTHER PUBLICATIONS

International Search Report mailed Oct. 23, 2007, issued in PCT/JP2007/063689.
Supplementary European Search Report dated Jun. 28, 2010, issued in European Patent Application No. 07790510.7.
McWhirter et al, "Antibodies selected from combinatorial libraries block a tumor antigen that plays a key role in immunomodulation." *PNAS*, Jan. 24, 2006, 103:1041-1046.
Onda et al, "New Monoclonal Antibodies to Mesothelin Useful for Immunohistochemistry, Fluorescence-Activated Cell Sorting, Western Blotting, and ELISA." *Clinical Cancer Research*, Aug. 15, 2005, 11:5840-5846.
Hellstrom et al, "Highly Tumor-reactive, Internalizing, Mouse Monoclonal Antibodies to Le$^y$-related Cell Surface Antigens," *Cancer Research*, 1990, 50:2183-2190.
Stancovski et al, "Mechanistic aspects of the opposing effects of monoclonal antibodies to the ERBB2 receptor on tumor growth." *PNAS*, 1991, 88:8691-8695.
Patibandla et al, "Flow Cytometric Analyses of Antibody Binding to Chinese Hamster Ovary Cells Expressing Human Thyrotropin Receptor." *JCEM*, 1997, 82:1885-1893.
Olafsen et al, "Characterization of engineered anti-p185$^{HER-2}$ (scFV-$C_H3$)$_2$ antibody fragments (minibodies) for tumor targeting." *Protein Engineering, Design & Selection*, 2004, 17:315-323.
Hurwitz et al, "Suppression and promotion of tumor growth by monoclonal antibodies to ErbB-2 differentially correlate with cellular uptake." *PNAS*, 1995, 92:3353-3357.
Kenneth A. Foon et al. "Preclinical and Clinical Evaluations of ABX-EGF, A Fully Human Anti-Epidermal Growth Factor Receptor Antibody", Int. J. Radiation Oncology Biol. Phys., vol. 58, No. 3, 2004, pp. 984-990.
Xiao-Dong Yang et al. "Eradication of Established Tumors by a Fully Human Monoclonal Antibody to the Epidermal Growth Factor Receptor without Concomitant Chemotherapy," Cancer Research 59, Mar. 15, 1999, pp. 1236-1243.
Motomu Kuroki et al., "Antobody-Based Cancer Therapies," Biotherapy 19(2) Mar. 2005, pp. 125-132.
Office Action mailed Dec. 19, 2014, issued for the Japanese patent application No. 2013-197808.
European Search Report mailed Oct. 20, 2015, issued for the European patent application No. 15 18 0578.5.
Linda F. Thompson et al., "Antibodies to 5'-Nucleotidase (CD73), A Glycosyl-Phosphatidylinositol-Anchored Protein, Cause Human Peripheral Blood T Cells to Proliferate," The Journal of Immunology, vol. 6, Sep. 15, 1989, pp. 1815-1821.
Frank Barry et al., "The SH-3 and SH-4 Antibodies Recognize Distinct Epitopes on CD73 from Human Mesenchymal Stem Cells", Biochemical and Biophysical Research Communications, vol. 289, Nov. 1, 2001, pp. 519-524.
K.H. Krüger et al., "Expression of ecto-5'-nucleotidase (CD73) in normal mammary gland and in breast carcinoma," Br. J. Cancer, vol. 63, 1991, pp. 114-118.
Karola Flocke et al., "Monoclonal antibodies against 5'-nucleotidase from a human pancreatic tumor cell line: their characterization and inhibitory capacity on tumor cell adhesion to fibronectin substratum," European Journal of Cell Biology, S8, 1992, pp. 62-70.
Office Action mailed Dec. 3, 2015, issued for the Japanese patent application No. 2015-018098.

* cited by examiner

Fig.7-1

```
pscFvCA9-E8VHdVLd

M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A  Q  V  Q  L  Q  Q  S  G  A  E  L  V  K
TTGTTATTACTCGCTGCCCAACCAGCGATGGCCCAGGTGCAGCTGCAGCAGTCTGGGGCAGAGCTTGTGAAG
                                         PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G  ————————  L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                   XbaI  EcoRI D  Y  G  N  F  D  Y  W  G  Q  G  T  T  V  T  V  S  R  G  G  G  G  S  G
TGATTACGGCAACTTTGACTACTGGGGCCAAGGCACCACGGTCACCGTCTCGAGAGGCGGTGGCGGATCAGG
                                         BstPI    XhoI G  G  G  S  G  G  G  G  S  M  A
TGGCGGTGGAAGTGGCGGTGGTGGGTCCATGGCC
                           NcoI D  I  E  L  T  Q  S  P  A  S  L  S  A  S  V  G  E  T  V  T  I  T
GACATCGAGCTCACCCAGTCTCCAGCCTCCCTTTCTGCGTCTGTGGGAGAAACTGTCACCATCAC
       SacI C  R  A  S  G  N  I  H  N  Y  L  A  ————————  K  L  E  I  K  R  A  D  A  A
ATGTCGAGCAAGTGGGAATATTCACAATTATTTAGCATGGTACCAAGCTCGAGATCAAACGGGCTGATGCTG
                                   KpnI    XhoI P  T  V  S  I  F  P  P  S  S  E  Q  L  T  S  G  G  A  S  V  V  C  F  L
CACCAACTGTATCCATCTTCCCACCATCCAGTGAGCAGTTAACATCTGGAGGTGCCTCAGTCGTGTGCTTCT N  S  F  Y  P  K  D  I  N  V  K  W  K  I  D  G  S  E  R  Q  N  G  V  L
TGAACAGCTTCTACCCCAAAGACATCAATGTCAAGTGGAAGATTGATGGCAGTGAACGACAAAATGGCGTCC N  S  W  T  D  Q  D  S  K  D  S  T  Y  S  M  S  S  T  L  T  L  T  K  D
TGAACAGTTGGACTGATCAGGACAGCAAAGACAGCACCTACAGCATGAGCAGCACCCTCACGTTGACCAAGG E  Y  E  R  H  N  S  Y  T  C  E  A  T  H  K  T  S  T  S  P  I  V  K  S
ACGAGTATGAACGACATAACAGCTATACCTGTGAGGCCACTCACAAGACATCAACTTCACCCATTGTCAAGA
```

Fig.7-2

```
   F  N  R  N  E  C  S  A  R  Q  S  T  P  F  V  C  E  Y  Q  G  Q  S  S  D
GCTTCAACAGGAATGAGTGTTCGGCGCGCCAGTCGACTCCATTCGTTTGTGAATATCAAGGCCAATCGTCTG
                      Ascl     Sa/l
   L  P  Q  P  P  V  N  A  G  G  G  S  G  G  G  S  G  G  G  S  E  G  G  G
ACCTGCCTCAACCTCCTGTCAATGCTGGCGGCGGCTCTGGTGGTGGTTCTGGTGGCGGCTCTGAGGGTGGTG S  E  G  G  G  S  E  G  G  G  S  E  G  G  G  S  G  G  G  S  G  S  G  D
GCTCTGAGGGTGGCGGTTCTGAGGGTGGCGGCTCTGAGGGAGGCGGTTCCGGTGGTGGCTCTGGTTCCGGTG F  D  Y  E  K  M  A  N  A  N  K  G  A  M  T  E  N  A  D  E  N  A  L  Q
ATTTTGATTATGAAAAGATGGCAAACGCTAATAAGGGGGCTATGACCGAAAATGCCGATGAAAACGCGCTAC S  D  A  K  G  K  L  D  S  V  A  T  D  Y  G  A  A  I  D  G  F  I  G  D
AGTCAGACGCTAAAGGCAAACTTGATTCTGTCGCTACTGATTACGGTGCTGCTATCGATGGTTTCATTGGTG V  S  G  L  A  N  G  N  G  A  T  G  D  F  A  G  S  N  S  Q  M  A  Q  V
ACGTTTCCGGCCTTGCTAATGGTAATGGTGCTACTGGTGATTTTGCTGGCTCTAATTCCCAAATGGCTCAAG G  D  G  D  N  S  P  L  M  N  N  F  R  Q  Y  L  P  S  L  P  Q  S  V  E
TCGGTGACGGTGATAATTCACCTTTAATGAATAATTTCCGTCAATATTTACCTTCCCTCCCTCAATCGGTTG C  R  P  F  V  F  G  A  G  K  P  Y  E  F  S  I  D  C  D  K  I  N  L  F
AATGTCGCCCTTTTGTCTTTGGCGCTGGTAAACCATATGAATTTTCTATTGATTGTGACAAAATAAACTTAT R  G  V  F  A  F  L  L  Y  V  A  T  F  M  Y  V  F  S  T  F  A  N  I  L
TCCGTGGTGTCTTTGCGTTTCTTTTATATGTTGCCACCTTTATGTATGTATTTTCTACGTTTGCTAACATAC R  N  K  E  S  *                             S  T  A  Q  H  D  E  A
TGCGTAATAAGGAGTCTTAATCATGCCAGTTCTTTTGGGTGCTAGCTGTCGACTGCGCAACACGATGAAGCC
                                               Nhel      Sa/l
   V  D  N  K  F  N  K  E  Q  Q  N  A  F  Y  E  I  L  H  L  P  N  L  N  E
GTAGACAACAAATTCAACAAAGAACAACAAAACGCGTTCTATGAGATCTTACATTTACCTAACTTAAACGAA E  Q  R  N  A  F  I  Q  S  L  K  D  D  P  S  Q  S  A  N  L  L  A  E  A
GAACAACGAAACGCCTTCATCCAAAGTTTAAAAGATGACCCAAGCCAAAGCGCTAACCTTTTAGCAGAAGCT K  K  L  N  D  A  Q  A  P  K  V  D  N  K  F  N  K  E  Q  Q  N  A  F  Y
AAAAAGCTAAATGATGCTCAGGCGCCGAAAGTAGACAACAAATTCAACAAAGAACAACAAAACGCGTTCTAT E  I  L  H  L  P  N  L  N  E  E  Q  R  N  A  F  I  Q  S  L  K  D  D  P
GAGATCTTACATTTACCTAACTTAAACGAAGAACAACGAAACGCCTTCATCCAAAGTTTAAAAGATGACCCA S  Q  S  A  N  L  L  A  E  A  K  K  L  N  D  A  Q  A  P  K  V  D  A  N
AGCCAAAGCGCTAACCTTTTAGCAGAAGCTAAAAAGCTAAATGATGCTCAGGCGCCGAAAGTAGACGCGAAT

*
TAGCTGGGAATTAATTC
```

Fig.8-1

```
pscFvCA-E8VHd

M  K  Y  L  L  P  T  A  A  A  G
AAGCTTGCATGCAAATTCTATTTCAAGGAGACAGTCATAATGAAATACCTATTGCCTACGGCAGCCGCTGGA
Hind III L  L  L  L  A  A  Q  P  A  M  A  Q  V  Q  L  Q  Q  S  G  A  E  L  V  K
TTGTTATTACTCGCGGCCCAGCCGGCCATGGCCCAGGTGCAGCTGCAGCAGTCTGGGGCAGAGCTTGTGAAG
          Sfi I          Nco I          Pst I P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G ———————— L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                       Xba I  EcoR I D  Y  G  N  F  D  Y  W  G  Q  G  T  T  V  T  V  S  S  G  G  G  G  S  G
TGATTACGGCAACTTTGACTACTGGGGCCAAGGCACCACGGTCACCGTCTCCTCAGGCGGTGGCGGATCAGG
                                          BstP I G  G  G  S  G  G  G  G  S  T  S  D  I  E  L  T  Q  S  P  A  S  L  S  A
TGGCGGTGGAAGTGGCGGTGGTGGGTCTACTAGTGACATCGAGCTCACCCAGTCTCCAGCCTCCCTTTCTGC
                                Spe I    Sac I S  V  G  E  T  V  T  I  T  C  R  A  S  G  N  I  H  N  Y  L  A  W  Y  Q
GTCTGTGGGAGAAACTGTCACCATCACATGTCGAGCAAGTGGGAATATTCACAATTATTTAGCATGGTACCA
                                                                  Kpn I Q  K  P  G  K  S  P  Q  L  L  V  Y  N  A  K  T  L  A  D  G  V  P  S  R
GCAGAAACCAGGGAAATCTCCTCAGCTCCTGGTCTATAATGCAAAAACCTTAGCAGATGGTGTGCCATCAAG F  S  G  S  G  S  G  T  Q  Y  S  L  K  I  N  S  L  Q  P  E  D  F  G  S
GTTCAGTGGCAGTGGATCCGGAACACAATATTCTCTCAAGATCAACAGCCTGCAGCCTGAAGATTTTGGGAG
             BamH I Y  Y  C  Q  H  F  W  S  T  P  W  T  F  G  G  G  T  K  I  E  S  T  P  F
TTATTACTGTCAACATTTTTGGAGTACTCCGTGGACGTTCGGTGGAGGTACCAAGCTCGAGTCGACTCCATT
                                              Kpn I      Xho I Sal I V  C  E  Y  Q  G  Q  S  S  D  L  P  Q  P  P  V  N  A  G  G  G  S  G  G
CGTTTGTGAATATCAAGGCCAATCGTCTGACCTGCCTCAACCTCCTGTCAATGCTGGCGGCGGCTCTGGTGG
```

Fig.8-2

```
  G   S   G   G   G   S   E   G   G   G   S   E   G   G   G   S   E   G   G   G   S   E   G   G
TGGTTCTGGTGGCGGCTCTGAGGGTGGTGGCTCTGAGGGTGGCGGTTCTGAGGGTGGCGGCTCTGAGGGAGG

G   S   G   G   G   S   G   S   G   D   F   D   Y   E   K   M   A   N   A   N   K   G   A   M
CGGTTCCGGTGGTGGCTCTGGTTCCGGTGATTTTGATTATGAAAAGATGGCAAACGCTAATAAGGGGGCTAT

T   E   N   A   D   E   N   A   L   Q   S   D   A   K   G   K   L   D   S   V   A   T   D   Y
GACCGAAAATGCCGATGAAAACGCGCTACAGTCAGACGCTAAAGGCAAACTTGATTCTGTCGCTACTGATTA

G   A   A   I   D   G   F   I   G   D   V   S   G   L   A   N   G   N   G   A   T   G   D   F
CGGTGCTGCTATCGATGGTTTCATTGGTGACGTTTCCGGCCTTGCTAATGGTAATGGTGCTACTGGTGATTT

A   G   S   N   S   Q   M   A   Q   V   G   D   G   D   N   S   P   L   M   N   N   F   R   Q
TGCTGGCTCTAATTCCCAAATGGCTCAAGTCGGTGACGGTGATAATTCACCTTTAATGAATAATTTCCGTCA

Y   L   P   S   L   P   Q   S   V   E   C   R   P   F   V   F   G   A   G   K   P   Y   E   F
ATATTTACCTTCCCTCCCTCAATCGGTTGAATGTCGCCCTTTTGTCTTTGGCGCTGGTAAACCATATGAATT

S   I   D   C   D   K   I   N   L   F   R   G   V   F   A   F   L   L   Y   V   A   T   F   M
TTCTATTGATTGTGACAAAATAAACTTATTCCGTGGTGTCTTTGCGTTTCTTTTATATGTTGCCACCTTTAT

Y   V   F   S   T   F   A   N   I   L   R   N   K   E   S   *
GTATGTATTTTCTACGTTTGCTAACATACTGCGTAATAAGGAGTCTTAATCATGCCAGTTCTTTTGGGTGCT
                                                                    NheI
        S   T   A   Q   H   D   E   A   V   D   N   K   F   N   K   E   Q   Q   N   A   F   Y   E
AGCTGTCGACTGCGCAACACGATGAAGCCGTAGACAACAAATTCAACAAAGAACAACAAAACGCGTTCTATG
       SalI

I   L   H   L   P   N   L   N   E   E   Q   R   N   A   F   I   Q   S   L   K   D   D   P   S
AGATCTTACATTTACCTAACTTAAACGAAGAACAACGAAACGCCTTCATCCAAAGTTTAAAAGATGACCCAA

Q   S   A   N   L   L   A   E   A   K   K   L   N   D   A   Q   A   P   K   V   D   N   K   F
GCCAAAGCGCTAACCTTTTAGCAGAAGCTAAAAAGCTAAATGATGCTCAGGCGCCGAAAGTAGACAACAAAT

N   K   E   Q   Q   N   A   F   Y   E   I   L   H   L   P   N   L   N   E   E   Q   R   N   A
TCAACAAAGAACAACAAAACGCGTTCTATGAGATCTTACATTTACCTAACTTAAACGAAGAACAACGAAACG

F   I   Q   S   L   K   D   D   P   S   Q   S   A   N   L   L   A   E   A   K   K   L   N   D
CCTTCATCCAAAGTTTAAAAGATGACCCAAGCCAAAGCGCTAACCTTTTAGCAGAAGCTAAAAAGCTAAATG

A   Q   A   P   K   V   D   A   N   *
ATGCTCAGGCGCCGAAAGTAGACGCGAATTAGCTGGGAATTAATTC
```

Fig.9

(A) HepG2 screening

| | input phage(cfu) | output phage(cfu) | recovery rate |
|---|---|---|---|
| 1st screening | $1 \times 10^{13}$ | $6.4 \times 10^6$ | $1/1.6 \times 10^6$ |
| 2nd screening | $1 \times 10^{10}$ | $3.9 \times 10^4$ | $1/2.6 \times 10^6$ |
| 3rd screening | $1 \times 10^9$ | $5.0 \times 10^6$ | $1/2.0 \times 10^2$ |

(B) Nuk-1 screening

| | input phage(cfu) | output phage(cfu) | recovery rate |
|---|---|---|---|
| 1st screening | $1 \times 10^{13}$ | $8.7 \times 10^7$ | $1/1.1 \times 10^5$ |
| 2nd screening | $2 \times 10^{10}$ | $2.1 \times 10^6$ | $1/9.5 \times 10^3$ |
| 3rd screening | $1 \times 10^9$ | $2.5 \times 10^6$ | $1/4.6 \times 10^2$ |

Fig.18

| antigen | antibody | HLF | SKOv3 | BT474 | 293T | PC-14 | HepG2 | ACHN | Caki-1 | CCF-RC1 | 040520IT | CHOK1SV | EBC-1 | A431 | NCI-H1373 |
|---|---|---|---|---|---|---|---|---|---|---|---|---|---|---|---|
| HER1 | 048-006 | ◎ | ◎ | × | △ | ◎ | △ | ◎ | △ | ◎ | ○ | × | ◎ | ◎ | ◎ |
| HER1 | 057-091 | △ | △ | / | / | △ | / | ◎ | × | ◎ | △ | × | △ | ○ | △ |
| HER1 | 059-152 | ◎ | ○ | / | / | ○ | / | / | / | ◎ | ○ | × | ○ | ◎ | ○ |
| HER2 | 015-126 | × | ◎ | ◎ | × | × | △ | × | × | × | × | × | / | / | / |
| CD46 | 035-224 | ○ | ◎ | ○ | ○ | ○ | ◎ | ○ | ○ | ○ | △ | × | / | / | / |
| CD46 | 045-011 | ○ | ◎ | △ | △ | △ | ◎ | ○ | ○ | ○ | △ | × | / | / | / |
| CD46 | 051-144 | ○ | ◎ | ○ | ○ | ○ | ◎ | / | / | / | / | / | / | / | / |
| CD46 | 052-053 | / | ○ | △ | ○ | △ | ○ | / | / | / | / | / | / | / | / |
| CD46 | 052-073 | ○ | ◎ | ○ | ○ | ○ | ◎ | / | / | / | / | / | / | / | / |
| CD46 | 053-049 | ◎ | ◎ | ○ | ○ | ○ | ◎ | / | / | / | / | / | / | / | / |
| ITGA3 | 015-003 | ◎ | ◎ | △ | × | △ | × | ◎ | ◎ | ○ | ◎ | × | / | / | / |
| ICAM1 | 052-033 | × | × | × | × | △ | ◎ | × | × | × | ○ | × | / | / | / |
| ICAM1 | 053-042 | × | × | × | × | △ | ◎ | / | / | / | / | / | / | / | / |
| ICAM1 | 053-051 | × | × | × | × | △ | ◎ | / | / | / | / | / | / | / | / |
| ICAM1 | 053-059 | × | × | × | × | △ | ◎ | / | / | / | / | / | / | / | / |
| ICAM1 | 053-085 | × | × | × | × | △ | ◎ | / | / | / | / | / | / | / | / |
| ALCAM | 035-234 | ◎ | ◎ | ◎ | ◎ | ◎ | ◎ | ◎ | ◎ | ◎ | ○ | ◎ | / | / | / |
| ALCAM | 040-107 | ◎ | ◎ | ◎ | ○ | ◎ | ◎ | / | / | / | / | / | / | / | / |
| ALCAM | 041-118 | ◎ | ◎ | ◎ | ○ | ◎ | ◎ | / | / | / | / | / | / | / | / |
| ALCAM | 066-174 | ○ | ◎ | / | / | △ | / | / | / | / | / | / | △ | × | ○ |
| ALCAM | 083-040 | / | / | / | / | / | / | / | / | / | / | / | / | / | / |
| CD147 | 059-053 | / | / | / | / | △ | / | ○ | ○ | ◎ | ○ | × | / | / | / |
| IgSF4 | 035-029 | △ | × | × | △ | × | ○ | × | × | × | × | × | / | / | / |
| IgSF4 | 035-130 | ○ | × | × | △ | × | ○ | × | × | × | × | × | / | / | / |
| IgSF4 | 035-169 | ○ | × | × | △ | × | ◎ | / | / | / | / | / | / | / | / |
| IgSF4 | 035-212 | ○ | × | × | △ | × | ◎ | △ | × | × | × | × | / | / | / |
| IgSF4 | 035-215 | ○ | × | × | △ | × | ◎ | / | / | / | / | / | / | / | / |
| IgSF4 | 035-273 | ◎ | × | × | △ | × | ◎ | / | / | / | / | / | / | / | / |
| IgSF4 | 035-283 | ○ | △ | × | △ | × | ◎ | / | / | / | / | / | / | / | / |
| IgSF4 | 040-131 | ◎ | × | × | ○ | × | ◎ | ○ | × | × | × | × | / | / | / |
| IgSF4 | 051-054 | △ | × | × | △ | × | ○ | / | / | / | / | / | / | / | / |
| IgSF4 | 051-181 | ◎ | × | × | ○ | × | ◎ | / | / | / | / | / | / | / | / |

*Fig.76A*  Ⓐ

| | origin organ | name of cell line | origin |
|---|---|---|---|
| liver | HCV+ | HepG2<br>Nuk-1<br>OCTH-16 | |
| | HBV+ | HT17 | poorly differentiated hepatic cell carcinoma |
| | HBV+ | Hep3B | |
| | immortalize liver cell | THLE-3 | |
| | | HLF | hepatic left lobe |
| | intrahepatic bile duct cancer | RBE | undifferentiated hepatic cell carcinoma |
| kidney | clear cell carcinoma | CCF-RC1<br>CCF-RC2<br>Caki-1<br>Caki-2 | |
| | adenocarcinoma<br>normal | ACHN<br>293<br>040520IT | established from abdominal dropsy |
| pancreas | | MIA-PaCa2 | |
| | | pANC-1 | |
| lung cancer | adenocarcinoma | A549<br>PC-14 | lung-derived poorly differentiated |
| | | NCI-N441 | papillary type adenocarcinoma |
| | | Calu-3 | abdominal dropsy |
| | squamous cell carcinoma line | EBC-1<br>RERF-LC-AI | |
| stomach cancer | adenocarcinoma | MKN-45 | solid-type gastric adenocarcinoma |
| | | SNU-5 | poorly differentiated adenocarcinoma |
| | | NCI-N87 | from highly differentiated liver metastatic focus |
| ovarian cancer | adenocarcinoma | SKOv3<br>KF28 | abdominal dropsy |
| | ovarian mesonephroma<br>ovarian mesonephroma | RMG-1<br>RMG-2 | |
| large bowel | colon adenocarcinoma | CACO-2<br>CW-2 | |

Ⓐ *Fig.76B*

| medium | subculture method |
|---|---|
| DMEM+10%FBS+NEAA or GIT<br>Williams+10%FBS<br>Williams+10%FBS<br>EMEM+2mM L-glutamine+10%FBS<br>(or Williams+1-%FBS)<br><br>EMEM+2mM L-glutamine+10%FBS<br>(or Williams+1-%FBS)<br><br>special medium<br>DMEM+10%FBS+100μg/ml Kanamycin<br>RPMI1640+10%FCS | 0.25%Trypsin<br><br><br><br><br><br><br><br><br>0.2%Trypsin+0.02%EDTA<br>0.25%Trypsin |
| RPMI1640<br>10%FBS<br>1%Pn-SM<br>MEM+10%FCS+NEAA<br>DMEM-F12+10%FBS+1%Pn-SM | Trypsin-EDTA<br>Trypsin-EDTA<br>Trypsin-EDTA<br>0.25%Trypsin<br>EDTA solution |
| DMEM(including 4mM L-glutamin·1.5g/L<br>sodium bicarbonate ·4.5g/L glucose)<br>+10%FBS+2.5%horse serum<br>RPMI1640+10%FCS or Eagle's MEM+10%FBS | 0.25%Trypsin, 0.53 mM EDTA solution<br><br>0.02%EDTA-PBS |
| DMEM+10%FBS<br>RPMI1640+10%FBS<br>RPMI1640<br>(2mM L=glutamine·1.5g/L NaHCO3·4.5g/L glucose·<br>10mM HEPES·1.0mMSodiumPyruvate)<br>+10%FBS<br>EMEM<br>(2mM L-glutamine·1.5g/L NaHC03·4.5g/L glucose·<br>10mM HEPES·1.0mMSodiumPyravate)<br>+10%FBS<br>MEM+10% FBS or RPMI1640+10% FBS<br>MEM+10%FBS | 0.25%Trypsin<br>Dilution<br><br>0.25%Trypsin+0.02%EDTA<br><br><br><br>0.25%Trypsin<br>+0.53mM EDTA<br><br><br>0.25%Trypsin<br>0.25%Trypsin |
| RPMI1640+10%FBS<br>Iscove's Modified Dulbecco's Medium (with 4mM L-<br>glutamine·1.5g/L NaHCO3)+20%FBS<br>RPMI1640<br>(2mM L-glutamine·1.5g/L NaHCO3·4.5g/L glucose·<br>10mM HEPES·1.0mMSodiumPyruvate)<br>+10%FBS | 0.25%Trypsin+0.02%EDTA<br><br>Dilution after centrifugation<br><br>0.25% Trypsin+0.53mM EDTA |
| ·1cCoy's 5a medium(with 1.5mM L-glutamine)<br>+10%FBS<br>Ham'sF12+10%FBS | 0.25%Trypsin+0.53mMEDTA<br><br>0.25% Trypsin-0.02% EDTA |
| MEM+20%FCS+NEAA<br>RPMI1640+10%FCS | 0.05%Trypsin+0.02%EDTA<br>0.25% Trypsin |

Fig.78
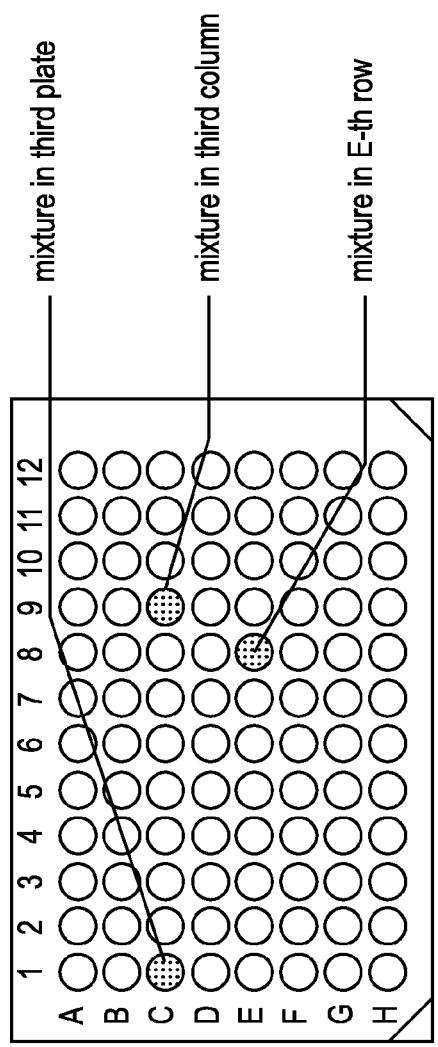
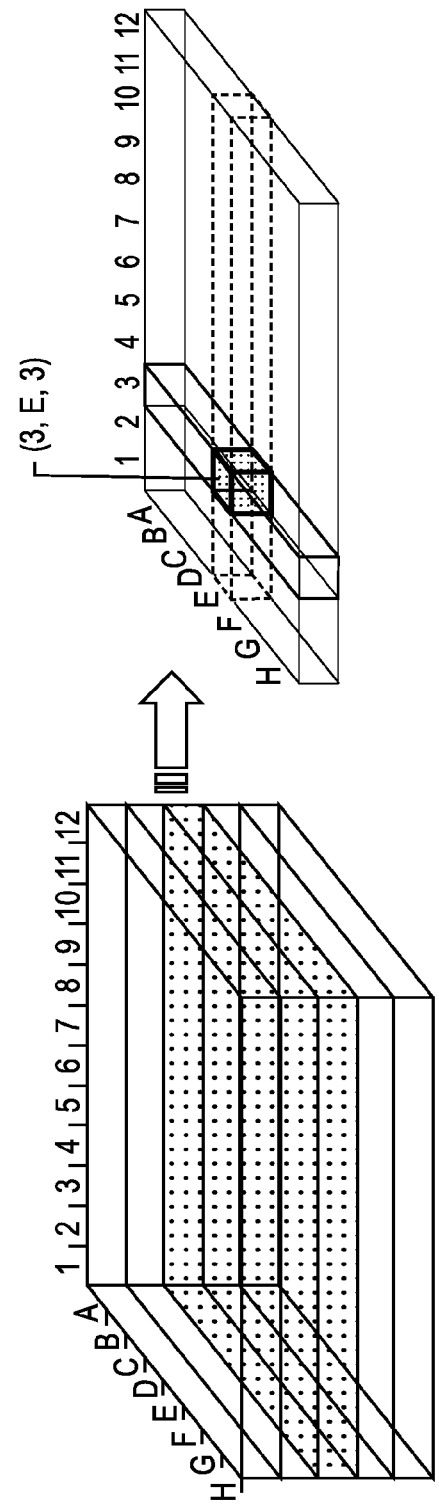

Fig.87

| subject antigen | name of clone | cancer tissue (clinical specimen) determined to be specific to cancer by immunostaining |
|---|---|---|
| HER1 | 048-006 | kidney, liver, lung, pancreas, stomach |
| | 057-091 | kidney |
| | 059-152 | kidney |
| HER2 | 015-126 | lung |
| HGFR | 067-126 | lung |
| | 067-133 | lung |
| | 067-287 | lung |
| LAR | 064-044 | kidney, liver, lung |
| | 065-030 | lung |
| | 065-358 | lung |
| | 066-019 | lung |
| | 079-085 | kidney, lung |
| IGSF4 | 035-029 | liver |
| | 035-130 | liver |
| | 035-169 | liver |
| | 035-212 | liver |
| | 035-215 | liver |
| | 035-273 | liver |
| | 035-283 | liver |
| | 040-131 | liver |
| | 051-054 | liver |
| | 051-181 | liver |
| ALCAM | 035-234 | kidney, liver, lung, large bowel |
| | 041-118 | kidney, liver, lung, stomach, large bowel |
| ICAM1 | 040-107 | liver, lung |
| | 052-033 | liver, lung |
| | 053-042 | liver |
| | 053-051 | liver, lung |
| | 053-059 | liver |
| | 053-085 | liver, lung |
| BCAM | 067-024 | lung |
| CD147 | 059-053 | kidney |
| ITGA3 | 015-003 | liver, lung |
| | 064-002 | lung |
| | 064-006 | kidney, lung, pancreas, |
| | 064-012 | kidney, lung, pancreas, |
| | 064-014 | lung |
| | 064-054 | lung |
| | 064-085 | lung |
| | 064-093 | lung |
| | 064-116 | lung |
| | 065-183 | lung |
| | 067-142 | lung |
| | 068-007 | lung |
| CD44 | 064-003 | lung |
| EpCAM | 067-153 | lung, stomach, large bowel |
| CD46 | 035-224 | liver, lung, stomach, large bowel |
| | 045-011 | liver, lung, large bowel |
| | 051-144 | kidney, liver, lung, stomach |
| | 052-053 | liver |
| | 052-073 | liver |
| | 053-049 | liver |
| | 3172-120 | liver, lung, pancreas, stomach |
| CD73 | 066-069 | lung |
| | 067-213 | lung |

Fig. 88

| antigen | antibody clone | squamous carcinoma | | adenosquamous carcinoma | alveolar adenocarcinoma | adenocarcinoma | | | | | | | | | | | large cell carcinoma | |
|---|---|---|---|---|---|---|---|---|---|---|---|---|---|---|---|---|---|---|
| | | 050707 | 050725 | 051219 | 050623 | 060501 | 060116 | 050823A | 060119 | 060214 | 051020 | 050822 | 060627 | 060608 | 051025 | 060515 | 050929 | 060413 |
| | | moderately differentiated | | | highly differentiated | papillary type highly differentiated | papillary type | papillary type | papillary type highly differentiated | papillary type highly differentiated | papillary type highly differentiated | mixed type | poorly differentiated | poorly differentiated | mixed type | mixed type | | |
| | | IA | IA | IB | IA | IA | IB | IB | IB | IB | IB | IB | IIB | IIIA | IIIA | IIIB | IIIA | IIIA |
| HER1 | 048-006 | + | + | - | - | + | + | + | + | +- | - | - | + | +- | + | + | + | + |
| HER2 | 015-126 | - | - | + | - | + | - | - | - | - | - | - | + | + | + | + | + | - |
| HGFR | 067-133 | - | - | - | - | + | - | - | - | - | - | - | - | - | - | + | - | - |
| LAR | 064-044 | + | - | - | - | - | - | - | + | - | - | + | - | + | - | - | + | - |
| IgSF4 | 076-048 | - | - | - | +- | + | - | + | + | +- | +- | +- | - | + | - | - | - | + |
| CD147 | 059-053 | - | - | - | - | + | - | - | - | - | - | - | + | + | + | + | + | - |

METHOD OF CLASSIFYING ANTIBODY, METHOD OF IDENTIFYING ANTIGEN, METHOD OF OBTAINING ANTIBODY OR ANTIBODY SET, METHOD OF CONSTRUCTING ANTIBODY PANEL AND ANTIBODY OR ANTIBODY SET AND USE OF THE SAME

CROSS REFERENCE TO RELATED APPLICATIONS

This application is divisional of U.S. Ser. No. 12/318,829, filed Jan. 9, 2009. U.S. Ser. No. 12/318,829 is a continuation-in-part of international application No. PCT/JP2007/063689, filed Jul. 9, 2007, which claims priority to Japanese applications No. 2006-189872, filed Jul. 10, 2007 and No. 2007-058458, filed Mar. 8, 2008. The contents of these above-identified applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created Feb. 5, 2014, is named 83289DIV305882_ST25.txt and is 479,195 bytes in size.

FIELD OF THE INVENTION

The present invention relates to a method of classifying a plurality of antibodies, a method of identifying antigen, a panel displaying characteristics of an antibody, and the like, as well as an antibody related to a disease and a use thereof.

BACKGROUND OF THE INVENTION

Success of Herceptin to breast cancer (see, non-patent document 1) and Rituxan (non-patent document 2) to malignant lymphoma B shows that an antibody is effective as a therapeutic agent to a cancer. Certain antibodies exhibit an ADCC effect (non-patent document 3) and/or a CDC effect (non-patent document 4) by forming a complex with an antigen molecule existing on the cell membrane and the effects kill a target cell (cell expressing an antigen). The ADCC effect or the CDC effect may cause apoptosis. Such an effect of an antibody is specific to an antigen. That is to say, an antibody acts on cells expressing an antigen which the antibody recognizes regardless of whether the cells are cancer cells or normal cells. Therefore, the success in development of antibody therapeutic agents to cancers is dependent on discovery of antigens expressing in a cancer-specific manner and recognized by an antibody so as to cause the ADCC effect or the CDC effect. An antibody against to such an antigen is a promising candidate of a therapeutic agent capable of reliably killing target cancer cells while minimizing the influence (side effect) on normal cells.

In antibody drug development, it is essential to obtain antibodies that recognize "intact state" target cancer antigens existing on the surface of a cell membrane. However, since the target cancer antigen is membrane protein, it has been difficult to obtain an antibody against even known cancer antigen. In order to solve these problems, present inventors have produced a huge human antibody library including as many as 100 billion independent clones and established a comprehensive acquisition method for antibodies to proteins (cell surface antigens) existing on the surface of the cell membrane of cancer cells and tissues by using the library (patent documents 1 to 3).

[Patent document 1] WO01/062907
[Patent document 2] WO2001/096401
[Patent document 3] Japanese Patent Unexamined Publication No. 2005-185281
[Non-patent document 1] Mass R, et al.: The Concordance Between the Clinical Trials Assay (CTA) and Fluorescence in Situ Hybridization (FISH) in the Herceptin Pivotal Trials.: Proc Am Soci Clin Oncol 19, 75a, 2000
[Non-patent document 2] Berinstein N L, Grillo-Lopez A J, White C A, Bence-Bruckler I, Maloney D, Czuczman M, et al. Association of serum Rituximab (IDEC-C2B8) concentration and anti-tumor response in the treatment of recurrent low-grade or follicular non-Hodgkin's lymphoma. Annals of Oncology 1998, 9:995-1001.
[Non-patent document 3] Bruggemann M., Williams G. T., Bindon C. I., Clark M. R., Walker M. R., Jefferis R., Waldmann H., Neuberger M. S. (1987). Comparison of the effector functions of human immunoglobulins using a matched set of chimeric antibodies. J. Exp. Med., 166, 1351-1361.
[Non-patent document 4] Loos M. (1982). The classical complement pathway: mechanism of activation of the first component by antigen-antibody complexes. Prog. Allergy, 30, 135-192. Mol Immunol. 1982 May; 19 (5): 651-7.

SUMMARY OF THE INVENTION

Currently, the present inventors can comprehensively obtain antibodies to cell surface antigens. As the next step, it is necessary to identify an antibody to each antibody and to screen useful antibodies. However, it will take a much labor and time and considerably high cost to individually identify an antigen for the comprehensively obtained antibodies.

Furthermore, the comprehensively obtained antibodies may include unnecessary antibodies from the viewpoint that they do not have sufficient affinity and reactivity, or they have substantially the same as the other antibodies. Therefore, method for efficiently screening useful antibodies has been demanded.

On the other hand, the comprehensively obtained antibodies may include antibodies such as candidates of diagnostic agents and therapeutic agents, which are extremely important from the medical viewpoint.

Under such circumstances, the present invention aims at the effective use of comprehensively obtained antibodies to cell surface antigens in medical fields and research fields, and has an object to provide a useful method therefor. That is to say, the present invention has an object to provide a method of classifying a plurality of antibodies to cell surface antigens rapidly. Also, the present invention has another object to provide a method of rapidly identifying an antigen for the antibody. Furthermore, the present invention has a further object to provide a method of promoting to use useful information obtained by such methods. The present invention has a yet further object to provide an antibody effective for treatment and diagnosis of cancers.

In view of the above-mentioned objects, the present inventors carry out an analysis of an antibody by the following approach: preparing cell lines that are expected to express cell surface antigens for the obtained antibodies; allowing each antibody to react with the cell lines; and carrying out the flow cytometry analysis. The present inventors focus on the histogram of the results of the flow cytometry analysis and classify the antibodies based on the similarity so as to obtain a plurality of antibodies groups. Then, it is confirmed that antigens to antibodies belonging to the same antibody group are common. This fact means that it is possible to determine antigens for all antibodies by selecting the respective antibody in each antibody group and identifying the antigen of the representative antibody. Thus, the present inventors have succeeded in finding a method for identifying antigens comprehensively and rapidly. On the other hand, the present inventors carry out classification of antibodies and identification of an antigen according to the above-mentioned technique and consider the reactivity between each antibody group and clinical samples so as to search for clinically applicable antibodies. As a result, the present inventors have succeeded in finding a novel antibody specific to certain kinds of cancers. Furthermore, they have reached the findings that information obtained by using a clinical sample (relationship between the antibody and disease) is extremely useful for establishing methods for diagnosis and treatment.

The present invention provides, for example, a method of classifying antibody, and the like, mentioned below based on the above-mentioned results and findings.

<Method of Classifying Antibody>

[1] A method of classifying antibody including the following steps:

(1) preparing a plurality of antibodies recognizing cell surface antigen;

(2) bringing each of the antibodies into contact with cells of the same kinds;

(3) analyzing each cell after step (2) by flow cytometry so as to obtain data showing reactivity between the antibody and the cell surface; and (4) comparing the obtained data and classifying antibodies based on the similarity of the data.

[2] The method of classifying antibody according to [1], wherein the cell surface antigen is an intact cell surface antigen.

[3] The classifying method according to [1] or [2], wherein the cell surface antigen is a cell surface antigen of a cancer cell.

[4] The classifying method according to [1], wherein the plurality of antibodies recognize cell surface antigen are composed of an assembly of antibodies derived from antibody clones selected as being capable of recognizing a cell surface antigen, from an antibody library.

[5] The classifying method according to [4], wherein the antibody library is a phage antibody library.

[6] The classifying method according to [1], wherein the antibody is an antibody to which a label material is bound or fused.

[7] The classifying method according to [1], wherein the antibody does not include a label material and the method includes a step of labeling the antibody bound to the cell after step (2).

[8] The classifying method according to [1], wherein the cell is an established cell line.

[9] The classifying method according to [1], wherein the cell is an established cancer cell line.

[10] The classifying method according to [1], wherein the data are shown in a histogram showing a relationship between a binding amount of antibodies and a number of cells, and the similarity of the data is determined by comparing the shapes of the histograms.

[11] The classifying method according to [1], wherein the data are shown in a histogram showing a relationship between a binding amount of antibodies and a number of cells, and the similarity of the data is determined based on one or more values selected from the group consisting of a median value, a mode, a maximum value, a range, a standard deviation, a kurtosis and a skewness of the histogram.

[12] The classifying method according to [11], wherein the similarity of the data is determined based on the values of the median value, the mode, and the kurtosis and a skewness of the histogram.

[13] The classifying method according to [10] or [11], wherein the binding amount of antibody is shown by a fluorescence intensity.

[14] The classifying method according to [1], wherein in step (4), a plurality of antibodies having the identical or high similar data are classified into one antibody group.

[15] The classifying method according to [1], wherein two or more kinds of cells are prepared and each kind of cell is subjected to steps (2) to (4).

[16] The classifying method according to [15], wherein a plurality of antibodies having the identical or high similar data with respect to two or more kinds of cells in the cells are classified into one antibody group.

[17] The classifying method according to [1], wherein an antibody that has been determined to have a low reactivity with respect to the cell surface antigen during classification or after classification is excluded.

[18] The classifying method according to [1], wherein classification results of antibodies are displayed as a panel.

[19] The classifying method according to any of [1] to [18], wherein after step (4), the following steps are carried out:

(i) associating the classified antibodies to a combination of n pieces of parameters including a first parameter, a second parameter, . . . , and an n-th parameter (wherein, n represents an integer of 2 or more, each parameter has two or more parameter values and the same parameter value is given to two or more antibodies in each parameter);

(ii) with respect to each parameter, preparing antibody mixtures of the antibodies having the same parameter value;

(iii) examining a reactivity of each of the antibody mixtures with a target antigen by an enzyme linked immunosorbent assay (ELISA) so as to specify the antibody mixture which shows reactivity;

(iv) specifying a combination of a parameter name and a parameter value that are common to the antibody group contained in the specified antibody mixture;

(v) selecting an antibody corresponding to the combination specified in the step (iv) in terms of all parameters among the antibodies subjected to step (i); and (vi) classifying the selected antibodies into one antibody group.

[20] The classifying method according to [19], wherein the steps (i) to (v) are repeated several times under the conditions in which the combination of parameters is different in each trial; an antibody in which results of all trials are not contradictory is selected; and the antibody is subjected to the step (vi).

[21] The classifying method according to [19], further including the following steps between the step (v) and the step (vi);

(v-1) newly associating the classified antibodies selected in step (v) with a combination of n pieces of parameters in a same manner as in the step (i);

(v-2) with respect to each parameter, preparing the antibody mixture of antibodies having the same parameter value for each parameter;

(v-3) examining a reactivity of each of the antibody mixtures with a target antigen by an enzyme linked immunosorbent assay (ELISA) so as to specify the antibody mixture showing the reactivity;

(v-4) determining a combination of a parameter name and a parameter value that are common to the antibody group contained in the specified antibody mixture; and (v-5) selecting an antibody having the combination specified in the step (v-4) in terms of all parameters among the antibodies subjected to the step (v-1).

[22] The classifying method according to [21], wherein the steps (v-1) to (v-4) are repeated twice or more.

[23] The classifying method according to any of [19] to [22], wherein n is 3.

[24] The classifying method according to any of [19] to [23], wherein two or more kinds of target antigens are prepared and the steps (iii) to (vi) are carried out by using each target antigen.

[25] The classifying method according to any of [19] to [24], wherein the target antigen is an antigen selected from the group consisting of HER1, HER2, CD46, ITGA3, ICAM1, ALCAM, CD147, IgSF4, BCAM, C1qR, CD44, CD73, LAR, EpCAM and HGFR.

<Identifying Method of Antigen>

[26] An identifying method of an antigen including the following steps:

(1) preparing a plurality of antibodies recognizing cell surface antigen;

(2) bringing each of the antibodies into contact with cells of the same kind;

(3) analyzing each cell after step (2) by flow cytometry so as to obtain data showing the reactivity between the antibody and the cell surface;

(4) comparing the obtained data and classifying antibodies based on the similarity of the data;

(5) selecting one or several antibodies from each antibody group formed in the step (4) and identifying an antigen thereof; and (6) associating the antigens identified in the step (5) with an antibody group, based on the estimation that antigens to antibodies belonging to the same antibody group are identical or have high relationship, and.

[27] The identification method according to [26], wherein in the step (5), one antibody is selected from each antibody group.

[28] The identification method according to [26], wherein in the step (5), from the results of a flow cytometry analysis, an antibody that is determined to have a high reactivity with respect to an antigen is selected.

[29] The identification method according to [26], wherein in the step (5), the identification of an antigen is carried out by one or more methods selected from the group consisting of an immunoprecipitation test, Western blotting, affinity chromatography, proteomics techniques (electrophoresis, mass spectrometry, genome data base retrieve, and analysis by bioinformatics), and an expression analysis of corresponding gene.

[30] The identification method according to [26], further including a step of examining a reactivity between an antigen identified in the step (5) and an antibody belonging to an antibody group with which the antigen is associated in the step (6) so as to confirm that the estimation is correct.

[31] The identification method according to [26], wherein an identification result of antigen is displayed as a panel.

[32] The identification method according to [31], wherein the panel is any of the following (a) to (c):

(a) a panel displaying a plurality of antibodies showing identical or high similar data in the flow cytometry analysis in the step (3) as one antibody group in which each antibody group is associated with its antigen;

(b) a panel displaying a plurality of antibodies showing identical or high similar data in the flow cytometry analysis in the step (3) as one antibody group in which each antibody group is associated with a cell expressing a cell surface antigen recognized by the each antibody group; and (c) a panel displaying a plurality of antibodies showing identical or high similar data in the flow cytometry analysis in the step (3) as one antibody group in which each antibody group, its antigen and a cell expressing a cell surface antigen recognized by the antibody group are associated with each other.

<Method of Obtaining Antibody or Antibody Set, Antibody or Antibody Set to be Obtained>

[33] A method of obtaining an antibody having a relationship with respect to a certain disease, the method comprising the following steps:

(1) selecting one or two or more of antibody groups from the plurality of antibody groups classified by the classifying method according to [1];

(2) with respect to one kind or two or more kinds of diseases, examining a reactivity between an antibody in each of the selected antibody groups and a certain disease; and (3) selecting an antibody in the antibody group, to which an antibody having a specific reactivity to any of diseases belongs, as a useful antibody.

[34] A method of obtaining an antibody having a relationship with respect to a certain disease, the method comprising the following steps:

(1) selecting one or two or more of antibody groups from the plurality of antibody groups classified by the classifying method according to [19];

(2) with respect to one kind or two or more kinds of diseases, examining a reactivity between an antibody in each of the selected antibody groups and a certain disease; and (3) selecting an antibody in the antibody group, to which an antibody having a specific reactivity to any of diseases belongs, as a useful antibody.

[35] A method of obtaining an antibody set having a relationship with respect to a certain disease, the method comprising the following steps:

(1) selecting one or two or more antibody groups from the plurality of antibody groups classified by the classifying method according to [1];

(2) with respect to one kind or two or more kinds of diseases, examining a reactivity between an antibody in each of the selected antibody groups and a certain disease; and (3') selecting a disease to which two or more antibodies show a specific reactivity, then selecting antibodies from the antibody group, to which the antibody having a specific reactivity to the disease belongs, and combining the selected antibodies.

[36] A method of obtaining an antibody set having a relationship with respect to a certain disease, the method comprising the following steps:

(1) selecting two or more antibody groups recognizing different antigens from the plurality of antibody groups classified by the classifying method according to [1];

(2) with respect to two kinds or more diseases, examining a reactivity between an antibody in each of the selected antibody groups and a certain disease; and (3) selecting antibodies from the antibody group, to which the antibody having a specific reactivity to any of disease belongs, and combining the selected antibodies.

[37] A method of obtaining an antibody set having a relationship with respect to a certain disease, the method comprising the following steps:

(1) selecting two or more antibody groups recognizing different antigens from the plurality of antibody groups classified by the classifying method according to [1];

(2) with respect to one kind or two or more kinds of diseases, examining a reactivity between an antibody in each of the selected antibody groups and a certain disease; and (3) selecting an antibody from the antibody group to which the antibody having a specific reactivity to any of diseases belongs, and an antibody belonging to other antibody group whose antigen is common to that of the antibody group, and combining the selected antibodies.

[38] A method of obtaining an antibody set having a relationship with respect to a certain disease, the method comprising the following steps:

(1) selecting two or more antibody groups recognizing the common antigen from the plurality of antibody groups classified by the classifying method according to [1];

(2) with respect to one kind or two or more kinds of pathologic conditions, examining a reactivity between an antibody in each of the selected antibody groups and a pathologic condition; and (3) connecting information about the reactivity and then combining the antibodies in the antibody groups.

[39] A method of obtaining an antibody set having a relationship with respect to a certain disease, the method comprising the following steps:

(1) selecting one or two or more antibody groups from the plurality of antibody groups classified by the classifying method according to [19];

(2) with respect to one kind or two or more kinds of diseases, examining a reactivity between an antibody in each of the selected antibody groups and a certain disease; and (3') selecting a disease to which two or more antibodies show a specific reactivity, then selecting antibodies from an antibody group which the antibodies showing a specific reactivity to the disease belong to, and combining the selected antibodies.

[40] A method of obtaining an antibody set having a relationship with respect to a certain disease, the method comprising the following steps:

(1) selecting two or more antibody groups recognizing different antigens from the plurality of antibody groups classified by the classifying method according to [19];

(2) with respect to two or more kinds of diseases, examining a reactivity between an antibody in each of the selected antibody groups and a certain disease in two or more kinds of diseases; and (3) selecting antibodies from the antibody group to which the antibody having a specific reactivity to any of diseases belong, and combining the selected antibodies.

[41] A method of obtaining an antibody set having a relationship with respect to a certain disease, the method comprising the following steps:

(1) selecting two or more antibody groups recognizing different antigens from the plurality of antibody groups classified by the classifying method according to [19];

(2) with respect to one kind or two or more kinds of diseases, examining a reactivity between an antibody in each of the selected antibody groups and a certain disease; and (3) selecting an antibody from the antibody group to which the antibody having a specific reactivity to any of disease belongs, and an antibody belonging to other antibody group whose antigen is common to that of the antibody group, and combining the selected antibodies.

[42] A method of obtaining an antibody set having a relationship with respect to a certain disease, the method comprising the following steps:

(1) selecting two or more antibody groups recognizing the common antigen from the plurality of antibody groups classified by the classifying method according to [19];

(2) with respect to one kind or two or more kinds of pathologic conditions, examining a reactivity between an antibody in each of the selected antibody groups and a pathologic condition; and (3) associating information about the reactivity and then combining the antibodies in the antibody groups.

[43] The obtaining method according any of [33] to [42], wherein the disease is selected from the group consisting of kidney cancer, hepatic cell carcinoma, gallbladder and liver cancer, alveolar cell carcinoma, lung squamous cell cancer, pulmonary adenocarcinoma, pancreas cancer, adenocarcinoma, and ovarian cancer.

[44] The obtaining method according any of [33] to [42], wherein in the step (2), the reactivity is examined by one or more methods selected from the group consisting of an immunostaining procedure, an immunoprecipitation method, a flow cytometry analysis, cell ELISA, an intermolecular interactive analysis between a disease-related molecule (disease causative gene product and the like) and an antibody, and application test to a disease model cell (or animal).

[45] An isolated antibody obtained by the method according to [33] or [34].

[46] An antibody set obtained by the method described in any of [35] to [42].

<Production Method of Panel, Panel, and Combination of Antibody or Antibody Set and Panel>

[47] A production method of a panel displaying a relationship between an antibody and a disease, the method comprising the following steps:

(1) selecting one or two or more of antibody groups from the plurality of antibody groups classified by the classifying method according to [1];

(2) with respect to one kind or two or more kinds of diseases, examining a reactivity between an antibody in each of the selected antibody groups and a certain disease; and (3) associating the results of the step (2) with each antibody and displaying by using a drawing or a tabular format.

[48] A production method of a panel displaying a relationship between an antibody and a disease, the method comprising the following steps:

(1) selecting two or more of antibody groups recognizing different antigens from the plurality of antibody groups classified by the classifying method according to [1];

(2) with respect to one kind or two or more kinds of diseases, examining a reactivity between an antibody in each of the selected antibody groups and a certain disease; and (3) associating the results of the step (2) with each antibody and displaying by using a drawing or a tabular format.

[49] A production method of a panel displaying a relationship between an antibody and a pathologic condition, the method comprising the following steps:

(1) selecting two or more of antibody groups recognizing a common antigen from the plurality of antibody groups classified by the classifying method according to [1];

(2) with respect to one kind or two or more kinds of pathologic condition, examining a reactivity between an antibody in each of the selected antibody groups and a certain pathologic condition of disease; and (3) associating the results of the step (2) with each antibody and displaying by using a drawing or a tabular format.

[50] A production method of a panel displaying a relationship between an antibody and a disease, the method comprising the following steps:

(1) selecting one or two or more of antibody groups from the plurality of antibody groups classified by the classifying method according to [19];

(2) with respect to one kind or two or more kinds of diseases, examining a reactivity between an antibody in each of the selected antibody groups and a certain disease; and (3) associating the results of the step (2) with each antibody and displaying by using a drawing or a tabular format.

[51] A production method of a panel displaying a relationship between an antibody and a disease, the method comprising the following steps:

(1) selecting two or more of antibody groups recognizing different antigens from the plurality of antibody groups classified by the classifying method according to [19];

(2) with respect to one kind or two or more kinds of diseases, examining a reactivity between an antibody in each of the selected antibody groups and a certain disease; and (3) associating the results of the step (2) with each antibody and displaying by using a drawing or a tabular format.

[52] A production method of a panel displaying a relationship between an antibody and a pathologic condition, the method comprising the following steps:

(1) selecting two or more of antibody groups recognizing a common antigen from the plurality of antibody groups classified by the classifying method according to [19];

(2) with respect to one kind or two or more kinds of pathologic condition, examining a reactivity between an antibody in each of the selected antibody groups and a certain pathologic condition of disease; and (3) associating the results of the step (2) with each antibody and displaying by using a drawing or a tabular format.

[53] A panel produced by the method according to any of [47] to [52].

[54] A combination of an antibody or an antibody set and a panel selected from the group consisting of the following (a) to (d);

(a) a combination of the isolated antibody obtained by the method according to [33] and the panel produced by the method according to [47];

(b) a combination of the antibody set obtained by the method according to [35] and the panel produced by the method according to [47];

(c) a combination of the antibody set obtained by the method according to [36] and the panel produced by the method according to [48];

(d) a combination of the antibody set obtained by the method according to [37] and the panel produced by the method according to [48];

(e) a combination of the antibody set obtained by the method according to [38] and the panel produced by the method according to [49];

(f) an isolated antibody obtained by the method according to [34] and the panel produced by the method according to [50];

(g) a combination of the antibody set obtained by the method according to [39] and the panel produced by the method according to [50];

(h) a combination of the antibody set obtained by the method according to [40] and the panel produced by the method according to [51];

(i) a combination of the antibody set obtained by the method according to [41] and the panel produced by the method according to [51]; and (j) a combination of the antibody set obtained by the method according to [42] and the panel produced by the method according to [52].

[55] A method of testing a disease in which a cell surface antigen is an indicator, the method comprising the following steps:

(1) preparing a cell or a tissue separated from a subject;

(2) examining a reactivity between the cell or the tissue and each antibody displayed on the panel according to [53]; and (3) collating the results in the step (2) with the panel.

<Method of Selecting Optimum Treatment Method>

[56] A method of selecting an optimum treatment method for a certain disease, the method comprising the following steps:

(1) preparing a cell or a tissue separated from a subject;

(2) examining a reactivity between the cell or the tissue and each antibody displayed on the panel according to [53];

(3) collating the results in the step (2) with the panel, and (4) selecting an effective antibody according to the results of collating.

[57] The method according to [56], wherein the effective antibody is an antibody showing a specific reactivity in the step (2) or an antibody equivalent thereto.

[58] The method according to [56] or [57], wherein the certain disease is a disease in which a cell surface antigen selected from the group consisting of HER1, HER2, CD46, ITGA3, ICAM1, ALCAM, CD147, IgSF4, BCAM, C1qR, CD44, CD73, LAR, EpCAM and HGFR is an indicator.

[59] The method according to any of [56] to [58], wherein the panel displays two or more antibodies selected from the group consisting of 048-006 antibody, 057-091 antibody, 059-152 antibody, 048-040 antibody, 054-101 antibody, 055-147 antibody, 059-173 antibody, 067-149 antibody, 067-176 antibody, 015-126 antibody, 015-044 antibody, 015-102 antibody, 015-136 antibody, 015-143 antibody, 015-209 antibody, 039-016 antibody, 053-216 antibody, 075-024 antibody, 075-110 antibody, 086-032 antibody, 086-035 antibody, 086-036 antibody, 086-061 antibody, 086-138 antibody, 086-182 antibody, 035-224 antibody, 045-011 antibody, 051-144 antibody, 052-053 antibody, 052-073 antibody, 053-049 antibody, 3172-120 antibody, 066-069 antibody, 015-003 antibody, 064-002 antibody, 064-006 antibody, 064-012a antibody, 064-012b antibody, 064-014 antibody, 064-054 antibody, 064-085 antibody, 064-093 antibody, 064-116 antibody, 065-183 antibody, 067-142 antibody, 068-007 antibody, 052-033 antibody, 053-042 antibody, 053-051 antibody, 053-059 antibody, 053-085 antibody, 035-234 antibody, 040-107 antibody, 041-118 antibody, 066-174 antibody, 083-040 antibody, 029-143 antibody, 045-134 antibody, 062-101 antibody, 062-109 antibody, 084-103 antibody, 052-274 antibody, 029-067 antibody, 083-131 antibody, 059-053 antibody, 064-003 antibody, 067-213 antibody, 067-153 antibody, 067-126 antibody, 067-133 antibody, 067-287 antibody, 064-044 antibody, 065-030 antibody, 065-358 antibody, 066-019 antibody, 079-085 antibody, 067-024 antibody and 076-048 antibody.

[60] A method of selecting an optimum treatment method of a certain disease, the method comprising the following steps:

(1) preparing a panel displaying a reactivity between one or more antibodies selected from the group consisting of 048-006 antibody, 015-126 antibody, 067-133 antibody, 064-044 antibody, 076-048 antibody and 059-053 antibody, and a clinical cancer tissue of one or more diseases selected from the group consisting of squamous carcinoma, adenosquamous carcinoma, alveolar adenocarcinoma, adenocarcinoma, and large cell carcinoma, and a cell or tissue separated from a subject;

(2) examining a reactivity between the cell or the tissue and each antibody displayed on the panel;

(3) collating the results in the step (2) with the panel, and (4) selecting an effective antibody according to the results of collating.

[61] The method according to [60], wherein the effective antibody is an antibody showing a specific reactivity in the step (2) or an antibody equivalent thereto.

[62] The method according to [60] or [61], wherein the certain disease is a disease selected from the group consisting of squamous carcinoma, adenosquamous carcinoma, alveolar adenocarcinoma, adenocarcinoma, and large cell carcinoma.
<Isolated Antibody>

[63] An isolated antibody having affinity to HER1, comprising:

a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) selected from the group consisting of the following (1) to (3);

heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) selected from the group consisting of the following (4) to (6);

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (7) to (9) and (13) to (18); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (10) to (12) and (19) to (24);

(1) SEQ ID NO: 4 and SEQ ID NO: 8
(2) SEQ ID NO: 12 and SEQ ID NO: 16
(3) SEQ ID NO: 20 and SEQ ID NO: 24
(4) SEQ ID NO: 3, SEQ ID NO: 4, SEQ ID NO: 7, and SEQ ID NO: 8
(5) SEQ ID NO: 11, SEQ ID NO: 12, SEQ ID NO: 15, and SEQ ID NO: 16
(6) SEQ ID NO: 19, SEQ ID NO: 20, SEQ ID NO: 23, and SEQ ID NO: 24
(7) SEQ ID NO: 2, SEQ ID NO: 3, SEQ ID NO: 4, SEQ ID NO: 6, SEQ ID NO: 7, and SEQ ID NO: 8
(8) SEQ ID NO: 10, SEQ ID NO: 11, SEQ ID NO: 12, SEQ ID NO: 14, SEQ ID NO: 15, and SEQ ID NO: 16
(9) SEQ ID NO: 18, SEQ ID NO: 19, SEQ ID NO: 20, SEQ ID NO: 22, SEQ ID NO: 23, and SEQ ID NO: 24
(10) SEQ ID NO: 1, and SEQ ID NO: 5
(11) SEQ ID NO: 9, and SEQ ID NO: 13
(12) SEQ ID NO: 17, and SEQ ID NO: 21
(13) SEQ ID NO: 484 (VH CDR1), SEQ ID NO: 485 (VH CDR2), SEQ ID NO: 486 (VH CDR3), SEQ ID NO: 488 (VL CDR1), SEQ ID NO: 489 (VL CDR2), and SEQ ID NO: 490 (VL CDR3)
(14) SEQ ID NO: 492 (VH CDR1), SEQ ID NO: 493 (VH CDR2), SEQ ID NO: 494 (VH CDR3), SEQ ID NO: 496 (VL CDR1), SEQ ID NO: 497 (VL CDR2), and SEQ ID NO: 498 (VL CDR3)
(15) SEQ ID NO: 500 (VH CDR1), SEQ ID NO: 501 (VH CDR2), SEQ ID NO: 502 (VH CDR3), SEQ ID NO: 504 (VL CDR1), SEQ ID NO: 505 (VL CDR2), and SEQ ID NO: 506 (VL CDR3)
(16) SEQ ID NO: 508 (VH CDR1), SEQ ID NO: 509 (VH CDR2), SEQ ID NO: 510 (VH CDR3), SEQ ID NO: 512 (VL CDR1), SEQ ID NO: 513 (VL CDR2), and SEQ ID NO: 514 (VL CDR3)
(17) SEQ ID NO: 516 (VH CDR1), SEQ ID NO: 517 (VH CDR2), SEQ ID NO: 518 (VH CDR3), SEQ ID NO: 520 (VL CDR1), SEQ ID NO: 521 (VL CDR2), and SEQ ID NO: 522 (VL CDR3)
(18) SEQ ID NO: 524 (VH CDR1), SEQ ID NO: 525 (VH CDR2), SEQ ID NO: 526 (VH CDR3), SEQ ID NO: 528 (VL CDR1), SEQ ID NO: 529 (VL CDR2), and SEQ ID NO: 530 (VL CDR3)
(19) SEQ ID NO: 483 (VH), and SEQ ID NO: 487 (VL)
(20) SEQ ID NO: 491 (VH), and SEQ ID NO: 495 (VL)
(21) SEQ ID NO: 499 (VH), and SEQ ID NO: 503 (VL)
(22) SEQ ID NO: 507 (VH), and SEQ ID NO: 511 (VL)
(23) SEQ ID NO: 515 (VH), and SEQ ID NO: 519 (VL), and
(24) SEQ ID NO: 523 (VH), and SEQ ID NO: 527 (VL)

[64] An isolated antibody having affinity to HER2, comprising:

a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) shown in the following (1);

heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) shown in the following (2);

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (3) and (5) to (19); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (4) and (20) to (34);

(1) SEQ ID NO: 28, and SEQ ID NO: 32
(2) SEQ ID NO: 27, SEQ ID NO: 28, SEQ ID NO: 31, and SEQ ID NO: 32
(3) SEQ ID NO: 26, SEQ ID NO: 27, SEQ ID NO: 28, SEQ ID NO: 30, SEQ ID NO: 31, and SEQ ID NO: 32

(4) SEQ ID NO: 25, and SEQ ID NO: 29
(5) SEQ ID NO: 532 (VH CDR1), SEQ ID NO: 533 (VH CDR2), SEQ ID NO: 534 (VH CDR3), SEQ ID NO: 536 (VL CDR1), SEQ ID NO: 537 (VL CDR2), and SEQ ID NO: 538 (VL CDR3)
(6) SEQ ID NO: 540 (VH CDR1), SEQ ID NO: 541 (VH CDR2), SEQ ID NO: 542 (VH CDR3), SEQ ID NO: 544 (VL CDR1), SEQ ID NO: 545 (VL CDR2), and SEQ ID NO: 546 (VL CDR3)
(7) SEQ ID NO: 548 (VH CDR1), SEQ ID NO: 549 (VH CDR2), SEQ ID NO: 550 (VH CDR3), SEQ ID NO: 552 (VL CDR1), SEQ ID NO: 553 (VL CDR2), and SEQ ID NO: 554 (VL CDR3)
(8) SEQ ID NO: 556 (VH CDR1), SEQ ID NO: 557 (VH CDR2), SEQ ID NO: 558 (VH CDR3), SEQ ID NO: 560 (VL CDR1), SEQ ID NO: 561 (VL CDR2), and SEQ ID NO: 562 (VL CDR3)
(9) SEQ ID NO: 564 (VH CDR1), SEQ ID NO: 565 (VH CDR2), SEQ ID NO: 566 (VH CDR3), SEQ ID NO: 568 (VL CDR1), SEQ ID NO: 569 (VL CDR2), and SEQ ID NO: 570 (VL CDR3)
(10) SEQ ID NO: 572 (VH CDR1), SEQ ID NO: 573 (VH CDR2), SEQ ID NO: 574 (VH CDR3), SEQ ID NO: 576 (VL CDR1), SEQ ID NO: 577 (VL CDR2), and SEQ ID NO: 578 (VL CDR3)
(11) SEQ ID NO: 580 (VH CDR1), SEQ ID NO: 581 (VH CDR2), SEQ ID NO: 582 (VH CDR3), SEQ ID NO: 584 (VL CDR1), SEQ ID NO: 585 (VL CDR2), and SEQ ID NO: 586 (VL CDR3)
(12) SEQ ID NO: 588 (VH CDR1), SEQ ID NO: 589 (VH CDR2), SEQ ID NO: 590 (VH CDR3), SEQ ID NO: 592 (VL CDR1), SEQ ID NO: 593 (VL CDR2), and SEQ ID NO: 594 (VL CDR3)
(13) SEQ ID NO: 596 (VH CDR1), SEQ ID NO: 597 (VH CDR2), SEQ ID NO: 598 (VH CDR3), SEQ ID NO: 600 (VL CDR1), SEQ ID NO: 601 (VL CDR2), and SEQ ID NO: 602 (VL CDR3)
(14) SEQ ID NO: 604 (VH CDR1), SEQ ID NO: 605 (VH CDR2), SEQ ID NO: 606 (VH CDR3), SEQ ID NO: 608 (VL CDR1), SEQ ID NO: 609 (VL CDR2), and SEQ ID NO: 610 (VL CDR3)
(15) SEQ ID NO: 612 (VH CDR1), SEQ ID NO: 613 (VH CDR2), SEQ ID NO: 614 (VH CDR3), SEQ ID NO: 616 (VL CDR1), SEQ ID NO: 617 (VL CDR2), and SEQ ID NO: 618 (VL CDR3)
(16) SEQ ID NO: 620 (VH CDR1), SEQ ID NO: 621 (VH CDR2), SEQ ID NO: 622 (VH CDR3), SEQ ID NO: 624 (VL CDR1), SEQ ID NO: 625 (VL CDR2), and SEQ ID NO: 626 (VL CDR3)
(17) SEQ ID NO: 628 (VH CDR1), SEQ ID NO: 629 (VH CDR2), SEQ ID NO: 630 (VH CDR3), SEQ ID NO: 632 (VL CDR1), SEQ ID NO: 633 (VL CDR2), and SEQ ID NO: 634 (VL CDR3)
(18) SEQ ID NO: 636 (VH CDR1), SEQ ID NO: 637 (VH CDR2), SEQ ID NO: 638 (VH CDR3), SEQ ID NO: 640 (VL CDR1), SEQ ID NO: 641 (VL CDR2), and SEQ ID NO: 642 (VL CDR3)
(19) SEQ ID NO: 644 (VH CDR1), SEQ ID NO: 645 (VH CDR2), SEQ ID NO: 646 (VH CDR3), SEQ ID NO: 648 (VL CDR1), SEQ ID NO: 649 (VL CDR2), and SEQ ID NO: 650 (VL CDR3)
(20) SEQ ID NO: 531 (VH), and SEQ ID NO: 535 (VL)
(21) SEQ ID NO: 539 (VH), and SEQ ID NO: 543 (VL)
(22) SEQ ID NO: 547 (VH), and SEQ ID NO: 551 (VL)
(23) SEQ ID NO: 555 (VH), and SEQ ID NO: 559 (VL)
(24) SEQ ID NO: 563 (VH), and SEQ ID NO: 567 (VL)
(25) SEQ ID NO: 571 (VH), and SEQ ID NO: 575 (VL)
(26) SEQ ID NO: 579 (VH), and SEQ ID NO: 583 (VL)
(27) SEQ ID NO: 587 (VH), and SEQ ID NO: 591 (VL)
(28) SEQ ID NO: 595 (VH), and SEQ ID NO: 599 (VL)
(29) SEQ ID NO: 603 (VH), and SEQ ID NO: 607 (VL)
(30) SEQ ID NO: 611 (VH), and SEQ ID NO: 615 (VL)
(31) SEQ ID NO: 619 (VH), and SEQ ID NO: 623 (VL)
(32) SEQ ID NO: 627 (VH), and SEQ ID NO: 631 (VL)
(33) SEQ ID NO: 635 (VH), and SEQ ID NO: 639 (VL), and
(34) SEQ ID NO: 643 (VH), and SEQ ID NO: 647 (VL)

[65] An isolated antibody having affinity to CD46 antigen, comprising:

a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) selected from the group consisting of the following (1) to (7);

heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) selected from the group consisting of the following (8) to (14);

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (15) to (22); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (23) to (30);
(1) SEQ ID NO: 36, and SEQ ID NO: 40
(2) SEQ ID NO: 44, and SEQ ID NO: 48
(3) SEQ ID NO: 52, and SEQ ID NO: 56
(4) SEQ ID NO: 60, and SEQ ID NO: 64
(5) SEQ ID NO: 68, and SEQ ID NO: 72
(6) SEQ ID NO: 76, and SEQ ID NO: 80
(7) SEQ ID NO: 84, and SEQ ID NO: 88
(8) SEQ ID NO: 35, SEQ ID NO: 36, SEQ ID NO: 39, and SEQ ID NO: 40
(9) SEQ ID NO: 43, SEQ ID NO: 44, SEQ ID NO: 47, and SEQ ID NO: 48
(10) SEQ ID NO: 51, SEQ ID NO: 52, SEQ ID NO: 55, and SEQ ID NO: 56
(11) SEQ ID NO: 59, SEQ ID NO: 60, SEQ ID NO: 63, and SEQ ID NO: 64
(12) SEQ ID NO: 67, SEQ ID NO: 68, SEQ ID NO: 71, and SEQ ID NO: 72
(13) SEQ ID NO: 75, SEQ ID NO: 76, SEQ ID NO: 79, and SEQ ID NO: 80
(14) SEQ ID NO: 83, SEQ ID NO: 84, SEQ ID NO: 87, and SEQ ID NO: 88

(15) SEQ ID NO: 34, SEQ ID NO: 35, SEQ ID NO: 36, SEQ ID NO: 38, SEQ ID NO: 39, and SEQ ID NO: 40
(16) SEQ ID NO: 42, SEQ ID NO: 43, SEQ ID NO: 44, SEQ ID NO: 46, SEQ ID NO: 47, and SEQ ID NO: 48
(17) SEQ ID NO: 50, SEQ ID NO: 51, SEQ ID NO: 52, SEQ ID NO: 54, SEQ ID NO: 55, and SEQ ID NO: 56
(18) SEQ ID NO: 58, SEQ ID NO: 59, SEQ ID NO: 60, SEQ ID NO: 62, SEQ ID NO: 63, and SEQ ID NO: 64
(19) SEQ ID NO: 66, SEQ ID NO: 67, SEQ ID NO: 68, SEQ ID NO: 70, SEQ ID NO: 71, and SEQ ID NO: 72
(20) SEQ ID NO: 74, SEQ ID NO: 75, SEQ ID NO: 76, SEQ ID NO: 78, SEQ ID NO: 79, and SEQ ID NO: 80
(21) SEQ ID NO: 82, SEQ ID NO: 83, SEQ ID NO: 84, SEQ ID NO: 86, SEQ ID NO: 87, and SEQ ID NO: 88
(22) SEQ ID NO: 756 (VH CDR1), SEQ ID NO: 757 (VH CDR2), SEQ ID NO: 758 (VH CDR3), SEQ ID NO: 760 (VL CDR1), SEQ ID NO: 761 (VL CDR2), and SEQ ID NO: 762 (VL CDR3)
(23) SEQ ID NO: 33, and SEQ ID NO: 37
(24) SEQ ID NO: 41, and SEQ ID NO: 45
(25) SEQ ID NO: 49, and SEQ ID NO: 53
(26) SEQ ID NO: 57, and SEQ ID NO: 61
(27) SEQ ID NO: 65, and SEQ ID NO: 69
(28) SEQ ID NO: 73, and SEQ ID NO: 77
(29) SEQ ID NO: 81, and SEQ ID NO: 85
(30) SEQ ID NO: 755 (VH), and SEQ ID NO: 759 (VL)

[66] An isolated antibody having affinity to ITAG3, comprising:
a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) shown in the following (1);
heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) shown in the following (2);
heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (3) and (5) to (16); or
a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (4) and (17) to (28);
(1) SEQ ID NO: 92, and SEQ ID NO: 96
(2) SEQ ID NO: 91, SEQ ID NO: 92, SEQ ID NO: 95, and SEQ ID NO: 96
(3) SEQ ID NO: 90, SEQ ID NO: 91, SEQ ID NO: 92, SEQ ID NO: 94, and SEQ ID NO: 95,
(4) SEQ ID NO: 89, and SEQ ID NO: 93
(5) SEQ ID NO: 676 (VH CDR1), SEQ ID NO: 677 (VH CDR2), SEQ ID NO: 678 (VH CDR3), SEQ ID NO: 680 (VL CDR1), SEQ ID NO: 681 (VL CDR2), and SEQ ID NO: 682 (VL CDR3)
(6) SEQ ID NO: 684 (VH CDR1), SEQ ID NO: 685 (VH CDR2), SEQ ID NO: 686 (VH CDR3), SEQ ID NO: 688 (VL CDR1), SEQ ID NO: 689 (VL CDR2), and SEQ ID NO: 690 (VL CDR3)
(7) SEQ ID NO: 692 (VH CDR1), SEQ ID NO: 693 (VH CDR2), SEQ ID NO: 694 (VH CDR3), SEQ ID NO: 696 (VL CDR1), SEQ ID NO: 697 (VL CDR2), and SEQ ID NO: 698 (VL CDR3)
(8) SEQ ID NO: 700 (VH CDR1), SEQ ID NO: 701 (VH CDR2), SEQ ID NO: 702 (VH CDR3), SEQ ID NO: 704 (VL CDR1), SEQ ID NO: 705 (VL CDR2), and SEQ ID NO: 706 (VL CDR3)
(9) SEQ ID NO: 708 (VH CDR1), SEQ ID NO: 709 (VH CDR2), SEQ ID NO: 710 (VH CDR3), SEQ ID NO: 712 (VL CDR1), SEQ ID NO: 713 (VL CDR2), and SEQ ID NO: 714 (VL CDR3)
(10) SEQ ID NO: 716 (VH CDR1), SEQ ID NO: 717 (VH CDR2), SEQ ID NO: 718 (VH CDR3), SEQ ID NO: 720 (VL CDR1), SEQ ID NO: 721 (VL CDR2), and SEQ ID NO: 722 (VL CDR3)
(11) SEQ ID NO: 724 (VH CDR1), SEQ ID NO: 725 (VH CDR2), SEQ ID NO: 726 (VH CDR3), SEQ ID NO: 728 (VL CDR1), SEQ ID NO: 729 (VL CDR2), and SEQ ID NO: 730 (VL CDR3)
(12) SEQ ID NO: 732 (VH CDR1), SEQ ID NO: 733 (VH CDR2), SEQ ID NO: 734 (VH CDR3), SEQ ID NO: 736 (VL CDR1), SEQ ID NO: 737 (VL CDR2), and SEQ ID NO: 738 (VL CDR3)
(13) SEQ ID NO: 740 (VH CDR1), SEQ ID NO: 741 (VH CDR2), SEQ ID NO: 742 (VH CDR3), SEQ ID NO: 744 (VL CDR1), SEQ ID NO: 745 (VL CDR2), and SEQ ID NO: 746 (VL CDR3)
(14) SEQ ID NO: 748 (VH CDR1), SEQ ID NO: 749 (VH CDR2), SEQ ID NO: 750 (VH CDR3), SEQ ID NO: 752 (VL CDR1), SEQ ID NO: 753 (VL CDR2), and SEQ ID NO: 754 (VL CDR3)
(15) SEQ ID NO: 764 (VH CDR1), SEQ ID NO: 765 (VH CDR2), SEQ ID NO: 766 (VH CDR3), SEQ ID NO: 768 (VL CDR1), SEQ ID NO: 769 (VL CDR2), and SEQ ID NO: 770 (VL CDR3)
(16) SEQ ID NO: 772 (VH CDR1), SEQ ID NO: 773 (VH CDR2), SEQ ID NO: 774 (VH CDR3), SEQ ID NO: 776 (VL CDR1), SEQ ID NO: 777 (VL CDR2), and SEQ ID NO: 778 (VL CDR3)
(17) SEQ ID NO: 675 (VH), and SEQ ID NO: 679 (VL)
(18) SEQ ID NO: 683 (VH), and SEQ ID NO: 687 (VL)
(19) SEQ ID NO: 691 (VH), and SEQ ID NO: 695 (VL)
(20) SEQ ID NO: 699 (VH), and SEQ ID NO: 703 (VL)
(21) SEQ ID NO: 707 (VH), and SEQ ID NO: 711 (VL)
(22) SEQ ID NO: 715 (VH), and SEQ ID NO: 719 (VL)
(23) SEQ ID NO: 723 (VH), and SEQ ID NO: 727 (VL)
(24) SEQ ID NO: 731 (VH), and SEQ ID NO: 735 (VL)
(25) SEQ ID NO: 739 (VH), and SEQ ID NO: 743 (VL)
(26) SEQ ID NO: 747 (VH), and SEQ ID NO: 751 (VL)
(27) SEQ ID NO: 763 (VH), and SEQ ID NO: 767 (VL), and
(28) SEQ ID NO: 771 (VH), and SEQ ID NO: 775 (VL)

[67] An isolated antibody having affinity to ICAM1, comprising:
a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) selected from the group consisting of the following (1) to (5);

heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) selected from the group consisting of the following (6) to (10);

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (11) to (15); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (16) to (20);

(1) SEQ ID NO: 100, and SEQ ID NO: 104
(2) SEQ ID NO: 108, and SEQ ID NO: 112
(3) SEQ ID NO: 116, and SEQ ID NO: 120
(4) SEQ ID NO: 124, and SEQ ID NO: 128
(5) SEQ ID NO: 132, and SEQ ID NO: 136
(6) SEQ ID NO: 99, SEQ ID NO: 100, SEQ ID NO: 103, and SEQ ID NO: 104
(7) SEQ ID NO: 107, SEQ ID NO: 108, SEQ ID NO: 111, and SEQ ID NO: 112
(8) SEQ ID NO: 115, SEQ ID NO: 116, SEQ ID NO: 119, and SEQ ID NO: 120
(9) SEQ ID NO: 123, SEQ ID NO: 124, SEQ ID NO: 127, and SEQ ID NO: 128
(10) SEQ ID NO: 131, SEQ ID NO: 132, SEQ ID NO: 135, SEQ ID NO: 136
(11) SEQ ID NO: 98, SEQ ID NO: 99, SEQ ID NO: 100, SEQ ID NO: 102, SEQ ID NO: 103, and SEQ ID NO: 104
(12) SEQ ID NO: 106, SEQ ID NO: 107, SEQ ID NO: 108, SEQ ID NO: 110, SEQ ID NO: 111, and SEQ ID NO: 112
(13) SEQ ID NO: 114, SEQ ID NO: 115, SEQ ID NO: 116, SEQ ID NO: 118, SEQ ID NO: 119, and SEQ ID NO: 120
(14) SEQ ID NO: 122, SEQ ID NO: 123, SEQ ID NO: 124, SEQ ID NO: 126, SEQ ID NO: 127, and SEQ ID NO: 128
(15) SEQ ID NO: 130, SEQ ID NO: 131, SEQ ID NO: 132, SEQ ID NO: 134, SEQ ID NO: 135, and SEQ ID NO: 136
(16) SEQ ID NO: 97, and SEQ ID NO: 101
(17) SEQ ID NO: 105, and SEQ ID NO: 109
(18) SEQ ID NO: 113, and SEQ ID NO: 117
(19) SEQ ID NO: 121, and SEQ ID NO: 125
(20) SEQ ID NO: 129, and SEQ ID NO: 133

[68] An isolated antibody having affinity to ALCAM, comprising:

a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) selected from the group consisting of the following (1) to (5);

heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) selected from the group consisting of the following (6) to (10);

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (11) to (15) and (21) to (28); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (16) to (20) and (29) to (36);

(1) SEQ ID NO: 140, and SEQ ID NO: 144
(2) SEQ ID NO: 148, and SEQ ID NO: 152
(3) SEQ ID NO: 156, and SEQ ID NO: 160
(4) SEQ ID NO: 164, and SEQ ID NO: 168
(5) SEQ ID NO: 172, and SEQ ID NO: 176
(6) SEQ ID NO: 139, SEQ ID NO: 140, SEQ ID NO: 143, and SEQ ID NO: 144
(7) SEQ ID NO: 147, SEQ ID NO: 148, SEQ ID NO: 151, and SEQ ID NO: 152
(8) SEQ ID NO: 155, SEQ ID NO: 156, SEQ ID NO: 159, and SEQ ID NO: 160
(9) SEQ ID NO: 163, SEQ ID NO: 164, SEQ ID NO: 167, and SEQ ID NO: 168
(10) SEQ ID NO: 171, SEQ ID NO: 172, SEQ ID NO: 175, and SEQ ID NO: 176
(11) SEQ ID NO: 138, SEQ ID NO: 139, SEQ ID NO: 140, SEQ ID NO: 142, SEQ ID NO: 143, and SEQ ID NO: 144
(12) SEQ ID NO: 146, SEQ ID NO: 147, SEQ ID NO: 148, SEQ ID NO: 150, SEQ ID NO: 151, and SEQ ID NO: 152
(13) SEQ ID NO: 154, SEQ ID NO: 155, SEQ ID NO: 156, SEQ ID NO: 158, SEQ ID NO: 159, and SEQ ID NO: 160
(14) SEQ ID NO: 162, SEQ ID NO: 163, SEQ ID NO: 164, SEQ ID NO: 166, SEQ ID NO: 167, and SEQ ID NO: 168
(15) SEQ ID NO: 170, SEQ ID NO: 171, SEQ ID NO: 172, SEQ ID NO: 174, SEQ ID NO: 175, and SEQ ID NO: 176
(16) SEQ ID NO: 137, and SEQ ID NO: 141
(17) SEQ ID NO: 145, and SEQ ID NO: 149
(18) SEQ ID NO: 153, and SEQ ID NO: 157
(19) SEQ ID NO: 161, SEQ ID NO: 165
(20) SEQ ID NO: 169, and SEQ ID NO: 173
(21) SEQ ID NO: 780 (VH CDR1), SEQ ID NO: 781 (VH CDR2), SEQ ID NO 782 (VH CDR3), SEQ ID NO: 784 (VL CDR1), SEQ ID NO: 785 (VL CDR2), and SEQ ID NO: 786 (VL CDR3)

(22) SEQ ID NO: 788 (VH CDR1), SEQ ID NO: 789 (VH CDR2), SEQ ID NO: 790 (VH CDR3), SEQ ID NO: 792 (VL CDR1), SEQ ID NO: 793 (VL CDR2), and SEQ ID NO: 794 (VL CDR3)
(23) SEQ ID NO: 796 (VH CDR1), SEQ ID NO: 797 (VH CDR2), SEQ ID NO: 798 (VH CDR3), SEQ ID NO: 800 (VL CDR1), SEQ ID NO: 801 (VL CDR2), and SEQ ID NO: 802 (VL CDR3)
(24) SEQ ID NO: 804 (VH CDR1), SEQ ID NO: 805 (VH CDR2), SEQ ID NO: 806 (VH CDR3), SEQ ID NO: 808 (VL CDR1), SEQ ID NO: 809 (VL CDR2), and SEQ ID NO: 810 (VL CDR3)
(25) SEQ ID NO: 812 (VH CDR1), SEQ ID NO: 813 (VH CDR2), SEQ ID NO: 814 (VH CDR3), SEQ ID NO: 816 (VL CDR1), SEQ ID NO: 817 (VL CDR2), and SEQ ID NO: 818 (VL CDR3)
(26) SEQ ID NO: 820 (VH CDR1), SEQ ID NO: 821 (VH CDR2), SEQ ID NO: 822 (VH CDR3), SEQ ID NO: 824 (VL CDR1), SEQ ID NO: 825 (VL CDR2), and SEQ ID NO: 826 (VL CDR3)
(27) SEQ ID NO: 828 (VH CDR1), SEQ ID NO: 829 (VH CDR2), SEQ ID NO: 830 (VH CDR3), SEQ ID NO: 832 (VL CDR1), SEQ ID NO: 833 (VL CDR2), and SEQ ID NO: 834 (VL CDR3)
(28) SEQ ID NO: 836 (VH CDR1), SEQ ID NO: 837 (VH CDR2), SEQ ID NO: 838 (VH CDR3), SEQ ID NO: 840 (VL CDR1), SEQ ID NO: 841 (VL CDR2), and SEQ ID NO: 842 (VL CDR3)
(29) SEQ ID NO: 779 (VH), and SEQ ID NO: 783 (VL)
(30) SEQ ID NO: 787 (VH), and SEQ ID NO: 791 (VL)
(31) SEQ ID NO: 795 (VH), and SEQ ID NO: 799 (VL)
(32) SEQ ID NO: 803 (VH), and SEQ ID NO: 807 (VL)
(33) SEQ ID NO: 811 (VH), and SEQ ID NO: 815 (VL)
(34) SEQ ID NO: 819 (VH), and SEQ ID NO: 823 (VL)
(35) SEQ ID NO: 827 (VH), and SEQ ID NO: 831 (VL), and
(36) SEQ ID NO: 835 (VH), and SEQ ID NO: 839 (VL)
[69] An isolated antibody having affinity to CD147 antigen, comprising:

a heavy chain variable region CDR3 and a light chain variable region CDR3 specified by a combination of SEQ ID NOs (SEQ ID NO showing an amino acid sequence of a heavy chain variable region CDR3 and SEQ ID NO showing an amino acid sequence of a light chain variable region CDR3) shown in the following (1);

heavy chain variable regions CDR2 and CDR3 and light chain variable regions CDR2 and CDR3 specified by a combination of SEQ ID NOs (SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR2, and SEQ ID NO showing an amino acid sequence of a light chain variable region CDR3) shown in the following (2);

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) shown in the following (3); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) shown in the following (4);

(1) SEQ ID NO: 180, and SEQ ID NO: 184
(2) SEQ ID NO: 179, SEQ ID NO: 180, SEQ ID NO: 183, and SEQ ID NO: 184
(3) SEQ ID NO: 178, SEQ ID NO: 179, SEQ ID NO: 180, SEQ ID NO: 182, SEQ ID NO: 183, and SEQ ID NO: 184, and
(4) SEQ ID NO: 177, and SEQ ID NO: 181

[70] An isolated antibody having affinity to C1qR, comprising:

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) shown in the following (1); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) shown in the following (2);

(1) SEQ ID NO: (VH CDR1) 452, SEQ ID NO: 453 (VH CDR2), SEQ ID NO: 454 (VH CDR3), SEQ ID NO: (VL CDR1) 456, SEQ ID NO: 457 (VL CDR2), and SEQ ID NO: 458 (VL CDR3), and
(2) SEQ ID NO: 451 (VH), and SEQ ID NO: 455 (VL)

[71] An isolated antibody having affinity to CD44, comprising:

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) shown in the following (1); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) shown in the following (2);

(1) SEQ ID NO: 460 (VH CDR1), SEQ ID NO: 461 (VH CDR2), SEQ ID NO: 462 (VH CDR3), SEQ ID NO: 464 (VL CDR1), SEQ ID NO: 465 (VL CDR2), and SEQ ID NO: 466 (VL CDR3), and
(2) SEQ ID NO: 459 (VH), and SEQ ID NO: 463 (VL)

[72] An isolated antibody having affinity to CD73, comprising:

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) shown in the following (1); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) shown in the following (2);
(1) SEQ ID NO: 468 (VH CDR1), SEQ ID NO: 469 (VH CDR2), SEQ ID NO: 470 (VH CDR3), SEQ ID NO: 472 (VL CDR1), SEQ ID NO: 473 (VL CDR2), and SEQ ID NO: 474 (VL CDR3), and
(2) SEQ ID NO: 467 (VH), and SEQ ID NO: 471 (VL)

[73] An isolated antibody having affinity to EpCAM, comprising:

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) shown in the following (1); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) shown in the following (2);
(1) SEQ ID NO: 476 (VH CDR1), SEQ ID NO: 477 (VH CDR2), SEQ ID NO: 478 (VH CDR3), SEQ ID NO: 480 (VL CDR1), SEQ ID NO: 481 (VL CDR2), and SEQ ID NO: 482 (VL CDR3), and
(2) SEQ ID NO: 475 (VH), and SEQ ID NO: 479 (VL)

[74] An isolated antibody having affinity to HGFR, comprising:

heavy chain variable regions CDR1 to CDR3 and light chain variable regions CDR1 to CDR3 specified by a combination of SEQ ID NOs (SEQ ID NO showing an amino acid sequence of a heavy chain variable region CDR1, SEQ ID NO showing an amino acid sequence of a heavy chain variable region CDR2, SEQ ID NO showing an amino acid sequence of a heavy chain variable region CDR3, SEQ ID NO showing an amino acid sequence of a light chain variable region CDR1, SEQ ID NO showing an amino acid sequence of a light chain variable region CDR2, and SEQ ID NO showing an amino acid sequence of a light chain variable region CDR3) selected from the group consisting of the following (1) to (3); or a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (4) to (6);
(1) SEQ ID NO: 652 (VH CDR1), SEQ ID NO: 653 (VH CDR2), SEQ ID NO: 654 (VH CDR3), SEQ ID NO: 656 (VL CDR1), SEQ ID NO: 657 (VL CDR2), and SEQ ID NO: 658 (VL CDR3)
(2) SEQ ID NO: 660 (VH CDR1), SEQ ID NO: 661 (VH CDR2), SEQ ID NO: 662 (VH CDR3), SEQ ID NO: 664 (VL CDR1), SEQ ID NO: 665 (VL CDR2), and SEQ ID NO: 666 (VL CDR3)
(3) SEQ ID NO: 668 (VH CDR1), SEQ ID NO: 669 (VH CDR2), SEQ ID NO: 670 (VH CDR3), SEQ ID NO: 672 (VL CDR1), SEQ ID NO: 673 (VL CDR2), and SEQ ID NO: 674 (VL CDR3)
(4) SEQ ID NO: 651 (VH), and SEQ ID NO: 655 (VL)
(5) SEQ ID NO: 659 (VH), and SEQ ID NO: 663 (VL), and
(6) SEQ ID NO: 667 (VH), and SEQ ID NO: 671 (VL)

[75] An isolated antibody having affinity to LAR, comprising:

a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) selected from the group consisting of the following (1) to (5);
(1) SEQ ID NO: 944 (VH), and SEQ ID NO: 945 (VL)
(2) SEQ ID NO: 946 (VH), and SEQ ID NO: 947 (VL)
(3) SEQ ID NO: 948 (VH), and SEQ ID NO: 949 (VL)
(4) SEQ ID NO: 950 (VH), and SEQ ID NO: 951 (VL), and
(5) SEQ ID NO: 952 (VH), and SEQ ID NO: 953 (VL)

[76] An isolated antibody having affinity to BCAM, comprising:

a heavy chain variable region and a light chain variable region specified by a combination of SEQ ID NOs (SEQ ID NO showing an amino acid sequence of a heavy chain variable region and SEQ ID NO showing an amino acid sequence of a light chain variable region) shown in the group consisting of the following (1);
(1) SEQ ID NO: 954(VH), and SEQ ID NO: 955(VL)

<Isolated Nucleic Acid Molecule, Vector, and the Like>

[77] An isolated nucleic acid molecule, which encodes the heavy chain variable region and/or the light chain variable region of the antibody according to any of [63] to [76].

[78] A vector including the nucleic acid molecule according to [77] in a form capable of being expressed.

[79] A transformant into which the nucleic acid molecule according to [77] is introduced.

[80] A cancer therapeutic agent comprising the antibody according to any of [63] to [76] as an effective ingredient.

[81] A reagent for examining or studying cancer comprising the antibody according to any of [63] to [76].

<Examination Method>

[82] A method for examining gallbladder and liver cancer or pancreas cancer, the method comprising the following steps:
(1) preparing subject cells or tissues separated from a living body; and
(2) detecting a CD46 antigen in the subject cells or tissues.

[83] A method for examining gallbladder and liver cancer or pancreas cancer, the method comprising the following steps:
(1) preparing subject cells or tissues separated from a living body; and
(2) detecting ITGA3 in the subject cells or tissues.

[84] A method for examining kidney cancer, hepatic cell carcinoma or gallbladder and liver cancer, the method comprising the following steps:
(1) preparing subject cells or tissues separated from a living body; and
(2) detecting ALCAM in the subject cells or tissues.

[85] A method for examining kidney cancer, the method comprising the following steps:
(1) preparing subject cells or tissues separated from a living body; and
(2) detecting a CD147 antigen in the subject cells or tissues.

BRIEF DESCRIPTION OF THE DRAWINGS

FIG. 7-1 shows a base sequence (SEQ ID NO: 401) of an insert part of pscFvCA9-E8VHdVLd and an amino acid sequence (SEQ ID NO: 402) encoded by the base sequence.

FIG. 7-2 shows a part continuing to FIG. 7-1.

FIG. 8-1 shows a base sequence (SEQ ID NO: 405) of an insert of pscFvCA-E8VHd and a restriction enzyme site and an amino acid sequence (SEQ ID NO: 406).

FIG. 8-2 shows a part continuing to FIG. 8-1.

FIG. 9 shows a process of screening of an antibody clone specific to liver cancer cell.

FIG. 18 is a table showing a classification of a plurality of antibody clones based on the results of the FCM analysis. Each reference mark in Table is shown by a shift amount from the histogram (reference histogram) provided by the negative control antibody. Double circle mark represents that the shift amount is 20 times or more (the peak value of the is 20 times or more of the reference histogram); "○" (circle mark) represents that the shift amount is 10 times or more; "Δ" (triangle mark) represents that the shift amount is 3 times or more; and "x" represents that the shift amount is less than 3, respectively (an oblique line means no data is obtained).

FIGS. 76 A and B is a table showing culture conditions of cell lines to be used in experiments.

FIG. 78 is a conceptual diagram of three-dimensional ELISA, showing a procedure of specifying an antibody clone.

FIG. 87 shows a correspondence between a tissue that has been diagnosed to be specific in immunostaining using a clinical cancer specimen and each antibody clone.

FIG. 88 shows a reactivity of a clinical cancer specimen and each antibody clone. + represents positive to the immunostaining; ± represents weakly positive to the immunostaining; and − represents negative to the immuno staining.

DETAILED DESCRIPTION OF THE INVENTION

Terms

Figure 1:
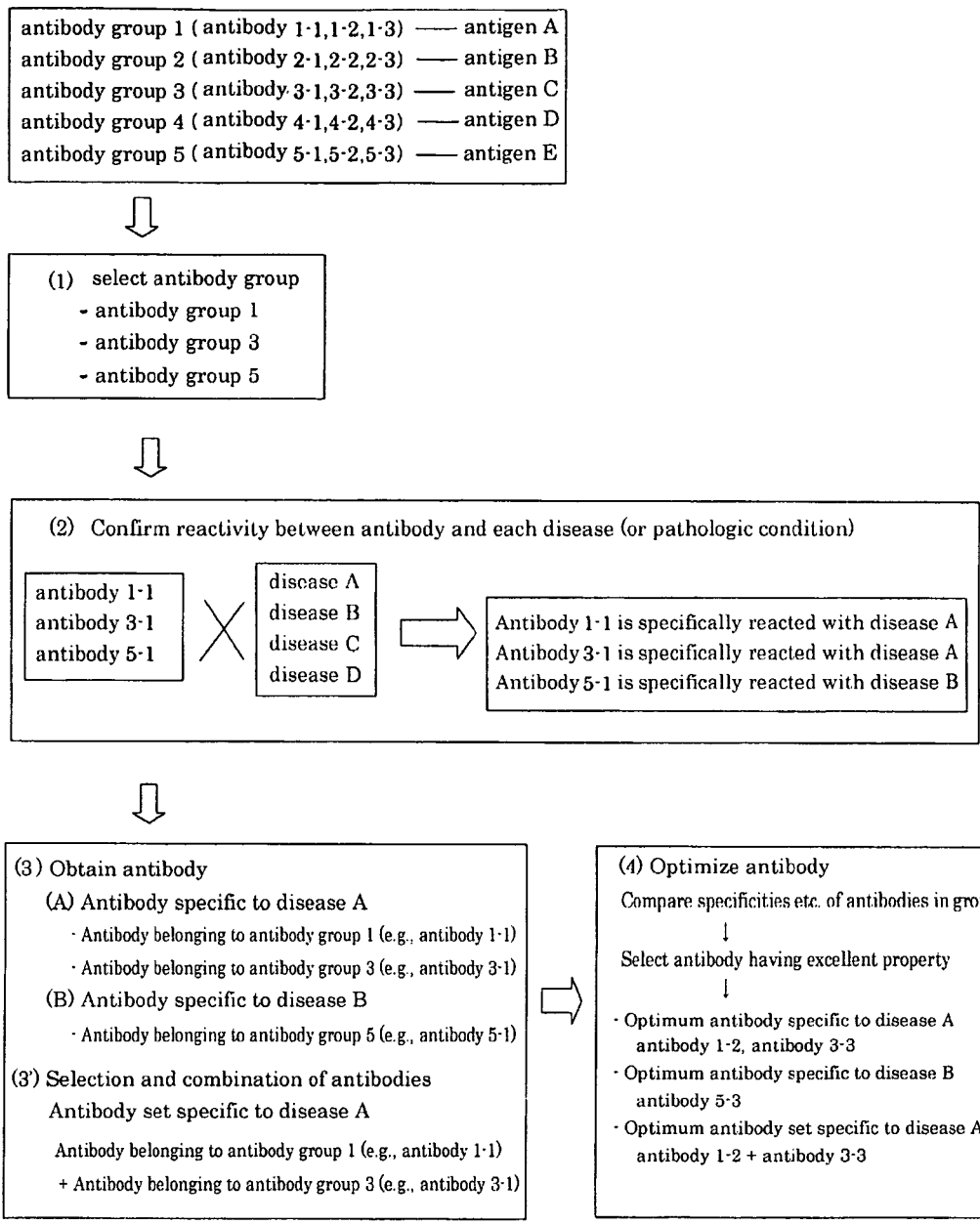
FIG. 1 shows one example of a method of obtaining an antibody or an antibody set related to a certain disease.

For convenience, certain terms employed in the specification are collected herein.

In the specification, the terms "comprise/include" and "comprising/including" are used to include the meaning of "consisting of." Therefore, for example, "a product (or method) comprising/including a plurality of elements (members)" necessarily includes also the terms "a product (or method) consisting of a plurality of elements (members)"

The term "disease" herein is used interchangeably with the terms meaning that some function failure occurs, for example, illness and sickness. Furthermore, unless otherwise noted, in this specification, this term is used to encompass the words meaning the condition (state) of disease such as condition, pathologic condition, symptom, and state of health. That is to say, the term "disease" is used interchangeably with the terms such as condition and pathologic condition.

The term "isolated" used herein means a state in which it is taken out from the original environment (for example, a natural environment in the case of a natural material), that is to say, means a state that is a different state from the original existing state by an artificial manipulation.

An "isolated antibody" does not include an antibody in a state in which it is natural state and no external manipulation (artificial manipulation) is given. It does not include an antibody produced in the individual body and remaining therein. An isolated antibody is typically present in a state in which other kinds of antibodies are not contaminated, that is, present singly (as an assembly of the same kinds of antibodies). In the case of an "isolated" state of the CDR region, in addition to the state which is present singly, a state which is present together with the other regions of the antibody is included. That is, the term "isolated CDR" includes not only a CDR that is present singly but also a CDR that is present as a part of an isolated antibody is included.

"HER1" is also referred to as erbB1, c-erbB-1, EGFR (Epidermal Growth Factor Receptor), or v-erbB. Originally, a gene corresponding to a cancer gene erbB found in the retrovirus that infects chicken and causes carcinogenesis (erythroleukemia) on the genome is isolated. And this gene is determined to be a receptor of EGF. By the way, EGF (Epidermal Growth Factor) as a ligand was found as a factor for promoting the cleavage of the eyelids of newly born mouse and development of an incisor in an extracted solution of the mouse submaxillary gland in 1962, and has been studied widely as cell proliferation, differentiation and survival factors. EGF is a peptide composed of 53 amino acids and has a characteristic structure including three disulfide loops formed of six cysteine residues. Thereafter, this structure has been found in a large number of proteins and is referred to as EGF-like domain. The EGF family has one or more EGF-like domains and directly binds to a receptor type tyrosine kinase EGF receptor (EGFR) family (another name: ErbB family) so as to activate this.

On the other hand, currently, four kinds of receptor ErbB families has been found and they are called EGFR (ErbB-1), ErbB-2, ErbB-3, and ErbB-4. ErbB-1 and ErbB-2 overexpress in various human tumors and are involved in the deterioration of the prognosis or survival rate. Furthermore, stimuli of these receptors are involved in cell proliferation and in turn involved in several processes related to progress, infiltration, and metastasis of tumor. To date, a phosphorylation inhibiting agent specific to EGFR have been approved as a therapeutic agent for lung cancer. They are found to highly express in many cancers. Cetuximab (ERBITUX, which is mouse/human chimeric antibody) has been developed by ImClone Systems and already marketed. ERBITUX inhibits the initial process of activation of the information transmission passage by the phosphorylation of dimerized-EGFR when it binds to a receptor of EGF as a ligand. Note here that the amino acid sequence of HER1 is shown in SEQ ID NO: 369.

"HER2" is also referred to as erbB-2, c-erbB-2, or neu. HER2 belongs to a receptor type tyrosine kinase family and its over-expression and gene amplification in the breast cancer, ovarian cancer, stomach cancer, and the like, have been reported. HER2 is a molecule that was found in 1985 when DNA containing a region of gene similar to EGFR was amplified (gene amplification) in the brain tumor and breast cancer derived from glia cells was observed. HER2 has low shedding level and is thought to be very effective as a target molecule in treating cancers. In many institutions, the monoclonal antibody (MoAb) showing effects of promoting or suppressing the tumor proliferation has been produced. MoAb showing a tumor proliferation suppressing effect is used for clinical test as a simple substance of the antibody or in combination with anti-cancer drugs such as cisplatin, and its efficacy has been reported. The EGFR family includes four kinds, but only EGFR (HER1) and HER4 have both the ligand binding sites and tyrosine phosphorylation enzymatic activity sites. HER2 does not have the ligand binding site. Instead using a ligand, HER2 has a structure that is activated from the first in terms of dimer formation ability. Incidentally, HER3 lacks the tyrosine phosphorylation activity. Therefore, HER2-HER3 hetero-dimer is a functional molecule. Genentech isolated 11 kinds of mouse monoclonal antibodies to HER2 in 1989. Among them, 4D5 was made into a humanized antibody and succeeded in developing Trastuzumab (Herceptin). Note here that the amino acid sequence of HER2 is shown in SEQ ID NO: 370.

"CD46 antigen" is an O-type sugar chain bonded non-disulfide bonded dimer protein having a molecule weight of 56 to 66 kDa, which is also referred to as MCP (Membrane Co-factor Protein), gp45-70, HuLY-m5, measles virus receptor, MIC10, TLX-B antigen, TRA2, trophoblast leucocyte common antigen, and trophoblast-lymphocyte cross-reactive antigen. This molecule binds to C3b or C4b and is known as Membrane Co-factor Protein (MCP) that is a co-factor for promoting the degradation by serine protease or I factor in plasma. It is also a receptor of the surface protein of measles virus agglutinin and Streptococcus group A. It has been reported that it is expressed in the thymus gland cells, T lymphocyte, B lymphocyte, monocyte, granulocyte, NK cells, platelet, endothelial cell, epithelium cells and fibroblast but does not express in the erythrocyte. On the assumption that only cells inducing the production of antibody to cancer specific antigen abnormally expressing in carcinogenicity and escaping from the attack of cancer tissue by complement (complement-dependent cytotoxicity, CDC) may actually grow into cancer, the expression of molecule group having an effect of inhibiting the complement has been analyzed in detail. There have been many reports about the abnormal expression of CD46 in cancer cells, however, few evidence showing that the production of antibody against antigen specific to cancer cells are induced. An amino acid sequence of CD46 antigen is shown in SEQ ID NO: 371.

"ITGA3 (integrin alpha 3)" is also referred to as alpha 3 beta 1 Epiligrin Receptor, alpha 3 beta 1 Integrin, Epiligrin Receptor, CD49c, VLA-3, Gap b3, Galactoprotein b3, or Laminin-5 Receptor in which integrin α3 chain having a molecular weight of 150 kDa and integrin β1 chain (CD29 molecule) having a molecular weight of 130 kDa are bonded to each other non-covalently to form a VLA-3 complex (α3β1 or CD49c/CD29). It is known as a receptor of laminin, collagen, fibronectin, invasion and epiligrin. Integrin is a hetero dimer molecule composed of α chain and β chain. Twenty four types of α chains and nine types of β chain form a variety of molecule groups by various combination and selective splicing. The extracellular domain binds to the extracellular matrix (for example, collagen, fibronectin, laminin). The side of cytoplasm is bonded to actin filament via talin, filanin, and α-actinin. It functions as an adhesive molecule and further functions as an important role as information transmission molecule. Above all, α3β1 molecule is associated with a tetraspanin molecule C151. Note here that the amino acid sequence of ITGA3 is shown in SEQ ID NO: 372.

The "ICAM1 (Intercellular adhesion molecule-1)" is also referred to Intercellular Adhesion Molecule 1 or CD54 Antigen and is transmembrane glycoprotein having seven binding sites of the N-bonding sugar chain. The molecular weight is 90 kDa. ICAM belongs to Ig-superfamily and is known to be mainly involved with adhesion of leukocyte. It also mediates T lymphocyte adhesion to an antigen presenting cell (APC) and is involved with the interaction between T cell and T cell or between T cell and B cell. It also involved with the adhesion to endothelial cell in which monocyte, lymphocyte, and neutrophil are activated. ICAM is bonded to integrin of LFA-1 (CD11a/CD18) and Mac-1 (CD11b/CD18). Furthermore, it also is a receptor of rhinovirus. It is expressed on various kinds of activated cells in addition to the endothelial cells. For example, it is expressed on the monocyte. On B- and T-lymphocytes, thymus gland cells, dendritic cells, endothelial cells, fibroblast, keratinocyte, chondrocyte and epithelium cells, expression is enhanced. The characteristics required to obtain during the cancerization process of epithelium cells include capability of invading into cells, and furthermore migrating and being fixed in metastasis. Therefore, it is thought that the expression of adhesion factor contributes to carcinogenesis. The adhesion factor is roughly classified into five groups, i.e., selectin (E-, P-, and L-), molecules (Ig-superfamily) having an immunoglobulin-like domain, integrin, Cadherin, and CD44. In cancerization, it is recognized that the expression of E Cadherin is suppressed. Abnormal expression in some cancer cases has been reported. Note here that the amino acid sequence of ICAM1 is shown in SEQ ID NO: 373.

"ALCAM (Activated leukocyte cell adhesion molecule)" is transmembrane protein that is also referred to as CD166 antigen, KG-CAM, CD6 Ligand, and Neurolin. ALCAM is an immunoglobulin superfamily molecule including ten N-bonding type sugar chain added sites. ALCAM has a molecular weight of 100 to 105 kDa and is composed of five extracellular Ig-like domains and the intracellular terminus having 32 amino acid, and short transmembrane region. ALCAM is one of the adhesive molecules, is present on the activated leukocyte and is identified as a ligand molecule to CD6 molecule (which functions as a signal receptor in T cells). ALCAM also functions as an adhesion factor in homophylic (ALCAM-ALCAM) or heterophylic (ALCAM-CD6) interaction. It is suggested that ALCAM can form oligomer at intercellular adhesion site via three C2-like domains near the membrane. The distribution of ALCAM is not restricted by cell strains and ALCAM is expressed in various types of cells such as hematopoietic cells, endothelial cells, epithelium cells of the thymic cortex and thymic medulla, mesenchymal cell of the bone marrow, fibroblast, liver cells, and the like. In the peripheral blood, it is weakly expressed in activated T- and B-cells, monocyte, circulated dendritic cells, and granulocyte. Although ALCAM shows wide dispersion of tissues, the expression of ALCAM is generally limited to cell populations involved in proliferation or migration. In the thymus gland, since ALCAM is expressed in CD6+thymus gland cells, and thymus gland epithelium cells, its interaction with CD6 molecule is thought to play a role in the differentiation of T cells. In addition, it is suggested that ALCAM adhesive molecules are involved in the fetal blood formation, differentiation of angioblastic cells, and capillary angiogenesis. The roles of ALCAM in cancerization is variously assumed (e.g., controlling of MMP activation, causing internalization and recycling, functioning as a substrate of ADM17 and ADAM10 (abbreviation of a disintegrin and metalloprotease), protecting from apoptosis and autophasy), however, no decisive roles have not reported. The interaction of ALCAM—CD6 is thought to be carried out in the both direction. The amino acid sequence of ALCAM is shown in SEQ ID NO: 374.

"CD147 antigen" is membrane glycoprotein belonging to an immunoglobulin superfamily and is also referred to as BSG, TCSF (Tumor cell-derived collagenase stimulatory factor), 5F7 protein, OK blood group protein, basigin protein, collagenase stimulatory factor protein, EMMPRIN (Extracellular matrix metalloproteinase Inducer), M6 activation antigen, human leukocyte activation antigen M6, or the like. D147 antigen has two aspects. One is observed when it functions on the cell surface, it exhibits the activation of MMP-1, 2, 3 (matrix metalloprotease) and the lectin activity recognizing oligomannose as membrane glycoprotein having two Ig domains. The activation of MMP receives much attention in cancers (which is also known as EMMPRIN in Europe and America). That is to say, CD147 antigen expressing in cancer cells activates MMP expressing in the surrounding fibroblast and contributes to the infiltration of cancers. On the other hand, the activation of oligomannose lectin is especially important in the interaction of nerve cells and indicated to have a relationship with respect to neurite outgrowth. The second aspect is a function in cells. CD147 antigen forms a homo dimer. It is reported that this formation needs N-terminal Ig domain and does not need addition of sugar chain. CD147 has the following interesting reports: integrin α3β1 and CD147 form a complex, and in this case, TM4SF (tetraspanin) molecule does not join the complex. In cancerization, the production of D147 changes anchorage-dependent growth to independent growth, which is promoted by the production of hyaluronic acid (hyaluronam). It is interesting that the receptor of hyaluronic acid includes CD44 and RHAMM. CD147 induces the production of MMP, and a part of CD147 is solubilized due to the effect of the MMP. CD147 acts on integrin so as to change the structure of cells. CD147 affects the angiogenesis. Furthermore, mass expression-cell proliferation of CD147 and Cyclophin A has been found.

The amino acid sequence of the CD147 antigen is shown in SEQ ID NO: 375.

"IgSF4" is an abbreviation of immunogloblin superfamily member 4 and is also referred to as BL2, ST17, NECL2, TSLC1, IGSF4A, SYNCAM, and sTSLC-1. IgSF4 has homology of NCAM (neural cell adhesion molecule) and amino acid sequence. IgSF4 is thought to be expressed from human 11-chromosome, 11q23.2. It has been reported that IgSF4 expressed as a suppression gene in a lung cancer specific manner and that IgSF4 is involved in the nerve adhesion in the brain (Biederer T et al. Science. 2002 Aug. 30; 297 (5586): 1525-31). The sequence information of IgSF4 is recorded in a NCBI-PUBMED database (Accession No. NM_01433, Definition: *Homo sapiens* immunoglobulin superfamily, member 4 (IGSF4), mRNA). As to the relationship with respect to the carcinogenesis, as shown by the name TSLC1 (tumor suppressor in lung cancer 1), it receives attention as a tumor suppressor gene. However, IgSF4 shows high expression in 100% adult T cell leukemia (ATL) cells and it is suggested that IgSF4 may work as oncogene. The amino acid sequence of IgSF4 is shown in SEQ ID NO: 376.

"C1qR" is a complement receptor encoding a type I membrane protein. This protein functions as a receptor for complement protein C1q, mannose binding lictin, and lung surfactant protein A. Two or more polypeptides of 70 kDa are bonded by disulfide bonding so as to form C1qR. Removing an immune complex is an important function of the complement and the C1q receptor is a functional receptor that is bonded to a collagen portion of C1q thereby linking the immune complex to phagocyte. It is suggested that C1qR forms complex with CD43. The amino acid sequence of C1qR is shown in SEQ ID NO: 446.

"CD44" is a transmembrane protein belonging to a hyaladherin family, which is cell surface glycoprotein related to cellular interaction, cell adhesion and cell migration. It is a hyaluronic acid receptor. It is thought that a wide variety of the structural and functional isoforms of proteins by the selective splicing or post-translation modification of this molecule may be involved in tumor metastasis. The CD44 molecule is expressed in almost all the cells and tissues. However, in general, it is not expressed in the platelet, liver cell, cardiac muscle, uridiferous tubule epithelium, testis, and skin. The amino acid sequence of CD44 is shown in SEQ ID NO: 447.

"CD73" is also referred to as 5-prime-ribonucleotide phosphohydrolase and transforms purine 5-prime mononucleotides into nucleosides at the neutral pH. The enzyme mediates glycosylphosphatidyl inositol to the surface of the outside of the plasma membrane and is bonded to the surface of the outside of the plasma membrane. CD73 is a homodimer composed of two 70 kDA subunits. CD73 is used as a marker of the lymphocyte differentiation. It has been known that the deletion of this gene is related to various immune defective diseases. The amino acid sequence of CD73 is shown in SEQ ID NO: 448.

"EpCAM" has 22 or more names as to only the number of names used and cited several times in research paper. This antigen exists on genome 2p21. This antigen is a protein having a full length of 314aa, and 34920 Da. In the documents in which this molecule is examined at the mRNA level, it is detected in healthy human individuals, 100% in the peripheral blood (PB) level and 40% in the bone marrow (BM) level. It has been reported that it can be detected in large intestine but cannot detected in the liver, prostate, and lung. In cancer cell line, in the relationship with respect to p53, the methylation of EpCAM is lost due to the mutation or deletion of p53 and the amplification is induced. The amino acid sequence of EpCAM is shown in SEQ ID NO: 449.

The first Met gene discovered as a search product of oncogene using NIH3T3 gene is HGFR (Hepatocyte growth factor receptor). HGF is also referred to as a scatter factor and is utterly independently isolated as a molecule having an extremely different apparent function. Similar to HER1 and PDGF, HGFR is a receptor having a ligand binding domain outside the cells and has a tyrosine phosphorylation enzymatic activity site at the cytoplasm side, however, the function is extremely different. In general, when the cell proliferation factor or a differentiation induction factor is bonded to a receptor so as to cause the phosphorylation of protein, it finally activates the transcription factor and expresses a certain gene set by way of some of the limited information transmission pathway (Ras/MAP kinase pathway, and the like). In this case, the type of the cell response is finally determined by transcription factor. Thus, when the cancerization may activate some of the proliferation factors-receptor, it is thought that changes other than cancerization are not likely to occur in the cells. Currently, as to the cancerization, the phenomenon called epithelial-mesenchymal transition (EMT) receives much attention and the factor plays a core role in the phenomenon. In such examples, since a large number of molecules cooperatively function, detail analysis is needed. The amino acid sequence of HGFR is shown in SEQ ID NO: 450.

LAR (Leukocyte common Antigen-Related) belongs to a PTP (protein tyrosine phosphatase) family. The PTPs are known to be molecules to modulate the process in the various aspects of the cancerization, division cycle, differentiation, cell growth, and the like. The structure thereof includes an extracellular region, mono-transmembrane region, and two tandem catalyzing domain in the cytoplasm (homolog of protein tyrosine phosphatase). The extracellular region has a structure similar to nerve cell adhesion factor, which includes three Ig-like domains and nine non-Ig like domains (homolog of NCAM). The function of this molecule is involved in the cell adhesion in the formation adherents junctions in the epithelium. Note here that it is confirmed that this molecule is highly expressed in insulin sensitive mast cells, and insulin resistant cells. Therefore, it is suggested that it is related to insulin. Furthermore, it is reported that anti-LAR antibody has an insulin receptor inhibitory activity of the insulin receptor forced expressing body (Knock-down of LAR protein tyrosine phosphatase induces insulin resistance: Mander A, Hodgkinson C P, Sale G J.: FEBS Lett. 2005 Jun. 6; 579 (14): 3024-8).

Furthermore, LAR is expressed on the membrane of all the leukocytes and is referred to as protein tyrosine phosphatase receptor type F (PTPRF) and protein sequence (SEQ ID NO: 941) thereof is registered as TDHULK in Protein sequence database of the Protein Information Resource (PIR).

BCAM (basal cell adhesion molecule) (Lutheran blood group) is referred to as CD239 antigen and its protein sequence is registered as Q86VC7 (UniProtKB/Swiss-Prot) and 13800 (PIR) (SEQ ID NO: 942). It produces a selective splicing product from a single gene in the chromosome 19q13.2-q13.3. It is a glycoprotein having an immunoglobulin-like domain. It is a mono-transmembrane type and expressed widely. Its expression in the pancreas is high and its expression in the brain is low. The BCAM antigen is modulated excessively in certain cells, thus inducing the malignant alteration of cancers. Also, it is shown that it is overexpressed in the living body with ovarian cancers.

In the present invention, "liver cancer" is intended to be widely interpreted and it includes liver carcinoma and liver sarcoma. Furthermore, the term "cancer" in the present invention is interchangeably with "tumor." Furthermore, in the stages before the pathological diagnosis is not established, that is, before whether the tumor is benign or malignant has not been determined, the term may include benign tumor, benign-malignant borderline lesion, and malignant tumor collectively.

Cancers are called under the name of the organs in which the cancers are developed or the name of development body tissue. Main examples include tongue cancer, gingival cancer, pharynx cancer, maxillary cancer, laryngeal cancer, salivary gland cancer, esophageal cancer, stomach cancer, small intestinal cancer, large bowel cancer, rectum cancer, liver cancer, biliary tract cancer, gallbladder cancer, pancreas cancer, lung cancer, breast cancer, thyroid gland cancer, adrenal gland cancer, hypophyseal tumor, pinealoma, uterine cancer, ovarian cancer, vaginal cancer, urinary bladder cancer, kidney cancer, prostate cancer, urethral cancer, retinoblastoma, conjunctival cancer, gliocystoma, glioblastoma, skin cancer, leukemia, malignant lymphoma, testicular tumor, osteo sarcoma, rhabdomyoblastoma, leiomyo sarcoma, blood vessel sarcoma, liposarcoma, chondrosarcoma, Ewing's sarcoma, and the like. Furthermore, depending upon the characteristics of the sites of the organs of development, cancers are subclassified into, for example, upper, middle, and lower pharynx cancers, upper, middle, and lower esophageal cancers, gastric cardia cancer, gastropyloric cancer, cervical cancer, cancer of uterine body, and the like. These cancers are included in the "cancers" of the present invention but the cancers are not limited to these alone.

In the specification, if necessary, the following abbreviations (in parentheses) are used according to the practice.

Heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), first complementarity determining region of heavy chain (VH CDR1), second complementarity determining region of heavy chain (VH CDR2), third complementarity determining region of heavy chain (VH CDR3), first complementarity determining region of light chain (VL CDR1), second complementarity determining region of light chain (VL CDR2), third complementarity determining region of light chain (VL CDR3)

The first aspect of the present invention relates to a method of classifying antibody. The classifying method of the present invention includes the following steps.

(1) preparing a plurality of antibodies recognizing cell surface antigen;

(2) bringing each of the antibodies into contact with cells of the same kinds;

(3) analyzing each cell after step (2) by flow cytometry so as to obtain data showing reactivity between the antibody and the cell surface; and (4) comparing the obtained data and classifying antibodies based on the similarity of the data.

Step (1)

In the classifying method of the present invention, firstly, a plurality of antibodies recognizing cell surface antigen are prepared. For convenience of explanation, the antibody classified by the classifying method of the present invention is also referred to as a "sample antibody."

In the present invention, the "cell surface antigen" is a molecule in which at least a part thereof exists outside the cell and which forms an antigenic determinant on the surface of the cell. For example, protein such as transmembrane type protein having a cell membrane transmembrane domain and an extracellular domain and GPI anchor type protein, which are linked to cell membrane via glycolipid and the like and existing on the surface of the extracellular surface, can form such an antigenic determinant. The cell surface antigen can be formed by a simple protein (basically, constituent includes only amino acids), a conjugated protein (constituent other than amino acid are contained. For example, glycoprotein and lipoprotein), or a modified protein (a protein modified by, for example, phosphorylation, acetylation, and methylation), and the like. Furthermore, two or more same types or different types of molecules may cooperatively form an antigen determinant.

The "cell surface antigen" of the present invention is not particularly limited to animal cells and may include cell surface antigens of plant cells, microorganism cells, and the like. Preferably, "cell surface antigen" of the present invention is the cell surface antigen of animal cells. It is known that the animal cells have various cell surface antigens. The "animal cells" herein include mammalian cells and non-mammalian cells, but preferably mammalian cells. Above all, human cells are preferable.

Preferably, a plurality of antibodies recognizing the intact cell surface antigen are prepared. The "intact state" means that the original state is maintained. It has the same meaning that "not denatured state."

The "antibody recognizing cell surface antigen" represents an antibody recognizing and binding the cell surface antigen with highly specific recognition mechanism between the antigen and the antibody. The origins, types, classes, forms and the like, of antibodies are not particularly limited. Therefore, the "antibody" in the present invention includes an antibody of non-human animals such as mouse and rat, a chimeric antibody in which a part of the region is substituted with that of other animal (including human), a humanized antibody, and human antibody. Preferably, human antibody or human type antibody (humanized antibody) are used. Antibody fragments such as Fab, Fab', F(ab')2, scFv, and dsFv antibody may be used. An antibody for treatment application includes an antibody in which VH and VL (Fv region) are converted into IgG type is included.

An antibody recognizing a cell surface antigen can be prepared by, for example, bringing an antibody library into contact with the cell surface antigens and recovering the antibodies bound to the cell surface antigens. One of such preparation methods is a method reported by the present inventors before (Japanese Patent Unexamined Publication No. 2005-185281). This method makes it possible to select an antibody clone recognizing intact cell surface antigen from the phage antibody library. The present invention can preferably use the antibody assembly derived from each antibody clone. The "assembly derived from each antibody clone" herein includes the selected antibody clone itself, or the product prepared by using the gene. The latter example includes an antibody in which genes of the selected antibody clone is transformed by an appropriate host (for example, *E. coli*) and the host is expressed, or an antibody to which further genetic engineering modification is added in the host or by the use of the host and then the modified antibody is expressed.

The above-mentioned publication discloses as the antibody having a human Fv region, scFv-CL-cp3 antibody (an antibody in which a phage protein cpIII is fused to scFV via the light chain constant region), scFv-CL-pp antibody (an antibody in which two proteins A are fused to scFV via the light chain constant region), scFv-CL-pp-Avi antibody (an antibody in which avidin is fused to scFv-CL-pp antibody), scFv-CL-Avi antibody (an antibody in which avidin is fused to scFV via the light chain constant region), scFv-CL-pp-Avi or antibody obtained by biotining scFv-CL-Avi antibody (an antibody in which biotin is bonded to an avidin part), and the like. The present invention can preferably use any of these types of antibodies. These antibodies having a human Fv region are very useful in providing an antibody for treatment (production of an antibody for treatment can be proceeded advantageously).

Note here that the contents disclosed Japanese Patent Unexamined Publication No. 2005-185281 are herein incorporated by reference in its entity.

A combination of separately prepared antibodies may be used as the "plurality of antibodies recognizing cell surface antigen" in the present invention. In this case, the preparation method of each antibody may be the same as or different from each other.

An antibody in which a label material has been bound or fused in advance (which is collectively referred to as "labeled sample antibody") may be used. The former example can include an antibody labeled with fluorescence pigment. The latter example can include an antibody in which fluorescence proteins (fluorescence protein fused antibody) such as GFP (Green Fluorescent Protein) and RFP (Red Fluorescent Protein) have been fused. Such fluorescence protein fused antibody can be prepared easily by using genetic engineering technique.

Step (2)

Next, the sample antibodies are brought into contact with cells of the same kinds, respectively. That is to say, cells to be used are determined, and then the cells are brought into contact with the sample antibody for each sample antibody. The sample antibody recognizing the surface antigen of the cells to be used binds to the cell surface. The binding amount of the sample antibody is dependent upon the expression amount of the cell surface antigen recognized by the antibody.

Cells that are brought into contact with the sample antibody are not particularly limited and may be arbitrarily selected from animal cells, plant cells, microorganism cells, and the like. For example, in one preferable embodiment, cells derived from a patent having a certain disease (or having a certain pathologic condition) are used. The "certain disease" includes various kinds of cancers, for example. The tissues or organs from which the cells are derived are not particularly limited. An example of the certain disease include kidney cancer, hepatic cell carcinoma, gallbladder and liver cancer, alveolar cell carcinoma, lung squamous cell cancer, pulmonary adenocarcinoma, pancreas cancer, adenocarcinoma, ovarian cancer, and the like.

Cells forming a highly uniform cell population are preferably used. It is preferable because such cells can provide easier or simpler data, facilitates the comparison of data and provides more reliable comparison results in the below-mentioned flow cytometry analysis. The typical example of such cells is established cell line (cell line). Preferable examples include established cancer cell line such as liver cancer cell line HepG2, undifferentiated liver cancer cell line HLF, liver cancer cell line OCTH, intrahepatic bile duct cancer cell line RBE, pancreatic cancer cell line PANC-1, pancreas cancer cell line MIA-Paca2, kidney cancer cell line CCFRC1, kidney cancer cell line Caki-1, kidney cancer cell line ACHN, kidney cancer cell line 293T, ovarian cancer cell line KF28, ovarian cancer cell line SKOv3, ovarian cancer cell line KF-28, ovarian cancer cell line RMG-1, ovarian cancer cell line RMG-2, breast cancer cell line BT474, vulvar mucosa epithelium cell line A431, stomach cancer cell line SNU-5, stomach cancer cell line MKN45, stomach cancer cell line NCI-N87, cancer cell line RERF-LC-AI, pulmonary adenocarcinoma cell line PC14, lung cancer cell line NCI-H441, lung squamous cell canceEBC1, pulmonary adenocarcinoma cell line H1373, pulmonary adenocarcinoma cell line A549, pulmonary adenocarcinoma cell line Calu-3, pulmonary adenocarcinoma cell line PC14, large bowel cancer cell line CaCo2, large bowel cancer cell line CW2, hamster ovarian cancer cell line CHO, and the like. Note here that cells whose uniformity is improved by culture operation is one of the most preferable cells.

Each sample antibody is brought into contact with cells in an appropriate solution. At this time, it is preferable that the conditions are set so that the properties of the sample antibody are not affected and cells are not damaged. For example, cells and the sample antibodies are co-existed in the culture solution suitable for the existence and proliferation of the cells, in the phosphoric acid buffer and citric acid buffer, in physiologic saline, or in a solution in which BSA for suppressing non-specific adsorption is added, at room temperature to low temperatures (for example, 0° C. to 25° C., preferably 4° C. to 15° C.), for 20 minutes to 3 hours. During this time, the solution may be stirred.

The conditions under which each sample antibody and cells are brought into contact with each other are made to be uniform in order to obtain highly reliable data.

After contacting operation mentioned above, labeling is carried out if necessary (other than the case when a labeled sample antibody is used). The "labeling" herein denotes labeling the sample antibody bound to the surface of the cells. For example, labeling can be carried out by reacting (contacting) an antibody having a specific binding ability to the sample antibody to which a label material has been bound (antibody to be detected) with cells after the contacting operation. Instead of directly binding an antibody to be detected to the sample antibody, other antibodies and the like may be interposed therebetween. Thus, various labeling techniques can be employed and a person skilled in the art can select an appropriate technique. In the flow cytometry analysis, in general, fluorescent dye is used as a label material. Fluorescent dye such as Alexa488, AMCA, Cascade Blue (registered trademark), FITC, PerCPTM, CyTM3, Texas Red (registered trademark), CyTM5, APC, TRITC, and the like, can be used.

Step (3)

Subsequently, cells after subjecting to the step (2) are analyzed by flow cytometry so as to obtain data showing the reactivity between the antibody and the cell surface. That is to say, cells after subjecting the contacting operation to the sample antibody are subjected to the flow cytometry analysis, and the binding property to the sample antibody is examined. Preferably, as the data showing the "reactivity" herein, histogram showing the relationship between the antibody binding amount and the number of cells is used. That is to say, one-parameter histogram in which the antibody binding amount is used as a parameter is used. The one-parameter histogram is one display method in the flow cytometry. The one-parameter histogram is generally shown in a graph in which X-axis represents one indicator (parameter) and Y-axis represents the number of cells. For the device used for the flow cytometry analysis, for example, devices from BECKMAN COULTER, Japan Becton, Dickinson and Company, and the like can be used in the present invention. The operation may be carried out according to the basic operation and analysis conditions attached to the device. Furthermore, many research paper and documents about the flow cytometry analysis are published. See, for example, Cao T M, et al. Cancer. 2001 Jun. 15; 91 (12): 2205-13., Storek K J, et al. Blood 97: 3380-3389, WEIR'S HANDBOOK OF EXPERIMENTAL IMMUNOLOGY Vol. II<Blackwell Science>, Little MT and R. Storb Nture Reviews Cancer 2002 2: 231-238.

Typical procedure of the flow cytometry analysis is described below. The sample antibody and cells are reacted with each other, then reacted with antibody to be detected labeled with fluorescent dye, so that cells are labeled with fluorescence. The amount of sample antibody to be bound varies depending upon the amount of antigen existing on the surface of the cells. As a result, the amount of fluorescent label of the cells becomes different. Therefore, by measuring the fluorescence intensity, the affinity between the antigen existing on the surface of the cell and the ample antibody and the amount of antigen can be estimated. In general, prior to the detection of the fluorescence intensity, forward scatter light (FSC) and side scatter light (SSC) are measured and gated, so that the fluorescence intensity of only the target cell population is measured. Specifically, for example, the forward scatter light and the side scatter light are shown in X-axis and Y-axis, respectively. The cell population (when established cell lines or cultured cells are used, the cell population becomes extremely uniform) that are assumed to be living cells from the data obtained by dot plot expansion are gated, and the fluorescence intensity within the gate is measured. The measurement result is shown in a form of, for example, histogram. Note here that the terms related to the histogram obtained in the flow cytometry analysis are mentioned below.

The "number of samples" denotes number of data and generally represented by n. The "total" denotes a total of data and generally represented by T. "Mean value" denotes an average of data and is calculated by dividing the total by the number of samples. The mean value is susceptible to abnormal data. The "median value" is a value located in the middle when the data are aligned in ascending numeric order. When the number of data is odd number, the average of two middle values is defined as a median value. The median value is less susceptible to abnormal data as compared with the mean value and shows the characteristics of the population more accurately. The "mode" denotes a value whose frequency is maximum in the data. In the case of the flow cytometry analysis, the mode is the same as a peak value. The mode is less susceptible to abnormal data as compared with the mean value. The "maximum value" is a maximum value of data and generally represented by Max. The "range value" is difference between the maximum value and the minimum value and generally called range and referred to as R. The "dispersion" is a value showing the degree of variation of data. The larger the dispersion is, the larger the variation is. In general, it is referred to as V. The dispersion is obtained by dividing the sum of squares deviation by the number of samples (in the case of sample survey, divided by (umber of samples-1)). The "standard deviation" denotes square root of the dispersion and is generally referred to as u. The "coefficient of variation" is a value obtained by dividing the standard deviation by an average value and is generally referred to as CV. Since the standard deviation does not clearly shows the degree of variation of data, the standard deviation is normalized by dividing it by the average value. In the flow cytometry analysis, it is frequently used as a value showing the resolving power of the device. The "kurtosis" is one of the indicators representing the distribution in the population and generally is referred to as H. The distribution in which the kurtosis is 0 is defined as normal distribution. When the kurtosis is larger than 0, the distribution has sharper apex than the normal distribution. When the kurtosis is smaller than 0, the distribution becomes more flatness than the normal distribution. The "skewness" denotes a value showing the left-right symmetry of the population and generally is referred to as G. When the skewness is 0, distribution becomes left-right symmetric. When the skewness is larger than 0, the distribution distorts in the right direction. When the skewness is smaller than 0, the distribution distorts in the left direction.

Step (4)

Next, the obtained data are compared and sample antibodies are classified based on the similarity of the obtained data. Herein, "based on the similarity" means that the similarly of data are used as a criterion of classification. An example of criterion (classification criterion) based on the similarity of data is shown below.

(a) A plurality of antibodies having the identical or highly similar data are classified into one antibody group. Specifically, for example, plurality of antibodies having extremely similar histogram is defined as one group when the shape of the histogram showing the distribution of cells is determined by the kurtosis, skewness and the like.

(b) An antibody providing specific data forms one antibody group by itself.

(c) An antibody having a low reactivity with respect to the antigen is excluded (the antibody does not belong to any groups).

In the present invention, each antibody is classified by one or two or more criteria selected from the above-mentioned classification criteria (a) to (c).

The similarity of data can be determined based on the parameter specifying the data. However, the specific determination method is dependent upon the types of data. In the case where data are represented by numeric values, it is possible to determine the similarity based on the degree of similarity of numeric values (for example, when 1, 2, and 5 are given as data, it is determined that the similarity between 1 and 2 has high similarity).

Furthermore, when a histogram is given as data, it is possible to determine the similarity of data based on the shape of the histogram. As a result of the investigation by the present inventors, it is determined that the shape of the histogram in the flow cytometry analysis is highly dependent upon the kinds of the antigen. In other words, when the antigens to be recognized are the same, regardless of the kinds of antibodies, it is determined that the histogram having an identity or high similarity can be obtained. Base on this fact, in one embodiment of the present invention, by comparing the shapes of the histogram showing the results of the flow cytometry analysis, the similarity of data is determined. Specifically, the similarity of data can be determined by comparison by visual observation or by comparison of one or two or more of parameters specifying the histogram. The parameters herein can employ one or more values selected from the group consisting of median value, mode, maximum value, range, standard deviation, kurtosis, and skewness of the histogram. Preferably, determination is carried out in terms of two or more values, furthermore preferably three or more values, and yet furthermore preferably four or more values. By increasing parameters to be used in determination, the determination accuracy can be improved. Among these parameters, it is said to be advantageous that the median value, mode, or kurtosis that are parameters deeply related to the shapes of the histogram are employed for carrying out the determination at high accuracy. Preferably, a combination of two or more of these parameters is used. Specifically, for example, the similarity of the histogram may be determined based on the median value, mode, and kurtosis.

When two data to be compared have similar values in terms of employed parameters, the similarity between the two data is determined to be high. When the difference between two values ($100\times(A-B)/A$ (%) when the two values are A, B ($A\geq B$)) is within 10%, preferably within 5%, and furthermore preferably within 3%, the two values are determined to be similar.

In one embodiment of the present invention, when or after the sample antibodies are classified, sample antibodies having a low reactivity to the cell surface antigen are removed. Thereby, an antibody group including highly useful sample antibodies can be formed. The degree of the reactivity of the antibody can be determined by using the results of the flow cytometry analysis. Specifically, the mode (peak value) of the histogram obtained with respect to the sample antibody to be determined and the mode (that is to say, the maximum mode in the group) of the histogram obtained with respect to the sample antibody having the maximum reactivity in the antibody group to which the sample antibody belongs. As a result, when the former is ½ or less of the latter, preferably ⅕ or less, furthermore preferably ⅒, it is determined that the sample antibody to be determined has low reactivity.

In one embodiment of the present invention, the reactivity of each sample antibody is examined in two or more kinds of cells and the sample antibodies are classified by using the results. That is to say, two or more kinds of cells are prepared and by using the prepared cells, steps (2) to (4) are carried out.

The expression amount, distribution, and the like of the cell surface antigens are dependent upon the kinds of cells. Therefore, two antibodies having high similarity in data obtained by using certain cells, that is, two antibodies having the common antigens should provide data having high similarity when the other cells are used. Thus, when the two antibodies to be compared provide data with high similarity with respect to more than two kinds of cells, the probability that the antibodies have the common antigens is extremely high. Furthermore, when such results are obtained, it can be easily determined that the two antibodies have the common antigens. Thus, the use of two kinds or more cells can make it accurate and easy to determine the identity of antigens.

In one preferable embodiment of the present invention, sample antibodies having identical or highly similar data with respect to at least two kinds of cells are classified into one antibody group.

Furthermore, by observing the classification results of the case where two or more kinds of cells are used, kinds or amount of antigens to be expressed can be compared between the cells. Therefore, more useful information can be provided in studying the properties of these cells.

In one embodiment of the present invention, a classification result is displayed as a panel. The "panel" in this specification is a product in which a plurality of elements (for example, antigen, antibody, antibody group, cell, name of disease, name of pathologic condition), are displayed in the form of tables or drawings, in which the elements are associated with each other, on media such as a display and paper. Each element is represented by general name, abbreviation, alias, or symbol or code representing thereof, and the like. The panel of the present invention shows the relationship with respect to two kinds or more of elements.

The term "associating to" in the present invention means that two or more elements are linked. Therefore, in the tabular format panel showing the association between an antigen and an antibody group, for example, both elements are displayed in adjacent to each other, or both elements are displayed in the same cells, or both elements are linked by a line or something, so that it can be understood that the both elements form a pair.

In the panel herein, typically, antibody groups are displayed in a way in which they are associated with each other for each antigen (or for each antigen having high association) expressed by the cells that have been subjected to the flow cytometry analysis. Therefore, this panel makes it possible to access antibodies useful for studying surface antigens of the cells. Thus, the panel itself of the present invention has a great value. A panel formed by using two kinds or more of cells makes it possible to understand the presence, expression amount, and the like, of antigens expressing between cells. Such a panel has further higher values.

In the panel of the present invention, antibodies may be arranged regularly in accordance with the reactivity to antigens. Thus, the difference in the reactivity between antibodies can be made obvious.

According to the classifying method in the present invention, a plurality of antibodies recognizing the same antigen (or antigens having high association) are associated with each other. In other words, for each antigen (or for each antigen having high association), antibody assembly (antibody group) recognizing the antigen can be obtained. These antibody groups are useful for studying cell surface antigen and have high usability. Furthermore, according to the classifying method of the present invention, a large number of antibodies can be classified rapidly for each antigen (or for each antigen having high association). That is to say, the classifying method of the present invention is useful for classification of a large number of antibodies and allows comprehensive classification of antibodies. The term "highly associated" or "having high association" used for antigen means that two or more antigens have a close association in a living body, for example, the antigens are not the same molecules but exhibit one function cooperatively (for example, two antigens are bound so as to form one complex functionally).

According to the classifying method of the present invention, typically, plurality of antibodies are associated with each other for each antigen (or for each antigen having high association). Therefore, in studying certain antigens, a plurality of antibodies can be used or suitable antibodies can be selectively used if necessary, which leads to better results or significant findings and means that studying can be proceeded advantageously.

On the other hand, by executing the classifying method of the present invention, it is possible to understand the expression amount of distribution of cell surface antigens (antigen are unknown) in certain cells (that is, cells that are brought into contact with the sample antibody). Thus, the classifying method of the present invention provides useful information on the properties of the certain cells and is useful for studying the cells (in particular, the surface antigens).

Note here that when antigens to all the sample antibodies are unknown, antigens to which each antibody group is associated are not identified. On the other hand, when some identified antigens are contained in a part of the sample antibodies, an antigen to which the antibody group containing the antibody becomes an identified antigen. Thus, it is also possible to associate an antibody group with the identified antigen.

According to the above-mentioned classifying method, antibodies are classified based on the reactivity between the antigens and certain cell surfaces and the antibody groups are formed. Therefore, antibodies belonging to the same antibody group have the same (or highly similar) reactivity to the surface of cells used for classification. However, it is not necessarily ensured that all the antibodies belonging to the same antibody group can recognize the same antigens. Even if the recognizing antigen is the same, the reactivity to cells expressing antigens on the cell surface may be different. Furthermore, the opposite case may occur (even if the recognizing antigen is different, the reactivity to cells expressing antigens on the cell surface may be the same, for example, one of the complex may be recognized).

Therefore, in order to form an antibody for each recognizing antigen, one embodiment of the present invention carries out the following steps (i) to (vi) after the step (4).

(i) associating the classified antibodies with a combination of n pieces of parameters including a first parameter, a second parameter, . . . , and an n-th parameter (wherein, n represents an integer of 2 or more, each parameter has two or more parameter values and the same parameter value is given to two or more antibodies in each parameter);

(ii) with respect to each parameter, preparing an antibody mixture of the antibodies having the same parameter value;

(iii) examining a reactivity of each of the antibody mixtures with a target antigen by an enzyme linked immunosorbent assay (ELISA) so as to specify the antibody mixture which shows reactivity;

(iv) specifying a combination of a parameter name and a parameter value that are common to the antibody group contained in the specified antibody mixture;

(v) selecting an antibody corresponding to the combination specified in the step (iv) in terms of all parameters among the antibodies subjected to step (i); and (vi) classifying the selected antibodies into one antibody group.

According to the classifying method of this embodiment, an antibody group can be formed for each antigen to be recognized. That is to say, antibody groups having various individualities recognizing the same antigen can be obtained. Furthermore, the combination of the plurality of parameters is associated with each antigen and then an antibody mixture is prepared according to a predetermined regulation. Then, based on the results of ELISA (Enzyme-Linked immunosorbent assay) using the antibody mixture, an antibody recognizing a target antigen is determined. By this unique technique, antibodies can be classified rapidly and efficiently. Furthermore, at the same time when the antibodies are classified, as to at least a part of the antibodies, an antigen is identified. That is to say, the classifying method of this embodiment is a method of rapidly and efficiently obtaining an antibody whose antigen has been identified, which dramatically promote the increase in the number of antibodies whose antigens have been identified. On the other hand, the classification results show the presence form or expression from on the cell surface used in flow cytometry analysis, which provides extremely useful information for study and development of the application of antibody (for example, treatment of cancer). Furthermore, when the presence of a certain antigen is clarified based on the classification results, it is possible to obtain an unknown antigen (for example, complex counterpart) that is thought to be possible to exist in a form of a complex with the antigen. That is to say, the classifying method of this embodiment efficiently functions as determining a novel antigen or novel molecule complex.

Hereinafter, each step is described in detail. For convenience of explanation, the classifying method of this embodiment is also referred to as "n dimensional ELISA method."

Step (i)

In this step, a combination of n pieces of parameters consisting of the first parameter, the second parameter, . . . , and the n-th parameter are associated with antibodies classified by the preceding steps (steps (1) to (4)). Thus, each antibody has n-dimensional address (a parameter value of the first parameter, a parameter value of the second parameter, . . . , and a parameter value of the n-th parameter).

In general, association is carried out with respect to all the antibodies that have been classified in the preceding steps, although the association is not limited to this. That is to say, the association may be carried out only a part of the antibodies that has been classified in the preceding steps. In this case, a part of antibodies are excluded from the antibodies to be classified.

Herein, "n" is an integer of two or more. That is to say, to each antibody, two or more combinations of parameters are associated. The number of "n" does not have an upper limit. When the number of "n" is too large, operations in the subsequent steps (for example, preparation of an antibody mixture, specification of an antibody mixture showing the reactivity) may be excessively complicated. Therefore, "n" is preferably three to five.

On the other hand, each parameter is made to have two or more parameter values and the same parameter values of each parameter are made to be provided to two or more kinds of antibodies. Specifically, parameter values of the first parameter may be 1, 2, 3 and 4, and each parameter value is provided to five kinds of antibodies, respectively. The number of the parameter values is set for each parameter. Furthermore, similar to the number of parameters, the number of the parameter values does not have an upper limit. In order to make the analysis in the following steps (iv) and (v) be efficient and improve the accuracy thereof, it is preferable that the kinds of antibodies contained in each antibody mixture are not excessively large number. Therefore, each parameter value may be set so that the kinds of antibodies contained in each antibody mixture is preferably 200 or less, and furthermore preferably, 100 or less. Specifically, for example, the number of the parameter values can be set to between 2 and 100. Note here that the kind of antibodies contained in each antibody mixture is dependent upon the setting of the parameter, and may not be equal between antibody mixtures.

Step (ii)

In this step, an antibody mixture, in which antibodies having the same parameter value are mixed, is prepared. The antibody mixture is prepared for each parameter. For example, when the values of the first parameter is 1, 2, 3 and 4, an antibody mixture mixing antibodies to which 1 is given as the first parameter, an antibody mixture mixing antibodies to which 2 is given as the first parameter, an antibody mixture mixing antibodies to which 3 is given as the first parameter, and an antibody mixture mixing antibodies to which 4 is given as the first parameter are prepared. By the same procedure, as to the remaining parameters, antibody mixtures are prepared. Thus, antibody mixtures in the same number as the total number of the number of the first parameter, the number of the second parameter, . . . , and the number of the n-th parameter are prepared.

In general, an antibody mixture, in which all antibodies having the same parameter values are mixed, are prepared although the antibody mixture is not limited to this. An antibody mixture may be prepared by selecting a part of all antibodies having the same parameter values and mixing thereof. Thus, the selection of antibodies may be carried out in this stage.

It is preferable that an antibody mixture is prepared so that all antibodies are contained in equal amount and the amount of each antibody (that is, concentration for each antibody) is equal between antibody mixtures. Adjusting the amount of antibodies in this way facilitates the specification of the antibody mixture based on the reactivity in the following ELISA.

Step (iii)

In this step, the reactivity between each of the antibody mixtures and the target antigen is examined by ELISA so as to specify the antibody mixture showing the reactivity. When at least one of the antibodies recognizing the target antigen is contained in the antibody to be used for preparing the antibody mixture, a plurality of antibody mixtures shows the reactivity. On the other hand, when the antibody recognizing the target antigen is not contained, any of the antibody mixtures will not show reactivity. In this case, the operation is terminated without continuing the following operations.

The target antigen herein may include HER1, HER2, CD46, ITGA3, ICAM1, ALCAM, CD147, IgSF4, BCAM, C1qR, CD44, CD73, LAR, EpCAM, HGFR, and the like. The target antigen can be arbitrarily selected. The antigen determined by the below-mentioned identification methods (step (5) and (6)) may be used as the target antigen herein.

Step (iv)

In this step, a combination of a parameter name and a parameter value that are common to the antibody group contained in the specified antibody mixture is specified. In the present invention, the combination specified herein is referred to as "positive combination." Specifically, the positive combination is specified like (first parameter, parameter value a1), (second parameter, parameter value a2), . . . , (the n-th parameter, parameter value an). When a plurality of antibody mixtures having the different degree of reactivity are recognized in the step (iii), similarly, specification may be carried out for each level of the reactivity. For example, the middle level of positive combination may be specified like (first parameter, parameter value a1), (second parameter, parameter value a2), . . . , (the n-th parameter, parameter value an); and the high level of positive combination may be specified like (first parameter, parameter value b1), (second parameter, parameter value b2), . . . , (the n-th parameter, parameter value bn).

Step (v)

In this step, antibodies corresponding to the combination specified in step (iv) as to all parameters are selected from the antibody subjected to step (i). That is to say, antibodies in which all parameters are positive combination are selected. For example, when (first parameter, parameter value a1), (second parameter, parameter value a2), . . . , (the n-th parameter, parameter value an) are specified as the positive combination, antibodies having (parameter value a1, parameter value a2, . . . , parameter value an) is selected.

Step (vi)

In this step, the selected antibodies are classified into one antibody group. Thus, an antibody group showing the reactivity to the target antigen can be made into one group. In other words, an antibody group whose antigen is determined can be obtained. Note here that when only one antibody is selected in the step (v), this only one antibody makes one an antibody group.

When two or more kinds of target antigens are prepared and the above-mentioned steps (iii) to (vi) are carried out by using each target antigen, two or more antibody groups recognizing different antigens can be obtained.

In one embodiment of the present invention, the steps (i) to (v) are tried a plurality of times under the conditions in which the combination of parameters is changed every trial. For example, in the first trial, analysis is carried out in which four parameter combinations composed of numeric values (for example, antibody 1 (001, 001, 001, 001), antibody 2 (002, 002, 002, 002), . . . ) are associated with each antibody. In the second trial, analysis is carried out in which three parameter combinations composed of alphabets (for example, antibody 1 (ααα, ααα, ααα), antibody 2 (βββ, βββ, βββ, βββ), . . . ) are associated with each antibody. Note here that each trial is carried out so that the antibody group formed in each trial is not completely identical. The "antibody group is completely identical" means that the numbers of groups are the same and the kinds of antibodies contained in each group are the same over the all groups.

After a plurality of times of trials, antibodies in which the results in all trials are not contradictory and which show the binding positive reaction to the target antigen are selected. Then, the step (vi) is carried out by using the selected antibody (a plurality of antibodies).

When trials are carried out at a plurality of times and only an antibody that provides not-contradictory (that is, consistent) results are selected, an antibody having a target antigen reactivity (intended antibody) can be efficiently obtained.

The number of times of trial in the steps (i) to (v) is not particularly limited. It may be arbitrarily set by considering the number of antibodies to be treated, the number of "positive combinations" that is anticipated at one trial. For example, the number of times of trial can be twice to five times.

In a further embodiment of the present invention, the following steps are carried out between the step (v) and the step (vi).

(v-1) newly associating the classified antibodies selected in step (v) with a combination of n pieces of parameters in a same manner as in the step (i);

(v-2) with respect to each parameter, preparing the antibody mixture of antibodies having the same parameter value;

(v-3) examining a reactivity of each of the antibody mixtures with a target antigen by an enzyme linked immunosorbent assay (ELISA) so as to specify the antibody mixture showing the reactivity;

(v-4) determining a combination of a parameter name and a parameter value that are common to the antibody group contained in the specified antibody mixture; and (v-5) selecting an antibody having the combination specified in the step (v-4) in terms of all parameters among the antibodies subjected to the step (v-1).

Note here that the steps (v-1) to (v-4) are repeated twice or more, if necessary.

In this embodiment, a combination of parameters is newly associated with antibodies selected in one trial. Then, the selection of antibody is carried out again. By repeating trials, the intended antibody is narrowed. Thus, classification accuracy is improved.

Figure 77:
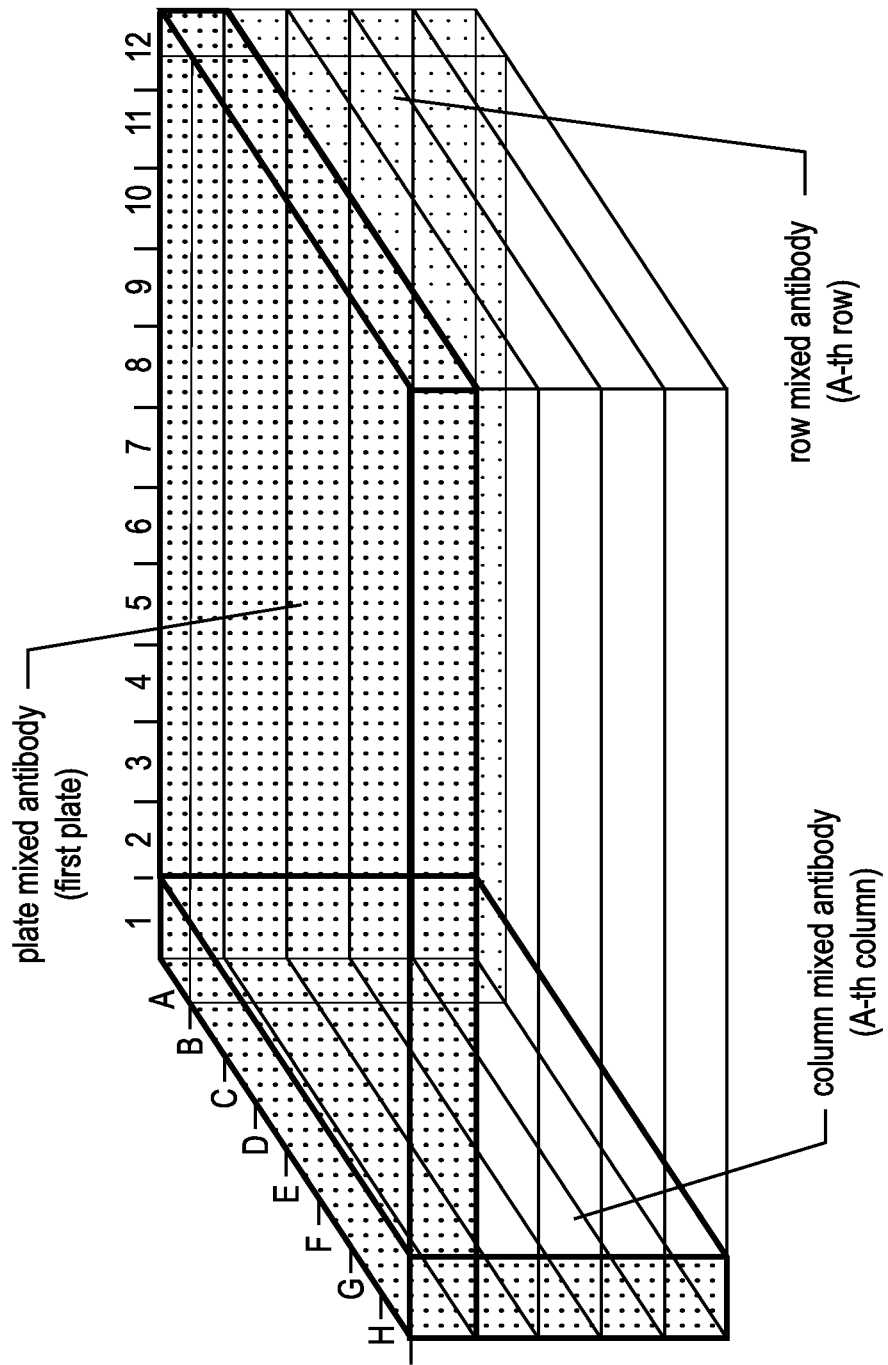
FIG. 77 is a conceptual diagram of three-dimensional ELISA, showing how each mixture antibody is prepared.

Herein, with reference to FIGS. 77 and 78, the principle of the n-dimensional ELISA method is described more particularly. FIGS. 77 and 78 are conceptual diagrams in a case where n is 3 (three dimensional ELISA method). In this example, a general-purposed 96-well microwell plate is used. Firstly, plates in the number necessary to the number of antibody clones are prepared. In this example, the number of antibody clones is made to be 4,800 and 50 plates (4,800 well in total) are prepared.

Next, the antibody clone is placed in the well sequentially and the antibody clones are arranged in the plate. Thus, each antibody clone is associated with an address consisting of a plate number (first parameter), a plate row name (second parameter), and a plate column number (third parameter). For example, the address of the antibody clone in the first plate, row A and first column in a well becomes (1, A, 1).

Subsequently, a mixture of antibody clones having the same plate number (referred to as a plate mixed antibody), a mixture of antibody clones having the same plate row name (referred to as a row mixed antibody), and a mixture of antibody clones having the same plate column number (referred to as a column mixed antibody) are prepared, respectively (FIG. 77). The number of the respective mixed antibodies are 50 (first plate mixed antibody to fifth plate mixed antibody), 8 (row A mixed antibody to row H mixed antibody), and 12 (first column mixed antibody to twelfth column mixed antibody), sequentially.

The mixed antibodies prepared as mentioned above are placed in wells in a newly prepared 96-well microwell plate sequentially, and the mixed antibodies are aligned in the plate. In this example, in the plate, the first to seventh columns are assigned to the plate mixed antibody, the eighth column is assigned to the row mixed antibody, and the ninth to tenth columns are assigned to the column mixed antibody (upper part of FIG. 78). The thus obtained plates are used and ELISA method is carried out. Then, by examining the well showing the reactivity, the address of the intended antibody clone (antibody clone showing the reactivity to the target antigen) is specified. In this example, a well in which the plate mixed antibody of the third plate is placed, a well in which the row mixed antibody of the row E is placed, and a well in which the column mixed antibody of the third column show the reactivity, (3, E, 3) is specified as an address of the intended antibody (lower part of FIG. 78). Finally, antibody clone to which the specified address is associated with is obtained as the intended antibody.

The second aspect of the present invention provides an identifying method of an antigen to each antibody classified in the classifying method of the present invention. In the identification method of the present invention, following the above-mentioned steps (1) to (4) in the classifying method of the present invention, the below-mentioned steps are carried out.

(5) selecting one or several antibodies from each antibody group formed in the step (4) and identifying an antigen thereof; and (6) associating the antigens identified in the step (5) with an antibody group, on the estimation that antigens to antibodies belonging to the same antibody group are identical or have high relationship, and.

Step (5)

In this step, antibodies to be identified are selected. The criteria of selection are not particularly limited, and antibodies that are judged to have high reactivity with respect to antigen from the results of the flow cytometry analysis may be selected. This is because when such an antibody is used, the identification operation using the antigen antibody reaction can be carried out advantageously.

The number of antibody to be selected is typically one, but the number is not necessarily limited to one. If necessary, several antibodies (for example, two or three antibodies) are selected. When a plurality of antibodies are selected from one antibody group, the identification results of antibodies can be compared with each other, and thereby the reliability of the identification results can be improved. On the other hand, when the identification operation is carried out by selecting a more than necessary number of antibodies, excessive workload is applied. As a result, the effect that is originally intended by the present invention is decreased. Then, it is preferable that the number of antibodies to be selected is small. Specifically, the number is preferably five or less, further preferably three or less, and the most preferably two or less. In order to maximize the effect of the present invention, the number of antibody to be selected from each antibody group is one.

Identification of an antigen to an selected antibody (hereinafter, referred to as "selected antibody") can be carried out by using a method such as mass spectrometry, immunoprecipitation test, Western blotting, affinity chromatography, RNAi, proteomics techniques (analysis by electrophoresis, mass spectrometry, genome data base retrieve, and bioinformatics), and analysis of expression of corresponding gene. Among them, a method by the proteomics technique based on the mass spectrometry is suitable for identification of unknown antigen and preferable for the identification method employed in the present invention. Note here that these methods are not exclusive to each other and two or more of them can be used if necessary.

The mass spectrometry is a method of determining the mass of samples by separating ions generated from samples such as protein and peptide according to mass/electric charge (m/z), and measuring the intensity thereof. Since soft ionization methods such as an ESI method (Electro Spray Ionization) and an MALDI method (Matrix Assisted Laser Deporption Ionization) are developed, the mass spectrometry is widely used for analyzing living body sample such as protein and peptide.

A mass spectrometer is generally composed of ion source, mass spectrometer, and detector. According to sample types and analysis purposes, various mass spectrometers are commercially available. For identification of protein or peptide, MS/MS (Mass spectrometry/mass spectrometry) by a tandem mass spectrometry such as ESI Q-TOF MS, MALDI-TOF MS, and the like are used. A measurement method combining liquid chromatography and mass spectrometer (LC-MAS (liquid chromatography/Electro Spray Ionization mass spectrometer), LC-MS/MS, etc.), and the like, can be also used.

In the tandem mass spectrometer, two mass spectrometers are linked in series in which ions generated in the ion source are separated in the first mass spectrometer (MS 1) and allowed to pass through only a single ion peak. Then, inactive gas particles are allowed to collide with the ions so as to be degraded into product ions. This product ion is analyzed by the second mass spectrometer (MS 2). According to the combination of the first mass spectrometer (MS 1) and the second mass spectrometer (MS 2), tandem mass spectrometers such as Q-TOF, TOF-TOF, Q-Q, and Q-IT (Iontrap) are present. Like Q-TOF (a tandem mass spectrometer in which Quadrupole mass spectrometer: Q-MS and TOF mass spectrometer (Time-of-flight mass spectrometer: TOF-MS are linked in series), hybrid type tandem mass spectrometer composed of two different kinds of mass spectrometers is excellent in MS/MS measurement ability and suitable for identifying the amino acid sequence of protein and peptide.

In order to identify the amino acid sequence from the results of the mass spectrometer, a PMF method (peptide mass fingerprinting method) of carrying out genome data search by using experiment results, MS/MS ion search method and the like, are used. Furthermore, de novo sequencing method of determining the amino acid sequence by mathematical operation from the MS/MS spectrum without carrying out genome data search may be used.

On the other hand, an immunoprecipitation test, Western blotting technique, affinity chromatography, RNAi, and the like, are effective method when a selected antibody is anticipated to recognize the known antigen. These methods can examine the reactivity between the selected antibody and well-known antigen. That is to say, in the immunoprecipitation test, it is examined whether or not the selected antibody and certain known antigen form an immunoprecipitate. When an immunoprecipitate is formed, the known antigen is determined to be the antigen of the selected antibody. On the other hand, in the Western blotting technique, it is examined whether or not the selected antibody can recognize an antigen protein transferred to a PVDF membrane etc. Furthermore, in the affinity chromatography, the adsorption property of the selective antibody to a column supporting a certain known antigen is examined. The presence or the degree of adsorption property is determined. Herein, as the known antigen, commercially available antigens, or antigens expressed from a gene and purified can be used. Furthermore, operations of the immunoprecipitation test, Western blotting technique, affinity chromatography, and the like, can be carried out in the usual manner. In the investigation in RNAi, RNAi of the known antigen is allowed to act on forcedly expressed cells or cells to which an antibody is reacted. It is determined that the subject antibody recognizes the subject antigen when the staining property FCM or the degree of cell immunostaining is reduced.

Step (6)

In the identification method of the present invention, following the step (5), it is assumed that antigens to each antigen belonging to the same antibody group are identical or have high association. According to the assumption, the antigens identified in the step (5) are associated with an antibody group. Thus, all antibodies belonging to the same antibody group are associated with one antigen.

In one embodiment of the present invention, the above assumption (estimation as to the association of antigen) is verified. That is to say, in this embodiment, the reactivity between the antigen identified in the step (5) and the antibody belonging to the antibody group with which the antigen is associated in the step (6) is examined so as to confirm that the above assumption is correct. Specifically, firstly, antibodies are selected from the antibody group that needs verification. Preferably, all the antibodies are selected, and the reactivity thereof is verified. Next, the reactivity of each antibody to the identified antigen (hereinafter, referred to as "identified antigen") is examined by using the immunoprecipitation test or ELISA (including cell ELISA), and RNAi. For example, in the immunoprecipitation test, by reacting the antibody to an solution or an extracted solution of cells that express the identified antigen, then, proteins recovered as the immunoprecipitates are detected by, for example, electrophoresis. Thereby, the reactivity of each antibody to the identified antigen can be confirmed. On the other hand, in ELISA, for example, by a series of operations including preparation of well in which an identified antigen is fixed, addition of antibody, addition of labeled antibody, and measurement amount of labeled antibodies, the reactivity of each antibody with respect to the identified antigen can be confirmed. Furthermore, also by examining the binding property to cells forcedly expressing the identified antigen, the reactivity of each antigen to the identified antigen can be confirmed. In the verification by RNAi, by allowing the known RNAi to act on cells forcedly expression the identified antigen or subjected cells showing the antibody reaction. When, the staining property of the subjected antibody in FCM and cell immunostaining is reduced, it is recognized that he subjected antigen is recognized.

Furthermore, when disease-related molecules (disease causative gene products, etc.) can be obtained in same forms such as purified protein or recombinant protein, the intermolecular interaction between such molecules and the antibodies can be examined in vitro (classical methods using fluorescence spectroscopy, gel filtration, and ultracentrifugation; a method using surface plasmon resonance phenomenon; a method using quartz-crystal resonator microbalance, and the like) or in vivo (monomolecular tracing method, fluorescence resonance energy metastasis (fluorescence resonance energy transfer: FRET) observation method, and the like).

When specific reactivity is observed between the identified antigen and each antibody, it is judged that the above assumption is correct.

In one embodiment of the present invention, identification results are displayed on a panel. Specifically, the panel is any of the following (a) to (c).

(a) a panel displaying as one antibody group a plurality of antibodies providing data identical to or similar to each other in the flow cytometry analysis in the step (3) in which each antibody group is associated with its antigen;

(b) a panel displaying as one antibody group a plurality of antibodies providing data identical to or similar to each other in the flow cytometry analysis in the step (3) in which each antibody in the antibody group is associated with a cell expressing a cell surface antigen recognized by the each antibody group; and (c) a panel displaying as one antibody group a plurality of antibodies providing histogram identical to or similar to each other in the flow cytometry analysis in the step (3) in which each antibody group, its antigen and a cell expressing a cell surface antigen recognized by the antibody are associated with each other.

The above-mentioned panels are useful for studying identified antigens, and for studying or classifying certain cells displayed on the panel.

The panel (a) displays the relationship between each antigen to the antibody group. Therefore, it is useful in searching an antibody to a certain antigen. The panel (a) can be formed by displaying by the use of diagrams or tabular formats the association between each antibody group and the antigen by using identification results by steps (5) and (6) of the present invention in which a plurality of antibodies providing identical or highly similar data in the flow cytometry analysis in the step (3) of the present invention are defined as one group.

The panel (b) shows the association between the antibody group and cells. Therefore, it is useful in searching an antibody to a certain cell surface antigen. Furthermore, when the panel displays the association between the antibody group and a plurality of cells, useful information on the distribution of cell surface antigen can be provided. The panel (b) can be formed by displaying by the use of diagrams or tabular formats the association between each antibody group and cells expression the cell surface antigen recognized thereby by using identification results by steps (5) and (6) of the present invention in which a plurality of antibodies providing identical or highly similar data in the flow cytometry analysis in the step (3) of the present invention are defined as one group.

The panel (c) combines the panel (a) and the panel (b). This panel shows that the kinds or distribution state of a cell surface antigen expressed by certain cells and allows easy and rapid search of antibodies to the antigens of interest. The panel (c) can be formed by displaying by the use of diagrams or tabular formats the association between each antibody group and cells expression the cell surface antigen recognized by the antigen and each antibody group by using identification results by steps (5) and (6) of the present invention in which a plurality of antibodies providing identical or highly similar histogram in the flow cytometry analysis in the step (3) of the present invention are defined as one group.

In the identification method of the present invention, identification of antigen with respect to only a part of the antibodies in the antibody group, and as to the other antibodies, antigens are determined by estimation. Therefore, as compared with the case where identification operation is carried out for each antibody, necessary labor and time can be radically reduced. In other words, according to the identification method of the present invention, antigen of each antibody can be determined rapidly and easily. Note here that as shown in the below-mentioned Examples, as far as the present inventors have investigated, error in estimation has not been confirmed. The reliability of this method has been confirmed.

On the other hand, according to the identification method of the present invention, it is possible to understand the kinds of surface antigens expressed by certain cells. Furthermore, information on the expression amount can be obtained. When the classification of antibodies is carried out by using two kinds or more cells, information on the distribution state of the cell surface antigens can be obtained. Thus, the identification method of the present invention brings useful information as to the cell surface antigen.

As a result, according to the identification method of the present invention, it is possible to obtain an assembly of antibodies capable of recognizing antigens for each identified antigen (or for each of the plurality of antigens having high association). These antibody groups are useful for study of the cell surface antigens, classification and diagnosis of diseases, and the like. These antibody groups are expected to be applied to the field of treatment.

The present invention further provides an application of information obtained by the classifying method or the identification method of the present invention. As one of the applications, the third aspect of the present invention relates to a method of obtaining an antibody or an antibody set having a association with respect to a certain disease. The method of obtaining the antibody of the present invention (the first embodiment of the third aspect) includes the following steps.

(1) selecting one or two or more of antibody groups from the plurality of antibody groups classified by the classifying method according to the present invention;

(2) with respect to one kind or two or more kinds of diseases examining a reactivity between an antibody in each of the selected antibody groups and a certain disease; and (3) selecting an antibody in the antibody group, to which an antibody having a specific reactivity to any of diseases belongs, as a useful antibody.

On the other hand, a method of obtaining an antibody set of the present invention (the second embodiment of the third aspect) includes the step (3') instead of the step (3):

(3') selecting diseases to which two or more antibodies show a specific reactivity, then selecting antibodies from the antibody group, to which the antibody having a specific reactivity to the disease belongs, and combining the selected antibodies.

Hereinafter, the detail of each step is described with reference to FIG. 1. For convenience of explanation, in FIG. 1, it is assumed that the antibody groups 1 to 5 are obtained by the classifying method of the present invention and three antibodies belong to each antibody group. Furthermore, in this example, it is assumed that antigens to each antibody group have been already identified.

Firstly, in the step (1), focused antibody group (antibody groups 1, 3, and 5) are selected (FIG. 1, (1)). As in this example, two or more antibody groups may be selected.

Next, in the step (2), the reactivity between an antibody to each of the selected antibody groups and a certain disease is examined. Specifically, a sample (cells or tissues) derived from a patient having a certain disease is prepared, and then, the reactivity of each antibody to the sample is examined (FIG. 1, (2)). Two or more antibodies from each of the selected antibody groups are selected, and thereby the reactivity of them may be examined. The "certain disease" herein is not particularly limited but it may include various kinds of cancers, for example, kidney cancer, hepatic cell carcinoma, gallbladder and liver cancer, alveolar cell carcinoma, lung squamous cell cancer, pulmonary adenocarcinoma, pancreas cancer, adenocarcinoma, or ovarian cancer. In the example shown in FIG. 1, the reactivity with respect to two kinds or more of diseases are examined simultaneously. However, the examination is not limited to this alone. The reactivity to one disease may be examined. Furthermore, the reactivity with respect to a certain pathologic condition in the certain disease may be examined.

The reactivity with respect to the samples derived from a patient can be detected and evaluated by using an immunohistochemical staining technique, an immunoprecipitation method, flow cytometry analysis, cell ELISA and the like. These methods are not exclusive to each other and therefore two or more of these methods can be used if necessary. Among them, it is preferable to employ the immunohistochemical staining technique. The immunohistochemical staining technique permits rapid and sensitive detection. Furthermore, its operation is relatively simple.

In the immunohistochemical staining technique, tissues collected from a patient and an antibody are brought into contact with each other, and then, specifically bonded antibodies are detected. Concretely, the method of the present invention can be carried out according to the following immunohistochemical staining technique.

The immunohistochemical staining of living tissue is generally carried out by the following procedures (a) to (j). Note here that the immunohistochemical staining of living tissue can be referred to as various documents and publications (for example, "Enzyme-labeled Antibody Method" 3rd revised edition, K. Watanabe and K. Nakane (ed), Gakusai Kikaku).

(a) Immobilization—Paraffin Embedding Method

Tissue surgically collected from a living body is immobilized in formalin, paraformaldehyde, absolute ethyl alcohol, and the like, and then embedded in paraffin. In general, it is dehydrated with alcohol, treated with xylene and embedded in paraffin. The paraffin embedded specimen is cut into a desired thickness (for example, 3 to 5 μm thick) and extended on a slide glass. Instead of the paraffin embedding specimen, an alcohol immobilized specimen, a dry sealed specimen, a frozen specimen, and the like may be used.

(b) Deparaffinization

In general, treatment is carried out with xylene, alcohol, and purified water sequentially in this order.

(c) Pretreatment (Antigen Activation)

If necessary, for antigen activation, for example, enzyme treatment, heat treatment and/or pressurization treatment are carried out.

(d) Removal of Endogeneous Peroxidase

When peroxidase is used as a labeling material for staining, endogeneous peroxidase activation is removed by carrying out with hydrogen peroxide solution.

(e) Non-Specific Reaction Inhibition

Non-specific reaction is inhibited by treating a section with bovine serum albumin solution (for example, 1% solution) for several minutes to several tens of minutes. Note here that this process may be omitted when the following primary antibody reaction is carried out by using an antibody solution impregnated with bovine serum albumin.

(f) Primary Antibody Reaction

An antibody diluted to an appropriate concentration is dropped on the slide glass and allowed to react for ten minutes to several hours. After reaction, the reacted produce is washed with an appropriate buffer solution such as phosphate buffer.

(g) Addition of Labeling Reagent

As the label material, peroxidase is frequently used. Secondary antibody bonded to peroxidase is dropped on the section and then allowed to react for ten minutes to several hours. After reaction, the reacted product is washed with an appropriate buffer solution such as phosphate buffer.

(h) Color Reaction

DAB (3,3'-diaminobenzidine) is dissolved in Tris buffer. Then, hydrogen peroxide solution is added. The thus prepared coloring solution is impregnated into a section for several minutes (for example, five minutes) so as to color the section. After coloring, the section is sufficiently washed with tapped water so as to remove DAB.

(i) Nuclear Staining

The section is subjected to nuclear staining by reacting it with Mayer hematoxylin for several seconds to several tens seconds. It was washed with flowing water for saddening (in general, for several minutes).

(j) Dehydration, Clearing, Encapsulation

The section is dehydrated with alcohol, clearing treated with xylene, and finally encapsulated with synthesized resin, glycerine, rubber syrup, and the like.

An antibody that is recognized to have specific reactivity to any of diseases can detect a cell surface antigen characterizing the disease with high sensitivity. Such an antibody is expected to be used as a diagnosis or treatment antibody of the disease. Then, in the step (3), an antibody of the antibody group including such an antibody is selected (FIG. 1 (3)). As a result, in this example, as to disease A, an antibody (antibody 1-1, 1-2 or 1-3) of the antibody group 1 and an antibody of the antibody group 3 (antibody 3-1, 3-2 or 3-3) are selected. As to disease B, an antibody (antibody 5-1, 5-2 or 5-3) of the antibody group 5 is selected. In this way, a specific antibody for a certain diseases can be obtained.

In the step (3'), a disease in which two or more antibodies show the specific reactivity is selected, and then, each antibody is selected from the antibody group to which the antibody showing the specific reactivity to the disease belongs, is selected, and the selective antibodies are combined (FIG. 1, (3')). That is to say, in this example, the disease A is selected and the antibodies of antibody groups 1 and 3, which are antibody groups to which the antibody showing the specific reactivity to the disease A belongs, are combined. Thus, the antibody set showing specific to a certain disease is obtained.

Herein, by comparing the specificities (cross reactivity) of the antibodies in the antibody group, an antibody having the most excellent property may be selected (in this example, antibody 1-2, antibody 3-3, and antibody 5-3 are selected. See, FIG. 1, (4)). By adding this step, more useful antibody or antibody set can be obtained.

Furthermore, an antibody set may be structured by combining an arbitrary antibody that does not have reactivity to the diseases with the antibodies selected as the antibodies showing the reactivity to a certain disease (in this example, for example, the antibody 4-1 is combined to an antibody of the antibody group 1 and antibody of antibody group 3). By using such an antibody set, detail characterization of the disease can be possible.

According to the obtaining method of the present invention, an antibody (or antibody set) to a disease-specific antigen can be obtained. The antibody (or antibody set), which are as it is or to which necessary modification is added, is useful for study, classifying, diagnosing and treating the disease or the pathologic condition. Thus, this method provides an extremely useful tool in the field of medicine.

The third embodiment of this aspect provides the obtaining method of antibody set including the following steps.

(1) selecting two or more antibody groups recognizing different antigens from the plurality of antibody groups classified by the classifying method according to the present invention;

(2) with respect to two kinds or more of diseases, examining a reactivity between an antibody in each of the selected antibody groups and a certain disease; and (3) selecting antibodies from the antibody group, to which the antibody having a specific reactivity to any of disease belongs, and combining the selected antibodies.

Hereinafter, the detail of each step is described with reference to FIG. 2. For convenience of explanation, in FIG. 2, it is assumed that the antibody groups 1 to 6 are obtained by the classifying method of the present invention and three antibodies belong to each antibody group. The antigens (antigen A) in the antibody groups 1 to 3 are common. Similarly, the antigens (antigen B) in the antibody groups 4 and 5 are also common.

Figure 2:
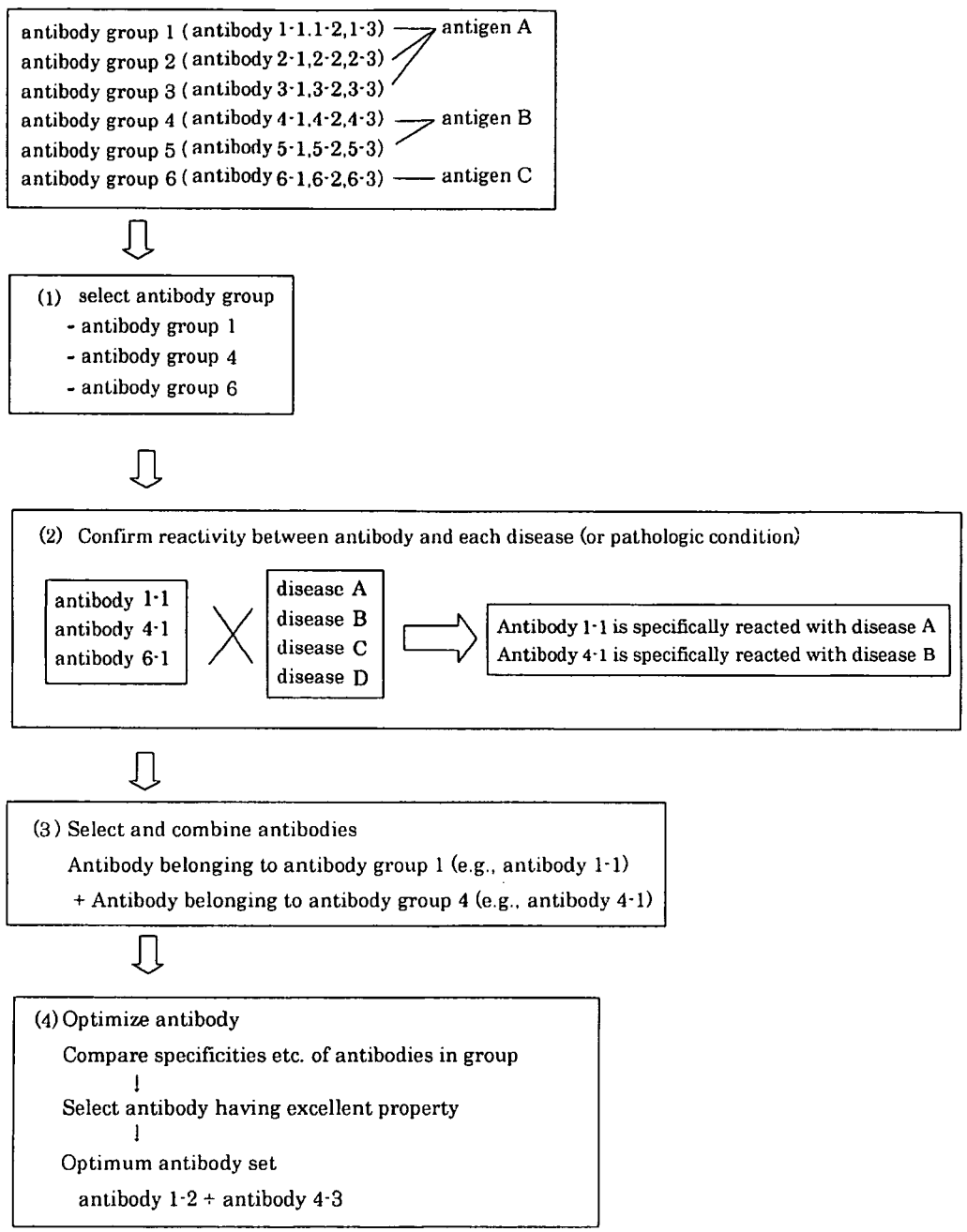
FIG. 2 shows another example of a method of obtaining an antibody set related to a certain disease.

In the step (1) of this embodiment, two or more antibody groups recognizing different antigens (antibody groups 1, 4, and 6) are selected (see, FIG. 2 (1)). In the following step (2), the reactivity between the antibodies (antibodies 1-1, 4-1, and 6-1) in each of the selected antibody groups and certain diseases (diseases A to D) are examined (FIG. 2, (2)). In the step (3), antibodies in the antibody groups to which the antibody belong showing specific reactivity to any of diseases are combined. That is to say, in this example, an antibody of antibody group 1 to which an antibody 1-1 showing specific reactivity to disease A and an antibody of antibody group 4 to which an antibody 4-1 showing specific reactivity to disease B are combined to form an antibody set (FIG. 2, (3)). Thus, an antibody set (the antibody 1-1 and the antibody 4-1) including an antibody specific to disease A and an antibody specific to disease B is obtained. This antibody set is useful for detecting, for example, disease A or disease B and this antibody is a reagent effective to the discrimination of the diseases A and B.

Note here that by comparing the specificity (cross reactivity) and the like between the antibodies in the antibody group, an antibody having the most excellent property may be selected (In this example, the antibody 1-2 and the antibody 4-3 are selected. FIG. 2, (4)). By adding this step, it is possible to obtain a more useful antibody set.

As a result of carrying out the classifying method and the identification method of the present invention, assuming that a plurality of antibodies groups recognizing the same antigen are obtained, the fourth embodiment of this aspect provides a obtaining method of an antibody set including the following steps.

(1) selecting two or more antibody groups recognizing different antigens from the plurality of antibody groups classified by the classifying method according to the present invention;

(2) with respect to one kind or two or more kinds of diseases, examining a reactivity between an antibody in each of the selected antibody groups and a certain disease; and (3) selecting an antibody from the antibody group to which the antibody having a specific reactivity to any of disease belongs, and an antibody belonging to other antibody group whose antigen is common to that of the antibody group, and combining the selected antibodies.

Hereinafter, the detail of each step is described with reference to FIG. 3. For convenience of explanation, in FIG. 3, it is assumed that the antibody groups 1 to 6 are obtained by the classifying method of the present invention and three antibodies belong to each antibody group. The antigens (antigen A) in the antibody groups 1 to 3 are common. Similarly, the antigens (antigen B) in the antibody groups 4 and 5 are also common.

Figure 3:
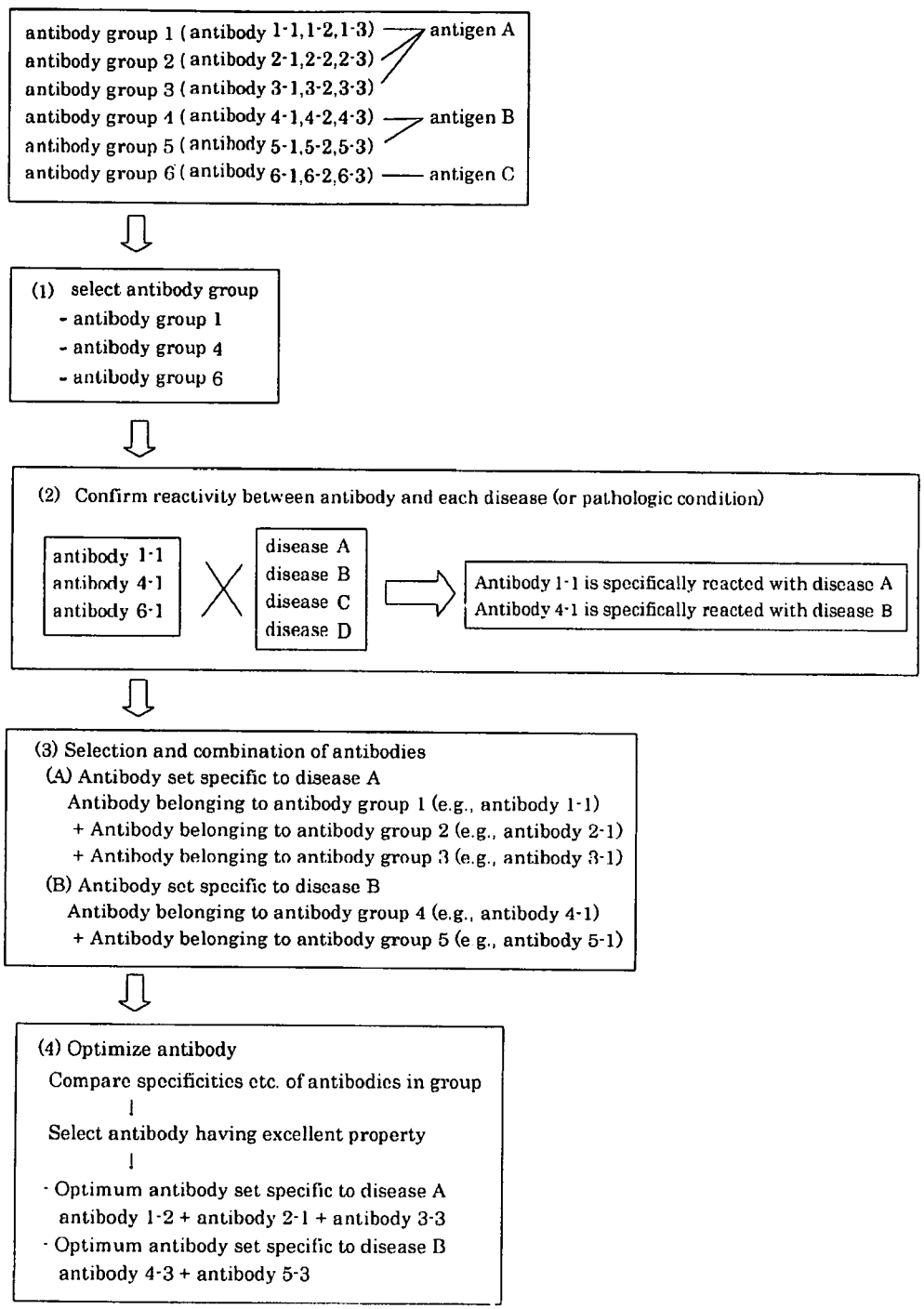
FIG. 3 shows a further example of a method of obtaining an antibody set related to a certain disease.

In the step (1) of this embodiment, two or more antibody groups recognizing different antigens (antibody groups 1, 4, and 6) are selected (see, FIG. 3 (1)). In the following step (2), the reactivity between the antibodies (antibodies 1-1, 4-1, and 6-1) in each of the selected antibody groups and certain diseases (diseases A to D) are examined (FIG. 3, (2)). In the step (3), an antibody of the antibody group to which an antibody showing the specific reactivity to any of diseases and an antibody belonging to other antibody group whose antigen is common to the group are selected, respectively. The selected antibodies are combined so as to form an antibody set (FIG. 3, (3)). That is to say, in this example, an antibody in antibody group 1 to which antibody 1-1 belongs showing specific reactivity to disease A and an antibody of the antibody groups 2 and 3 whose antigens are common are combined. Thus, an antibody set specific to the disease A is obtained. Similarly, an antibody in antibody group 4 to which antibody 4-1 belongs showing specific reactivity to disease B and an antibody of the antibody group 5 whose antigen is common to that of antibody group 4. Thus, an antibody set specific to the disease B is obtained. As shown in this example, "another antibody group" herein is not particularly one but a plurality antibody groups may be present.

Herein, even in the case of cancers of the same organ, depending upon patients, the pathologic condition (grade of malignancy) may be largely different. The difference in such pathologic conditions is thought to be involved to the expression forms of the specific antigens. On the other hand, the antibody sets obtained in this embodiment are not different in the level recognized by an antigen but include antibodies that are different in the level of epitope. That is to say, this is an antibody set including a plurality of antibodies that are different in the epitope to be recognized. Such an antibody set permits multilateral detection or evaluation of expression forms of antigen. For example, such an antibody set is useful for detection of certain pathologic conditions in, for example, cancers, or a determination of the grade of malignancy.

Note here that by comparing the specificity (cross reactivity) and the like in the antibodies in the antibody group, an antibody having the most excellent property may be finally selected (FIG. 3, (4)). By adding this step, it is possible to obtain a more useful antibody set.

As a result of carrying out the classifying method and the identification method of the present invention, assuming that a plurality of antibodies groups recognizing the same antigen are obtained, the fifth embodiment of this aspect provides a obtaining method of an antibody set including the following steps.

(1) selecting two or more antibody groups recognizing the same antigen from the plurality of antibody groups classified by the classifying method according to the present invention;

(2) with respect to one kind or two or more kinds of pathologic conditions, examining a reactivity between an antibody in each of the selected antibody groups and a pathologic condition; and (3) associating information about the reactivity and then combining the antibodies in the antibody groups.

Hereinafter, the detail of each step is described with reference to FIG. 4. For convenience of explanation, in FIG. 4, it is assumed that the antibody groups 1 to 6 are obtained by the classifying method of the present invention and three antibodies belong to each antibody group. The antigens (antigen A) in the antibody groups 1 to 3 are common. Similarly, the antigens (antigen B) in the antibody groups 4 and 5 are also common.

Figure 4:
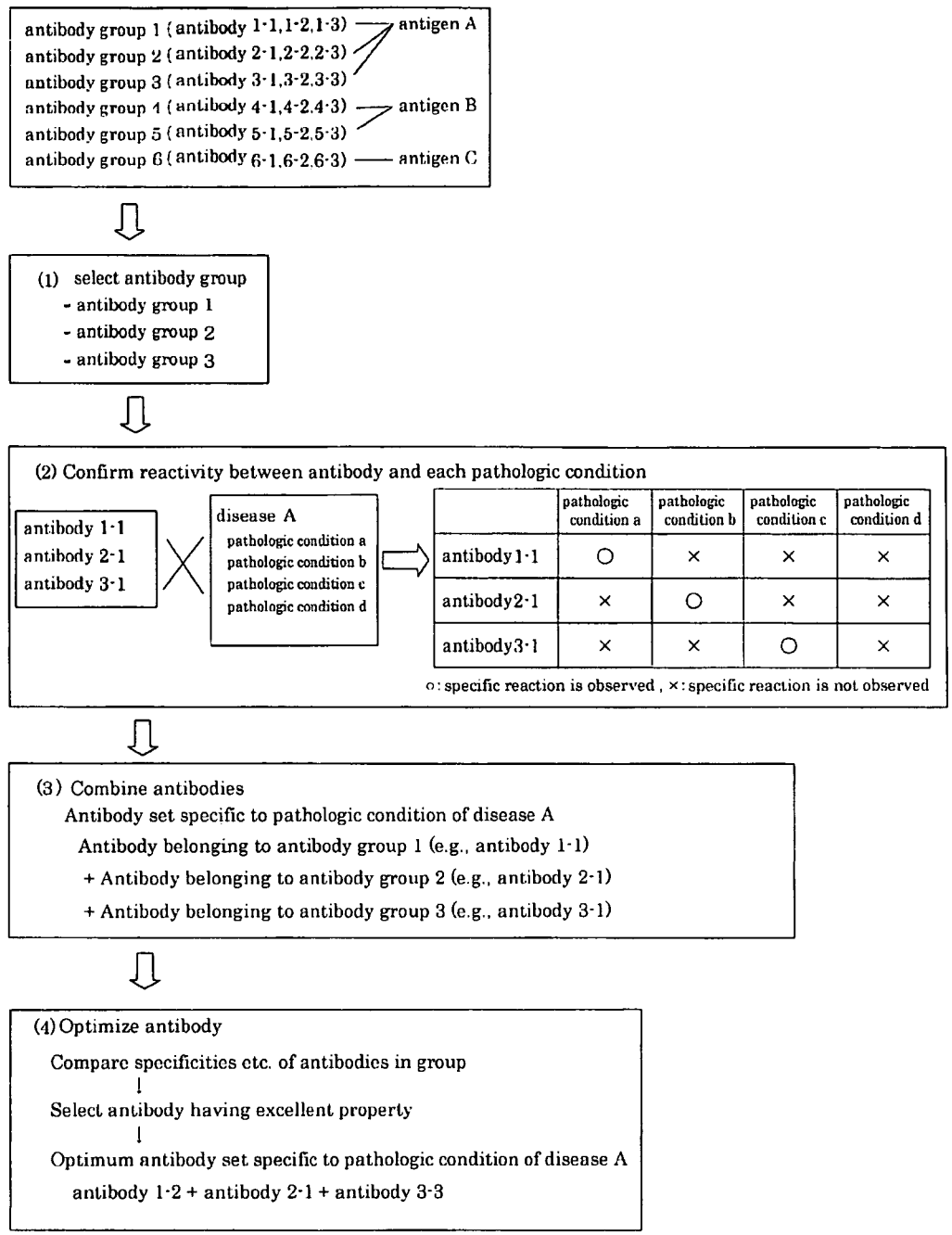
FIG. 4 shows a yet further example of a method of obtaining an antibody set related to a certain disease.

In the step (1) of this embodiment, two or more antibody groups recognizing common antigen (antibody groups 1 to 3) are selected (see, FIG. 4 (1)). In the following step (2), the reactivity between the antibodies (antibodies 1-1, 2-1, and 3-1) in each of the selected antibody groups and certain various diseases are examined (FIG. 4, (2)). Specifically, as to various pathologic conditions of certain disease, samples (cells or tissue) derived from a patient are prepared, and the reactivity between the samples and each antibody is examined. In the step (3), the obtained reactivity is associated with each other (FIG. 4, (2), right column), and then antibodies of each of the selected antibody groups (antibody groups 1 to 3) are combined so as to form an antibody set (FIG. 4, (3)). Thus, antibody sets specific to the certain pathologic condition of certain disease is obtained (in this example, an antibody set specific to pathologic condition of disease A including antibodies of the antibody groups 1 to 3 is obtained). The antibody set obtained in this embodiment is typically not different in the level of an antigen but include antibodies that are different in the level of epitope. Therefore, similar to the antibody set according to the above-mentioned embodiment, for example, the antibody set is useful detecting the certain pathologic condition in, for example, cancer, or a determination of the grade of malignancy. Note here that it is preferable that an antibody set is constructed by excluding antibodies showing no specific reactivity with respect to any pathologic conditions.

By comparing the specificity (cross reactivity) and the like in the antibodies in the antibody group, an antibody having the most excellent property may be finally selected (in this example, antibodies 1-2, 2-1 and 3-3 are selected, FIG. 4, (4)). By adding this step, it is possible to obtain a more useful antibody set.

A further aspect of the present invention provides a production method of a panel displaying a association between an antibody and a disease (or pathologic condition). In the first embodiment of this aspect, the following steps are carried out.

(1) selecting one or two or more of antibody groups from the plurality of antibody groups classified by the classifying method according to the present invention;

(2) with respect to one kind or two or more kinds of diseases, examining a reactivity between an antibody in each of the selected antibody groups and a certain disease; and (3) associating the results of the step (2) with each antibody and displaying by using a drawing or a tabular format.

When one antibody group is selected in the step (1), as to one antibody or a plurality of antibodies whose antigen is common, a panel displaying the association with respect to a certain disease can be obtained. In the latter case, as to a plurality of antibodies whose antigen is common antigen, from the viewpoint of the association with respect to the disease, difference or points of difference (one caused by the cross reactivity and the like) can be read out. That is to say, the panel gives an important suggestion as to the property of the antibody. On the other hand, when two or more antibody groups are selected in the step (1), as to a plurality of antibodies whose antigen is different (however, when several antibodies from each antibody group in the step (1), antibodies whose antigen is common is contaminated), a panel displaying the association with respect to the certain disease is obtained. This panel gives information on the antibody group useful for study, classification and diagnosis. The panel itself has a great value. Form this panel, the association between a plurality of antigen and disease can be read out. That is to say, the panel gives an important suggestion as to the association between each antigen and disease.

Herein, in the step (2), it is preferable to examine the reactivity of the antibody as to two or more diseases. Thus, a panel displaying the association (linkage) between each antibody and two or more diseases can be obtained. The panel displays more pieces of information and further displays the association between diseases. Suggestion that is useful and important for study, classification and diagnosis of the diseases can be obtained.

In the second embodiment of this aspect, the following steps are carried out.

(1) selecting two or more of antibody groups recognizing different antigens from the plurality of antibody groups classified by the classifying method according to the present invention;

(2) with respect to one kind or two or more kinds of diseases, examining a reactivity between an antibody in each of the selected antibody groups and a certain disease; and (3) associating the results of the step (2) with each antibody and displaying by using a drawing or a tabular format.

In this embodiment, a panel displaying the association between a plurality of antibodies whose antigen is different and a certain disease can be obtained. This panel gives information on an antibody group useful for study, classification and diagnosis for a disease and the panel itself has a great value. Form this panel, the association (linkage) between a plurality of antigens and disease can be read out. That is to say, the panel gives important suggestions as to the association between each antigen and disease as well as the association between antigens.

Herein, in the step (2), it is preferable to examine the reactivity of the antibody as to two or more diseases. Thus, a panel displaying the association between each antibody and two or more diseases can be obtained. The panel displays more pieces of information and further displays the association between diseases. Suggestion that is useful and important for study, classification and diagnosis of the diseases can be obtained.

In the third embodiment of this aspect, the following steps are carried out.

(1) selecting two or more of antibody groups recognizing a common antigen from the plurality of antibody groups classified by the classifying method according to the present invention;

(2) with respect to one kind or two or more kinds of pathologic condition, examining a reactivity between an antibody in each of the selected antibody groups and a certain pathologic condition of disease; and (3) associating the results of the step (2) with each antibody and displaying by using a drawing or a tabular format.

In this embodiment, as to a plurality of antibodies whose antigen is common, a panel displaying the association with respect to a pathologic condition of a certain disease can be obtained. This panel gives information on antibody group that is useful for study of each pathologic condition, study of difference between pathologic conditions, classification of pathologic conditions, or diagnosis on the level of the pathologic condition. The panel itself has a great value.

Herein, in the step (2), it is preferable to examine the reactivity of the antibody as to two or more pathologic conditions. Thus, a panel displaying the association between each antibody and two or more pathologic conditions can be obtained. This panel displays not only more pieces of information but also the association between the pathologic conditions. Suggestion that is useful and important to study, classification and diagnosis of each pathologic condition can be obtained.

Note here that the first embodiment of this aspect corresponds to the first and second embodiments of the third aspect. Similarly, the third aspect of the second embodiment corresponds to the third and fourth embodiments of the third aspect, respectively. Therefore, as to the matters that are not specifically noted in this aspect, the explanation of the corresponding third aspect is employed.

In the panel of the present invention, the term "association between antibody and disease (or pathologic condition)" is displayed by characters showing subject diseases (or pathologic conditions) are positive or negative to the antibody (for example, "to positive," "to negative," "positive," and "negative") or marks (for example, "o," "x," "P," and "N") etc. The display is not limited to two-stage display and, display may be carried out in four stages, for example, strongly positive, moderate positive, weak positive, and negative.

The number of antibodies displayed in one panel is not particularly limited. For example, the number is 1 to 1000, preferably 2 to 100, and further preferably 5 to 59.

Furthermore, in addition to the association between an antibody and a certain disease (or pathologic condition), an antigen to each antibody may be shown.

The combination of the panel of this aspect and the antibody (or antibody set) obtained in the above-mentioned obtaining method of the present invention becomes an effective tool for study, classification and diagnosis of diseases, pathologic conditions, or the like. That is to say, according to the combination, both information, i.e., an antibody (or an antibody set) specific to a disease or a pathologic condition and the association between the antibody (or the antibody set) and the disease or the pathologic condition can be obtained simultaneously.

The present invention further relates to a method of testing a disease in which a cell surface antigen is an indicator, the method comprising the following steps.

(1) preparing a cell or a tissue separated from a subject;

(2) examining a reactivity between the cell or the tissue and each antibody displayed on the panel (panel displaying the association between an antibody and a disease (or a pathologic condition)) according to the present invention; and (3) collating the results in the step (2) with the panel.

According to the testing method of the present invention, as to a disease or a pathologic condition to be tested (hereinafter, referred to as "diseased to be tested"), information about the presence of contraction of a subject, contraction risk, pathologic conditions, and the like, can be obtained. That is to say, the testing method of the present invention is effective means for diagnosing the subjected disease. Furthermore, when the testing method of the present invention is carried out along with the treatment, the therapeutic effect can be evaluated based on the testing results. Thus, the testing method of the present invention may be used for monitoring the therapeutic effect.

In the step (1), cells or tissue separated from a subject (that is, a living body) (hereinafter, referred to as "subject cell, and the like") are prepared. The term "separated from a subject" means a state in which a part of cells or tissue of a subject is extracted and completely isolated form a subject as a living body. A person who needs information about a disease to be tested is a subject. A subject may be a patient of a disease to be tested or may be an apparent healthy person. The "apparent healthy person" means a person who has not recognized to be a patient of a disease to be tested prior to the application of the testing method of the present invention.

In the step (2), the reactivity between the subject cells and the like and each antibody displayed on the panel of the present invention is examined. That is to say, by using an immunologic procedure (for example, immunohistochemical staining technique), whether or not the tested cells express an antigen recognized by each antibody is examined. According to the immunologic procedure, in general, information on the expression amount of antigens can be obtained. Therefore, in addition to the presence of expression antigen, the expression amount may be also examined. An example of the immunologic procedure includes ELISA method, radioimmunoassay, flow cytometry analysis, immunoprecipitation method, immune-blotting, and the like.

In the step (3), the results of the step (2) (reactivity of each antibody) is collated with the panel of the present invention. The panel of the present invention displays the association between each antibody and a disease or a pathologic condition. Therefore, this step clarifies the association between the tested cells etc. and the disease via the reactivity with respect to each antibody.

A further application of the above-mentioned panel also includes the following method of the present invention, that is, the optimum method of treating certain diseases, which includes the following steps.

(1) preparing a cell or a tissue separated from a subject;

(2) examining a reactivity between the cell or the tissue and each antibody displayed on the panel (a panel displaying the association between the antibody and disease (or pathologic condition)) according to the present invention;

(3) collating the results in the step (2) with the panel, and (4) selecting an effective antibody according to the results of collating.

In the selection method of the present invention, similar to the above-mentioned testing method, after the steps (1) to (3) are carried out, according to the collation results, an effective antibody is selected (the step (4)). As the effective antibody, typically, an antibody showing a specific reactivity in the step (2) is selected. An antibody equivalent to the antibody showing a specific reactivity in the step (2) may be also selected. The "equivalent antibody" means an antibody having equivalent properties (reactivity or activity) to the reference antibody. An example of the equivalent antibody may be an antibody in which the sequence of the heavy chain variable region and the sequence of the light chain variable region are not substantially different from that of the reference antibody (completely identical, or slightly different so that the reactivity or activity is not affected). Another example of the equivalent antibody may be an antibody in which no difference is observed in all of the sequence of each CDR constituting heavy chain variable region and the sequence of each CDR constituting light chain variable region when it is compared with the reference antibody.

Diseases to which the selection method of the present invention is applied is a disease in which cell surface antigen selected from the group consisting of HER1, HER2, CD46, ITGA3, ICAM1, ALCAM, CD147, IgSF4, BCAM, C1qR, CD44, CD73, LAR, EpCAM and HGFR is an indicator. That is to say, for selecting optimum treatment methods suitable for various diseases characterized by the expression of the cell surface antigen, the present invention can be used. According to the present invention, optimum treatment method suitable for each patient can be selected. Thus, tailor-made medicine can be realized.

It is preferable that the panel used in the selection method of the present invention displays two or more antibodies selected from the group consisting of 048-006 antibody, 057-091 antibody, 059-152 antibody, 048-040 antibody, 054-101 antibody, 055-147 antibody, 059-173 antibody, 067-149 antibody, 067-176 antibody, 015-126 antibody, 015-044 antibody, 015-102 antibody, 015-136 antibody, 015-143 antibody, 015-209 antibody, 039-016 antibody, 053-216 antibody, 075-024 antibody, 075-110 antibody, 086-032 antibody, 086-035 antibody, 086-036 antibody, 086-061 antibody, 086-138 antibody, 086-182 antibody, 035-224 antibody, 045-011 antibody, 051-144 antibody, 052-053 antibody, 052-073 antibody, 053-049 antibody, 3172-120 antibody, 066-069 antibody, 015-003 antibody, 064-002 antibody, 064-006 antibody, 064-012a antibody, 064-012b antibody, 064-014 antibody, 064-054 antibody, 064-085 antibody, 064-093 antibody, 064-116 antibody, 065-183 antibody, 067-142 antibody, 068-007 antibody, 052-033 antibody, 053-042 antibody, 053-051 antibody, 053-059 antibody, 053-085 antibody, 035-234 antibody, 040-107 antibody, 041-118 antibody, 066-174 antibody, 083-040 antibody, 029-143 antibody, 045-134 antibody, 062-101 antibody, 062-109 antibody, 084-103 antibody, 052-274 antibody, 029-067 antibody, 083-131 antibody, 059-053 antibody, 064-003 antibody, 067-213 antibody, 067-153 antibody, 067-126 antibody, 067-133 antibody, 067-287 antibody, 064-044 antibody, 065-030 antibody, 065-358 antibody, 066-019 antibody, 079-085 antibody, 067-024 antibody, and 076-048 antibody.

In one embodiment of the selecting method of the present invention, the following steps are carried out.

(1) preparing a panel displaying a reactivity between one or more antibodies selected from the group consisting of 048-006 antibody, 015-126 antibody, 067-133 antibody, 064-044 antibody, 076-048 antibody and 059-053 antibody, and a clinical cancer tissue of one or more diseases selected from the group consisting of squamous carcinoma, adenosquamous carcinoma, alveolar adenocarcinoma, adenocarcinoma, and large cell carcinoma, and a cell or tissue separated from a subject;

(2) examining reactivity between the cell or the tissue and each antibody displayed on the panel;

(3) collating the results in the step (2) with the panel, and (4) selecting an effective antibody according to the results of collating.

In the step (1) of this embodiment, a panel displaying the reactivity between an antibody successfully obtained by the present inventor and clinical cancer tissue of a certain disease is prepared. In addition, cells or tissue separated from a subject are prepared. The step (2) or later are carried out similar to the above-mentioned embodiments. Note here that, a specific example of the panel to be used in this embodiment is a panel shown in FIG. 69.

Also in this embodiment, an antibody showing the specific reactivity in the step (2) or the equivalent antibody thereto is selected as an effective antibody. The selection method of this embodiment is preferred for selecting the suitable treatment method of squamous carcinoma, adenosquamous carcinoma, alveolar adenocarcinoma, adenocarcinoma, or large cell carcinoma.

As a further aspect of the present invention provides an isolated antibody (or an antibody set) obtained in the above-mentioned obtaining method of an antibody (or an obtaining method of an antibody set). As shown in the below-mentioned Examples, the present inventors have succeeded in actually obtaining by the method of the present invention, an antibody relevant to HER1, an antibody relevant to HER2, an antibody relevant to CD46, an antibody relevant to ITGA3, an antibody relevant to ICAM1, an antibody relevant to ALCAM, an antibody relevant to CD147, an antibody relevant to C1qR, an antibody relevant to CD44, an antibody relevant to CD73, an antibody relevant to EpCAM, an antibody relevant to HGFR, an antibody relevant to LAR, and an antibody relevant to BCAM. Furthermore, in the current testing method, it is possible to obtain an antibody capable of recognizing two clinical specimen s that are determined to have the same disease (pathologic condition). With this antibody, a certain disease can be newly classified based on the expression state of an antigen and further such a disease can be examined.

A further aspect of the present invention provides an antibody successfully obtained by the present inventors and the application thereof. As shown in the below-mentioned Examples, the present inventors succeeded in obtaining nine kinds of antibodies to HER1 (048-006 antibody, 057-091 antibody, 059-152 antibody, 048-040 antibody, 054-101 antibody, 055-147 antibody, 059-173 antibody, 067-149 antibody, and 067-176 antibody), 16 kinds of antibodies to HER2 (015-126 antibody, 015-044 antibody, 015-102 antibody, 015-136 antibody, 015-143 antibody, 015-209 antibody, 039-016 antibody, 053-216 antibody, 075-024 antibody, 075-110 antibody, 086-032 antibody, 086-035 antibody, 086-036 antibody, 086-061 antibody, 086-138 antibody, and 086-182 antibody), eight kinds of antibodies to CD46 (035-224 antibody, 045-011 antibody, 051-144 antibody, 052-053 antibody, 052-073 antibody, 053-049 antibody, 3172-120 antibody, and 066-069 antibody), 13 kinds of antibodies to ITGA3 (015-003 antibody, 064-002 antibody, 064-006 antibody, 064-012a antibody, 064-012b antibody, 064-014 antibody, 064-054 antibody, 064-085 antibody, 064-093 antibody, 064-116 antibody, 065-183 antibody, 067-142 antibody, and 068-007 antibody), five kinds of antibodies to ICAM1 (052-033 antibody, 053-042 antibody, 053-051 antibody, 053-059 antibody, and 053-085 antibody), 13 kinds of antibodies to ALCAM (035-234 antibody, 040-107 antibody, 041-118 antibody, 066-174 antibody, 083-040 antibody, 029-143 antibody, 045-134 antibody, 062-101 antibody, 062-109 antibody, 084-103 antibody, 052-274 antibody, 029-067 antibody, and 083-131 antibody), one kind of antibody to CD147 antibody (059-053 antibody), one kind of antibody to C1qR (070-016 antibody), one kind of antibody to CD44 (064-003 antibody), one kind of antibody to CD73 (067-213 antibody), one kind of antibody to EpCAM (067-153 antibody), three kinds of antibodies to HGFR (067-126 antibody, 067-133 antibody, and 067-287 antibody), five kinds of antibodies to LAR (064-044 antibody, 065-030 antibody, 065-358 antibody, 066-019 antibody, and 079-085 antibody), and one kind of antibody to BCAM (067-024 antibody). Since these antibodies are recognize an extracellular domain of antigen in a state in which it is expressed on the surface of the cell membrane, they are useful for staining cells and tissues, and the like. As a result of analysis of sequences of each antibody, the following sequence information is obtained. Note here that, following to the antibody name, the amino acid sequence of the heavy chain variable region; the amino acid sequence of the heavy chain CDR1; the amino acid sequence of the heavy chain CDR2; the amino acid sequence of the heavy chain CDR3; the amino acid sequence of the light chain variable region; the amino acid sequence of the light chain CDR1; the amino acid sequence of the light chain CDR2; and the amino acid sequence of the light chain CDR3 are described sequentially in this order.

1. Antibody to HER1

A plurality of antibodies clones are obtained. Among them, antibodies having the same amino acid sequence are included. As to the below-mentioned nine kinds of antibody clones, the sequences are analyzed.

048-006 antibody: SEQ ID NO: 1 (VH); SEQ ID NO: 2 (VH CDR1); SEQ ID NO: 3 (VH CDR2); SEQ ID NO: 4 (VH CDR3); SEQ ID NO: 5 (VL); SEQ ID NO: 6 (VL CDR1); SEQ ID NO: 7(VL CDR2); SEQ ID NO: 8(VL CDR3)

057-091 antibody: SEQ ID NO: 9 (VH); SEQ ID NO: 10 (VH CDR1); SEQ ID NO: 11 (VH CDR2); SEQ ID NO: 12 (VH CDR3); SEQ ID NO: 13 (VL); SEQ ID NO: 14 (VL CDR1); SEQ ID NO: 15 (VL CDR2); SEQ ID NO: 16 (VL CDR3)

059-152 antibody: SEQ ID NO: 17 (VH); SEQ ID NO: 18 (VH CDR1); SEQ ID NO: 19 (VH CDR2); SEQ ID NO: 20 (VH CDR3); SEQ ID NO: 21 (VL); SEQ ID NO: 22 (VL CDR1); SEQ ID NO: 23 (VL CDR2); SEQ ID NO: 24 (VL CDR3)

048-040 antibody: SEQ ID NO: 483 (VH); SEQ ID NO: 484 (VH CDR1); SEQ ID NO: 485 (VH CDR2); SEQ ID NO: 486 (VH CDR3); SEQ ID NO: 487 (VL); SEQ ID NO: 488 (VL CDR1); SEQ ID NO: 489 (VL CDR2); SEQ ID NO: 490 (VL CDR3)

054-101 antibody: SEQ ID NO: 491 (VH); SEQ ID NO: 492 (VH CDR1); SEQ ID NO: 493 (VH CDR2); SEQ ID NO: 494 (VH CDR3); SEQ ID NO: 495 (VL); SEQ ID NO: 496 (VL CDR1); SEQ ID NO: 497 (VL CDR2); SEQ ID NO: 498 (VL CDR3)

055-147 antibody: SEQ ID NO: 499 (VH); SEQ ID NO: 500 (VH CDR1); SEQ ID NO: 501 (VH CDR2); SEQ ID NO: 502 (VH CDR3); SEQ ID NO: 503 (VL); SEQ ID NO: 504 (VL CDR1); SEQ ID NO: 505 (VL CDR2); SEQ ID NO: 506 (VL CDR3)

059-173 antibody: SEQ ID NO: 507 (VH); SEQ ID NO: 508 (VH CDR1); SEQ ID NO: 509 (VH CDR2); SEQ ID NO: 510 (VH CDR3); SEQ ID NO: 511 (VL); SEQ ID NO: 512 (VL CDR1); SEQ ID NO: 513 (VL CDR2); SEQ ID NO: 514 (VL CDR3)

067-149 antibody: SEQ ID NO: 515 (VH); SEQ ID NO: 516 (VH CDR1); SEQ ID NO: 517 (VH CDR2); SEQ ID NO: 518 (VH CDR3); SEQ ID NO: 519 (VL); SEQ ID NO: 520 (VL CDR1); SEQ ID NO: 521 (VL CDR2); SEQ ID NO: 522 (VL CDR3)

067-176 antibody: SEQ ID NO: 523 (VH); SEQ ID NO: 524 (VH CDR1); SEQ ID NO: 525 (VH CDR2); SEQ ID NO: 526 (VH CDR3); SEQ ID NO: 527 (VL); SEQ ID NO: 528 (VL CDR1); SEQ ID NO: 529 (VL CDR2); SEQ ID NO: 530 (VL CDR3)

As mentioned in the below-mentioned Examples, the relationships between these antibodies and pancreatic cancer cell line PANC-1, kidney cancer cell line CCFRC1, kidney cancer cell line Caki-1, ovarian cancer cell line KF28, stomach cancer cell line SNU-5, lung squamous cell carcinoma line RERF-LC-AI, ovarian cancer cell line RMG-1, undifferentiated hepatic cell carcinoma cancer cell line HLF, ovarian cancer cell line SKOv3, pulmonary adenocarcinoma cell line PC14, kidney cancer cell line ACHN, lung squamous cell carcinoma line EBC1, vulva mucosal epithelial cell line A431, pulmonary adenocarcinoma cell line H1373, hepatic cell carcinoma cell line HepG2, and kidney cancer clinical specimen established cell line (as to the above mention, based on the results of the cell line staining), as well as the relationships between these antibodies and kidney cancer, hepatic cell carcinoma, gallbladder and liver cancer, lung squamous cell cancer, pulmonary adenocarcinoma, and pancreas cancer (as to the above mention, based on the results of the tissue staining) are experimentally confirmed.

2. Antibody to HER2

A plurality of antibodies clones are obtained. Among them, antibodies having the same amino acid sequence are included. As to the below-mentioned 16 kinds of antibody clones, the sequences are analyzed.

015-126 antibody SEQ ID NO: 25 (VH); SEQ ID NO: 26 (VH CDR1); SEQ ID NO: 27 (VH CDR2); SEQ ID NO: 28 (VH CDR3); SEQ ID NO: 29 (VL); SEQ ID NO: 30 (VL CDR1); SEQ ID NO: 31 (VL CDR2); SEQ ID NO: 32 (VL CDR3)

015-044 antibody SEQ ID NO: 531 (VH); SEQ ID NO: 532 (VH CDR1); SEQ ID NO: 533 (VH CDR2); SEQ ID NO: 534 (VH CDR3); SEQ ID NO: 535 (VL); SEQ ID NO: 536 (VL CDR1); SEQ ID NO: 537 (VL CDR2); SEQ ID NO: 538 (VL CDR3)

015-102 antibody SEQ ID NO: 539 (VH); SEQ ID NO: 540 (VH CDR1); SEQ ID NO: 541 (VH CDR2); SEQ ID NO: 542 (VH CDR3); SEQ ID NO: 543 (VL); SEQ ID NO: 544 (VL CDR1); SEQ ID NO: 545 (VL CDR2); SEQ ID NO: 546 (VL CDR3)

015-136 antibody SEQ ID NO: 547 (VH); SEQ ID NO: 548 (VH CDR1); SEQ ID NO: 549 (VH CDR2); SEQ ID NO: 550 (VH CDR3); SEQ ID NO: 551 (VL); SEQ ID NO: 552 (VL CDR1); SEQ ID NO: 553 (VL CDR2); SEQ ID NO: 554 (VL CDR3)

015-143 antibody SEQ ID NO: 555 (VH); SEQ ID NO: 556 (VH CDR1); SEQ ID NO: 557 (VH CDR2); SEQ ID NO: 558 (VH CDR3); SEQ ID NO: 559 (VL); SEQ ID NO: 560 (VL CDR1); SEQ ID NO: 561 (VL CDR2); SEQ ID NO: 562 (VL CDR3)

015-209 antibody SEQ ID NO: 563 (VH); SEQ ID NO: 564 (VH CDR1); SEQ ID NO: 565 (VH CDR2); SEQ ID NO: 566 (VH CDR3); SEQ ID NO: 567 (VL); SEQ ID NO: 568 (VL CDR1); SEQ ID NO: 569 (VL CDR2); SEQ ID NO: 570 (VL CDR3)

039-016 antibody SEQ ID NO: 571 (VH); SEQ ID NO: 572 (VH CDR1); SEQ ID NO: 573 (VH CDR2); SEQ ID NO: 574 (VH CDR3); SEQ ID NO: 575 (VL); SEQ ID NO: 576 (VL CDR1); SEQ ID NO: 577 (VL CDR2); SEQ ID NO: 578 (VL CDR3)

053-216 antibody SEQ ID NO: 579 (VH); SEQ ID NO: 580 (VH CDR1); SEQ ID NO: 581 (VH CDR2); SEQ ID NO: 582 (VH CDR3); SEQ ID NO: 583 (VL); SEQ ID NO: 584 (VL CDR1); SEQ ID NO: 585 (VL CDR2); SEQ ID NO: 586 (VL CDR3)

075-024 antibody SEQ ID NO: 587 (VH); SEQ ID NO: 588 (VH CDR1); SEQ ID NO: 589 (VH CDR2); SEQ ID NO: 590 (VH CDR3); SEQ ID NO: 591 (VL); SEQ ID NO: 592 (VL CDR1); SEQ ID NO: 593 (VL CDR2); SEQ ID NO: 594 (VL CDR3)

075-110 antibody SEQ ID NO: 595 (VH); SEQ ID NO: 596 (VH CDR1); SEQ ID NO: 597 (VH CDR2); SEQ ID NO: 598 (VH CDR3); SEQ ID NO: 599 (VL); SEQ ID NO: 600 (VL CDR1); SEQ ID NO: 601 (VL CDR2); SEQ ID NO: 602 (VL CDR3)

086-032 antibody SEQ ID NO: 603 (VH); SEQ ID NO: 604 (VH CDR1); SEQ ID NO: 605 (VH CDR2); SEQ ID NO: 606 (VH CDR3); SEQ ID NO: 607 (VL); SEQ ID NO: 608 (VL CDR1); SEQ ID NO: 609 (VL CDR2); SEQ ID NO: 610 (VL CDR3)

086-035 antibody SEQ ID NO: 611 (VH); SEQ ID NO: 612 (VH CDR1); SEQ ID NO: 613 (VH CDR2); SEQ ID NO: 614 (VH CDR3); SEQ ID NO: 615 (VL); SEQ ID NO: 616 (VL CDR1); SEQ ID NO: 617 (VL CDR2); SEQ ID NO: 618 (VL CDR3)

086-036 antibody SEQ ID NO: 619 (VH); SEQ ID NO: 620 (VH CDR1); SEQ ID NO: 621 (VH CDR2); SEQ ID NO: 622 (VH CDR3); SEQ ID NO: 623 (VL); SEQ ID NO: 624 (VL CDR1); SEQ ID NO: 625 (VL CDR2); SEQ ID NO: 626 (VL CDR3)

086-061 antibody SEQ ID NO: 627 (VH); SEQ ID NO: 628 (VH CDR1); SEQ ID NO: 629 (VH CDR2); SEQ ID NO: 630 (VH CDR3); SEQ ID NO: 631 (VL); SEQ ID NO: 632 (VL CDR1); SEQ ID NO: 633 (VL CDR2); SEQ ID NO: 634 (VL CDR3)

086-138 antibody SEQ ID NO: 635 (VH); SEQ ID NO: 636 (VH CDR1); SEQ ID NO: 637 (VH CDR2); SEQ ID NO:

638 (VH CDR3); SEQ ID NO: 639 (VL); SEQ ID NO: 640 (VL CDR1); SEQ ID NO: 641 (VL CDR2); SEQ ID NO: 642 (VL CDR3)

086-182 antibody SEQ ID NO: 643 (VH); SEQ ID NO: 644 (VH CDR1); SEQ ID NO: 645 (VH CDR2); SEQ ID NO: 646 (VH CDR3); SEQ ID NO: 647 (VL); SEQ ID NO: 648 (VL CDR1); SEQ ID NO: 649 (VL CDR2); SEQ ID NO: 650 (VL CDR3)

As mentioned in the below-mentioned Examples, the relationships between these antibodies and pulmonary adenocarcinoma cell line Calu-3, ovarian cancer cell line SKOv3, and breast cancer cell line BT474 (based on the results of the cell line staining) are experimentally confirmed.

3. Antibody to CD46

A plurality of antibodies clones are obtained. Among them, antibodies having the same amino acid sequence are included. Finally 87 kinds of antibody clones are identified. As to the below-mentioned eight kinds of antibody clones, the sequences are analyzed.

035-224 antibody SEQ ID NO: 33 (VH); SEQ ID NO: 34 (VH CDR1); SEQ ID NO: (VH CDR2); SEQ ID NO: 36 (VH CDR3); SEQ ID NO: 37 (VL); SEQ ID NO: 38 (VL CDR1); SEQ ID NO: 39 (VL CDR2); SEQ ID NO: 40 (VL CDR3)

045-011 antibody SEQ ID NO: 41 (VH); SEQ ID NO: 42 (VH CDR1); SEQ ID NO: 43 (VH CDR2); SEQ ID NO: 44 (VH CDR3); SEQ ID NO: 45 (VL); SEQ ID NO: 46 (VL CDR1); SEQ ID NO: 47 (VL CDR2); SEQ ID NO: 48 (VL CDR3)

051-144 antibody SEQ ID NO: 49 (VH); SEQ ID NO: 50 (VH CDR1); SEQ ID NO: 51 (VH CDR2); SEQ ID NO: 52 (VH CDR3); SEQ ID NO: 53 (VL); SEQ ID NO: 54 (VL CDR1); SEQ ID NO: 55 (VL CDR2); SEQ ID NO: 56 (VL CDR3)

052-053 antibody SEQ ID NO: 57 (VH); SEQ ID NO: 58 (VH CDR1); SEQ ID NO: 59 (VH CDR2); SEQ ID NO: 60 (VH CDR3); SEQ ID NO: 61 (VL); SEQ ID NO: 62 (VL CDR1); SEQ ID NO: 63 (VL CDR2); SEQ ID NO: 64 (VL CDR3)

052-073 antibody SEQ ID NO: 65 (VH); SEQ ID NO: 66 (VH CDR1); SEQ ID NO: 67 (VH CDR2); SEQ ID NO: 68 (VH CDR3); SEQ ID NO: 69 (VL); SEQ ID NO: 70 (VL CDR1); SEQ ID NO: 71 (VL CDR2); SEQ ID NO: 72 (VL CDR3)

053-049 antibody SEQ ID NO: 73 (VH); SEQ ID NO: 74 (VH CDR1); SEQ ID NO: 75 (VH CDR2); SEQ ID NO: 76 (VH CDR3); SEQ ID NO: 77 (VL); SEQ ID NO: 78 (VL CDR1); SEQ ID NO: 79 (VL CDR2); SEQ ID NO: 80 (VL CDR3)

3172-120 antibody SEQ ID NO: 81 (VH); SEQ ID NO: 82 (VH CDR1); SEQ ID NO: 83 (VH CDR2); SEQ ID NO: 84 (VH CDR3); SEQ ID NO: 85 (VL); SEQ ID NO: 86 (VL CDR1); SEQ ID NO: 87 (VL CDR2); SEQ ID NO: 88 (VL CDR3)

066-069 antibody SEQ ID NO: 755 (VH); SEQ ID NO: 756 (VH CDR1); SEQ ID NO: 757 (VH CDR2); SEQ ID NO: 758 (VH CDR3); SEQ ID NO: 759 (VL); SEQ ID NO: 760 (VL CDR1); SEQ ID NO: 761 (VL CDR2); SEQ ID NO: 762 (VL CDR3)

As mentioned in the below-mentioned Examples, the relationships between these antibodies and large bowel cancer cell line CaCo2, stomach cancer cell line MKN45, undifferentiated hepatic cell carcinoma cell line HLF, liver cancer cell line HepG2, intrahepatic bile duct cell cancer cell line RBE, pancreas cancer cell line PANC1, kidney cancer cell line CCFRC1, kidney cancer cell line Caki-1, lung cancer cell line NCI-H441, lung squamous cell cancer EBC1, stomach cancer cell line NCI-N87, stomach cancer cell line SNU-5, lung squamous cell carcinoma line RERF-LC-AI, hepatic cell carcinoma clinical specimen s, breast cancer cell line BT474, kidney cancer cell line 293T, pulmonary adenocarcinoma cell line PC14, kidney cancer cell line ACHN, and pulmonary adenocarcinoma cell line H1373 (as to the above mention, based on the results of the cell line staining), as well as the relationships between these kidney cancer, hepatic cell carcinoma, gallbladder and liver cancer, pulmonary adenocarcinoma, and pancreas cancer (as to the above mention, based on the results of the tissue staining) are experimentally confirmed.

4. Antibody to ITGA3

A plurality of antibodies clones are obtained. Among them, antibodies having the same amino acid sequence are included. As to the below-mentioned 13 kinds of antibody clones, the sequences are analyzed.

015-003 antibody SEQ ID NO: 89 (VH); SEQ ID NO: 90 (VH CDR1); SEQ ID NO: 91 (VH CDR2); SEQ ID NO: 92 (VH CDR3); SEQ ID NO: 93 (VL); SEQ ID NO: 94 (VL CDR1); SEQ ID NO: 95 (VL CDR2); SEQ ID NO: 96 (VL CDR3)

064-002 antibody SEQ ID NO: 675 (VH); SEQ ID NO: 676 (VH CDR1); SEQ ID NO: 677 (VH CDR2); SEQ ID NO: 678 (VH CDR3); SEQ ID NO: 679 (VL); SEQ ID NO: 680 (VL CDR1); SEQ ID NO: 681 (VL CDR2); SEQ ID NO: 682 (VL CDR3)

064-006 antibody SEQ ID NO: 683 (VH); SEQ ID NO: 684 (VH CDR1); SEQ ID NO: 685 (VH CDR2); SEQ ID NO: 686 (VH CDR3); SEQ ID NO: 687 (VL); SEQ ID NO: 688 (VL CDR1); SEQ ID NO: 689 (VL CDR2); SEQ ID NO: 690 (VL CDR3)

064-012a antibody SEQ ID NO: 691 (VH); SEQ ID NO: 692 (VH CDR1); SEQ ID NO: 693 (VH CDR2); SEQ ID NO: 694 (VH CDR3); SEQ ID NO: 695 (VL); SEQ ID NO: 696 (VL CDR1); SEQ ID NO: 697 (VL CDR2); SEQ ID NO: 698 (VL CDR3)

064-012b antibody SEQ ID NO: 699 (VH); SEQ ID NO: 700 (VH CDR1); SEQ ID NO: 701 (VH CDR2); SEQ ID NO: 702 (VH CDR3); SEQ ID NO: 703 (VL); SEQ ID NO: 704 (VL CDR1); SEQ ID NO: 705 (VL CDR2); SEQ ID NO: 706 (VL CDR3)

064-014 antibody SEQ ID NO: 707 (VH); SEQ ID NO: 708 (VH CDR1); SEQ ID NO: 709 (VH CDR2); SEQ ID NO: 710 (VH CDR3); SEQ ID NO: 711 (VL); SEQ ID NO: 712 (VL CDR1); SEQ ID NO: 713 (VL CDR2); SEQ ID NO: 714 (VL CDR3)

064-054 antibody SEQ ID NO: 715 (VH); SEQ ID NO: 716 (VH CDR1); SEQ ID NO: 717 (VH CDR2); SEQ ID NO: 718 (VH CDR3); SEQ ID NO: 719 (VL); SEQ ID NO: 720 (VL CDR1); SEQ ID NO: 721 (VL CDR2); SEQ ID NO: 722 (VL CDR3)

064-085 antibody SEQ ID NO: 723 (VH); SEQ ID NO: 724 (VH CDR1); SEQ ID NO: 725 (VH CDR2); SEQ ID NO: 726 (VH CDR3); SEQ ID NO: 727 (VL); SEQ ID NO: 728 (VL CDR1); SEQ ID NO: 729 (VL CDR2); SEQ ID NO: 730 (VL CDR3)

064-093 antibody SEQ ID NO: 731 (VH); SEQ ID NO: 732 (VH CDR1); SEQ ID NO: 733 (VH CDR2); SEQ ID NO: 734 (VH CDR3); SEQ ID NO: 735 (VL); SEQ ID NO: 736 (VL CDR1); SEQ ID NO: 737 (VL CDR2); SEQ ID NO: 738 (VL CDR3)

064-116 antibody SEQ ID NO: 739 (VH); SEQ ID NO: 740 (VH CDR1); SEQ ID NO: 741 (VH CDR2); SEQ ID NO: 742 (VH CDR3); SEQ ID NO: 743 (VL); SEQ ID NO: 744 (VL CDR1); SEQ ID NO: 745 (VL CDR2); SEQ ID NO: 746 (VL CDR3)

065-183 antibody SEQ ID NO: 747 (VH); SEQ ID NO: 748 (VH CDR1); SEQ ID NO: 749 (VH CDR2); SEQ ID NO: 750 (VH CDR3); SEQ ID NO: 751 (VL); SEQ ID NO: 752 (VL CDR1); SEQ ID NO: 753 (VL CDR2); SEQ ID NO: 754 (VL CDR3)

067-142 antibody SEQ ID NO: 763 (VH); SEQ ID NO: 764 (VH CDR1); SEQ ID NO: 765 (VH CDR2); SEQ ID NO: 766 (VH CDR3); SEQ ID NO: 767 (VL); SEQ ID NO: 768 (VL CDR1); SEQ ID NO: 769 (VL CDR2); SEQ ID NO: 770 (VL CDR3)

068-007 antibody SEQ ID NO: 771 (VH); SEQ ID NO: 772 (VH CDR1); SEQ ID NO: 773 (VH CDR2); SEQ ID NO: 774 (VH CDR3); SEQ ID NO: 775 (VL); SEQ ID NO: 776 (VL CDR1); SEQ ID NO: 777 (VL CDR2); SEQ ID NO: 778 (VL CDR3)

As mentioned in the below-mentioned Examples, the relationships between these antibodies and undifferentiated hepatic cell carcinoma cell line HLF, ovarian cancer cell line SKOv3, kidney cancer cell line ACHN, kidney cancer cell line Caki-1, pulmonary adenocarcinoma cell line H1373, lung squamous cell cancer EBC1, vulva mucosal epithelial cell line A431, breast cancer cell line BT474, pulmonary adenocarcinoma cell line PC14, kidney cancer cell line CCFRC1, hepatic cell carcinoma cell line OCTH, intrahepatic bile duct cell cancer RBE, pancreas cancer cell line PANC-1, pancreas cancer cell line MIA-Paca2, pulmonary adenocarcinoma cell line A549, pulmonary adenocarcinoma cell line NCI-N441, lung squamous cell carcinoma line Calu-3, lung squamous cell carcinoma line RERF-LC-AI, stomach cancer cell line SNU5, stomach cancer cell line MKN45, stomach cancer cell line NCI-N87, large bowel cancer cell line CW2, ovarian cancer cell line SKOv3, ovarian cancer cell line KF-28, ovarian cancer cell line RMG-1, and ovarian cancer cell line RMG-2 (as to the above mention, based on the results of the cell line staining), as well as the relationships between these antibodies and gallbladder and liver cancer and pancreas cancer (as to the above mention, based on the results of the tissue staining) are experimentally confirmed.

5. Antibody to ICAM1

A plurality of antibodies clones are obtained. Among them, antibodies having the same amino acid sequence are included. Finally, 22 kinds of antibody clones are identified. As to the below-mentioned five kinds of antibody clones, the sequences are analyzed.

052-033 antibody SEQ ID NO: 97 (VH); SEQ ID NO: 98 (VH CDR1); SEQ ID NO: 99 (VH CDR2); SEQ ID NO: 100 (VH CDR3); SEQ ID NO: 101 (VL); SEQ ID NO: 102 (VL CDR1); SEQ ID NO: 103 (VL CDR2); SEQ ID NO: 104 (VL CDR3)

053-042 antibody SEQ ID NO: 105 (VH); SEQ ID NO: 106 (VH CDR1); SEQ ID NO: 107 (VH CDR2); SEQ ID NO: 108 (VH CDR3); SEQ ID NO: 109 (VL); SEQ ID NO: 110 (VL CDR1); SEQ ID NO: 111 (VL CDR2); SEQ ID NO: 112 (VL CDR3)

053-051 antibody SEQ ID NO: 113 (VH); SEQ ID NO: 114 (VH CDR1); SEQ ID NO: 115 (VH CDR2); SEQ ID NO: 116 (VH CDR3); SEQ ID NO: 117 (VL); SEQ ID NO: 118 (VL CDR1); SEQ ID NO: 119 (VL CDR2); SEQ ID NO: 120 (VL CDR3)

053-059 antibody SEQ ID NO: 121 (VH); SEQ ID NO: 122 (VH CDR1); SEQ ID NO: 123 (VH CDR2); SEQ ID NO: 124 (VH CDR3); SEQ ID NO: 125 (VL); SEQ ID NO: 126 (VL CDR1); SEQ ID NO: 127 (VL CDR2); SEQ ID NO: 128 (VL CDR3)

053-085 antibody SEQ ID NO: 129 (VH); SEQ ID NO: 130 (VH CDR1); SEQ ID NO: 131 (VH CDR2); SEQ ID NO: 132 (VH CDR3); SEQ ID NO: 133 (VL); SEQ ID NO: 134 (VL CDR1); SEQ ID NO: 135 (VL CDR2); SEQ ID NO: 136 (VL CDR3)

As mentioned in the below-mentioned Examples, the relationships between these antibodies and liver cancer cell line HepG2, pulmonary adenocarcinoma cell line PC14, and cell line established from kidney clinical specimen (as to the above mention, based on the results of the cell line staining), as well as the relationships between these antibodies and hepatic cell carcinoma (as to the above mention, based on the results of the tissue staining) are experimentally confirmed.

6. Antibody to ALCAM

A plurality of antibodies clones are obtained. Among them, antibodies having the same amino acid sequence are included. As to the below-mentioned 13 kinds of antibody clones, the sequences are analyzed.

035-234 antibody SEQ ID NO: 137 (VH); SEQ ID NO: 138 (VH CDR1); SEQ ID NO: 139 (VH CDR2); SEQ ID NO: 140 (VH CDR3); SEQ ID NO: 141 (VL); SEQ ID NO: 142 (VL CDR1); SEQ ID NO: 143 (VL CDR2); SEQ ID NO: 144 (VL CDR3)

040-107 antibody SEQ ID NO: 145 (VH); SEQ ID NO: 146 (VH CDR1); SEQ ID NO: 147 (VH CDR2); SEQ ID NO: 148 (VH CDR3); SEQ ID NO: 149 (VL); SEQ ID NO: 150 (VL CDR1); SEQ ID NO: 151 (VL CDR2); SEQ ID NO: 152 (VL CDR3)

041-118 antibody SEQ ID NO: 153 (VH); SEQ ID NO: 154 (VH CDR1); SEQ ID NO: 155 (VH CDR2); SEQ ID NO: 156 (VH CDR3); SEQ ID NO: 157 (VL); SEQ ID NO: 158 (VL CDR1); SEQ ID NO: 159 (VL CDR2); SEQ ID NO: 160 (VL CDR3)

066-174 antibody SEQ ID NO: 161 (VH); SEQ ID NO: 162 (VH CDR1); SEQ ID NO: 163 (VH CDR2); SEQ ID NO: 164 (VH CDR3); SEQ ID NO: 165 (VL); SEQ ID NO: 166 (VL CDR1); SEQ ID NO: 167 (VL CDR2); SEQ ID NO: 168 (VL CDR3)

083-040 antibody SEQ ID NO: 169 (VH); SEQ ID NO: 170 (VH CDR1); SEQ ID NO: 171 (VH CDR2); SEQ ID NO: 172 (VH CDR3); SEQ ID NO: 173 (VL); SEQ ID NO: 174 (VL CDR1); SEQ ID NO: 175 (VL CDR2); SEQ ID NO: 176 (VL CDR3)

029-143 antibody SEQ ID NO: 779 (VH); SEQ ID NO: 780 (VH CDR1); SEQ ID NO: 781 (VH CDR2); SEQ ID NO 782 (VH CDR3); SEQ ID NO: 783 (VL); SEQ ID NO: 784 (VL CDR1); SEQ ID NO: 785 (VL CDR2); SEQ ID NO: 786 (VL CDR3)

045-134 antibody SEQ ID NO: 787 (VH); SEQ ID NO: 788 (VH CDR1); SEQ ID NO: 789 (VH CDR2); SEQ ID NO: 790 (VH CDR3); SEQ ID NO: 791 (VL); SEQ ID NO: 792 (VL CDR1); SEQ ID NO: 793 (VL CDR2); SEQ ID NO: 794 (VL CDR3)

062-101 antibody SEQ ID NO: 795 (VH); SEQ ID NO: 796 (VH CDR1); SEQ ID NO: 797 (VH CDR2); SEQ ID NO: 798 (VH CDR3); SEQ ID NO: 799 (VL); SEQ ID NO: 800 (VL CDR1); SEQ ID NO: 801 (VL CDR2); SEQ ID NO: 802 (VL CDR3)

062-109 antibody SEQ ID NO: 803 (VH); SEQ ID NO: 804 (VH CDR1); SEQ ID NO: 805 (VH CDR2); SEQ ID NO: 806 (VH CDR3); SEQ ID NO: 807 (VL); SEQ ID NO: 808 (VL CDR1); SEQ ID NO: 809 (VL CDR2); SEQ ID NO: 810 (VL CDR3)

084-103 antibody SEQ ID NO: 811 (VH); SEQ ID NO: 812 (VH CDR1); SEQ ID NO: 813 (VH CDR2); SEQ ID NO: 814 (VH CDR3); SEQ ID NO: 815 (VL); SEQ ID NO: 816 (VL CDR1); SEQ ID NO: 817 (VL CDR2); SEQ ID NO: 818 (VL CDR3)

052-274 antibody SEQ ID NO: 819 (VH); SEQ ID NO: 820 (VH CDR1); SEQ ID NO: 821 (VH CDR2); SEQ ID NO: 822 (VH CDR3); SEQ ID NO: 823 (VL); SEQ ID NO: 824 (VL CDR1); SEQ ID NO: 825 (VL CDR2); SEQ ID NO: 826 (VL CDR3)

029-067 antibody SEQ ID NO: 827 (VH); SEQ ID NO: 828 (VH CDR1); SEQ ID NO: 829 (VH CDR2); SEQ ID NO: 830 (VH CDR3); SEQ ID NO: 831 (VL); SEQ ID NO: 832 (VL CDR1); SEQ ID NO: 833 (VL CDR2); SEQ ID NO: 834 (VL CDR3)

083-131 antibody SEQ ID NO: 835 (VH); SEQ ID NO: 836 (VH CDR1); SEQ ID NO: 837 (VH CDR2); SEQ ID NO: 838 (VH CDR3); SEQ ID NO: 839 (VL); SEQ ID NO: 840 (VL CDR1); SEQ ID NO: 841 (VL CDR2); SEQ ID NO: 842 (VL CDR3)

As mentioned in the below-mentioned Examples, the relationships between these antibodies and liver cancer cell line (HepG2, OCTH, Hep3B, and HLF), kidney cancer cell line (Caki-1, CCFRC1, ACHN, 293T, and cell line established from the clinical specimen), lung cancer cell line (PC14, NCI-H441, EBC-1, RERF-LC-AI, A549, and H1373), ovarian cancer cell line (SKOv3, KF-28, RMG1, and RMG2), stomach cancer cell line (NCI-N87), large bowel cancer cell line (CW2), breast cancer cell line (BT474), acute myelocytic leukemia AML clinical specimen, and hamster ovarian cancer cell line CHO (as to the above mention, based on the results of the cell line staining), as well as the relationships between these antibodies and kidney cancer, hepatic cell carcinoma, gallbladder and liver cancer, lung squamous cell cancer, alveolar cell carcinoma, and adenocarcinoma (as to the above mention, based on the results of the tissue staining) are experimentally confirmed.

7. Antibody to CD147

A plurality of antibodies clones are obtained. Among them, antibodies having the same amino acid sequence are included. As to the below-mentioned one kind of antibody clone, the sequence is analyzed.

059-053 antibody SEQ ID NO: 177 (VH); SEQ ID NO: 178 (VH CDR1); SEQ ID NO: 179 (VH CDR2); SEQ ID NO: 180 (VH CDR3); SEQ ID NO: 181 (VL); SEQ ID NO: 182 (VL CDR1); SEQ ID NO: 183 (VL CDR2); SEQ ID NO: 184 (VL CDR3)

As mentioned in the below-mentioned Examples, the relationships between this antibody the and liver cancer cell line HepG2, kidney cancer cell line CCFRC1, kidney cancer cell line ACHN, kidney cancer cell line Caki-1, pulmonary adenocarcinoma PC14, and cell line established from kidney cancer clinical specimen (as to the above mention, based on the results of the cell line staining), as well as the relationships between these antibodies and kidney cancer (as to the above mention, based on the results of the tissue staining) are experimentally confirmed.

8. Antibody to C1qR

A plurality of antibodies clones are obtained. Among them, antibodies having the same amino acid sequence are included. As to the below-mentioned one kind of antibody clone, the sequence is analyzed.

070-016 antibody SEQ ID NO: 451 (VH); SEQ ID NO: (VH CDR1)452; SEQ ID NO: 453 (VH CDR2); SEQ ID NO: 454 (VH CDR3); SEQ ID NO: 455 (VL); SEQ ID NO: (VL CDR1)456; SEQ ID NO: 457 (VL CDR2); SEQ ID NO: 458 (VL CDR3)

The relationship between this antibody and leukemia is experimentally confirmed. That is to say, in cell line staining using this antibody, leukemia AML cell line Nohno 1 and leukemia AML clinical specimen shows a strong positive property (MFI=20 or more). Furthermore, in the process of growing the leukemia cell line, this antibody is added to the growing temperature, rapid aggregation of cancer cells can be confirmed. Moreover, the antibody amount necessary to cause these phenomena is relatively low concentration.

9. Antibody to CD44

A plurality of antibodies clones are obtained. Among them, antibodies having the same amino acid sequence are included. As to the below-mentioned one kind of antibody clone, the sequence is analyzed.

064-003 antibody SEQ ID NO: 459 (VH); SEQ ID NO: 460 (VH CDR1); SEQ ID NO: 461 (VH CDR2); SEQ ID NO: 462 (VH CDR3); SEQ ID NO: 463 (VL); SEQ ID NO: 464 (VL CDR1); SEQ ID NO: 465 (VL CDR2); SEQ ID NO: 466 (VL CDR3)

The relationships between this antibody and liver cancer, lung cancer, ovarian cancer, and stomach cancer are experimentally confirmed. That is to say, in the cell staining using this antibody, hepatic cell carcinoma HLF, pulmonary adenocarcinoma cell line PC14, pulmonary adenocarcinoma cell line NCI-H1373, and ovary adenocarcinoma cell line SKOv3 show the strong positive property (MFI=20 or more), and epidermoid cancer cell line A431 and lung squamous cell cancer EBC1 show the weak positive property (MFI=3 or more). Furthermore, in immunostaining using this antibody, a case in which a pulmonary adenocarcinoma clinical specimen shows cancer specific stained image is observed, and cancer portions of alveolar cell carcinoma and lung squamous cell cancer show the weak positive property.

10. Antibody to CD73

A plurality of antibodies clones are obtained. Among them, antibodies having the same amino acid sequence are included. As to the below-mentioned one kind of antibody clone, the sequence is analyzed.

067-213 antibody SEQ ID NO: 467 (VH); SEQ ID NO: 468 (VH CDR1); SEQ ID NO: 469 (VH CDR2); SEQ ID NO: 470 (VH CDR3); SEQ ID NO: 471 (VL); SEQ ID NO: 472 (VL CDR1); SEQ ID NO: 473 (VL CDR2); SEQ ID NO: 474 (VL CDR3)

The relationships between this antibody and liver cancer, lung cancer, and ovarian cancer are experimentally confirmed. That is to say, in the cell staining using this antibody, pulmonary adenocarcinoma cell line NCI-H1373, and lung squamous cell cancer EBC1 show the strong positive property (MFI=20 or more), and liver cancer cell line HLF, ovary adenocarcinoma cell line SKOv3, and pulmonary adenocarcinoma cell line PC14 show the weak positive property (MFI=3 or more). Furthermore, in immunostaining using this antibody, a cancer-specific stained image is obtained in a pulmonary adenocarcinoma clinical specimen and a stained image showing the weak positive property to a cancer portion is obtained in lung squamous cell cancer.

11. Antibody to EpCAM

A plurality of antibodies clones are obtained. Among them, antibodies having the same amino acid sequence are included. As to the below-mentioned one kind of antibody clone, the sequence is analyzed.

067-153 antibody SEQ ID NO: 475 (VH); SEQ ID NO: 476 (VH CDR1); SEQ ID NO: 477 (VH CDR2); SEQ ID NO: 478 (VH CDR3); SEQ ID NO: 479 (VL); SEQ ID NO: 480 (VL CDR1); SEQ ID NO: 481 (VL CDR2); SEQ ID NO: 482 (VL CDR3)

The relationships between this antibody and liver cancer, lung cancer, ovarian cancer, stomach cancer, and large bowel cancer are experimentally confirmed. That is to say, in the cell staining using this antibody, pulmonary adenocarcinoma cell line NCI-H1373 and lung squamous cell carcinoma line LK-2 show the strong positive property (MFI=20 or more); lung squamous cell cancer EBC1 and pulmonary adenocarcinoma cell line PC14 show the positive property (MFI=10 or more); and ovary adenocarcinoma cell line SKOv3 shows the weak positive property (MFI=3 or more). Furthermore, in immunostaining using this antibody, an extremely excellent cancer-specific stained image is obtained in each clinical specimen of large bowel cancer, pulmonary adenocarcinoma, lung squamous cell cancer, stomach cancer. A stained image having a weak cancer specific positive property is obtained in a part of hepatic cell carcinoma clinical specimens.

12. Antibody to HGFR

A plurality of antibodies clones are obtained. Among them, antibodies having the same amino acid sequence are included. Finally 87 kinds of antibody clones are identified. As to the below-mentioned three kinds of antibody clones, the sequences are analyzed.

067-126 antibody SEQ ID NO: 651 (VH); SEQ ID NO: 652 (VH CDR1); SEQ ID NO: 653 (VH CDR2); SEQ ID NO: 654 (VH CDR3); SEQ ID NO: 655 (VL); SEQ ID NO: 656 (VL CDR1); SEQ ID NO: 657 (VL CDR2); SEQ ID NO: 658 (VL CDR3)

067-133 antibody SEQ ID NO: 659 (VH); SEQ ID NO: 660 (VH CDR1); SEQ ID NO: 661 (VH CDR2); SEQ ID NO: 662 (VH CDR3); SEQ ID NO: 663 (VL); SEQ ID NO: 664 (VL CDR1); SEQ ID NO: 665 (VL CDR2); SEQ ID NO: 666 (VL CDR3)

067-287 antibody SEQ ID NO: 667 (VH); SEQ ID NO: 668 (VH CDR1); SEQ ID NO: 669 (VH CDR2); SEQ ID NO: 670 (VH CDR3); SEQ ID NO: 671 (VL); SEQ ID NO: 672 (VL CDR1); SEQ ID NO: 673 (VL CDR2); SEQ ID NO: 674 (VL CDR3)

The relationships between this antibody and lung cancer, liver cancer, ovarian cancer, large bowel cancer, and stomach cancer are experimentally confirmed. That is to say, in cell line staining using this antibody, lung squamous cell cancer EBC1 shows a strong positive property (MFI=20 or more); alveolar adenocarcinoma NCI-H1373 shows the positive property (MFI=10 or more); and epidermoid cancer cell line A431, ovary adenocarcinoma cell line SKOv3, pulmonary adenocarcinoma cell line PC14, and hepatic cell carcinoma HLF show the weak positive property (MFI=3 or more). Furthermore, in immunostaining using this antibody, a weak positive property to cancer portion in a part of lung squamous cell cancer clinical specimen is obtained.

13. Antibody to LAR

A plurality of antibodies clones are obtained. Among them, antibodies having the same amino acid sequence are included. As to the below-mentioned five kinds of antibody clones, the sequence is analyzed.

064-044 antibody SEQ ID NO: 944 (VH); and SEQ ID NO: 945 (VL) 065-030 antibody SEQ ID NO: 946 (VH); and SEQ ID NO: 947 (VL)

065-358 antibody SEQ ID NO: 948 (VH); and SEQ ID NO: 949 (VL)

066-019 antibody SEQ ID NO: 950 (VH); and SEQ ID NO: 951 (VL)

079-085 antibody SEQ ID NO: 952 (VH); and SEQ ID NO: 953 (VL)

In the immunostaining using these antibodies, a positive property is observed in a cancer portion in a part of the lung cancer clinical specimens.

14. Antibody to BCAM

A plurality of antibodies clones are obtained. Among them, antibodies having the same amino acid sequence are included. As to the below-mentioned one kind of antibody clone, the sequence is analyzed.

067-024 antibody SEQ ID NO: 954 (VH); and SEQ ID NO: 955 (VL)

In the immunostaining using these antibodies, a positive property is observed in a cancer portion in a part of the clinical specimens of lung cancer, liver cancer, and kidney cancer.

The first embodiment of this aspect provides an isolated antibody having a specific binding property to HER1. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) selected from the group consisting of the following (1) to (3). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) selected from the group consisting of the following (4) to (6). Furthermore, preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) selected from the group consisting of the following (7) to (9) and (13) to (18). The most preferably, it includes the heavy chain variable region and the light chain variable region specified by the combination of SEQ ID NOs (SEQ ID NO showing the heavy chain variable region and SEQ ID NO showing the light chain variable region) selected from the group consisting of the following (10) to (12) and (19) to (24).

(Combination of CDR3)
(1) SEQ ID NO: 4, SEQ ID NO: 8
(2) SEQ ID NO: 12, SEQ ID NO: 16
(3) SEQ ID NO: 20, SEQ ID NO: 24
(Combination of CDR2 and CDR3)
(4) SEQ ID NO: 3, SEQ ID NO: 4, SEQ ID NO: 7, SEQ ID NO: 8
(5) SEQ ID NO: 11, SEQ ID NO: 12, SEQ ID NO: 15, SEQ ID NO: 16
(6) SEQ ID NO: 19, SEQ ID NO: 20, SEQ ID NO: 23, SEQ ID NO: 24
(Combination of CDR1 to CDR3)
(7) SEQ ID NO: 2, SEQ ID NO: 3, SEQ ID NO: 4, SEQ ID NO: 6 SEQ ID NO: 7, SEQ ID NO: 8
(8) SEQ ID NO: 10, SEQ ID NO: 11, SEQ ID NO: 12, SEQ ID NO: 14, SEQ ID NO: 15, SEQ ID NO: 16
(9) SEQ ID NO: 18, SEQ ID NO: 19, SEQ ID NO: 20, SEQ ID NO: 22, SEQ ID NO: 23, SEQ ID NO: 24
(13) SEQ ID NO: 484 (VH CDR1), SEQ ID NO: 485 (VH CDR2), SEQ ID NO: 486 (VH CDR3), SEQ ID NO: 488 (VL CDR1), SEQ ID NO: 489 (VL CDR2), SEQ ID NO: 490 (VL CDR3)

(14) SEQ ID NO: 492 (VH CDR1), SEQ ID NO: 493 (VH CDR2), SEQ ID NO: 494 (VH CDR3), SEQ ID NO: 496 (VL CDR1), SEQ ID NO: 497 (VL CDR2), SEQ ID NO: 498 (VL CDR3)
(15), SEQ ID NO: 500 (VH CDR1), SEQ ID NO: 501 (VH CDR2), SEQ ID NO: 502 (VH CDR3), SEQ ID NO: 504 (VL CDR1), SEQ ID NO: 505 (VL CDR2), SEQ ID NO: 506 (VL CDR3)
(16) SEQ ID NO: 508 (VH CDR1), SEQ ID NO: 509 (VH CDR2), SEQ ID NO: 510 (VH CDR3), SEQ ID NO: 512 (VL CDR1), SEQ ID NO: 513 (VL CDR2), SEQ ID NO: 514 (VL CDR3)
(17) SEQ ID NO: 516 (VH CDR1), SEQ ID NO: 517 (VH CDR2), SEQ ID NO: 518 (VH CDR3), SEQ ID NO: 520 (VL CDR1), SEQ ID NO: 521 (VL CDR2), SEQ ID NO: 522 (VL CDR3)
(18) SEQ ID NO: 524 (VH CDR1), SEQ ID NO: 525 (VH CDR2), SEQ ID NO: 526 (VH CDR3), SEQ ID NO: 528 (VL CDR1), SEQ ID NO: 529 (VL CDR2), SEQ ID NO: 530 (VL CDR3)
(Combination of Heavy Chain Variable Region and Light Chain Variable Region)
(10) SEQ ID NO: 1, SEQ ID NO: 5
(11) SEQ ID NO: 9, SEQ ID NO: 13
(12) SEQ ID NO: 17, SEQ ID NO: 21
(19) SEQ ID NO: 483 (VH), SEQ ID NO: 487 (VL)
(20) SEQ ID NO: 491 (VH), SEQ ID NO: 495 (VL)
(21) SEQ ID NO: 499 (VH), SEQ ID NO: 503 (VL)
(22) SEQ ID NO: 507 (VH), SEQ ID NO: 511 (VL)
(23) SEQ ID NO: 515 (VH), SEQ ID NO: 519 (VL)
(24) SEQ ID NO: 523 (VH), SEQ ID NO: 527 (VL)

Note here that (1), (4), (7), and (10) correspond to 048-006 antibody; (2), (5), (8), and (11) correspond to 057-091 antibody; (3), (6), (9), and (12) correspond to 059-152 antibody; (13) and (19) correspond to 048-040 antibody; (14) and (20) correspond to 054-101 antibody; (15) and (21) correspond to 055-147 antibody; (16) and (22) correspond to 059-173 antibody; (17) and (23) correspond to 067-149 antibody; as well as (18) and (24) correspond to 067-176 antibody. Therefore, the antibody of the present invention is expected to have high specificity to HER1.

The second embodiment of this aspect provides an isolated antibody having a specific binding property to HER2. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) shown in the following (1). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) selected from the following (2). Furthermore, preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) selected from the group consisting of the following (3) and (5) to (19). The most preferably, it includes the heavy chain variable region and the light chain variable region specified by the combination of SEQ ID NOs (SEQ ID NO showing the heavy chain variable region and SEQ ID NO showing the light chain variable region) selected from the group consisting of the following (4) and (20) to (34).
(Combination of CDR3)
(1) SEQ ID NO: 28, SEQ ID NO: 32
(Combination of CDR2 and CDR3)
(2) SEQ ID NO: 27, SEQ ID NO: 28, SEQ ID NO: 31, SEQ ID NO: 32
(Combination of CDR1 to CDR3)
(3) SEQ ID NO: 26, SEQ ID NO: 27, SEQ ID NO: 28, SEQ ID NO: 30, SEQ ID NO: 31, SEQ ID NO: 32
(5) SEQ ID NO: 532 (VH CDR1), SEQ ID NO: 533 (VH CDR2), SEQ ID NO: 534 (VH CDR3), SEQ ID NO: 536 (VL CDR1), SEQ ID NO: 537 (VL CDR2), SEQ ID NO: 538 (VL CDR3)
(6) SEQ ID NO: 540 (VH CDR1), SEQ ID NO: 541 (VH CDR2), SEQ ID NO: 542 (VH CDR3), SEQ ID NO: 544 (VL CDR1), SEQ ID NO: 545 (VL CDR2), SEQ ID NO: 546 (VL CDR3)
(7) SEQ ID NO: 548 (VH CDR1), SEQ ID NO: 549 (VH CDR2), SEQ ID NO: 550 (VH CDR3), SEQ ID NO: 552 (VL CDR1), SEQ ID NO: 553 (VL CDR2), SEQ ID NO: 554 (VL CDR3)
(8) SEQ ID NO: 556 (VH CDR1), SEQ ID NO: 557 (VH CDR2), SEQ ID NO: 558 (VH CDR3), SEQ ID NO: 560 (VL CDR1), SEQ ID NO: 561 (VL CDR2), SEQ ID NO: 562 (VL CDR3)
(9) SEQ ID NO: 564 (VH CDR1), SEQ ID NO: 565 (VH CDR2), SEQ ID NO: 566 (VH CDR3), SEQ ID NO: 568 (VL CDR1), SEQ ID NO: 569 (VL CDR2), SEQ ID NO: 570 (VL CDR3)
(10) SEQ ID NO: 572 (VH CDR1), SEQ ID NO: 573 (VH CDR2), SEQ ID NO: 574 (VH CDR3), SEQ ID NO: 576 (VL CDR1), SEQ ID NO: 577 (VL CDR2), SEQ ID NO: 578 (VL CDR3)
(11) SEQ ID NO: 580 (VH CDR1), SEQ ID NO: 581 (VH CDR2), SEQ ID NO: 582 (VH CDR3), SEQ ID NO: 584 (VL CDR1), SEQ ID NO: 585 (VL CDR2), SEQ ID NO: 586 (VL CDR3)
(12) SEQ ID NO: 588 (VH CDR1), SEQ ID NO: 589 (VH CDR2), SEQ ID NO: 590 (VH CDR3), SEQ ID NO: 592 (VL CDR1), SEQ ID NO: 593 (VL CDR2), SEQ ID NO: 594 (VL CDR3)
(13) SEQ ID NO: 596 (VH CDR1), SEQ ID NO: 597 (VH CDR2), SEQ ID NO: 598 (VH CDR3), SEQ ID NO: 600 (VL CDR1), SEQ ID NO: 601 (VL CDR2), SEQ ID NO: 602 (VL CDR3)
(14) SEQ ID NO: 604 (VH CDR1), SEQ ID NO: 605 (VH CDR2), SEQ ID NO: 606 (VH CDR3), SEQ ID NO: 608 (VL CDR1), SEQ ID NO: 609 (VL CDR2), SEQ ID NO: 610 (VL CDR3)
(15) SEQ ID NO: 612 (VH CDR1), SEQ ID NO: 613 (VH CDR2), SEQ ID NO: 614 (VH CDR3), SEQ ID NO: 616 (VL CDR1), SEQ ID NO: 617 (VL CDR2), SEQ ID NO: 618 (VL CDR3)
(16) SEQ ID NO: 620 (VH CDR1), SEQ ID NO: 621 (VH CDR2), SEQ ID NO: 622 (VH CDR3), SEQ ID NO: 624 (VL CDR1), SEQ ID NO: 625 (VL CDR2), SEQ ID NO: 626 (VL CDR3)

(17) SEQ ID NO: 628 (VH CDR1), SEQ ID NO: 629 (VH CDR2), SEQ ID NO: 630 (VH CDR3), SEQ ID NO: 632 (VL CDR1), SEQ ID NO: 633 (VL CDR2), SEQ ID NO: 634 (VL CDR3)
(18) SEQ ID NO: 636 (VH CDR1), SEQ ID NO: 637 (VH CDR2), SEQ ID NO: 638 (VH CDR3), SEQ ID NO: 640 (VL CDR1), SEQ ID NO: 641 (VL CDR2), SEQ ID NO: 642 (VL CDR3)
(19) SEQ ID NO: 644 (VH CDR1), SEQ ID NO: 645 (VH CDR2), SEQ ID NO: 646 (VH CDR3), SEQ ID NO: 648 (VL CDR1), SEQ ID NO: 649 (VL CDR2), SEQ ID NO: 650 (VL CDR3)
(Combination of Heavy Chain Variable Region and Light Chain Variable Region)
(4) SEQ ID NO: 25, SEQ ID NO: 29
(20) SEQ ID NO: 531 (VH), SEQ ID NO: 535 (VL)
(21) SEQ ID NO: 539 (VH), SEQ ID NO: 543 (VL)
(22) SEQ ID NO: 547 (VH), SEQ ID NO: 551 (VL)
(23) SEQ ID NO: 555 (VH), SEQ ID NO: 559 (VL)
(24) SEQ ID NO: 563 (VH), SEQ ID NO: 567 (VL)
(25) SEQ ID NO: 571 (VH), SEQ ID NO: 575 (VL)
(26) SEQ ID NO: 579 (VH), SEQ ID NO: 583 (VL)
(27) SEQ ID NO: 587 (VH), SEQ ID NO: 591 (VL)
(28) SEQ ID NO: 595 (VH), SEQ ID NO: 599 (VL)
(29) SEQ ID NO: 603 (VH), SEQ ID NO: 607 (VL)
(30) SEQ ID NO: 611 (VH), SEQ ID NO: 615 (VL)
(31) SEQ ID NO: 619 (VH), SEQ ID NO: 623 (VL)
(32) SEQ ID NO: 627 (VH), SEQ ID NO: 631 (VL)
(33) SEQ ID NO: 635 (VH), SEQ ID NO: 639 (VL)
(34) SEQ ID NO: 643 (VH), SEQ ID NO: 647 (VL)

Note here that (1) to (4) correspond to 015-126 antibody; (5) and (20) correspond to 015-044 antibody; (6) and (21) correspond to 015-102 antibody; (7) and (22) correspond to 015-136 antibody; (8) and (23) correspond to 015-143 antibody; (9) and (24) correspond to 015-209 antibody; (10) and (25) correspond to 039-016 antibody; (11) and (26) correspond to 053-216 antibody; (12) and (27) correspond to 075-024 antibody; (13) and (28) correspond to 075-110 antibody; (14), (29) correspond to 086-032 antibody; (15) and (30) correspond to 086-035 antibody; (16) and (31) correspond to 086-036 antibody; (17) and (32) correspond to 086-061 antibody; (18) and (33) correspond to 086-138 antibody; as well as (19) and (34) correspond to 086-182 antibody. Therefore, the antibody of the present invention is expected to have high specificity to HER2.

The third embodiment of this aspect provides an isolated antibody having a specific binding property to CD46 antigen. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) selected from the following the group consisting of (1) to (7). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) selected from the following the group consisting of (8) to (14). Furthermore preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) selected from the following group consisting of (15) to (21). The most preferably, it includes the heavy chain variable region and the light chain variable region specified by the combination of SEQ ID NOs (SEQ ID NO showing the amino acid sequence of the heavy chain variable region and SEQ ID NO showing the amino acid sequence of the light chain variable region) selected from the following the group consisting of (22) to (28).
(Combination of CDR3)
(1) SEQ ID NO: 36, SEQ ID NO: 40
(2) SEQ ID NO: 44, SEQ ID NO: 48
(3) SEQ ID NO: 52, SEQ ID NO: 56
(4) SEQ ID NO: 60, SEQ ID NO: 64
(5) SEQ ID NO: 68, SEQ ID NO: 72
(6) SEQ ID NO: 76, SEQ ID NO: 80
(7) SEQ ID NO: 84, SEQ ID NO: 88
(Combination of CDR2 and CDR3)
(8) SEQ ID NO: 35, SEQ ID NO: 36, SEQ ID NO: 39, SEQ ID NO: 40
(9) SEQ ID NO: 43, SEQ ID NO: 44, SEQ ID NO: 47, SEQ ID NO: 48
(10) SEQ ID NO: 51, SEQ ID NO: 52, SEQ ID NO: 55, SEQ ID NO: 56
(11) SEQ ID NO: 59, SEQ ID NO: 60, SEQ ID NO: 63, SEQ ID NO: 64
(12) SEQ ID NO: 67, SEQ ID NO: 68, SEQ ID NO: 71, SEQ ID NO: 72
(13) SEQ ID NO: 75, SEQ ID NO: 76, SEQ ID NO: 79, SEQ ID NO: 80
(14) SEQ ID NO: 83, SEQ ID NO: 84, SEQ ID NO: 87, SEQ ID NO: 88
(Combination of CDR1 to CDR3)
(15) SEQ ID NO: 34, SEQ ID NO: 35, SEQ ID NO: 36, SEQ ID NO: 38, SEQ ID NO: 39, SEQ ID NO: 40
(16) SEQ ID NO: 42, SEQ ID NO: 43, SEQ ID NO: 44, SEQ ID NO: 46, SEQ ID NO: 47, SEQ ID NO: 48
(17) SEQ ID NO: 50, SEQ ID NO: 51, SEQ ID NO: 52, SEQ ID NO: 54, SEQ ID NO: 55, SEQ ID NO: 56
(18) SEQ ID NO: 58, SEQ ID NO: 59, SEQ ID NO: 60, SEQ ID NO: 62, SEQ ID NO: 63, SEQ ID NO: 64
(19) SEQ ID NO: 66, SEQ ID NO: 67, SEQ ID NO: 68, SEQ ID NO: 70, SEQ ID NO: 71, SEQ ID NO: 72
(20) SEQ ID NO: 74, SEQ ID NO: 75, SEQ ID NO: 76, SEQ ID NO: 78, SEQ ID NO: 79, SEQ ID NO: 80
(21) SEQ ID NO: 82, SEQ ID NO: 83, SEQ ID NO: 84, SEQ ID NO: 86, SEQ ID NO: 87, SEQ ID NO: 88
(22) SEQ ID NO: 756 (VH CDR1), SEQ ID NO: 757 (VH CDR2), SEQ ID NO: 758 (VH CDR3), SEQ ID NO: 760 (VL CDR1), SEQ ID NO: 761 (VL CDR2), SEQ ID NO: 762 (VL CDR3)
(Combination of Heavy Chain Variable Region and Light Chain Variable Region)
(23) SEQ ID NO: 33, SEQ ID NO: 37
(24) SEQ ID NO: 41, SEQ ID NO: 45
(25) SEQ ID NO: 49, SEQ ID NO: 53
(26) SEQ ID NO: 57, SEQ ID NO: 61
(27) SEQ ID NO: 65, SEQ ID NO: 69
(28) SEQ ID NO: 73, SEQ ID NO: 77
(29) SEQ ID NO: 81, SEQ ID NO: 85
(30) SEQ ID NO: 755 (VH), SEQ ID NO: 759 (VL)

Note here that (1), (8), (15) and (23) correspond to 035-224 antibody; (2), (9), (16), and (24) correspond to 045-011 antibody; (3), (10), (17), and (25) correspond to 051-144 antibody; (4), (11), (18), and (26) correspond to 052-053 antibody; (5), (12), (19), and (27) correspond to 052-073 antibody; (6), (13), (20), and (28) correspond to 053-049 antibody; (7), (14), (21), and (29) correspond to 3172-120 antibody; as well as (22) and (30) correspond to 066-069 antibody. Therefore, the antibody of the present invention is expected to have high specificity to a CD46 antigen.

The fourth embodiment of this aspect provides an isolated antibody having a specific binding property to ITGA3. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) shown in the following (1). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) shown in the following (2). Furthermore, preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) selected from the group consisting of the following (3) and (5) to (17). The most preferably, it includes the heavy chain variable region and the light chain variable region specified by the combination of SEQ ID NOs (SEQ ID NO showing the heavy chain variable region and SEQ ID NO showing the light chain variable region) selected from the group consisting of the following (4) and (18) to (30).

(Combination of CDR3)
(1) SEQ ID NO: 92, SEQ ID NO: 96
(Combination of CDR2 and CDR3)
(2) SEQ ID NO: 91, SEQ ID NO: 92, SEQ ID NO: 95, SEQ ID NO: 96
(Combination of CDR1 to CDR3)
(3) SEQ ID NO: 90, SEQ ID NO: 91, SEQ ID NO: 92, SEQ ID NO: 94, SEQ ID NO: 95, SEQ ID NO: 96
(5) SEQ ID NO: 676 (VH CDR1), SEQ ID NO: 677 (VH CDR2), SEQ ID NO: 678 (VH CDR3), SEQ ID NO: 680 (VL CDR1), SEQ ID NO: 681 (VL CDR2), SEQ ID NO: 682 (VL CDR3)
(6) SEQ ID NO: 684 (VH CDR1), SEQ ID NO: 685 (VH CDR2), SEQ ID NO: 686 (VH CDR3), SEQ ID NO: 688 (VL CDR1), SEQ ID NO: 689 (VL CDR2), SEQ ID NO: 690 (VL CDR3)
(7) SEQ ID NO: 692 (VH CDR1), SEQ ID NO: 693 (VH CDR2), SEQ ID NO: 694 (VH CDR3), SEQ ID NO: 696 (VL CDR1), SEQ ID NO: 697 (VL CDR2), SEQ ID NO: 698 (VL CDR3)
(8) SEQ ID NO: 700 (VH CDR1), SEQ ID NO: 701 (VH CDR2), SEQ ID NO: 702 (VH CDR3), SEQ ID NO: 704 (VL CDR1), SEQ ID NO: 705 (VL CDR2), SEQ ID NO: 706 (VL CDR3)
(9) SEQ ID NO: 708 (VH CDR1), SEQ ID NO: 709 (VH CDR2), SEQ ID NO: 710 (VH CDR3), SEQ ID NO: 712 (VL CDR1), SEQ ID NO: 713 (VL CDR2), SEQ ID NO: 714 (VL CDR3)
(10) SEQ ID NO: 716 (VH CDR1), SEQ ID NO: 717 (VH CDR2), SEQ ID NO: 718 (VH CDR3), SEQ ID NO: 720 (VL CDR1), SEQ ID NO: 721 (VL CDR2), SEQ ID NO: 722 (VL CDR3)
(11) SEQ ID NO: 724 (VH CDR1), SEQ ID NO: 725 (VH CDR2), SEQ ID NO: 726 (VH CDR3), SEQ ID NO: 728 (VL CDR1), SEQ ID NO: 729 (VL CDR2), SEQ ID NO: 730 (VL CDR3)
(12) SEQ ID NO: 732 (VH CDR1), SEQ ID NO: 733 (VH CDR2), SEQ ID NO: 734 (VH CDR3), SEQ ID NO: 736 (VL CDR1), SEQ ID NO: 737 (VL CDR2), SEQ ID NO: 738 (VL CDR3)
(13) SEQ ID NO: 740 (VH CDR1), SEQ ID NO: 741 (VH CDR2), SEQ ID NO: 742 (VH CDR3), SEQ ID NO: 744 (VL CDR1), SEQ ID NO: 745 (VL CDR2), SEQ ID NO: 746 (VL CDR3)
(14) SEQ ID NO: 748 (VH CDR1), SEQ ID NO: 749 (VH CDR2), SEQ ID NO: 750 (VH CDR3), SEQ ID NO: 752 (VL CDR1), SEQ ID NO: 753 (VL CDR2), SEQ ID NO: 754 (VL CDR3)
(15) SEQ ID NO: 764 (VH CDR1), SEQ ID NO: 765 (VH CDR2), SEQ ID NO: 766 (VH CDR3), SEQ ID NO: 768 (VL CDR1), SEQ ID NO: 769 (VL CDR2), SEQ ID NO: 770 (VL CDR3)
(16) SEQ ID NO: 772 (VH CDR1), SEQ ID NO: 773 (VH CDR2), SEQ ID NO: 774 (VH CDR3), SEQ ID NO: 776 (VL CDR1), SEQ ID NO: 777 (VL CDR2), SEQ ID NO: 778 (VL CDR3)
(Combination of Heavy Chain Variable Region and Light Chain Variable Region)
(4) SEQ ID NO: 89, SEQ ID NO: 93
(17) SEQ ID NO: 675 (VH), SEQ ID NO: 679 (VL)
(18) SEQ ID NO: 683 (VH), SEQ ID NO: 687 (VL)
(19) SEQ ID NO: 691 (VH), SEQ ID NO: 695 (VL)
(20) SEQ ID NO: 699 (VH), SEQ ID NO: 703 (VL)
(21) SEQ ID NO: 707 (VH), SEQ ID NO: 711 (VL)
(22) SEQ ID NO: 715 (VH), SEQ ID NO: 719 (VL)
(23) SEQ ID NO: 723 (VH), SEQ ID NO: 727 (VL)
(24) SEQ ID NO: 731 (VH), SEQ ID NO: 735 (VL)
(25) SEQ ID NO: 739 (VH), SEQ ID NO: 743 (VL)
(26) SEQ ID NO: 747 (VH), SEQ ID NO: 751 (VL)
(27) SEQ ID NO: 763 (VH), SEQ ID NO: 767 (VL)
(28) SEQ ID NO: 771 (VH), SEQ ID NO: 775 (VL)

Note here that (1) to (4) correspond to 015-003 antibody; (5) and (17) correspond to 064-002 antibody; (6) and (18) correspond to 064-006 antibody; (7) and (19) correspond to 064-012a antibody; (8) and (20) correspond to 064-012b antibody; (9) and (21) correspond to 064-014 antibody; (10) and (22) correspond to 064-054 antibody; (11) and (23) correspond to 064-085 antibody; (12) and (24) correspond to 064-093 antibody; (13) and (25) correspond to 064-116 antibody; (14) and (26) correspond to 065-183 antibody; (15) and (27) correspond to 067-142 antibody; as well as (16) and (28) correspond to 068-007 antibody. Therefore, the antibody of the present invention is expected to have high specificity to ITGA3.

The fifth embodiment of this aspect provides an isolated antibody having a specific binding property to ICAM1. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) selected from the following the group consisting of (1) to (5). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) selected from the following the group consisting of (6) to (10). Furthermore preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) selected from the following the group consisting of (11) to (15). The most preferably, it includes the heavy chain variable region and the light chain variable region specified by the combination of SEQ ID NOs (SEQ ID NO showing the amino acid sequence of the heavy chain variable region and SEQ ID NO showing the amino acid sequence of the light chain variable region) selected from the following the group consisting of (16) to (20).

(Combination of CDR3)
(1) SEQ ID NO: 100, SEQ ID NO: 104
(2) SEQ ID NO: 108, SEQ ID NO: 112
(3) SEQ ID NO: 116, SEQ ID NO: 120
(4) SEQ ID NO: 124, SEQ ID NO: 128
(5) SEQ ID NO: 132, SEQ ID NO: 136
(Combination of CDR2 and CDR3)
(6) SEQ ID NO: 99, SEQ ID NO: 100, SEQ ID NO: 103, SEQ ID NO: 104
(7) SEQ ID NO: 107, SEQ ID NO: 108, SEQ ID NO: 111, SEQ ID NO: 112
(8) SEQ ID NO: 115, SEQ ID NO: 116, SEQ ID NO: 119, SEQ ID NO: 120
(9) SEQ ID NO: 123, SEQ ID NO: 124, SEQ ID NO: 127, SEQ ID NO: 128
(10) SEQ ID NO: 131, SEQ ID NO: 132, SEQ ID NO: 135, SEQ ID NO: 136
(Combination of CDR1 to CDR3)
(11) SEQ ID NO: 98, SEQ ID NO: 99, SEQ ID NO: 100, SEQ ID NO: 102, SEQ ID NO: 103, SEQ ID NO: 104
(12) SEQ ID NO: 106, SEQ ID NO: 107, SEQ ID NO: 108, SEQ ID NO: 110, SEQ ID NO: 111, SEQ ID NO: 112
(13) SEQ ID NO: 114, SEQ ID NO: 115, SEQ ID NO: 116, SEQ ID NO: 118, SEQ ID NO: 119, SEQ ID NO: 120
(14) SEQ ID NO: 122, SEQ ID NO: 123, SEQ ID NO: 124, SEQ ID NO: 126, SEQ ID NO: 127, SEQ ID NO: 128
(15) SEQ ID NO: 130, SEQ ID NO: 131, SEQ ID NO: 132, SEQ ID NO: 134, SEQ ID NO: 135, SEQ ID NO: 136
(Combination of Heavy Chain Variable Region and Light Chain Variable Region)
(16) SEQ ID NO: 97, SEQ ID NO: 101
(17) SEQ ID NO: 105, SEQ ID NO: 109
(18) SEQ ID NO: 113, SEQ ID NO: 117
(19) SEQ ID NO: 121, SEQ ID NO: 125
(20) SEQ ID NO: 129, SEQ ID NO: 133

Note here that (1), (6), (11) and (16) correspond to 052-033 antibody; (2), (7), (12), and (17) correspond to 053-042 antibody; (3), (8), (13), and (18) correspond to 053-051 antibody; (4), (9), (14), and (19) correspond to 053-059 antibody; as well as (5), (10), (15), and (20) correspond to 053-085 antibody. Therefore, the antibody of the present invention is expected to have high specificity to ICAM1.

The sixth embodiment of this aspect provides an isolated antibody having a specific binding property to ALCAM. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) selected from the group consisting of the following (1) to (5). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) selected from the group consisting of the following (6) to (10). Furthermore, preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) selected from the group consisting of the following (11) to (15) and (21) to (28). The most preferably, it includes the heavy chain variable region and the light chain variable region specified by the combination of SEQ ID NOs (SEQ ID NO showing the heavy chain variable region and SEQ ID NO showing the light chain variable region) selected from the group consisting of the following (16) to (20) and (29) to (36).

(Combination of CDR3)
(1) SEQ ID NO: 140, SEQ ID NO: 144
(2) SEQ ID NO: 148, SEQ ID NO: 152
(3) SEQ ID NO: 156, SEQ ID NO: 160
(4) SEQ ID NO: 164, SEQ ID NO: 168
(5) SEQ ID NO: 172, SEQ ID NO: 176
(Combination of CDR2 and CDR3)
(6) SEQ ID NO: 139, SEQ ID NO: 140, SEQ ID NO: 143, SEQ ID NO: 144
(7) SEQ ID NO: 147, SEQ ID NO: 148, SEQ ID NO: 151, SEQ ID NO: 152
(8) SEQ ID NO: 155, SEQ ID NO: 156, SEQ ID NO: 159, SEQ ID NO: 160
(9) SEQ ID NO: 163, SEQ ID NO: 164, SEQ ID NO: 167, SEQ ID NO: 168
(10) SEQ ID NO: 171, SEQ ID NO: 172, SEQ ID NO: 175, SEQ ID NO: 176
(Combination of CDR1 to CDR3)
(11) SEQ ID NO: 138, SEQ ID NO: 139, SEQ ID NO: 140, SEQ ID NO: 142, SEQ ID NO: 143, SEQ ID NO: 144
(12) SEQ ID NO: 146, SEQ ID NO: 147, SEQ ID NO: 148, SEQ ID NO: 150, SEQ ID NO: 151, SEQ ID NO: 152

(13) SEQ ID NO: 154, SEQ ID NO: 155, SEQ ID NO: 156, SEQ ID NO: 158, SEQ ID NO: 159, SEQ ID NO: 160
(14) SEQ ID NO: 162, SEQ ID NO: 163, SEQ ID NO: 164, SEQ ID NO: 166, SEQ ID NO: 167, SEQ ID NO: 168
(15) SEQ ID NO: 170, SEQ ID NO: 171, SEQ ID NO: 172, SEQ ID NO: 174, SEQ ID NO: 175, SEQ ID NO: 176
(21) SEQ ID NO: 780 (VH CDR1), SEQ ID NO: 781 (VH CDR2), SEQ ID NO 782 (VH CDR3), SEQ ID NO: 784 (VL CDR1), SEQ ID NO: 785 (VL CDR2), SEQ ID NO: 786 (VL CDR3)
(22) SEQ ID NO: 788 (VH CDR1), SEQ ID NO: 789 (VH CDR2), SEQ ID NO: 790 (VH CDR3), SEQ ID NO: 792 (VL CDR1), SEQ ID NO: 793 (VL CDR2), SEQ ID NO: 794 (VL CDR3)
(23) SEQ ID NO: 796 (VH CDR1), SEQ ID NO: 797 (VH CDR2), SEQ ID NO: 798 (VH CDR3), SEQ ID NO: 800 (VL CDR1), SEQ ID NO: 801 (VL CDR2), SEQ ID NO: 802 (VL CDR3)
(24) SEQ ID NO: 804 (VH CDR1), SEQ ID NO: 805 (VH CDR2), SEQ ID NO: 806 (VH CDR3), SEQ ID NO: 808 (VL CDR1), SEQ ID NO: 809 (VL CDR2), SEQ ID NO: 810 (VL CDR3)
(25) SEQ ID NO: 812 (VH CDR1), SEQ ID NO: 813 (VH CDR2), SEQ ID NO: 814 (VH CDR3), SEQ ID NO: 816 (VL CDR1), SEQ ID NO: 817 (VL CDR2), SEQ ID NO: 818 (VL CDR3)
(26) SEQ ID NO: 820 (VH CDR1), SEQ ID NO: 821 (VH CDR2), SEQ ID NO: 822 (VH CDR3), SEQ ID NO: 824 (VL CDR1), SEQ ID NO: 825 (VL CDR2), SEQ ID NO: 826 (VL CDR3)
(27) SEQ ID NO: 828 (VH CDR1), SEQ ID NO: 829 (VH CDR2), SEQ ID NO: 830 (VH CDR3), SEQ ID NO: 832 (VL CDR1), SEQ ID NO: 833 (VL CDR2), SEQ ID NO: 834 (VL CDR3)
(28) SEQ ID NO: 836 (VH CDR1), SEQ ID NO: 837 (VH CDR2), SEQ ID NO: 838 (VH CDR3), SEQ ID NO: 840 (VL CDR1), SEQ ID NO: 841 (VL CDR2), SEQ ID NO: 842 (VL CDR3)
(Combination of Heavy Chain Variable Region and Light Chain Variable Region)
(16) SEQ ID NO: 137, SEQ ID NO: 141
(17) SEQ ID NO: 145, SEQ ID NO: 149
(18) SEQ ID NO: 153, SEQ ID NO: 157
(19) SEQ ID NO: 161, SEQ ID NO: 165
(20) SEQ ID NO: 169, SEQ ID NO: 173
(29) SEQ ID NO: 779 (VH), SEQ ID NO: 783 (VL)
(30) SEQ ID NO: 787 (VH), SEQ ID NO: 791 (VL)
(31) SEQ ID NO: 795 (VH), SEQ ID NO: 799 (VL)
(32) SEQ ID NO: 803 (VH), SEQ ID NO: 807 (VL)
(33) SEQ ID NO: 811 (VH), SEQ ID NO: 815 (VL)
(34) SEQ ID NO: 819 (VH), SEQ ID NO: 823 (VL)
(35) SEQ ID NO: 827 (VH), SEQ ID NO: 831 (VL)
(36) SEQ ID NO: 835 (VH), SEQ ID NO: 839 (VL)

Note here that (1), (6), (11), and (16) correspond to 035-234 antibody; (2), (7), (12), and (17) correspond to 040-107 antibody; (3), (8), (13), and (18) correspond to 041-118 antibody; (4), (9), (14), and (19) correspond to 066-174 antibody; (5), (10), (15), and (20) correspond to 083-040 antibody; (21) and (29) correspond to 029-143 antibody; (22) and (30) correspond to 045-134 antibody; (23) and (31) correspond to 062-101 antibody; (24) and (32) correspond to 062-109 antibody; (25) and (33) correspond to 084-103 antibody; (26) and (34) correspond to 052-274 antibody; (27) and (35) correspond to 029-067 antibody; as well as (28) and (36) correspond to 083-131 antibody. Therefore, the antibody of the present invention is expected to have high specificity to ALCAM.

The seventh embodiment of this aspect provides an isolated antibody having a specific binding property to a CD147 antigen. The antibody of this form includes the heavy chain variable region CDR3 and the light chain variable region CDR3 specified by the combination of SEQ ID NOs (SEQ ID NO showing the amino acid sequence of the heavy chain variable region CDR3, and SEQ ID NO showing the amino acid sequence of the light chain variable region CDR3) shown in the following (1). Preferably, it includes the heavy chain variable regions CDR2 and CDR3 and the light chain variable regions CDR2 and CDR3 specified by the combination of SEQ ID NOs (SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR2, and SEQ ID NO showing the amino acid sequence of the light chain variable region CDR3) selected from the following (2). Furthermore, preferably, it includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2, and SEQ ID NO showing the amino acid sequence of the light chain variable region CDR3) shown in the following (3). The most preferably, it includes the heavy chain variable region and the light chain variable region specified by the combination of SEQ ID NOs (SEQ ID NO showing the heavy chain variable region and SEQ ID NO showing the light chain variable region) shown in the following (4).
(Combination of CDR3)
(1) SEQ ID NO: 180, SEQ ID NO: 184
(Combination of CDR2 and CDR3)
(2) SEQ ID NO: 179, SEQ ID NO: 180, SEQ ID NO: 183, SEQ ID NO: 184
(Combination of CDR1 to CDR3)
(3) SEQ ID NO: 178, SEQ ID NO: 179, SEQ ID NO: 180, SEQ ID NO: 182, SEQ ID NO: 183, SEQ ID NO: 184
(Combination of Heavy Chain Variable Region and Light Chain Variable Region)
(4) SEQ ID NO: 177, SEQ ID NO: 181

Note here that (1) to (4) correspond to 059-053 antibody. Therefore, the antibody of the present invention is expected to have high specificity to a CD147 antigen.

The eighth embodiment of this aspect provides an isolated antibody having a specific binding property to C1qR. The antibody of this form includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2 and SEQ ID NO showing the amino acid sequence of the light chain variable region CDR3) shown in the following (1). Preferably, it includes the heavy chain variable region and the light chain variable region specified by the combination of SEQ ID NOs (SEQ ID NO showing the heavy chain variable region and SEQ ID NO showing the light chain variable region) shown in the following (2).
(Combination of CDR3)
(1) SEQ ID NO: (VH CDR1)-452, SEQ ID NO: 453 (VH CDR2), SEQ ID NO: 454 (VH CDR3), SEQ ID NO: (VL CDR1)-456, SEQ ID NO: 457 (VL CDR2), SEQ ID NO: 458 (VL CDR3)
(Combination of Heavy Chain Variable Region and Light Chain Variable Region)
(2) SEQ ID NO: 451 (VH), SEQ ID NO: 455 (VL)

Note here that (1) and (2) correspond to 070-016 antibody. Therefore, the antibody of the present invention is expected to have high specificity to C1qR.

The ninth embodiment of this aspect provides an isolated antibody having a specific binding property to CD44. The antibody of this form includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2 and SEQ ID NO showing the amino acid sequence of the light chain variable region CDR3) shown in the following (1). Preferably, it includes the heavy chain variable region and the light chain variable region specified by the combination of SEQ ID NOs (SEQ ID NO showing the heavy chain variable region and SEQ ID NO showing the light chain variable region) shown in the following (2).
(Combination of CDR1 to CDR3)
(1) SEQ ID NO: 460 (VH CDR1), SEQ ID NO: 461 (VH CDR2), SEQ ID NO: 462 (VH CDR3), SEQ ID NO: 464 (VL CDR1), SEQ ID NO: 465 (VL CDR2), SEQ ID NO: 466 (VL CDR3)
(Combination of Heavy Chain Variable Region and Light Chain Variable Region)
(2) SEQ ID NO: 459 (VH), SEQ ID NO: 463 (VL)

Note here that (1) and (2) correspond to 064-003 antibody. Therefore, the antibody of the present invention is expected to have high specificity to CD44.

The tenth embodiment of this aspect provides an isolated antibody having a specific binding property to CD73. The antibody of this form includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2 and SEQ ID NO showing the amino acid sequence of the light chain variable region CDR3) shown in the following (1). Preferably, it includes the heavy chain variable region and the light chain variable region specified by the combination of SEQ ID NOs (SEQ ID NO showing the heavy chain variable region and SEQ ID NO showing the light chain variable region) shown in the following (2).
(Combination of CDR1 to CDR3)
(1) SEQ ID NO: 468 (VH CDR1), SEQ ID NO: 469 (VH CDR2), SEQ ID NO: 470 (VH CDR3), SEQ ID NO: 472 (VL CDR1), SEQ ID NO: 473 (VL CDR2), SEQ ID NO: 474 (VL CDR3)
(Combination of Heavy Chain Variable Region and Light Chain Variable Region)
(2) SEQ ID NO: 467 (VH), SEQ ID NO: 471 (VL)

Note here that (1) and (2) correspond to 067-213 antibody. Therefore, the antibody of the present invention is expected to have high specificity to CD73.

The eleventh embodiment of this aspect provides an isolated antibody having a specific binding property to EpCAM. The antibody of this form includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2 and SEQ ID NO showing the amino acid sequence of the light chain variable region CDR3) shown in the following (1). Preferably, it includes the heavy chain variable region and the light chain variable region specified by the combination of SEQ ID NOs (SEQ ID NO showing the heavy chain variable region and SEQ ID NO showing the light chain variable region) shown in the following (2).
(Combination of CDR1 to CDR3)
(1) SEQ ID NO: 476 (VH CDR1), SEQ ID NO: 477 (VH CDR2), SEQ ID NO: 478 (VH CDR3), SEQ ID NO: 480 (VL CDR1), SEQ ID NO: 481 (VL CDR2), SEQ ID NO: 482 (VL CDR3)
(Combination of Heavy Chain Variable Region and Light Chain Variable Region)
(2) SEQ ID NO: 475 (VH),
SEQ ID NO: 479 (VL)

Note here that (1) and (2) correspond to 067-153 antibody. Therefore, the antibody of the present invention is expected to have high specificity to EpCAM.

The twelfth embodiment of this aspect provides an isolated antibody having a specific binding property to HGFR. The antibody of this form includes the heavy chain variable regions CDR1 to CDR3 and the light chain variable regions CDR1 to CDR3 specified by the combination of SEQ ID NOs (SEQ ID NO showing the amino acid sequence of the heavy chain variable region CDR1, SEQ ID NO showing the amino acid sequence of the heavy chain variable region CDR2, SEQ ID NO showing the amino acid sequence of the heavy chain variable region CDR3, SEQ ID NO showing the amino acid sequence of the light chain variable region CDR1, SEQ ID NO showing the amino acid sequence of the light chain variable region CDR2 and SEQ ID NO showing the amino acid sequence of the light chain variable region CDR3) selected from the group consisting of the following (1) to (3). Preferably, it includes the heavy chain variable region and the light chain variable region specified by the combination of SEQ ID NOs (SEQ ID NO showing the heavy chain variable region and SEQ ID NO showing the light chain variable region) selected from the group consisting of the following (4) to (6).
(Combination of CDR1 to CDR3)
(1) SEQ ID NO: 652 (VH CDR1), SEQ ID NO: 653 (VH CDR2), SEQ ID NO: 654 (VH CDR3), SEQ ID NO: 656 (VL CDR1), SEQ ID NO: 657 (VL CDR2), SEQ ID NO: 658 (VL CDR3)
(2) SEQ ID NO: 660 (VH CDR1), SEQ ID NO: 661 (VH CDR2), SEQ ID NO: 662 (VH CDR3), SEQ ID NO: 664 (VL CDR1), SEQ ID NO: 665 (VL CDR2), SEQ ID NO: 666 (VL CDR3)

(3) SEQ ID NO: 668 (VH CDR1), SEQ ID NO: 669 (VH CDR2), SEQ ID NO: 670 (VH CDR3), SEQ ID NO: 672 (VL CDR1), SEQ ID NO: 673 (VL CDR2), SEQ ID NO: 674 (VL CDR3)
(Combination of Heavy Chain Variable Region and Light Chain Variable Region)
(4) SEQ ID NO: 651 (VH), SEQ ID NO: 655 (VL)
(5) SEQ ID NO: 659 (VH), SEQ ID NO: 663 (VL)
(6) SEQ ID NO: 667 (VH), SEQ ID NO: 671 (VL)

Note here that (1) and (4) correspond to 067-126 antibody; (2) and (5) correspond to 067-133 antibody; and (3) and (6) correspond to 067-287 antibody. Therefore, the antibody of the present invention is expected to have high specificity to HGFR.

The 13rd embodiment of this aspect provides an isolated antibody having a specific binding property to LAR. The antibody of this form includes the heavy chain variable region and the light chain variable region specified by the combination of SEQ ID NOs (SEQ ID NO showing the heavy chain variable region and SEQ ID NO showing the light chain variable region) selected from the group consisting of the following (1) to (5).
(Combination of Heavy Chain Variable Region and Light Chain Variable Region)
(1) SEQ ID NO: 944 (VH), SEQ ID NO: 945 (VL)
(2) SEQ ID NO: 946 (VH), SEQ ID NO: 947 (VL)
(3) SEQ ID NO: 948 (VH), SEQ ID NO: 949 (VL)
(4) SEQ ID NO: 950 (VH), SEQ ID NO: 951 (VL)
(5) SEQ ID NO: 952 (VH), SEQ ID NO: 953 (VL)

Note here that (1) corresponds to 064-044 antibody; (2) corresponds to 065-030 antibody; (3) corresponds to 065-358 antibody; (4) corresponds to 066-019 antibody; and (5) corresponds to 079-085 antibody. Therefore, the antibody of the present invention is expected to have high specificity to LAR.

The 14th embodiment of this aspect provides an isolated antibody having a specific binding property to BCAM. The antibody of this form includes the heavy chain variable region and the light chain variable region specified by the combination of SEQ ID NOs (SEQ ID NO showing the heavy chain variable region and SEQ ID NO showing the light chain variable region) shown in the following (1).
(Combination of Heavy Chain Variable Region and Light Chain Variable Region)
(1) SEQ ID NO: 954 (VH), SEQ ID NO: 955 (VL)

Note here that (1) corresponds to 067-024 antibody. Therefore, the antibody of the present invention is expected to have high specificity to BCAM.

In the variable region of the antibody of the present invention, the sequence of the framework region (FR region) is not particularly limited as long as it does not substantially affect the specific binding property with respect to corresponding antigen. For example, when the antibody of the present invention is constructed as a humanized antibody, the FR region of a known human antibody can be used. Furthermore, when the antibody of the present invention is constructed as an antibody used as a reagent for detection or used for application to non-human animal species, in some cases, an effect can be expected even if the human antibody FR region is not used, or the use of the human antibody FR region may not appropriate. In such cases, the FR region from non-human animal species (for example, mouse or rat) can be used.

In one embodiment of the antibody of the present invention, a constant region (for example, in the case of an IgG type antibody) is included in addition to the variable region. The sequence of the constant region in this embodiment is not particularly limited. For example, as mentioned below, when the antibody of the present invention is constructed as a humanized antibody, the constant region of a known human antibody can be used. Furthermore, similar to the above-mentioned FR region, a constant region from non-human animal species (for example, mouse or rat) can be used.

One embodiment of the antibody of the present invention relates to a humanized antibody. The "humanized antibody" herein denotes an antibody that is allowed to resemble the structure of the human antibody. It includes a humanized chimeric antibody in which only a constant region is replaced by that of human antibody, and a humanized CDR-grafted antibody in which a part other than the CDR (complementarity determining region) existing in the constant region and the variable region is replaced by that of human antibody (P. T. Johons et al., Nature 321, 522 (1986)). In order to improve the antigen binding activity of the humanized CDR-grafted antibody, improved techniques of a method of selecting a human antibody FR that is highly homologous to a mouse antibody, a method of producing a humanized antibody having high homology, and a method of transplanting a human antibody to a mouse CDR and then replacing amino acid in the FR region have been already developed (see, for example, U.S. Pat. Nos. 5,585,089, 5,693,761, 5,693,762, and 6,180,370, European Patent Nos. 451216 and 682040, and Patent No. 2828340) and such techniques can be used for producing the humanized antibody of the present invention.

The humanized chimeric antibody can be produced by, for example, replacing the constant region of an antibody having the above-mentioned structure of H chain variable region and/or structure of L chain variable region by the constant region of a human antibody. As the constant region of the human antibody, known region can be employed. Hereinafter, one example of the method of producing the humanized chimeric antibody is described.

Firstly, mRNA is extracted from the hybridoma producing a mouse antibody to certain antigens (for example, antigens expressing certain cancers, which have been determined this time, HER1, HER2, CD46, ITGA3, ICAM1, ALCAM, CD147, or the like), and cDNA is synthesized according to the usual procedure. The synthesized cDNA is inserted into a vector so as to construct a cDNA library. From this cDNA library, an H chain gene fragment and an L chain gene fragment are used as a probe, a vector containing an H chain gene and an L chain gene is selected. By sequencing the insertion sequence of the selected vector, the sequences of the gene in the H chain variable region and the L chain variable region can be determined. Based on the thus obtained sequence data, DNA encoding H chain variable region is produced by a chemical synthesis, biochemical cleavage/recombination and the like. DNA encoding the obtained H chain variable region is ligated with DNA encoding a human H chain constant region so as to incorporate it into an expression vector. Thereby, H chain expression vector is produced. As the expression vector, for example, an SV40 virus based vector, an EB virus based vector, and a BPV (papilloma virus) based vector can be used but not limited to these vectors alone. On the other hand, by the similar method, an L chain expression vector is produced. With such H chain expression vector and L chain expression vector, host cells are co-transformed. As the host cell, CHO cell (Chinese hamster ovary cell) (A. Wright & S. L. Morrison, J. Immunol. 160, 3393-3402 (1998)), SP2/0 cell (myeloma) (K. Motmans et al., Eur. J. Cancer Prev. 5, 512-519 (1996), R. P. Junghans et al., Cancer Res. 50, 1495-1502 (1990)), and the like can be suitably used. Furthermore, for transformation, a Lipofectin method (R. W. Malone et al., Proc. Natl. Acad. Sci. USA 86, 6077 (1989), P. L. Felgner et al., Proc. Natl. Acad. Sci. USA 84, 7413 (1987), an electroporation method, a calcium phosphate method (F.

L. Graham & A. J. van der Eb, Virology 52, 456-467 (1973)), a DEAE-Dextran method, and the like, are suitably used.

After the transformant is cultured, a humanized chimeric antibody is separated from the cells of transformant or the culture solution. For separation and purification, methods such as centrifugation, ammonium sulfate fractionation, salting out, ultrafiltration, affinity chromatography, ion-exchange chromatography, and gel filtration chromatography can be appropriately combined and used.

On the other hand, the humanized CDR-grafted antibody can be produced by, for example, the following method. Firstly, by the method described in the production method of chimeric antibody, the amino acid sequences of the H chain variable region and L chain variable region of the antibody to the certain antigen and the base sequences encoding the amino acid sequences are determined. In addition, the amino acid sequence and the base sequence of each CDR region are determined.

As the base sequence of the specific CDRs, any of the following combinations are used. Note here that they are shown by SEQ ID NO showing the base sequence of the heavy chain variable region CDR1, SEQ ID NO showing the base sequence of the heavy chain variable region CDR2, SEQ ID NO showing the base sequence of the heavy chain variable region CDR3, SEQ ID NO showing the base sequence of the light chain variable region CDR1, SEQ ID NO showing the base sequence of the light chain variable region CDR2, and SEQ ID NO showing the base sequence of the light chain variable region CDR3, in this order.

(1) SEQ ID NO 186, SEQ ID NO 187, SEQ ID NO 188, SEQ ID NO 190, SEQ ID NO 191, SEQ ID NO 192
(2) SEQ ID NO 194, SEQ ID NO 195, SEQ ID NO 196, SEQ ID NO 198, SEQ ID NO 199, SEQ ID NO 200
(3) SEQ ID NO: 202, SEQ ID NO: 203, SEQ ID NO: 204, SEQ ID NO: 206, SEQ ID NO: 207, SEQ ID NO: 208
(4) SEQ ID NO: 210, SEQ ID NO: 211, SEQ ID NO: 212, SEQ ID NO: 214, SEQ ID NO: 215, SEQ ID NO: 126
(5) SEQ ID NO: 218, SEQ ID NO: 219, SEQ ID NO: 220, SEQ ID NO: 222, SEQ ID NO: 223, SEQ ID NO: 224
(6) SEQ ID NO: 226, SEQ ID NO: 227, SEQ ID NO: 228, SEQ ID NO: 230, SEQ ID NO: 231, SEQ ID NO: 232
(7) SEQ ID NO: 234, SEQ ID NO: 235, SEQ ID NO: 236, SEQ ID NO: 238, SEQ ID NO: 239, SEQ ID NO: 240
(8) SEQ ID NO: 242, SEQ ID NO: 243, SEQ ID NO: 244, SEQ ID NO: 246, SEQ ID NO: 247, SEQ ID NO: 248
(9) SEQ ID NO: 250, SEQ ID NO: 251, SEQ ID NO: 252, SEQ ID NO: 254, SEQ ID NO: 255, SEQ ID NO: 256
(10) SEQ ID NO: 258, SEQ ID NO: 259, SEQ ID NO: 260, SEQ ID NO: 262, SEQ ID NO: 263, SEQ ID NO: 264
(11) SEQ ID NO: 266, SEQ ID NO: 267, SEQ ID NO: 268, SEQ ID NO: 270, SEQ ID NO: 271, SEQ ID NO: 272
(12) SEQ ID NO: 274, SEQ ID NO: 275, SEQ ID NO: 276, SEQ ID NO: 278, SEQ ID NO: 279, SEQ ID NO: 280
(13) SEQ ID NO: 282, SEQ ID NO: 283, SEQ ID NO: 284, SEQ ID NO: 286, SEQ ID NO: 287, SEQ ID NO: 288
(14) SEQ ID NO: 290, SEQ ID NO: 291, SEQ ID NO: 292, SEQ ID NO: 294, SEQ ID NO: 295, SEQ ID NO: 296
(15) SEQ ID NO: 298, SEQ ID NO: 299, SEQ ID NO: 300, SEQ ID NO: 302, SEQ ID NO: 303, SEQ ID NO: 304
(16) SEQ ID NO: 306, SEQ ID NO: 307, SEQ ID NO: 308, SEQ ID NO: 310, SEQ ID NO: 311, SEQ ID NO: 312
(17) SEQ ID NO: 314, SEQ ID NO: 315, SEQ ID NO: 316, SEQ ID NO: 318, SEQ ID NO: 319, SEQ ID NO: 320
(18) SEQ ID NO: 322, SEQ ID NO: 323, SEQ ID NO: 324, SEQ ID NO: 326, SEQ ID NO: 327, SEQ ID NO: 328
(19) SEQ ID NO: 330, SEQ ID NO: 331, SEQ ID NO: 332, SEQ ID NO: 334, SEQ ID NO: 335, SEQ ID NO: 336
(20) SEQ ID NO: 338, SEQ ID NO: 339, SEQ ID NO: 340, SEQ ID NO: 342, SEQ ID NO: 343, SEQ ID NO: 344
(21) SEQ ID NO: 346, SEQ ID NO: 347, SEQ ID NO: 348, SEQ ID NO: 350, SEQ ID NO: 351, SEQ ID NO: 352
(22) SEQ ID NO: 354, SEQ ID NO: 355, SEQ ID NO: 356, SEQ ID NO: 358, SEQ ID NO: 359, SEQ ID NO: 360
(23) SEQ ID NO: 362, SEQ ID NO: 363, SEQ ID NO: 364, SEQ ID NO: 366, SEQ ID NO: 367, SEQ ID NO: 368

Note here that these combinations correspond to the combination in CDR1 to CDR3 in 048-006 antibody, 057-091 antibody, and 059-152 antibody (which are antibodies to HER1), 015-126 antibody (which is antibody to HER2), 035-224 antibody, 045-011 antibody, 051-144 antibody, 052-053 antibody, 052-073 antibody, 053-049 antibody, and 3172-120 antibody (which are antibodies to CD46), 015-003 antibody (which is antibody to ITGA3), 052-033 antibody, 053-042 antibody, 053-051 antibody, 053-059 antibody, and 053-085 antibody (which are antibodies to ICAM1), 035-234 antibody, 040-107 antibody, 041-118 antibody, 066-174 antibody, and 083-040 antibody (which are antibodies to ALCAM), 059-053 antibody (which is antibody to CD147).

Next, FRs (framework regions) sandwiching the CDR region are selected. For selecting the FR, approximately three methods can be employed. The first method is a method using a human antibody frame whose three dimensional structure has been already identified, for example, NEWM, REI, and the like (Riechmann L. et al., Nature 332, 323-3Z7 (1988); Tempst, P R. et al., Protein Engineering 7, 1501-1507 (1994); Ellis J H. et al., J. Immunol 155, 925-937 (1995)). The second method includes selecting a variable region of a human antibody having the highest homology to a variable region of the intended mouse antibody from database, and using the FR thereof (Queen C. et al., Proc Natl Acad Sci USA 86, 10029-10033 (1989); Rozak M J. et al., J Biol Chem 271, 22611-22618 (1996); Shearman C W. et al., J. Immunol 147, 4366-4373 (1991)). The third method is a method of selecting amino acid most commonly used in the FR of the human antibody (Sato K. et al., Mol Immunol 31, 371-381 (1994); Kobinger F. et al., Protein Engineering 6, 971-980 (1993); Kettleborough Calif. et al., Protein Engineering 4, 773-783 (1991)). The present invention can use any of these methods.

Even if the amino acid sequence is an amino acid sequence obtained by modifying the amino acid sequence of the selected human FR, it can be used as an amino acid sequence of the FR as long as a finally obtained humanized CDR-grafted antibody has a specific binding property to the corresponding antigens (HER1, HER2, CD46, ITGA3, ICAM1, ALCAM, CD147, and the like). In particular, a part of the amino acid of the selected human FR is changed to the amino acid of the FR of the antibody of the origin of CDR, the property of the antibody may be maintained. The number of the amino acid to be modified is preferably 30% or less relative to the entire FR, further preferably 20% or less relative to the entire FR, and yet further preferably 10% or less relative to the entire FR.

Next, by combining the FR selected by any of these methods and the above-mentioned CDR, DAN encoding the H chain variable region and L chain variable region is designed. Based on this design, DNA encoding H chain variable region and DNA encoding L chain variable region are produced by the chemical synthesis, biochemical cleavage/recombination, and the like, respectively. Then, DAN encoding the H chain variable region together with the DNA encoding H chain constant region of a human immunoglobulin is incorporated into an expression vector so as to construct an H chain expression vector. Similarly, DAN encoding the L chain variable region together with the DNA encoding L chain constant region of a human immunoglobulin is incorporated into an expression vector so as to construct an L chain expression vector. As the expression vector, for example, an SV40 virus based vector, an EB virus based vector, a BPV (papilloma virus) based vector, and the like can be used but not necessarily limited to these vectors.

With the H chain expression vector and L chain expression vector that are produced by the above-mentioned method, host cells are co-transformed. As the host cell, CHO cell (Chinese hamster ovary cell) (A. Wright & S. L. Morrison, J. Immunol. 160, 3393-3402 (1998)), SP2/0 cell (myeloma) (K. Motmans et al., Eur. J. Cancer Prev. 5, 512-519 (1996), R. P. Junghans et al., Cancer Res. 50, 1495-1502 (1990)), and the like can be suitably used. Furthermore, for transformation, a Lipofectin method (R. W. Malone et al., Proc. Natl. Acad. Sci. USA 86, 6077 (1989), P. L. Felgner et al., Proc. Natl. Acad. Sci. USA 84, 7413 (1987), an electroporation method, a calcium phosphate method (F. L. Graham & A. J. van der Eb, Virology 52, 456-467 (1973)), a DEAE-Dextran method, and the like, are suitably used.

After the transformant is cultured, a humanized CDR-grafted antibody is separated from the cells of transformant or the culture solution. For separation and purification, methods such as centrifugation, ammonium sulfate fractionation, salting out, ultrafiltration, affinity chromatography, ion-exchange chromatography, and gel filtration chromatography can be appropriately combined and used.

Based on the antibody of the present invention or based on the sequence information on the genes encoding the antibody of the present invention, an antibody fragment can be produced. The antibody fragment can include Fab, Fab', F(ab')$_2$, scFv, and dsFv antibodies.

Fab is a fragment that is obtained by digesting IgG with papain in the presence of cysteine; includes L chain and H chain variable regions as well as an H chain fragment consisting of a $C_H1$ domain and a part of hinge portion; and has a molecular weight of about 50000. In the present invention, it can be obtained by digesting the antibody with papain. Furthermore, DNA encoding a part of the H chain of the above-mentioned antibody and L chain is incorporated into an appropriate vector, and the vector is used for transforming so as to obtain a transformant. From this transformant, Fab can be prepared.

Fab' is a fragment having a molecular weight of about 50000, which can be obtained by cleaving the disulfide bond between H chains of F(ab')$_2$ mentioned below. In the present invention, it can be obtained by digesting the above-mentioned antibody with pepsin and cleaving the disulfide bond by the use of a reducing agent. Furthermore, similar to Fab, it can also be prepared by gene engineering with the use of DNA encoding Fab'.

F(ab')$_2$ is a fragment that is obtained by digesting IgG with pepsin; a fragment (Fab') is linked by disulfide bond including L chain and H chain variable regions as well as an H chain fragment consisting of a $C_H1$ domain and a part of hinge portion; and has a molecular weight of about 100000. In the present invention, it can be obtained by digesting the antibody with pepsin. Furthermore, similar to Fab, it can also be prepared by gene engineering with the use of DNA encoding F(ab')$_2$.

scFv is an antibody fragment obtained by linking Fv including an H chain variable region and an L chain variable region to C terminal of one of the chains and N terminal of the other of the chains by using an appropriate peptide linker so as to produce a single chain antibody fragment. As the peptide linker, for example, highly flexible (GGGGS)$_3$ can be used. For example, DNA encoding an scFv antibody is constructed by using DNA encoding H chain variable region and L chain variable region of the above-mentioned antibody and DNA encoding the peptide linker is constructed. This is incorporated into an appropriate vector and this vector is used to obtain a transformant. From this transformant, scFv can be prepared.

dsFv is an Fv fragment obtained by introducing a Cys residue into an appropriate positions of the H chain variable region and L chain variable region and stabilizing the H chain variable region and chain variable region by disulfide bond. The position in which the Cys residue is introduced in each chain can be determined based on the three dimensional structure anticipated by molecule modeling. In the present invention, for example, the three dimensional structure is anticipated from the amino acid sequence of the H chain variable region and the L chain variable region of the above-mentioned antibody. DNA encoding the H chain variable region and L chain variable region into which difference based on such anticipation is constructed and the constructed DNA is incorporated into the appropriate vector. The vector is used to obtain a transformant. From this transformant, dsFv can be prepared.

Note here that an antibody fragment can be multimerized by linking an scFv antibody and a dcFv antibody and the like with the use of an appropriate linker, or by allowing streptavidin to be fused.

By fusing or linking a low molecule compound, protein, a label material, and the like to the antibody of the present invention (including an antibody fragment), a fused antibody or labeled antibody can be formed. An example of the label material may include radioactive material such as $^{125}$I, peroxidase, β-D-galactosidase, micro peroxidase, horseradish peroxidase (HRP), fluorescein isothiocyanate (FITC), rhodamine isothiocyanate (RITC), alkaline phosphatase, biotin, and the like.

The antibody of the present invention (including an antibody fragment) specifically binds to a cancer cell that specifically expresses the antigen by the specific binding property to the corresponding antigen. The use of this property makes it possible to label and detect a cancer cell (or cancer tissue). By gene recombination technology, VH and VL having such a specific binding capacity can be fused to a constant region (Fc region) of IgG so as to transform into an IgG type antibody. The thus obtained IgG type antibody is expected to exhibit a cytotoxic effect via Fc receptor on NK cells. The IgG constant region has subclass. As to the binding of Fc receptor of each IgG subclass of human, IgG1 and IgG3 have the strongest binding, IgG4 has moderate binding and IgG2 has weak binding. In transforming into IgG type antibodies, it is preferable to select a constant region in consideration of this point. Note here that the present inventors have proposed an assay of cytotoxic effect via the secondary antibody instead of IgG type antibody in the previous applications (Japanese Patent Unexamined Publication No. 2005-185281 and PCT/JP2006/303195).

Actually, as shown in the below-mentioned Examples, since 015-003 antibody as anti-ITGA3 antibody, 048-006 antibody as anti-HER1 antibody, and 015-126 antibody as anti-HER2 antibody are recognized to have an ADCC activity, they themselves can be used for damaging (killing) cancer cells. Herein, when the antibody of the present invention that has transformed into human or human IgG antibody is used, it is less attacked and excluded by the immune system, thus enabling the expected effect to be well exhibited and serious side effects to be avoided.

Furthermore, the antibody of the present invention can be used as a medium (carrier) for delivering a drug, and the like, to a specific cancer. That is to say, an anticipated application of use of the antibody of the present invention includes DDS (Drug delivery system) targeting a specific cancer cell.

Note here that each application of the antibody of the present invention is described in detail below.

(Diagnosis Application)

Another aspect of the present invention relates to a use as a diagnosis marker of based on the findings of the expression (distribution) of CD46 antigen, ITGA3, ALCAM and CD147 antigen. Specifically, one embodiment of this aspect provides a testing method of gallbladder and liver cancer or pancreas cancer based on the findings that a CD46 antigen is expressed in the gallbladder and liver cancer and the pancreas cancer. The method includes the following steps.

Step (1): preparing subject cells or tissues separated from a living body.

Step (2): detecting a CD46 antigen in the subject cells or tissues.

Information obtained by the testing method of the present invention is useful for diagnosis of gallbladder and liver cancer or pancreas cancer. For example, information obtained by subjecting the above-mentioned method to patients with gallbladder and liver cancer can be used for evaluating or grasping the pathologic condition of patients and for evaluating the therapeutic effect. For example, when the present invention is carried out concurrently with the treatment of gallbladder and liver cancer, based on the resultant information, the therapeutic effect can be evaluated. Specifically, when the method of the present invention is carried out after administering drugs, the change in the expression amount of CD46 antigen in the liver cells is examined and the therapeutic effect can be determined from the increase and decrease of the expression amount. Thus, the method of the present invention may be used for monitoring the therapeutic effect.

On the other hand, information obtained when the subjects are persons other than the patient, that is, persons that have not recognized to have gallbladder and liver cancer can be used for determination of the presence or absence of contraction of gallbladder and liver cancer, evaluation of contraction risk, and the like. Since the method of the present invention permits diagnosis of liver cancer based on the amount of expression amount of genes, i.e., an objective indicator, its value is extremely high.

Hereinafter, the steps constituting the present invention are respectively described in detail.

1. Step (1)

In the step (1), cells or tissues separated from a subject (a subject person, a living body) are prepared. The subjects herein may include not only patients (gallbladder and liver cancer patients or pancreas cancer patients) but also healthy persons (including persons having a risk of contracting gallbladder and liver cancer or pancreas cancer). For example, a part of tissues collected from a subject by biopsy can be used as subject cells or tissues in the method of the present invention.

The "subject cells or tissues" in the present invention are cells or tissues that are samples (subjects) in the detection in the method of the present invention. The subject cells or tissues are separated from a living body. That is to say, the present invention is applied to the subject cells or tissues in the state in which it is separated from the living body. The term "separated from a living body" means a state in which a part of the living tissue in which subject cells or tissues exist is extracted, thereby the subject cells or tissues are completed separated from the origin living body. In the step (2), when an immunological detection method is employed, the subject cells are generally prepared in a state in which they are present in a living body, that is, in a state in which they are linked to the surrounding cells (as tissue), and used for the method of the present invention. Note here that the subject cells may be used for the method of the present invention after they are separated (isolated) from the surrounding cells.

2. Step (2)

In the step (2), a CD46 antigen is detected in the prepared subject cells or tissues as subjects. The term "CD46 antigen is detected" means examining whether or not the CD46 antigen is expressed (presence or absence of expression), or figuring out the expression amount of the CD46 antigen as an absolute value or a relative value. The reference of the relative amount herein can be, for example, an amount of CD46 antigen of the reference samples prepared according to the grade of malignancy. In general, the presence of expression of CD46 antigen and the amount if expressed are examined. In detecting the CD46 antigen, it is not essential to determine the amount of CD46 antigens strictly.

In one embodiment of the present invention, a detection method targeting mRNA that is a transcriptional product of the CD46 antigen is carried out. For the detection (measurement) of mRNA, routine procedures such as an RT-PCR method and various hybridization methods using specific probes (for example, northern hybridization, in situ hybridization) can be employed. In another embodiment of the present invention, a detection method targeting the expression product of the CD46 antigen (protein) is carried out.

It is preferable that CD46 antigen is detected by immunologic procedures (for example, immunohistochemical staining technique). In the immunologic procedure, anti-CD46 antigen antibody is used, CD46 antigen protein is detected by using the bonding property (binding amount) of the antibodies as an indicator. The immunological detection method permits rapid and sensitive detection. Also, the operation is simple. An example of the detection methods may include ELISA method, radioimmunoassay, FCM, an immunoprecipitation method, immunoblotting, and the like.

The immunohistochemical staining technique permits rapid and sensitive detection of CD46 antigens. Also, the operation is simple. Therefore, burdens to a subject person (patient) accompanying the detection of CD46 antigen is reduced.

In the immunohistochemical staining technique, in general, firstly, a step of bringing the subject cells into contact with the anti-CD46 antibody is carried out. Then, the binding amount of the anti-CD46 antibody is examined. Specifically, according to the above-mentioned immunohistochemical staining technique, the method of the present invention can be carried out.

The kind or origin of the anti-CD46 antibody to be used in immunostaining procedure is not particularly limited as long as it has a specific binding property to the CD46 antigen. The anti-CD46 antibody may be any of a polyclonal antibody, an oligoclonal antibody (a mixture of several kinds to several tens of antibodies) and a monoclonal antibody. As the polyclonal antibody or the oligoclonal antibody, affinity purification antibody by antigen can be used besides an IgG fraction derived from anti-serum obtained by immunizing an animal so as to obtain. The anti-CD46 antibody may be antibody fragments such as Fab, Fab', F(ab')$_2$, scFv, and dsFv antibodies.

The anti-CD46 antibody can be prepared by using an immunologic procedure, phage display technique, ribosome display method, and the like.

The preparation of a polyclonal antibody by the immunologic procedure can be prepared by the following procedures. An antigen (CD46 or a part thereof) is prepared. An animal such as a rabbit is immunized with this antigen. As this antigen, not only human CD46 but also non-human CD46 such as mouse CD46 can be used. Such CD46 can be obtained by purifying a living body sample. Furthermore, recombinant CD46 may be used. The recombinant human CD46 can be prepared by, for example, introducing a gene encoding CD46 (which may include a part of gene) in an appropriate host by using a vector and expressing the gene within the obtained recombinant cells.

In order to strengthen the immunity inducing effect, an antigen to which a carrier protein is attached may be used. As the carrier protein, KLH (Keyhole Limpet Hemocyanin), BSA (Bovine Serum Albumin), OVA (Ovalbumin), and the like are used. For binding of the carrier protein, a carbodiimide method, a glutaraldehyde method, a diazo condensation method, an MBS (maleimidobenzoyl oxy succinimide) method, and the like, can be used. On the other hand, an antigen expressing CD46 (or a part thereof) as fusion protein with GST, β galactosidase, maltose bonded protein, or histidine (His) tag, and the like, can be used. Such a fusion protein can be purified by a general method in a simple manner.

If necessary, immunization is repeated. When the antibody titer is sufficiently increased, blood is collected and subjected to centrifugation so as to obtain serum. The obtained antiserum is subjected to affinity purification. Thus, a polyclonal antibody is obtained.

On the other hand, a monoclonal antibody can be prepared by the following procedures. Firstly, an immunization operation is carried out by the similar method to the above-mentioned procedures. If necessary, immunization is repeated. When the antibody titer is sufficiently increased, antibody-producing cells are extracted from an immunized animal. Next, the obtained antibody-producing cells and myeloma cells are fused to each other so as to obtain a hybridoma. Subsequently, this hybridoma is made to be monoclonal. Then, a clone producing antibody showing high specificity to the target protein is selected. A culture solution of the selected clone is purified, thereby the target antibody can be obtained. On the other hand, hybridoma is proliferated into a predetermined number of more, then, transplanted in the abdominal cavity of an animal (for example, mouse), proliferated in the abdominal dropsy. By purifying the abdominal dropsy, the target antibody can be obtained. For purification of the above-mentioned culture solution or purification of the abdominal dropsy, affinity chromatography using protein G, protein A, and the like, is preferably used. Furthermore, affinity chromatography in which an antigen is made into a solid phase can be used. Furthermore, methods such as ion-exchange chromatography, gel filtration chromatography, ammonium sulfate fractionation, and centrifugation can be used. These methods are used singly or in arbitrary combination thereof.

On the conditions that the specific binding property to CD46 antigen is maintained, the obtained antibody may be subjected to various modifications. In the present invention, such a modified antibody may be used.

When a labeled antibody is used as an anti-CD46 antibody, the amount of bound antibody can be directly detected by using the labeled amount as an indicator. Therefore, the method is more simplified. On the contrary, it is necessary to prepare an anti-CD46 antibody to which a label material is bound and furthermore, and furthermore, the detection sensitivity is generally reduced. Therefore, it is preferable that indirect methods such as a method using a secondary antibody to which a label material is linked, a method using a polymer to which a secondary antibody and a label material are linked are used. The secondary antibody herein is an antibody having a specific binding property to the anti-CD46 antibody. For example, when an anti-CD46 antibody is prepared as a rabbit antibody, an anti-rabbit IgG antibody can be used. Label secondary antibodies that can be used for various species such as rabbit, goat, and mouse are commercially available (for example, Funakoshi Corporation, COSMO BIO Co., Ltd., etc.). Proper antibodies can be appropriately selected depending upon the anti-CD46 antibody used in the present invention.

For the label material, the label material arbitrarily selected from the group consisting of peroxidase, β-D-galactosidase, micro peroxidase, horseradish peroxidase (HRP), fluorescein isothiocyanate (FITC), rhodamine isothiocyanate (RITC), alkaline phosphatase, biotin, and radioactive material is preferably used. In particular, a method of using biotin as the label material and reacting avidin peroxidase permits highly sensitive detection.

The above-mentioned antibody of the present invention may be used as the anti-CD46 antibody. Specifically, for example, antibodies (035-224 antibody, 045-011 antibody, 051-144 antibody, 052-053 antibody, 052-073 antibody, 053-049 antibody, or 3172-120 antibody), which the present inventors have succeeded in obtaining, can be used.

Another embodiment of this aspect provides a testing method of gallbladder and liver cancer or pancreas cancer based on the findings that ITGA3 is expressed in gallbladder and liver cancer and pancreas cancer. The method includes the following steps.

Step (1): preparing subject cells or tissues separated from a living body

Step (2): detecting ITGA3 in the subject cells or tissues

Information obtained by the testing method of the present invention is useful for diagnosis of gallbladder and liver cancer or diagnosis of pancreas cancer. Since the using method and details of each step are the same as in the case of the CD46 antigen, the description thereof is not mentioned here.

A further embodiment of this aspect provides an obtaining method of information for diagnosis of kidney cancer, hepatic cell carcinoma or gallbladder and liver cancer based on the findings that ALCAM is expressed in kidney cancer, hepatic cell carcinoma and gallbladder and liver cancer. The method includes the following steps.

Step (1): preparing subject cells or tissues separated from a living body

Step (2): detecting ALCAM in the subject cells or tissues

Information obtained by the testing method of the present invention is useful for diagnosis of kidney cancer, diagnosis of hepatic cell carcinoma, or diagnosis of gallbladder and liver cancer. Since the using method and details of each step are the same as in the case of the CD46 antigen, the description thereof is not mentioned here.

A yet further embodiment of this aspect provides a testing method of kidney cancer based on the findings that CD147 antigen is expressed in kidney cancer. The method includes the following steps.

Step (1): preparing subject cells or tissues separated from a living body

Step (2): detecting a CD147 antigen in the subject cells or tissues

Information obtained by the testing method of the present invention is useful for diagnosis of kidney cancer. Since the using method and details of each step are the same as in the case of the CD46 antigen, the description thereof is not mentioned here.

(Treatment Application)

As mentioned in the below-mentioned Examples, the present inventor have succeeded in obtaining antibodies exhibiting Antibody-Dependent Cell-mediated Cytotoxicity (hereinafter, abbreviated as "ADCC") activity to certain antibodies. Furthermore, the present inventors have transformed these antibodies into IgG type and investigated the probability of application to an antibody therapeutic agent. Any antibodies show excellent anti-tumor effect. Based on these findings, the further aspect of the present invention relates to an application of the antibodies successfully obtained by the present inventors in treatment of cancer.

This aspect firstly provides a drug (cancer therapeutic agent) capable of affecting and damaging in a cancer cell-specific manner using by using ITGA3, HER1, HER2, ALCAM, EpCAM or HGFR as a target, and the treatment method using the same. One embodiment of the drug of the present invention contains anti-ITGA3 antibody as an active ingredient. One preferable embodiment of the drug of the present invention contains an anti-ITGA3 antibody having an ADCC activity as an active ingredient. The drugs of this embodiment can obtain the therapeutic effect by the cytotoxicity using the ADCC activity. As anti-ITGA3 antibody having the ADCC activity, 015-003 antibody (the specific binding property to ITGA3 and it may be partially modified as long as the ADCC activity is maintained) shown in the below-mentioned Examples or different types of antibodies constructed based on the 015-003 antibody (for example, IgG type antibody) can be used. This antibody has both the specific binding property to ITGA3 and the ADCC activity. Therefore, it specifically binds to the cancer cells expressing ITGA3 and then expresses the ADCC activity. Thus, it can damage a cancer cell. The target cancer cell of the drug of this embodiment is not particularly limited, but can target, for example, gallbladder and liver cancer cells and pancreas cancer cells.

In another embodiment of the present invention, an anti-HER1 antibody is contained as an active ingredient. In the drug of one preferable embodiment of the present invention, anti-HER1 antibody having an ADCC activity is contained as an active ingredient. In the drug of this embodiment, the therapeutic effect can be obtained by the cytotoxicity using the ADCC activity. In the drug of the further preferable embodiment, in addition to the cytotoxicity using the ADCC activity, since inhibition of binding of EGF as a ligand to HER1 and/or inhibition of phosphorylation signal by HER1 are provided, higher therapeutic effect can be obtained. As anti-HER1 antibody having such an ADCC activity, 048-006 antibody, 059-152 antibody, 055-147 antibody or 059-173 antibody shown in the below-mentioned Example (which may be partially modified as long as the specific binding property to HER1 and the ADCC activity are maintained) or different types of antibodies constructed based on them (for example, IgG type) can be used. These antibodies have the specific binding property to HER1, inhibition of binding of EGF to HER1, inhibition of phosphorylation signal of HER1 and ADCC activity. Therefore, they can specifically bind to a cancer cell expressing HER1 and inhibit HER1 activity by inhibition of binding of EGF to HER1 and/or inhibition of phosphorylation signal of HER1, thereafter, exhibit the ADCC activity so as to damage a cancer cell. Furthermore, it is confirmed that the antibody exhibits suppression effect to cancer cells and an anti-tumor effect in animal model, so that the antibody is greatly expected to be used in antibody medicine. The target cancer cell by the drug of this embodiment is not particularly limited, but it can target, for example, cells of kidney cancer, hepatic cell carcinoma, gallbladder and liver cancer, lung squamous cell carcinoma, pulmonary adenocarcinoma, and pancreas cancer.

In a further embodiment of the present invention, an anti-HER2 antibody is contained as an active ingredient. In the drug of one preferable embodiment of the present invention, anti-HER2 antibody having an ADCC activity is contained as an active ingredient. In the drug of this embodiment, the therapeutic effect can be obtained by the cytotoxicity using the ADCC activity. As anti-HER2 antibody having such an ADCC activity, 015-126 antibody shown in the below-mentioned Example (which may be partially modified as long as the specific binding property to HER2 and the ADCC activity are maintained) or different types of antibodies constructed based on them (for example, IgG type) can be used. This antibody has the specific binding property to HER2 and ADCC activity. Therefore, they can specifically bind to a cancer cell expressing HER2 then exhibits the ADCC activity so as to damage a cancer cell. Furthermore, it is confirmed that the antibody exhibits suppression effect to cancer cells, so that the antibody is greatly expected to be used in antibody medicine. The target cancer cell by the drug of this embodiment is not particularly limited, but it can target, for example, cells of kidney cancer, liver cancer, and pulmonary adenocarcinoma.

In a further embodiment of the present invention, an anti-ALCAM antibody is contained as an active ingredient. In the drug of one preferable embodiment of the present invention, anti-ALCAM antibody having an ADCC activity is contained as an active ingredient. As anti-ALCAM antibody having such an ADCC activity, 041-118 antibody or 066-174 antibody shown in the below-mentioned Example (which may be partially modified as long as the specific binding property to ALCAM and the ADCC activity are maintained) or different types of antibodies constructed based on them (for example, IgG type) can be used. This antibody has the specific binding property to ALCAM and ADCC activity. Therefore, they can specifically bind to a cancer cell expressing ALCAM then exhibits the ADCC activity so as to damage a cancer cell. The target cancer cell by the drug of this embodiment is not particularly limited, but it can target, for example, cells of pulmonary adenocarcinoma, ovarian cancer, and large bowel cancer.

In a yet further embodiment of the present invention, an anti-EpCAM antibody is contained as an active ingredient. In the drug of one preferable embodiment of the present invention, anti-EpCAM antibody having an ADCC activity is contained as an active ingredient. As anti-EpCAM antibody having such an ADCC activity, 067-153 antibody shown in the below-mentioned Example (which may be partially modified as long as the specific binding property to EpCAM and the ADCC activity are maintained) or different types of antibodies constructed based on them (for example, IgG type) can be used. This antibody has the specific binding property to EpCAM and ADCC activity. Therefore, they can specifically bind to a cancer cell expressing EpCAM then exhibits the ADCC activity so as to damage a cancer cell. The target cancer cell by the drug of this embodiment is not particularly limited, but it can target, for example, cells of gastric solid-type adenocarcinoma, colon adenocarcinoma, and pulmonary adenocarcinoma cell.

In a yet further embodiment of the present invention, an anti-CD147 antibody is contained as an active ingredient. In the drug of one preferable embodiment of the present invention, anti-CD147 antibody having an ADCC activity is contained as an active ingredient. As anti-CD147 antibody having such an ADCC activity, 059-053 antibody shown in the below-mentioned Example (which may be partially modified as long as the specific binding property to CD147 and the ADCC activity are maintained) or different types of antibodies constructed based on them (for example, IgG type) can be used. This antibody has the specific binding property to CD147 and ADCC activity. Therefore, they can specifically bind to a cancer cell expressing CD147 then exhibits the ADCC activity so as to damage a cancer cell. The target cancer cell by the drug of this embodiment is not particularly limited, but it can target, for example, kidney cancer cells.

In a yet further embodiment of the present invention, an anti-CD44 antibody is contained as an active ingredient. In the drug of one preferable embodiment of the present invention, anti-CD44 antibody having an ADCC activity is contained as an active ingredient. As anti-CD44 antibody having such an ADCC activity, 064-003 antibody shown in the below-mentioned Example (which may be partially modified as long as the specific binding property to CD44 and the ADCC activity are maintained) or different types of antibodies constructed based on them (for example, IgG type) can be used. This antibody has the specific binding property to CD44 and ADCC activity. Therefore, they can specifically bind to a cancer cell expressing CD44 then exhibits the ADCC activity so as to damage a cancer cell. The target cancer cell by the drug of this embodiment is not particularly limited, but it can target, for example, pulmonary adenocarcinoma cells.

In a yet further embodiment of the present invention, an anti-HGFR antibody is contained as an active ingredient. In the drug of one preferable embodiment of the present invention, anti-HGFR antibody having an ADCC activity is contained as an active ingredient. As anti-HGFR antibody having such an ADCC activity, 067-133 antibody shown in the below-mentioned Example (which may be partially modified as long as the specific binding property to HGFR and the ADCC activity are maintained) or different types of antibodies constructed based on them (for example, IgG type) can be used. This antibody has the specific binding property to HGFR and ADCC activity. Therefore, they can specifically bind to a cancer cell expressing HGFR then exhibits the ADCC activity so as to damage a cancer cell. The target cancer cell by the drug of this embodiment is not particularly limited, but it can target, for example, pulmonary adenocarcinoma cells.

The present invention furthermore provides a method of reducing the grade of malignancy of a target cell or promoting the normalization by damaging or suppressing the expression of HER1, HER2, CD46, ITGA3, ICAM1, ALCAM, or CD147 in the target cell.

Herein, the present inventors have investigated and recognized specific expression of CD46 in gallbladder and liver cancer and pancreas cancer, which had not been particularly reported about the relationship with respect to CD46 (see the below-mentioned Example). Similarly, the relationship between gallbladder and liver cancer and pancreas cancer and the expression of ITGA3; the relationship between kidney cancer, hepatic cell carcinoma and gallbladder and liver cancer and ALCAM; as well as the relationship between kidney cancer and CD147 have been clarified (see the below-mentioned Example). Based on the findings, a novel and effective target cell of CD46 is a gallbladder and liver cancer cell and a pancreas cancer cell; a novel and effective target cell of ITGA3 is a gallbladder and liver cancer cell and a pancreas cancer cell; and a novel and effective target cell of CD147 is a kidney cancer cell.

Note here that the inhibition or suppression of each antigen can be carried out by using an antisense method or RNA interference, or by using ribozyme.

In the case where expression inhibition by the antisense method is carried out, for example, when transcription is carried out in the target cell, an antisense-construct for generating RNA that is complementary to a portion specific to mRNA encoding this protein is used. Such an antisense—construct is introduced into the target cells, for example, in a form of an expression plasmid. On the other hand, when it is introduced in to the target cells as the antisense—construct, it is possible to employ an oligonucleotide—probe that is hybridized with mRNA or genome DNA sequence encoding this protein and inhibits the expression thereof. As such an oligonucleotide—probe, one having a low resistance to endogenous nuclease such as exonuclease and/or endonuclease is preferably used.

When DNA molecule is used as an antisense nucleic acid, it is preferable that oligodeoxyribonucleotide derived from a region (for example, a region from −10 to +10) including a translation initiation site of mRNA encoding this protein is used.

It is preferable that the complementation between the antisense nucleic acid and the target nucleic acid is strict. However, some mismatch may be accepted. The hybridization performance of the antisense nucleic acid with respect to the target nucleic acid is generally dependent upon both the degree of complementation of both nucleic acids and the length thereof. In general, as the antisense nucleic acid to be used is longer, even if the number of mismatch is increased, stable two heavy chains (or three heavy chains) can be formed between the antisense nucleic acid and the target nucleic acid. Persons skilled in the art can confirm the degree of permissible degree of the mismatch by using a standard technique.

The antisense nucleic acid may be DNA, RNA or a chimera mixture thereof, or derivative or modified type thereof. Furthermore, it may be single stranded or double stranded. By modifying a base portion, a sugar portion or a skeleton portion of phosphoric acid, the stability and hybridization performance and the like of the antisense nucleic acid can be improved. Furthermore, to the antisense nucleic acid, materials for urging the cell membrane transportation (for example, see Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or materials capable of enhancing the affinity with respect to certain cells may be added.

The antisense nucleic acid can be synthesized by a conventional method, for example, by using commercially available automated DNA synthesizer (for example, Applied Biosystems, and the like). For producing the modulated product or derivative of nucleic acid, you can see, for example, Stein et al. (1988), Nucl. Acids Res. 16:3209, or Sarin et al., (1988), Proc. Natl. Acad. Sci. U.S.A. 85:7448-7451.

In order to enhance the effect of antisense nucleic acid in the target cells, a strong promoter such as pol II and pol III can be used. That is to say, if a construct including antisense nucleic acid disposed under control of such promoters is introduced into the target cells, it is possible to secure the transcription of sufficient amount of antisense nucleic acid by the effect of the promoter.

The antisense nucleic acid can be expressed by using any promoters (derivative promoters or constitutive promoters) known to function in the mammalian cells (preferably, human cells). For example, promoters such as a SV40 initial promoter region (Bernoist and Chambon, 1981, Nature 290:304-310), a promoter derived from the 3'-terminal region of Rous sarcoma virus (Yamamoto et al., 1980, Cell 22:787-797), a Herpetic Thymidine Kinase promoter (Wagner et al., 1981, Proc. Natl. Acad. Sci. U.S.A. 78: 1441-1445), and the like, can be used.

In one embodiment of the present invention, the expression of the protein is inhibited by RNA interference (RNAi). RNAi is a process of a sequence specific post-transcriptional gene suppression that can be caused in the eukaryote. In the RNA interference, double stranded RNA (dsRNA) having a sequence corresponding to the sequence of the target mRNA is used. It is known that mammalian cells have two routes (a sequence specific route and a sequence nonspecific route) affected by dsRNA. In the sequence specific route, relatively long dsRNA is divided into short interference RNAs (siRNAs). Each of the siRNAs has sense and antisense chains of about 21 nucleotides that form siRNA of about 19 nucleotides having protruding portions at the 3' terminal portion. On the other hand, it is thought that a sequence nonspecific route can be caused by arbitrary dsRNA regardless of the sequence as long as it has a predetermined length or longer. In this route, dsRNA, two enzymes, that is, PKR, which becomes an active from and stops whole synthesis of proteins by phosphorylating the translation initiation factor eIF2, and 2', 5' oligoadenylate synthetase, which is involved in the synthesis of an RNAase L activated molecule are activated. In the method of the present invention, in order to minimize the progress of this nonspecific route, it is preferable to use dsRNA including about 30 base pairs or less (see, for example, Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

Note here that it is confirmed that RNAi is an effective means for reducing the gene expression in various cells (for example, a HeLa cell, a NIH/3T3 cell, a COS cell, a 293 cell, and the like). Furthermore, in general, it can inhibit expression more effectively than by the antisense method.

The dsRNA used in RNAi can be prepared in vitro or in vivo by chemical synthesis or by using an appropriate expression vector. In the latter method, it is particularly effective to prepare a relatively long dsRNA. For designing dsRNA, in general, sequence peculiar to the target nucleic acid (continuous sequence) is used. Note here that a program and algorithm for selecting an appropriate target sequence have been developed.

In another embodiment of the present invention, the expression of ITGA3 is carried out by using ribozyme. By using ribozyme for cleave mRNA at the site specific recognition sequence, it is possible to destroy mRNA encoding the protein. However, preferably, a hammerhead ribozyme is used. A method for constructing the hammerhead ribozyme can be seen in, for example, Haseloff and Gerlach, 1988, Nature, 334: 585-591.

Similar to the antisense method, for example, for the purpose of the stability and target performance, by using a modified oligonucleotide, ribozyme may be constructed. In order to produce an effective amount of ribozyme in the target cells, for example, under the control of a strong promoter (for example, pol II and pol III), it is preferable that the nucleic acid construct in which DNA encoding ribozyme is disposed is used.

Drugs used for the treatment method (including a method of urging to reducing or normalizing the grade of malignancy of cancer cells, and the like) of the present invention can be formulated according to the conventional method. In formulation, other ingredients acceptable for formulation (for example, carrier, vehicle, disintegrating agents, buffer agent, emulsifying agent, suspending agent, soothing agent, stabilizer, preservative, preservative, physiological saline, and the like) can be contained. An example of the vehicle may include lactose, starch, sorbitol, D-mannitol, and sucrose. An example of the disintegrating agents may include starch, carboxymethyl cellulose, calcium carbonate, and the like. An example of the buffer agent may include phosphate, citrate, acetate, and the like. An example of the emulsifying agent may include gum Arabic, alginate sodium, tragacanth, and the like. An example of the suspending agent may include glyceryl monostearate, aluminum monostearate, methylcellulose, carboxymethyl cellulose, hydroxymethyl cellulose, sodium lauryl sulfate, and the like. An example of the soothing agent may include benzyl alcohol, chlorobutanol, sorbitol, and the like. An example of the stabilizer may include propylene glycol, diethylene sulfite, ascorbic acid, and the like. An example of the preservative may include phenol, benzalkonium chloride, benzyl alcohol, chlorobutanol, methylparaben, and the like. An example of the preservative may include benzalkonium chloride, parahydroxybenzoate, chlorobutanol, and the like.

The dosage form in the formulation is not particularly limited. An example of the dosage form may include tablet, powdered drug, fine subtilae, granule, capsules, syrup, injectable drug, external preparation, and suppository.

In the treatment using the drug of the present invention, the drug of the present invention is administered to a subject (patient) with a cancer cell or adult T cell leukemia. The drug of the present invention can be administered to a subject (patient) by oral administration or parenteral administration (intravenous, intra-arterial, subcutaneous, intramuscular, intraperitoneal injection, direct introduction to the target cell, and the like) depending upon the dosage form.

The dosage amount of the drug of the present invention will vary depending on the symptoms, age, sex, body weight, and the like, of the patient, but the person skilled in the art can set an appropriate dosage amount. For example, the dosage amount can be set so that the dosage amount of effective ingredient for adult (body weight: about 60 kg) per day is about 0.001 mg to about 100 mg. The administration schedule can include, for example, once to several times a day, once per two days, or once per three days. For setting the administration schedule, conditions of a patient, efficacy duration time of the drug, and the like, can be considered.

In another embodiment, the drug of the present invention uses anti-HER1 antibody, anti-HER2 antibody, anti-CD46 antibody, anti-ITGA3 antibody, anti-ICAM1 antibody, anti-ALCAM antibody, anti-CD147 antibody as a carrier for DDS. That is to say, this embodiment provides an immunocomplex obtained by combining a drug (cytotoxin and the like), radioactive isotope, or the like (these are also referred to as "active ingredient" together) to anti-HER1 antibody, and others. The immunocomplex containing a drug (cytotoxin) having a cell-killing activity or a cytotoxic activity is generally referred to as immunotoxin. An example of the cytotoxin may include Taxol, cytochalasin B, gramicidin D, ethidium bromide, emetine, mitomycin, etoposide, tenoposide, vincristine, vinblastine, colchicines, doxorubicin, daunorubicin, dihydroxy-anthracene-dione, mitoxantrone, methramycin, actinomycin D, 1-dehydrotestosterone, glucocorticoid, procaine, tetracaine, lidocaine, propranolol, and puromycin as well as analogue or homologue thereof.

As the active ingredient contained in the immunocomplex of the present invention, protein or peptide having a desirable biological activity may be used. An example of the candidate for protein and the like that can be used for such a purpose may include abrin, ricin A, *Pseudomonas*-exotoxin, diphteria toxin, tumor necrosis factor, interferon-γ, interleukin 1 (IL-1), interleukin 2 (IL-2), interleukin 6 (IL-6), a granulocyte macrophage colony stimulating factor (GM-CSF), a granulocyte colony stimulating factor (G-CSF) lymphokine.

A technology for combining an active component to an antibody is well known and you can see it, for example, Monoclonal Antibodies And Cancer Therapy, Reisfeld et al. (eds.), pp. 243-56 (Alan R. Liss, Inc. 1985), Controlled Drug Delivery (2nd edition), Robinson et al. (eds.), pp. 623-53

(Marcel Dekker, Inc. 1987), Monoclonal Antibodies For Cancer Detection And Therapy, Baldwin et al. (eds.), pp. 303-16 (Academic Press 1985), Thorpe et al., "The Preparation And Cytotoxic Properties Of antibody-Toxin Conjugates", Immunol. Rev., 62:119-58 (1982).

(Kit Used in the Present Invention)

Each method of the present invention (a method for obtaining information for diagnosis, and the like) may be carried out by using a kit of reagent and the like. Another aspect of the present invention provides a kit used for such a purpose. For example, nucleic acid (probe and primer), reaction reagent, dilution, a reactor vessel, and the like, that are used for the method of the present invention can be contained in the kit. Note here that the kit of the present invention is generally includes instruction.

The user of a kit makes it possible to allow the method of the present invention to be carried out in a simple way and for a short time.

EXAMPLE

Figure 5:
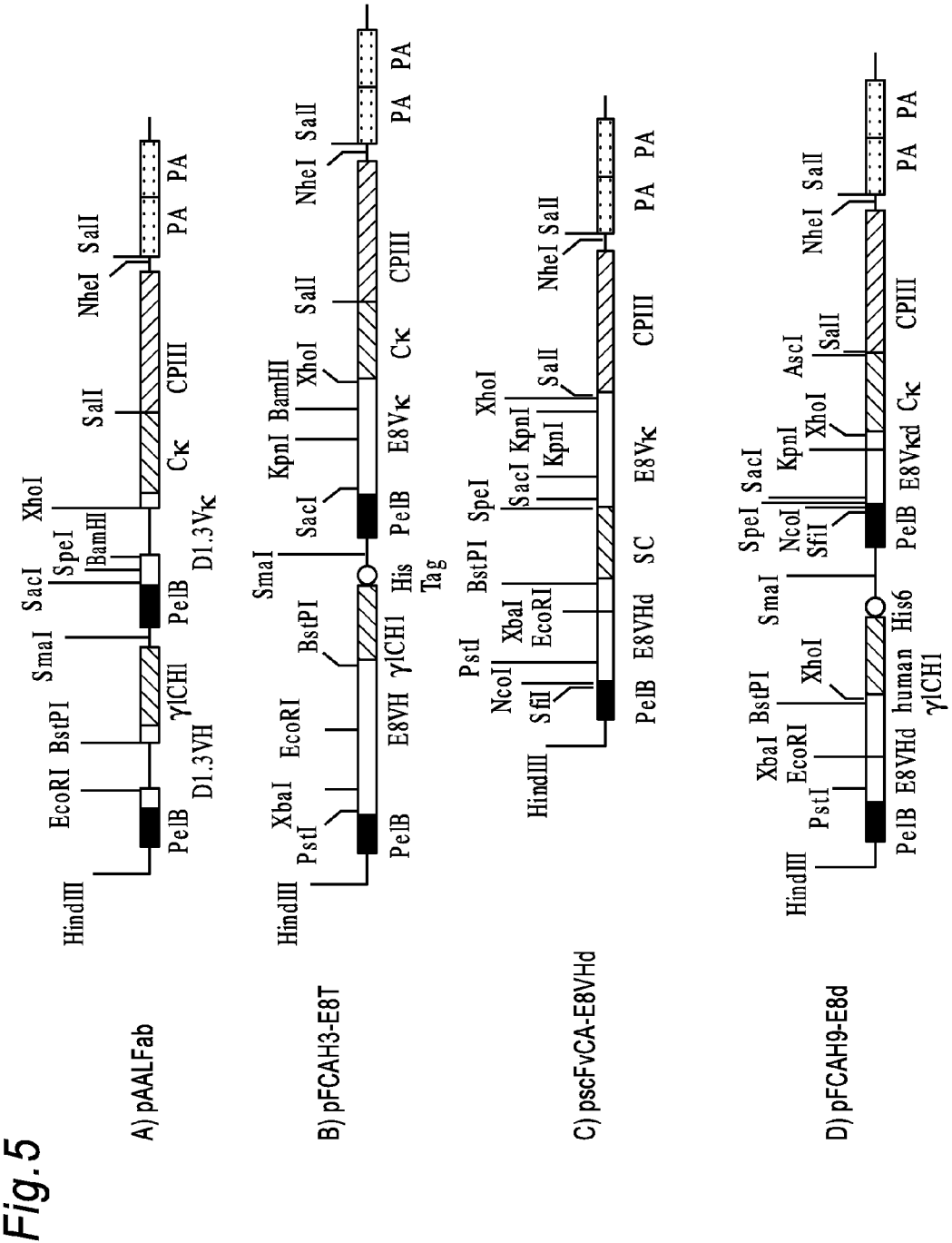
FIG. 5 is a schematic view showing a vector used for producing an scFv antibody gene library.

1. Production of Vector for Producing scFv Antibody Gene Library 1-1 Production of Vector for Producing scFv Antibody Gene Library As conceptually shown in FIG. 5, pelB (signal sequence) of M13 phage, His6 tag sequence, cp3 protein of M13 phage (Δcp3 (198aa-406aa) N-terminal deleted capsid protein 3) sequence, protein A protein sequence were incorporated in an appropriate restriction enzyme site of a pTZ19R phagemid vector (Pharmacia) so as to from a vector pAALFab (see Iba Y. et al., Gene 194: 35-46, 1997). A vector pFCAH9-E8d for incorporation was produced from this pAALFab.

Genes of a heavy chain and a light chain are inserted into the predetermined position of this vector, thereby completing an actual antibody protein expression vector. The shape of the antibody expressed by the completed vector is a scFv and a light chain constant region CL gene is bonded to the aforementioned cp3 gene. As a result, expression protein has a shape of scFv-CL-cp3. Specifically, the below-mentioned operation is carried out.

Used Primer:

```
527 Reverse (SEQ ID NO: 377):
5'-CAGGAAACAGCTATGAC-3'

599 E8VHf-PstR: (SEQ ID NO: 378)
3'-CGGCTCCAAGTCGACGTCGTCA-5'

544 E8VHf-PstF: (SEQ ID NO: 379)
5'-CAGCTGCAGCAGTCTGGGGCAGAGCTTGTGAAGCCAGGGGCCTCAGT

CAAGTTGTCCTGCACAGCTTCTGGCTTCAACATTAA-3'

545 E8VHf-XbaR: (SEQ ID NO: 380)
3'-AGACCGAAGTTGTAATTTCTGTGGATATACGTGACCCACTTCGTCTC

CGGACTTTTCCCAGATCTCACCTAACCTTCCTAA-5'

546 E8VHf-XbaF: (SEQ ID NO: 381)
5'-AAGGGTCTAGAGTGGATTGGAAGGATTGATCCTGCGAGTGGTAATAC

TAAATATGACCCGAAGGACAAGGCCACTATAACAGCA-3'

547 E8VHf-EcoR (SEQ ID NO: 382)
3'-TTCCTGTTCCGGTGATATTGTCGTCTGTGTAGGAGGTTGTGTCGGAT

GGATGTCGACTTAAGGGAC-5'
```

```
548 E8VHf-EcoF (SEQ ID NO: 383)
5'-CAGCTGAATTCCCTGACATCTGAGGACACTGCCGTCTATTACTGTGC

TGGT-3'

549 E8VHf-BstR (SEQ ID NO: 384):
3'-CAGATAATGACACGACCAATACTAATGCCGTTGAAACTGATGACCCC

GGTTCCGTGGTGCCAGTGGCACAAGG-5'

590 His6-SmaR (SEQ ID NO: 385):
3'-GGTTCTCTAACAGTAGTGGTAGTAGTGGTAATTATTCTCGATAGGGC

CCTCGAA-5'

542 E8VLf-SacF (SEQ ID NO: 386):
5'-GACATCGAGCTCACCCAGTCTCCAGCCTCCCTTTCTGCGTCTGTGGG

AGAAACTGTCACCATCACATGT-3'

539 E8VLf-KpnR (SEQ ID NO: 387):
3'-TGACAGTGGTAGTGTACAGCTCGTTCACCCTTATAAGTGTTAATAAA

TCGTACCATGGTCGTC-5'

542 E8VLf-KpnF (SEQ ID NO: 388):
5'-GCATGGTACCAGCAGAAACCAGGGAAATCTCCTCAGCTCCTGGTCTA

T-3'

543 E8VLf-BamR (SEQ ID NO: 389):
3'-GGAGTCGAGGACCAGATATTACGTTTTTGGAATCGTCTACCACACGG

TAGTTCCAAGTCACCGTCACCTAGGCCTTGTGTT-5'

562 E8VLf-XhoR (SEQ ID NO: 390):
3'-TCATGAGGCACCTGCAAGCCACCTCCGTGGTTCGAGCTCTAGTTT-5'

563 E8VLf-XhoF (SEQ ID NO: 391):
5'-AGTACTCCGTGGACGTTCGGTGGAGGCACCAAGCTCGAGATCAAA-3'

613 NheR (SEQ ID NO: 392):
3'-ATCGACAGCT-5'

600 E8VLKpnXhoR (SEQ ID NO: 393):
3'-AAGCCACCTCCATGGTTCGAGCTCTAGTTT-5'

LCP3ASC (SEQ ID NO: 394):
3'-TCGAAGTTGTCCTTACTCACAAGCCGCGCGGTCAGCTGAGGTAA-5' hCH1Bst (SEQ ID NO: 395):
5'-ACCCTGGTCACCGTCTCCTCAGCCTCCACCAAGGGCCCATCGGTCTT

CCCCCTGG-3' hCH1midAS (SEQ ID NO: 396):
3'-GGGAGTCGTCGCAGCACTGGCACGGGAGGTCGTCGAA-5' hCH1midS (SEQ ID NO: 397):
5'-GGACTCTACTCCCTCAGCAGCGTCGTGACCGTGCCC-3' hCH1H6 (SEQ ID NO: 398):
3'-GGGTCGTTGTGGTTCCACCTGTTCTTTCAACTCGGGTTTAGAACAGT

AGTGGTAGTAGTGGTA-5' hCH1H6Sma (SEQ ID NO: 399):
3'-GGGTTTAGAACAGTAGTGGTAGTAGTGGTAATTATTCTCGATAGGGC

CCTCGAACG-5'

702 BstXhoF (SEQ ID NO: 400):
5'-GGCACCACGGTCACCGTCTCGAGCGCCTCCACC-3'
```

<Production of pFCAH3-E8T H Chain Part>

1) By using pAALFab as a template, PCR using 527-599 and PCR using 547-590 were carried out so as to produce a DNA fragment.

2) PCR using 544-545, 546-547, and 548-549 was carried out so as to produce a DNA fragment.

Figure 6:
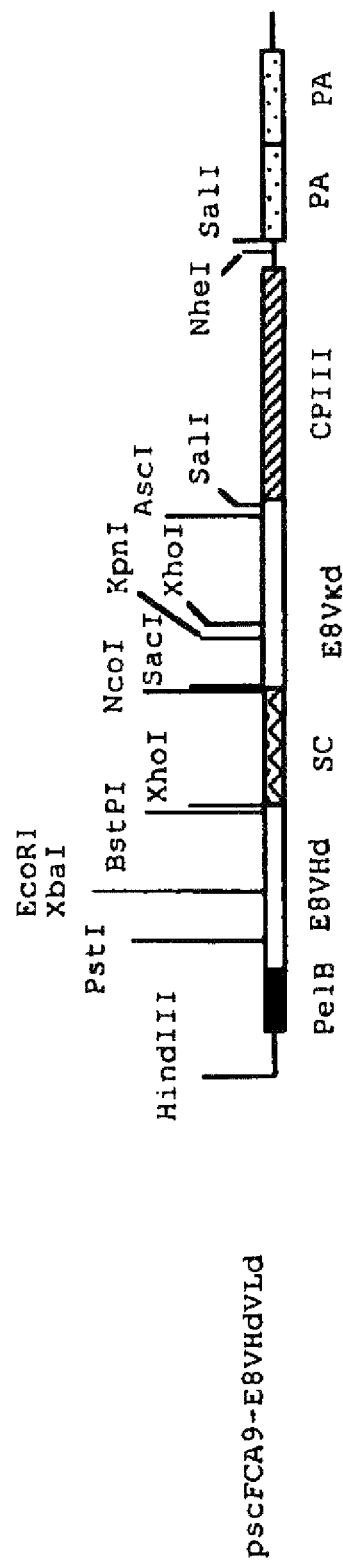
FIG. 6 is a schematic view showing a structure of pscFvCA9-E8VHdVLd.

3) 1) and 2) were mixed and PCR by 527,590 was carried out, which was cloned to a HindIII-SmaI site of pAALFab.
<pFCAH3-E8T L Chain Part>
4) PCR using 542-562 and 561-613 was carried out so as to produce a DNA fragment.
5) PCR using 538-539 and 542-543 was carried out so as to produce a DNA fragment.
6) 4) and 5) were mixed and PCR by 538, 562 was carried out, which was cloned to a SacI-NheI site of pAALFab.
<pFCAH9-E8d>
7) Production of VH Stuffer Part
pFCAH3-E8T was digested with XbaI and EcoRI and a klenow fragment was acted thereon so as to be blunted. Thereafter, the self ligation was carried out so as to produce a stuffer of the VH part.
8) Production of VL stuffer part
By using pFCAH3-E8T as a template, PCR with 527-600 was carried out, which was cloned to the HindIII-XhoI site in 7).
9) This was digested with KpnI and subjected to self-ligation so as to produce a stuffer of a VL part.
10) Introduction of SfiI, NcoI, SpeI sites
By using pFCAH3-E8T as a template, PCR with 527-663 was carried out, which was cloned to the HindIII-SacI site in 1).
11) Introduction of AscI site
By using pFCAH3-E8T as a template, PCR with 527-LCP3ASC was carried out, which was cloned to 2) which was completely digested with SacI and partially digested with SalI.
12) Transform of gammaCH1 part into human gene
Since human gamma CH1 part has BstPI site, cloning was carried out so as to design this site. By using tonsil cDNA as a template, PCR with hCH1Bst-hCH1midS, hCH1midAS-hCH1H6 was carried out and then mixed. PCR with hCH1Bst-hCH16Sma was carried out and the DNA fragment was cloned to the BstPI-Sma site in 3).
13) Introduction of Xho site
By using 12) as a template, PCR with 702-663 was carried out and this was cloned to the BstPI-SacI site in 12).
<Production of pscFvCA9-E8VHdVLd>
pFCAH9-E8d 3 µg (3 µL) (see FIG. 5D) was mixed with BstPI (3 U/µL) (3 µL), 10×H buffer (5 µL), DW (39 µL) and subjected to restriction enzyme treatment at 37° C. for two hours. After treatment, precipitates obtained by ethanol precipitation were dissolved in 10 µL of TE buffer. To this solution, SacI (10 U/µL) (1 µL), 10×L buffer (5 µL) and DW (34 µL) were mixed. Then, this mixture was subjected to restriction enzyme treatment at 37° C. for two hours and to agarose gel electrophoresis. Thus, 4.7 kb fragment was recovered. The recovered products were subjected to ethanol precipitation to give 10 µL (pFCAH9-E8d BstPI-SacI fragment).
On the other hand, a primer linF (100 pmol/µL) (5 µL) and a primer linR (100 pmol/µL) (5 µL) were mixed and heated at 94° C. for 5 minutes, and then annealed at 80° C. for 5 minutes, at 70° C. for 5 minutes, and at room temperature for 30 minutes. Two µL of which was mixed with the above-obtained pFCAH9-E8d BstPI-SacI fragment (1 µL), 10× ligation buffer (1.5 µL), DW (9.5 µL), and T4DNA ligase (1 µL) and reacted at 16° C. for 16 hours. After reaction, the reacted product was subjected to ethanol precipitation to concentrate to 3 µL. 1.5 µL of them was used to transform E. coli DH12S competent cells (20 µL) by electroporation. The obtained plasmid clone was extracted and the base sequence thereof was confirmed. This was named pscFvCA9-E8VHdVLd. FIG. 6 schematically shows a structure of pscFvCA9-E8VHdVLd. Furthermore, FIGS. 7-1 to 7-2 show the base sequence (SEQ ID NO: 401) of the insert part of pscFvCA9-E8VHdVLd and the amino acid sequence (SEQ ID NO: 402) encoded thereby, respectively.

```
primer linF
                                        (SEQ ID NO: 403)
GTCACCGTCTCGAGAGGCGGTGGCGGATCAGGTGGCGGTGGAAGTGGCGG

TGGTGGGTCCATGGCCGACATCGAGCT primer linR
                                        (SEQ ID NO: 404)
CGATGTCGGCCATGGACCCACCACCGCCACTTCCACCGCCACCTGATCCG

CCACCGCCTCTCGAGACG
```

1-2 Production of Vector for Temporarily Cloning Heavy Chain Variable Region (VH)
According to the well-known technique (see Iba Y. et al., Gene 194:35-46, 1997), firstly, a pAALFab vector (FIG. 5A) was produced. A portion between XbaI and EcoRI was deleted from the pAALFab vector, and the restriction enzyme cut sites Kpn I, Sfi I, Nco I, and Spe I were newly added. Through pFCAH3-E8T (FIG. 5B), a vector pscFvCA-E8VHd (FIG. 5C) capable of cloning VH (heavy chain variable region) was produced. Thus, a vector for temporarily cloning the heavy chain variable region (VH) was obtained. FIGS. 8-1 to 8-2 show the base sequence (SEQ ID NO: 405) of the insert of pscFvCA-E8VHd, the restriction enzyme site and the amino acid sequence (SEQ ID NO: 406) encoded by the base sequence.
Specifically, the primer 610 and the primer 611 were annealed and annealed produced was cloned to a BstPI-SacI site of pFCAH3-E8T. Thus, a single chain was produced. Furthermore, PCR with the primer 527 and the primer 619 was carried out and this was further cloned to a HindIII-PstI site. Thus, introduction of SfiI, NcoI site was carried out. Hereinafter, primer sequences used for producing the vector are shown.

```
610 scBstSpeSacF (SEQ ID NO: 407):
5'-CACCACGGTCACCGTCTCCTCAGGCGGTGGCGGATCAGGTGGCGGTG

GAAGTGGCGGTGGTGGGTCTACTAGTGACATCGAGCTCACCCAG-3'

611 scBstSpeSacR (SEQ ID NO: 408):
3'-GTGGTGCCAGTGGCAGAGGAGTCCGCCACCGCCTAGTCCACCGCCAC

CTTCACCGCCACCACCCAGATGATCACTGTAGCTCGAGTGGGTC-5'

527 Reverse (SEQ ID NO: 409):
5'-CAGGAAACAGCTATGAC-3'

619 E8VHf-SfiNcoPstR (SEQ ID NO: 410):
3'-GACGCCGGGTCGGCCGGTACCGGCTCCAAGTCGACGTCGTCA-5'
```

2. Production of Immunoglobulin Light Chain Library 2-1 Isolation of Immunoglobulin Light Chain Gene by Using PCR
From bone marrow cells (sample No. 59) 4×10⁷ cells, and lymphocytes of cord blood and peripheral blood, by using a commercially available kit (Pharmacia Biotech, QuickPrep Micro mRNA Purification Kit), 2.6 µg of mRNA was obtained. From this mRNA, cDNA was produced. The cDNA was produced by using SuperScriptPreamplification System (GibcoBRL). As a primer, oligo dT was used. PCR using the obtained cDNA as a template was carried out by using 5' primer (κ1-κ6, λ1-λ6) and 3' primer (hCKASC primer or hCLASC primer) for obtaining light chain genes. The PCR product was treated with phenol, subjected to ethanol precipitation and suspended in 10 µL of TE buffer. The base sequence of primer and conditions of PCR are shown below. In the base sequence of a primer for obtaining light chain genes, underline part represents NcoI site and AscI site.

5' primer κ1-κ6
hVK1a (SEQ ID NO: 411):
GTCCTCGCAACTGCGGCCCAGCCGGCCATGGCC

GACATCCAGATGACCCAGTCTCC hVK2a (SEQ ID NO: 412):
GTCCTCGCAACTGCGGCCCAGCCGGCCATGGCC

GATGTTGTGATGACTCAGTCTCC hVK3a (SEQ ID NO: 413):
GTCCTCGCAACTGCGGCCCAGCCGGCCATGGCC

GAAATTGTGTTGACGCAGTCTCC hVK4a (SEQ ID NO: 414):
GTCCTCGCAACTGCGGCCCAGCCGGCCATGGCC

GACATCGTGATGACCCAGTCTCC hVK5a (SEQ ID NO: 415):
GTCCTCGCAACTGCGGCCCAGCCGGCCATGGCC

GAAACGACACTCACGCAGTCTCC hVK6a (SEQ ID NO: 416):
GTCCTCGCAACTGCGGCCCAGCCGGCCATGGCC

GAAATTGTGCTGACTCAGTCTCC

5' primer λ1-λ6
hVL1 (SEQ ID NO: 417):
GTCCTCGCAACTGCGGCCCAGCCGGCCATGGCC

CAGTCTGTGTTGACGCAGCCGCC hVL2 (SEQ ID NO: 418):
GTCCTCGCAACTGCGGCCCAGCCGGCCATGGCC

CAGTCTGCCCTGACTCAGCCTGC hVK3a (SEQ ID NO: 419):
GTCCTCGCAACTGCGGCCCAGCCGGCCATGGCC

TCCTATGTGCTGACTCAGCCACC hVL3b (SEQ ID NO: 420):
GTCCTCGCAACTGCGGCCCAGCCGGCCATGGCC

TCTTCTGAGCTGACTCAGGACCC hVL4 (SEQ ID NO: 421):
GTCCTCGCAACTGCGGCCCAGCCGGCCATGGCC

CACGTTATACTGACTCAACCGCC hVL5 (SEQ ID NO: 422):
GTCCTCGCAACTGCGGCCCAGCCGGCCATGGCC

CAGGCTGTGCTCACTCAGCCGCC hVL6 (SEQ ID NO: 423):
GTCCTCGCAACTGCGGCCCAGCCGGCCATGGCC

AATTTTATGCTGACTCAGCCCCA

3'- primer hCKASC (SEQ ID NO: 424):
TCGACTGGCGCGCCGAACACTCTCCCCTGTTGAAGCTCTTTGTG 3'- primer HCLASC (SEQ ID NO: 425):
TCGACTGGCGCGCCGAACATTCTGTAGGGGCCACTGTCTTCTC Conditions of PCR

| cDNA | 2 μL |
| 10 × buffer #1 (attached to KOD) | 10 μL |
| dNTP mix (2.0 mM) | 10 μL |
| 25 mM MgCl2 | 4 μL |
| 5' side primer (100 pmol/μL) | 1 μL |
| 3' side primer (100 pmol/μL) | 1 μL |
| sterilized MilliQ | 71 μL |
| KOD DNA polymerase (TYOBO CO LTD., 2.5 U/μL) | 1 μL |

35 cycles, each cycle includes 94° C. for one minute, 55° C. for two minutes and 74° C. for one minute 2-2-1 Incorporation of Light Chain Gene into Phagemid The PCR product obtained in 1 was treated with a restriction enzyme in the following conditions.

| PCR product | 10 μL |
| 10 × NEB4 (attached to AscI) | 5 μL |
| Sterilized MilliQ | 33 μL |
| AscI (NEB, 10 U/μL) | 1 μL |
| NcoI (TAKARA SHUZO, 10 U/μL) | 1 μL |

After the reaction at 37° C. for one hour and at 50° C. for one hour, 10 μL of the reacted product was subjected to agarose gel electrophoresis and 600 bp band was cut out to be purified by using geneclean II kit (Funakoshi Corporation). Similar to the PCR product, restriction enzyme-treated pscFvCA9-E8VHdVLd was purified by using geneclean II kit and reacted with the restriction enzyme-treated PCR product at 16° C. for four hours to overnight in the following conditions, thereby carrying out ligation.

| restriction enzyme-treated pscFvCA9-E8VHdVLd | 2 μL |
| restriction enzyme-treated PCR product | 1 μL |
| 10 × ligation buffer (attached to T4 DNA ligase) | 1.5 μL |
| 10 mM ATP | 1.5 μL |
| sterilized MilliQ | 8 μL |
| T4 DNA ligase (TAKARA SHUZO 10 U/μL) | 1 μL |

2-2-2 Introduction of Phagemid into *E. coli*

The obtained ligated DNA was used so as to transform *E. coli* DH12S as follows. That is to say, ligated DNA was subjected to ethanol precipitation once, and dissolved in 3 μL of ⅕ TE (TE that was 5-fold diluted with sterilized MilliQ). 1.5 μL of them was suspended in 20 μL of competent cell DH12S (GIBCO BRL), which was subjected to electroporation in the following conditions.

Electroporator
Cell-Porator (Cat. series 1600), product of BRL

| Setting conditions; voltage booster | 4 kΩ |
| capacitance | 330 μF |
| DC volts | LowΩ |
| charge rate | Fast |

The above-mentioned transformed *E. coli* was planted on a transformation medium (SOB) (2 mL) and shaking cultured at 37° C. for one hour. Then, a part of the cultured product was planted on agar medium (Amp plate) and a remaining part was cultured in a 2×TY medium containing 0.1% glucose and 100 μg/mL ampicillin to form glycerine stock. The agar medium was incubated at 30° C. and growing colony was separated by picking by a picker. A plasmid was prepared, respectively. Then, the light chain gene and the base sequence were examined.

SOB medium: to 950 mL of purified water, the following components were added and shaken so as to be dissolved completely. Thereafter, 250 mM KCl solution (10 mL) was added so as to adjust to pH 7.0 with 5N NaOH. Purified water was added to adjust to 1000 mL, then sterilized for 20 minutes in the autoclave. Immediately before the use, 5 mL of 2M sterilized MgCl$_2$ was added.

| bacto-tryptone | 20 g |
|---|---|
| bacto-yeast extract | 5 g |
| NaCl | 0.5 g |

2×YT medium: to 900 mL of purified water, the following components were added and shaken so as to be dissolved completely. Thereafter, 5 N NaOH was added so as to adjust to pH 7.0 with 5N NaOH. Purified water was added to adjust to 1000 mL, then sterilized for 20 minutes in the autoclave and used.

| bacto-tryptone | 16 g |
|---|---|
| bacto-yeast extract | 10 g |
| NaCl | 5 g |

The other reagents were purchased form the following suppliers.
(Manufacture/Product Name are Described in this Order)
SIGMA/ampicillin sodium
Wako Pure Chemical/phenol
SIGMA/BSA
DIFCO/2×YT medium
Wako Pure Chemical/kanamycin sulfate
nacalai tesque/polyethylene glycol 6000
nacalai tesque/Tween 20
KATAYAMA CHEMICAL/NaCl
Wako Pure Chemical/IPTG
Wako Pure Chemical/skim milk
Wako Pure Chemical/sodium azide
Wako Pure Chemical/triethylamine
Wako Pure Chemical/hydrogen peroxide
Wako Pure Chemical/OPD tablet
Wako Pure Chemical/ethanol The above-mentioned operation is carried out with respect to all of κ1, κ2, κ3, κ4, κ5, and κ6, as well as λ1, λ2, λ3a, λ3b, λ4, λ5, λ6, λ7, λ8, λ9, and λ10 are operated so as to confirm whether or not the intended clones are obtained. Then, for example, κ1 and κ2, clones in each group, were mixed so that the ratio becomes near the frequency of use. The rate of expression of each group of these light chains in an actual living body is already known. These gene clones amplified by PCR method and incorporated into a vector are mixed so that the ratio becomes near the frequency of use. Thus, VL library was obtained. Constituent ratio in each family in VL library is shown below.

TABLE 1

Vκ

| family | Usage frequency in vivo(%)* | Constitutive ratio in VL library(%) | Constitutive ratio in KL200(%) |
|---|---|---|---|
| Vκ1 | 39 | 37 | 30.7 |
| Vκ2 | 12 | 12 | 19.8 |
| Vκ3 | 36 | 35 | 33.7 |
| Vκ4 | 12 | 12 | 10.9 |
| Vκ5 | 1 | 2 | 5.0 |
| Vκ6 | —** | 2*** | 0.0 |

*Griffith A D et al. EMBO J. (1994) 13, 3245-60.
**Published data is not shown
***equal amount of cDNA produced with primer VK6-2 and cDNA produced with primer VK6-3 were mixed.

TABLE 2

Vλ

| family | Usage frequency in vivo(%)* | Constitutive ratio in VL library(%) | Constitutive ratio in KL200(%) |
|---|---|---|---|
| Vλ1 | 43 | 41 | 34.1 |
| Vλ2 | 15 | 15*[3] | 15.2 |
| Vλ3 | 34 | 32*[4] | 25.3 |
| Vλ4 | 0 | 1.5*[5] | 0.0 |
| Vλ5 | 0 | 1.0*[6] | 11.1 |
| Vλ6 | 0 | 1.0 | 14.1 |
| Vλ7 | 6 | 6 | 0.0 |
| Vλ8 | 1 | 1 | 0.0 |
| Vλ9 | 1 | 1 | 0.0 |
| Vλ10 | —*[2] | 1 | 0.0 |

*Griffith A D et al. EMBO J. (1994) 13, 3245-60.
*[2]Published data is not shown
*[3]cDNA produced with primer VL2 (5%) and cDNA produced with primer VL2-2 (10%) were mixed.
*[4]cDNA produced with primer VL3a-2 (17%) and cDNA produced with primer VL3b (15%)
*[5]cDNA produced with primer VL4a (0.5%), cDNA produced with primer VL4b (0.5%) and cDNA produced with primer VL4c (0.5%) were mixed.
*[6]cDNA produced with primer VL5abde (0.5%) and cDNA produced with cDNA (0.5%) were mixed.

3. Production of Combinatorial Library of Light Chain Gene Library and Heavy Chain Gene Library (scFv Antibody Gene Library)

3-1-1 Isolation of Immunoglobulin Heavy Chain Gene Using PCR

By the procedure similar to 2-1, cDNA was prepared by using cord blood, bone marrow fluid, and lymphocyte of peripheral blood as well as a human μ primer (below-mentioned primer, 634) from the tonsil or random hexamer. By using this cDNA as a template, a mixture of equal amount of 5' primer (VH1 to VH7) and 3' primer (four kinds of human JH primers are mixed in equal amount, below-mentioned primers 697 to 700) for obtaining a human antibody heavy chain gene, or human μ primer (below-mentioned primer 634) were subjected to PCR. In Table, underlined parts show the SfiI site. Since hVH2a did not correspond to a germ line VH2 family, VH2a-2 was newly designed. Furthermore, since hhVH4a did not correspond to the entire VH4 family, hVH4a-2 was newly designed. Also, VH5a did not correspond to a germ line VH5 subfamily, VH5a-2 was newly designed. Furthermore, as a primer corresponding to VH7, hVH7 was designed. These were also subjected to gene amplification and incorporated into pscFvCA-E8VHd. Then, as to the obtained genes, the base sequence was determined. Since the sequence of hVH5a-2 is extremely similar to that of hVH1a and it is expected that the gene product similar to that amplified with hVH1a, this was not used. The PCR products were subjected to phenol treatment and then ethanol precipitation, and thereafter suspended in 10 μL of TE buffer.

```
634 hum μ CH1R (SEQ ID NO: 426):
    ATGGAGTCGGGAAGGAAGTC
```

Primers used for amplification of each VH family

Human VH primer, SfiI site is underlined.

```
628 hVH1a (SEQ ID NO: 427):
GTCCTCGCAACTGCGGCCCAGCCGGCCATGGCC

CAGGTGCAGCTGGTGCAGTCTGG
```

```
-continued
629 hVH2a (SEQ ID NO: 428):
GTCCTCGCAACTGCGGCCCAGCCGGCCATGGCC

CAGGTCAACTTAAGGGAGTCTGG 630 hVH3a (SEQ ID NO: 429):
GTCCTCGCAACTGCGGCCCAGCCGGCCATGGCC

GAGGTGCAGCTGGTGGAGTCTGG 631 hVH4a (SEQ ID NO: 430):
GTCCTCGCAACTGCGGCCCAGCCGGCCATGGCC

CAGGTGCAGCTGCAGGAGTCGGG 632 hVH5a (SEQ ID NO: 431):
GTCCTCGCAACTGCGGCCCAGCCGGCCATGGCC

CAGGTGCAGCTGTTGCAGTCTGC 633 hVH6a (SEQ ID NO: 432):
GTCCTCGCAACTGCGGCCCAGCCGGCCATGGCC

CAGGTACAGCTGCAGCAGTCAGG 629-2 hVH2a-2 (SEQ ID NO: 433):
GTCCTCGCAACTGCGGCCCAGCCGGCCATGGCC

CAGRTCACCTTGAAGGAGTCTGG TCC 631-2 hVH4a-2 (SEQ ID NO: 434):
GTCCTCGCAACTGCGGCCCAGCCGGCCATGGCC

CAGGTGCAGCTACAGCAGTGGGG 632-2 hVH5a-2 (SEQ ID NO: 435):
GTCCTCGCAACTGCGGCCCAGCCGGCCATGGCC

GAGGTGCAGCTGGTGCAGTCTGG 712 hVH7 (SEQ ID NO: 436):
GTCCTCGCAACTGCGGCCCAGCCGGCCATGGCC

CAGGTGCAGCTGGTGCAATCTGG GTCTGAGT
```

Human JH primer, BstPI and XhoI sites underlined.

```
697 hJH1-2 (SEQ ID NO: 437):
GGTGGAGGCACTCGAGACGGTGACCAGGGTGC 698 hJH3 (SEQ ID NO: 438):
GGTGGAGGCACTCGAGACGGTGACCATTGTCC 699 hJH4-5 (SEQ ID NO: 439):
GGTGGAGGCACTCGAGACGGTGACCAGGGTTC 700 hJH6 (SEQ ID NO: 440):
GGTGGAGGCACTCGAGACGGTGACCGTGGTCC
```

| cDNA | 2 μL |
|---|---|
| 10 × buffer #1 (attached to KOD) | 10 μL |
| dNTP mix (2.0 mM) | 10 μL |
| 25 mM MgCl2 | 4 μL |
| 5' primer (100 pmol/μL) | 1 μL |
| 3' primer (100 pmol/μL) | 1 μL |
| sterilized MilliQ | 71 μL |
| KOD DNA polymerase (TYOBO CO LTD., 2.5 U/μL) | 1 μL |

PCR conditions: 35 cycles, each cycle includes 94° C. for one minute, 55° C. for two minutes and 74° C. for one minute 3-1-2 Production of Heavy Chain Gene Library The PCR product obtained in 3-1-1 was treated with a restriction enzyme in the following conditions.

| PCR product | 10 μL |
|---|---|
| 10 × K buffer NEB4 (TAKARA SHUZO) | 5 μL |
| Sterilized MilliQ | 33 μL |
| SfiI (NEB, 10 U/μL) | 1 μL |
| XhoI (TAKARA SHUZO, 12 U/μL) | 1 μL |

After the reaction at 37° C. for two hours, 10 μL of the reacted product was subjected to agarose electrophoresis and 400 bp band was cut out to be purified by using geneclean II kit (Funakoshi Corporation). Similar to the PCR product, restriction enzyme-treated pscFvCA-E8VHd was purified by using geneclean II kit and reacted with the restriction enzyme-treated PCR product at 16° C. for four hours to overnight in the following conditions, thereby carrying out ligation.

| restriction enzyme-treated pscFvCA-E8VHd | 2 μL |
|---|---|
| restriction enzyme-treated PCR product | 1 μL |
| 10 × ligation buffer (attached to T4 DNA ligase) | 1.5 μL |
| 10 mM ATP | 1.5 μL |
| sterilized MilliQ | 8 μL |
| T4 DNA ligase (TAKARA SHUZO 10 U/μL) | 1 μL |

3-1-3 Introduction of Phagemid into *E. coli*

The obtained DNA was transformed into *E. coli* DH12S. Specifically, DNA was subjected to ethanol precipitation once, and dissolved in 3 μL of ⅕ TE (TE that was 5-fold diluted with sterilized MilliQ). 1.5 μL of them was suspended in 20 μL of competent cell DH12S (GIBCO BRL), which was subjected to electroporation.

Electroporator

| Cell-Porator (Cat. series 1600), product of BRL | |
|---|---|
| Setting conditions; voltage booster | 4 kΩ |
| capacitance | 330 μF |
| DC volts | Low Ω |
| charge rate | Fast |

The above-mentioned transformed *E. coli* was planted on a transformation medium (SOB) (2 mL) and shaking cultured at 37° C. for one hour. Then, a part of the cultured product was planted on agar medium (Amp plate) and a remaining part was cultured in a 2×YT medium containing 0.1% glucose and 100 μg/mL ampicillin to form glycerine stock. The agar medium was incubated at 30° C. and growing colony was separated by picking by a picker. A plasmid was prepared, respectively. Then, the heavy chain gene and the base sequence were examined. All of the VH1 to VH7 were treated in the same way to confirm whether or not the target clone was obtained. These clones of each group (family) were mixed so that the ratio was near the use frequency in vivo. Thus, VH library was produced. The constitution ratio of each family in the VH library is shown below.

TABLE 3

| family | Usage frequency in vivo(%)* | Constitutive ratio in VH library(%) |
|---|---|---|
| VH1 | 25 | 29** |
| VH2 | 6.6 | 7 |
| VH3 | 40 | 40 |
| VH4 | 19 | 19*** |
| VH5 | 5 | —** |

TABLE 3-continued

| family | Usage frequency in vivo(%)* | Constitutive ratio in VH library(%) |
|---|---|---|
| VH6 | 3.8 | 4 |
| VH7 | 1.2 | 2 |

*Griffith A D et al. EMBO J. (1994) 13, 3245-60.
**Actually, since VH1 and VH5 are amplified with the same primer, they cannot be counted separately.
***cDNA produced with VH4 primer and cDNA produced with VH4-2 primer were mixed in this ratio.

3-2 Production of Combinatorial Gene Library

VH library (200 µg) was digested with HindIII and XhoI under the following conditions and heavy chain gene is cut out and purified by using geneclean II kit.

| | |
|---|---|
| VH library 200 µg | 100 µL |
| 10 × K buffer (TAKARA SHUZO) | 40 µL |
| sterilized MilliQ | 205 µL |
| HindIII (TAKARA SHUZO 40 U/µL) | 30 µL |
| XhoI (TAKARA SHUZO 50 U/µL) | 25 µL |

A vector pscFvCA9-E8VHdVLd in which a VL library had been inserted was digested with HindIII and XhoI under the following conditions, and a fragment containing a light chain gene was purified by using geneclean II kit.

| | |
|---|---|
| pscFvCA9-E8VHdVLd in which a VL library had been inserted | 100 µg, 100 µL |
| 10 × K buffer (TAKARA SHUZO) | 40 µL |
| sterilized Milli-Q | 230 µL |
| HindIII (TAKARA SHUZO 40 U/µL) | 15 µL |
| XhoI (TAKARA SHUZO 50 U/µL) | 15 µL |

Next, a VH gene library fragment and a pscFvCA9-E8VHdVLd vector into which a light chain gene has been inserted were reacted at 16° C. overnight in the following conditions so as to be ligated.

| | |
|---|---|
| restriction enzyme-treated VH library fragment | 10 µg 50 µL |
| pscFvCA9-E8VHdVLd containing restriction enzyme-treated VL library fragment | 40 µg 50 µL |
| 10 × ligation buffer (attached to T4 DNA ligase) | 100 µL |
| 10 mM ATP | 100 µL |
| Sterilized MilliQ | 670 µL |
| T4 DNA ligase (TAKARA SHUZO 10 U/µL) | 30 µL |

The DNA in which the reaction had been completed was used to transform *E. coli* DH12S. Specifically, DNA was subjected to ethanol precipitation once, and dissolved in 30 µL of ⅕ TE (TE 5-fold diluted with sterilized MilliQ). This was suspended in 500 µL of competent cell DH12S (GIBCO BRL), and electroporation was carried out.
Electroporator

| Cell-Porator (Cat. series 1600), product of BRL | |
|---|---|
| Setting conditions; voltage booster | 4 kΩ |
| capacitance | 330 µF |
| DC volts | LowΩ |
| charge rate | Fast |

The above-mentioned transformed *E. coli* was planted on a transformation medium (SOB) (12 mL) and shaking cultured at 37° C. for one hour. Then, a part of the cultured product was planted on agar medium (Amp plate) and a remaining part was cultured in a 2×YT medium (500 mL) containing 0.1% glucose and 100 µg/mL ampicillin to form glycerine stock. The agar medium was incubated at 30° C. and the number of clones were estimated from the number of growing colonies. $8.5 \times 10^{10}$ clones were obtained.

4. Production of scFv-CL Antibody Phage Library from scFv-CL Antibody Gene Library To 16 of 5-liter flasks containing 300 mL of 2×YT medium to which 1% glucose and 100 µg/mL ampicillin had been added, 2.5 mL of AIMS-5 suspension was added and shaking cultured at 37° C. Every one hour, the absorbance at the wavelength of 600 nm was measured and the culture solution was proliferated until the absorbance became 1.0. To the culture solution, 12 mL each of helper phage solution (M13KO7) was added for each flask so as to infect the helper phage, culture at 37° C. for two hours. Thus, phage infected DH12S was obtained.

To 24 of 5-L flasks, 2×YT medium (600 mL), 100 µg/mL ampicillin (0.6 mL), 50 µg/m 38 L kanamycin (0.8 mL), and helper phage infected DH12S (200 mL) were added and shaking cultured at 37° C. for 20 hours.

The bacterial cells were centrifuged at 8000 rpm at 4° C. for 10 minutes, and supernatant was recovered. 4 L of 20% polyethylene glycol/2.5M NaCl was added to the supernatant, after it was quietly stirred for about 20 minutes, centrifuged at 8000 rpm at 4° C. for 20 minutes. The precipitate was dissolved in 1 L of PBS, 200 mL of 20% polyethylene glycol/2.5M NaCl was added thereto, after it was quietly stirred for about 20 minutes, and centrifuged at 8000 rpm at 4° C. for 20 minutes. The supernatant was discarded and further, centrifuged at 8000 rpm at 4° C. for 3 minutes, and the precipitate was recovered. The precipitate was dissolved in PBS to which 0.05% $NaN_3$ was added, after it was centrifuged at 1000 rpm at 4° C. for 15 minutes and the supernatant was recovered, further, centrifuged at 8000 rpm at 4° C. for 3 minutes and the supernatant was recovered.

The titer of the recovered phage solution was checked as followings: the phage solution was diluted with PBS in $10^6$, $10^7$ and $10^8$-fold, out of these, 10 µL was infected with 990 µL of DH12S, cultured at 37° C. for one hour. 100 µL of them was plated on LBGA plate and cultured at 30° C. for 18 hours. The titer of the stock solution before dilution was calculated by counting the number of colonies. The stock solution of the phage solution was suspended in PBS containing 0.05% $NaN_3$ so as to be $2 \times 10^{14}$/mL.

5. Obtaining of Antibody Clone Specific to Cancer Cell

5-1 Phage Antibody Screening Using Cancer Cell Line

Phage antibodies of various cancer cell lines or clinical specimens were isolated by the following procedure. Kinds of used cell lines are described below. The culture conditions of the cell line are show in Table of FIG. 38.

pancreatic cancer cell lines PANC-1, MIA-Paca2
kidney cancer cell lines CCFRC1, Caki-1, CCFRC1, Caki-1, ACHN
ovarian cancer cell lines KF28, RMG-1, RMG-2, SKOv3
stomach cancer cell lines SNU-5, MKN45, NCI-N87
lung squamous cell carcinoma lines RERF-LC-AI, EBC1
pulmonary adenocarcinoma cell lines Calu-3, NCI-H441, A549, PC14
hepatic cell carcinoma cell lines HepG2, OCTH, Hep3B
hepatic cell carcinoma clinical specimen (HCV positive), intrahepatic bile duct cell carcinoma cell line RBE
stomach cancer cell lines SNU5, MKN45, NCI-N87
large bowel cancer cell lines CW2, CaCo2
acute myelocytic leukemia, AML clinical specimen An adherent cell line group in 6 well plate (Falcon 3516) and a suspended cell line such as ATL-derived cell line in suspended culture flask (70 ml (slant neck)), which had been cultured in a medium (RPMI-1640: Sigma-Aldrich, 10% fetal calf serum, 1% penicillin-streptomycin solution) in a $CO_2$ incubator at 37° C., were used.

The adherent cell line was dissociated from culture dish with 2 mg/ml collagenase I (Gibco BRL)/cell dissociation buffer (Gibco BRL), and then recovered with 10% FBS/DMEM. On the other hand, the suspended cells were, as they were, centrifuged (400×g, 4° C., two minutes) to remove the medium once.

After such operation, each cell was washed with 1% BSA, 0.05% $NaN_3$/PBS (BSA solution) and centrifuged (400×g, 4° C., two minutes) to remove the supernatant.

Cells from the clinical specimen derived from clinical tissue material prepared in 6 well plate (Falcon 3516), which had been cultured in a medium (RPMI-1640: Sigma-Aldrich, 10% fetal calf serum, 1% penicillin-streptomycin solution) in a $CO_2$ incubator at 37° C., were used.

Cells were washed with cooled PBS and $4 \times 10^7$ of cells were used for screening. This was mixed with $1 \times 10^{13}$ cfu of human antibody phage library, so that the final concentration of the reaction solution was made to be 1% BSA-0.1% $NaN_3$/MEM and the volume was made to be 1.6 ml. The reaction was carried out while rotating slowly at 4° C. for four hours. After the reaction was completed, the reaction solution was divided into two parts and each part was stratified on 0.6 ml of organic solution (dibutyl phtalate cycloheximide 9:1) and subjected to centrifugation at centrifugal force of 3000 rpm by using a micro-centrifugal machine for two minutes, so that cells were allowed to precipitate at the bottom of the tube. From each tube, the solution was discarded and cells were suspended in 0.7 ml of 1% BSA/MEM, stratified on 0.7 ml of organic solvent and subjected to centrifugation. This operation was repeated again. Then the solution was discarded and cells were suspended in 0.3 ml PBS, frozen with liquid nitrogen and melted at 37° C.

This was infected with 20 ml of E. coli DH12S (OD 0.5) for one hour, the part of it was plated on an Ampicillin plate and the titer of the collected phage was calculated. Phage infected E. coli was cultured over night in 600 ml of 2×YTGA culture medium (2×YT, 200 µg/ml ampicillin sulfate, 1% glucose) at 30° C. overnight. The cultured product (10 ml) that had been cultured over night was mixed with 200 ml of 2×YTA culture medium (2×YT, 200 µg/ml ampicillin sulfate) and cultured at 37° C. for 1 hour. Thereafter, helper phage KO7 ($1 \times 10^{11}$) was placed and cultured at 37° C. for 1.5 hour. Then, 800 ml of 2×YTGAK (2×YT, 200 µg/ml ampicillin sulfate, 0.05% glucose, 50 µg/ml kanamycin) was placed and cultured over night at 30° C. This was centrifuged at 8000 rpm for ten minutes so as to prepare 1 l of supernatant. To this, 200 ml of PEG solution (20% polyetyleneglycol 6000, 2.5M NaCl) was mixed and agitated sufficiently. Thereafter, the mixture was centrifuged at 8000 rpm for 10 minutes so as to precipitate phage. This was suspended in 10 ml of PBS/0.05% $NaN_3$ and the part of it was used so as to examine the number of infected E. coli. This is the phase of the 1st screening.

For the 2nd screening, $2 \times 10^7$ of cells and $1 \times 10^{10}$ cfu of the 1st screening phages were used, so that the volume of the reaction solution was made to be 0.8 ml. The reaction solution was 1% BSA-0.1% $NaN_3$/MEM and the entire scale was carried out equal to that of the 1st screening.

The 3rd screening was carried out in the same conditions as those of the 2nd screening except that $1 \times 10^9$ cfu of 2nd phages were used.

When the recovering rate of the phages is increased, the screening round is stopped at the time. When the recovering rate is not increased, the 4th screening or later are carried out in the same manner by using the phage recovered immediately before round and by using $1 \times 10^9$ cfu of phages.

The screening of various cell lines was carried out by the same method as that of the screening mentioned above.

5-2 Selection of Antibody Clone

In the screening of HepG2 as an example, because the recovering rate of HepG2 was increased in the 3rd screening (FIG. 9), it was judged that HepG2 cell specific antibody clone was concentrated in this stage, and several hundreds clones were picked up. Next, when the base sequence of H-chain portions of these positive clones was analyzed, antibodies obtained by removing the overlap from the kinds of base sequences were classified. These were examined for expression. Furthermore, expression positive clones were selected by the following procedures.

6. Base Sequence Determination of Antibody Clone

E. coli, infected with antibody phage, obtained by screening was diluted and plated on a nutrient agar medium containing 100 µg/ml of ampicillin. The obtained colonies were picked up and cultured in 2×YTGA culture medium at 30° C. overnight. DNA was extracted by using KURABO PI-50 and the base sequence was determined by a dideoxy method. The overlapped clones having the same base sequence were removed. Furthermore, this culture medium cultured overnight (0.05 ml) was plated on 1.2 ml of 2×YTAI (2×YT, 200 µg/ml ampicillin sulfate, 0.5 mM IPTG) and cultured overnight at 30° C., centrifuged by using a micro-centrifugal machine at 15000 rpm for 5 minutes, and supernatant was obtained.

7. Confirmation of Expression of Antibody Clone 7-1 Selection of Antibody Clone

Since the antibody was expressed as cp3 fused protein, the expression using the protein was examined. That is to say, firstly, the supernatant obtained in the previous paragraph was reacted in Maxisorp (NUNC) at 37° C. for two hours, liquid was discarded, and blocking was carried out by reacting 5% BSA/PBS/0.05% $NaN_3$ at 37° C. for two hours. The liquid was discarded and a rabbit anti-cp3 antibody (Medical & Biological Laboratories Co., Ltd.) that had been diluted 5000-fold with 0.05% Tween/PBS was reacted at room temperature for one hour, followed by washing with PBS. Then, a HRP labeled goat anti-rabbit IgG antibody (Medical & Biological Laboratories Co., Ltd.) that had been diluted 2000-fold with 0.05% Tween/PBS was reacted at room temperature for one hour, followed by washing with PBS. Then, 100 µl of OPD solution was reacted at room temperature for 2 to 10 minutes, and the reaction was terminated by using 2N sulfuric acid, and by using SPECTRAmax 340PC (Molecular Devices), the absorbance at 492 nm of wavelength was measured.

In negative well in which the supernatant was not reacted was made to be a control. It was judged that a control whose absorbance did not become two times or more did not express. Such a control was removed from the later analysis.

7-2 Preparation of Antibody Sample 7-2-1 Production of cp Type Antibody Expression E. coli E. coli (10 ml) infected with phage corresponding to expressing antibody clones was introduced was plated on YTGA and shaking cultured at 30° C. one day and one night (pre-culture solution). This was added to 4 l of YT 0.05GA and cultured at 30° C. When O.D. of the bacterial cells became 0.5, 4 ml of 1M IPTG was added and shaking cultured at 30° C. one day and one night. After the culture was terminated, the bacterial cells were centrifuged by using a cooling centrifugal machine at 10000 g, 4° C. for 10 minutes. To the obtained culture supernatant, an equal amount of saturated ammonium sulfate aqueous solution was added and stirred at room temperature for one hour. This solution was centrifuged by using a cooling centrifugal machine at 10000 g, 4° C. for 15 minutes, then supernatant was discarded, the obtained precipitate was suspended in 20 ml of PBS-$NaN_3$ solution, centrifuged by using a cooling centrifugal machine at 10000 g, 4° C. for 5 minutes, and supernatant was recovered. This was dialyzed with PBS one day and one night. To this, a supernatant antibody cp3 mouse monoclonal antibody (Medical & Biological Laboratories Co., Ltd.) that had been balanced with 0.05% $NaN_3$/PBS was chemically immobilized. Antibody affinity column was produced by using sepharose beads. The supernatant was naturally dropped, and the components that had not reacted with beads were allowed to pass through the column. This column was washed with 100 ml of PBS twice, washed with 0.1% Tween 20/PBS (30 ml) four times, and washed with 100 ml of PBS twice. To this, 0.2M Glycine-HCl (pH 3, 4 ml) was slowly added three times and the eluted component was recovered. Then, 3M Tris (80 µl) was added and neutralize (antibody solution). This was filtrated through a MILLEX-GP 0.22 filter, O.D. was measured, and the yield of antibodies was calculated.

7-2-2 Production of pp Type Antibody Expressing *E. coli*

The obtained antibody clone is originally cp3 type clone. This DNA was extracted by using KURABO PI-50, digested with a restriction enzyme SalI, self reconnected, then, introduced into *E. coli* DH12S for transformation. Then, it was plated on a LBGA plate and cultured at 30° C. overnight at. The obtained *E. coli* colonies were cultured in 2×YTGA overnight and a pp type antibody expressing *E. coli* solution was obtained.

*E. coli* (10 ml) into which a plasmid expressing pp type antibody clones was introduced was plated on YTGA and shaking cultured at 30° C. one day and one night (pre-culture solution). This was added to 4 l of YT 0.05GA and cultured at 30° C. When O.D. of the bacterial cells became 0.5, 4 ml of 1M IPTG was added and shaking cultured at 30° C. one day and one night. After the culture was terminated, the bacterial cells were centrifuged by using a cooling centrifugal machine at 10000 g, 4° C. for 10 minutes. To the obtained culture supernatant, an equal amount of saturated ammonium sulfate aqueous solution was added and stirred at room temperature for one hour. This solution was centrifuged by using a cooling centrifugal machine at 10000 g, 4° C. for 15 minutes, then supernatant was discarded, the obtained precipitate was suspended in 20 ml of PBS-$NaN_3$ solution, centrifuged by using a cooling centrifugal machine at 10000 g, 4° C. for 5 minutes, and supernatant was recovered. This was dialyzed with PBS one day and one night. To this, 2 ml of IgG sepharose 6 Fast Flow (Amersham Biosciences) balanced with 0.05% $NaN_3$/PBS was added and reacted while shaking at 4° C. one day and one night. This mixture solution was transferred to a column and naturally dropped. The components that were not reacted with beads were allowed to pass through the column. This column was washed with 100 ml of PBS twice, washed with 0.1% Tween 20/PBS (30 ml) four times, and washed with 100 ml of PBS twice. To this, 0.2M Glycine-HCl (pH 3, 4 ml) was slowly added three times and the eluted component was recovered. Then, 3M Tris (80 µl) was added and neutralize (antibody solution). This was filtrated through a MILLEX-GP 0.22 µm filter, O.D. was measured, and the yield of antibodies was calculated.

8. Reactivity to Various Cell Lines of Antibody Clone 8-1 FCM (Flow Cytometry) Analysis The reactivity of various isolated antibody clones to various cell lines was confirmed by FCM. Experiment operation was as follows. Firstly, an adherent cell line in 6 well plate (Falcon 3516) and a suspended cell line such as ATL-derived cell line in suspended culture flask (70 ml (slant neck)), which had been cultured in a medium (RPMI-1640: Sigma-Aldrich, 10% fetal calf serum, 1% penicillin-streptomycin solution) in a $CO_2$ incubator at 37° C., were used.

i) Adherent cell line was dissociated from a culture plate with 2 mg/ml collagenase I (Gibco BRL)/cell dissociation buffer (Gibco BRL), and then recovered with 10% FBS/DMEM. On the other hand, the suspended cells were, as they were, centrifuged (400×g, 4° C., two minutes) to remove the medium once. After such operation, each cell was washed with 2.5% BSA, 0.05% $NaN_3$/PBS (BSA solution), suspended in 100 µl of 2.5% normal goat serum/BSA solution and stood still on ice for 30 minutes, dispensed to $10^6$ cells/well, and then centrifuged (400×g, 4° C., two minutes) to remove the supernatant.

ii-1) In the case of cp3 antibodies, they were added so that the concentration became 5 µg/ml and left on ice for one hour. This was washed with a BSA solution once, then suspended in 100 µl of 5 µg/ml BSA solution of anti-cp3 mouse monoclonal antibody (Medical & Biological Laboratories Co., Ltd.) and left on ice for one hour. This was washed with a BSA solution once, then suspended in 100 µl of 5 µg/ml BSA solution of Alexa 488 binding anti-mouse IgG goat antibody (Molecularprobe) and left on ice for one hour. This was washed with BSA solution twice, and then suspended in 500 µl of BSA solution. To this solution, 50 µl of fixation solution (formaldehyde) was added and it was left for 10 minutes. Thereafter, 150 µl of PBS was added, treated by using Cell Strainer (Becton Dickinson), and then the fluorescence intensity of the group of cells was analyzed by using FACScaliver (FCM) (Becton Dickinson) ((1) to (3)).

ii-2) In the case of the pp type (protein A type) antibodies, they were added so that the concentration became 5 µg/ml and left on ice for one hour. This was washed with a BSA solution once, then suspended in 100 µl of 5 µg/ml BSA solution of Alexa 488 binding anti-mouse IgG goat antibody (Molecularprobe) and left on ice for one hour. This was washed with BSA solution twice, and then suspended in 500 µl of BSA solution. To this solution, 50 µl of fixation solution (formaldehyde) was added and it was left for 10 minutes. Thereafter, 150 µl of PBS was added, treated by using Cell Strainer (Becton Dickinson), and then the fluorescence intensity of the group of cells was analyzed by using FACScaliver (FCM) (Becton Dickinson).

In the analysis, detection antibody was labeled with fluorescent dye (Alexa 488, etc.) in advance. After sample antibodies and cells were reacted, they were reacted with detection antibodies. The difference in the antibody amount occurs depending upon the amount of antigen existing on the surface of the cell, and as a result, the fluorescence intensity became different. Thus, the affinity with respect to the antigen existing on the surface of the cells and the amount of antigen can be estimated. Furthermore, in order to remove dead cells and debris, and the like, Forward Scatter: FSC is expressed in X-axis and Side Scatter: SSC is expressed in Y-axis, and a group of living cells (substantially the same group because cultured cells were used) in data obtained by dot plot expansion were gated, the fluorescence intensity only in this gate was measured.

8-2 Production of Panel

From the results of FCM, a histogram showing the relationship between the antibody binding amount and the number of cells was formed. One-parameter histogram using the antibody binding amount a parameter was drawn. The one-parameter histogram is one of the display methods in the flow cytometry. The one-parameter histogram is generally shown in a graph in which X-axis represents one indicator (parameter) and Y-axis represents the number of cells.

Figure 10:
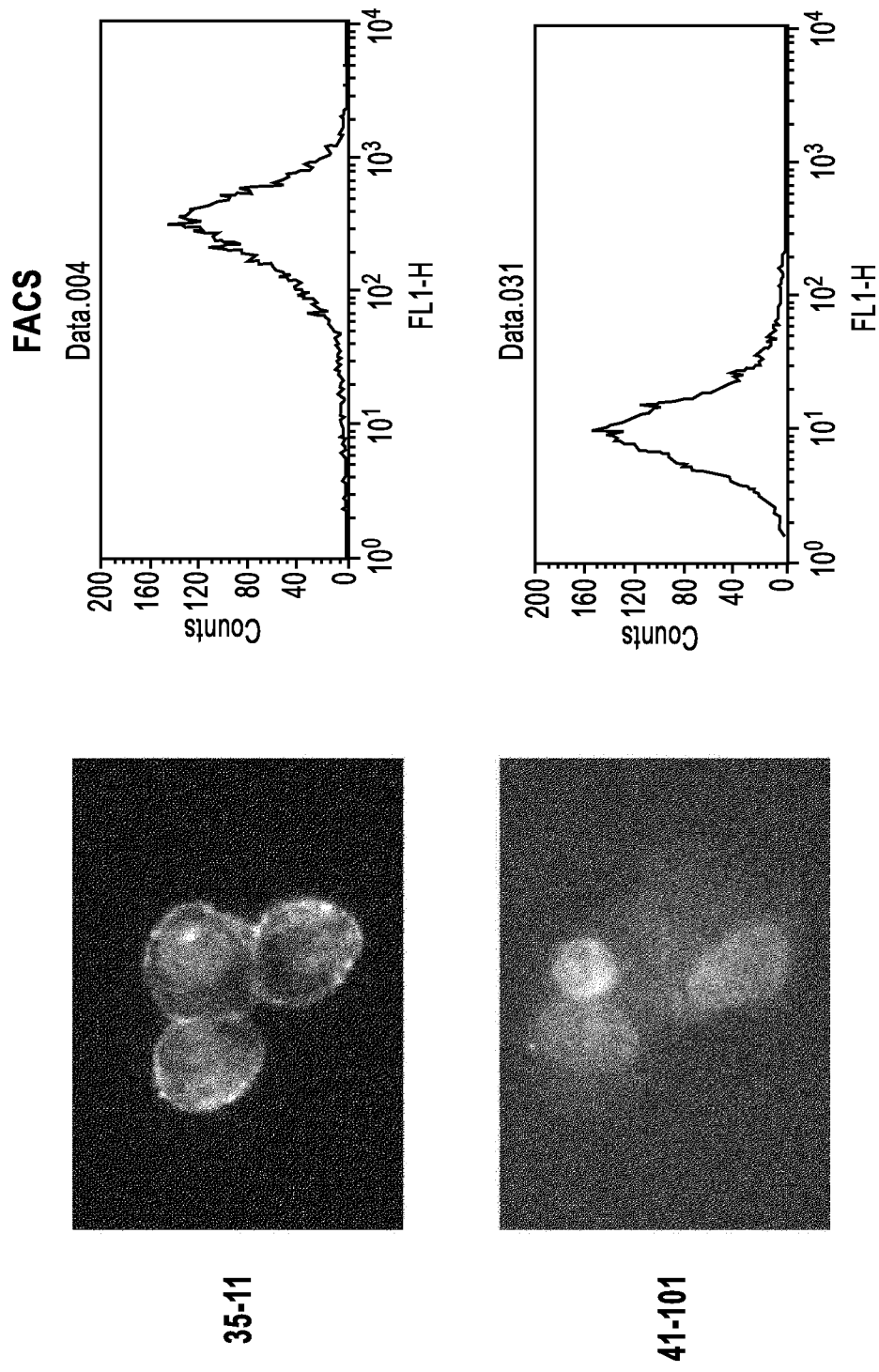
FIG. 10 shows an FCM reactivity (representative example) of an antibody clone, showing histogram (right) and cell fluorescence cytology image (left) showing the reactivity between an antibody clones 035-011 and 041-101 and undifferentiated malignant liver cancer cell line HLF.
Figure 11:
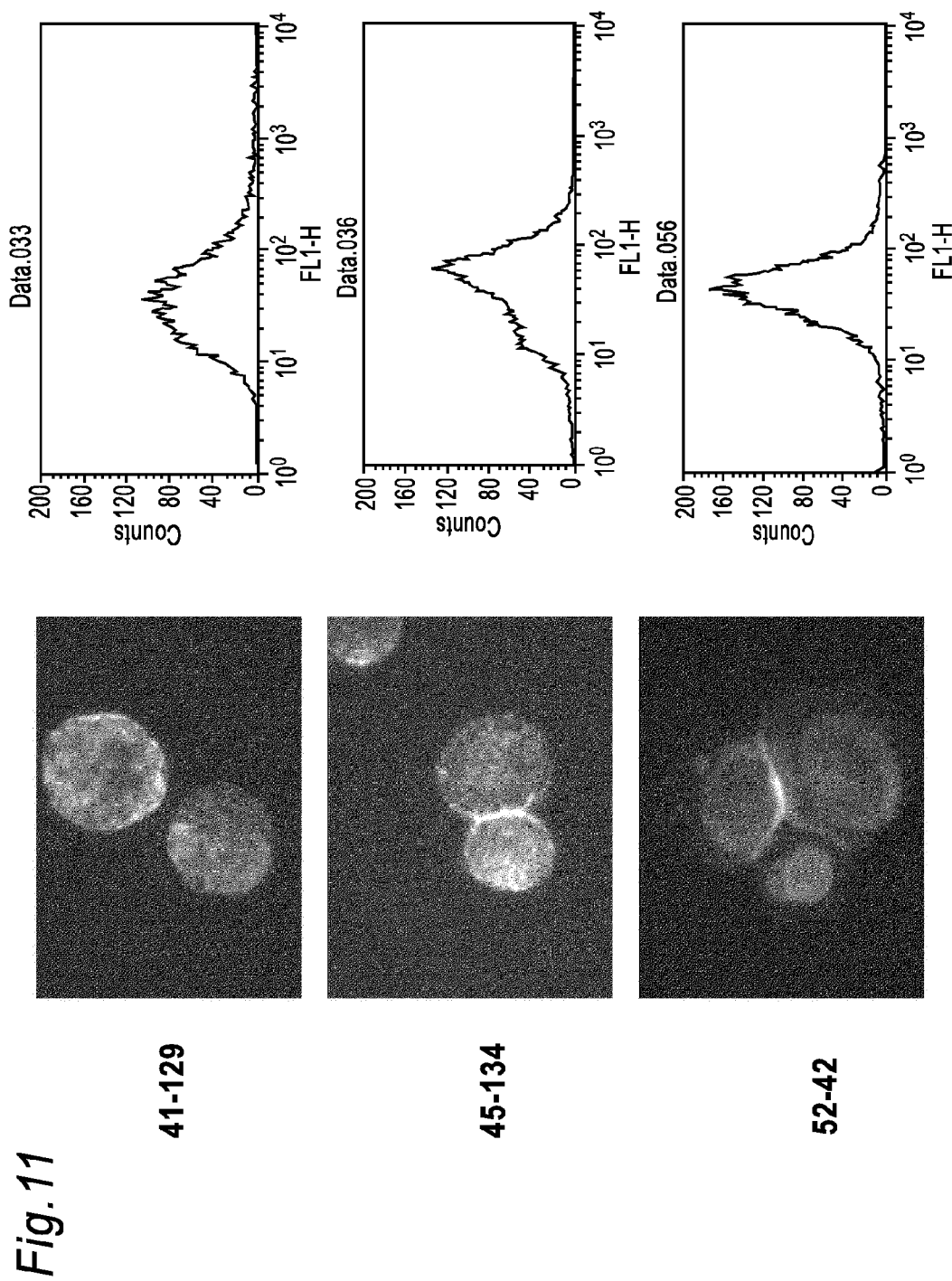
FIG. 11 shows an FCM reactivity (representative example) of an antibody clone, showing histogram (right) and cell fluorescence cytology image (left) showing the reactivity between an antibody clones 041-129, 045-134 and 052-042 and undifferentiated malignant liver cancer cell line HLF.
Figure 12:
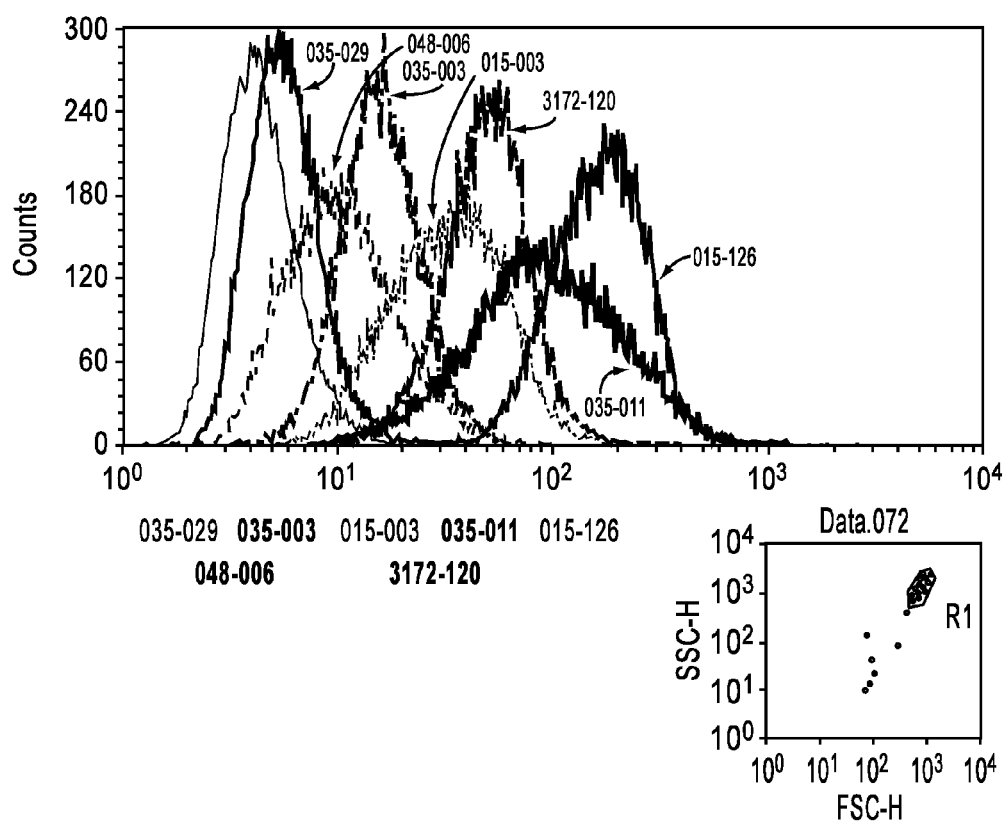
FIG. 12 shows histograms obtained by FCM of seven kinds of antibodies, which are overwritten onto each other. This shows that each histogram has a unique shape.
Figure 13:
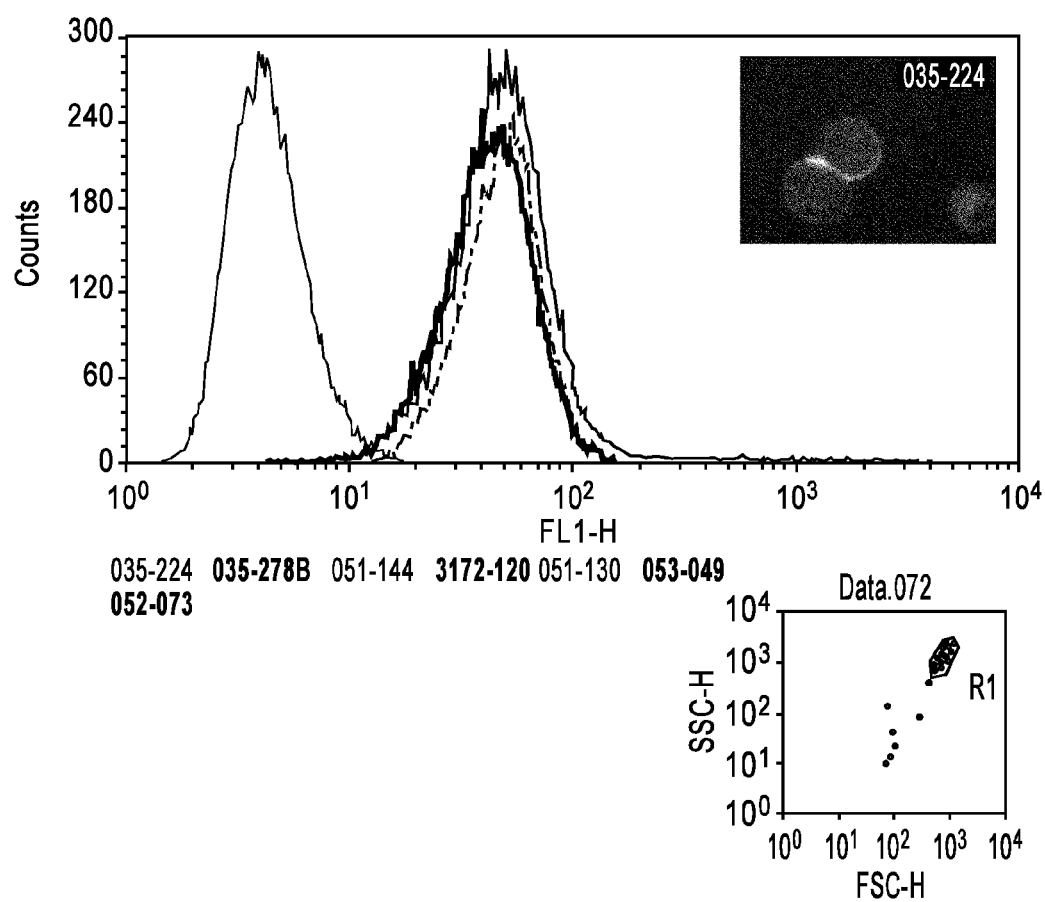
FIG. 13 shows histograms obtained by FCM of seven kinds of antibodies, which are overwritten onto each other. This shows that all the histograms have high similarity to each other.
Figure 14:
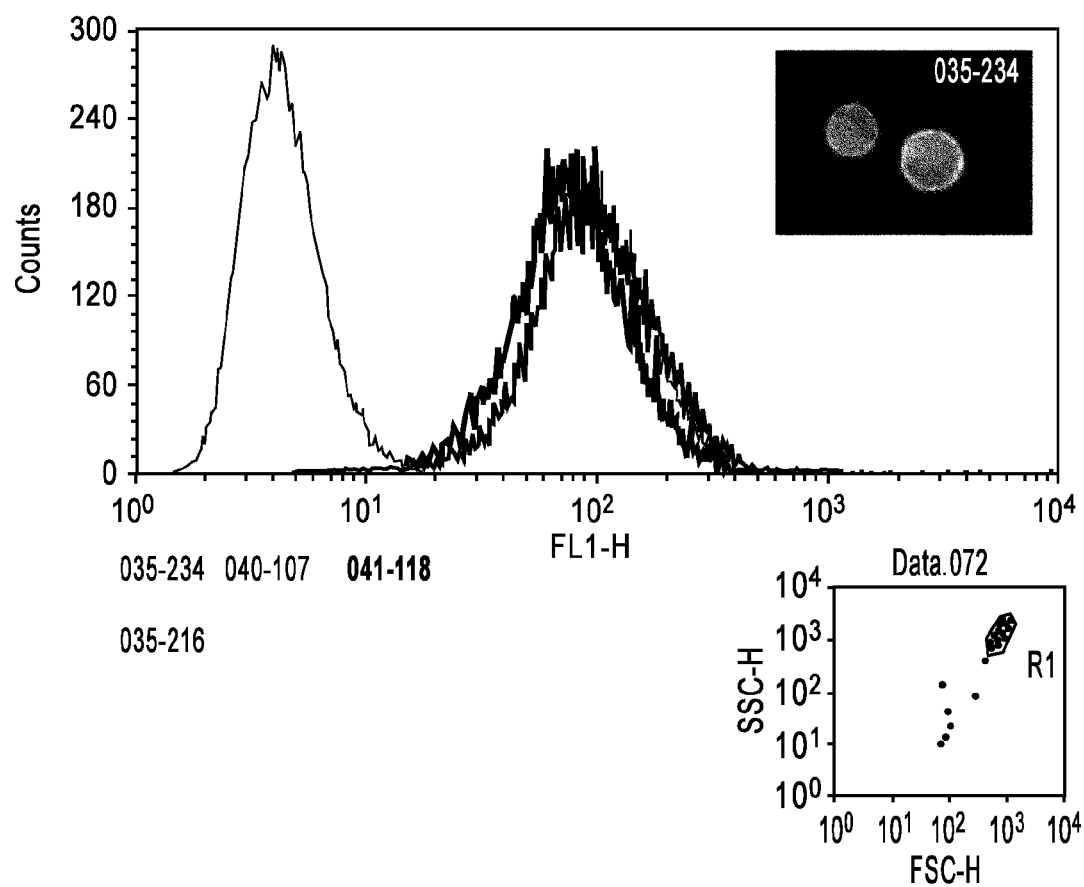
FIG. 14 shows histograms obtained by FCM of four kinds of antibodies, which are overwritten onto each other. This shows that all the histograms have high similarity to each other.
Figure 15:
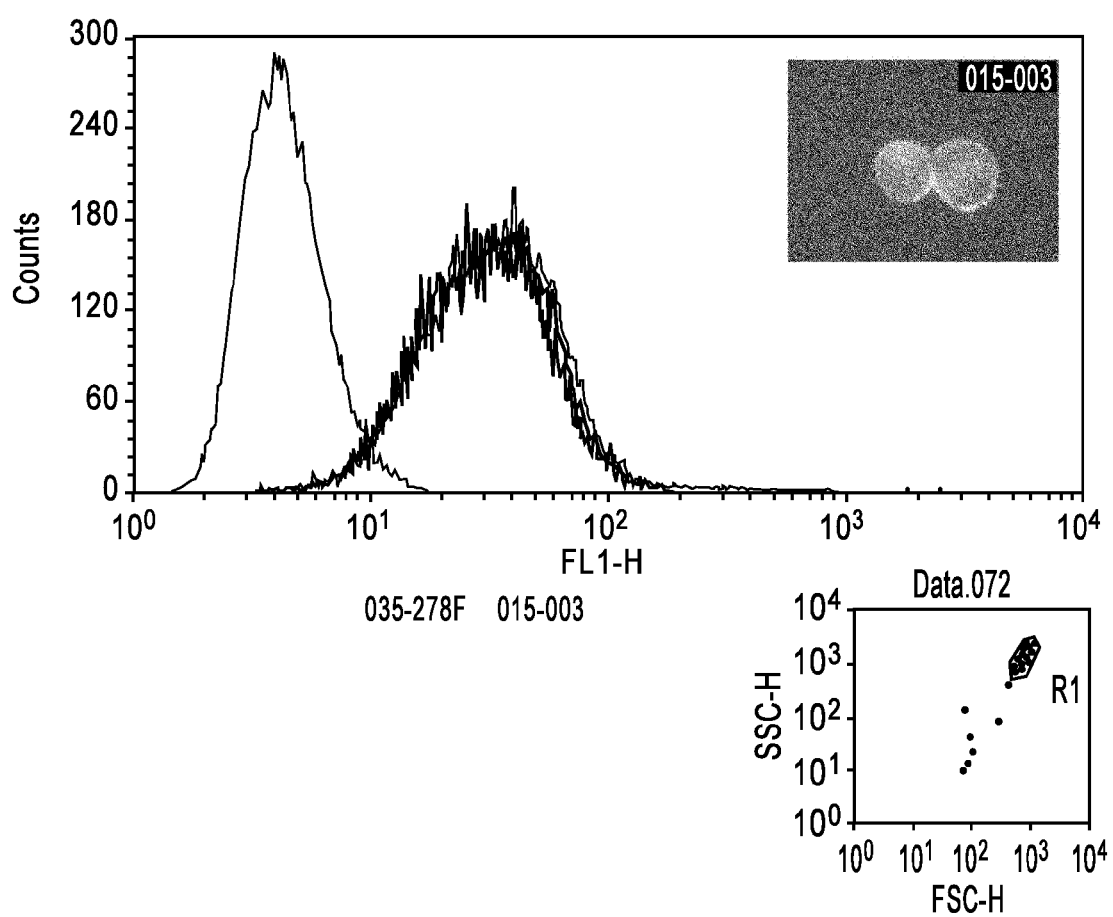
FIG. 15 shows histograms obtained by FCM of two kinds of antibodies, which are overwritten onto each other. This shows that two histograms have high similarity to each other.
Figure 16:
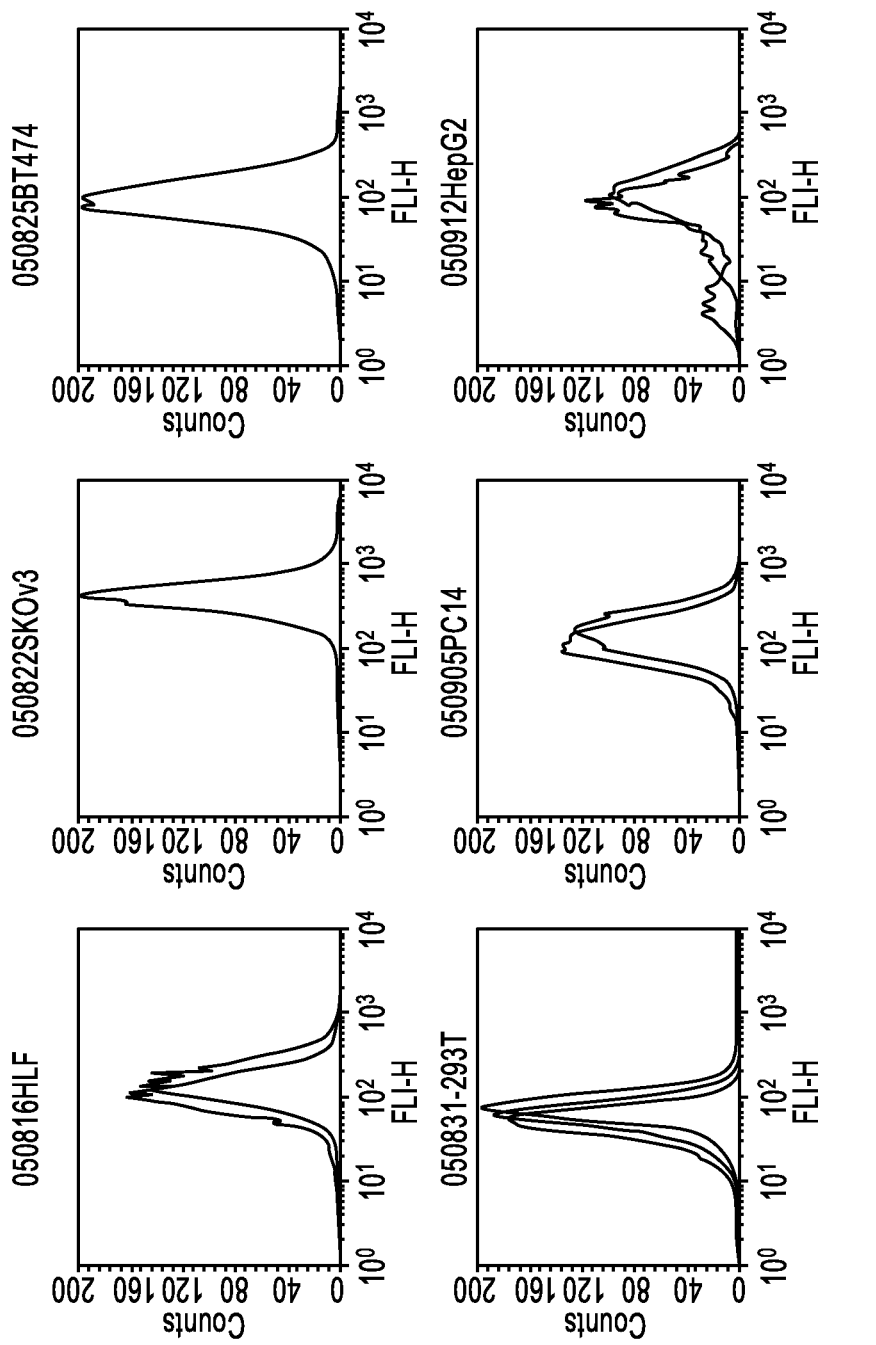
FIG. 16 shows histograms obtained by FCM of three kinds of antibodies in various cells, which are overwritten onto each other. This shows that even when any cells are used, these antibodies provide histograms having a high similarity to each other.

Typical examples of the results of FCM are shown in FIGS. 10 to 12. As shown in these figures, basically, the behavior of the FCM becomes unique according to the combination of cells and antibodies. FIGS. 10 and 11 show histogram (right) and cell fluorescence cytology image (left), respectively, which show the reactivity between the scFv antibody and the undifferentiated malignant liver cancer cell line HLF obtained in the above-mentioned method. In all the antibodies (five antibodies), positive patterns are obtained but each has very unique shape of peak. Such shapes of peaks are thought to reflect the uniqueness of epitope of antigen. FIG. 12 shows a plurality of histograms (antibodies to be used was different in each case) which are overwritten. It is shown that the peak of each histogram has its own unique shape. However, during the comprehensive FCM analysis, an antibody group providing histogram having an extremely high similarity as shown in FIGS. 13 to 15 are observed. Furthermore, as shown in FIG. 16, an antibody group consistently providing histogram having a high similarity regardless of cell lines to be used in the FCM analysis was observed. FIG. 16 show comparison of histograms obtained in three kinds of antibodies (035-234 antibody, 040-107 antibody, and 041-118 antibody). According to the later investigation, it is determined that these three kinds of antibodies recognize ALCAM.

Figure 17:
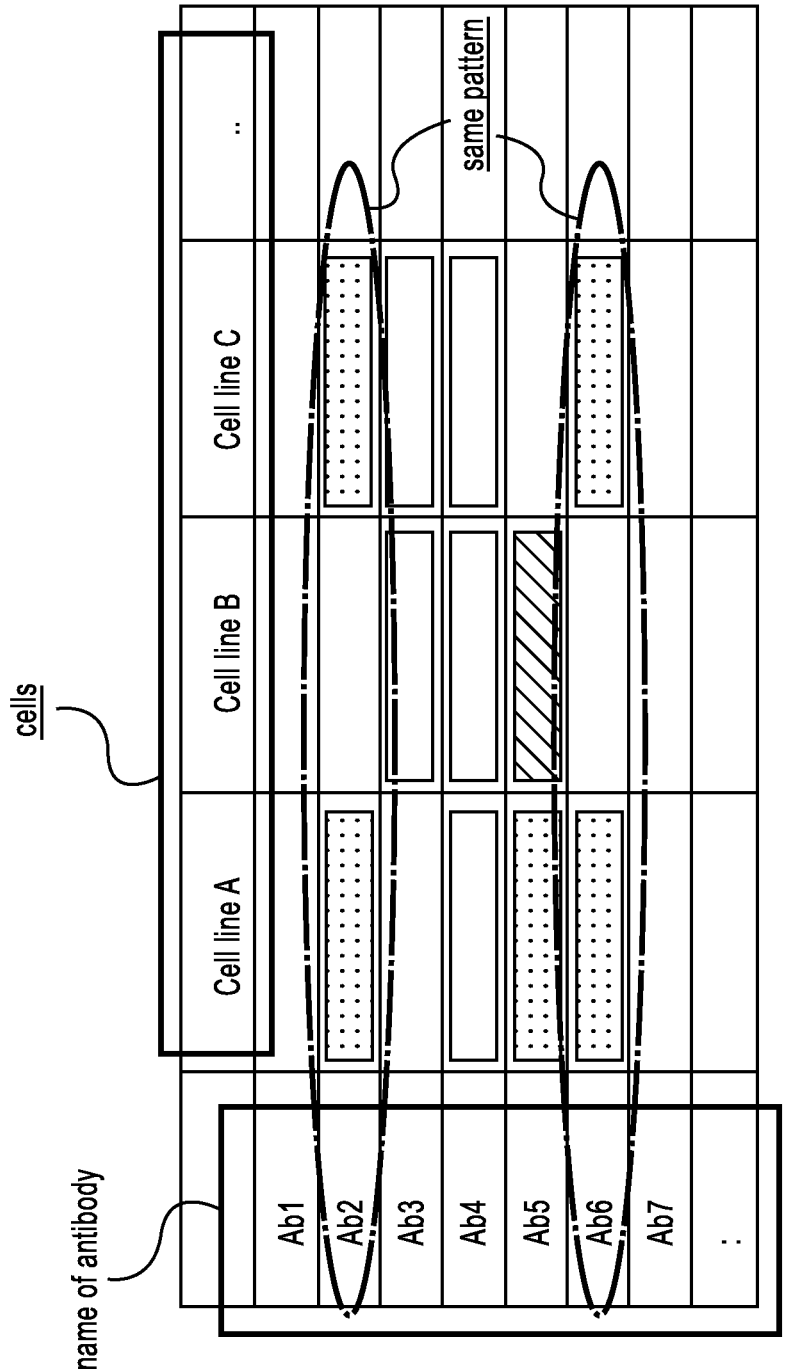
FIG. 17 shows a method for classifying the antibody group into groups based on the results of the FCM analysis.

FIG. 17 shows a method for classifying the antibody group based on the results of the FCM analysis. That is to say regardless of kinds of cells to be used, a plurality of antibodies having similar behavior (shape of histogram) in the FCM analysis are shown as the same group in a panel. Basically, a plurality of antibodies having the same shape of histogram (peaks are overlapped when the shapes are overwritten) are defined as one group. However, a plurality of antibodies may be classified into groups on the basis of the factors such as the median value, mode (peak value), and kurtosis of the histogram.

A plurality of antibodies are classified based on the above-mentioned technique. Firstly, the histograms obtained in the antibody clones are overwritten for each cell line to be used, and thereby the histograms are compared with each other. Thus, similarly between the antibody clones and the reactivity between antibody clones are obtained. Then, based on the similarity and the reactivity, antibody clones are classified and summarized in table (FIG. 18). Thus, eight antibody groups (in the description hereinafter, groups are named 1, 2, 3, 4, 5, 6, 7, and 8 sequentially in this order) are obtained. In FIG. 18, information on antigen identified later is also displayed. Each mark in Table shows a shift amount relative from the histogram (reference histogram) of the negative control antibody. Double circle mark represents that the shift amount is 20 times or more (the peak value of the is 20 times or more of the reference histogram); "○" (circle mark) represents that the shift amount is 10 times or more; "Δ" (triangle mark) represents that the shift amount is 3 times or more; and "x" represents that the shift amount is less than 3, respectively (an oblique line means no data is obtained). The larger the shift amount is, the higher the reactivity is.

Next, by the following procedure, it is verified that antigens of each antibody group in the produced panel are common.

9. Identification of Protein (Antigen) Recognized by Antibody Clone 9-1 Preparation of Solid Phase Antibody for Immunoprecipitation Firstly, a pp type antibody solution was dialyzed with a coupling buffer solution (0.1M $NaHCO_3$—NaOH, pH 9). That is to say, an antibody solution was enclosed with a dialysis membrane (Snake Skin Pleated Dialysis Tubing 10,000 MWCO) and this was allowed to be sunk in 1.5 L of the coupling buffer solution (0.1M $NaHCO_3$—NaOH, pH 9) and stirred by using a stirrer at 4° C. for two to three hours. Then, the buffer solution was replaced with new one and dialyzed for two to three hours. Thereafter, the buffer solution was replaced with new one again and dialyzed one day and one night.

Next, activated CNBr-activated Sepharose 4B used for making solid phase was adjusted. That is to say, CNBr-activated Sepharose 4B (Amersham Biosciences) was swollen with 1 mM HCl, then sucked by using an aspirator. To this, 50 ml of coupling buffer solution was added, stirred, and then sucked by using an aspirator. In this sucked state, a coupling buffer solution was added.

An antibody was made to be solid phased as follows. That is to say, to 5 mg antibody solution (10 ml), activated gel (1 ml) was added to cause a reaction at room temperature for two hours. After the reaction was terminated, the gel was transferred to a column and washed with a coupling buffer solution (1 ml) ten times. The presence of non-reacted antibodies was confirmed by measuring the O.D. The solid phased gel was substituted by 0.2M Glycine-NaOH pH8 solution (5 ml) twice, the same solution (5 ml) was further added and left at room temperature for two hours, this solution was naturally dropped, to this, 0.2M Glycine-HCl (pH 3, 5 ml) was added and substituted, the same solution (5 ml) was further added and left for 5 minutes, and then naturally dropped. Finally, the column was substituted by 20 ml of PBS, then naturally dropped, and 1% NP40, protease inhibitor, and 0.05% $NaN_3$/PBS were added, and gel was recovered.

9-2 Biotin Label of Protein on Cell Membrane and Production of Cell Lysate

Biotin labeling of the cultured liver cancer cell line was carried out as follows. That is to say, cultured cells HLF that had been cultured in five 15 cm-dishes were washed with PBS twice, and collagenase I (GIBCO) whose concentration had been adjusted to 5 mg/ml by using a cell dissociation buffer (GIBCO) was added and reacted in a $CO_2$ incubator at 37° C., so that cells were liberated. Thereafter, cells were recovered in a culture medium and washed with PBS(−) twice. Then, the number of cells was counted by using a hemocytometer. The cells were suspended in PBS(−) so that the counted number became about $5 \times 10^7$/ml. To this, an equal amount of EZ-Link Sulfo-NHS-LC-Biotinylation Kit (PIERCE) was added so that the concentration had been adjusted to 1 mg/ml with PBS, left at room temperature for 30 minutes and then washed with PBS twice.

The cell lysate of biotin labeled cells was adjusted as follows. That is to say, to the above-mentioned biotin labeled cells, 4 ml of lysis buffer (1% NP40/detergent base solution, the composition of the detergent base solution: 20 mM HEPES, pH 8.0, 140 mM NaCl, protease inhibitor) was added and cells were suspended. This suspension was placed and homogenized in a cooled Dounce homogenizer. To the solution, ½ amount (2 ml) of a detergent mix solution (1% NP40, tritonX-100, b-D-Maltoside, n-Octyl b-D-Glucoside, n-Octyl b-D-Maltoside, n-Decyl b-D-Maltoside, deoxycholic acid, each 0.5%/detergent base solution) was added and mixed at 4° C. for four hours. This solution was centrifuged at 100,000 rpm for 30 minutes and filtrated through MILLEX-GP 0.22 µm filter.

9-3 Immunoprecipitation Reaction

Firstly, about 60 µl parts (about 150 µl solution parts) of the solid-phased antibodies (hereinafter, referred to as "antibody beads") were placed in a 2 ml-tube and ¹/₁₀ volume (about 15 µl) of 4 mM biotin was added to the tube. A mixture of 0.5 culture dishs of lysate (600 µl) and 60 µl of biotin solution was added to the tube and reacted while stirring at 4° C. for several hours. Then, the tube was centrifuged (5500 g, one minute, 4° C.) and supernatant was removed. To this, 800 µl of washing biotin/lysis-T buffer (0.5 mM biotin, 0.1% Tween 20/PBS) was added and mixed while falling two or three times, then the tube was centrifuged (5500 g, one minute, 4° C.), and supernatant was removed. This washing operation was carried out again, then 30 µl of citric acid solution (50 mM citric acid, pH 2.5) for elution was added to the antibody beads and stirred. Then, the tube was centrifuged (5500 g, 1 min, 4° C.) and supernatant was recovered. To the remaining antibody beads, 30 µl of citric acid solution for elution was added and stirred. The tube was centrifuged (5500 g, 1 min, 4° C.) and supernatant was recovered. This elution operation was repeated further three times, and a sample solution was recovered and 3M Tris was added to the solution for neutralization. This sample was migrated by SDS-PAGE so as to confirm the band by silver staining. At the same time, this sample was subjected to western blotting by using streptavidin—HRP (Anti-Streptavidin, IgG Fraction, Conjugated to Peroxidase CORTEX biochem) so as to detect a band of the biotin membrane protein.

9-4 Mass Spectrometry of Cut-Out Band 9-4-1 Trypsin Digestion in Gel

A portion corresponding to detected membrane protein was digested with trypsin in a gel and peptide was recovered. SDS polyacrylamide gel electrophoresis was carried out in accordance with a usual method and a band that had been obtained by staining with Coomassie Brilliant Blue was cut out. This was soaked in 200 mM ammonium bicarbonate 50% acetonitrile solution, shaken at 37° C. for 45 minutes. Then, the solution was discarded and the operation was repeated twice, thereby removing the Coomassie Brilliant Blue. This gel was dried under reduced pressure, and 4 µl of trypsin (20 µg/ml) dissolved in 40 mM ammonium bicarbonate (pH 8.1)-10% acetonitrile was added per unit area (mm²) of gel slice, and left at room temperature for one hour and sufficiently infiltrated. To this, a trypsin solution was added in an amount that was 25 times as much as the previously added amount, and left at 37° C. for 18 hours. This was filtrated by a tube having a filter whose power size was 0.22 and peptide in which an antigen had been cut with trypsin was recovered.

9-4-2 Identification of Antigen by Mass Spectrometry

A specimen obtained by in-gel trypsin digestion was subjected to HPLC linked with an electrospray ionization type ion trap quadrupole mass spectrometer. From the reversed phase chromatography column of HPLC, according to the change of linear concentration gradient of 0% to 80% acetonitrile containing 0.1% TFA, each peptide that had been eluted sequentially depending upon the hydrophobic property was ionized by an electrospray method. The mass of each peptide was analyzed.

At the same time, the mass of limited digested product of each peptide generated by collision with helium atoms placed in the middle of the fight route of ions was analyzed. When one amino acid is removed by limited digestion, since ion that is smaller by a part of the mass of the removed amino acid is observed, the kind of the removed amino acid can be identified according to the difference in mass. Furthermore, another amino acid is removed, since ion that is smaller by a part of the mass of the removed amino acid is observed, the kind of the removed amino acid can be identified according to the difference in mass. By proceeding the same analysis of the experimental data, an inner amino acid sequence can be determined. The set of the inner sequence of the obtained amino acid was retrieved by using a published amino acid sequence database and antigen was identified. As a result, as shown below, antigen of each antibody clone was identified and it is confirmed that the antibodies in the same group have the common antigen. The identification results was confirmed because the total amount of the identified protein that had been analogized from the amino acid sequence was not contradictory to the experimental data of the molecular weight of the SDS polyacrylamide electrophoresis of antigen before carrying out the trypsin digestion.

Antigen of antibodies belonging to group 1: HER1 (also known as: ErbB1, c-erbB-1, EGFR (Epidermal Growth Factor Receptor), v-erbB)

Antigen of antibodies belonging to group 2: HER-2 (also known as: ErbB2, c-erbB-2, neu)

Antigen of antibodies belonging to group 3: CD46 antigen (also known as: MCP (membrane cofactor protein), gp45-70, HuLY-m5, measles virus receptor, MIC10, TLX-B antigen, TRA2, trophoblast leucocyte common antigen, trophoblast-lymphocyte cross-reactive antigen)

Antigen of antibodies belonging to group 4: ITGA3 (integrin alpha3) (also known as: alpha3beta1 Epiligrin Receptor, alpha3beta1 Integrin, Epiligrin Receptor, CD49c, VLA-3, Gap b3, Galactoprotein b3, Laminin-5 Receptor)

Antigen of antibodies belonging to group 5: ICAM1 (Intercellular adhesion molecule-1) (also known as: Intercellular Adhesion Molecule 1, CD54 Antigen)

Antigen of antibodies belonging to group 6: ALCAM (Activated leukocyte cell adhesion molecule) (also known as: KG-CAM, CD166 Antigen, CD6 Ligand, Activated Leukocyte Cell Adhesion Molecule, Neurolin)

Antigen of antibodies belonging to group 7: CD147 antigen (also known as: BSG, TCSF (Tumor cell-derived collagenase stimulatory factor), 5F7 protein, OK blood group protein, basigin protein, collagenase stimulatory factor protein, EMMPRIN (Extracellular matrix metalloproteinase Inducer), M6 activation antigen, human leukocyte activation antigen M6)

Antigen of antibodies belonging to group 8: IgSF4 (also known as: BL2, ST17, NECL2, TSLC1, IGSF4A, SYNCAM, sTSLC-1)

From the above-mentioned identification results, it has been clarified that it was possible obtain three antibody clones to HER1 (048-006 antibody, 057-091 antibody, and 059-152 antibody), one antibody clone to HER-2 (015-126 antibody), seven antibody clones to CD46 antigen (035-224 antibody, 045-011 antibody, 051-144 antibody, 052-053 antibody, 052-073 antibody, 053-049 antibody, and 3172-120 antibody), one antibody clone to ITGA3 (015-003 antibody), five antibody clones to ICAM1 (052-033 antibody, 053-042 antibody, 053-051 antibody, 053-059 antibody, and 053-085 antibody), five antibody clones to ALCAM (035-234 antibody, 040-107 antibody, 041-118 antibody, 066-174 antibody, and 083-040 antibody), one antibody clone to CD147 antigen (059-053 antibody), and ten antibody clones to IgSF4. The Note here that the amino acid sequences of the antibody clones have been identified as mentioned below (antibody clones to IgSF4 are omitted).

<Antibodies Belonging to Group 1>
(1) 048-006 Antibody
SEQ ID NO: 1 (VH), SEQ ID NO: 2 (VH CDR1), SEQ ID NO: 3 (VH CDR2), SEQ ID NO: 4 (VH CDR3), SEQ ID NO: 5 (VL), SEQ ID NO: 6 (VL CDR1), SEQ ID NO: 7 (VL CDR2), SEQ ID NO: 8 (VL CDR3)
(2) 057-091 Antibody
SEQ ID NO: 9 (VH), SEQ ID NO: 10 (VH CDR1), SEQ ID NO: 11 (VH CDR2), SEQ ID NO: 12 (VH CDR3), SEQ ID NO: 13 (VL), SEQ ID NO: 14 (VL CDR1), SEQ ID NO: 15 (VL CDR2), SEQ ID NO: 16 (VL CDR3)
(3) 059-152 Antibody
SEQ ID NO: 17 (VH), SEQ ID NO: 18 (VH CDR1), SEQ ID NO: 19 (VH CDR2), SEQ ID NO: 20 (VH CDR3), SEQ ID NO: 21 (VL), SEQ ID NO: 22 (VL CDR1), SEQ ID NO: 23 (VL CDR2), SEQ ID NO: 24 (VL CDR3)

<Antibody Belonging to Group 2>
(1) 015-126 Antibody
SEQ ID NO: 25 (VH), SEQ ID NO: 26 (VH CDR1), SEQ ID NO: 27 (VH CDR2), SEQ ID NO: 28 (VH CDR3), SEQ ID NO: 29 (VL), SEQ ID NO: 30 (VL CDR1), SEQ ID NO: 31 (VL CDR2), SEQ ID NO: 32 (VL CDR3)

<Antibodies Belonging to Group 3>
(1) 035-224 Antibody
SEQ ID NO: 33 (VH), SEQ ID NO: 34 (VH CDR1), SEQ ID NO: 35 (VH CDR2), SEQ ID NO: 36 (VH CDR3), SEQ ID NO: 37 (VL), SEQ ID NO: 38 (VL CDR1), SEQ ID NO: 39 (VL CDR2), SEQ ID NO: 40 (VL CDR3)
(2) 045-011 Antibody
SEQ ID NO: 41 (VH), SEQ ID NO: 42 (VH CDR1), SEQ ID NO: 43 (VH CDR2), SEQ ID NO: 44 (VH CDR3), SEQ ID NO: 45 (VL), SEQ ID NO: 46 (VL CDR1), SEQ ID NO: 47 (VL CDR2), SEQ ID NO: 48 (VL CDR3)
(3) 051-144 Antibody
SEQ ID NO: 49 (VH), SEQ ID NO: 50 (VH CDR1), SEQ ID NO: 51 (VH CDR2), SEQ ID NO: 52 (VH CDR3), SEQ ID NO: 53 (VL), SEQ ID NO: 54 (VL CDR1), SEQ ID NO: 55 (VL CDR2), SEQ ID NO: 56 (VL CDR3)
(4) 052-053 Antibody
SEQ ID NO: 57 (VH), SEQ ID NO: 58 (VH CDR1), SEQ ID NO: 59 (VH CDR2), SEQ ID NO: 60 (VH CDR3), SEQ ID NO: 61 (VL), SEQ ID NO: 62 (VL CDR1), SEQ ID NO: 63 (VL CDR2), SEQ ID NO: 64 (VL CDR3)
(5) 052-073 Antibody
SEQ ID NO: 65 (VH), SEQ ID NO: 66 (VH CDR1), SEQ ID NO: 67 (VH CDR2), SEQ ID NO: 68 (VH CDR3), SEQ ID NO: 69 (VL), SEQ ID NO: 70 (VL CDR1), SEQ ID NO: 71 (VL CDR2), SEQ ID NO: 72 (VL CDR3)
(6) 053-049 Antibody
SEQ ID NO: 73 (VH), SEQ ID NO: 74 (VH CDR1), SEQ ID NO: 75 (VH CDR2), SEQ ID NO: 76 (VH CDR3), SEQ ID NO: 77 (VL), SEQ ID NO: 78 (VL CDR1), SEQ ID NO: 79 (VL CDR2), SEQ ID NO: 80 (VL CDR3)
(7) 3172-120 Antibody
SEQ ID NO: 81 (VH), SEQ ID NO: 82 (VH CDR1), SEQ ID NO: 83 (VH CDR2), SEQ ID NO: 84 (VH CDR3), SEQ ID NO: 85 (VL), SEQ ID NO: 86 (VL CDR1), SEQ ID NO: 87 (VL CDR2), SEQ ID NO: 88 (VL CDR3)

<Antibody Belonging to Group 4>
(1) 015-003 Antibody
SEQ ID NO: 89 (VH), SEQ ID NO: 90 (VH CDR1), SEQ ID NO: 91 (VH CDR2), SEQ ID NO: 92 (VH CDR3), SEQ ID NO: 93 (VL), SEQ ID NO: 94 (VL CDR1), SEQ ID NO: 95 (VL CDR2), SEQ ID NO: 96 (VL CDR3)

<<Antibodies Belonging to Group 5>
(1) 052-033 Antibody
SEQ ID NO: 97 (VH), SEQ ID NO: 98 (VH CDR1), SEQ ID NO: 99 (VH CDR2), SEQ ID NO: 100 (VH CDR3), SEQ ID NO: 101 (VL), SEQ ID NO: 102 (VL CDR1), SEQ ID NO: 103 (VL CDR2), SEQ ID NO: 104 (VL CDR3)
(2) 053-042 Antibody
SEQ ID NO: 105 (VH), SEQ ID NO: 106 (VH CDR1), SEQ ID NO: 107 (VH CDR2), SEQ ID NO: 108 (VH CDR3), SEQ ID NO: 109 (VL), SEQ ID NO: 110 (VL CDR1), SEQ ID NO: 111 (VL CDR2), SEQ ID NO: 112 (VL CDR3)
(3) 053-051 Antibody
SEQ ID NO: 113 (VH), SEQ ID NO: 114 (VH CDR1), SEQ ID NO: 115 (VH CDR2), SEQ ID NO: 116 (VH CDR3), SEQ ID NO: 117 (VL), SEQ ID NO: 118 (VL CDR1), SEQ ID NO: 119 (VL CDR2), SEQ ID NO: 120 (VL CDR3)
(4) 053-059 Antibody
SEQ ID NO: 121 (VH), SEQ ID NO: 122 (VH CDR1), SEQ ID NO: 123 (VH CDR2), SEQ ID NO: 124 (VH CDR3), SEQ ID NO: 125 (VL), SEQ ID NO: 126 (VL CDR1), SEQ ID NO: 127 (VL CDR2), SEQ ID NO: 128 (VL CDR3)
(5) 053-085 Antibody
SEQ ID NO: 129 (VH), SEQ ID NO: 130 (VH CDR1), SEQ ID NO: 131 (VH CDR2), SEQ ID NO: 132 (VH CDR3), SEQ ID NO: 133 (VL), SEQ ID NO: 134 (VL CDR1), SEQ ID NO: 135 (VL CDR2), SEQ ID NO: 136 (VL CDR3)

<Antibodies Belonging to Group 6>
(1) 035-234 Antibody
SEQ ID NO: 137 (VH), SEQ ID NO: 138 (VH CDR1), SEQ ID NO: 139 (VH CDR2), SEQ ID NO: 140 (VH CDR3), SEQ ID NO: 141 (VL), SEQ ID NO: 142 (VL CDR1), SEQ ID NO: 143 (VL CDR2), SEQ ID NO: 144 (VL CDR3)
(2) 040-107 Antibody
SEQ ID NO: 145 (VH), SEQ ID NO: 146 (VH CDR1), SEQ ID NO: 147 (VH CDR2), SEQ ID NO: 148 (VH CDR3), SEQ ID NO: 149 (VL), SEQ ID NO: 150 (VL CDR1), SEQ ID NO: 151 (VL CDR2), SEQ ID NO: 152 (VL CDR3)
(3) 041-118 Antibody
SEQ ID NO: 153 (VH), SEQ ID NO: 154 (VH CDR1), SEQ ID NO: 155 (VH CDR2), SEQ ID NO: 156 (VH CDR3), SEQ ID NO: 157 (VL), SEQ ID NO: 158 (VL CDR1), SEQ ID NO: 159 (VL CDR2), SEQ ID NO: 160 (VL CDR3)
(4) 066-174 Antibody
SEQ ID NO: 161 (VH), SEQ ID NO: 162 (VH CDR1), SEQ ID NO: 163 (VH CDR2), SEQ ID NO: 164 (VH CDR3), SEQ ID NO: 165 (VL), SEQ ID NO: 166 (VL CDR1), SEQ ID NO: 167 (VL CDR2), SEQ ID NO: 168 (VL CDR3)
(5) 083-040 Antibody
SEQ ID NO: 169 (VH), SEQ ID NO: 170 (VH CDR1), SEQ ID NO: 171 (VH CDR2), SEQ ID NO: 172 (VH CDR3), SEQ ID NO: 173 (VL), SEQ ID NO: 174 (VL CDR1), SEQ ID NO: 175 (VL CDR2), SEQ ID NO: 176 (VL CDR3)

<<Antibody Belonging to Group 7>
(1) 059-053 Antibody
SEQ ID NO: 177 (VH), SEQ ID NO: 178 (VH CDR1), SEQ ID NO: 179 (VH CDR2), SEQ ID NO: 180 (VH CDR3), SEQ ID NO: 181 (VL), SEQ ID NO: 182 (VL CDR1), SEQ ID NO: 183 (VL CDR2), SEQ ID NO: 184 (VL CDR3)

10. Confirmation of Antigen by RNAi and Immunostaining

In order to reconfirm that the isolated antibodies recognize the identified antigen, double stranded oligo RNA was allowed to act on cells so as to carry out antigen gene knock-down. Thus, the immunostaining property of the antibody identified by the isolated antigen with respect to the cell was examined.

Firstly, cells were cultured in a 6-well culture dish to about 30% confluent. To this, a mixture including Lipofectamin 2000 (5 µl) (Invitrogen) and the following oligo RNA (100 pmol) was acted. At day 2, cells were peeled off by using collagenase and recovered. To this, cp3 type purified antibody for verification was acted at the concentration of 5 µg/ml. After washing, a rabbit anti-cp3 antibody was acted at the concentration of 2 µg/ml. After washing, Alexa488 labeled anti-rabbit IgG was acted at 2 µg/ml. This was washed and then immobilized in OptiLyse (NOTECH) (50 µl) for ten minutes. This was diluted by adding 1 ml of PBS and this was measured by using FACS Caliver (Beckmann). As the antibody reaction solution and washing solution, 2.5% BSA/PBS solution was used.

Subject antigen: CD147
Sequence of the used oligo RNA:

(SEQ ID NO: 441)
CAGAGCUACACAUUGAGAACCUGAA

Subject cell: clear cell renal cell carcinoma CCFRC1 cell
Verified antibody: 059-053 cp3 antibody
Subject antigen: CD166
Sequence of the used oligo RNA:

(SEQ ID NO: 442)
UACCUAUGUGCAGAGGAAUUAUGAU

Subject cell: clear cell renal cell carcinoma CCFRC1 cell
Verified antibody: 035-234 cp3 antibody
Subject antigen: CD166
Sequence of the used oligo RNA:

(SEQ ID NO: 443)
GCAACCAUCUAAACCUGAAAUUGUA

Subject cell: hepatic cell carcinoma HLF cell
Verified antibody: 048-006 cp3 antibody
Subject antigen: HER2
Sequence of the used oligo RNA:

(SEQ ID NO: 444)
UAAUAGAGGUUGUCGAAGGCUGGGC

Subject cell: ovarian cancer SKOv-3 cell
Verified antibody: 015-126 cp3 antibody
Subject antigen: IgSF4
Sequence of the used oligo RNA:

(SEQ ID NO: 445)
CCCAACAGGCAGACCAUUUAUUUCA

Figure 19:
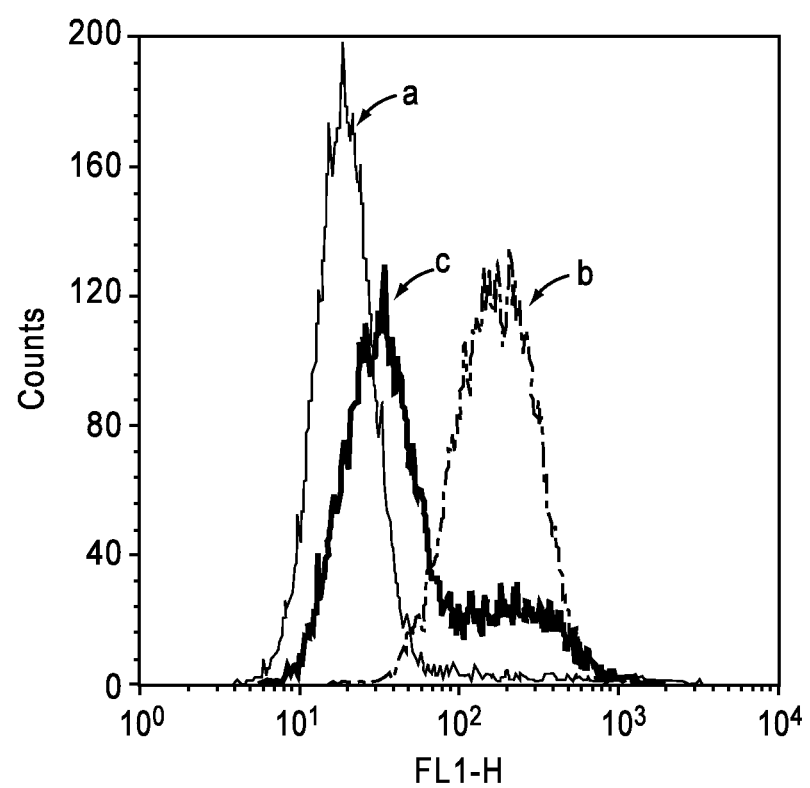
FIG. 19 shows the results of RNAi in which CD147 is a subject antigen. Gray color (a); cells that have not subjected to RNAi are stained with an anti-influenza antibody YA14cp3 as a primary antibody; Green color (b); cells that have not subjected to RNAi are stained with 059-053cp3 as a primary antibody; Red color (c); cells that have subjected to RNAi are stained with 059-053cp3 as a primary antibody.
Figure 20:
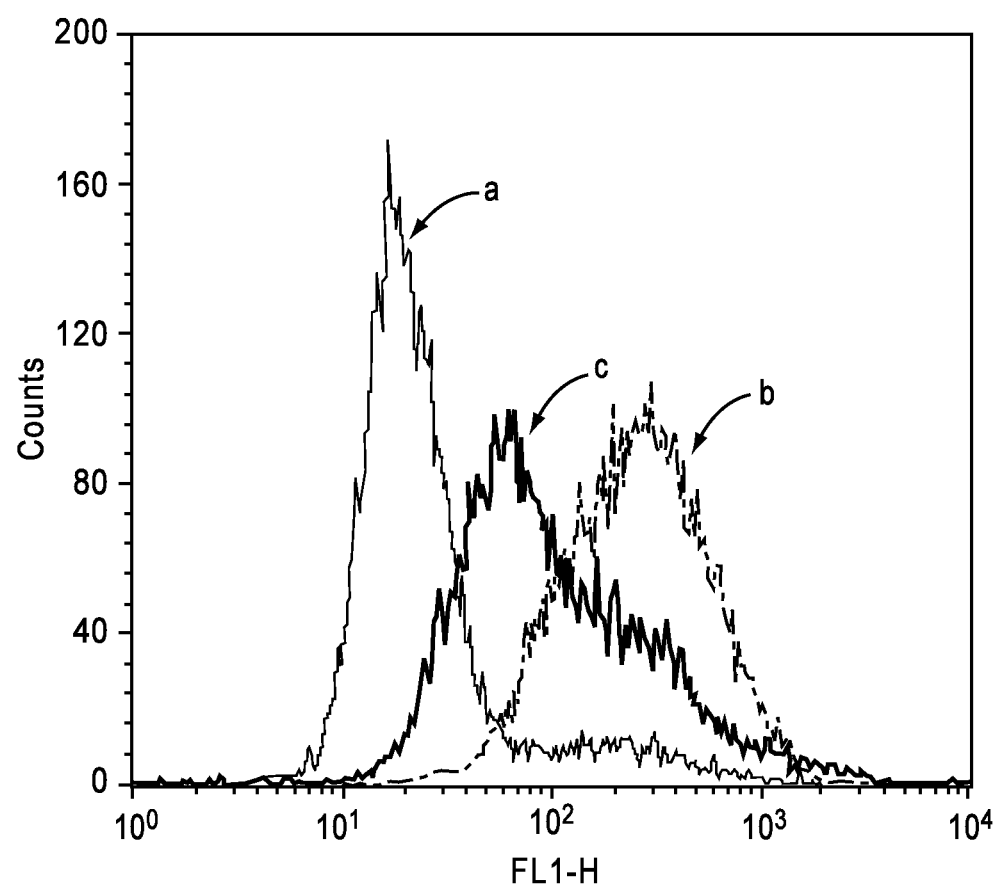
FIG. 20 shows the results of RNAi in which CD166 is a subject antigen. Gray color (a); cells that have not subjected to RNAi are stained with an anti-influenza antibody YA14cp3 as a primary antibody; Green color (b); cells that have not subjected to RNAi are stained with 035-234cp3 as a primary antibody; Red color (c); cells that have subjected to RNAi are stained with 035-234cp3 as a primary antibody.
Figure 21:
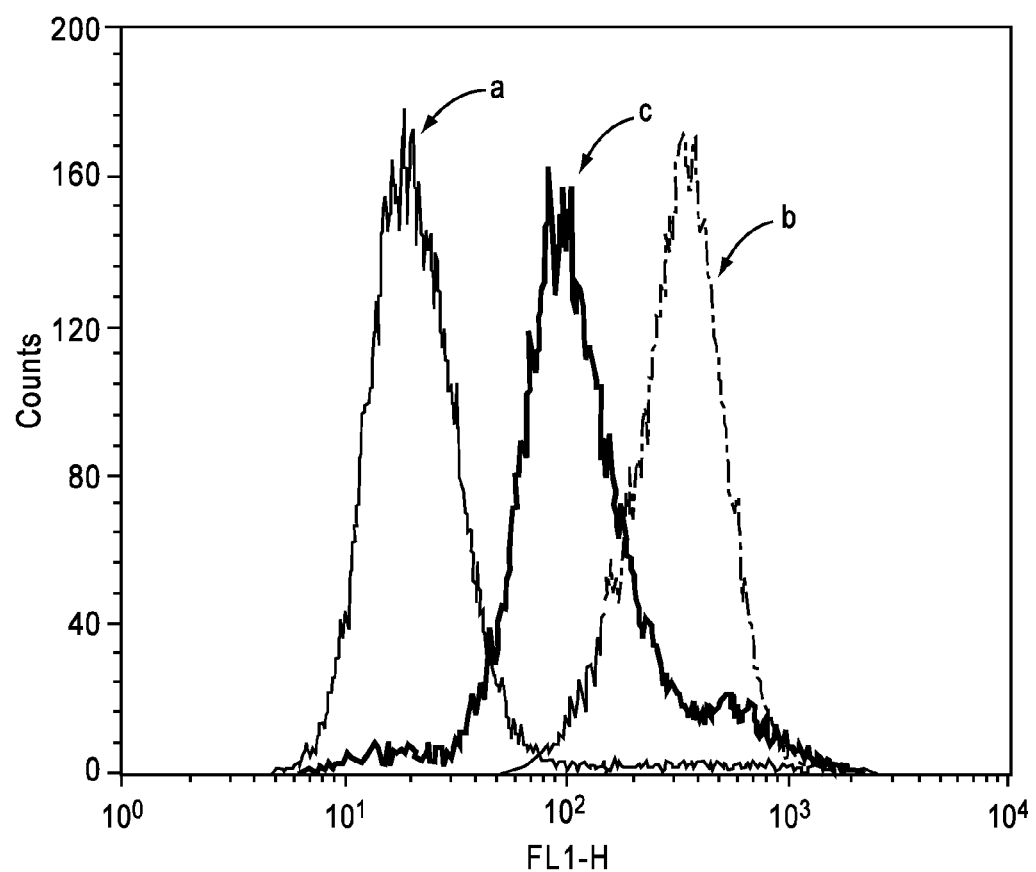
FIG. 21 shows the results of RNAi in which HER1 is a subject antigen. Gray color (a); cells that have not subjected to RNAi are stained with an anti-influenza antibody YA14cp3 as a primary antibody; Green color (b); cells that have not subjected to RNAi are stained with 048-006cp3 as a primary antibody; Red color (c); cells that have subjected to RNAi are stained with 048-006cp3 as a primary antibody.
Figure 22:
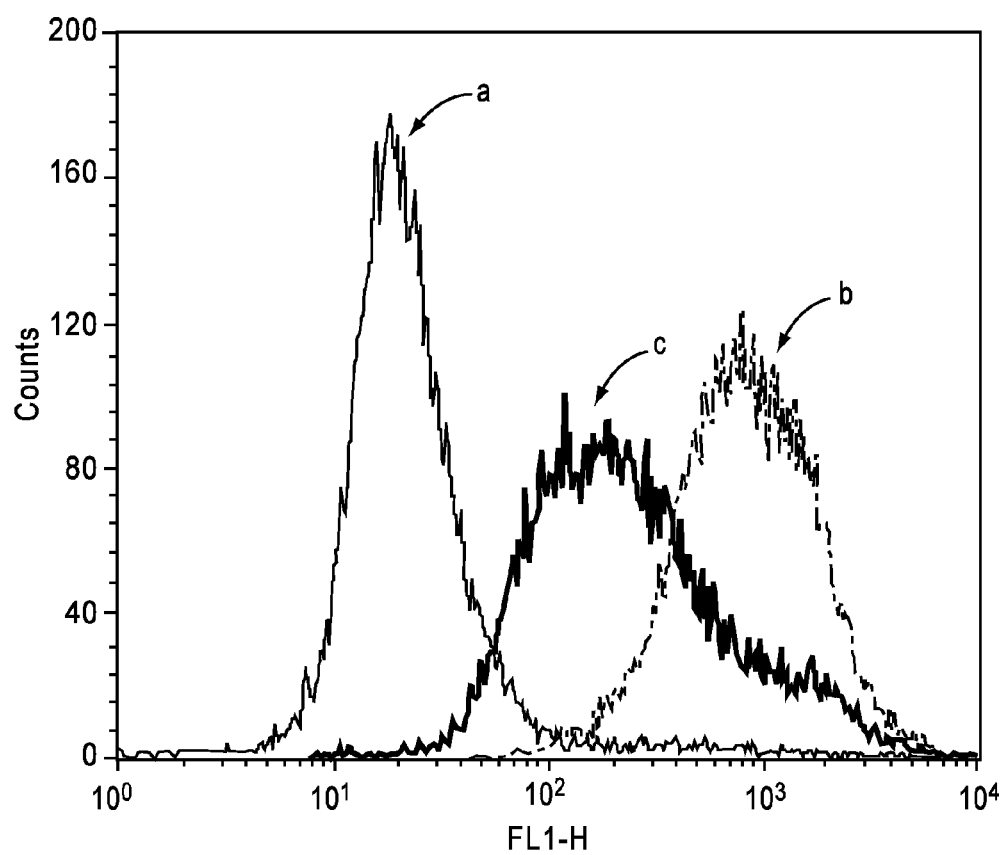
FIG. 22 shows the results of RNAi in which HER2 is a subject antigen. Gray color (a); cells that have not subjected to RNAi are stained with an anti-influenza antibody YA14cp3 as a primary antibody; Green color (b); cells that have not subjected to RNAi are stained with 015-126cp3 as a primary antibody; Red color (c); cells that have subjected to RNAi are stained with 015-126cp3 as a primary antibody.
Figure 23:
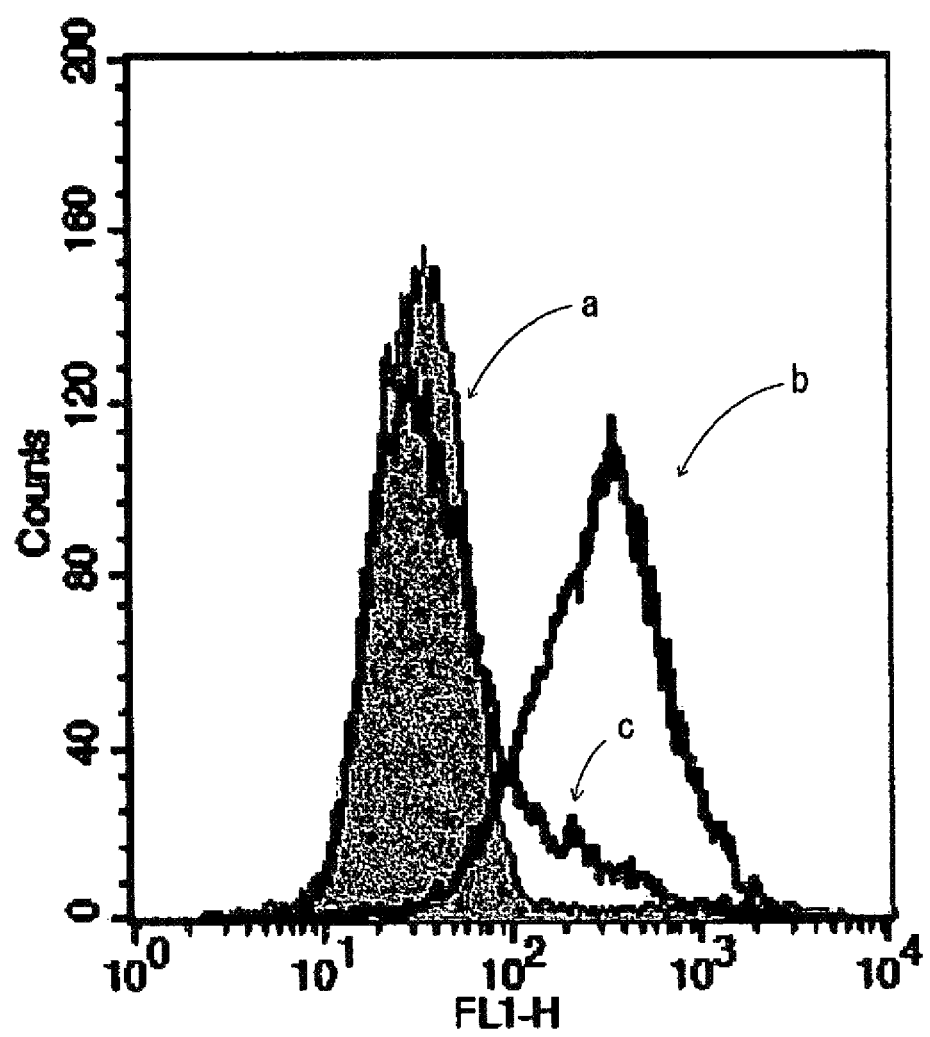
FIG. 23 shows the results of RNAi in which IgSF4 is a subject antigen. Gray color (a); cells that have not subjected to RNAi are stained with an anti-influenza antibody YA14cp3 as a primary antibody; light blue color (b); cells that have not subjected to RNAi are stained with 035-273cp3 as a primary antibody; orange color (c); cells that have subjected to RNAi are stained with 035-273cp3 as a primary antibody.

Subject cell: hepatic cell carcinoma HLF cell
Verified antibody: 035-273 cp3 antibody Results are shown in FIGS. 19 to 23. FIG. 19 shows the results of RNAi in which CD147 is a subject antigen. FIG. 20 shows the results of RNAi in which CD166 is a subject antigen. FIG. 21 shows the results of RNAi in which HER1 is a subject antigen. FIG. 22 shows the results of RNAi in which HER2 is a subject antigen. FIG. 23 shows the results of RNAi in which IgSF4 is a subject antigen. As is apparent from these results, in any of the verified antibodies, in the cell population that had been subjected to RNAi, as compared with the cell population that had not been subjected to RNAi, the staining property by antibodies (i.e., reactivity) was significantly reduced. In this way, by RNAi experiment using oligo RNA for knocking down the corresponding antigen it is reconfirmed again that each of the isolated antibodies recognizes the identified antigen.

11. Investigation of Reactivity of Each Antibody by Cell Staining and Tissue Staining 11-1 Experiment Method
(1) Cell Staining Cells were dissociated from a culture dish by using 2 mg/ml collagenase I (Gibco BRL)/cell dissociation buffer (Gibco BRL), then collected by using 10% FBS/DMEM, and $1 \times 10^5$ of the cells were used. These were washed with 2.5% BSA, 0.05% $NaN_3$/PBS (BSA solution), then suspended in 100 µl of 2.5% normal goat serum/BSA solution and left on ice for 30 minutes. Thereafter, cp3 type antibodies were added so that the concentration was 5 µg/ml and left on ice for one hour. This was washed with a BSA solution once, then suspended in 100 µl of 5 µg/ml BSA solution of anti-cp3 mouse monoclonal antibody (Medical & Biological Laboratories Co., Ltd.) and left on ice for one hour. This was washed with a BSA solution once, then suspended in 100 µl of 5 µg/ml BSA solution of ALEXA488 binding anti-mouse IgG goat antibody (Molecularprobe), and left on ice for one hour. This was washed with BSA solution twice, and then supernatant was discarded. To this, 50 µl of OptiLyse B (BECKMAN COULTER) was added and left at room temperature for ten minutes so as to fix the cells. To this, 950 µl of 1 ng DAPI/BSA solution was added, left at room temperature for 10 minutes, and subjected to centrifugation for collecting cells. The cells were mounted on MULTITEST SLIDE (ICN) and observed under microscopy.

(2) Tissue Staining
(2-1) Preparation of Antibody Sample

*E. coli* solution cultured overnight (0.5 ml) was planted in 6 ml of 2×YTAI (2×YT, 200 µg/ml ampicillin sulfate, 0.5 mM IPTG), cultured overnight at 30° C. and centrifuged at 10000 rpm for 5 minutes by using a micro-centrifugal machine, and supernatant was recovered. To this, an equal amount of saturated ammonium sulfate was added and left at room temperature for 30 minutes. Then, it was centrifuged at room temperature at 10000 rpm for 5 minutes and supernatant was discarded. The obtained precipitates were suspended in 0.6 ml of PBS-0.05% $NaN_3$, complete solution and centrifuged at 4° C. at 15000 rpm for 5 minutes, and supernatant was recovered.

(2) Production of Section

The extracted tissue was cut into about 5 mm×5 mm×10 mm, placed in 4% PFA/0.01% glutaraldehyde/0.1 Mcacodylic acid buffer (4° C.) (PFA is a product by Wako Pure Chemical Institute, glutaraldehyde is a product by KANTO CHEMICAL CO., INC., sodium cacodylate is a product by SIGMA). By using a microwave oven (SHARP), it was microwave-fixed. Then, it was fixed again in this fixation solution at 4° C. for one hour. Then, it was transferred into 10% sucrose/PBS and immersed therein at 4° C. for four hours, then substituted by 15% sucrose/PBS and immersed therein at 4° C. for four hours, and then substituted by 20% sucrose/PBS and immersed at one night. It was embedded in an OTC compound and rapidly frozen in dry ice/hexane. This was thinly cut into 4 µm thickness by using cryostat (Reichert-Jung 2800 FRIGCUT E), attached to silane coated slide glass (MATSUNAMI) and dried by using a cold wind drier for 30 minutes.

(2-3) Staining

The slide glass to which a section was attached was immersed in PBS three times for five minutes each so as to make hydrophilic. Next, 50 µl of 0.3% $H_2O_2$/0.1% $NaN_3$ was dropped so as to cause a reaction at room temperature for ten minutes and blocking of endogenous peroxidase was carried out. Then, it was washed with PBS three times for five minutes each. Then, it was reacted in 2% BSA/PBS at room temperature for 10 minutes, and blocking of a non-specific reaction was carried out. Then, excess liquid was dropped off and 50 µl of antibody sample was dropped thereto so as to cause a reaction at room temperature for one hour, followed by washing with PBS three times for 5 minutes each. Next, 50 µl of anti-CP3 rabbit antibody (5 µg/ml) was dropped to cause a secondary antibody reaction at room temperature for 45 minutes, followed by washing with PBS three times for 5 minutes each. Then, 50 µl of peroxidase labeled dextran binding anti-rabbit immunoglobulin—goat polyclonal antibody (DAKO) was dropped so as to cause a tertiary antibody reaction. This was washed with PBS three times for 5 minutes each, and the 50 µl of DAB—$H_2O$ coloring solution was dropped. After the color became brown, this was transferred to a vat filled with distilled water so as to terminate the reaction. Thereafter, obtained product was washed with water for 10 minutes, followed by staining nuclear with hematoxylin. Thereafter, dehydration and penetration were carried out, encapsulation with marinol and observation under microscopy were carried out.

11-2 Experiment Results (1) Anti-HER1 Antibody Group (Group 1)

Cancers showing positive in the cell line staining (containing FACS):
pancreatic cancer cell line PANC-1, kidney cancer cell line CCFRC1, kidney cancer cell line Caki-1, ovarian cancer cell line KF28, stomach cancer cell line SNU-5, lung squamous cell carcinoma line RERF-LC-AI, ovarian cancer cell line RMG-1, undifferentiated hepatic cell carcinoma cell line HLF, ovarian cancer cell line SKOv3, pulmonary adenocarcinoma cell line PC14, kidney cancer cell line ACHN, lung squamous cell carcinoma line EBC1, vulva mucosal epithelial cell line A431, pulmonary adenocarcinoma cell line H1373, hepatic cell carcinoma cell line HepG2, cell line established from kidney clinical specimen Cancers showing negative in the cell line staining (containing FACS):
breast cancer cell line BT474, hamster ovarian cancer cell line CHO Cancers showing positive in the tissue staining:
kidney cancer, hepatic cell carcinoma, intrahepatic bile duct cancer, lung squamous cell cancer, pulmonary adenocarcinoma, pancreas cancer (2) Anti-HER2 Antibody Group (Group 2)

Cancers showing positive in the cell line staining (containing FACS):
pulmonary adenocarcinoma cell line Calu-3, ovarian cancer cell line SKOv3, breast cancer cell line BT474

Cancers showing negative in the cell line staining (containing FACS):
hepatic cell carcinoma cell line HLF, pulmonary adenocarcinoma cell line PC14, kidney cancer cell line ACHN, kidney cancer cell line 293T, hamster ovarian cancer cell line CHO, kidney cancer cell line Caki-1, kidney and stomach cancer cell line CCFRC1, cell line established from kidney clinical specimen (3) Anti-CD46 Antibody Group Cancers showing positive in the cell line staining (containing FACS):
large bowel cancer cell line CaCo2, stomach cancer cell line MKN45, undifferentiated hepatic cell carcinoma cell line HLF, liver cancer cell line HepG2, intrahepatic bile duct cell cancer cell line RBE, pancreas cancer cell line PANC1, kidney cancer cell line CCFRC1, kidney cancer cell line Caki-1, pulmonary adenocarcinoma cell line NCI-H441, lung squamous cell cancer EBC1, stomach cancer cell line NCI-N87, stomach cancer cell line SNU-5, lung squamous cell carcinoma line RERF-LC-AI, hepatic cell carcinoma clinical specimen, breast cancer cell line BT474, kidney cancer cell line 293T, pulmonary adenocarcinoma cell line PC14, kidney cancer cell line ACHN, pulmonary adenocarcinoma cell line H1373

Cancers showing negative in the cell line staining (containing FACS):
hamster ovarian cancer cell line CHO, vulva mucosal epithelial cell line A431

Cancers showing positive in the tissue staining:
kidney cancer, hepatic cell carcinoma, intrahepatic bile duct cancer, pulmonary adenocarcinoma, pancreas cancer Specific expression of CD46 in intrahepatic bile duct cancer and pancreas cancer, which had not been particularly reported about the relationship with respect to CD46 was recognized.

(4) Anti-ITGA3 Antibody Group (Group 4)

Cancers showing positive in the cell line staining (containing FACS):
undifferentiated hepatic cell carcinoma cell line HLF, ovarian cancer cell line SKOv3, kidney cancer cell line ACHN, kidney cancer cell line Caki-1, pulmonary adenocarcinoma cell line H1373, lung squamous cell cancer EBC1, vulva mucosal epithelial cell line A431, breast cancer cell line BT474, pulmonary adenocarcinoma cell line PC14, kidney cancer cell line CCFRC1, hepatic cell carcinoma cell line OCTH, intrahepatic bile duct cell cancer cell line RBE, pancreas cancer cell line PANC-1, pancreas cancer cell line MIA-Paca2, pulmonary adenocarcinoma cell line A549, pulmonary adenocarcinoma cell line NCI-N441, pulmonary adenocarcinoma cell line Calu-3, lung squamous cell carcinoma line RERF-LC-AI, stomach cancer cell line SNU5, stomach cancer cell line MKN45, stomach cancer cell line NCI-N87, large bowel cancer cell line CW2, ovarian cancer cell line SKOv3, ovarian cancer cell line KF-28, ovarian cancer cell line RMG-1, ovarian cancer cell line RMG-2

Cancers showing negative in the cell line staining (containing FACS):
kidney cancer cell line 293T, hepatic cell carcinoma cell line HepG2, hamster ovarian cancer cell line CHO Cancers showing positive in the tissue staining:
intrahepatic bile duct cancer, pancreas cancer Specific expression of ITGA3 in gallbladder and liver cancer and pancreas cancer, which had not been particularly reported about the relationship with respect to ITGA3 was recognized.

(5) Anti-ICAM1 Antibody Group (Group 5)

Cancers showing positive in the cell line staining (containing FACS):
Liver cancer cell line HepG2, pulmonary adenocarcinoma cell line PC14, cell line established from kidney clinical specimen Cancers showing negative in the cell line staining (containing FACS):
undifferentiated hepatic cell carcinoma cell line HLF, ovarian cancer cell line SKOv3, breast cancer cell line BT474, kidney cancer cell line 293T, kidney cancer cell line ACHN, kidney cancer cell line Caki-1, pulmonary adenocarcinoma cell line PC14, kidney cancer cell line CCFRC1, hamster ovarian cancer cell line CHO
Cancers showing positive in the tissue staining:
hepatic cell carcinoma
(6) Anti-ALCAM Antibody Group (Group 6)
Cancers showing positive in the cell line staining (containing FACS):
Liver cancer cell line HepG2, OCTH, Hep3B, and HLF, kidney cancer cell line Caki-1, CCFRC1, ACHN, 293T, and cell line established from clinical specimen, lung cancer cell line PC14, NCI-H441, EBC-1, RERF-LC-AI, A549, and H1373, ovarian cancer cell line SKOv3, KF-28, RMG1, and RMG2, stomach cancer cell line NCI-N87, large bowel cancer cell line CW2, breast cancer cell line BT474, acute myelocytic leukemia AML-clinical specimen, hamster ovarian cancer cell line CHO
Cancers showing negative in the cell line staining (containing FACS):
vulva mucosal epithelial cell line A431
Cancers showing positive in the tissue staining:
kidney cancer, hepatic cell carcinoma, intrahepatic bile duct cancer, lung squamous cell cancer, alveolar cell carcinoma, adenocarcinoma
Specific expression of ALCAM in kidney cancer, hepatic cell carcinoma, and gallbladder and liver cancer, which had not been particularly reported about the relationship with respect to ALCAM was recognized.
(7) Anti-CD147 Antibody Group (Group 7)
Cancers showing positive in the cell line staining (containing FACS):
liver cancer cell line HepG2, kidney cancer cell line CCFRC1, kidney cancer cell line ACHN, kidney cancer cell line Caki-1, pulmonary adenocarcinoma PC14, cell line established from kidney cancer clinical specimen
Cancers showing negative in the cell line staining (containing FACS):
hamster ovarian cancer cell line CHO
Cancers showing positive in the tissue staining:
kidney cancer
Specific expression of CD147 in kidney cancer, which had not been particularly reported about the relationship with respect to CD147 was recognized.

12. Conversion into IgG Type Antibody 12-1 Construction of IgG Type Antibody Gene
In order to investigate the efficacy as an antibody medicine, a part of antibodies is converted into IgG type
Firstly, by using VH and VL genes of scFVcp3 type antibody, it is confirmed that there was not a restriction enzyme site necessary for cloning them to Fc region of IgG1 and the base sequence of the gene. PCR was carried out by using an antibody gene as a template and using a primer for amplifying the H chain and L chain were used. The amplified product was ligated to the downstream of CMV promoter of the IgG1 construction vector and a plasmid DNA containing an IgG type antibody gene was obtained.
12-2 Expression of IgG Type Antibody
For transfection of plasmid DNA into CHO-K1 cell, GenePORTER Reagent (Gene Therapy Systems: T201007) was used. Firstly, CHO-K1 cells were prepared in a 60 mm-culture dish the day before the transfection so that they became $2 \times 10^4$ cells/ml (a medium, in which α-MEM (Invitrogen: 12561-056) to which 10% FCS (Equitech: 268-1) had been added, was used).
The plasmid DNA (8 μg) was dissolved in 250 μL of serum free medium (hereinafter, abbreviate as "SFM") (Invtrogen: 12052-098 CHO-S-SFMII)) and subjected to 0.22 μm filter. GenePORTER Reagent (40 μL) was added to SFM (250 μL).
The plasmid DNA and GenePORTER Reagent dissolved in SFM were rapidly stirred and stood still at room temperature for 30 minutes.
The cells were washed with SFM (2 ml) twice, and the plasmid DNA-GenePORTER mixture (Transfection Medium) was slowly poured in a plate containing cells and cultured in an incubator at 37° C. for five hours.
The medium for transfection was sucked and washed with αMEM 10% FCS twice, then 5 ml of αMEM 10% FCS was added, which was cultured in an incubator at 37° C. for 48 hours.
The medium was replaced by a medium (10 mL) of αMEM 10% FCS+700 μg/ml G418 (Sigma: G7034) and selection was started (hereinafter, as a medium, αMEM 10% FCS+700 μg/mL G418 was used). After cultured at 37° C. for 48 hours, cells were washed with PBS (10 mL), treated with 0.25% Trypsin-EDTA (Sigma T4049) (750 μL), αMEM (5 mL) was added. Then, cultured product was peeled off and recovered from the plate. The number of cells was measured. Based on the results, limiting dilution was carried out under the conditions of 10 cells/200 μL/well (two sheets of 96 well plates). After culturing for 14 days, ELISA was carried out by using a culture supernatant of each well and the expression of an IgG type antibody was confirmed.
12-3 Purification of Expression Protein (IgG) from Culture Supernatant
Protein G Sepharose 4 Fast Flow (amersham pharmacia biotech: 17-0618-01) (1 mL) was packed in a column and balanced in PBS (5 mL). The culture supernatant was applied, sent at the flow rate of 1 drop/2 seconds, and allowed the expressed protein (IgG) to be bonded to a column. PBS (10 mL) was sent at the flow rate of 1 drop/2 seconds, non-adsorbed components were washed, then 6 mL of elute buffer (0.2M glycine-HCl, pH 3) was sent at the flow rate of 1 drop/second, and 1 mL each of eluate was collected in a 1.5 ml tube. To the collection tube, neutralizing buffer (3M Tris-HCl) (400 μL) was added in advance. Neutralization was carried out at the same time of collection. The eluate was collected and concentrated to 750 μL, and solution substitution (PBS, complete, 0.01% NaN3) was carried out. Then, the concentration of the antibody protein was calculated by SDS-PAGE.

13. Experiment of Inhibition of Binding of EGF by Successfully Obtained Anti-HER1 Antibody (048-006 Antibody)

13-1 Experimental Procedure
A431 cells were cultured in 15φ culture dish (medium: DMEM containing 10% FBS and 1% PS), and the cells were peeled off with the use of cell dissociation buffer (GIBCO: 13151-014) and recovered at 90% confluence. Two ml of PBS containing 1.0% BSA and 0.05% $NaN_3$ was added and the recovered cells were suspended. The suspension was stood still at 4° C. for 30 minutes and then 100 μl each (about $2.5 \times 10^5$ cells) was dispensed into each well of a 96-well V-bottom plate. It was centrifuged (650 G) for 2 minutes, and the cells were precipitated to remove the supernatant. Each antibody solution (HR1-007 [10 μg/ml], 48-006 [10 μg/ml, 5

μg/ml, 1 μg/ml], and 59-152 [10 μg/ml, 5 μg/ml, 1 μg/ml]) (200 μl), which had been prepared by using PBS containing 1.0% BSA, was added and the cells were suspended. The suspension was stood still at 4° C. for one hour, and then, biotin labeled EGF (biotinated EGF: 50 μg/ml) was added to each well so that the final concentration became 1 μg/ml, so that the cells were suspended. Note here that the biotinated EGF was produced by the following method. Firstly, to EGF (prepared to 1 mg/ml with PBS(−); AUSTRAL Biologicals: GF-010-5) (50 EZ-Link Sulfo-NHS-LC-Biotin (prepared to 2 mg/ml with PBS(−); PIERCE: 21335) (25 μl) was added. After it was stood still at room temperature for 30 minutes, 1M glycine (pH=7.0 to 8.0) (10 μl) was added. After it was stood still at room temperature for 30 minutes, PBS(−) (15 μl) was added and stored at 4° C. (final concentration: 500 μg/ml). This was 10-fold diluted with PBS containing 1.0% BSA and used for experiment.

This was stood still at 4° C. for one hour, and centrifuged (650 G) for 2 minutes so as to remove the supernatant. PBS containing 1.0% BSA (180 μl) was added and centrifuged (650 G) for 2 minutes so as to remove the supernatant. HRP-labeled streptavidin (0.2 μg/ml (PBS containing 1.0% BSA); PIERCE: 21126) (100 μl) was added and cells were suspended at 4° C. for one hour, and centrifuged (650 G) for 2 minutes so as to remove the supernatant. PBS containing 1.0% BSA (180 μl) was added and centrifuged (650 G) for 2 minutes so as to remove the supernatant. This operation was carried out again. OPD (Wako: 154-01673) coloring solution (100 μl) was added and cells were suspended. After four minutes at room temperature, coloring stop solution (2N $H_2SO_4$) (100 μl) was added and centrifuged (650 G) for 2 minutes. Then, the supernatant was transferred to a flat-bottom plate. By using a plate reader, the absorbance at 192 nm (A492) was measured and represented by a numeric value.

13-2 Results

Figure 24:
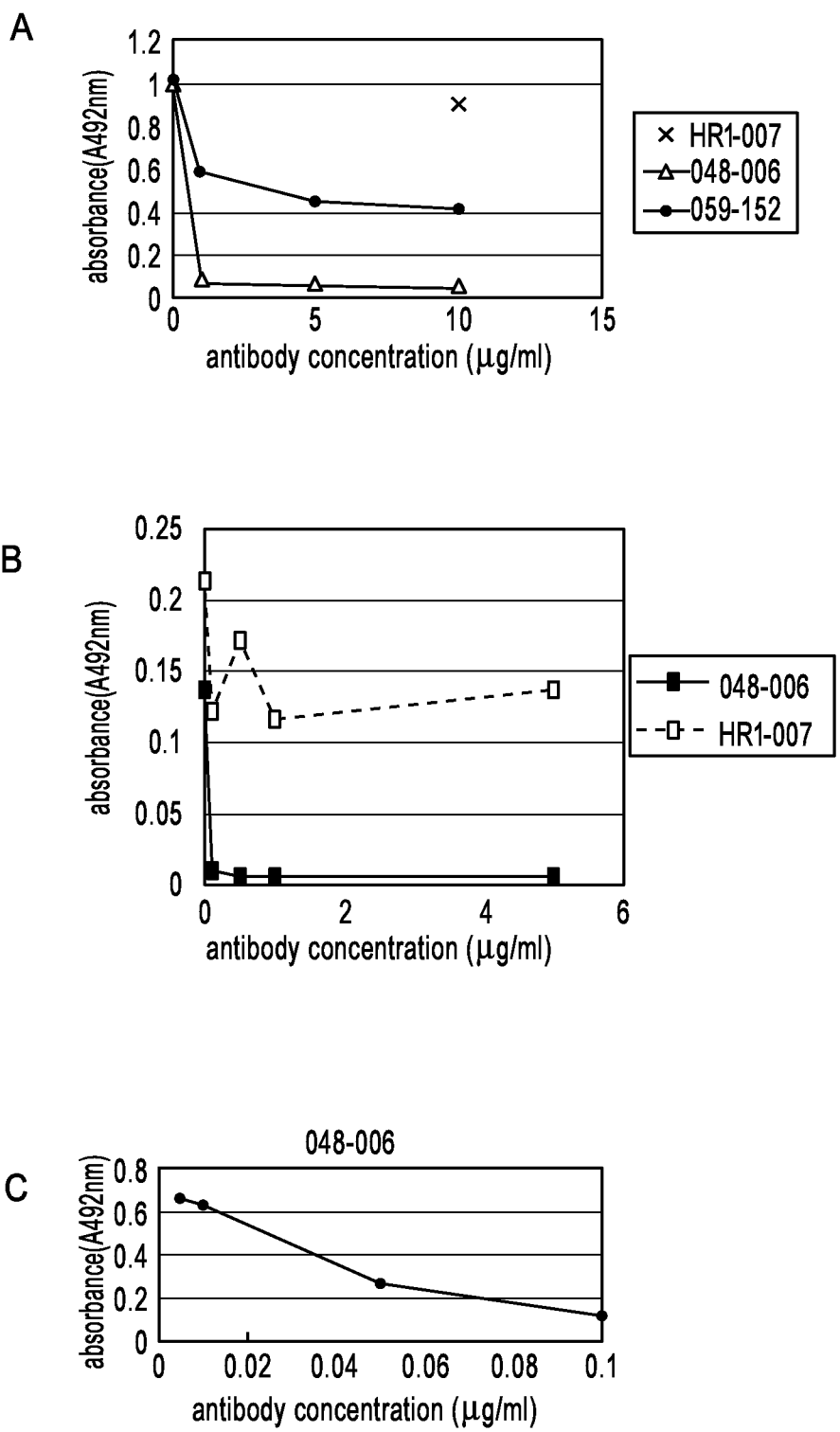
FIG. 24 shows A: an EGF binding inhibitory activity (using A431 cells) of 048-006 antibody and 059-152 antibody; B: an EGF binding inhibitory activity of 048-006 antibody (using low concentration range, A431 cells), and C: an EGF binding inhibitory activity of 048-006 antibody (using low concentration range, A431 cells).

The results are shown in FIG. 24. HR1-007 as a control does not affect the binding of EGF. 048-006 antibody and 059-152 antibody inhibit the binding of EGF. 048-006 antibody can inhibit the binding of EGF substantially completely while 059-152 antibody cannot completely inhibit the binding even if the temperature is increased. Note here that 048-006 antibody shows an inhibition effect even at the low level of about 0.02 μg/ml (FIG. 24C).

The results suggest that the antagonism activity between each antibody (048-006 antibody and 059-152 antibody) and EGF provides a part of the pharmacological effect such as anti-tumor property.

14. Experiment of Phosphorylation Signal Inhibition of HER1 by Successfully Obtained Anti-HER1 Antibody (048-006 antibody)

By using a phosphorylation antibody, it was determined whether or not be successfully obtained anti-HER1 antibody (048-006 antibody) inhibited the phosphorylation signal of HER1. Specifically, by using three kinds of cells (renal cell carcinoma (CCF-RC1, Caki-1) and epidermoid cancer (A431)), the inhibition effect of 048-006 antibody and 059-152 antibody and the inhibition effect of ERBITUX were compared with each other.

14-1 Experimental Procedure

Each of cells was cultured in 6-well culture dish, and at 60% confluence, a medium (DMEM containing 10% FBS and 1% PS) was substituted to DMEM. After 16 hours, each antibody (HR1-007, 048-006, 059-152 (prepared to 2 mg/ml with PBS(−))) and ERBITUX were added to each well so that the final concentration became 10 μg/ml or 1 μg/ml. After 30 minutes, EGF (prepared to 20 μg/ml with PBS(−)) was added to each well so that the final concentration became 1 μg/ml. After 30 minutes, each well was washed with PBS(−) and quickly frozen together with the culture dish by using liquid nitrogen. To each well, lysis buffer (50 mM Tris (pH 7.4), 150 mM NaCl, 1 mM Na3VO4, 10 mM NaF, 1% TritonX100, complete (Roche: 11836145001)) were added, and the cells were suspended and transferred to centrifugation tube. Centrifugation (10000G) was carried out for 10 minutes so as to precipitate cell debris. A part of the supernatant was subjected to SDS-PAGE, which was transferred to a membrane. Western blotting using an anti-phosphorylation tyrosine antibody (1 μg/ml; upstate: 05-321) or an anti-β-actin antibody (1 μg/ml; abcam: ab25139) as a primary antibody, and a secondary antibody reaction: HRP labeled anti-mouse IgG as a secondary antibody was carried out. A431 cells were required to be exposed to light for 1 to 2 seconds; CCF-RC1 for 10 seconds; and Caki-1 for one minute (there was originally large difference in cell sensitivity to external stimulation).

14-2 Results

Figure 25:
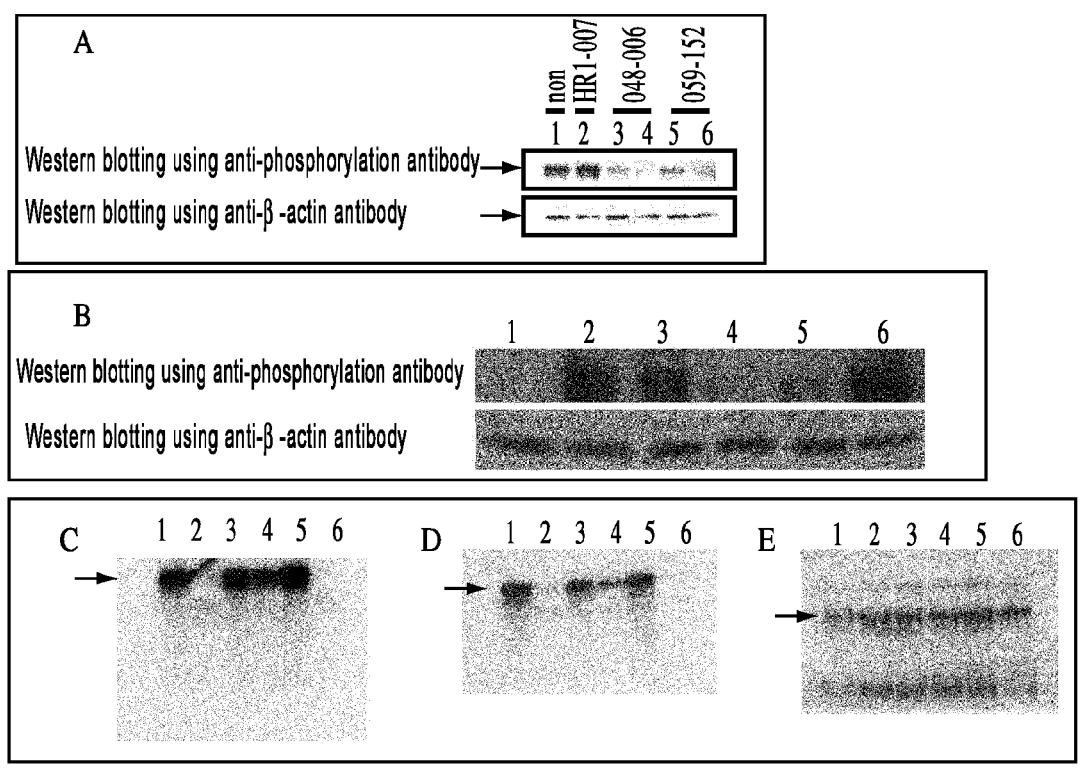
FIG. 25 shows A: HER1 phosphorylation signal inhibitory activity of 048-006 antibody and 059-152 antibody (results of Western blotting). Lane 1; antibody is not added, lane 2; HR1-007 added (10 µg/ml), lane 3; 048-006 antibody added (10 µg/ml), lane 4; 048-006 antibody added (10 µg/ml), lane 5; 059-152 antibody added (10 µg/ml), lane 6; and 059-152 antibody added (10 µg/ml). Upper part shows the results of Western blotting by using anti-phosphorylation tyrosine antibody (mouse monoclonal antibody). Lower part shows the results of Western blotting by using anti-β actin antibody (rabbit polyclonal antibody). B: HER1 phosphorylation signal inhibitory activity of a 048-006 antibody (low concentration range). Lane 1; not treated, lane 2; antibody is not added, lane 3; HR1-007 is added (1 µg/ml), lane 4; 048-006 antibody added (0.5 µg/ml), lane 5; 048-006 antibody added (0.1 µg/ml), lane 6; and 048-006 antibody added (0.05 µg/ml). After incubation with an antibody for 30 minutes, Her1 was added. Upper part shows the results of Western blotting by using anti-phosphorylation tyrosine antibody (mouse monoclonal antibody). Lower part shows the results of Western blotting by using anti-β actin antibody (rabbit polyclonal antibody). C: Comparison of HER1 phosphorylation signal inhibition effects of 048-006 antibody, 059-152 antibody and ERBITUX (using A-431 cells. Lane 1; HR1-007, lane 2; 048-006 antibody, lane 3; 059-152 antibody, lane 4; ERBITUX, lane 5; antibody is not added (EGF (+)), lane 6; antibody is not added (EGF (−)). D: Comparison of HER1 phosphorylation signal inhibition effects of 048-006 antibody, 059-152 antibody and ERBITUX (using CCF-RC1 cells). Lane 1; HR1-007, lane 2; 048-006 antibody, lane 3; 059-152 antibody, lane 4; ERBITUX, lane 5; antibody is not added (EGF (+)), lane 6; antibody is not added (EGF (−)). E: Comparison of HER1 phosphorylation signal inhibition effects of 048-006 antibody and 059-152 antibody clone and ERBITUX (using Caki-1 cells). Lane 1; HR1-007, lane 2; 048-006 antibody, lane 3; 059-152 antibody, lane 4; ERBITUX, lane 5; antibody is not added (EGF (+)), lane 6; antibody is not added (EGF (−)).

The results are shown in FIG. 25 (A and B: the results of Western blotting using A431 cells; C to E: comparison effect of inhibiting HER1 phosphorylation signal between the successfully obtained antibody and ERBITUX). In CCF-RC1 and A-431 cell lines, HR1-007 as a control does not affect the phosphorylation signal of HER1. However, 048-006 antibody and 059-152 antibody inhibit signal in a concentration-dependent manner. 048-006 antibody can inhibits the binding of EGF substantially completely and also inhibit self phosphorylation of HER1 substantially completely. 059-152 antibody inhibits the binding of EGF about 50%. Furthermore, 059-152 antibody inhibits self phosphorylation of HER1 although it is weaker than 048-006 antibody. 048-006 antibody and 059-152 antibody have inhibition capabilities superior to that by ERBITUX. In particular, the inhibition capability of 048-006 antibody is remarkable.

The sensitivity to external stimulation by EGF differs depending upon the kinds of cells. Therefore, when a cell like Caki-1 that does not show sensitivity to external stimulation by EGF is used, the difference in signal inhibition effect by the antibody is not observed.

The results suggest that each antibody (048-006 antibody and 059-152 antibody) has an activity of suppress the tyrosine kinase circuit of HER1 with respect to sensitive cells of HER1 by EGF, and exhibits pharmacological effects such as proliferation suppression and anti-tumor property.

15. Measurement of Binding Constant by BIAcore

As to the successfully obtained antibodies 048-006 and 059-152, the dissociation constant with respect to the expression Her1 was measured.

15-1 Experimental Procedure (1) Forced Expression of Partial Sequence of Her1

A sequence from a region after the signal of HER1 to immediately before the transmembrane region (621 amino acid of the expression sites from positions 26 to 645 (SEQ ID NO: 943) was cloned. For cloning and expression, a pSec-TagII vector (Invetrogen) was used. When this vector is inserted, myc and his tags are added.

(2) Recovering of Expressed Cells

One 15φ-culture dish (80 confluent) in which 293T cells were cultured was prepared. The medium was replaced with new one so that cells were not peeled off, and then cultured. Thus, a state in which cells were aggregated at 90-100% confluence was formed. The day before recovering cells, final medium replacement was carried out. DNA (75 μl) was added to D-MEM (serum free) (1.9 ml) and subjected to tapping adjustment so as to make the solution A. Furthermore, Lipo (75 µl) was added to D-MEM (serum free) (1.9 ml) and subjected to tapping adjustment (50 ml, Falcon) so as to make the solution B.

One minute after the formation of the solution B, the solution B was added to the solution A by using a 5 ml-pipette, subjected to pipetting, and incubated at room temperature for 20 minutes. 22.5 ml of D-MEM (serum free) was measured and taken out into a 50 ml culture container (Falcon) and 2.5 ml of serum was added thereto, which was incubated at 37° C. for 15 minutes so as to obtain D-MEM (containing serum).

The medium was removed from a 15φ-culture dish in which 293T cells were aggregated, and D-MEM (serum free) (25 ml) was added along the wall of the dish carefully so that cells are not peeled off. The added D-MEM (serum free) was sucked by using an aspirator and D-MEM (containing serum) (25 ml) was added.

Twenty minutes after D-MEM (containing serum) was formed, the mixture solution (3.8 ml) of solution A and solution B was added to the cells by using 25 ml-pipette and the cells were peeled off. The cells were separated from each other by pipetting, the cells were stood still in a $CO_2$ incubator for 2 days. Two days after, the supernatant was recovered and subjected to protein purification.

(3) Secretory Protein Purification (Ni-NTA)

Ni-NTA agarose gel (QIAGEN) (2 ml) (bed volume of 1 ml) was packed in a column and balanced in PBS. Then, the culture supernatant recovered in (2) was applied thereto. A flow-through solution was again applied to a column. The column was washed with 5 ml of PBS, and eluted in stages with 20, 50, 100, 250, and 500 mM imidazole/PBS (5 ml each) so that the absorbance (280 nm)<0.005 was satisfied. Furthermore, it was eluted with 0.5M EDTA/PBS (10 ml). The solution was replaced by new one by dialysis so as to obtain BIAcore immobilized sample.

(4) BIAcore Measurement

The interaction between the antibody clone and the expressed Her1 was examined so as to determine KD (dissociation constant; kd/ka). For analysis, BIAcore 1000 biosensor device was used.

A carboxymethyldextran (Sensor Chip CM5, Research grade, BIACORE) sensor chip was used. With the electrostatic adsorption to a CM5 matrix and a covalent linkage between a lysyl group on CM5 and an activated carboxyl group, antigen (Her1) was immobilized on the chip. By EDC/NHS coupling chemical reaction, a carboxyl group was activated.

In the condition of HBS-EP (BIACORE) at a flow rate of 5 µL/minute by using EDC/NHS (amine coupling kit, BIACORE was mixed with equal amount of EDC and NHS), after the lysyl group on CM5 was activated (contact time: 2.4 minutes), chip was washed with HBS-EP (BIACORE). Subsequently, Her1 (20 µg/mL: Sigma, 0.6 mg protein/ml was diluted with 10 mM acetic acid (pH 4.0)) was added to the chip. The chip was washed with HBS-EP, then, 1M ethanolamine (pH 8.5) was added so as to deactivate the remaining activated carboxyl group. Thereafter, the chip was washed with 50 mM NaOH so as to remove all Her1 that were not linked covalently. Note here that all the analysis experiments were carried out under the conditions of HBS-EP (BIACORE) at a flow rate of 35 µl/minute at 25° C. Reproduction was carried out by using 50 mM NaOH (one minute).

059-152 antibody or 048-006 antibody were reacted at each concentration shown in the figure and HBS-EP at flow rate of 35 µl/minute, so that the binding constant was analyzed.

15-2 Results

Figure 26:
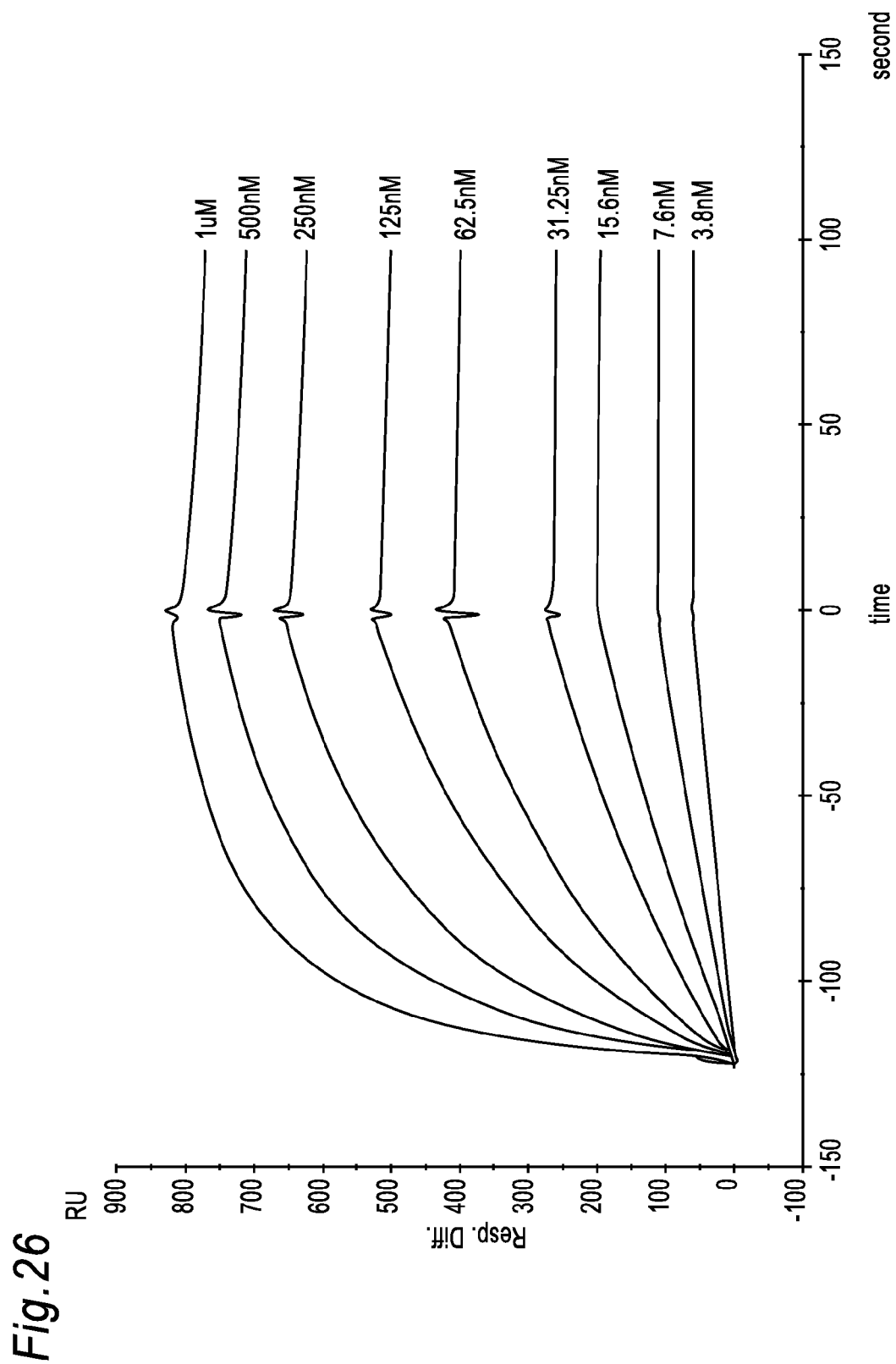
FIG. 26 shows a result of BIACORE experiment. Fixation method: CM5 chip of BIAcore is used and NHS is used so as to fix a partial sequence of HER1 to sensor. 048-006 antibody is allowed to flow at the above-mentioned concentration to observe signals.

The results are shown in FIG. 26. 048-006 antibody shows extremely strong binding force of more than KD=10-11 (M) at every measurement point. The actual value of Global fitting based on each detection value was $4.8 \times 10^{-13}$ (M). This is beyond the reliable measurement limit of BIAcore. As to 059-152 antibody, a bond dissociation curve cannot be detected. This is thought to be because this antibody cannot recognize the higher-order structure of artificially produced forced expression product. In other words, it is suggested that this antibody recognize a higher-order structure of a complex or a higher-order structure that can be observed only on an intact membrane.

16. Cytotoxicity Test of Anti-HER1 Antibody, Anti-HER2 Antibody, Anti-ITGA3 Antibody, Anti-ALCAM Antibody, and Anti-ICAM Antibody (ADCC Activity Measurement)

Antibody-Dependent Cell-mediated Cytotoxicity (ADCC) is an immune reaction of killing and attacking cells harmful to a human body, for example, virus infected cells, in which "effector cells" mainly consisting of natural-killer cell or monocyte attacks cells to which antibodies are bonded widely on the membrane surface as a target. The cytotoxicity by ADCC occurs depending upon the combination of an antibody specifically bonded to a surface of the cell membrane antigen and an effector cell.

Some of antibodies specifically bonded to a tumor surface antigen have an anti-tumor effect and a therapeutic effect to cancer and sold as antibody medicine. It has been reported that the main mechanism of action of these antibodies are ADCC. Then, in order to evaluate whether or not the cancer antigen specific antibodies successfully isolated by the present inventor have an anti-tumor effect, that is, they have promising as a cancer treatment antibody, the detection of ADCC was carried out. In the below-mentioned experiments, human IgG type antibody clone recognizing a subject antigen is reacted to a target cell to present it to an effector cell. In the detection of ADCC, the degree of cytotoxicity is calculated by using a cytotoxicity detection kit which, in principle, detects the enzymatic activity of lactate dehydrogenase leaking into the medium from the target cancer cell attached by the effector cell by using the coloring of the reagent.

16-1 Induction of ADCC 1 (Case of 015-003 Antibody as Anti-ITGA3 Antibody: scFVcp3 Type Antibody is Used)

Regarding 015-003 antibody as anti-ITGA3 antibody, a scFVcp3 type antibody was used and the ADCC activity was investigated by an assay combining an anti-M13 pIII rabbit antibody. Furthermore, liver cancer HLF cell is used as the target subject cultured cell. The operation procedure is described below.

(1) By the following procedures, peripheral blood is collected from a volunteer and mononucleosis is separated. Firstly, heparin-added peripheral blood (30 ml) collected from a volunteer is diluted with PBS to 80 ml and superposed quietly on 10 ml each of lymphocyte isolation reagent Ficoll Paque Plus (Amersham Bioscience), which have been dispensed in four centrifugation tubes, and centrifuged (400×g, 20° C. for 40 minutes). The mononucleosis fractions (including lymphocyte and monocyte) are recovered, diluted with cooled PBS to 80 ml and centrifuged (200×g, 4° C. for 15 minutes).

(2) (1) is suspended in a cooled cytotoxicity test medium (Cytotoxic Medium, hereinafter, abbreviated as "CTM", RPMI-1640 medium, 1% (v/v) fetal calf serum, 1% (v/v) Penicillin-Streptomycin Solution, 1% (v/v) 1M HEPES buffer (pH 7.0): Invitrogen) so that the final density becomes 5.0×10^6 cells/ml to obtain an effector cell.

(3) In a culture dish having a diameter of 150 mm, a target subject cultured cell is grown in a culture medium 1 (Minimum Essential Medium Alpha Medium:Invitrogen, 10% (v/v) fetal calf serum: Equitic-Bio, 1% (v/v) Penicillin-Streptomycin Solution: Sigma-Aldrich). A liquid medium is removed and cells are washed with PBS (10 ml) twice so as to remove the solution. Thereafter, 4% (w/v) collagenase Type IV (Invitrogen) (5 ml) is added and stored keeping warm at 37° C. for 10 minutes, so that cells are peeled off from the culture dish. Furthermore, 5 ml of liquid medium 2 (RPMI-1640, 10% (v/v) fetal calf serum, 1% (v/v) Penicillin-Streptomycin Solution:Sigma-Aldrich) (RPMI-1640: Sigma-Aldrich, 10% fetal calf serum, 1% penicillin-streptomycin solution) is added to stop a collagenase reaction. Then, suspended cells are recovered to obtain cell suspension.

(4) The cell density of the cell suspension of (3) is measured. The supernatant is removed by centrifugation and the cells are suspended in a cooled CTM medium so that the final density becomes $1.5 \times 10^5$ cells/ml.

(5) 100 µl each of target cells is dispensed in a 96-well V-bottom multi plate on ice.

(6) 2 µg/ml scFv-pIII phage antibody-CTM solution (100 µl each) is dispensed and reacted on ice for 60 minutes.

(7) Centrifugation (Swing rotor: 500×g, 4° C. for 10 min) is carried out to remove the supernatant.

(8) Cell pellet is suspended in 5 µg/ml anti-M13 pIII rabbit polyclonal antibody-CTM solution (150 µl each), a part of 100 µl is transferred to a 96-well U-bottom multi plate.

(9) The effector cell of (2) (or 2% Triton X-100-CTM solution) is added and then centrifuged (Swing rotor: 50×g, 4° C. for 5 min).

(10) Reaction is carried out in 5% $CO_2$ at 37° C. for 4 hours.

(11) After the reaction, centrifugation (Swing rotor: 500×g, 4° C. for 10 min) is carried out and the supernatant (100 µl) is transferred to a flat-bottom 96 well multi plate.

(12) LDH activity measurement reagent (Roche) (100 µl) is added and reaction is carried out at room temperature for 30 min.

(13) OD490 and OD690 are measured by using a micro plate absorptiometer.

16-2 Induction of ADCC 2 (Case of 048-006 Antibody as Anti-HER1 Antibody, 015-126 Antibody as Anti-HER2 Antibody, 066-174 Antibody, 035-234 Antibody and 041-118 Antibody as Anti-ALCAM Antibody, 053-051 Antibody, 053-059 Antibody and 053-085 Antibody as Anti-ICAM1 Antibody, 067-153 Antibody as Anti-EpCAM Antibody, 067-133 Antibody as Anti-HGFR Antibody: IgG Type Antibody is Used)

Regarding 048-006 antibody as anti-HER1 antibody, an IgG type antibody was used and the ADCC activity was investigated. A-431 and A549 (epidermoid tumor), ACHN and CCF-RC-1 (kidney cancer), NCI-H1373 (lung cancer), as well as SK-OV-3 (ovarian cancer) were used as the target subject cultured cell.

Also regarding 015-126 antibody as anti-HER2 antibody, an IgG type antibody was used, and the ADCC activity was investigated. Breast cancer BT-474 was used as the target subject cultured cell.

Regarding 066-174 antibody and 035-234 antibody as anti-ALCAM antibody, an IgG type antibody was used, and the ADCC activity was investigated. NCI-H1373 (pulmonary adenocarcinoma), CW2 (large bowel cancer), or NCI-H441 (lung cancer) was used as the target subject cultured cell.

Regarding 053-051 antibody, 053-059 antibody and 053-085 antibody as anti-ICAM1 antibody, an IgG type antibody was used, and the ADCC activity was investigated. HepG2 (hepatic cell carcinoma) and NCI-H441 (lung cancer) were used as the target subject cultured cell.

Furthermore, regarding the effect of 048-006 antibody or 059-152 antibody as anti-HER1 antibody on CCF-RC-1 (kidney cancer), NCI-H1373 (lung cancer) and A-431 (epidermoid cancer), the antibody dosage dependence of the ADCC activity was investigated so that the final concentration of the IgG type antibody was in the range from 0.01 to 10 µg/ml.

Regarding 041-118 antibody as anti-ALCAM antibody, an IgG type antibody was used and the antibody dosage dependence of the ADCC activity was investigated. NCI-H1373 (pulmonary adenocarcinoma) was used as the target subject cultured cell.

Regarding 067-153 antibody as anti-EpCAM antibody, an IgG type antibody was used and the antibody dosage dependence of the ADCC activity was investigated. MKN-45 (solid-type gastric adenocarcinoma), HT-29 (colon adenocarcinoma) and NCI-H1373 (lung cancer) were used as the target subject cultured cell.

Regarding 067-133 antibody as anti-HGFR antibody, an IgG type antibody was used and the antibody dosage dependence of the ADCC activity was investigated. NCI-H1373 (lung cancer) was used as antibody dosage dependence of the ADCC activity.

The antibody dosage dependence of the ADCC activity was basically measured at the E/T Ratio (ratio of effector cell:target cell) of 80:1 at final antibody concentration in the solution of 0.01 µg/ml to 10 µg/ml or $10^{-6}$ µg/ml to 10 µg/ml.

At each measurement point, the antibody and the effector cell were added to the target cell, and four hours later, the ADCC activity was measured. Regarding NCI-H1373, the ADCC activity was measured at the E/T Ratio of 100:1.

The operation procedure was carried out in accordance with the procedures described in 16-1. The detail of the reaction was made to be as follows. 66 µl/well of the target cells ($2 \times 10^4$ cells) were placed in 96-well U-bottom plate (Becton Dickinson) and 66 µl of IgG type antibody (3 µg/ml) was added and then 66 µl of peripheral blood mononucleosis suspension ($7.5 \times 10^5$ cells) was added. The E/T Ratio (ratio of effector cell:target cell) was made to be 20. In order to promote the association of cells, centrifugation (60×g, 4° C., 5 minutes) so as to allow the cells to sink, which was stored keeping warm 240 minutes in a culture container that had been set to the conditions of 37° C. and 5% $CO_2$. Thus ADCC reaction was induced. Each antibody sample was prepared as a CTM solution. Furthermore, in each sample, CTM was used as a negative control and target cell to which 100 µl of 2% Triton X-100—CTM solution was added was used as a control of maximum liberation of lactate dehydrogenase (cells had been destroyed by Triton X-100 in advance). Furthermore, three wells were used for each experiment groups.

16-3 Measurement of ADCC Activity

In both the assay using a scFVcp3 type antibody and assay using an IgG type antibody, the ADCC activity was an indicator of the damage to the target cell, which is in proportion to the degree of coloring, that is, the concentration of lactate dehydrogenase liberating to the culture supernatant. Thirty minutes after the coloring starts, absorbance (OD490-OD620 (background absorbance)) was measured by using a spectrophotometer. In each experiment group, absorbance values in the three wells were averaged to calculate the cytotoxic Index. In advance, the absorbance of only a medium was subtracted and the calculation was carried out by the following calculation equation.

Relative LDH activity=OD490-OD690

LDH activity derived from cell=experimental value−(control containing only solution)

Cytotoxicity (%)=(experimental value−effector cell control−target cell control)/(cell+Triton $X$-100 control−target cell control)×100    [Equation 1]

Note here that when the antibody does not have any cytotoxic activity, the cytotoxicity calculated by this method may be minus value due to a measurement error because the measurement is carried in experiments using the living body components.

16-4 Measurement Result

Figure 27:
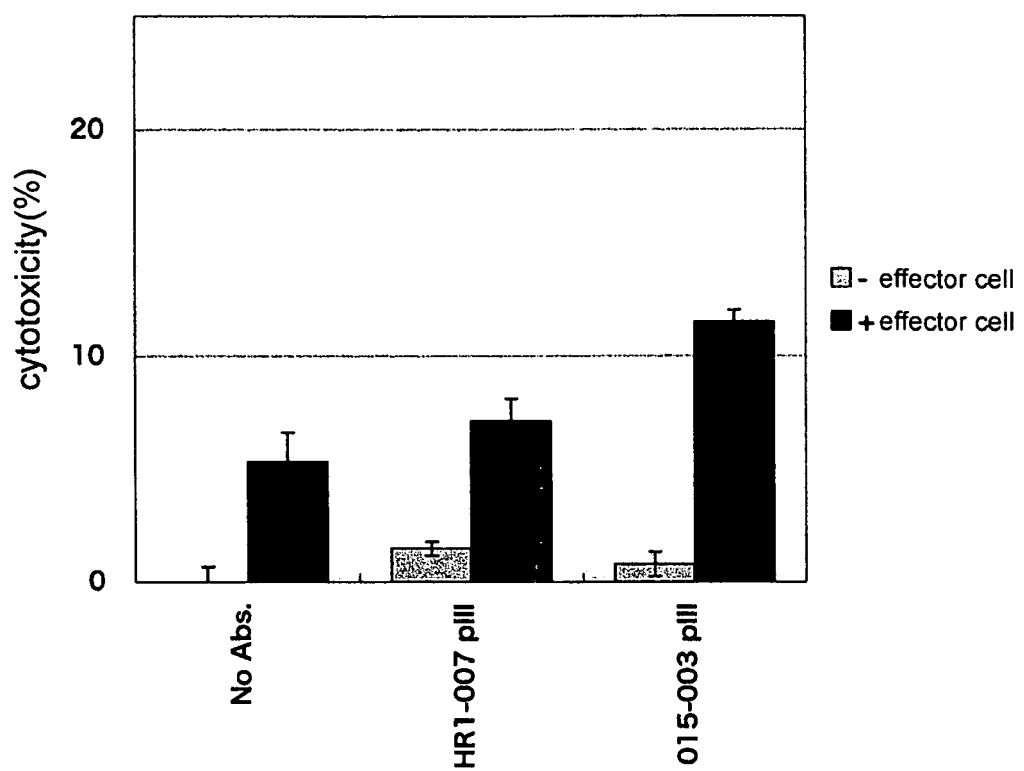
FIG. 27 shows a result of an ADCC activity test. An antibody to be used: anti-ITGA3 antibody, a target culture cell: HLF.
Figure 28:
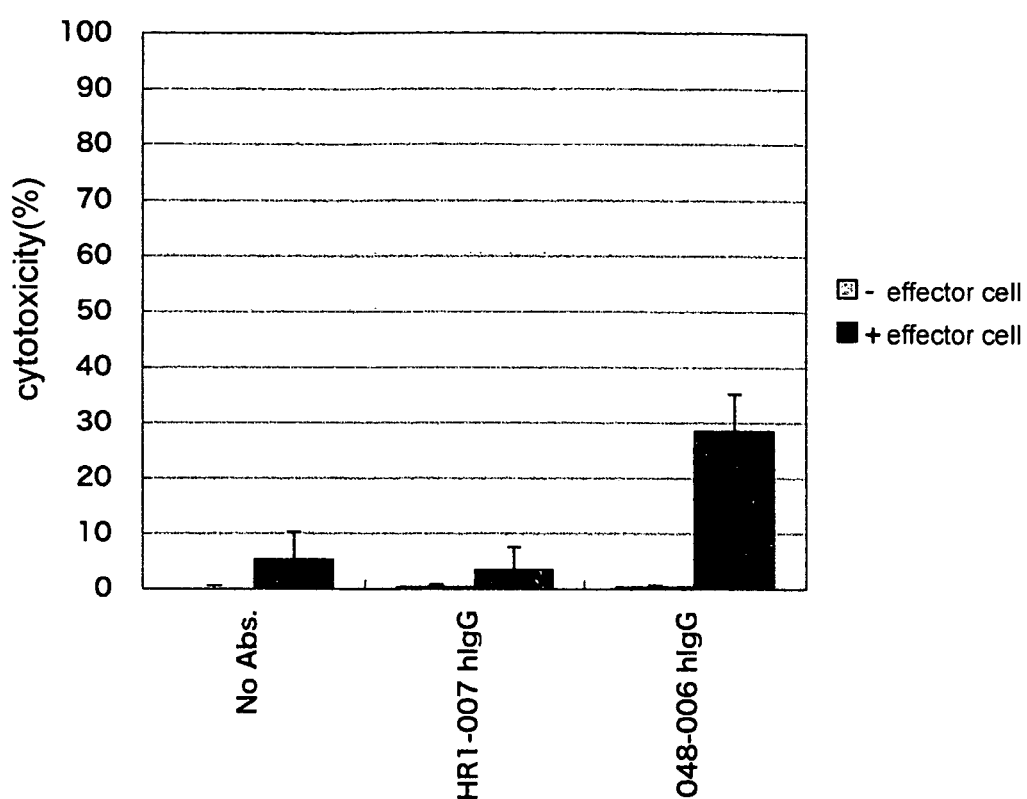
FIG. 28 shows a result of an ADCC activity test. An antibody to be used: anti-HER1 antibody, a target culture cell: A-431.
Figure 29:
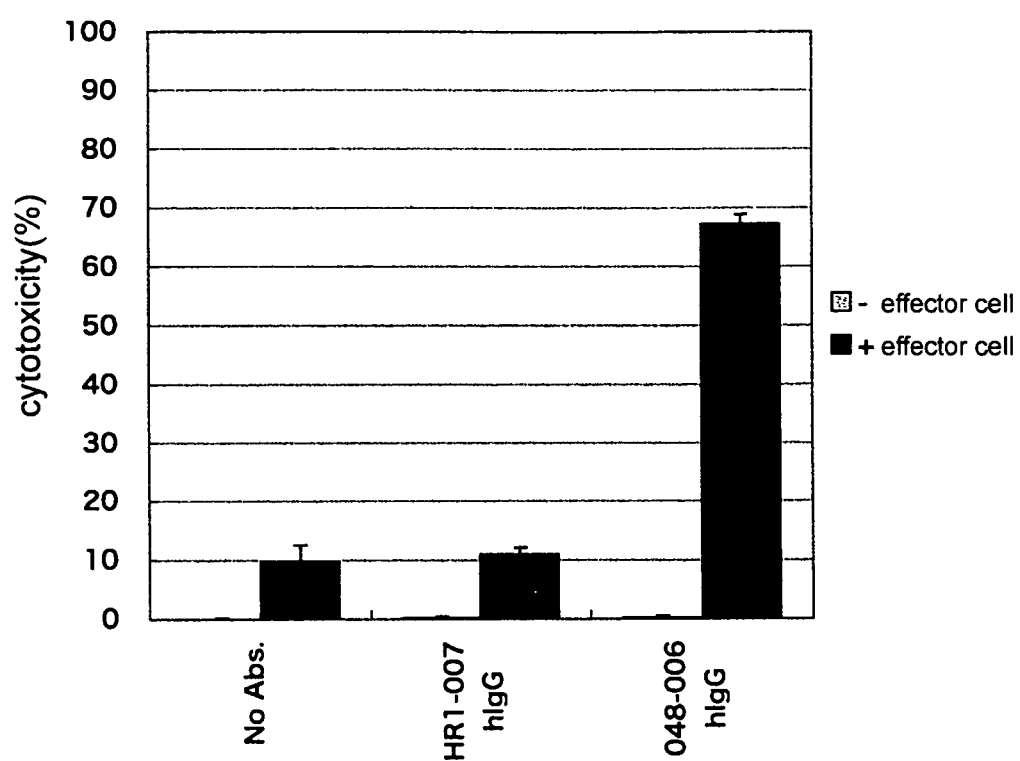
FIG. 29 shows a result of an ADCC activity test. An antibody to be used: anti-HER1 antibody, a target culture cell: A549.
Figure 30:
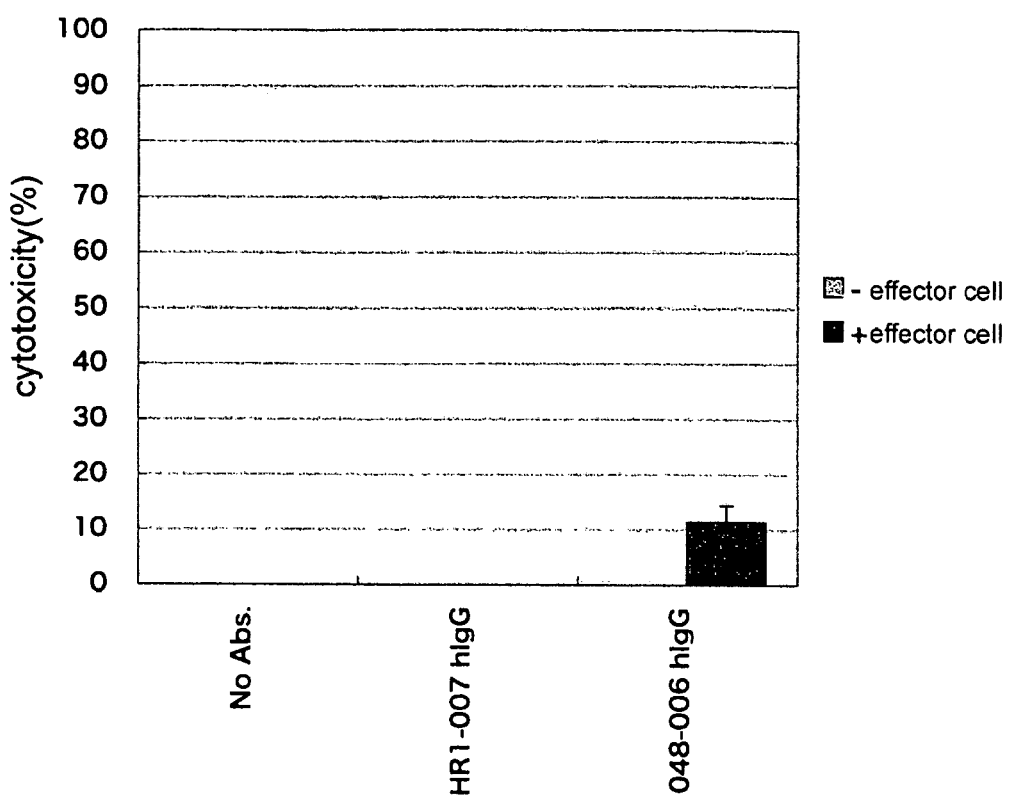
FIG. 30 shows a result of an ADCC activity test. An antibody to be used: anti-HER1 antibody, a target culture cell: ACHN.
Figure 31:
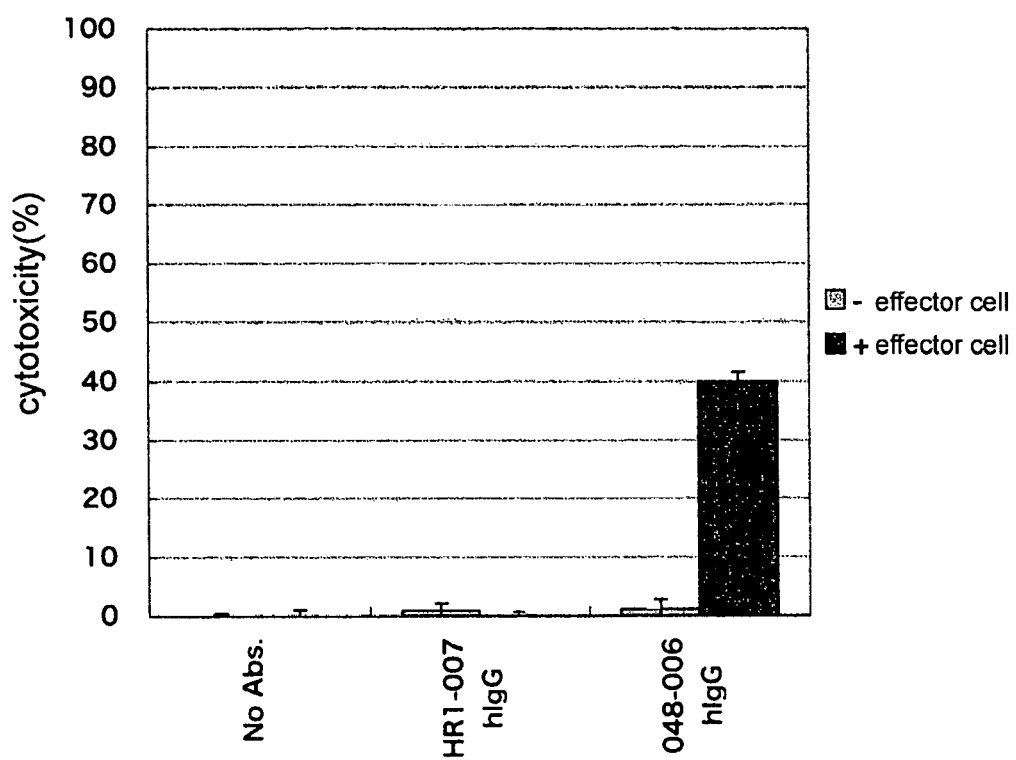
FIG. 31 shows a result of an ADCC activity test. An antibody to be used: anti-HER1 antibody, a target culture cell: CCF-RC-1.
Figure 32:
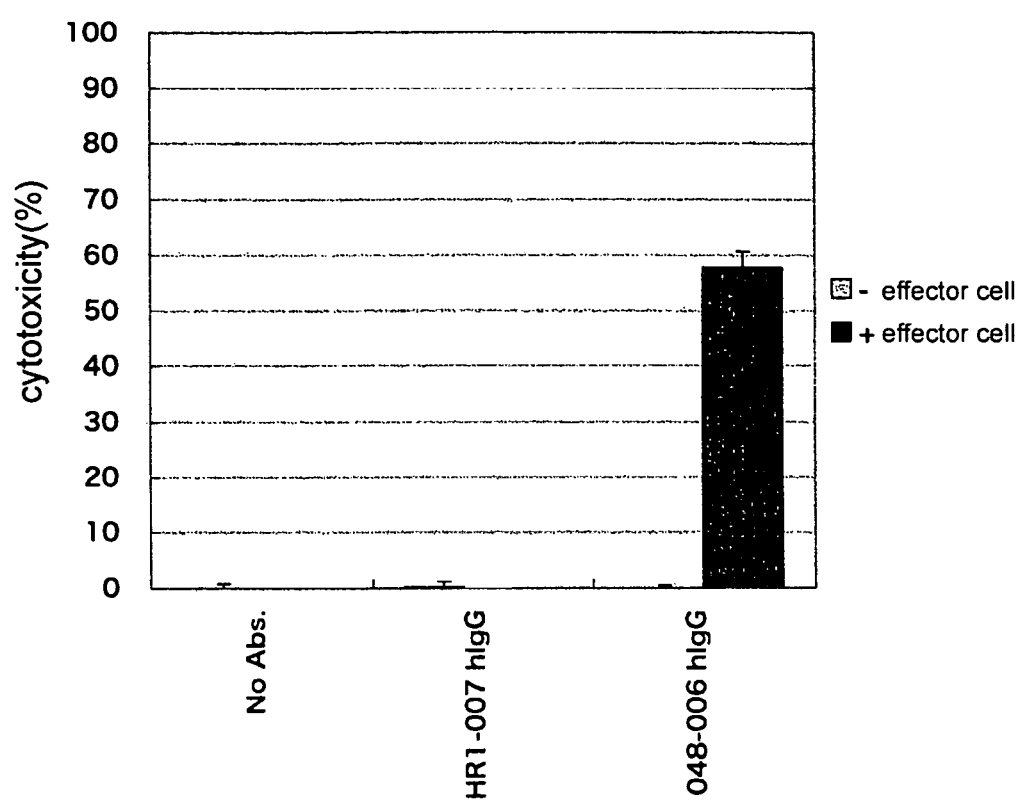
FIG. 32 shows a result of an ADCC activity test. An antibody to be used: anti-HER1 antibody, a target culture cell: NCI-H1373.
Figure 33:
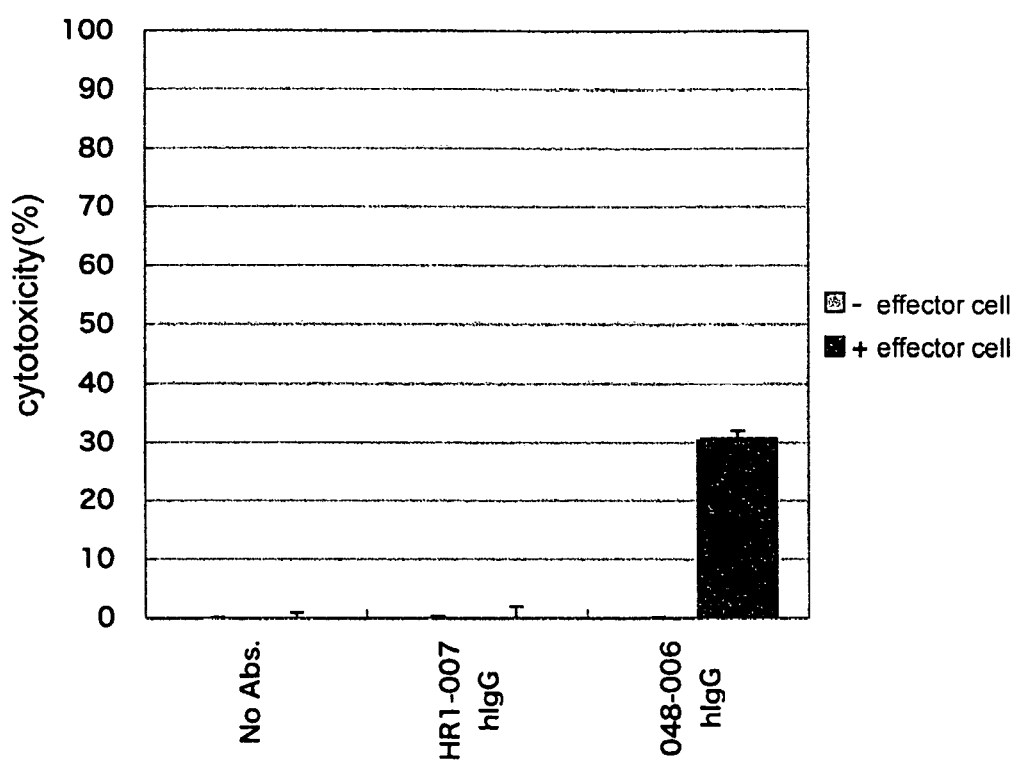
FIG. 33 shows a result of an ADCC activity test. An antibody to be used: anti-HER1 antibody, a target culture cell: SK-OV-3.
Figure 34:
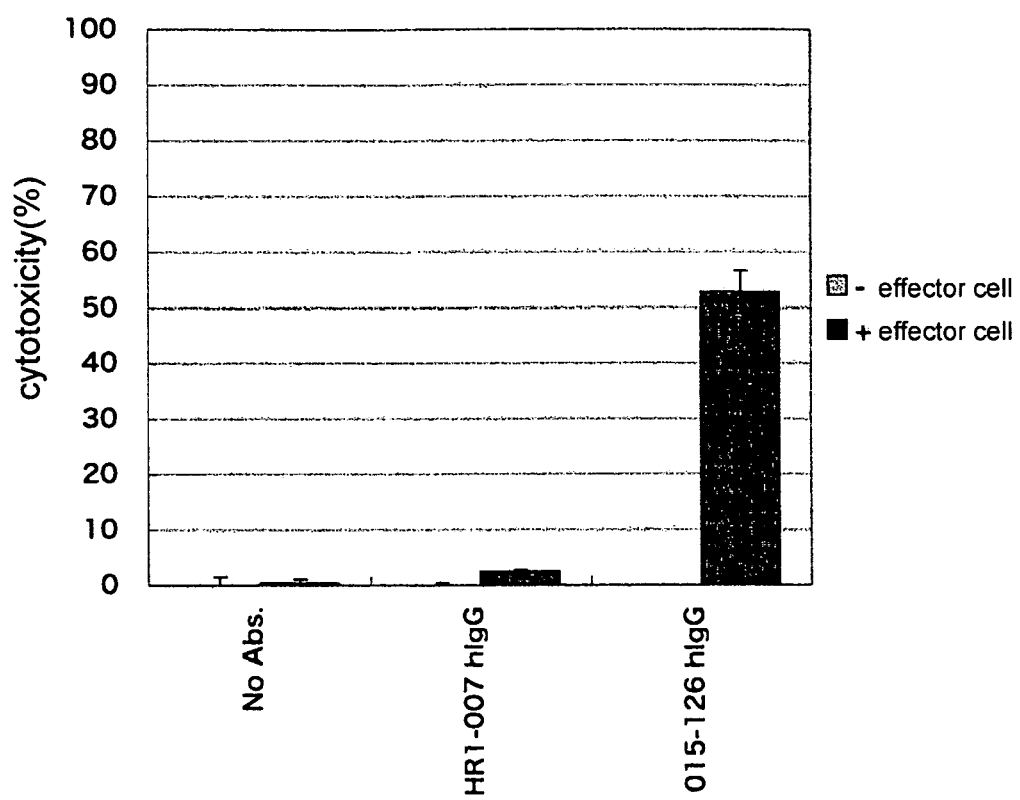
FIG. 34 shows a result of an ADCC activity test. An antibody to be used: anti-HER2 antibody, a target culture cell: BT-474.
Figure 35:
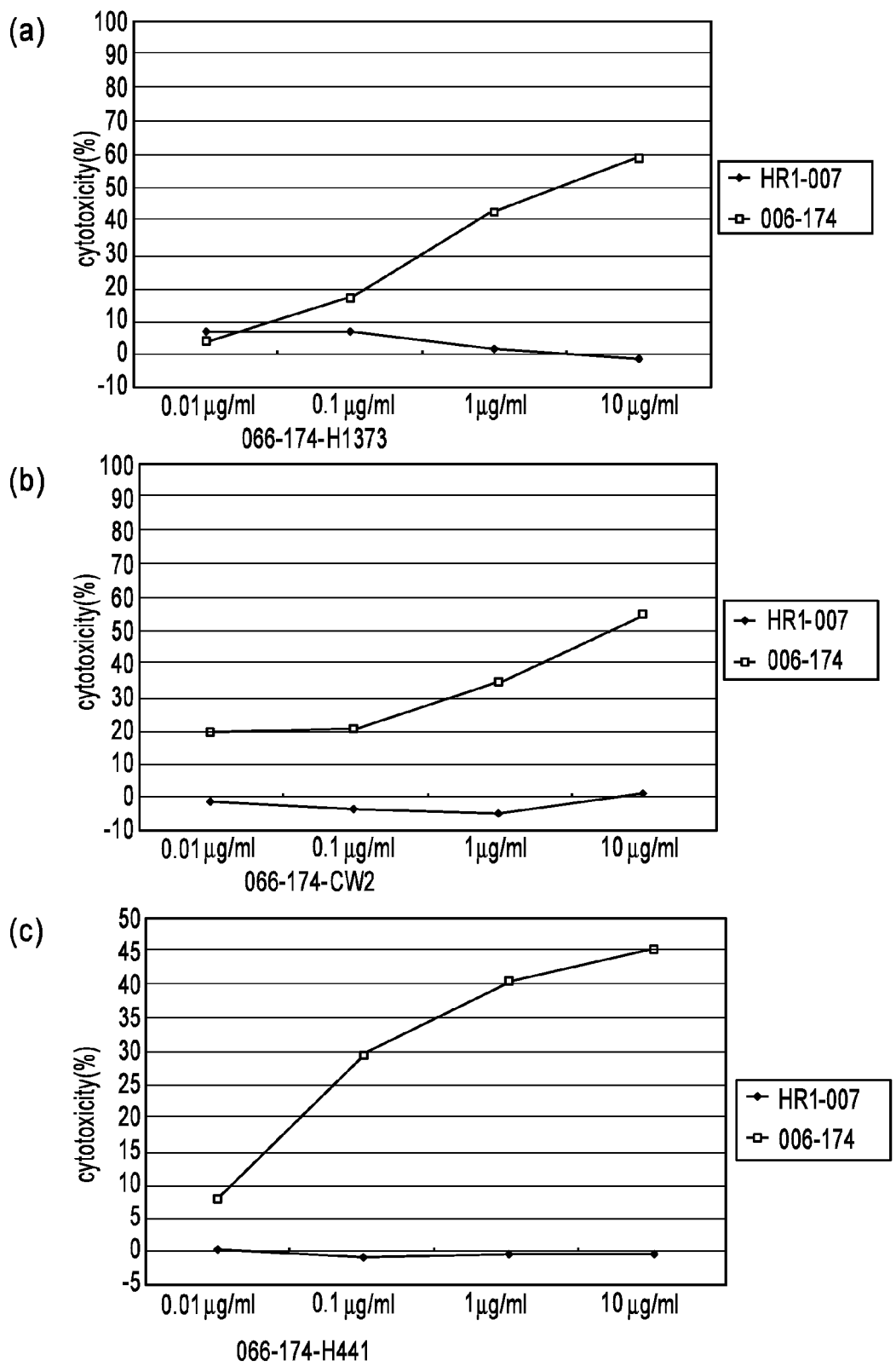
FIG. 35 shows a result of an ADCC activity test. (a) An antibody to be used: anti-ALCAM antibody, 066-174 whose, a target culture cell: NCI-H1373. (b) An antibody to be used: anti-ALCAM antibody, 066-174, target culture cell: CW2. (c) An antibody to be used: anti-ALCAM antibody, 066-174, target culture cell: NCI-H441.
Figure 36:
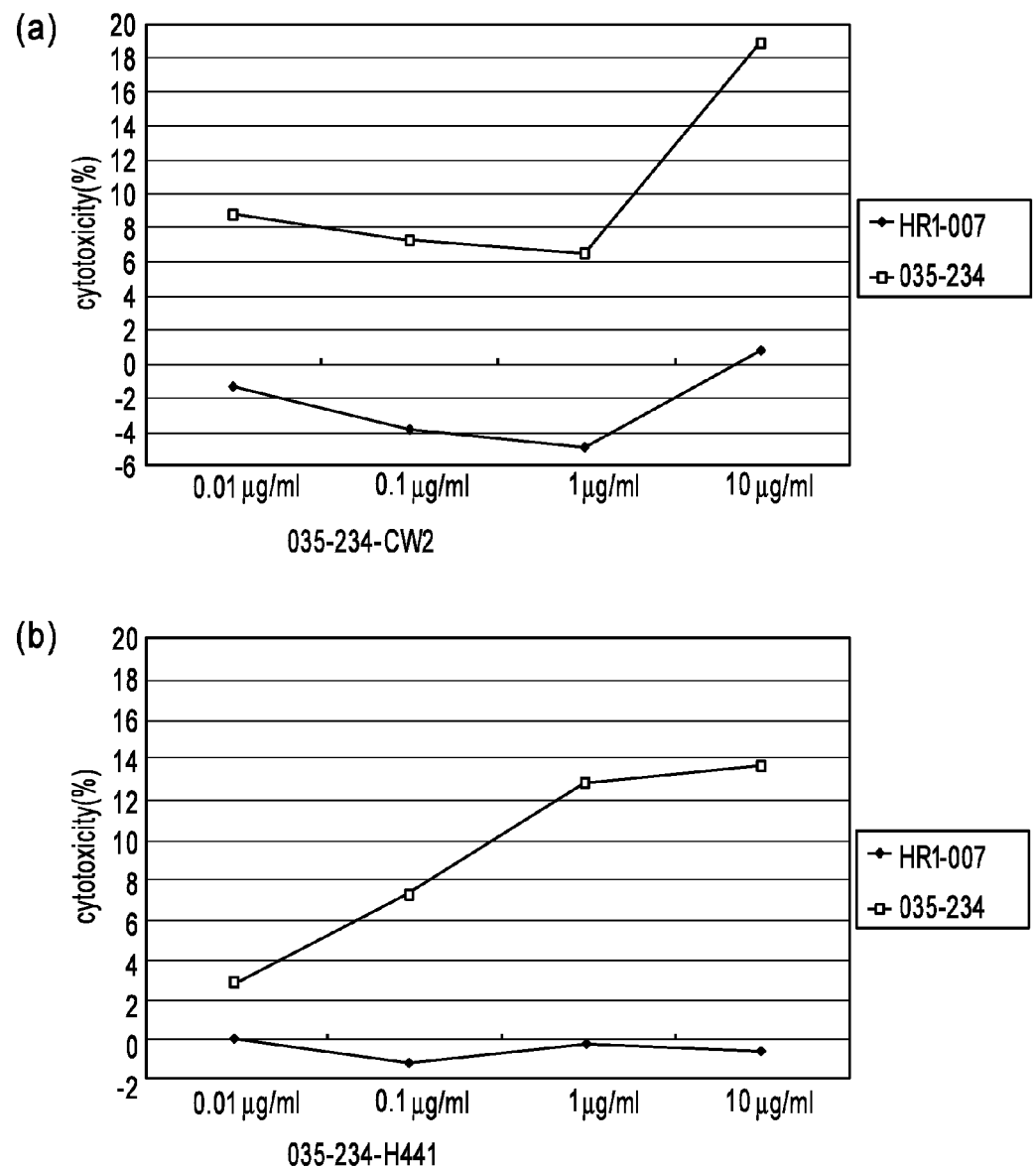
FIG. 36 shows a result of an ADCC activity test. (a) An antibody to be used: anti-ALCAM antibody, 035-234, target culture cell: CW2. (b) An antibody to be used: anti-ALCAM antibody, 035-234, target culture cell: NCI-H441.
Figure 37:
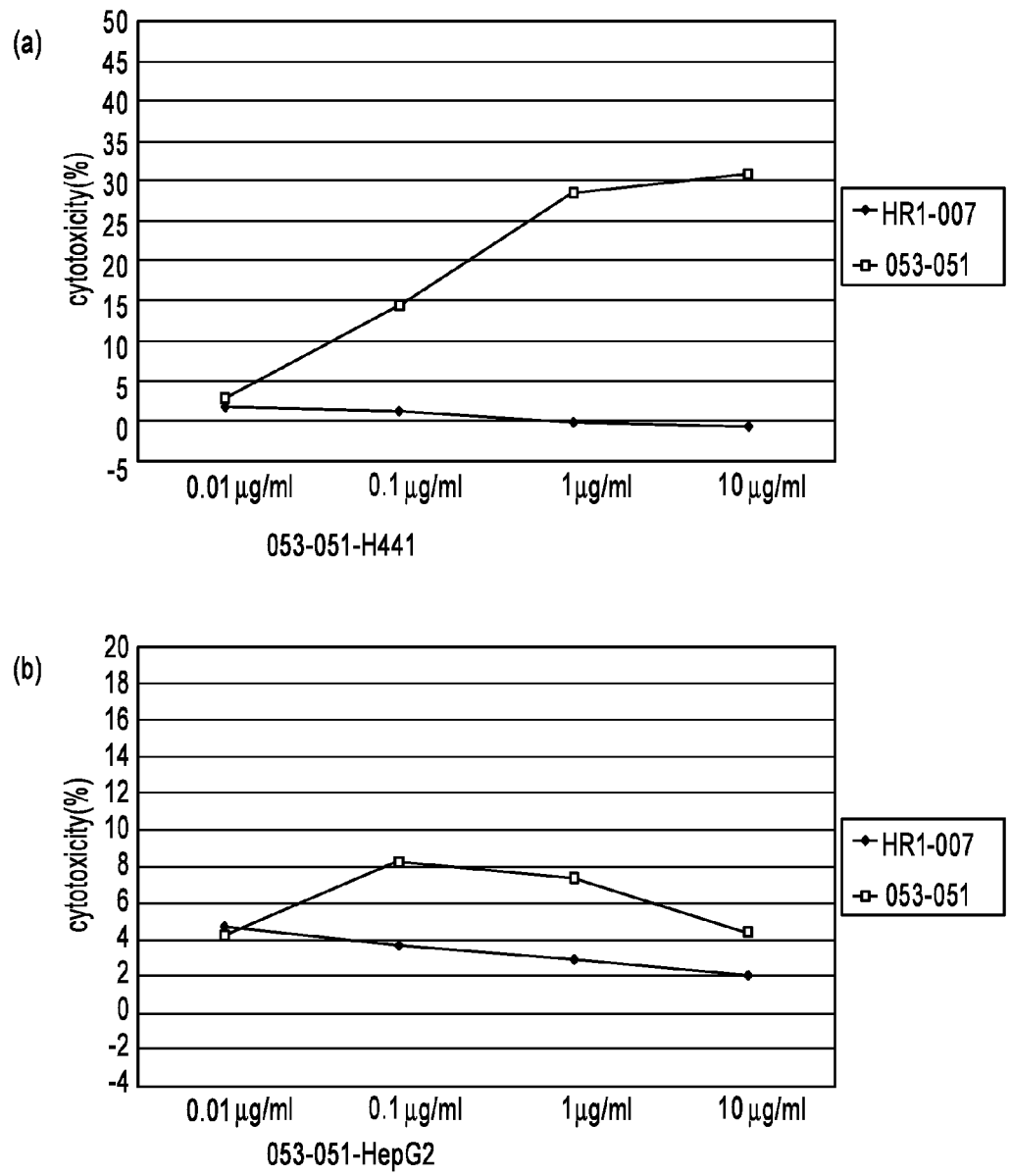
FIG. 37 shows a result of an ADCC activity test. (a) An antibody to be used: anti-ICAM1 antibody, 053-051, target culture cell: NCI-H441. (b) An antibody to be used: anti-ICAM1 antibody, 053-051, target culture cell: HepG2.
Figure 38:
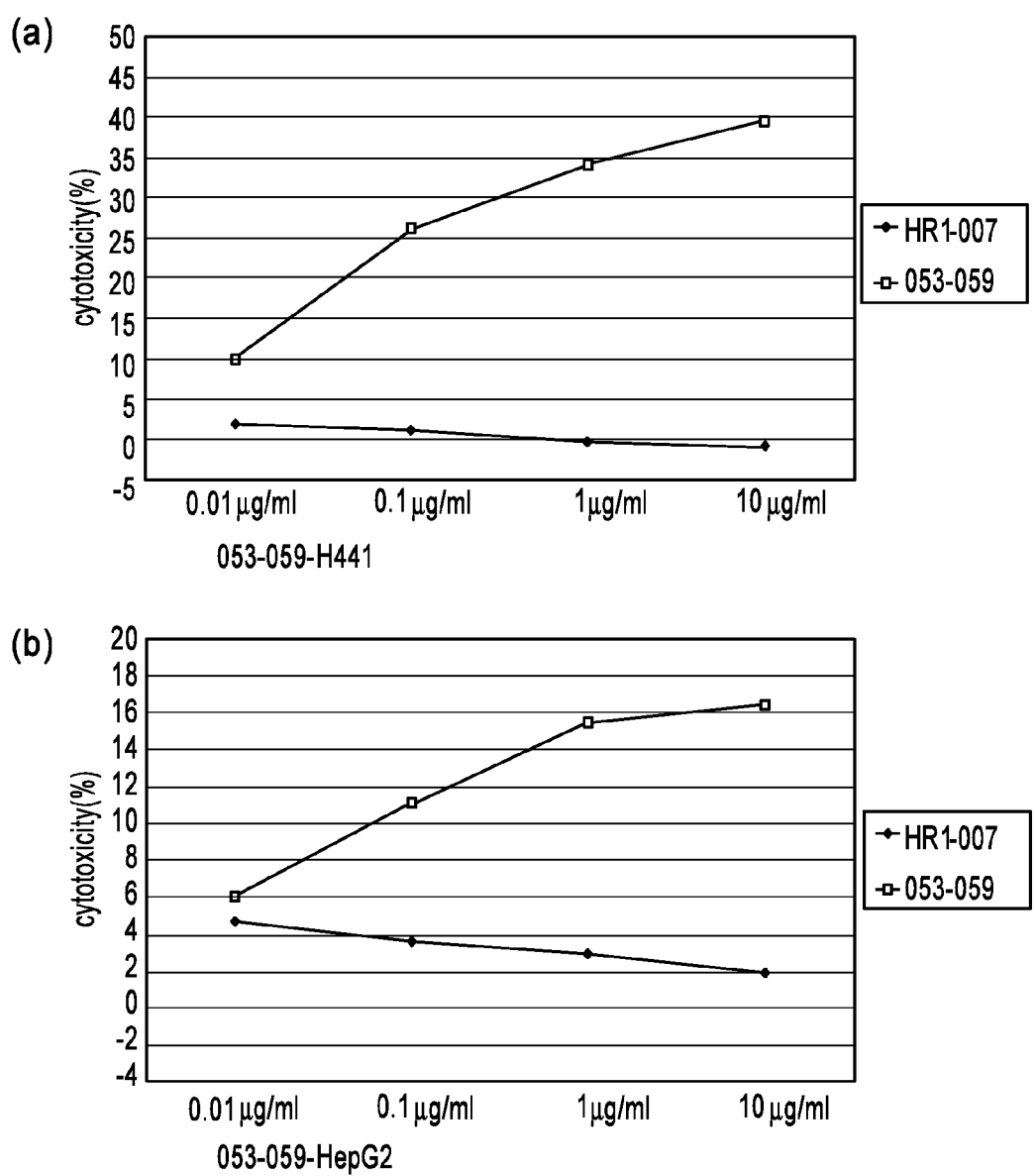
FIG. 38 shows a result of an ADCC activity test. (a) An antibody to be used: anti-ICAM1 antibody, 053-059, target culture cell: NCI-H441. (b) An antibody to be used: anti-ICAM1 antibody, 053-059, target culture cell: HepG2.
Figure 39:
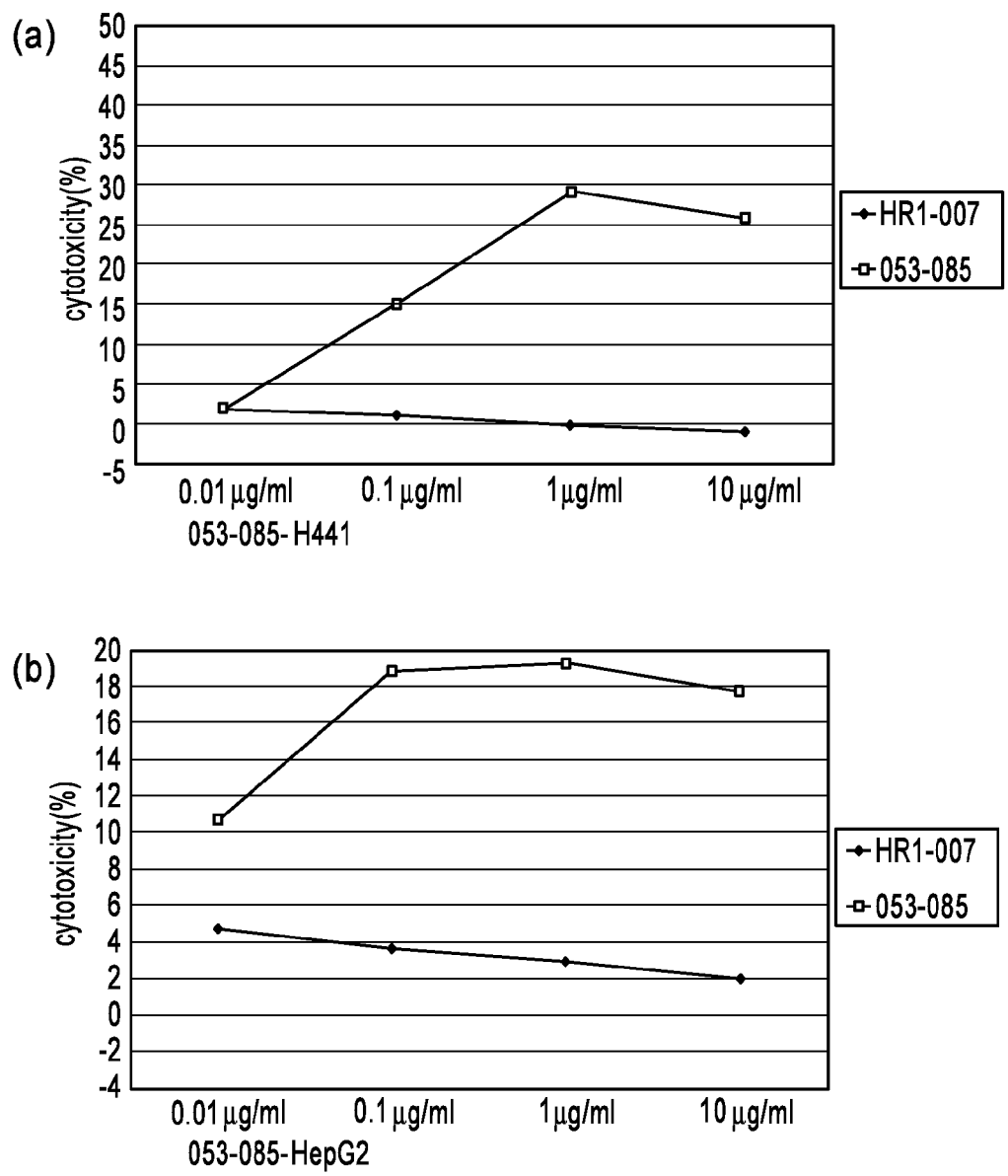
FIG. 39 shows a result of an ADCC activity test. (a) An antibody to be used: anti-ICAM1 antibody, 053-085, target culture cell: NCI-H441. (b) An antibody to be used: anti-ICAM1 antibody, 053-085, target culture cell: HepG2.
Figure 40:
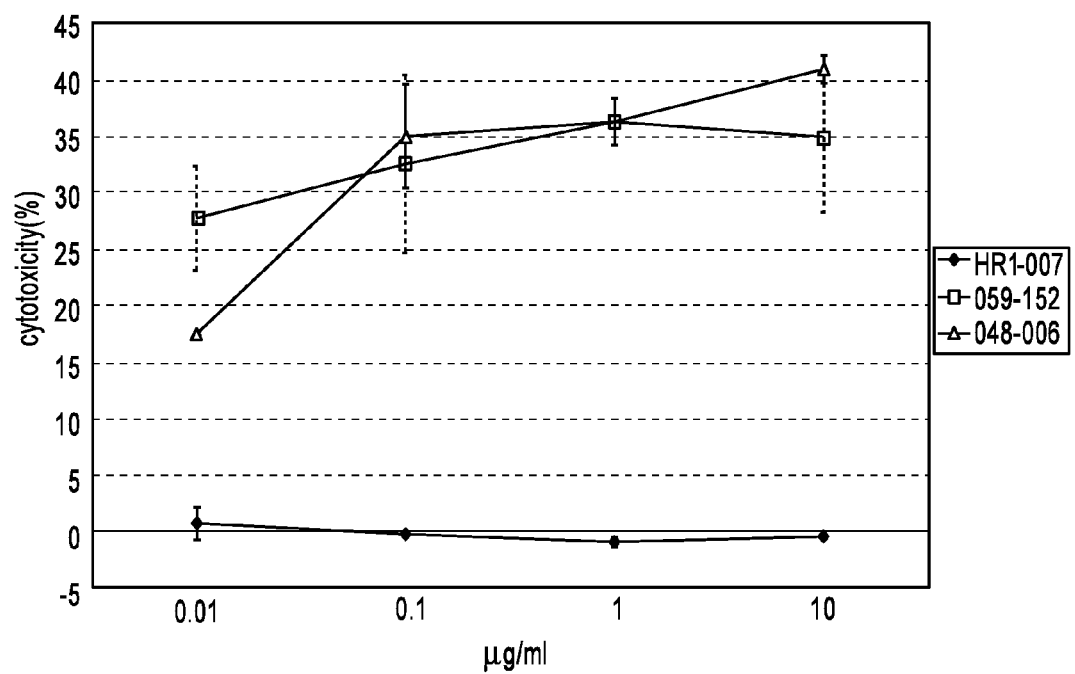
FIG. 40 shows antibody dosage dependence of the ADCC activity. An antibody to be used: anti-HER1 antibody, 048-006 antibody or 059-152 antibody, target culture cell: CCF-RC-1.
Figure 41:
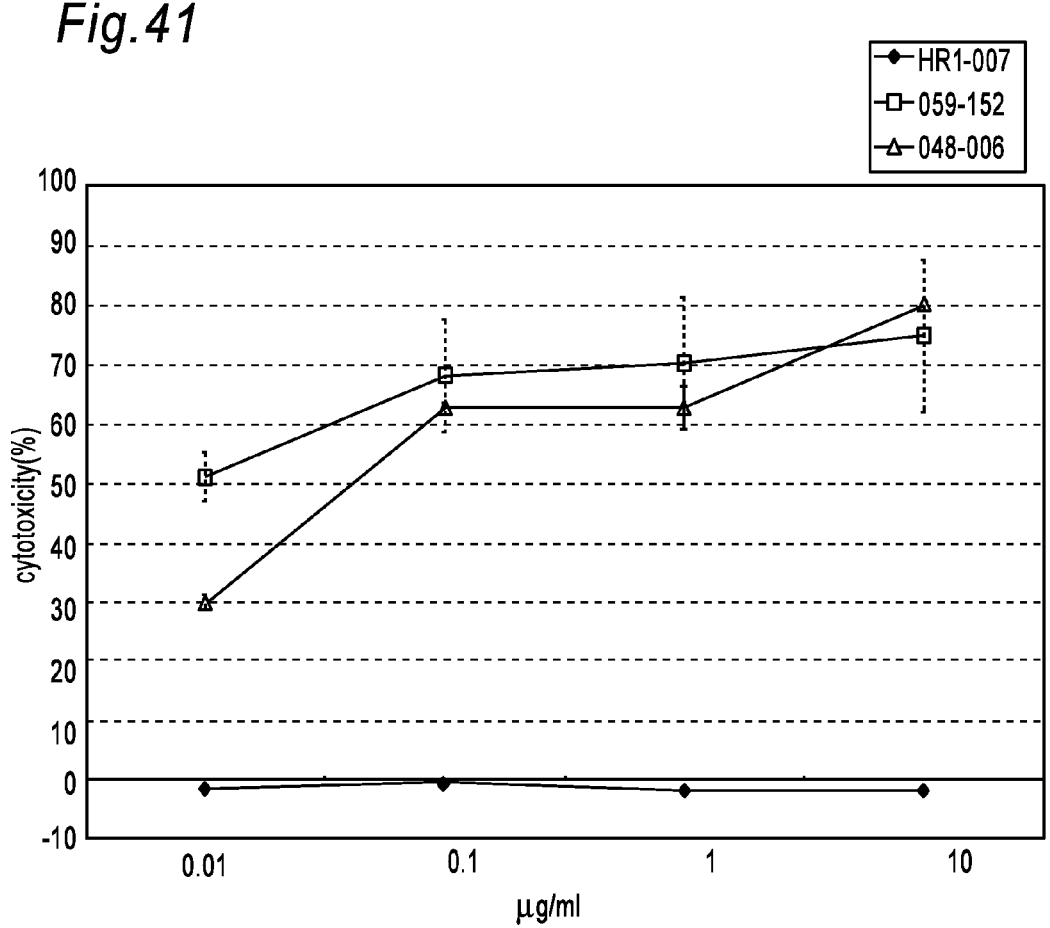
FIG. 41 shows antibody dosage dependence of the ADCC activity. An antibody to be used: anti-HER1 antibody, 048-006 antibody or 059-152 antibody, target culture cell: NCI-H1373.
Figure 42:
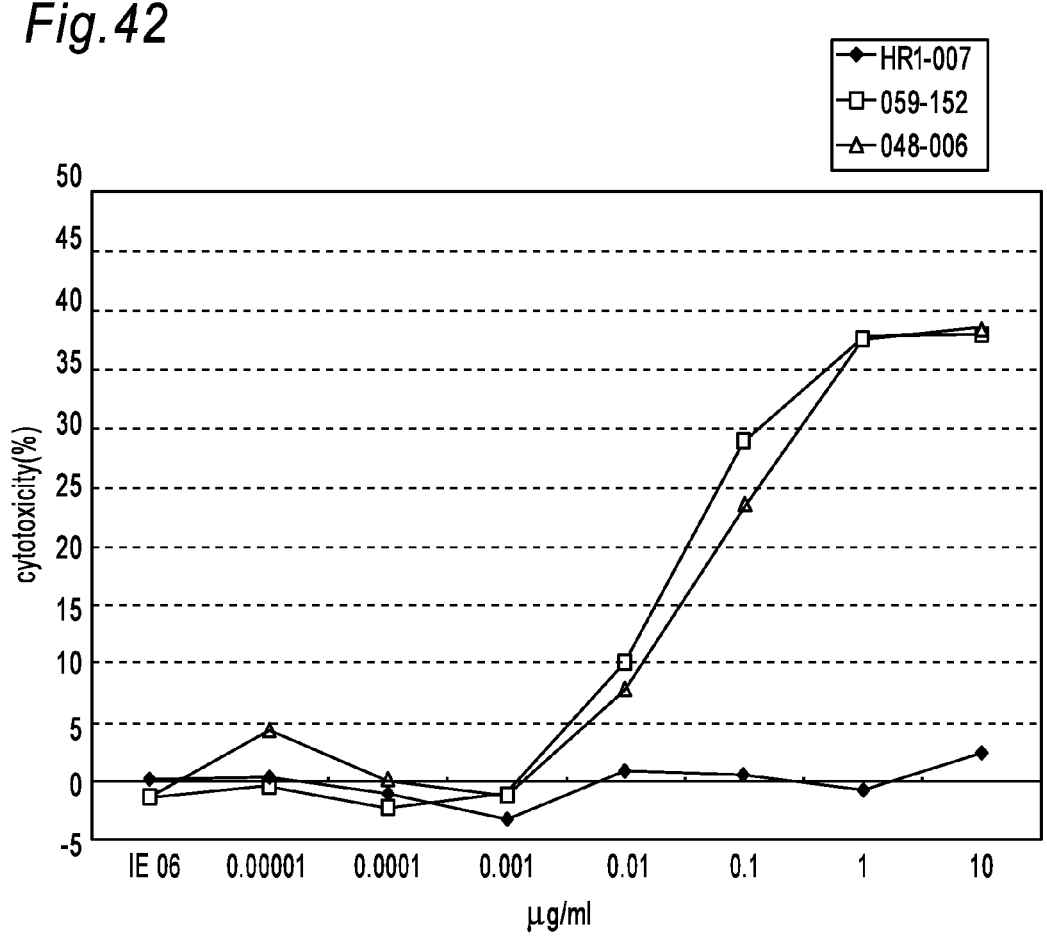
FIG. 42 shows antibody dosage dependence of the ADCC activity. An antibody to be used: anti-HER1 antibody, 048-006 antibody or 059-152 antibody, target culture cell: A-431.
Figure 43:
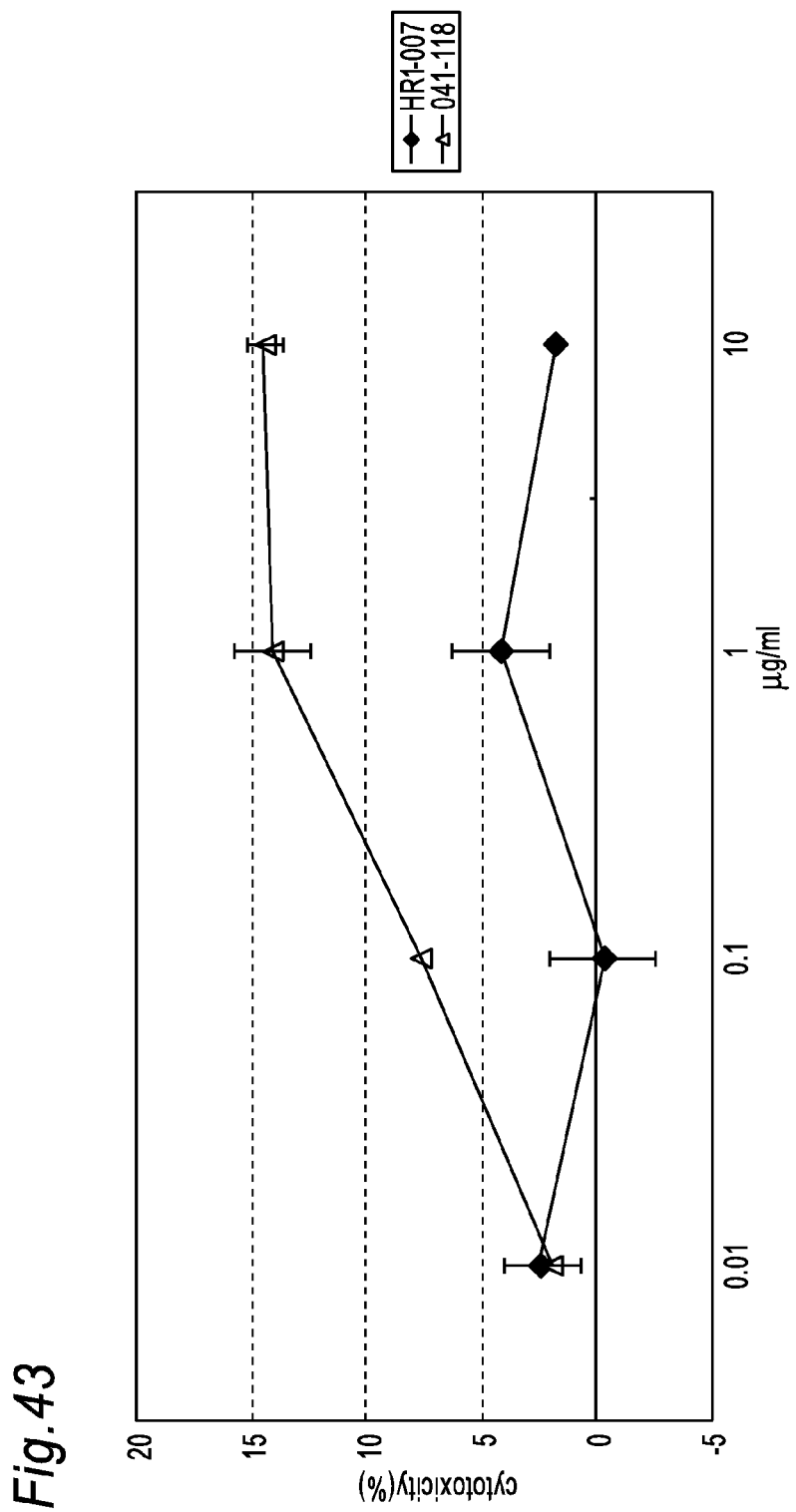
FIG. 43 shows antibody dosage dependence of the ADCC activity. An antibody to be used: anti-ALCAM antibody, 041-118 antibody, target culture cell: NCI-H1373.
Figure 44:
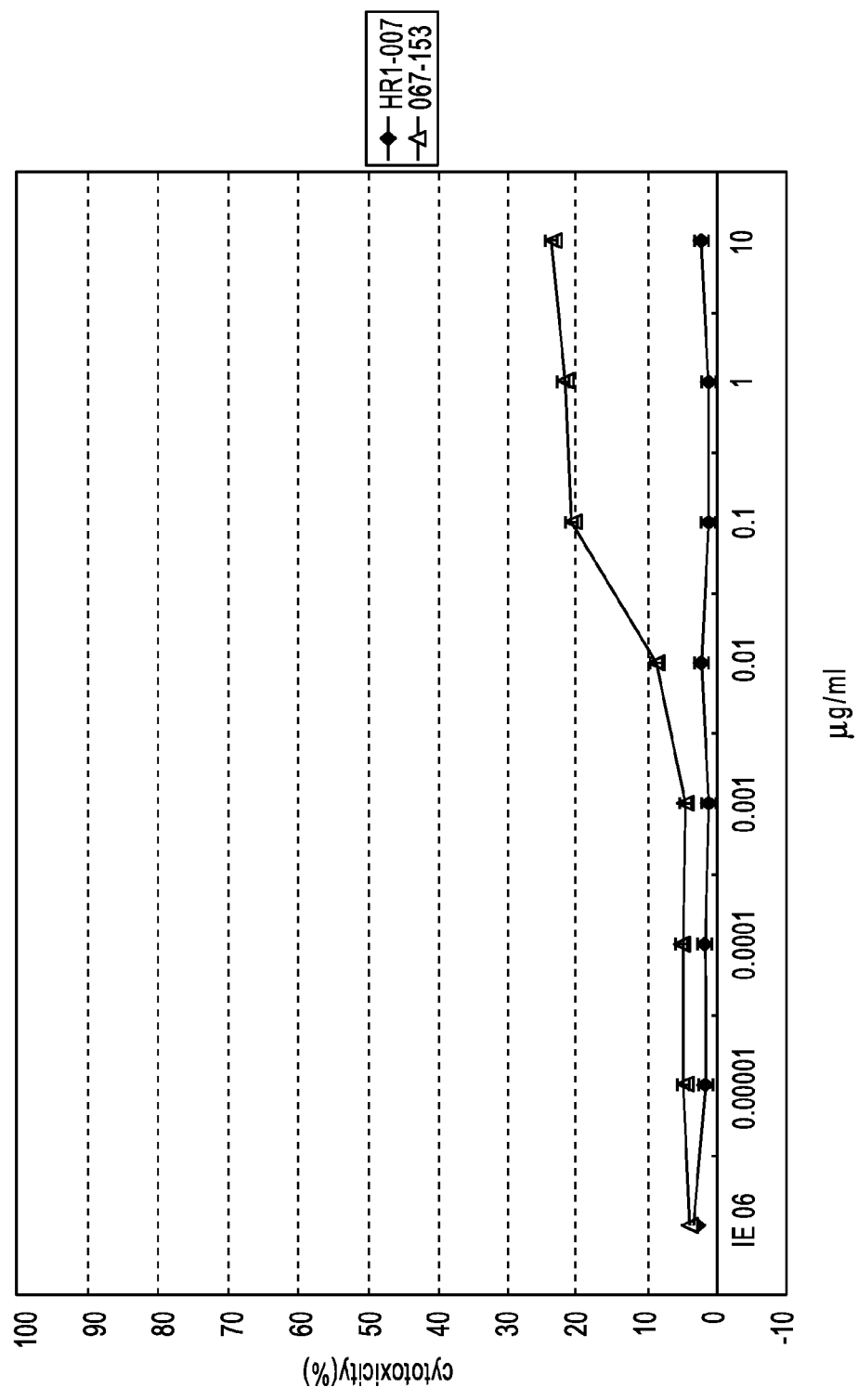
FIG. 44 shows antibody dosage dependence of the ADCC activity. An antibody to be used: anti-EpCAM antibody, 067-153 antibody, target culture cell: MKN-45.
Figure 45:
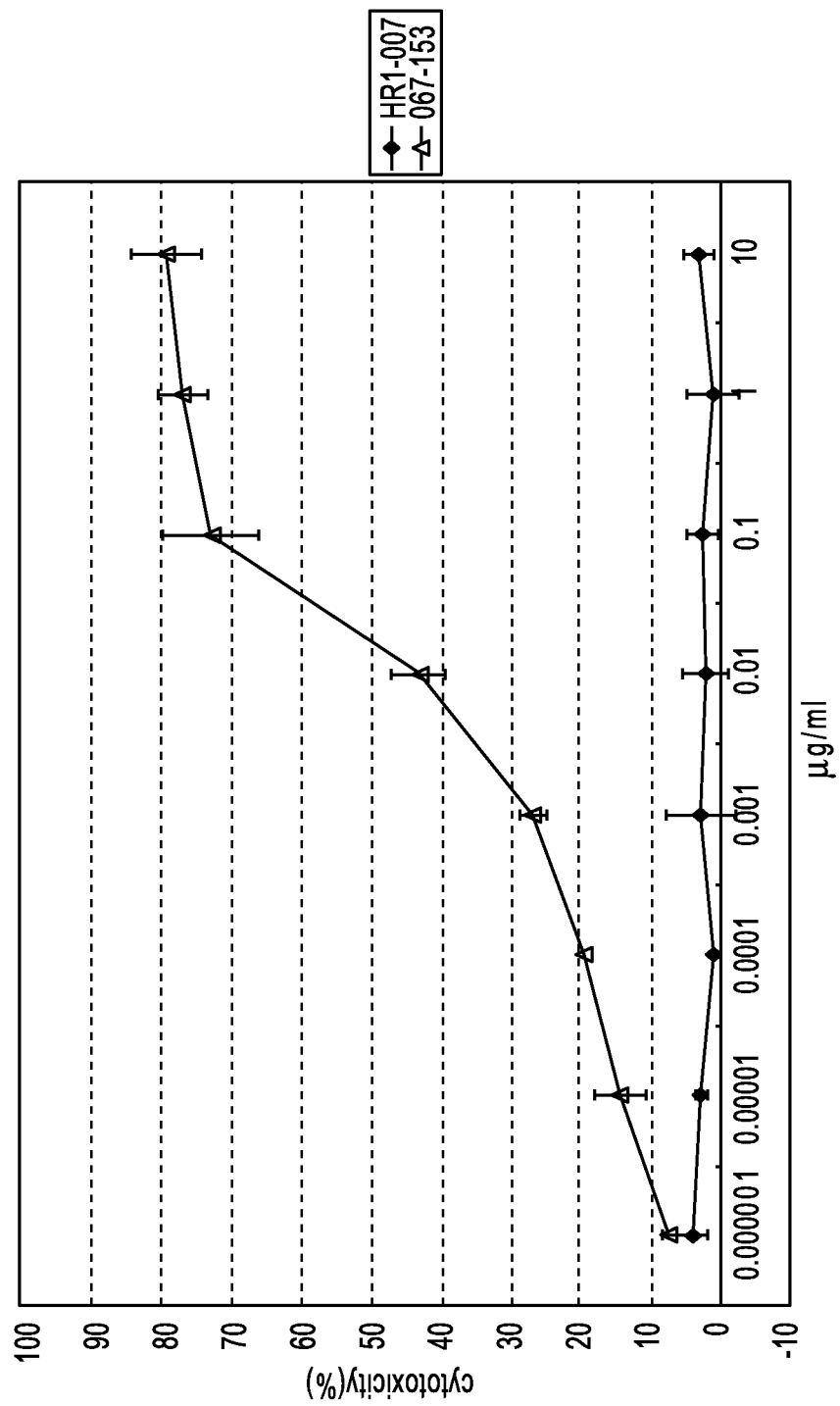
FIG. 45 shows antibody dosage dependence of the ADCC activity. An antibody to be used: anti-EpCAM antibody, 067-153 antibody, target culture cell: HT-29.
Figure 46:
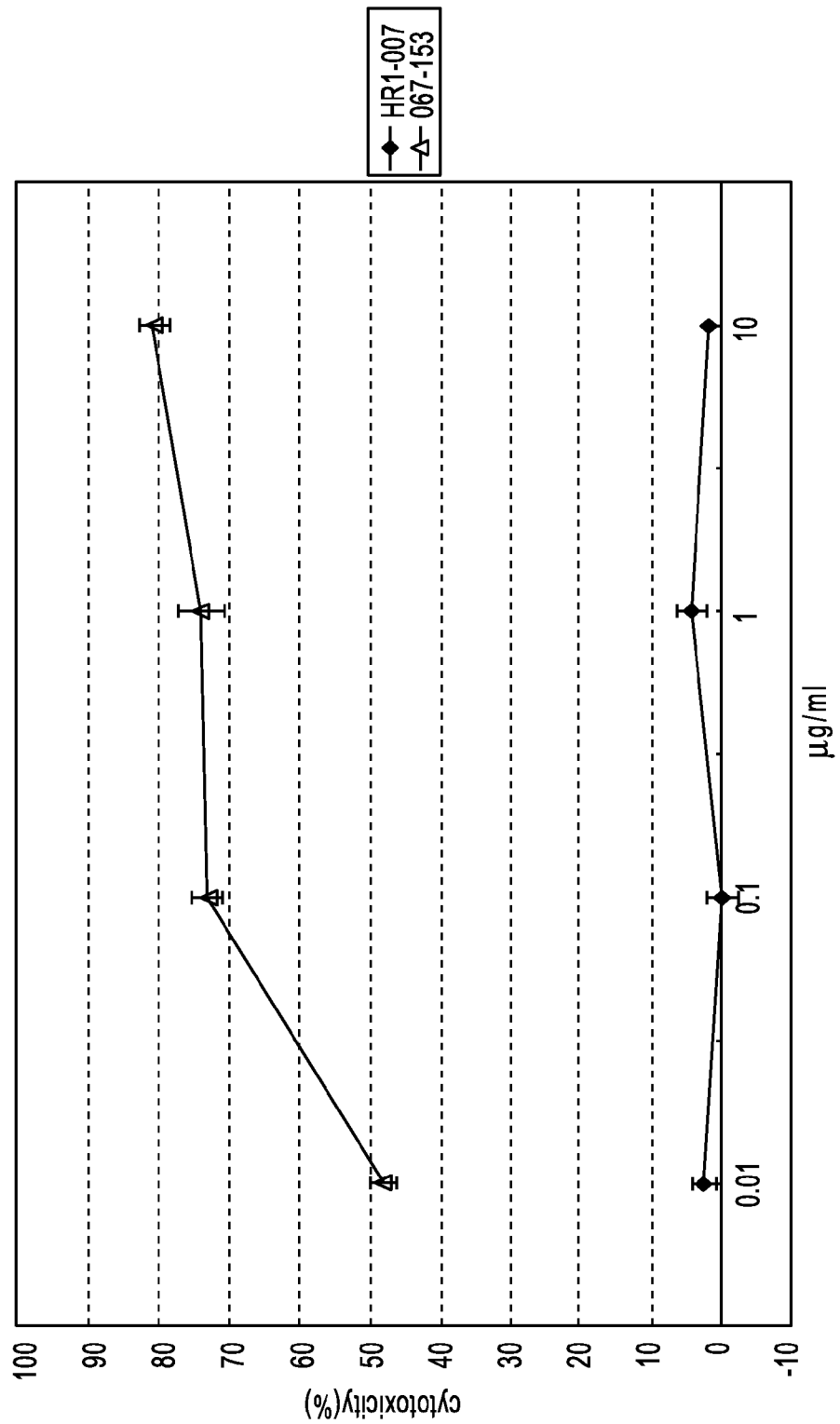
FIG. 46 shows antibody dosage dependence of the ADCC activity. An antibody to be used: anti-EpCAM antibody, 067-153 antibody, target culture cell: NCI-H1373.
Figure 47:
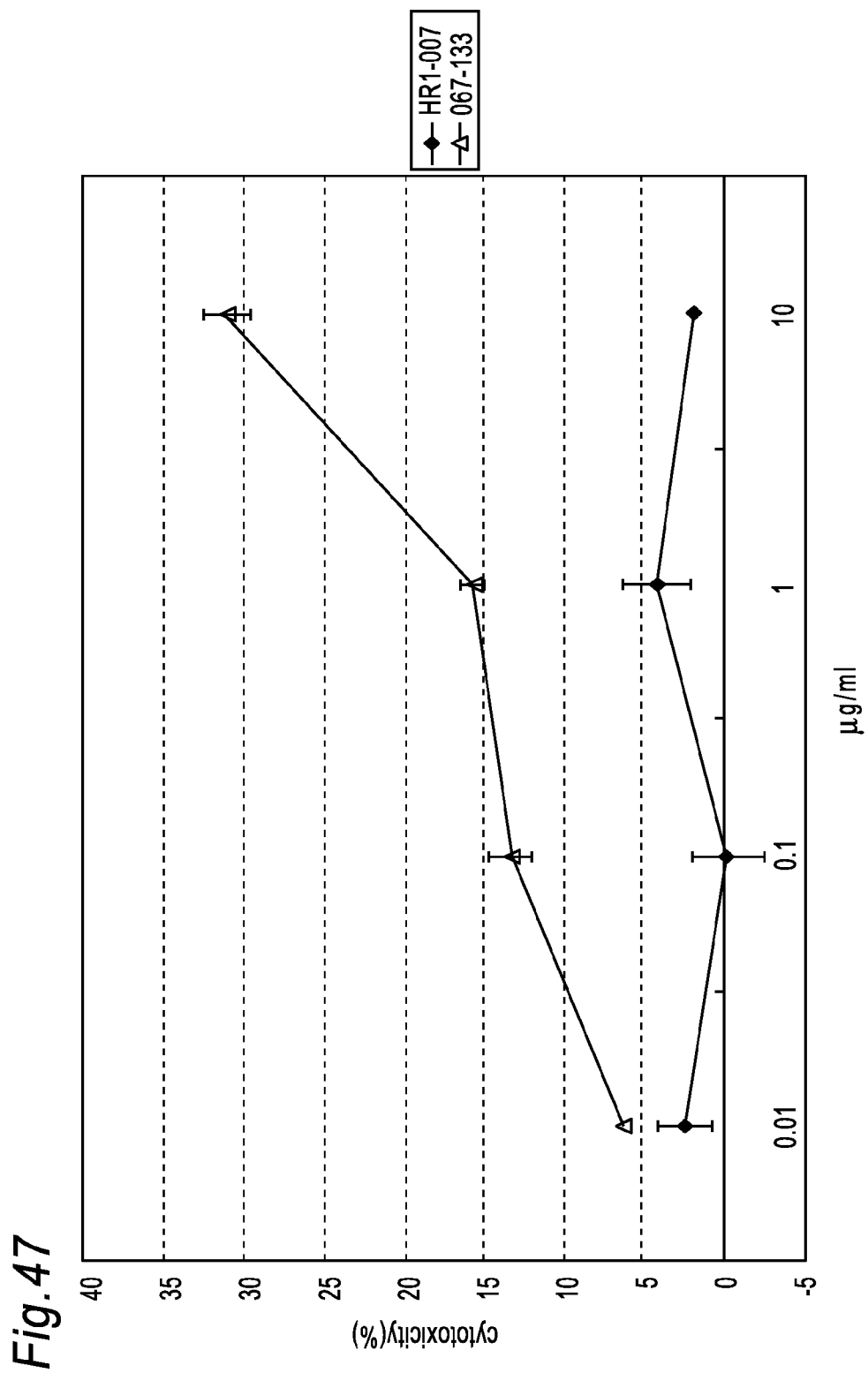
FIG. 47 shows antibody dosage dependence of the ADCC activity. An antibody to be used: anti-HGFR antibody, 067-133 antibody, target culture cell: NCI-H1373.

The measurement results of the ADCC activity are shown in FIG. 27 (anti-ITGA3 antibody was used; the target culture cell was HLF), FIG. 28 (anti-HER1 antibody was used; the target culture cell was A-431), FIG. 29 (anti-HER1 antibody was used; the target culture cell was A549), FIG. 30 (anti-HER1 antibody was used; the target culture cell was ACHN), FIG. 31 (anti-HER1 antibody was used; the target culture cell was CCF-RC-1), FIG. 32 (anti-HER1 antibody was used; the target culture cell was NCI-H1373), FIG. 33 (anti-HER1 antibody was used; the target culture cell was SK-OV-3), FIG. 34 (anti-HER2 antibody was used; the target culture cell was BT-474), FIG. 35 (066-174 as anti-ALCAM antibody was used; the target culture cell was NCI-H1373, CW2, or NCI-H441), FIG. 36 (035-234 as anti-ALCAM antibody was used; the target culture cell was CW2 or NCI-H441), FIG. 37 (053-051 as anti-ICAM1 antibody was used; the target culture cell was NCI-H441 and HepG2), FIG. 38 (053-059 as anti-ICAM1 antibody was used; the target culture cell was NCI-H441 and HepG2), and FIG. 39 (053-085 as anti-ICAM1 antibody was used; the target culture cell was NCI-H441 and HepG2). The measurement results of the antibody dosage dependence of the ADCC activity are shown in FIG. 40 (048-006 or 059-152 antibody as anti-HER1 antibody was used; the target culture cell was CCF-RC-1), FIG. 41 (048-006 or 059-152 antibody as anti-HER1 antibody was used; the target culture cell was NCI-H1373), FIG. 42 (048-006 or 059-152 antibody as anti-HER1 antibody was used; the target culture cell was A-431), FIG. 43 (041-118 antibody as anti-ALCAM antibody was used; the target culture cell was NCI-H1373), FIG. 44 (067-153 antibody as anti-EpCAM antibody was used; the target culture cell was MKN-45), FIG. 45 (067-153 antibody as anti-EpCAM antibody was used; the target culture cell was HT-29), FIG. 46 (067-153 antibody as anti-EpCAM antibody was used; the target culture cell was NCI-H1373), and FIG. 47 (067-133 antibody as anti-HGFR antibody was used; the target culture cell was NCI-H1373).

Figure 48:
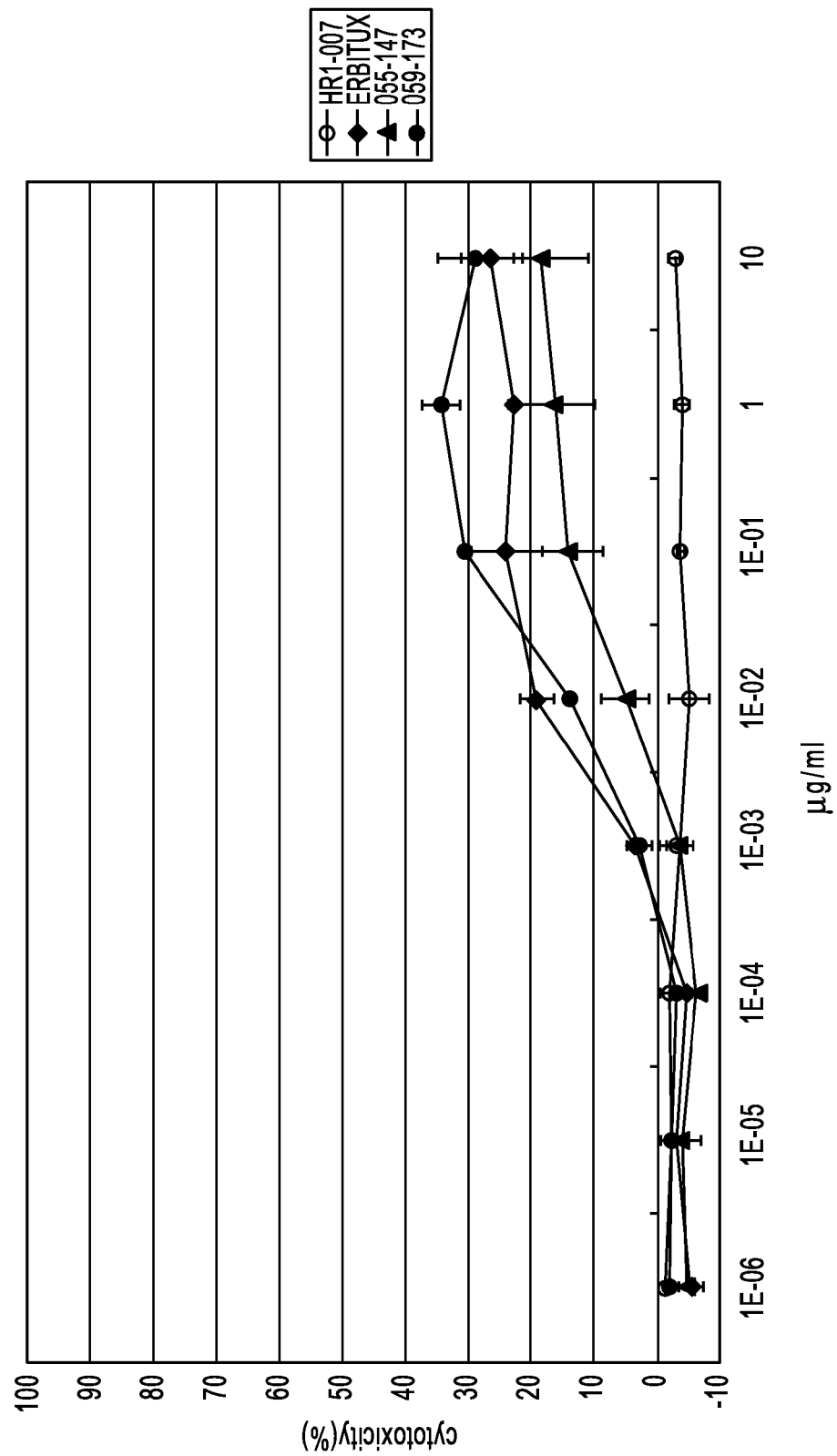
FIG. 48 shows antibody dosage dependence of the ADCC activity. An antibody to be used: anti-HER1 antibody, 055-147 antibody or 059-173 antibody, target culture cell: CCF-RC1.
Figure 49:
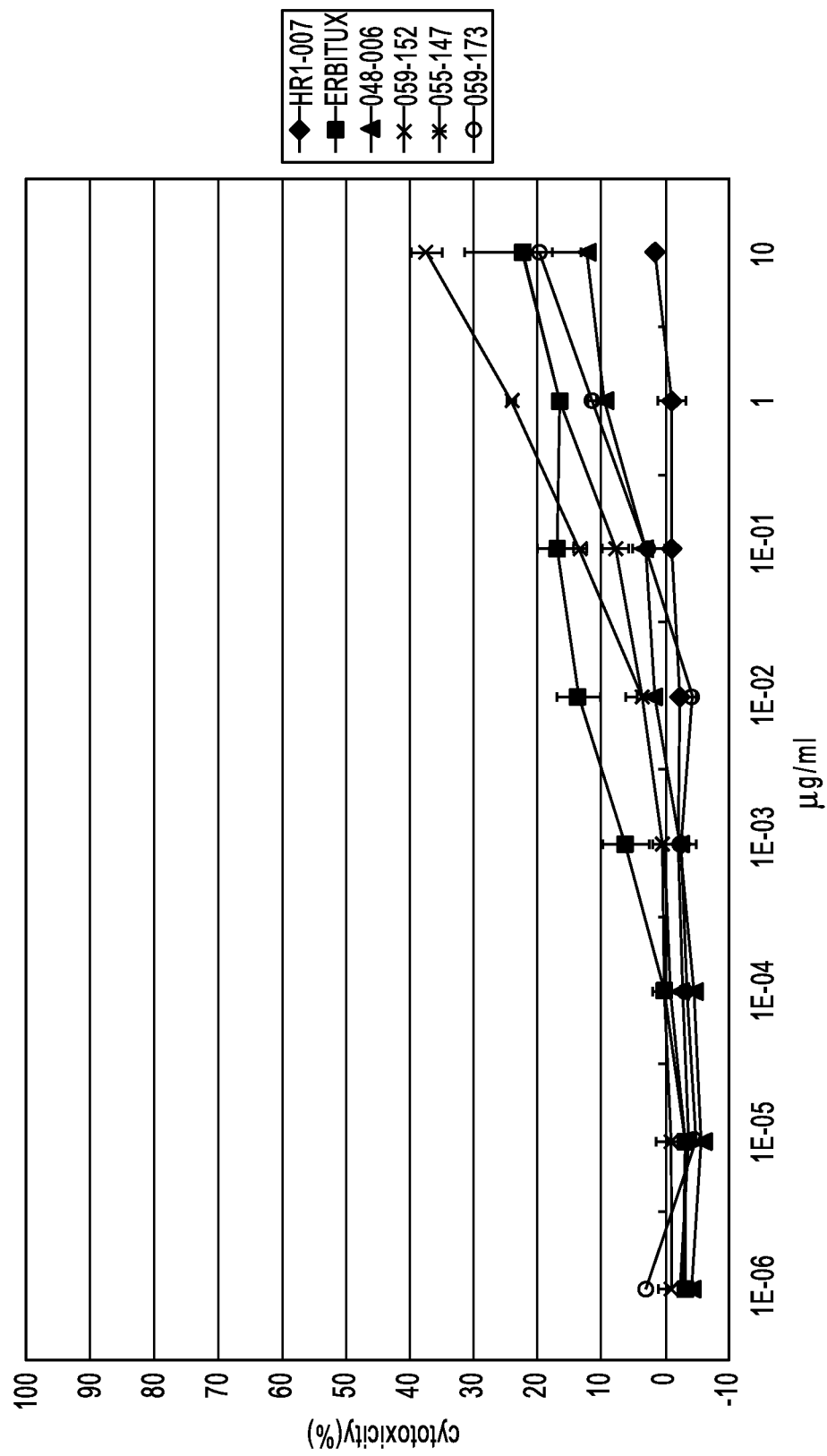
FIG. 49 shows antibody dosage dependence of the ADCC activity. An antibody to be used: anti-HER1 antibody, 048-006 antibody, 059-152 antibody, 055-147 antibody or 059-173 antibody, target culture cell: HT-29.
Figure 50:
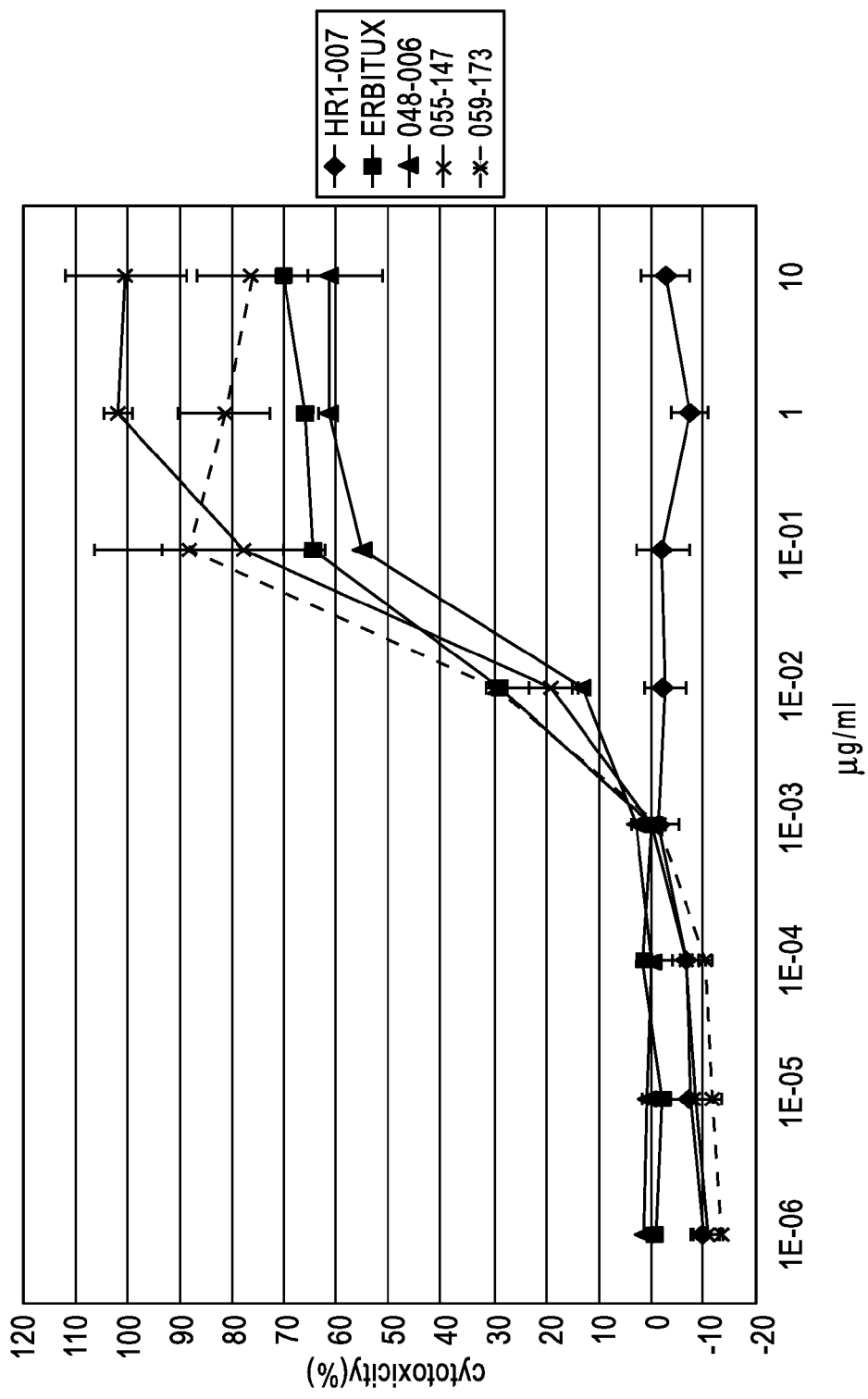
FIG. 50 shows antibody dosage dependence of the ADCC activity. An antibody to be used: anti-HER1 antibody, 048-006 antibody, 055-147 antibody or 059-173 antibody, target culture cell: A431.
Figure 51:
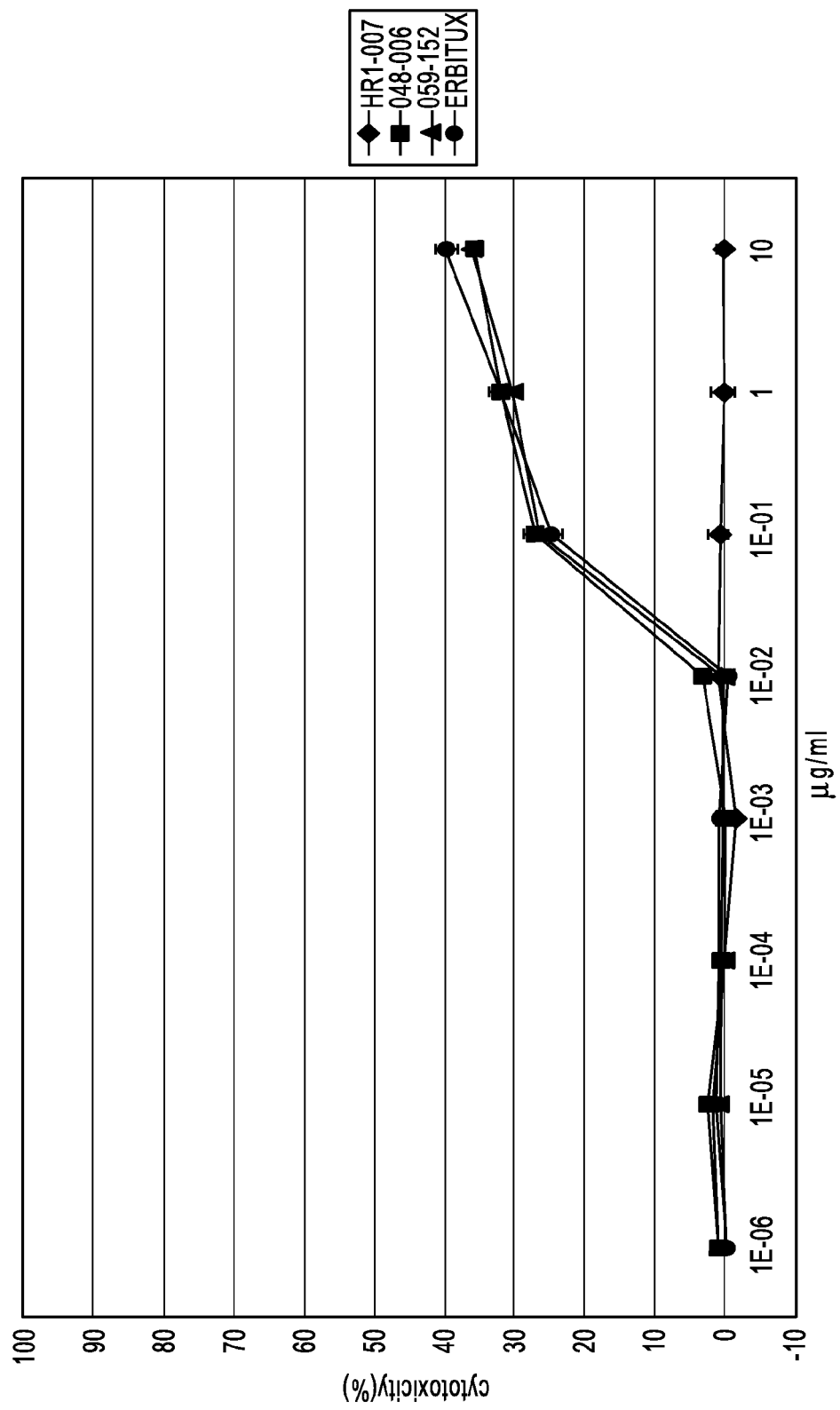
FIG. 51 shows antibody dosage dependence of the ADCC activity. An antibody to be used: anti-HER1 antibody, 048-006 antibody or 059-152 antibody, target culture cell: ACHN.
Figure 52:
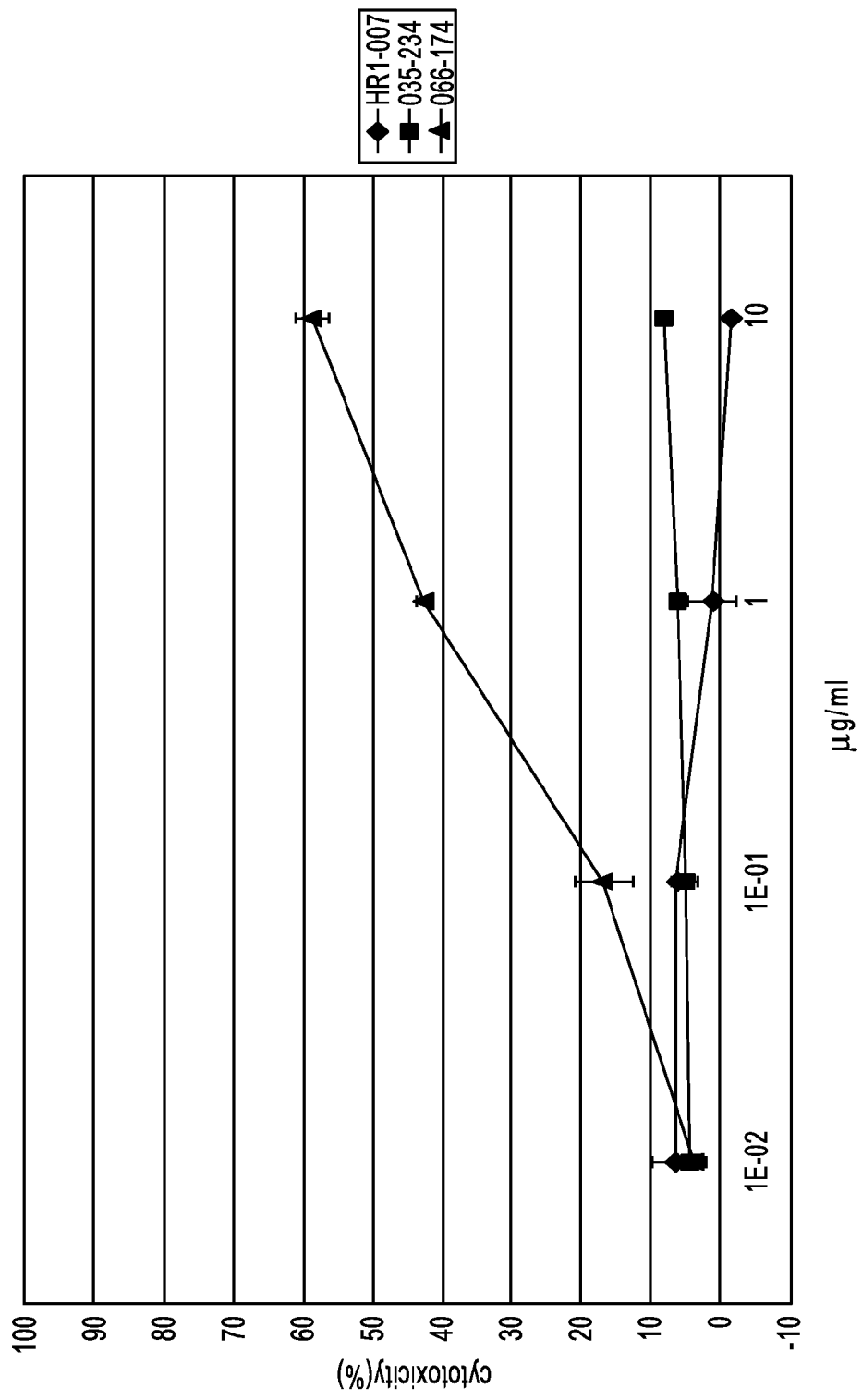
FIG. 52 shows antibody dosage dependence of the ADCC activity. An antibody to be used: anti-ALCAM antibody, 035-234 antibody or 066-174 antibody, target culture cell: NCI-H1373.
Figure 53:
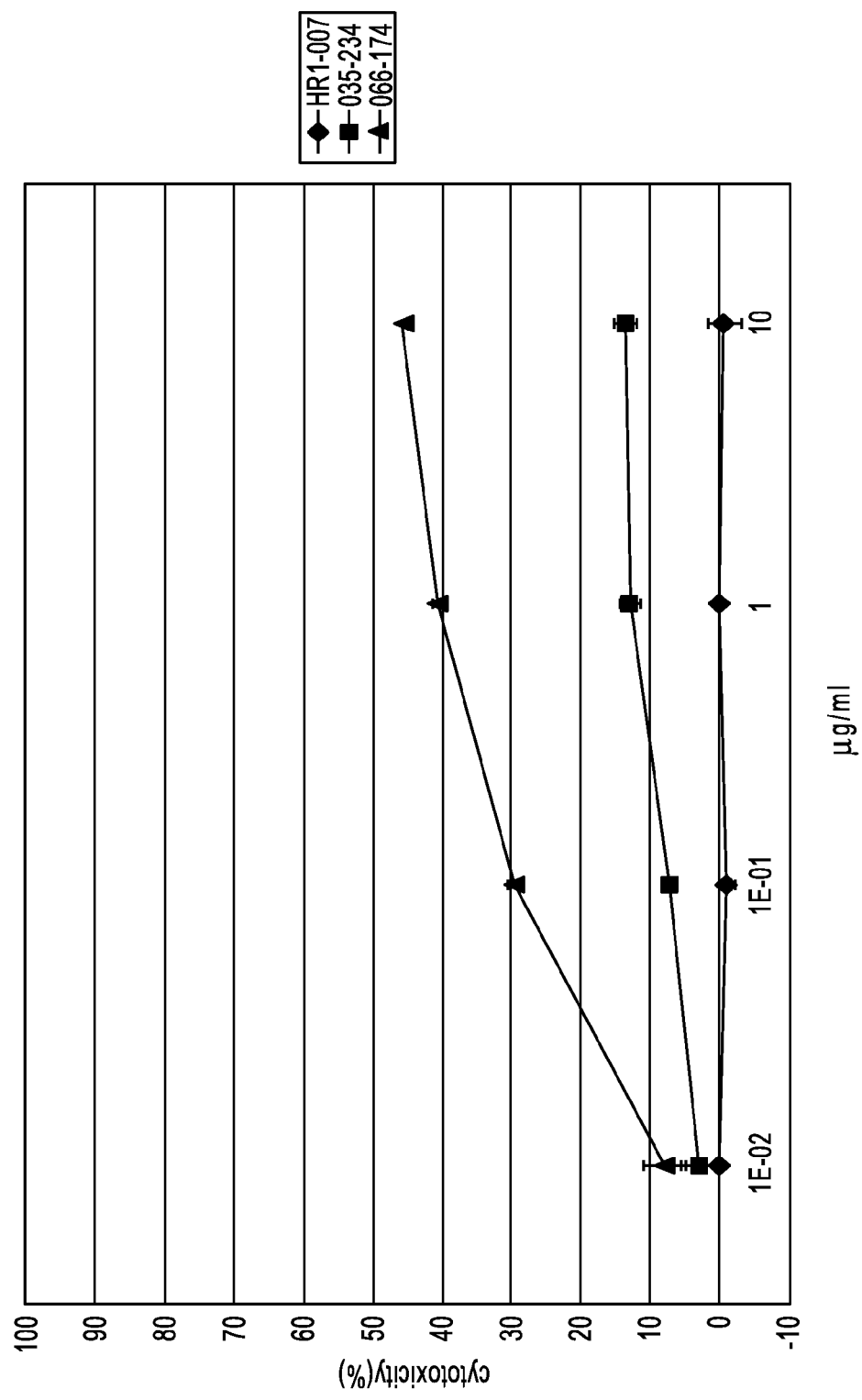
FIG. 53 shows antibody dosage dependence of the ADCC activity. An antibody to be used: anti-ALCAM antibody, 035-234 antibody or 066-174 antibody, target culture cell: SKOv3.
Figure 54:
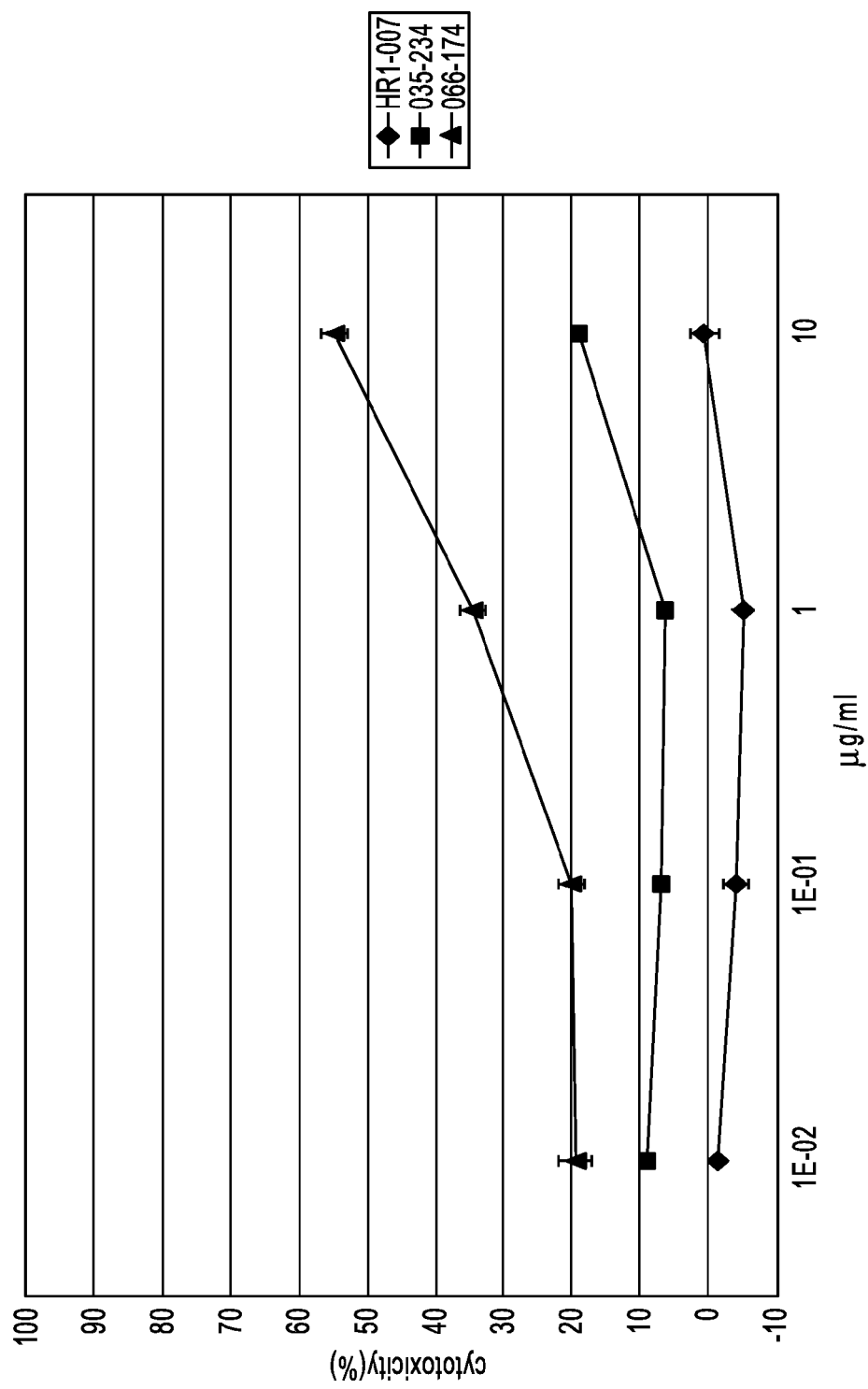
FIG. 54 shows antibody dosage dependence of the ADCC activity. An antibody to be used: anti-ALCAM antibody, 035-234 antibody or 066-174 antibody, target culture cell: CW-2.
Figure 55:
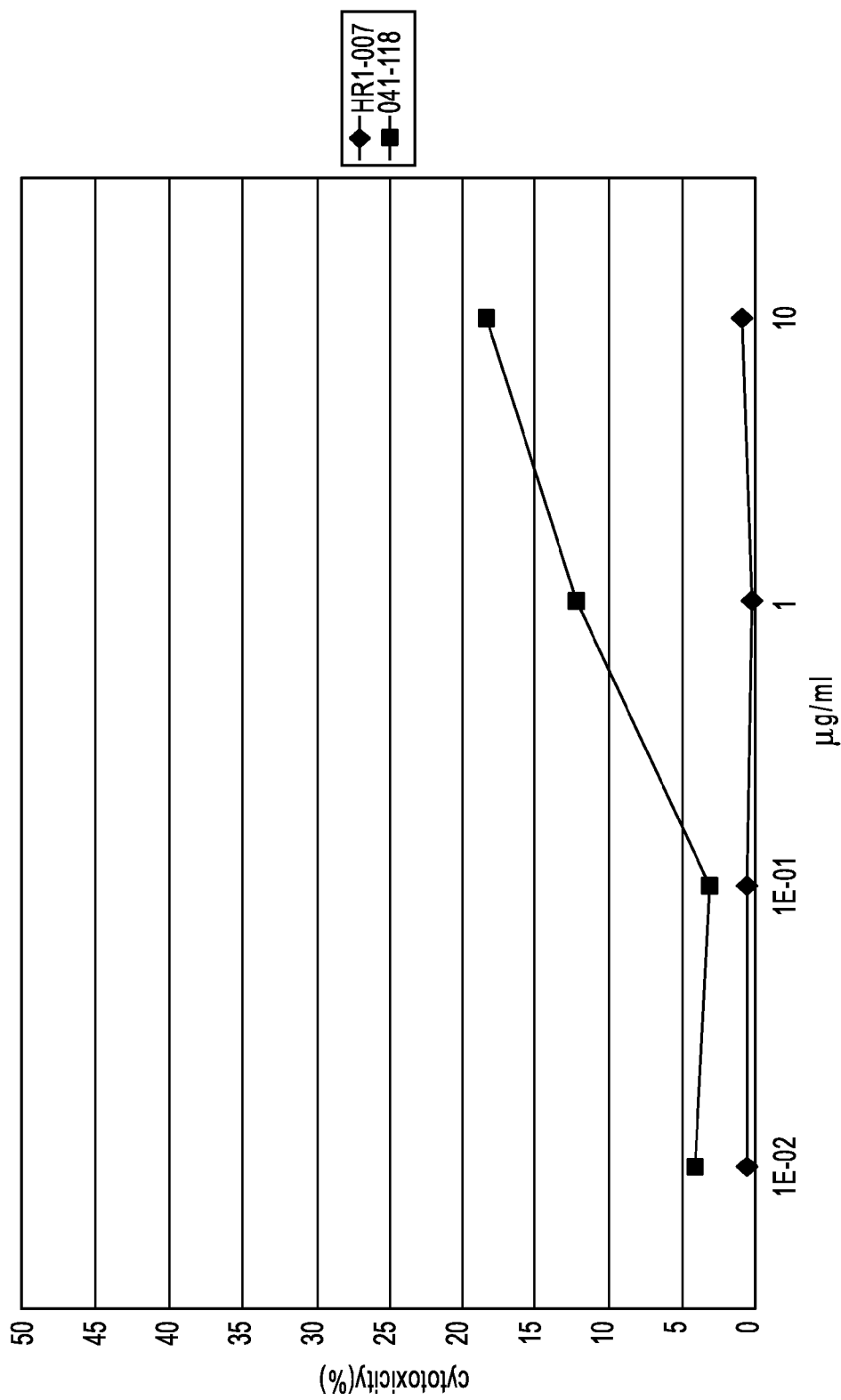
FIG. 55 shows antibody dosage dependence of the ADCC activity. An antibody to be used: anti-ALCAM antibody, 041-118 antibody, target culture cell: EBC-1.
Figure 56:
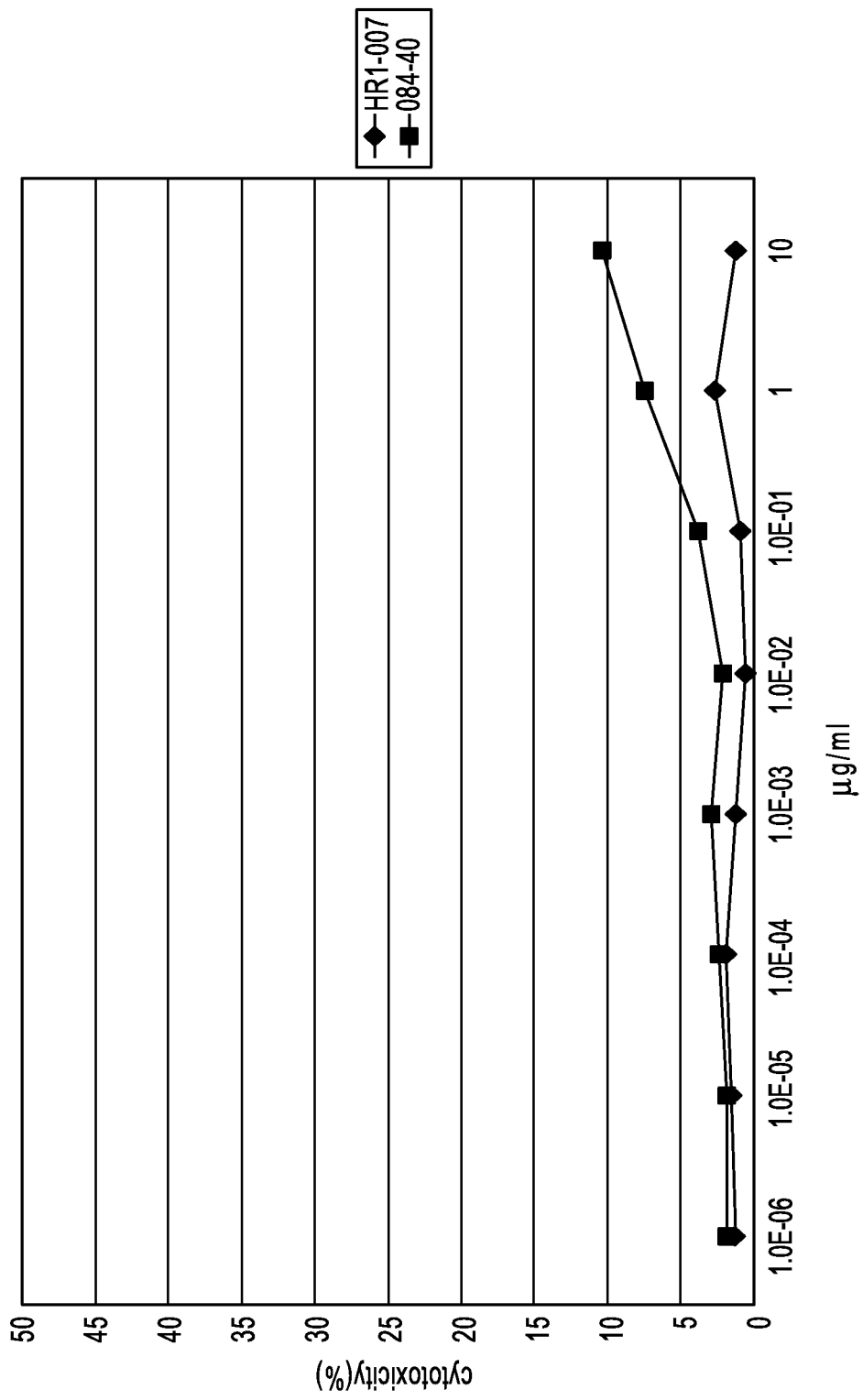
FIG. 56 shows antibody dosage dependence of the ADCC activity. An antibody to be used: anti-ALCAM antibody, 080-040 antibody, target culture cell: NCI-H1373.
Figure 57:
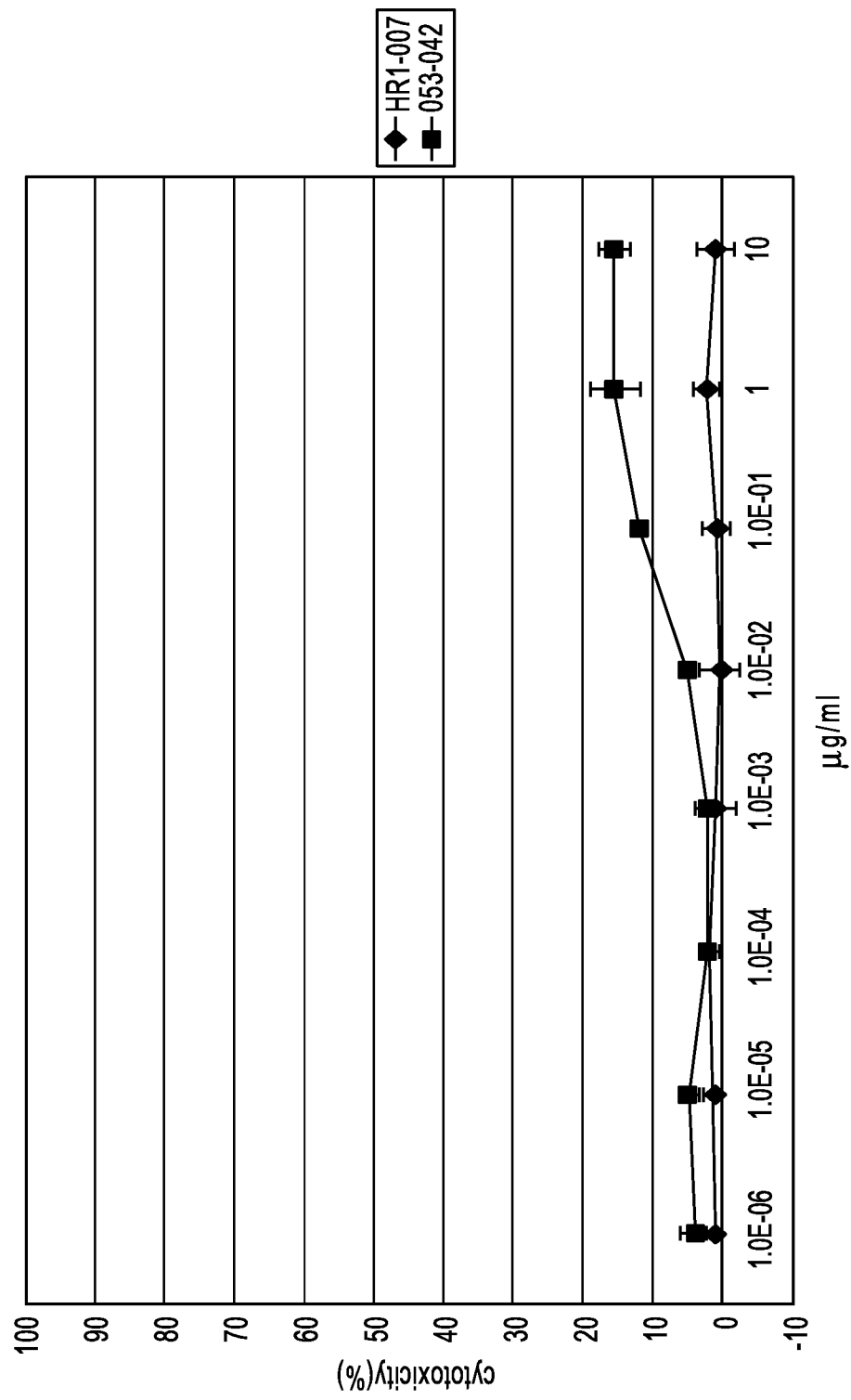
FIG. 57 shows antibody dosage dependence of the ADCC activity. An antibody to be used: anti-ICAM1 antibody, 053-042 antibody, target culture cell: NCI-H1373.
Figure 58:
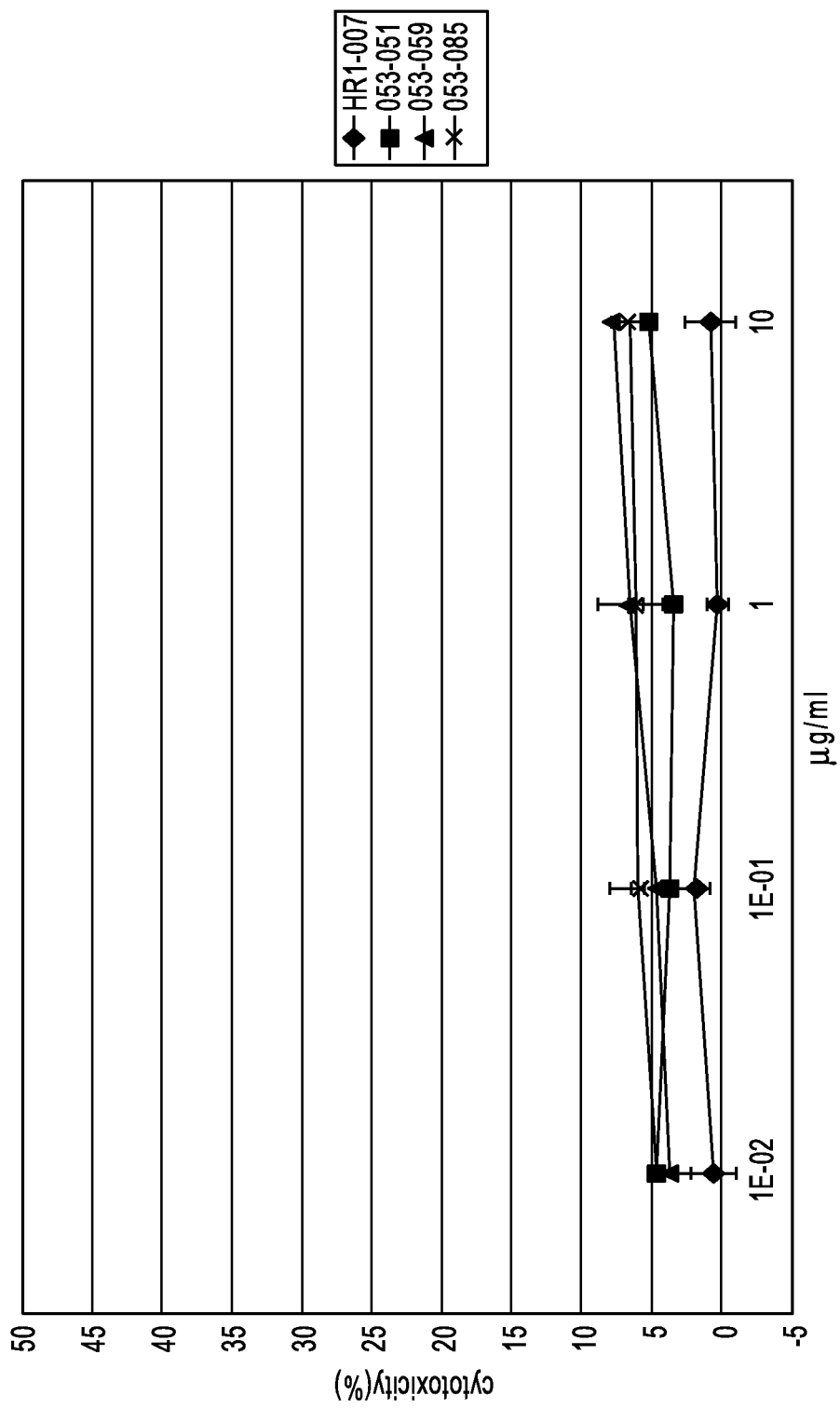
FIG. 58 shows antibody dosage dependence of the ADCC activity. An antibody to be used: anti-ICAM1 antibody, 053-051 antibody, 053-059 antibody or 053-085 antibody, target culture cell: NCI-H1373.
Figure 59:
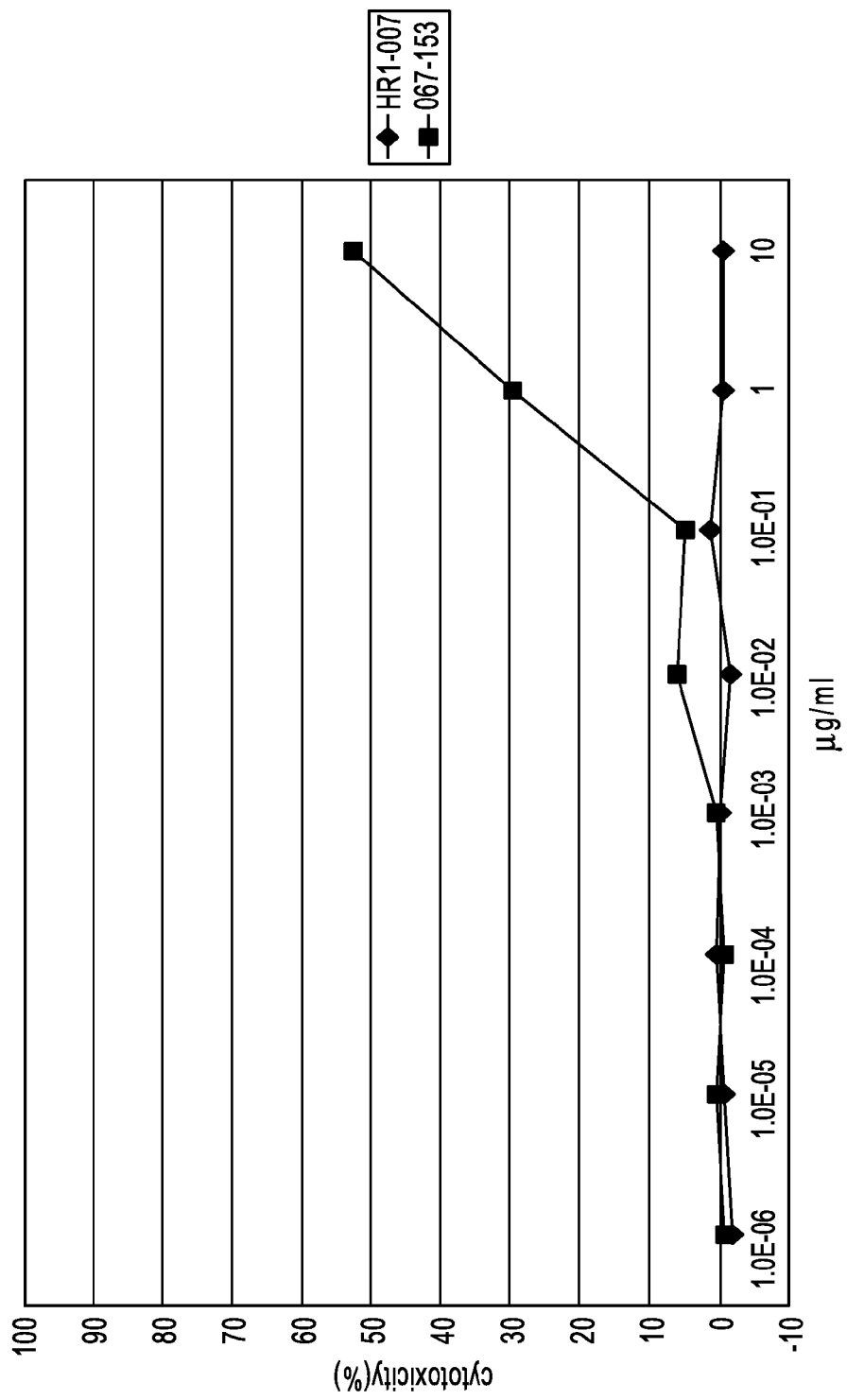
FIG. 59 shows antibody dosage dependence of the ADCC activity. An antibody to be used: anti-EpCAM antibody, 067-153 antibody, target culture cell: EBC-1.
Figure 60:
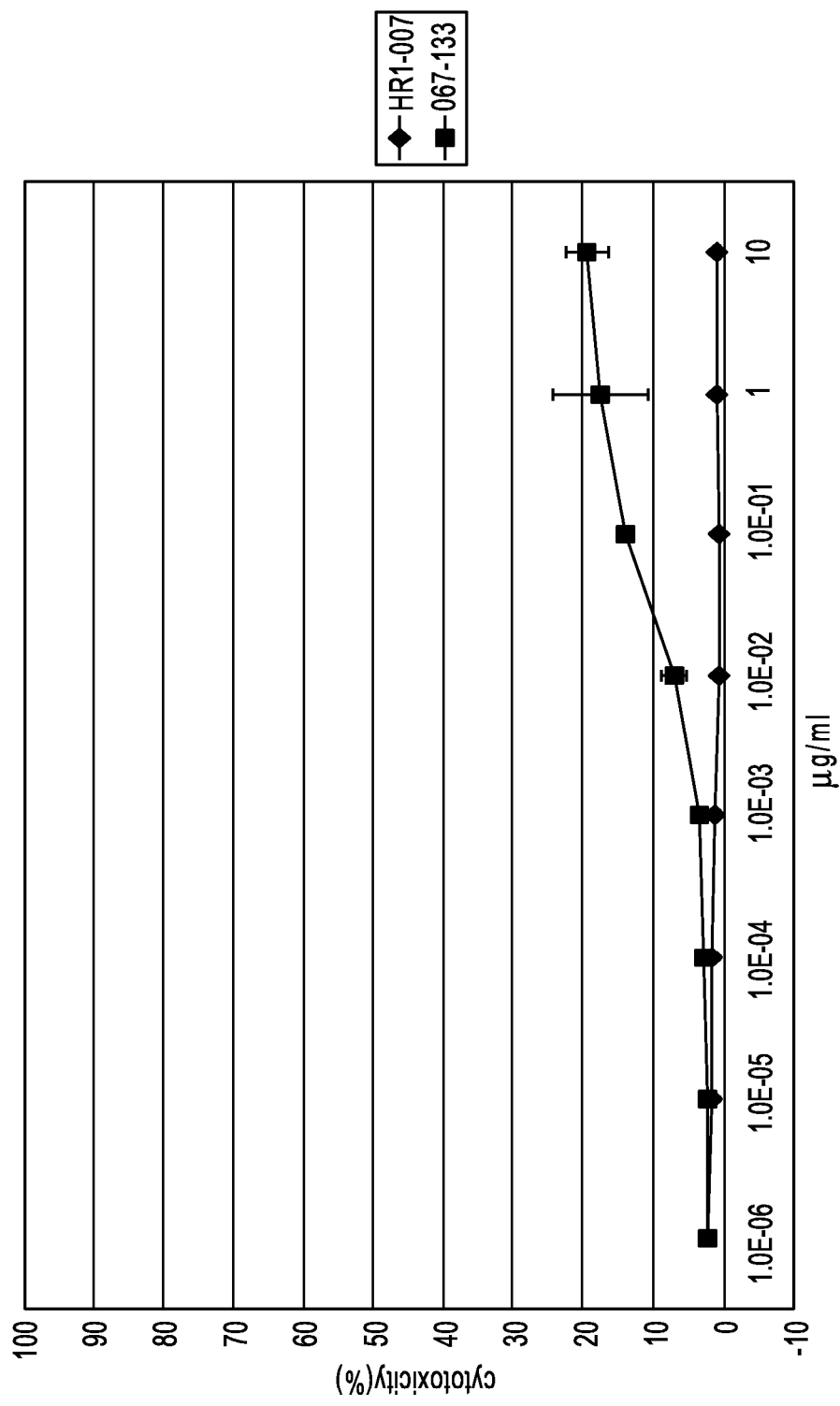
FIG. 60 shows antibody dosage dependence of the ADCC activity. An antibody to be used: anti-HGFR antibody 067-133 antibody, target culture cell: MKN-45.
Figure 61:
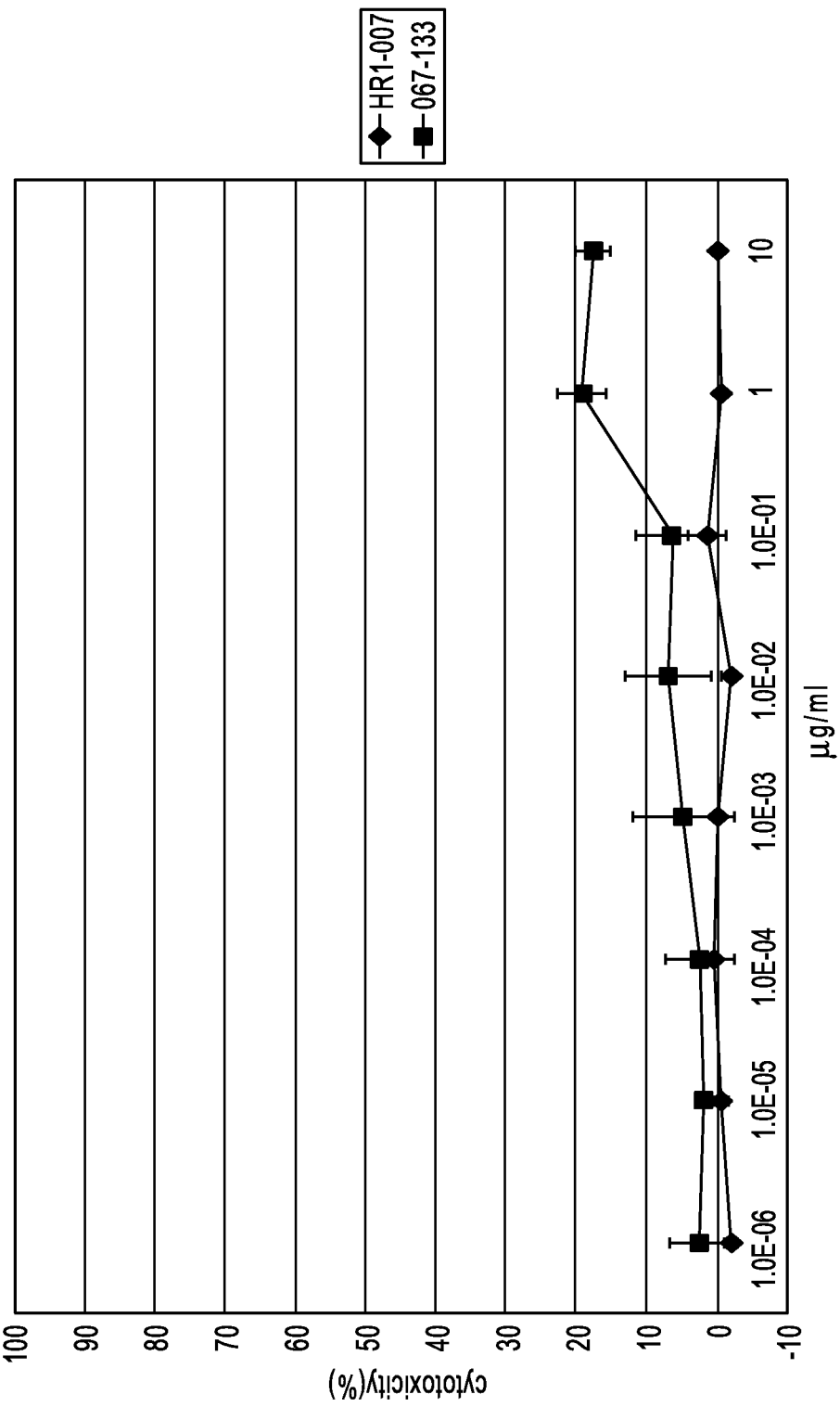
FIG. 61 shows antibody dosage dependence of the ADCC activity. An antibody to be used: anti-HGFR antibody 067-133 antibody, target culture cell: EBC-1.
Figure 62:
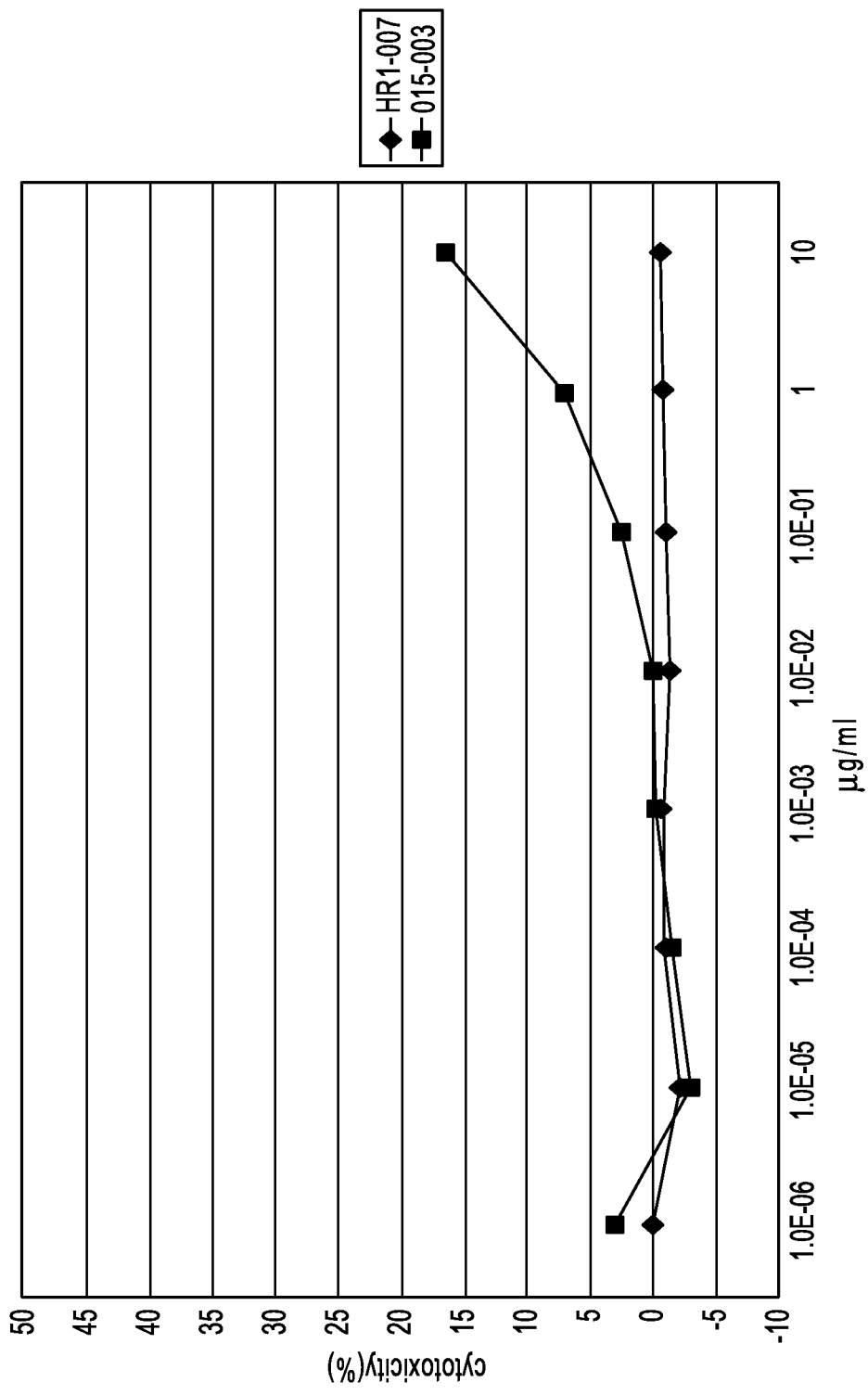
FIG. 62 shows antibody dosage dependence of the ADCC activity. An antibody to be used: anti-ITGA3 antibody, 015-003 antibody, target culture cell: ACHN.
Figure 63:
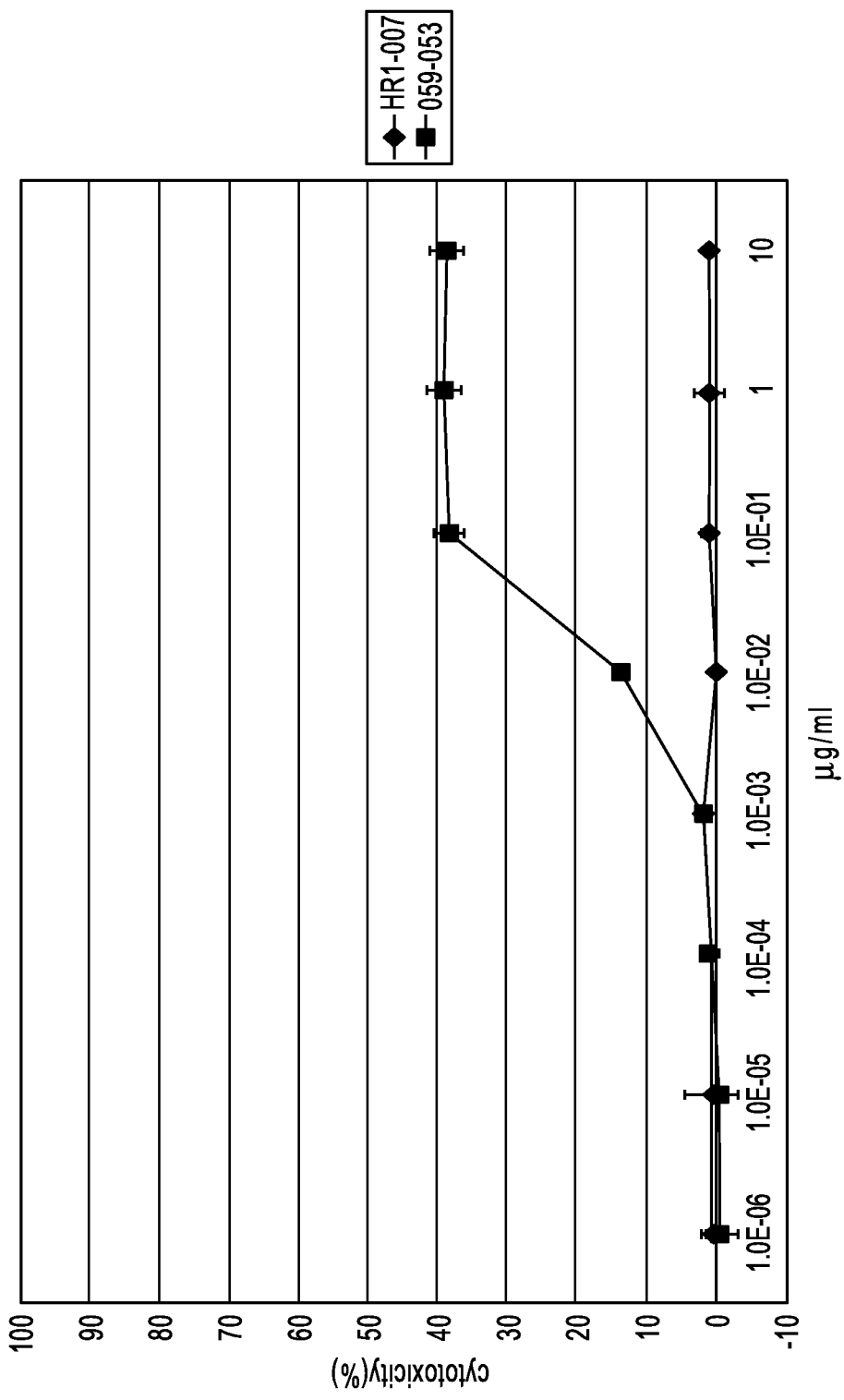
FIG. 63 shows antibody dosage dependence of the ADCC activity. An antibody to be used: anti-CD147 antibody, 059-053 antibody, target culture cell: CCF-RC1.
Figure 64:
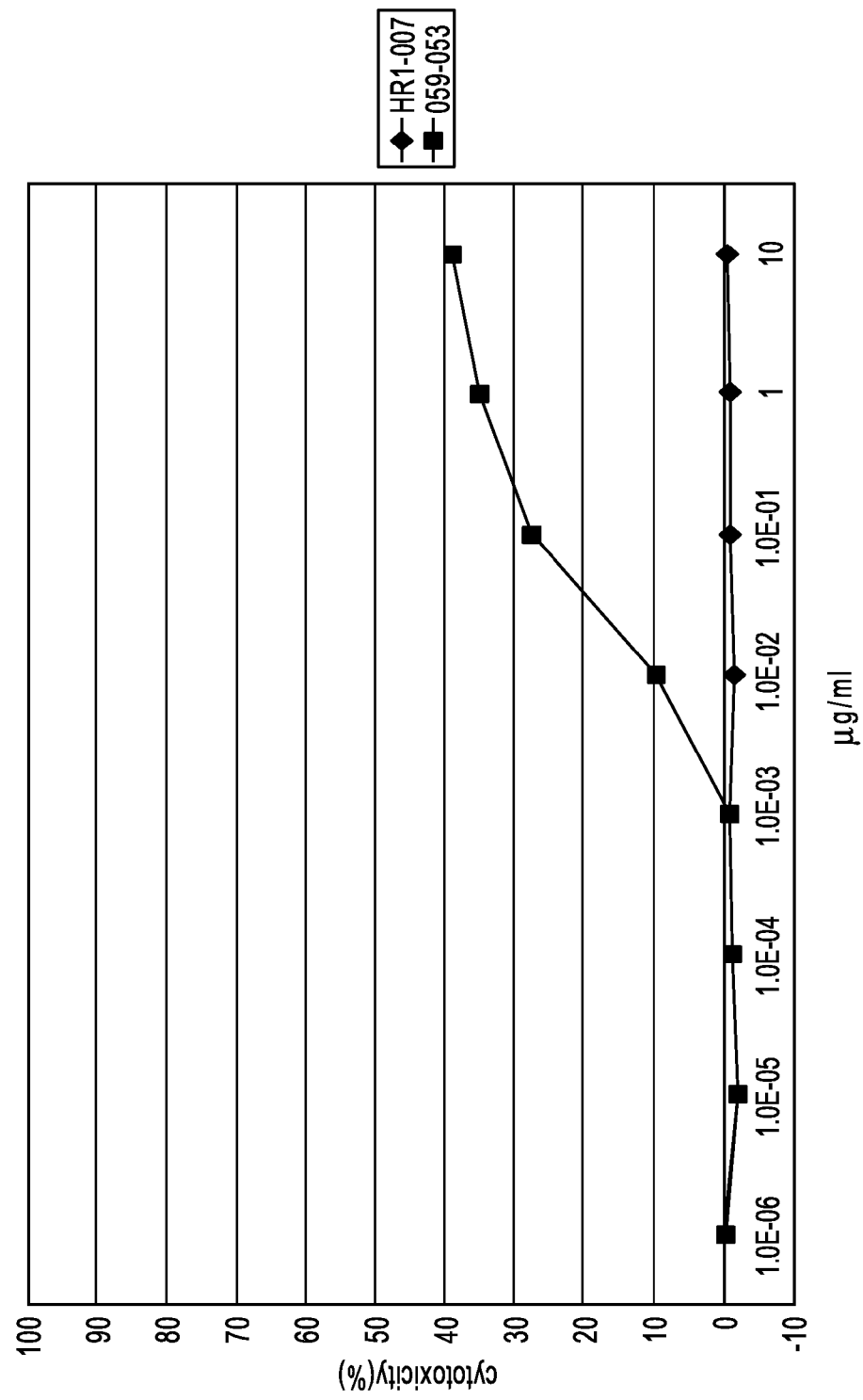
FIG. 64 shows antibody dosage dependence of the ADCC activity. An antibody to be used: anti-CD147 antibody, 059-053 antibody, target culture cell: ACHN.
Figure 65:
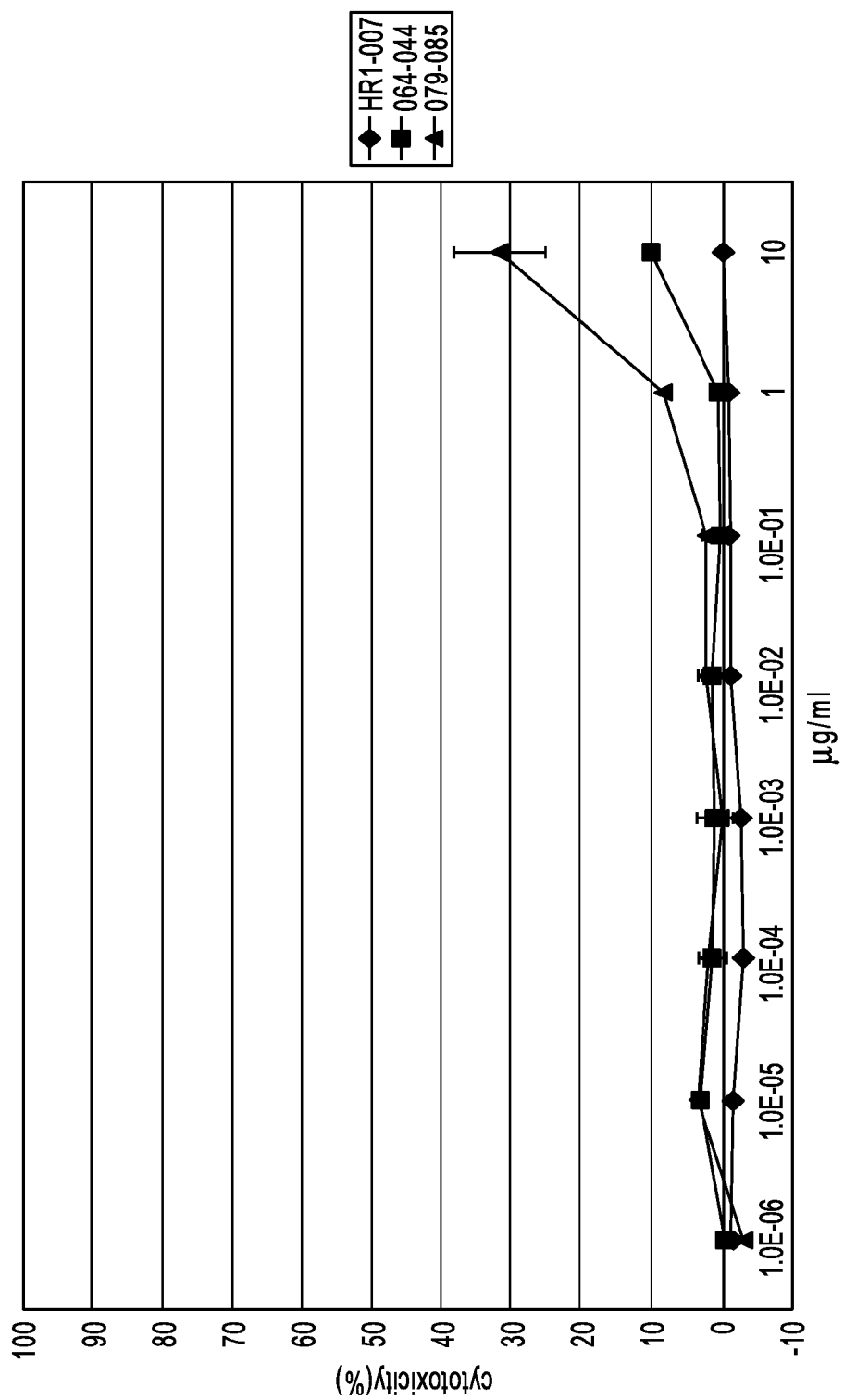
FIG. 65 shows antibody dosage dependence of the ADCC activity. An antibody to be used: anti-PTP-LAR antibody, 064-044 antibody or 079-085 antibody, target culture cell: PC-14.
Figure 66:
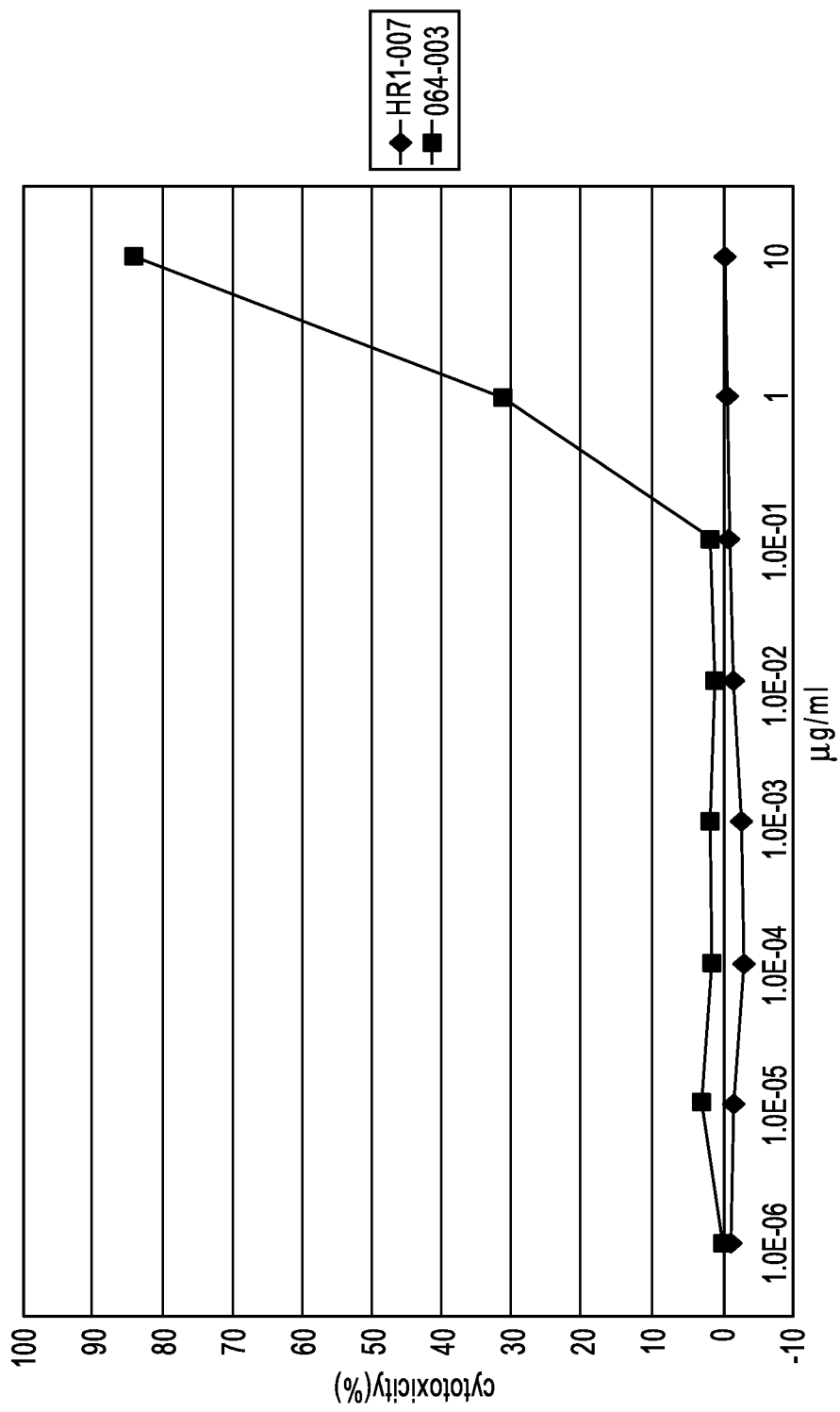
FIG. 66 shows antibody dosage dependence of the ADCC activity. An antibody to be used: anti-CD44 antibody. 064-003 antibody, target culture cell: PC-14.

Similarly, the measurement results of the antibody dosage dependence of the ADCC activity are shown in FIG. 48 (055-147 antibody or 059-173 antibody as anti-HER1 antibody was used; the target culture cell was CCF-RC1), FIG. 49 (048-006 antibody, 059-152 antibody, 055-147 antibody or 059-173 antibody as anti-HER1 antibody was used; the target culture cell was HT-29), FIG. 50 (048-006 antibody, 055-147 antibody or 059-173 antibody as anti-HER1 antibody was used; the target culture cell was A431), FIG. 51 (048-006 antibody or 059-152 antibody as anti-HER1 antibody was used; the target culture cell was ACHN), FIG. 52 (035-234 antibody or 066-174 antibody as anti-ALCAM antibody was used; the target culture cell was NCI-H1373), FIG. 53 (035-234 antibody or 066-174 antibody as anti-ALCAM antibody was used; the target culture cell was target cell SKOv3), FIG. 54 (035-234 antibody or 066-174 antibody as anti-ALCAM antibody was used; the target culture cell was CW-2), FIG. 55 (041-118 antibody as anti-ALCAM antibody was used; the target culture cell was EBC-1), FIG. 56 (080-040 antibody as anti-ALCAM antibody was used; the target culture cell was NCI-H1373), FIG. 57 (053-042 antibody as anti-ICAM1 antibody was used; the target culture cell was NCI-H1373), FIG. 58 (053-051 antibody, 053-059 antibody or 053-085 antibody as anti-ICAM1 antibody was used; the target culture cell was NCI-H1373), FIG. 59 (067-153 antibody as anti-EpCAM antibody was used; the target culture cell was EBC-1), FIG. 60 (067-133 antibody as anti-HGFR antibody was used; the target culture cell was MKN-45), FIG. 61 (067-133 antibody as anti-HGFR antibody was used; the target culture cell was EBC-1), FIG. 62 (015-003 antibody as anti-ITGA3 antibody was used; the target culture cell was ACHN), FIG. 63 (059-053 antibody as anti-CD147 antibody was used; the target culture cell was CCF-RC1), FIG. 64 (059-053 antibody as anti-CD147 antibody was used; the target culture cell was ACHN), FIG. 65 (064-044 antibody or 079-085 antibody as anti-PTP-LAR antibody was used; the target culture cell was PC-14), and FIG. 66 (064-003 antibody as anti-CD44 antibody was used; the target culture cell was PC-14).

In any of anti-ITGA3 antibody (015-003), anti-HER1 antibody (048-006) and anti-HER2 antibody (015-126), anti-CD44 antibody (064-003), the cytotoxicity was increased in the experiment groups in which the effector cell was added. That is to say, in any of the antibodies, the cytotoxic activity caused by the effector cell that recognizes an antibody to which a target cell has been specifically bound and attacks the target cell was observed.

Note here that an anti-habu venom antibody (control antibody) HR1-007 that is not related to the surface antigen or the experiment group in which the antibody clone is not added, the increase in the cytotoxicity is not observed.

In any of anti-ALCAM antibodies (066-174, 035-234, 041-118, and 083-040), anti-ICAM1 antibody (053-051, 053-059, 053-085, and 053-042), and anti-CD147 antibody (059-053), the cytotoxicity is increased more significantly than in the anti-habu venom antibody (control antibody) HR1-007 experiment group. As mentioned above, it is clearly shown that the antibody dependent cytotoxicity is higher than that of the control antibody (HR1-007) with a significant difference.

From the above-mentioned results, it has been confirmed that an antibody capable of specifically recognizing a cancer cell and exhibiting a damaging effect by the ADCC activity has been obtained for each of HER1, HER2, ITGA3, ALCAM, ICAM, CD44, CD147, EPCAM and HGFR. In other words, an antibody that is a promising as the antibody medicine targeting each of cancer cells has been obtained.

In the results of the antibody dosage dependence test, anti-HER1 antibody (048-006) shows a significant effect even if the dosage is 0.01 µg/ml. It is determined that the effect is expected with low dosage.

It is observed that the 048-006 antibody and 059-152 antibody tend to have a strong ADCC activity in the cell line in which HER1 is expressed. However, the activity differs depending upon the concentration range of the antibody to be used or the kinds of antibodies. To A431 cell, with 0.001 µg/ml, the difference in the activity was observed. Generally, in the low concentration range, the activity of 059-152 antibody was more significant than that of 048-006 antibody. Furthermore, 055-147 antibody and 059-173 antibody shows higher ADCC activity than ERBITUX™ that is commercially available drug and is more useful.

Furthermore, 067-153 antibody as anti-EpCAM antibody shows an excellent ADCC activity to MKN-45 (solid-type gastric adenocarcinoma) cell line at the concentration of 0.01 µg/ml or more, and it shows an excellent ADCC activity to HT-29 (colon adenocarcinoma) cell line at the concentration of 10 pg/ml or more with an amazing score of 80% or more in the ADCC activity in the concentration range of about 1 µg/ml. It shows an amazing score of 50% or more in the ADCC activity in NCI-H1373 (pulmonary adenocarcinoma) cell line at the concentration of 0.01 µg/ml or more.

Furthermore, 041-118 antibody as anti-ALCAM antibody shows a remarkable effect to NCI-H1373 (pulmonary adenocarcinoma) cell line at the concentration of 0.01 μg/ml or more. It is determined that the effect can be expected with low dosage.

Furthermore, 066-174 antibody as anti-ALCAM antibody shows high ADCC activity to various cells such as NCI-H1373 (pulmonary adenocarcinoma) cell line, SKOv3 (ovarian cancer) cell line, and CW-2 (large bowel cancer) cell line. Wide application is expected.

Furthermore, 067-133 antibody as anti-HGFR antibody shows a remarkable effect to NCI-H1373 (pulmonary adenocarcinoma) cell line at the concentration of 0.01 μg/ml or more with strong activity of 40% or more at the concentration of 10 μg/ml or more.

Furthermore, 059-053 antibody as anti-CD147 antibody shows an excellent ADCC effect to CCF-RC1 (kidney cancer) cell line and ACHN (kidney cancer) cell line, which shows near the upper limit value at the low concentration. Therefore, it can be expected to show the maximum activity at a low concentration.

From the above-mentioned results, it is confirmed that a promising antibody group showing a sufficient ADCC activity even with low dosage (at low concentration) can be obtained successfully. Also in the similar experiments using a plurality of lymphocyte fractions derived from human, the same results as mentioned above can be obtained. The high reproducibility is confirmed.

17. Cancer Cell Proliferation Inhibition Test

Some antibody medicines exhibit the efficacy by an effect of inhibiting the proliferation of cancer instead of the ADCC effect (or in addition to the ADCC effect). Thus, in order to further investigate the efficacy of antibody medicine, the activity of inhibiting the proliferation of cancer by antibodies that have been successfully isolated have been investigated according to the following procedure.

17-1 Testing Method
(1) Target culture cells that have grown in a culture dish are peeled off with 4% Collagenase and suspended in the used medium.
(2) The cell density is measured and then the supernatant is removed by centrifugation and suspended in a RPMI-1640 (10% FBS, 1% Penicillin-Streptomycin) medium so that the final density is $1.0 \times 10^4$ cells/ml.
(3) 100 μl each of target cells is dispensed in a flat-bottom 96 well multi plate.
(4) 100 μl each of 20 μg/ml human IgG monoclonal antibody solution is dispensed.
(5) Reaction is carried out in 5% $CO_2$ at 37° C. for 5 days.
(6) Medium is removed, and living cell measurement reagent (XTT: Roche) is dispensed in each well (150 μl each).
(7) Reaction is carried out in 5% $CO_2$ at 37° C. for 4 hours.
(8) After reaction, OD490 and OD690 are measured by using a micro plate absorptiometer. Then, the number of living cells is calculated according to the following equation.

XTT reduction amount(degree of coloring)=OD490−OD690

XTT reducing activity derived from cells=(experimental value)−(control value using only a solution)     [Equation 2]

Note here that the XTT reducing activity derived from cells is in proportion to the number of living cells.

17-2 Results

Figure 67:
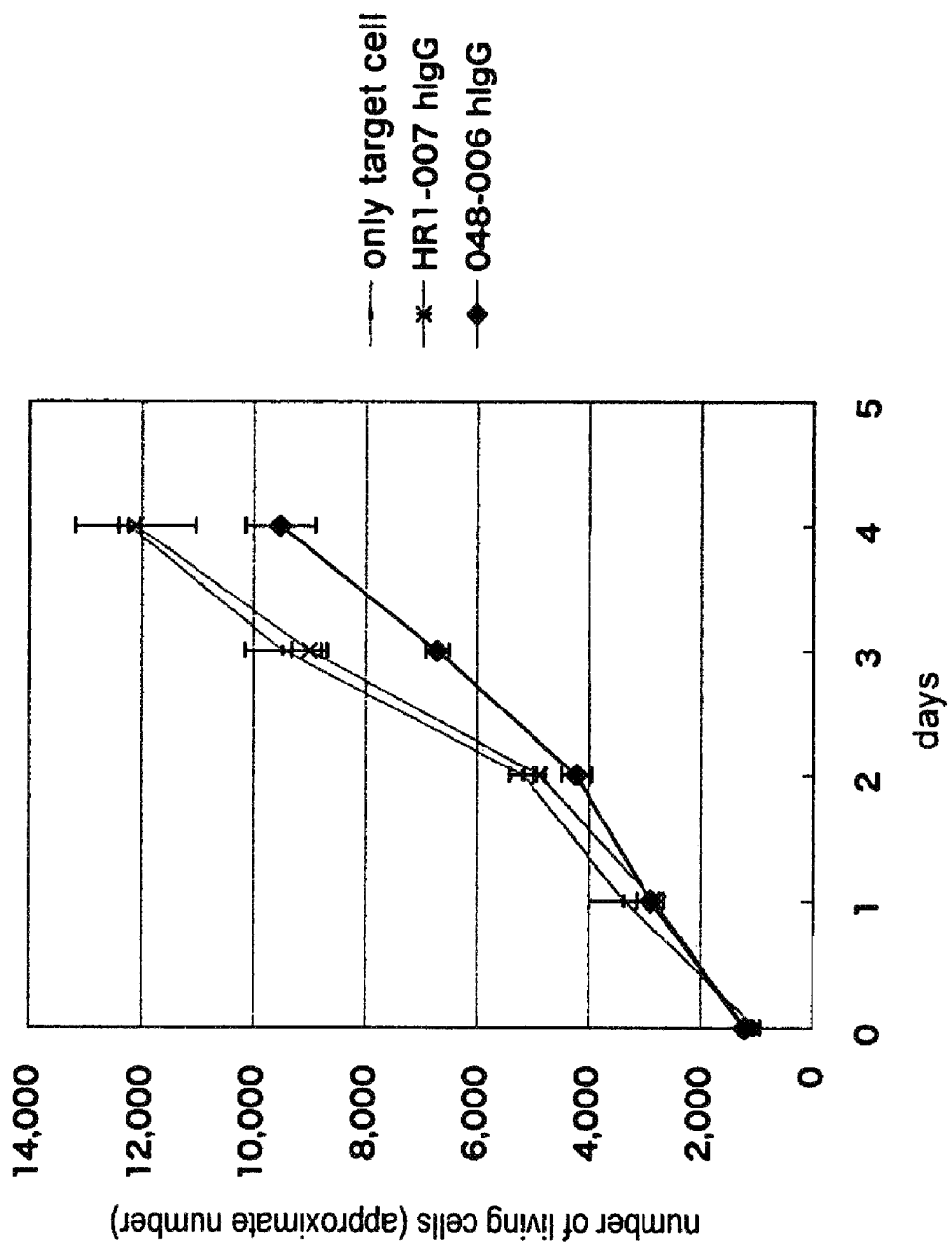
FIG. 67 shows a result of a cell proliferation inhibition test. An antibody to be used: anti-HER1 antibody (048-006), target subjected cultured cell: A-431.
Figure 68:
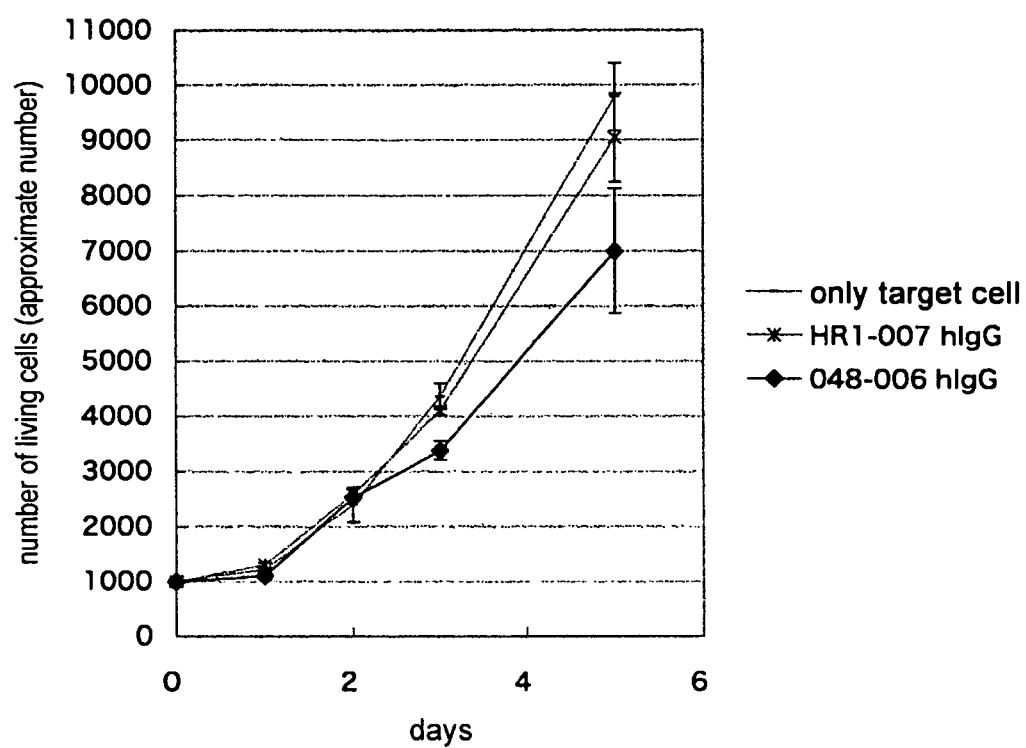
FIG. 68 shows a result of a cell proliferation inhibition test. An antibody to be used: anti-HER1 antibody (048-006), target subjected cultured cell: ACHN.
Figure 69:
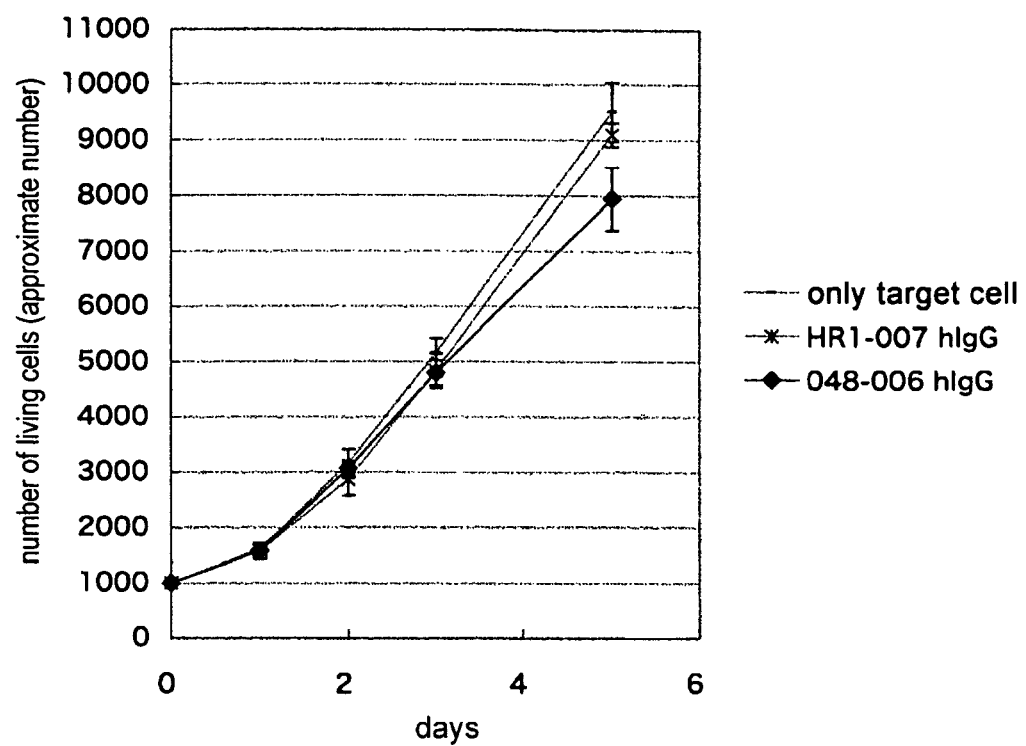
FIG. 69 shows a result of a cell proliferation inhibition test. An antibody to be used: anti-HER1 antibody (048-006), target subjected cultured cell: NCI-H1373.
Figure 70:
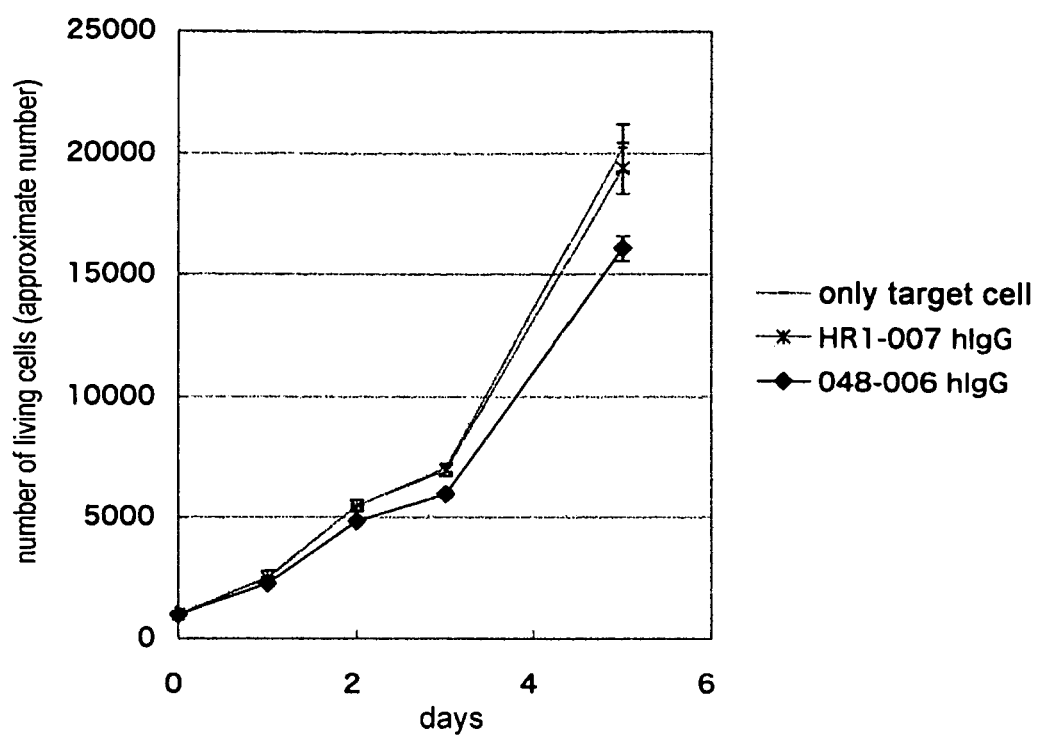
FIG. 70 shows a result of a cell proliferation inhibition test. An antibody to be used: anti-HER1 antibody (048-006), target subjected cultured cell: SK-OV-3.
Figure 71:
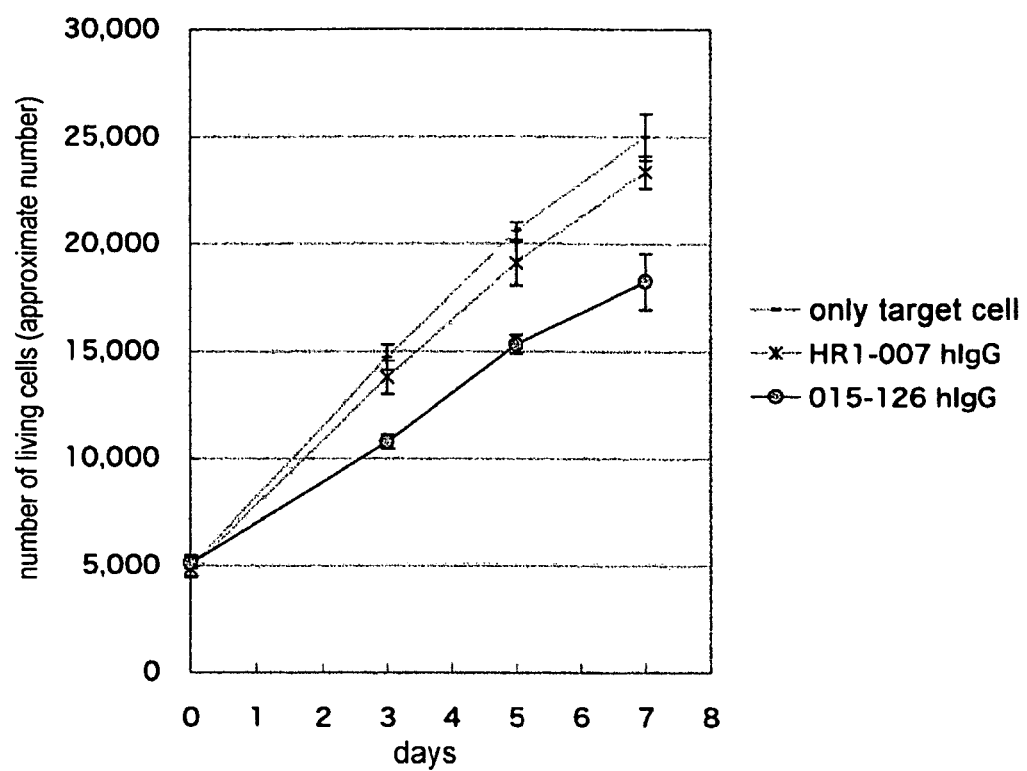
FIG. 71 shows a result of a cell proliferation inhibition test. An antibody to be used: anti-HER2 antibody (015-126), target subjected cultured cell: BT-474.
Figure 72:
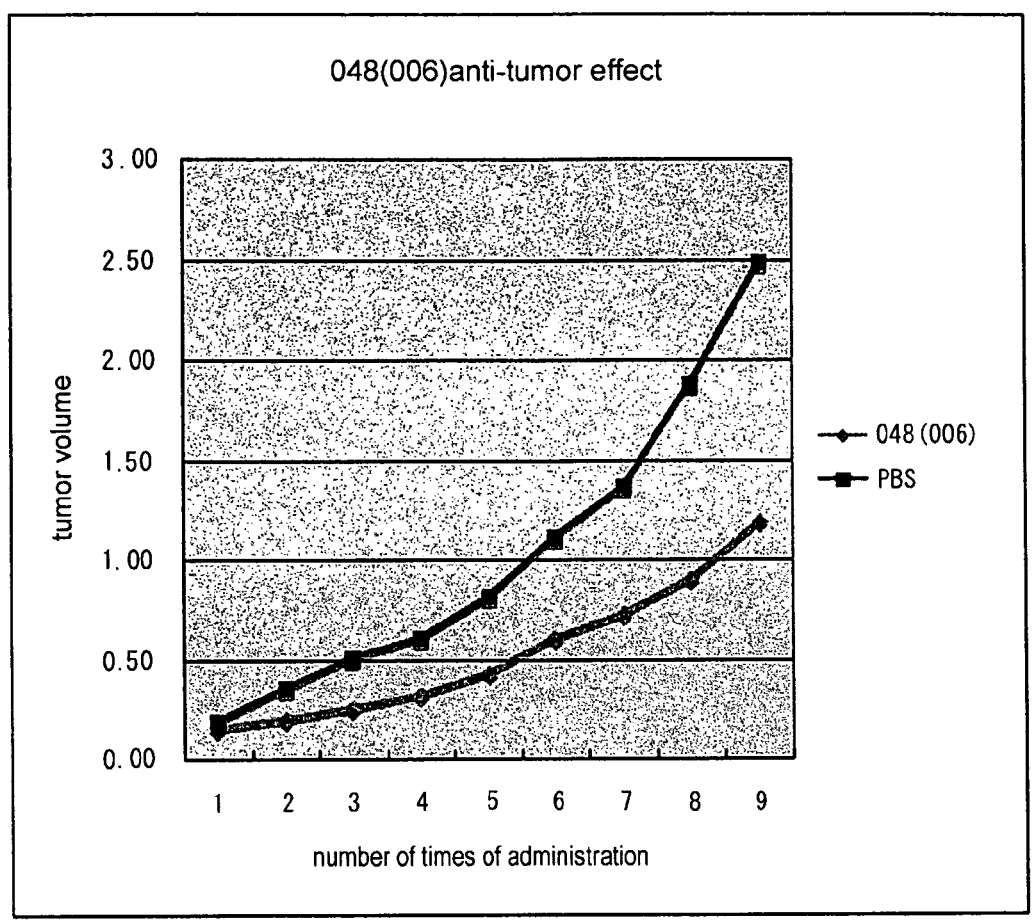
FIG. 72 shows a result of an antitumor experiment using mouse. An antibody to be used: anti-HER1 antibody (048-006), subject transplant cell: human lung cancer cell H1373 cell.
Figure 73:
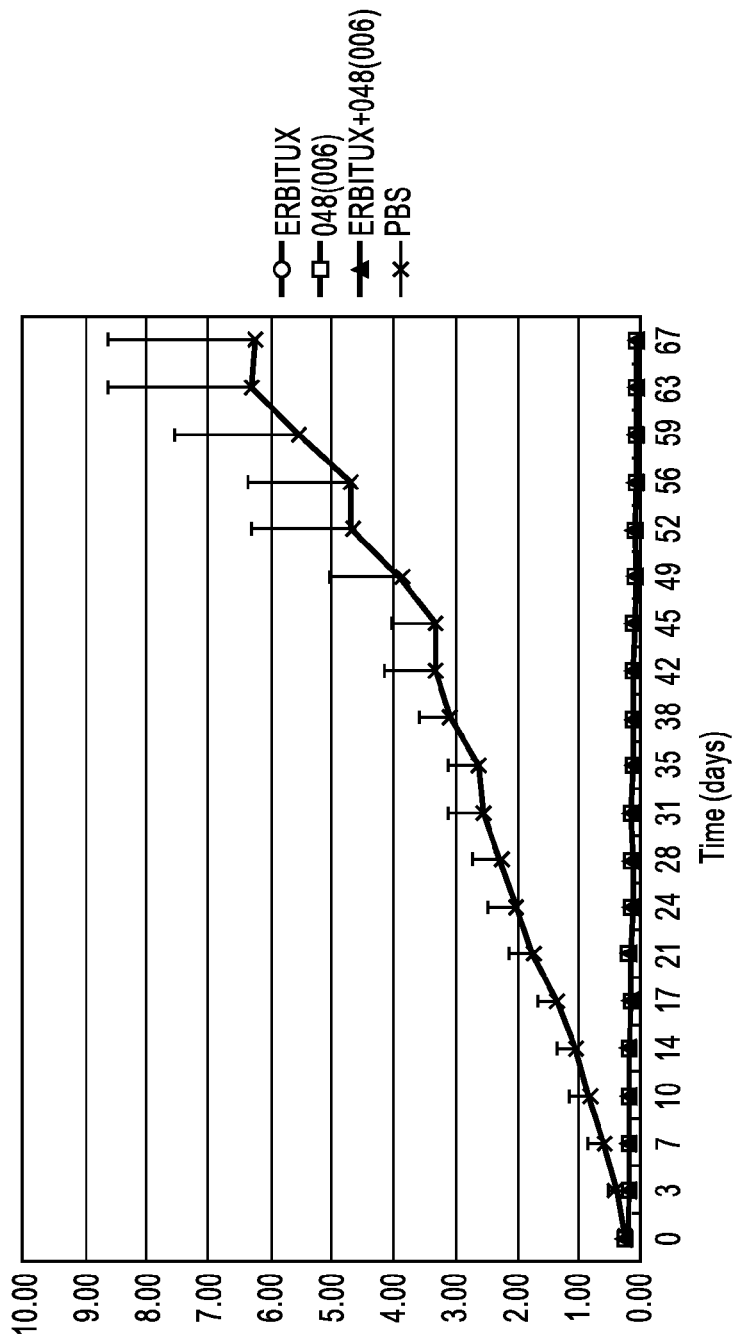
FIG. 73 shows a result of an antitumor experiment using mouse. An antibody to be used: anti-HER1 antibody (048-006), subject transplant cell: epidermoid tumor A-431.
Figure 74:
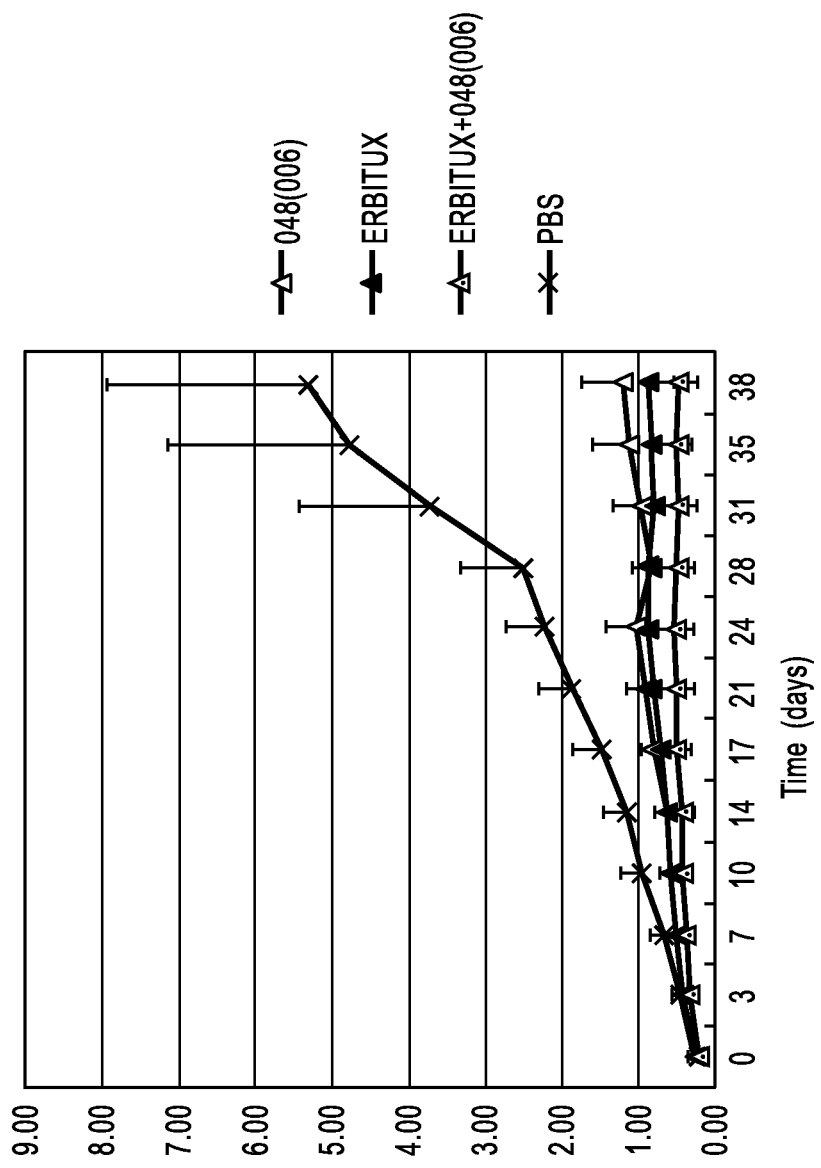
FIG. 74 shows a result of an antitumor experiment using mouse. An antibody to be used: anti-HER1 antibody (048-006), subject transplant cell: epidermoid tumor A-431.

The results are shown in FIG. 67 (anti-HER1 antibody (048-006) was used; the target subject cultured cell was A-431), FIG. 68 (anti-HER1 antibody (048-006) was used; the target subject cultured cell was ACHN), FIG. 69 (anti-HER1 antibody (048-006) was used; the target subject cultured cell was NCI-H1373), FIG. 70 (anti-HER1 antibody (048-006) was used; the target subject cultured cell was SK-OV-3), and FIG. 71 (anti-HER2 antibody (015-126) was used; the target subject cultured cell was BT-474).

As is apparent from these drawings, it is confirmed that the antibodies inhibiting the proliferation of cancer cell can be successfully obtained. In other words, it is shown that these antibodies may be effective as antibody medicine of suppressing the proliferation of cancer cells.

18. Antitumor Experiment Using Mouse

Next, whether or not the antibodies that have been successfully isolated show an anti-tumor activity in vivo is confirmed by using a cancer cell-transplanted mouse.

18-1 Animals and Cell Line to be Used

Four-week old female BALB/c nude mouse (Charles River Japan) was acclimated and bred for one week and then used for experiment. The animals were bred under the SPF environment and fed with sterilized water and feed.

Human lung cancer cell H1373 or epidermoid tumor A-431, which had been subcultured in a RPMI medium containing 10% FBS at 37° C. in the presence of 5% $CO_2$, were used.

18-2 Method of Antitumor Experiment

Human lung cancer cells, H1373 cells ($1 \times 10^7$ cells) were transplanted in the dorsolateral subcutaneous portion of a nude mouse so as to produce a tumor. At the time the tumor volume was 1 $cm^3$, the tumor was cut into a size of 3 mm×3 mm, and is was successive-transplanted to the dorsal subcutaneous portion of the prepared nude mouse. After transplantation, when a volume of the tumor was estimated to be 200 $mm^3$, administration of the antibody was started. The diameter of the tumor and body weight were measure twice a week, estimated tumor volume was calculated from the equation: $W = a \times b^2/2$ (W: estimated tumor volume ($mm^3$), a: major axis (mm), b: minor axis (mm)). The experiment group was divided into a control group (PBS was administered) and 048-006 IgG administered group (0.5 mg/individual). The administration pathway was made to be an intraperitoneal administration. Administration was carried out twice a week eight times in total. Then, the anti-tumor effect was examined.

Furthermore, ERBITUX (Cetuximab, Bristol-Myers Squibb Company) was used as a comparative group or an additivity examining group. When ERBITUX is used singly, the dosage amount was made to be 0.25 mg/individual. ERBITUX was used together with 048-006 IgG, the dosage amount of ERBITUX was made to be 0.25 mg/individual and the dosage amount of 048-006 IgG was made to be 0.25 mg/individual. After administration, the follow-up was carried out.

When epidermoid tumor A-431 is used, epidermoid tumors A-431 ($5 \times 10^6$) were similarly transplanted in the dorsolateral subcutaneous portion of a five-week old female BALB/c nude mouse nude mouse so as to produce a tumor. At the time the tumor volume was estimated to be 200 $mm^3$, administration of the antibody was started. The administration pathway was made to be an intraperitoneal administration. 048-006 IgG type antibody was administered twice a week six times in total. Then, the anti-tumor effect was examined. 059-152 IgG type antibody administered group (0.25 mg or 1.00 mg of antibody was diluted in 0.5 ml PBS/individual) twice a week six times in total. Then, the anti-tumor effect was examined. And the follow up was also carried out.

18-3 Results

Figure 75:
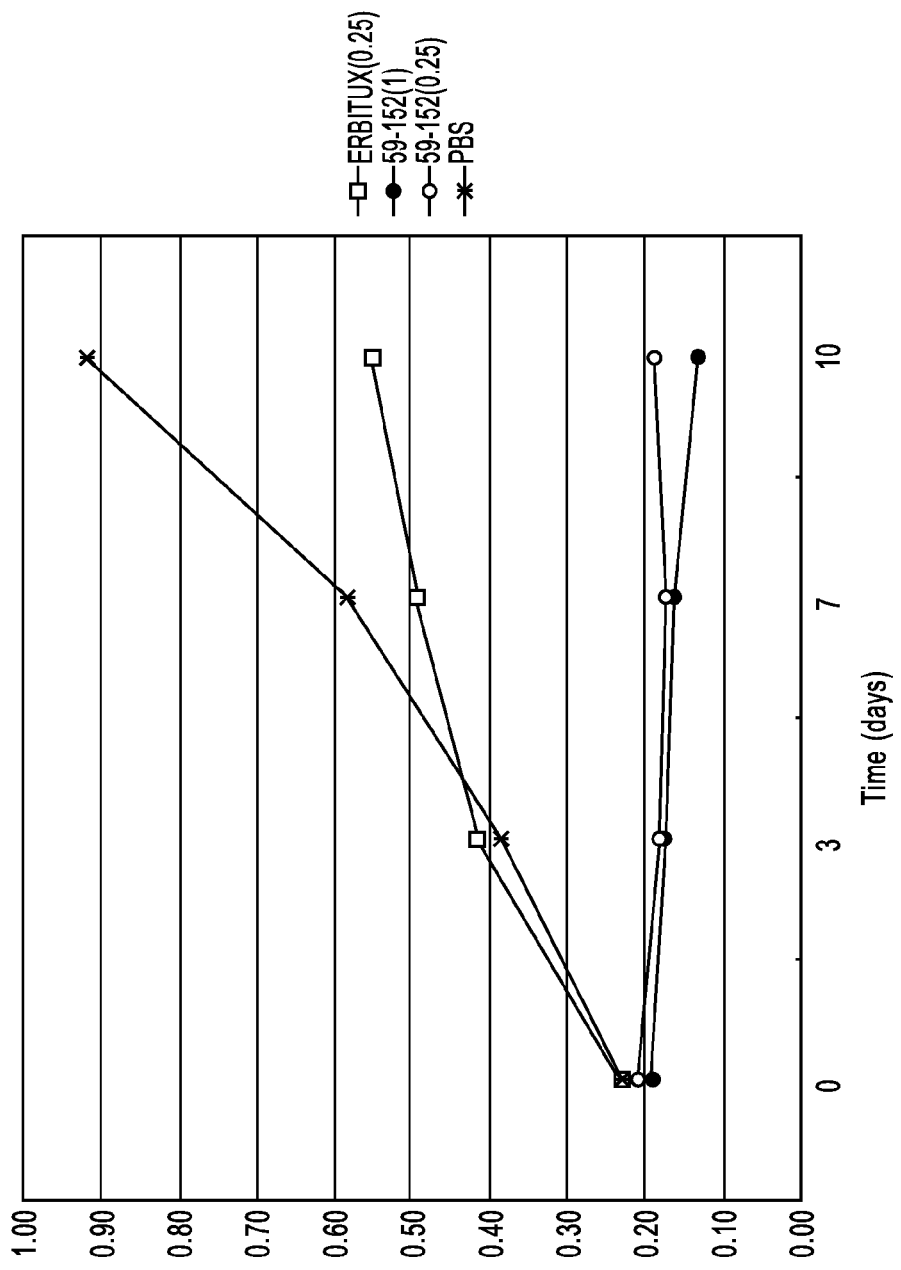
FIG. 75 shows a result of an antitumor experiment using mouse. An antibody to be used: anti-HER1 antibody (059-152), subject transplant cell: epidermoid tumor A-431.

In the antibody (048-006 IgG type antibody) administered group, estimated tumor volume was significantly reduced as compared with the control group (PBS was administered), showing a clear anti-tumor effect. It was confirmed that the effect was comparative to ERBITUX (see FIGS. 72 to 75). On the other hand, in the antibody (059-152 IgG type antibody) administered group, estimated tumor volume was significantly reduced as compared with the control group (PBS was administered), showing a clear anti-tumor effect. The effect was more excellent than that of ERBITUX (see FIG. 75). 059-152 antibody shows stronger tumor suppression effect than 048-006 antibody and commercially available ERBITUX. Thus, it was confirmed that the successfully obtained antibodies exhibited the anti-tumor effect in also in vivo model. In other words, they are shown to be an extremely promising as the antibody medicine.

19. Analysis by Three Dimensional ELISA (1) Expression of Antibody by Culturing Screened Clone Group and Preparation of Antibody Mixture Clones (about 4000 clones) of phage-infected *E. coli*, which were screened by the methods described in 1 to 5, were transferred to 41 sheets of 96-well plates at 1 clone/well, and they were shaking cultured in 100 µl/well YTGA medium (YT medium+1% Glucose+200 µg/ml Ampicillin) at 30° C. overnight. Next, 10 µl each of culture solution was mixed in all wells of the first to sixth columns for each plate to make one group (however, as to the 28th plate, the first to seventh columns are made to be one group). Forty-one plates of the mixed antibodies were obtained in total. As to 7th to 12th columns were also made into one group (excluding the 28th plate and 35th plate). Thirty-nine plates of the mixed antibodies in total were obtained. Furthermore, after the plates were divided into 7 groups (3, 6 or 7 sheets per group), for each group, 10 µl each of culture solution was mixed in all wells in each row and they were made to one group. Thus, 56 rows of the mixed antibodies in total were obtained. Finally, after the plates were divided into 5 groups (3, 9 or 10 sheets per group), for each group, 10 µl each of culture solution was mixed in all wells in each column and they were made to one group. Thus, 54 columns of the mixed antibodies in total (in a part, two columns were made to one group) were obtained.

A YT0.05GA medium (YT medium+0.05% Glucose+200 µg/ml Ampicillin) (100 ml) was added to each mixed antibody, and shaking cultured at 30° C. until OD600 nm was about 0.3 to 0.5. Thereafter, IPTG was added so that the final concentration was 0.5 mM and further shaking cultured at 30° C. The mixture was centrifuged at 10000 rpm at 4° C. for 15 minutes, and the culture supernatant was recovered. Then, ammonium sulfate (29.1 g) was slowly added and mixed, mixture was centrifuged at 10000 rpm at 4° C. for 20 minutes, and sediment was recovered. The sediment was suspended in 5 ml of PBS/NaN3/complete. The suspension was centrifuged at 10000 rpm at 4° C. for 20 minutes, and the culture supernatant was recovered. Thus, 20-fold concentrated mixed antibodies (190 types) were obtained.

(2) Measurement by Three-Dimensional ELISA

Three dimensional ELISA was carried out by using the obtained 20-fold concentrated mixed antibodies (190 types). Firstly, 50 µl/well of antigen whose concentration was adjusted to be 20 µg/ml with PBS was added to Maxisorp (Nunc) and reacted at 37° C. for two hours to be sensitized. After the liquid in each well was removed, 5% skim milk/PBS (200 µl/well) was added and reacted at 37° C. for two hours for blocking. The liquid in each well was removed and washed with PBS, and 20-fold concentrated mixed antibody (100 µl/well) was added and reacted at 37° C. for one hour. The reacted product was washed with PBS, and a rabbit anti-cp3 antibody (MBL) that had been 5000-fold diluted with 0.05% Tween/PBS was added (100 µl/well) and reacted at 37° C. for one hour. The mixture was washed with PBS, and an HRP labeled goat anti-rabbit IgG antibody (MBL) that had been 2000-fold diluted with 0.05% Tween/PBS was added (100 µl/well) and reacted at 37° C. for one hour. The reacted product was washed with PBS and a substrate solution (100 µl/well) was added. The substrate solution was produced as followed. That is to say, to 12 ml of 0.1M citric acid-disodium hydrogen-phosphate (pH 5.1), $H_2O_2$ was added so that the final concentration became 0.01% and furthermore, OPD tablet (Wako Pure Chemical) was added.

2N sulfuric acid (100 µl/well) was added to stop the reaction and the absorbance at 492 nm was measured by using a plate reader (Wako Pure Chemical, SUNRISE Remote).

Figure 79:
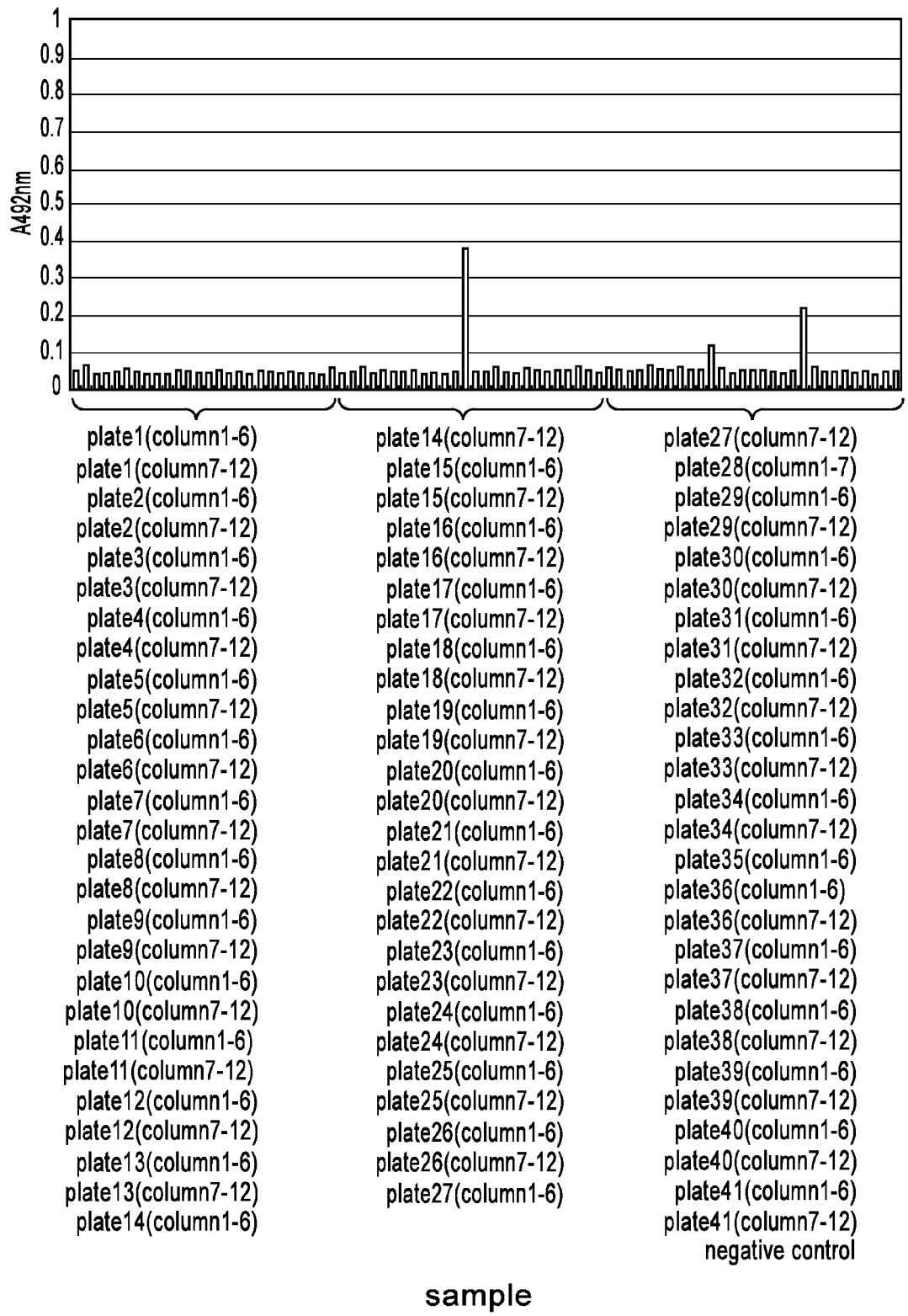
FIG. 79 shows a result of ELISA using a plate mixed antibody (antigen is CD147).
Figure 80:
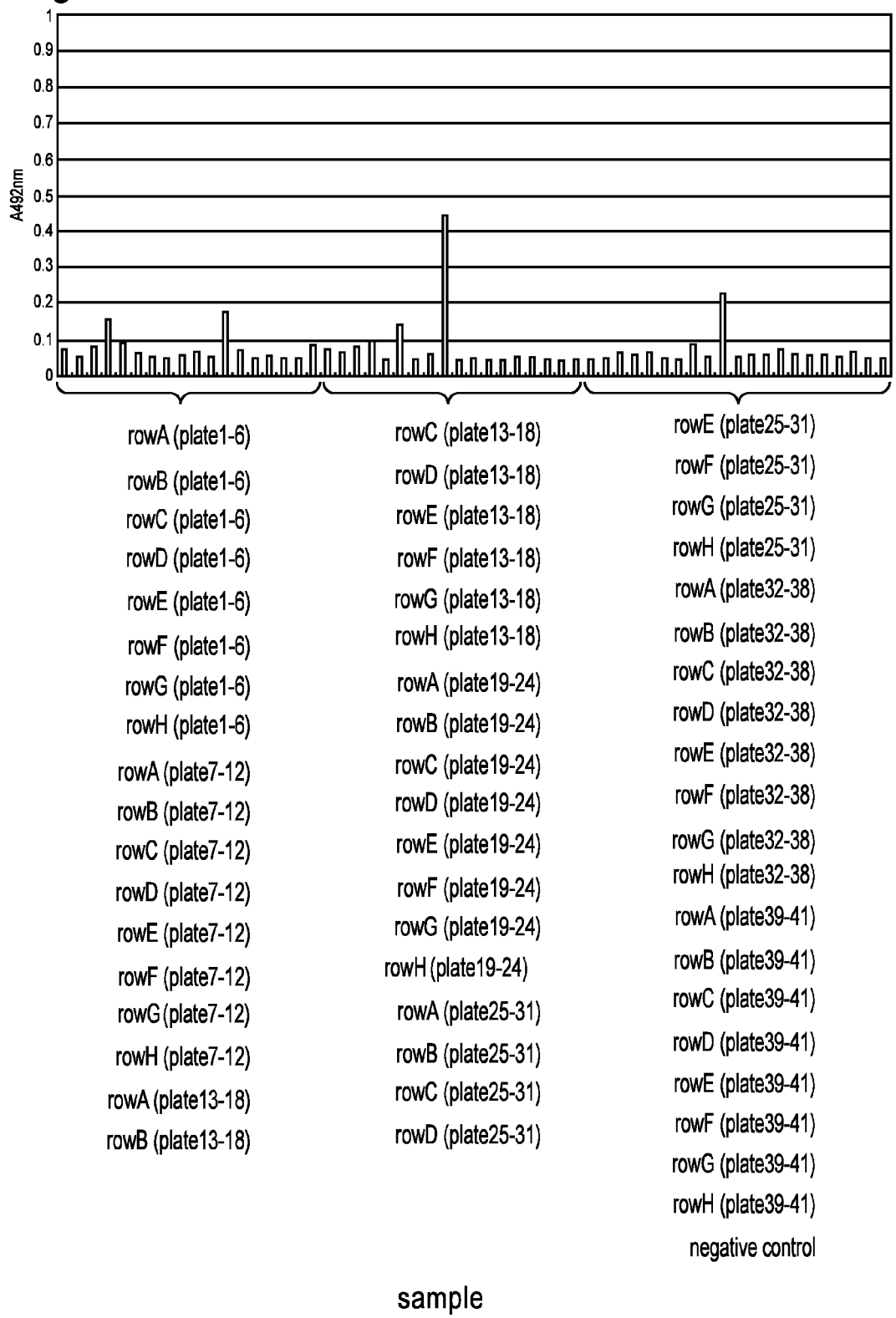
FIG. 80 shows a result of ELISA using a row mixed antibody (antigen is CD147).
Figure 81:
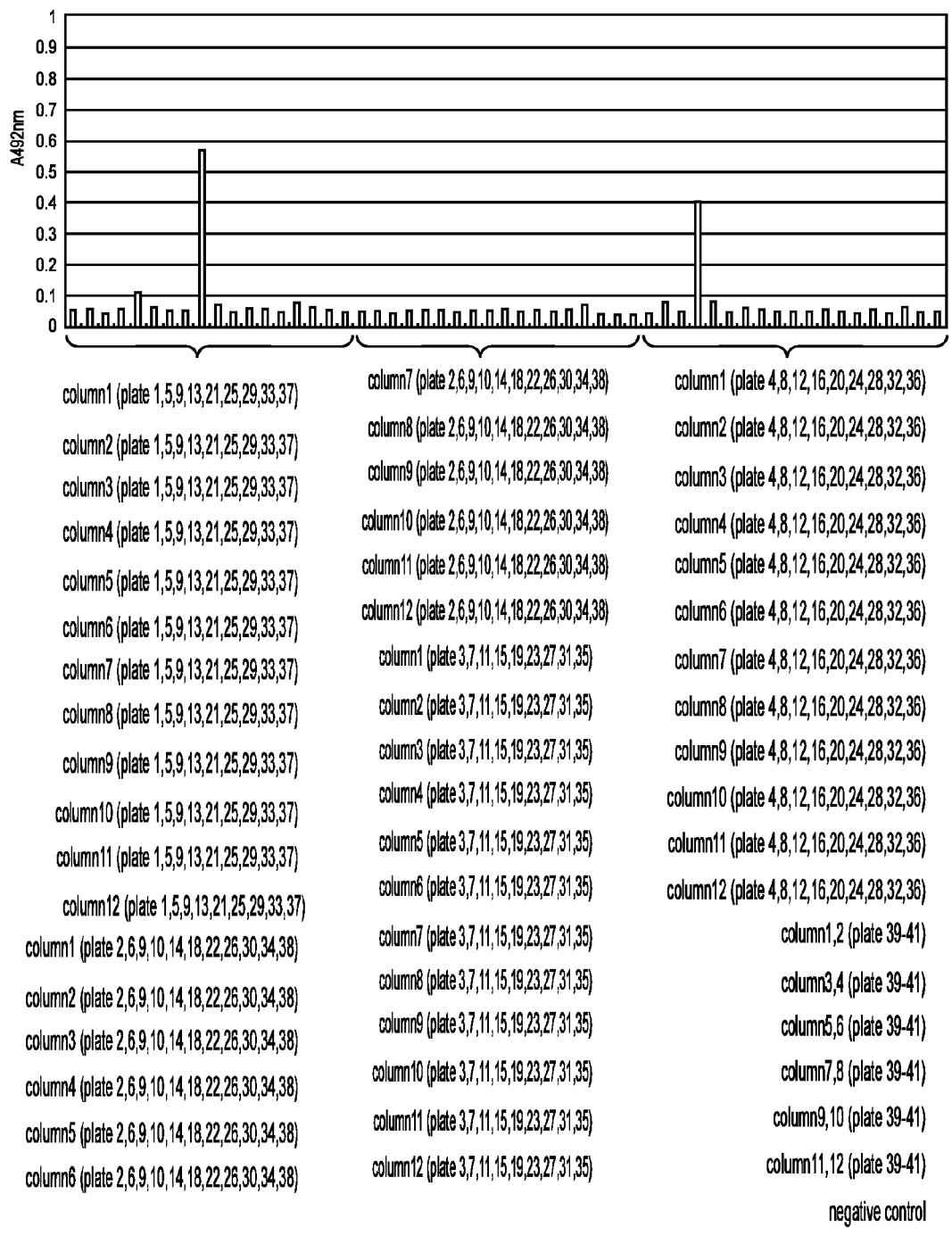
FIG. 81 shows a result of ELISA using a column mixed antibody (antigen is CD147).
Figure 82:
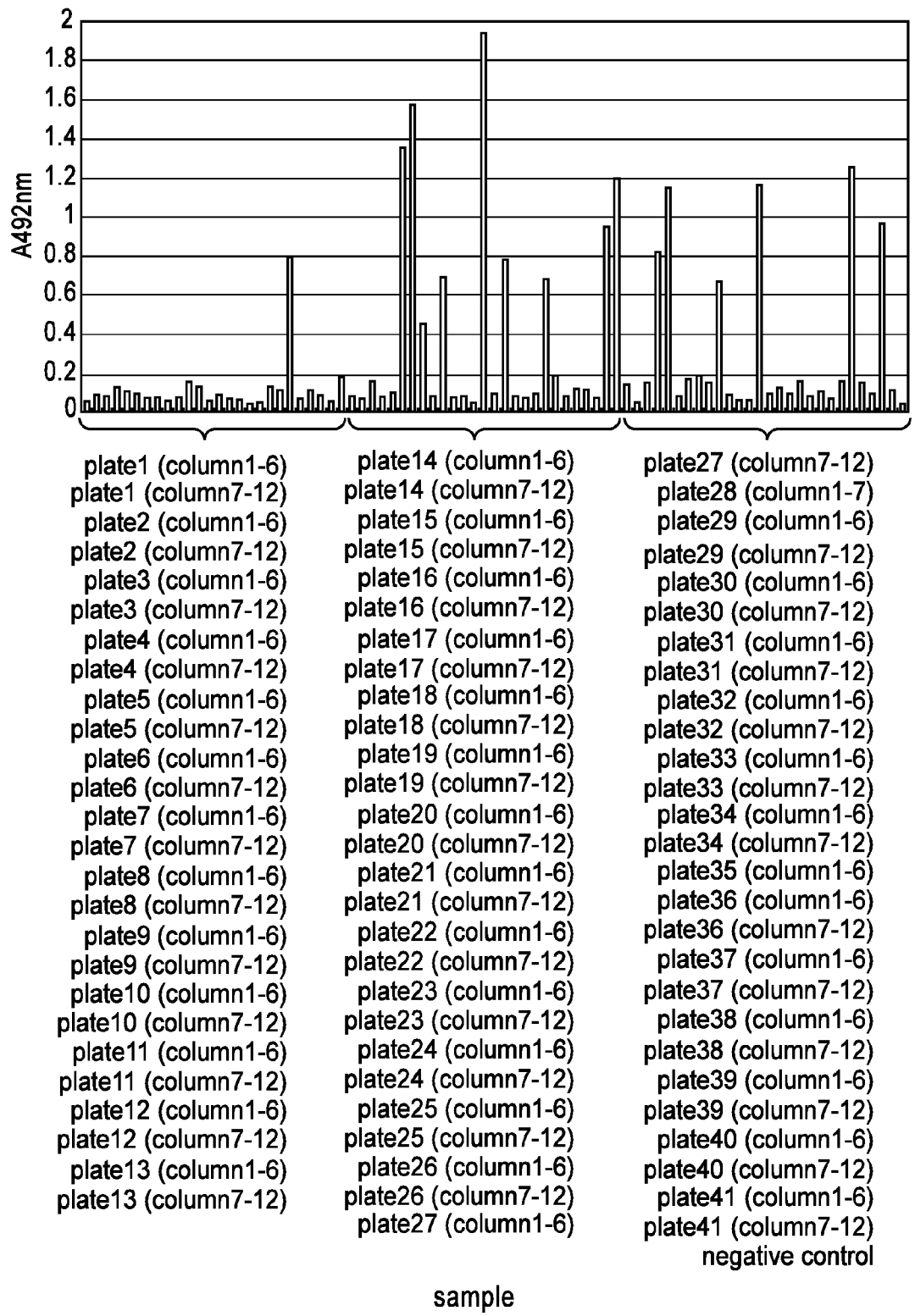
FIG. 82 shows a result of ELISA using a plate mixed antibody (antigen is HER1).
Figure 83:
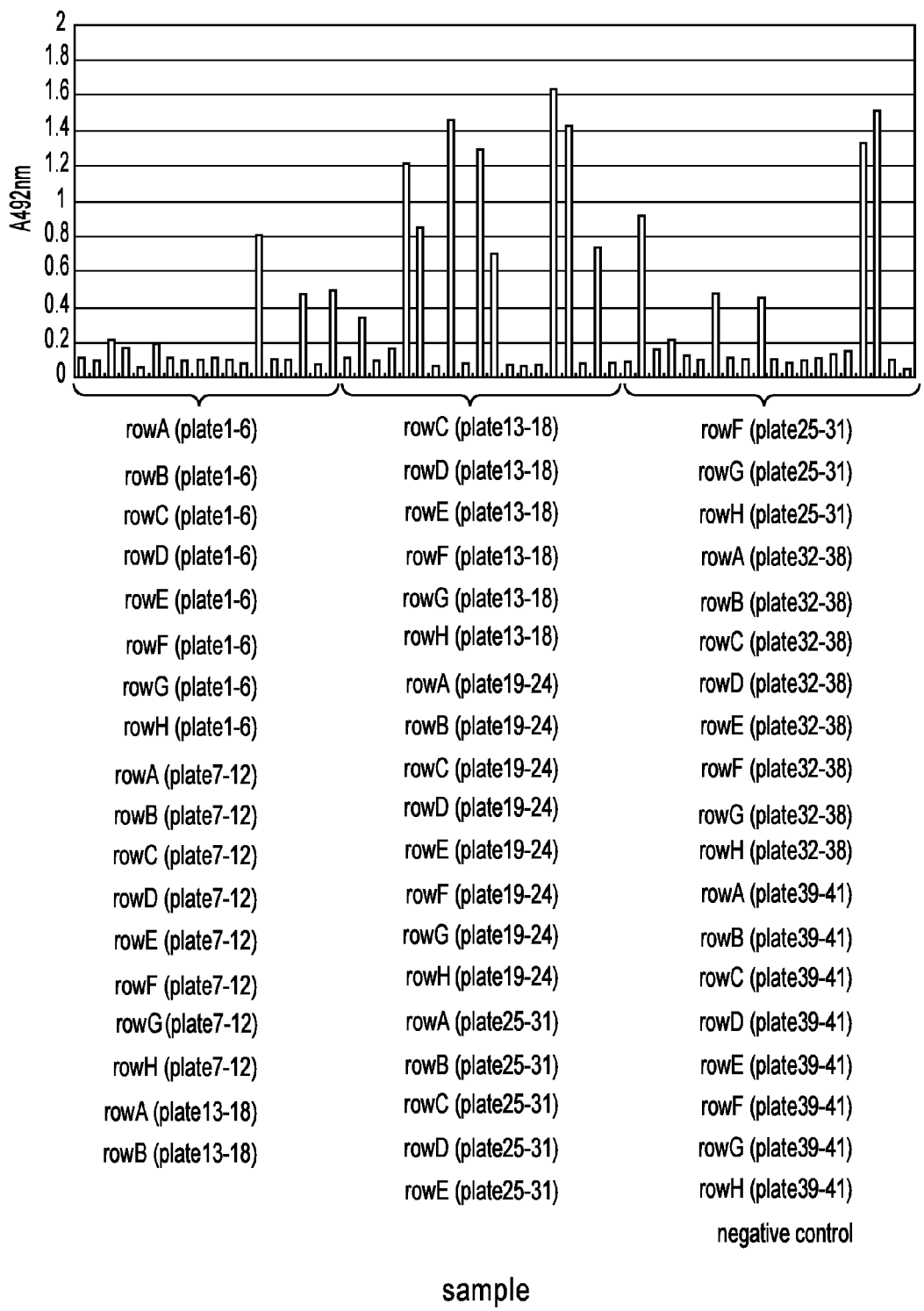
FIG. 83 shows a result of ELISA using a row mixed antibody (antigen is HER1).
Figure 84:
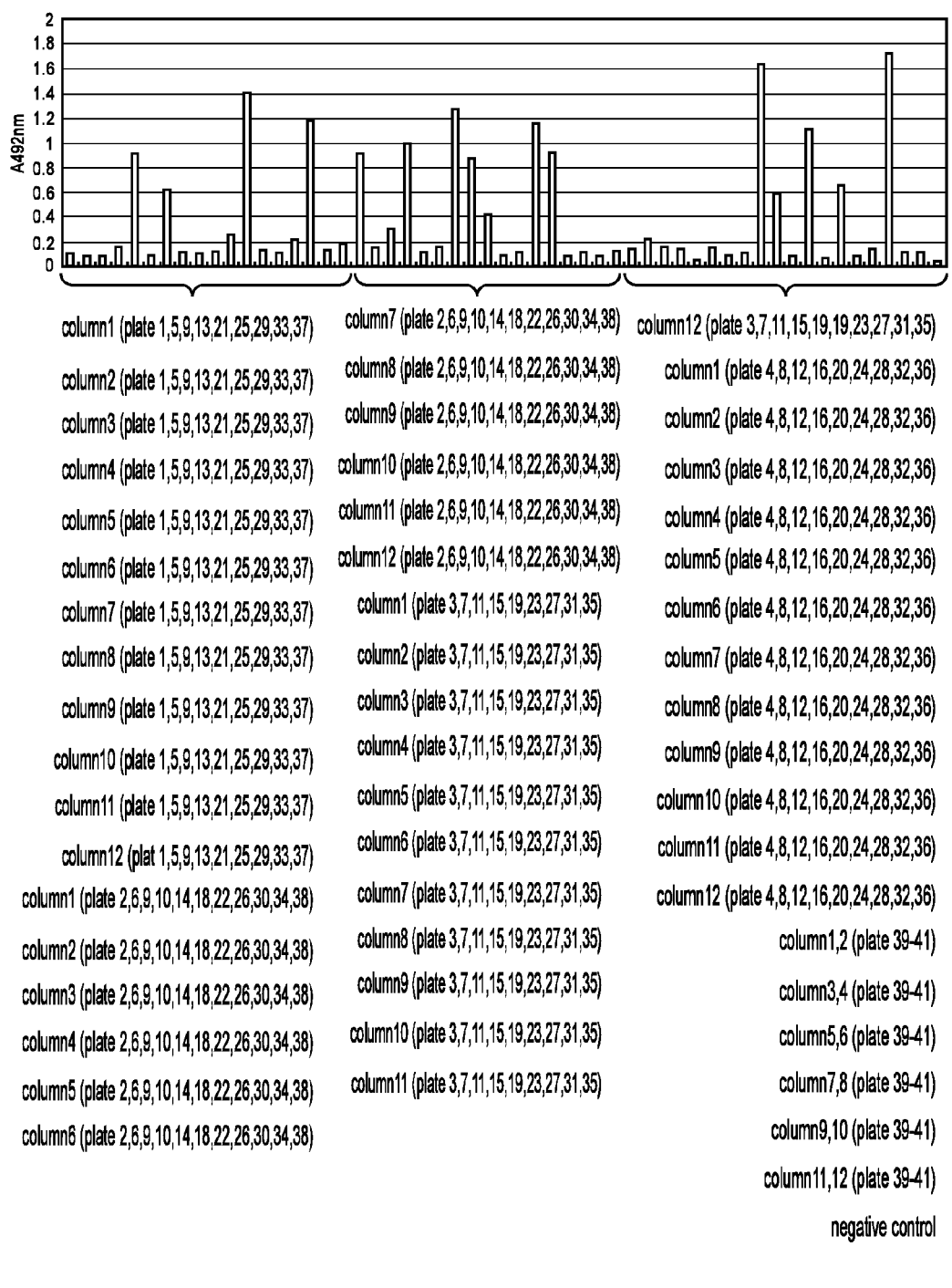
FIG. 84 shows a result of ELISA using a column mixed antibody (antigen is HER1).

The measurement results are shown in FIGS. 79 to 81 (ELISA using CK147 as an antigen) and FIGS. 82 to 84 (ELISA using HER1 as an antigen).

Based on the results of the above-mentioned three dimensional ELISA, positive clones were selected. That is to say, from information of plate, row and column providing positive results, intersection point was searched and antibody clones existing in the intersection point were selected. The selected antibody clones were shaking cultured in 75 µl/well YTGA medium at 30° C. overnight. In 200 µl/well YT0.05GA medium, the culture solution was plated and standing cultured at 37° C. for four hours. Thereafter, IPTG was added so that the final concentration became 1 mM and shaking cultured at 30° C. overnight. The culture was centrifuged at 3000 rpm at 4° C. for 10 minutes and the culture supernatant was recovered.

(3) Reactivity of Selected Antibody Clones

Figure 85:
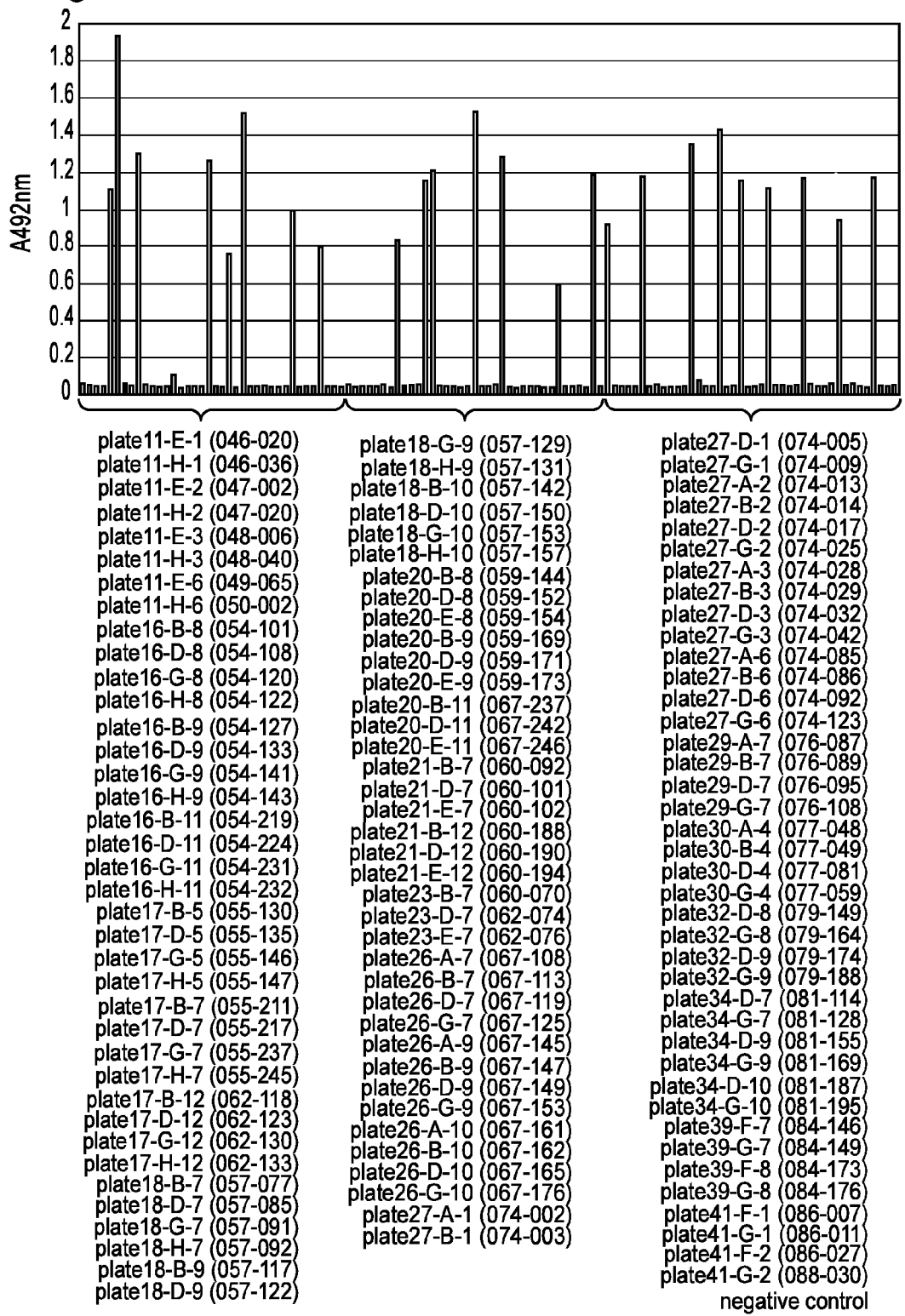
FIG. 85 shows a result of ELISA using a selected antibody clone (antigen is HER1).

50 µl/well of antigen (CD147 or HER1) whose concentration was adjusted to be 10 µg/ml with PBS was added to Maxisorp (Nunc) and reacted at 37° C. for two hours to be sensitized. After the liquid in each well was removed, 5% skim milk/PBS (200 µl/well) was added and reacted at 37° C. for two hours for blocking. The liquid in each well was removed and washed with PBS. The culture supernatant of the selected clones (100 µl/well) was added and reacted at 37° C. for one hour. The reacted product was washed with PBS, and a rabbit anti-cp3 antibody (MBL) that had been 5000-fold diluted with 0.05% Tween/PBS was added (100 µl/well) and reacted at 37° C. for one hour. The mixture was washed with PBS, and an HRP labeled goat anti-rabbit IgG antibody (MBL) that had been 2000-fold diluted with 0.05% Tween/PBS was added (100 µl/well) and reacted at 37° C. for one hour. The reacted product was washed with PBS and a substrate solution (100 µl/well) was added. 2N sulfuric acid (100 µl/well) was added to stop the reaction and the absorbance at 492 nm was measured by using a plate reader (Wako Pure Chemical, SUNRISE Remote). The results of ELISA using HER1 as an antigen is show in FIG. 85. As is apparent from the graph of FIG. 85, a large number of monoclonal antibodies to HER1 were obtained.

20. Newly Obtained Antibodies

By using the classifying method and identification method of the present invention, it was possible to obtain the following antibodies successfully.

(1) Antibody to C1qR 070-016 antibody (a) Amino Acid Sequence

SEQ ID NO: 451 (VH); SEQ ID NO: (VH CDR1) 452; SEQ ID NO: 453 (VH CDR2); SEQ ID NO: 454 (VH CDR3),

SEQ ID NO: 455 (VL); SEQ ID NO: (VL CDR1) 456; SEQ ID NO: 457 (VL CDR2); and SEQ ID NO: 458(VL CDR3)
(b) Base Sequence
SEQ ID NO: 843 (VH); and SEQ ID NO: 844 (VL)
(2) Antibody to CD44
064-003 antibody
(a) Amino Acid Sequence
SEQ ID NO: 459 (VH); SEQ ID NO: 460 (VH CDR1); SEQ ID NO: 461 (VH CDR2); SEQ ID NO: 462 (VH CDR3); SEQ ID NO: 463 (VL); SEQ ID NO: 464 (VL CDR1); SEQ ID NO: 465 (VL CDR2); and SEQ ID NO: 466 (VL CDR3)
(b) Base Sequence
SEQ ID NO: 845 (VH); and SEQ ID NO: 846(VL)
(3) Antibody to CD73
067-213 antibody
(a) Amino Acid Sequence
SEQ ID NO: 467 (VH); SEQ ID NO: 468 (VH CDR1); SEQ ID NO: 469 (VH CDR2); SEQ ID NO: 470 (VH CDR3); SEQ ID NO: 471 (VL); SEQ ID NO: 472 (VL CDR1); SEQ ID NO: 473 (VL CDR2); and SEQ ID NO: 474 (VL CDR3)
(b) Base Sequence
SEQ ID NO: 847 (VH); and SEQ ID NO: 848 (VL)
(4) Antibody to EpCAM
067-153 antibody
(a) Amino Acid Sequence
SEQ ID NO: 475 (VH); SEQ ID NO: 476 (VH CDR1); SEQ ID NO: 477 (VH CDR2); SEQ ID NO: 478 (VH CDR3); SEQ ID NO: 479 (VL); SEQ ID NO: 480 (VL CDR1); SEQ ID NO: 481 (VL CDR2); and SEQ ID NO: 482 (VL CDR3)
(b) Base Sequence
SEQ ID NO: 849 (VH); and SEQ ID NO: 850 (VL)
(5) Antibody to HER1
048-040 antibody
(a) Amino Acid Sequence
SEQ ID NO: 483 (VH); SEQ ID NO: 484 (VH CDR1); SEQ ID NO: 485 (VH CDR2); SEQ ID NO: 486 (VH CDR3); SEQ ID NO: 487 (VL); SEQ ID NO: 488 (VL CDR1); SEQ ID NO: 489 (VL CDR2); and SEQ ID NO: 490 (VL CDR3)
(b) Base Sequence
SEQ ID NO: 851 (VH); and SEQ ID NO: 852 (VL)
054-101 antibody
(a) Amino Acid Sequence
SEQ ID NO: 491 (VH); SEQ ID NO: 492 (VH CDR1); SEQ ID NO: 493 (VH CDR2); SEQ ID NO: 494 (VH CDR3); SEQ ID NO: 495 (VL); SEQ ID NO: 496 (VL CDR1); SEQ ID NO: 497 (VL CDR2); and SEQ ID NO: 498 (VL CDR3)
(b) Base Sequence
SEQ ID NO: 853(VH); and SEQ ID NO: 854(VL) 055-147 antibody
(a) Amino Acid Sequence
SEQ ID NO: 499 (VH); SEQ ID NO: 500 (VH CDR1); SEQ ID NO: 501 (VH CDR2); SEQ ID NO: 502 (VH CDR3); SEQ ID NO: 503 (VL); SEQ ID NO: 504 (VL CDR1); SEQ ID NO: 505 (VL CDR2); and SEQ ID NO: 506 (VL CDR3)
(b) Base Sequence
SEQ ID NO: 855(VH); and SEQ ID NO: 856(VL) 059-173 antibody
(a) Amino Acid Sequence
SEQ ID NO: 507 (VH); SEQ ID NO: 508 (VH CDR1); SEQ ID NO: 509 (VH CDR2); SEQ ID NO: 510 (VH CDR3); SEQ ID NO: 511 (VL); SEQ ID NO: 512 (VL CDR1); SEQ ID NO: 513 (VL CDR2); and SEQ ID NO: 514 (VL CDR3)
(b) Base Sequence
SEQ ID NO: 857(VH); and SEQ ID NO: 858(VL)
067-149 antibody
(a) Amino Acid Sequence
SEQ ID NO: 515 (VH); SEQ ID NO: 516 (VH CDR1); SEQ ID NO: 517 (VH CDR2); SEQ ID NO: 518 (VH CDR3); SEQ ID NO: 519 (VL); SEQ ID NO: 520 (VL CDR1); SEQ ID NO: 521 (VL CDR2); and SEQ ID NO: 522 (VL CDR3)
(b) Base Sequence
SEQ ID NO: 859(VH); and SEQ ID NO: 860(VL)
067-176 antibody
(a) Amino Acid Sequence
SEQ ID NO: 523 (VH); SEQ ID NO: 524 (VH CDR1); SEQ ID NO: 525 (VH CDR2); SEQ ID NO: 526 (VH CDR3); SEQ ID NO: 527 (VL); SEQ ID NO: 528 (VL CDR1); SEQ ID NO: 529 (VL CDR2); and SEQ ID NO: 530 (VL CDR3)
(b) Base Sequence
SEQ ID NO: 861(VH); and SEQ ID NO: 862(VL)
(6) Antibody to HER2
015-044 antibody
(a) Amino Acid Sequence
SEQ ID NO: 531 (VH); SEQ ID NO: 532 (VH CDR1); SEQ ID NO: 533 (VH CDR2); SEQ ID NO: 534 (VH CDR3); SEQ ID NO: 535 (VL); SEQ ID NO: 536 (VL CDR1); SEQ ID NO: 537 (VL CDR2); and SEQ ID NO: 538 (VL CDR3)
(b) Base Sequence
SEQ ID NO: 863(VH); and SEQ ID NO: 864(VL)
015-102 antibody
(a) Amino Acid Sequence
SEQ ID NO: 539 (VH); SEQ ID NO: 540 (VH CDR1); SEQ ID NO: 541 (VH CDR2); SEQ ID NO: 542 (VH CDR3); SEQ ID NO: 543 (VL); SEQ ID NO: 544 (VL CDR1); SEQ ID NO: 545 (VL CDR2); and SEQ ID NO: 546 (VL CDR3)
(b) Base Sequence
SEQ ID NO: 865 (VH); and SEQ ID NO: 866 (VL) 015-136 antibody
(a) Amino Acid Sequence
SEQ ID NO: 547 (VH); SEQ ID NO: 548 (VH CDR1); SEQ ID NO: 549 (VH CDR2); SEQ ID NO: 550 (VH CDR3); SEQ ID NO: 551 (VL); SEQ ID NO: 552 (VL CDR1); SEQ ID NO: 553 (VL CDR2); and SEQ ID NO: 554 (VL CDR3)
(b) Base Sequence
SEQ ID NO: 867 (VH); SEQ ID NO: 868 (VL)
015-143 antibody
(a) Amino Acid Sequence
SEQ ID NO: 555 (VH); SEQ ID NO: 556 (VH CDR1); SEQ ID NO: 557 (VH CDR2); SEQ ID NO: 558 (VH CDR3); SEQ ID NO: 559 (VL); SEQ ID NO: 560 (VL CDR1); SEQ ID NO: 561 (VL CDR2); SEQ ID NO: 562 (VL CDR3)
(b) Base Sequence
SEQ ID NO: 869 (VH); SEQ ID NO: 870 (VL)
015-209 antibody
(a) Amino Acid Sequence
SEQ ID NO: 563 (VH); SEQ ID NO: 564 (VH CDR1); SEQ ID NO: 565 (VH CDR2); SEQ ID NO: 566 (VH CDR3); SEQ ID NO: 567 (VL); SEQ ID NO: 568 (VL CDR1); SEQ ID NO: 569 (VL CDR2); SEQ ID NO: 570 (VL CDR3)
(b) Base Sequence
SEQ ID NO: 871 (VH); SEQ ID NO: 872 (VL)
039-016 antibody
(a) Amino Acid Sequence
SEQ ID NO: 571 (VH); SEQ ID NO: 572 (VH CDR1); SEQ ID NO: 573 (VH CDR2); SEQ ID NO: 574 (VH CDR3); SEQ ID NO: 575 (VL); SEQ ID NO: 576 (VL CDR1); SEQ ID NO: 577 (VL CDR2); SEQ ID NO: 578 (VL CDR3)
(b) Base Sequence
SEQ ID NO: 873 (VH); and SEQ ID NO: 874 (VL)
053-216 antibody
(a) Amino Acid Sequence
SEQ ID NO: 579 (VH); SEQ ID NO: 580 (VH CDR1); SEQ ID NO: 581 (VH CDR2); SEQ ID NO: 582 (VH CDR3);

SEQ ID NO: 583 (VL); SEQ ID NO: 584 (VL CDR1); SEQ ID NO: 585 (VL CDR2); SEQ ID NO: 586 (VL CDR3)
(b) Base Sequence
SEQ ID NO: 875 (VH); SEQ ID NO: 876 (VL)
075-024 antibody
(a) Amino Acid Sequence
SEQ ID NO: 587 (VH); SEQ ID NO: 588 (VH CDR1); SEQ ID NO: 589 (VH CDR2); SEQ ID NO: 590 (VH CDR3); SEQ ID NO: 591 (VL); SEQ ID NO: 592 (VL CDR1); SEQ ID NO: 593 (VL CDR2); SEQ ID NO: 594 (VL CDR3)
(b) Base Sequence
SEQ ID NO: 877 (VH); SEQ ID NO: 878 (VL)
075-110 antibody
(a) Amino Acid Sequence
SEQ ID NO: 595 (VH); SEQ ID NO: 596 (VH CDR1); SEQ ID NO: 597 (VH CDR2); SEQ ID NO: 598 (VH CDR3); SEQ ID NO: 599 (VL); SEQ ID NO: 600 (VL CDR1); SEQ ID NO: 601 (VL CDR2); SEQ ID NO: 602 (VL CDR3)
(b) Base Sequence
SEQ ID NO: 879 (VH); SEQ ID NO: 880 (VL)
086-032 antibody
(a) Amino Acid Sequence
SEQ ID NO: 603 (VH); SEQ ID NO: 604 (VH CDR1); SEQ ID NO: 605 (VH CDR2); SEQ ID NO: 606 (VH CDR3); SEQ ID NO: 607 (VL); SEQ ID NO: 608 (VL CDR1); SEQ ID NO: 609 (VL CDR2); SEQ ID NO: 610 (VL CDR3)
(b) Base Sequence
SEQ ID NO: 881 (VH); SEQ ID NO: 882 (VL)
086-035 antibody
(a) Amino Acid Sequence
SEQ ID NO: 611 (VH); SEQ ID NO: 612 (VH CDR1); SEQ ID NO: 613 (VH CDR2); SEQ ID NO: 614 (VH CDR3); SEQ ID NO: 615 (VL); SEQ ID NO: 616 (VL CDR1); SEQ ID NO: 617 (VL CDR2); SEQ ID NO: 618 (VL CDR3)
(b) Base Sequence
SEQ ID NO: 883 (VH); SEQ ID NO: 884 (VL)
086-036 antibody
(a) Amino Acid Sequence
SEQ ID NO: 619 (VH); SEQ ID NO: 620 (VH CDR1); SEQ ID NO: 621 (VH CDR2); SEQ ID NO: 622 (VH CDR3); SEQ ID NO: 623 (VL); SEQ ID NO: 624 (VL CDR1); SEQ ID NO: 625 (VL CDR2); SEQ ID NO: 626 (VL CDR3)
(b) Base Sequence
SEQ ID NO: 885 (VH); SEQ ID NO: 886 (VL)
086-061 antibody
(a) Amino Acid Sequence
SEQ ID NO: 627 (VH); SEQ ID NO: 628 (VH CDR1); SEQ ID NO: 629 (VH CDR2); SEQ ID NO: 630 (VH CDR3); SEQ ID NO: 631 (VL); SEQ ID NO: 632 (VL CDR1); SEQ ID NO: 633 (VL CDR2); SEQ ID NO: 634 (VL CDR3)
(b) Base Sequence
SEQ ID NO: 887 (VH); SEQ ID NO: 888 (VL)
086-138 antibody
(a) Amino Acid Sequence
SEQ ID NO: 635 (VH); SEQ ID NO: 636 (VH CDR1); SEQ ID NO: 637 (VH CDR2); SEQ ID NO: 638 (VH CDR3); SEQ ID NO: 639 (VL); SEQ ID NO: 640 (VL CDR1); SEQ ID NO: 641 (VL CDR2); SEQ ID NO: 642 (VL CDR3)
(b) Base Sequence
SEQ ID NO: 889 (VH); SEQ ID NO: 890 (VL)
086-182 antibody
(a) Amino Acid Sequence
SEQ ID NO: 643 (VH); SEQ ID NO: 644 (VH CDR1); SEQ ID NO: 645 (VH CDR2); SEQ ID NO: 646 (VH CDR3); SEQ ID NO: 647 (VL); SEQ ID NO: 648 (VL CDR1); SEQ ID NO: 649 (VL CDR2); SEQ ID NO: 650 (VL CDR3)
(b) Base Sequence
SEQ ID NO: 891 (VH); SEQ ID NO: 892 (VL)
(7) Antibody to HGFR
067-126 antibody
(a) Amino Acid Sequence
SEQ ID NO: 651 (VH); SEQ ID NO: 652 (VH CDR1); SEQ ID NO: 653 (VH CDR2); SEQ ID NO: 654 (VH CDR3); SEQ ID NO: 655 (VL); SEQ ID NO: 656 (VL CDR1); SEQ ID NO: 657 (VL CDR2); SEQ ID NO: 658 (VL CDR3)
(b) Base Sequence
SEQ ID NO: 893 (VH); SEQ ID NO: 894 (VL)
067-133 antibody
(a) Amino Acid Sequence
SEQ ID NO: 659 (VH); SEQ ID NO: 660 (VH CDR1); SEQ ID NO: 661 (VH CDR2); SEQ ID NO: 662 (VH CDR3); SEQ ID NO: 663 (VL); SEQ ID NO: 664 (VL CDR1); SEQ ID NO: 665 (VL CDR2); SEQ ID NO: 666 (VL CDR3)
(b) Base Sequence
SEQ ID NO: 895 (VH); SEQ ID NO: 896 (VL)
067-287 antibody
(a) Amino Acid Sequence
SEQ ID NO: 667 (VH); SEQ ID NO: 668 (VH CDR1); SEQ ID NO: 669 (VH CDR2); SEQ ID NO: 670 (VH CDR3); SEQ ID NO: 671 (VL); SEQ ID NO: 672 (VL CDR1); SEQ ID NO: 673 (VL CDR2); SEQ ID NO: 674 (VL CDR3)
(b) Base Sequence
SEQ ID NO: 897 (VH); SEQ ID NO: 898 (VL)
(8) Antibody to ITGA3
064-002 antibody
(a) Amino Acid Sequence
SEQ ID NO: 675 (VH); SEQ ID NO: 676 (VH CDR1); SEQ ID NO: 677 (VH CDR2); SEQ ID NO: 678 (VH CDR3); SEQ ID NO: 679 (VL); SEQ ID NO: 680 (VL CDR1); SEQ ID NO: 681 (VL CDR2); SEQ ID NO: 682 (VL CDR3)
(b) Base Sequence
SEQ ID NO: 899 (VH); SEQ ID NO: 900 (VL)
064-006 antibody
(a) Amino Acid Sequence
SEQ ID NO: 683 (VH); SEQ ID NO: 684 (VH CDR1); SEQ ID NO: 685 (VH CDR2); SEQ ID NO: 686 (VH CDR3); SEQ ID NO: 687 (VL); SEQ ID NO: 688 (VL CDR1); SEQ ID NO: 689 (VL CDR2); SEQ ID NO: 690 (VL CDR3)
(b) Base Sequence
SEQ ID NO: 901 (VH); SEQ ID NO: 902 (VL)
064-012a antibody
(a) Amino Acid Sequence
SEQ ID NO: 691 (VH); SEQ ID NO: 692 (VH CDR1); SEQ ID NO: 693 (VH CDR2); SEQ ID NO: 694 (VH CDR3); SEQ ID NO: 695 (VL); SEQ ID NO: 696 (VL CDR1); SEQ ID NO: 697 (VL CDR2); SEQ ID NO: 698 (VL CDR3)
(b) Base Sequence
SEQ ID NO: 903 (VH); SEQ ID NO: 904 (VL)
064-012b antibody
(a) Amino Acid Sequence
SEQ ID NO: 699 (VH); SEQ ID NO: 700 (VH CDR1); SEQ ID NO: 701 (VH CDR2); SEQ ID NO: 702 (VH CDR3); SEQ ID NO: 703 (VL); SEQ ID NO: 704 (VL CDR1); SEQ ID NO: 705 (VL CDR2); SEQ ID NO: 706 (VL CDR3)
(b) Base Sequence
SEQ ID NO: 905 (VH); SEQ ID NO: 906 (VL)
064-014 antibody
(a) Amino Acid Sequence
SEQ ID NO: 707 (VH); SEQ ID NO: 708 (VH CDR1); SEQ ID NO: 709 (VH CDR2); SEQ ID NO: 710 (VH CDR3);

SEQ ID NO: 711 (VL); SEQ ID NO: 712 (VL CDR1); SEQ ID NO: 713 (VL CDR2); SEQ ID NO: 714 (VL CDR3)
(b) Base Sequence
  SEQ ID NO: 907 (VH); SEQ ID NO: 908 (VL)
  064-054 antibody
(a) Amino Acid Sequence
  SEQ ID NO: 715 (VH); SEQ ID NO: 716 (VH CDR1); SEQ ID NO: 717 (VH CDR2); SEQ ID NO: 718 (VH CDR3); SEQ ID NO: 719 (VL); SEQ ID NO: 720 (VL CDR1); SEQ ID NO: 721 (VL CDR2); SEQ ID NO: 722 (VL CDR3)
(b) Base Sequence
  SEQ ID NO: 909 (VH); SEQ ID NO: 910 (VL)
  064-085 antibody
(a) Amino Acid Sequence
  SEQ ID NO: 723 (VH); SEQ ID NO: 724 (VH CDR1); SEQ ID NO: 725 (VH CDR2); SEQ ID NO: 726 (VH CDR3); SEQ ID NO: 727 (VL); SEQ ID NO: 728 (VL CDR1); SEQ ID NO: 729 (VL CDR2); SEQ ID NO: 730 (VL CDR3)
(b) Base Sequence
  SEQ ID NO: 911 (VH); SEQ ID NO: 912 (VL)
  064-093 antibody
(a) Amino Acid Sequence
  SEQ ID NO: 731 (VH); SEQ ID NO: 732 (VH CDR1); SEQ ID NO: 733 (VH CDR2); SEQ ID NO: 734 (VH CDR3); SEQ ID NO: 735 (VL); SEQ ID NO: 736 (VL CDR1); SEQ ID NO: 737 (VL CDR2); SEQ ID NO: 738 (VL CDR3)
(b) Base Sequence
  SEQ ID NO: 913 (VH); SEQ ID NO: 914 (VL)
  064-116 antibody
(a) Amino Acid Sequence
  SEQ ID NO: 739 (VH); SEQ ID NO: 740 (VH CDR1); SEQ ID NO: 741 (VH CDR2); SEQ ID NO: 742 (VH CDR3); SEQ ID NO: 743 (VL); SEQ ID NO: 744 (VL CDR1); SEQ ID NO: 745 (VL CDR2); SEQ ID NO: 746 (VL CDR3)
(b) Base Sequence
  SEQ ID NO: 915 (VH); SEQ ID NO: 916 (VL)
  065-183 antibody
(a) Amino Acid Sequence
  SEQ ID NO: 747 (VH); SEQ ID NO: 748 (VH CDR1); SEQ ID NO: 749 (VH CDR2); SEQ ID NO: 750 (VH CDR3); SEQ ID NO: 751 (VL); SEQ ID NO: 752 (VL CDR1); SEQ ID NO: 753 (VL CDR2); SEQ ID NO: 754 (VL CDR3)
(b) Base Sequence
  SEQ ID NO: 917 (VH); SEQ ID NO: 918 (VL)
  067-142 antibody
(a) Amino Acid Sequence
  SEQ ID NO: 763 (VH); SEQ ID NO: 764 (VH CDR1); SEQ ID NO: 765 (VH CDR2); SEQ ID NO: 766 (VH CDR3); SEQ ID NO: 767 (VL); SEQ ID NO: 768 (VL CDR1); SEQ ID NO: 769 (VL CDR2); SEQ ID NO: 770 (VL CDR3)
(b) Base Sequence
  SEQ ID NO: 921 (VH); SEQ ID NO: 922 (VL)
  068-007 antibody
(a) Amino Acid Sequence
  SEQ ID NO: 771 (VH); SEQ ID NO: 772 (VH CDR1); SEQ ID NO: 773 (VH CDR2); SEQ ID NO: 774 (VH CDR3); SEQ ID NO: 775 (VL); SEQ ID NO: 776 (VL CDR1); SEQ ID NO: 777 (VL CDR2); SEQ ID NO: 778 (VL CDR3)
(b) Base Sequence
  SEQ ID NO: 923 (VH); SEQ ID NO: 924 (VL)
(9) Antibody to ALCAM
  029-143 antibody
(a) Amino Acid Sequence
  SEQ ID NO: 779 (VH); SEQ ID NO: 780 (VH CDR1); SEQ ID NO: 781 (VH CDR2); SEQ ID NO 782 (VH CDR3); SEQ ID NO: 783 (VL); SEQ ID NO: 784 (VL CDR1); SEQ ID NO: 785 (VL CDR2); SEQ ID NO: 786 (VL CDR3)
(b) Base Sequence
  SEQ ID NO: 925 (VH); SEQ ID NO: 926 (VL)
  045-134 antibody
(a) Amino Acid Sequence
  SEQ ID NO: 787 (VH); SEQ ID NO: 788 (VH CDR1); SEQ ID NO: 789 (VH CDR2); SEQ ID NO: 790 (VH CDR3); SEQ ID NO: 791 (VL); SEQ ID NO: 792 (VL CDR1); SEQ ID NO: 793 (VL CDR2); SEQ ID NO: 794 (VL CDR3)
(b) Base Sequence
  SEQ ID NO: 927 (VH); SEQ ID NO: 928 (VL)
  062-101 antibody
(a) Amino Acid Sequence
  SEQ ID NO: 795 (VH); SEQ ID NO: 796 (VH CDR1); SEQ ID NO: 797 (VH CDR2); SEQ ID NO: 798 (VH CDR3); SEQ ID NO: 799 (VL); SEQ ID NO: 800 (VL CDR1); SEQ ID NO: 801 (VL CDR2); SEQ ID NO: 802 (VL CDR3)
(b) Base Sequence
  SEQ ID NO: 929 (VH); SEQ ID NO: 930 (VL)
  062-109 antibody
(a) Amino Acid Sequence
  SEQ ID NO: 803 (VH); SEQ ID NO: 804 (VH CDR1); SEQ ID NO: 805 (VH CDR2); SEQ ID NO: 806 (VH CDR3); SEQ ID NO: 807 (VL); SEQ ID NO: 808 (VL CDR1); SEQ ID NO: 809 (VL CDR2); SEQ ID NO: 810 (VL CDR3)
(b) Base Sequence
  SEQ ID NO: 931 (VH); SEQ ID NO: 932 (VL)
  084-103 antibody
(a) Amino Acid Sequence
  SEQ ID NO: 811 (VH); SEQ ID NO: 812 (VH CDR1); SEQ ID NO: 813 (VH CDR2); SEQ ID NO: 814 (VH CDR3); SEQ ID NO: 815 (VL); SEQ ID NO: 816 (VL CDR1); SEQ ID NO: 817 (VL CDR2); SEQ ID NO: 818 (VL CDR3)
(b) Base Sequence
  SEQ ID NO: 933 (VH); SEQ ID NO: 934 (VL)
  052-274 antibody
(a) Amino Acid Sequence
  SEQ ID NO: 819 (VH); SEQ ID NO: 820 (VH CDR1); SEQ ID NO: 821 (VH CDR2); SEQ ID NO: 822 (VH CDR3); SEQ ID NO: 823 (VL); SEQ ID NO: 824 (VL CDR1); SEQ ID NO: 825 (VL CDR2); SEQ ID NO: 826 (VL CDR3)
(b) Base Sequence
  SEQ ID NO: 935 (VH); SEQ ID NO: 936 (VL)
  029-067 antibody
(a) Amino Acid Sequence
  SEQ ID NO: 827 (VH); SEQ ID NO: 828 (VH CDR1); SEQ ID NO: 829 (VH CDR2); SEQ ID NO: 830 (VH CDR3); SEQ ID NO: 831 (VL); SEQ ID NO: 832 (VL CDR1); SEQ ID NO: 833 (VL CDR2); SEQ ID NO: 834 (VL CDR3)
(b) Base Sequence
  SEQ ID NO: 937 (VH); SEQ ID NO: 938 (VL)
  083-131 antibody
(a) Amino Acid Sequence
  SEQ ID NO: 835 (VH); SEQ ID NO: 836 (VH CDR1); SEQ ID NO: 837 (VH CDR2); SEQ ID NO: 838 (VH CDR3); SEQ ID NO: 839 (VL); SEQ ID NO: 840 (VL CDR1); SEQ ID NO: 841 (VL CDR2); SEQ ID NO: 842 (VL CDR3)
(b) Base Sequence
  SEQ ID NO: 939 (VH); SEQ ID NO: 940 (VL)
(10) Antibody to CD46
  066-069 antibody
(a) Amino Acid Sequence
  SEQ ID NO: 755 (VH); SEQ ID NO: 756 (VH CDR1); SEQ ID NO: 757 (VH CDR2); SEQ ID NO: 758 (VH CDR3);

SEQ ID NO: 759 (VL); SEQ ID NO: 760 (VL CDR1); SEQ ID NO: 761 (VL CDR2); SEQ ID NO: 762 (VL CDR3)
(b) Base Sequence
SEQ ID NO: 919 (VH); SEQ ID NO: 920 (VL)
(11) Antibody to LAR
064-044 antibody
(a) Amino Acid Sequence
SEQ ID NO: 944 (VH); SEQ ID NO: 945 (VL)
(b) Base Sequence
SEQ ID NO: 956 (VH); SEQ ID NO: 957 (VL)
065-030 antibody
(a) Amino Acid Sequence
SEQ ID NO: 946 (VH); SEQ ID NO: 947 (VL)
(b) Base Sequence
SEQ ID NO: 958 (VH); SEQ ID NO: 959 (VL)
065-358 antibody
(a) Amino Acid Sequence
SEQ ID NO: 948 (VH); SEQ ID NO: 949 (VL)
(b) Base Sequence
SEQ ID NO: 960 (VH); SEQ ID NO: 961 (VL)
066-019 antibody
(a) Amino Acid Sequence
SEQ ID NO: 950 (VH); SEQ ID NO: 951 (VL)
(b) Base Aequence
SEQ ID NO: 962 (VH); SEQ ID NO: 963 (VL)
079-085 antibody
(a) Amino Acid Sequence
SEQ ID NO: 952 (VH); SEQ ID NO: 953 (VL)
(b) Base Sequence
SEQ ID NO: 964 (VH); SEQ ID NO: 965 (VL)
(12) Antibody to BCAM
067-024 antibody
(a) Amino Acid Sequence
SEQ ID NO: 954 (VH); SEQ ID NO: 955 (VL)
(b) Base Sequence
SEQ ID NO: 966 (VH); SEQ ID NO: 967 (VL)
(13) Antibody to IgSF4
076-048 antibody
(a) Amino Acid Sequence
SEQ ID NO: 968 (VH); SEQ ID NO: 969 (VL)
(b) Base Sequence
SEQ ID NO: 970 (VH); SEQ ID NO: 971 (VL)
21. Experiment to Confirm ITGA3 Antibody From the results of the immunoprecipitation—mass spectrometry, a part of the antibody group, it was shown that the antibody included therein recognized a VLA complex. However, in a strict sense, it was not possible to determine what the antibody was, that is, whether the antigen was ITGA3 or ITGB1 or other molecules forming a complex such as CD151. Then, the antibody clones (015-003, 064-002, 064-006, 064-012, 064-014, 064-054, 064-085, 064-091, 064-093, 064-116, 065-183, 067-142, and 068-007) were subjected to RNAi in order to confirm antigens.

21-1 Experiment Procedure

ITGA3 stealth oligo RNA (400 pmol) purchased from Invitrogen and lipofect RNAi MAX (100 μl) (product of Invitrogen) were mixed with Opti-MEMI (8 ml) (product of GIBCO-BRL) and the mixture was stood still at a room temperature for 10 minutes. To this mixture, 4 ml of SKOv-3 cell solution ($2 \times 10^6$ cells) and 28 ml of RPMI1640-10% FBS were added. This mixture was planted on four 10-cm culture dishes and cultured in a $CO_2$ incubator for two days. 1% trypsin solution was allowed to act on the cultured cells so as to liberate cells. The cells were recovered in 5% BSA/PBS solution so as to produce 1 ml of cell suspension. The same experiment was carried out with respect to ITGB1. As to a group without RNAi (control group), the same experiment was carried out except that stealth oligo is not allowed to act.

To the recovered cells (50 μl), 2.5 μl of normal goat serum was added, and then primary antibody solution was added, so that the final amount was made to be 100 μl by using 5% BSA/PBS. The using amount of the primary antibody (anti-ITGA3 antibody or anti-ITGB1 antibody (mouse monoclonal antibody, product of CHEMICON)) was made to be 1 μl. As to the subjected sample (for example, 015-003 cp3 type antibody), 7 μl of 10-fold concentrated supernatant was used.

Next, the mixture was stood still at a room temperature for 10 minutes and then subjected to centrifugation. The supernatant was discarded, followed by washing with 5% BSA/PBS (200 μl). Next, as to the sample 015-003cp3 type antibody, 100 μl of anti-cp3 mouse monoclonal antibody (MBL), which had been diluted with 5% BSA/PBS so that the concentration became 5 μg/ml, was added. The mixture was stood still at a room temperature for 10 minutes. After centrifugation, the supernatant was discarded, followed by washing with 5% BSA/PBS (200 μl). Then, ALEXA488 labeled anti-mouse IgG goat antibody (100 μl), which had been 1000-folded diluted with 5% BSA/PBS, was reacted. The reacted product was stood still at a room temperature for 10 minutes and then subjected to centrifugation. The supernatant was discarded, followed by washing with 5% BSA/PBS (200 μl). The thus obtained cells were suspended in 50 μl of OptilyseB (BECKMAN COULTER). This was stood still for 10 minutes, and then 600 μl of PBS was added to be diluted. Subsequently, the diluted product was treated with Cell-Strainer (BD Falcon) and subjected to measurement using FACS Caliber (BECKMAN COULTER).

21-2 Results

Figure 86:
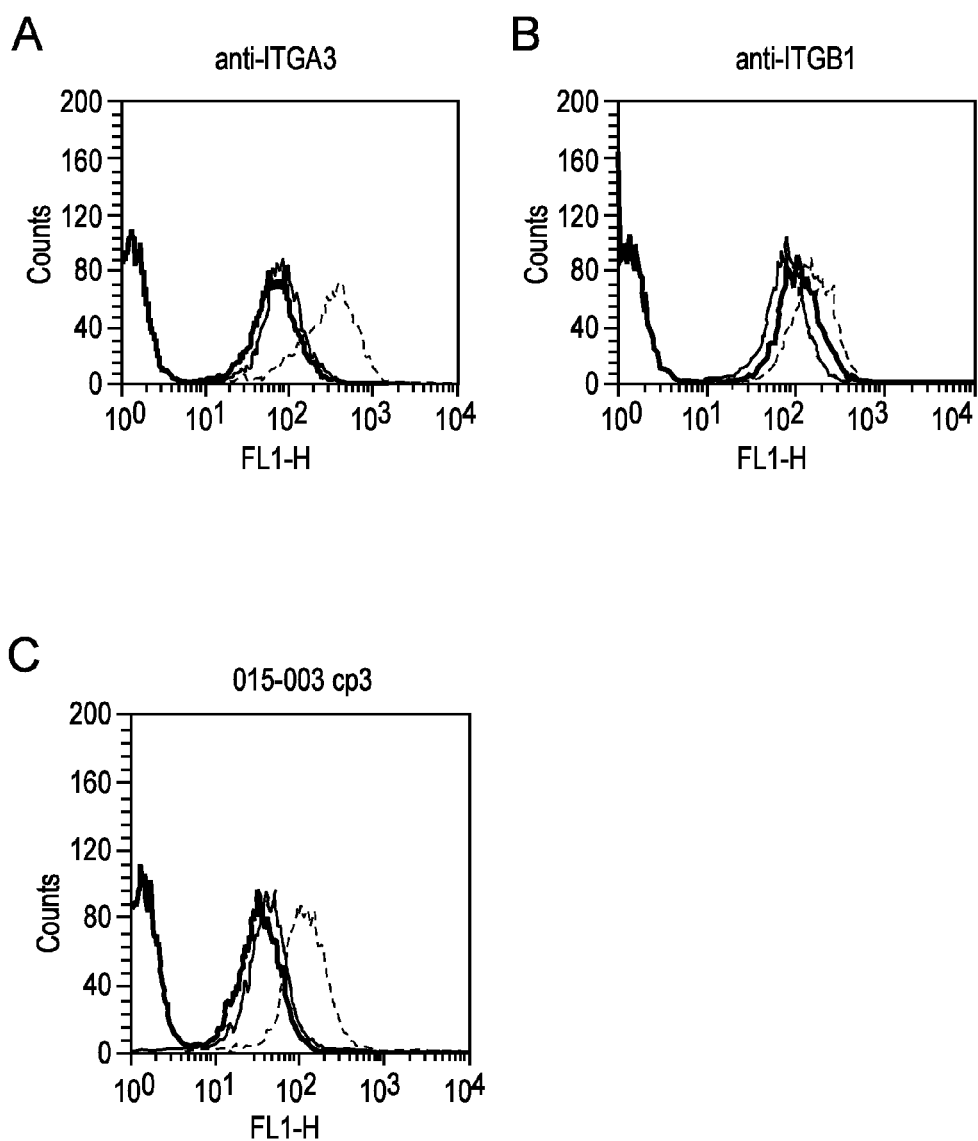
FIG. 86 shows a RNAi effect on SKOv-3 cells. A: anti-ITGA3 antibody, B: anti-ITGB1 antibody, C: 015-003cp3 antibody. Broken line: no RNAi, solid line: ITGA3 RNAi, light-colored solid line: ITGB1 RNAi, gray: and no primary antibody.

The results of the above-mentioned RNAi experiment are shown in FIG. 86. It is shown that A (results of FCM using anti-ITGA3 antibody) and B (results of FCM using anti-ITGB1 antibody) have different peak patterns. The samples (015-003, 064-002, 064-006, 064-012, 064-014, 064-054, 064-085, 064-091, 064-093, 064-116, 065-183, 067-142, and 068-007) show the peak patterns (C) similar to A. From this result, it is confirmed that antigen recognized by these antibody clones is ITGA3.

When the same RNAi experiment is carried out in each antibody obtained as an anti-HER1 antibody, an anti-HER2 antibody, an anti-HGFR antibody, an anti-IgSF4 antibody, an anti-EpCAM antibody, an anti-CD147 antibody, an anti-CD166 antibody, or anti-MCP antibody, antigen is not wrong, and it is confirmed that the method (method using a panel, three-dimensional ELISA)) of the present invention is useful.

22. Cancer Tissue Specificity of Each Antibody Clone

When the immunostaining property of the obtained antibody clones with respect to clinical cancer specimens were examined by the same method as described in the above column 11, results shown in FIG. 87 were obtained. These antibody clones are useful for studying and diagnosing the corresponding cancers.

Furthermore, clinical specimens in different stages in some cancers were prepared and the immunostaining property of the antibody clones with respect to the specimens was obtained. As a result, some antibody clones showed the staining property specific to stages in addition to the staining property specific to cancer (see FIG. 88). Thus, in the actual clinical tissues, there are differences in the reactivity to each antibody clone even if the tissue is from the same cancer or in the same grade of malignancy. This results show that the use of the antibody set provided by the present invention enables new tailor-maid diagnosis in cancers to be carried out and diagnosis that is more detail than conventional criterion to be carried out. In other words, it is shown that staging of cancer and re-classification of pathologic conditions can be realized. On the other hand, the staging of cancer and the re-classification of pathologic conditions by using the antibody set are useful for determining a treatment plan. Furthermore, antibodies recognized to have specific reactivity can be useful as antibodies for treatment and useful as a tool for drug screening. Thus, the antibody set provided by the present invention can realize not only tailor-made diagnosis of cancers but also tailor-made treatment of cancers. Thus, the antibody set provides extremely great values and significance.

INDUSTRIAL APPLICABILITY

The present invention provides a method of classifying a plurality of antibodies to cell surface antigens rapidly. Also, the present invention provides a method of rapidly identifying an antigen to an antibody. The use of these methods makes it possible to obtain an antibody useful for treatment and diagnosis of cancers, or study of the onset mechanism of cancers, and the like. Furthermore, when the classifying method and the identification method of an antigen of the present invention are used, a panel on which a useful antibody set and its characteristics are displayed can be provided, which is expected to greatly contribute to tailor-made medicine.

On the other hand, the present invention provides antibodies recognizing antigens expressing in a cancer-specific manner. Such antibodies are expected to be used as antibody for treatment, antibody for diagnosis, antibody for study, and the like, which target cancer cells specifically expressing cancer surface membrane protein recognized by the antibodies.

The present invention is not limited only to the description of the above embodiments. A variety of modifications which are within the scopes of the following claims and which are achieved easily by a person skilled in the art are included in the present invention.

Contents of the theses, Publication of Patent Applications, Patent Publications, and other published documents referred to in this specification are herein incorporated by reference in its entity.

SEQUENCE LISTING

```
<160> NUMBER OF SEQ ID NOS: 971

<210> SEQ ID NO 1
<211> LENGTH: 120
<212> TYPE: PRT
<213> ORGANISM: Homo sapiens

<400> SEQUENCE: 1

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Pro Trp Glu Leu Leu Ala Phe Asp Ile Trp Gly Gln
            100                 105                 110

Gly Thr Met Val Thr Val Ser Arg
        115                 120

<210> SEQ ID NO 2
<211> LENGTH: 7
<212> TYPE: PRT
<213> ORGANISM: Homo sapiens

<400> SEQUENCE: 2

Ser Gly Gly Tyr Tyr Trp Ser
1               5

<210> SEQ ID NO 3
<211> LENGTH: 16
<212> TYPE: PRT
<213> ORGANISM: Homo sapiens
```

```
<400> SEQUENCE: 3

Tyr Ile Tyr Tyr Ser Gly Ser Thr Tyr Tyr Asn Pro Ser Leu Lys Ser
1               5                   10                  15

<210> SEQ ID NO 4
<211> LENGTH: 10
<212> TYPE: PRT
<213> ORGANISM: Homo sapiens

<400> SEQUENCE: 4

Thr Pro Trp Glu Leu Leu Ala Phe Asp Ile
1               5                   10

<210> SEQ ID NO 5
<211> LENGTH: 109
<212> TYPE: PRT
<213> ORGANISM: Homo sapiens

<400> SEQUENCE: 5

Ser Tyr Glu Leu Thr Gln Pro Pro Ser Val Ser Val Ala Pro Gly Lys
1               5                   10                  15

Thr Thr Arg Ile Thr Cys Gly Gly Asn Asn Ile Gly Ser Lys Ser Ala
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly
            100                 105

<210> SEQ ID NO 6
<211> LENGTH: 11
<212> TYPE: PRT
<213> ORGANISM: Homo sapiens

<400> SEQUENCE: 6

Gly Gly Asn Asn Ile Gly Ser Lys Ser Ala His
1               5                   10

<210> SEQ ID NO 7
<211> LENGTH: 7
<212> TYPE: PRT
<213> ORGANISM: Homo sapiens

<400> SEQUENCE: 7

Tyr Asp Ser Asp Arg Pro Ser
1               5

<210> SEQ ID NO 8
<211> LENGTH: 9
<212> TYPE: PRT
<213> ORGANISM: Homo sapiens

<400> SEQUENCE: 8

Gln Val Trp Asp Ser Ser Ser Asp His
1               5
```

```
<210> SEQ ID NO 9
<211> LENGTH: 126
<212> TYPE: PRT
<213> ORGANISM: Homo sapiens

<400> SEQUENCE: 9

Gln Val Gln Leu Val Gln Ser Gly Ala Glu Val Lys Lys Thr Gly Ser
1               5                   10                  15

Ser Val Lys Val Ser Cys Lys Ala Ser Gly Gly Ser Phe Ser Ser Ser
            20                  25                  30

Ala Ile Ser Trp Val Arg Gln Ala Pro Gly His Gly Leu Glu Trp Leu
        35                  40                  45

Gly Gly Ile Ile Pro Thr Phe Gly Thr Pro Asn His Ala Gln Lys Phe
    50                  55                  60

Gln Gly Arg Val Thr Ile Thr Ala Asp Glu Ser Thr Gly Thr Ala Tyr
65                  70                  75                  80

Met Glu Leu Ser Gly Leu Arg Ser Glu Asp Thr Ala Val Tyr Tyr Cys
                85                  90                  95

Ala Arg Ala His Cys Gly Gly Gly Arg Cys Tyr Asp Tyr Thr Asp Ala
            100                 105                 110

Phe His Phe Trp Gly Gln Gly Thr Met Val Thr Val Ser Arg
        115                 120                 125

<210> SEQ ID NO 10
<211> LENGTH: 5
<212> TYPE: PRT
<213> ORGANISM: Homo sapiens

<400> SEQUENCE: 10

Ser Ser Ala Ile Ser
1               5

<210> SEQ ID NO 11
<211> LENGTH: 17
<212> TYPE: PRT
<213> ORGANISM: Homo sapiens

<400> SEQUENCE: 11

Gly Ile Ile Pro Thr Phe Gly Thr Pro Asn His Ala Gln Lys Phe Gln
1               5                   10                  15

Gly

<210> SEQ ID NO 12
<211> LENGTH: 17
<212> TYPE: PRT
<213> ORGANISM: Homo sapiens

<400> SEQUENCE: 12

Ala His Cys Gly Gly Gly Arg Cys Tyr Asp Tyr Thr Asp Ala Phe His
1               5                   10                  15

Phe

<210> SEQ ID NO 13
<211> LENGTH: 109
<212> TYPE: PRT
<213> ORGANISM: Homo sapiens

<400> SEQUENCE: 13

Ser Tyr Glu Leu Thr Gln Pro Pro Ser Val Ser Val Ala Pro Gly Lys
1               5                   10                  15
```

```
Thr Ala Arg Ile Thr Cys Gly Gly Asp Asn Ile Gly Asn Arg Ser Val
            20                  25                  30

His Trp Tyr Gln Gln Lys Pro Gly Gln Ala Pro Val Leu Leu Ile Tyr
        35                  40                  45

Tyr Asp Ser Asp Arg Pro Ser Gly Ile Pro Lys Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Thr Ser Asp His
                85                  90                  95

Val Val Phe Gly Gly Gly Thr Lys Leu Thr Val Leu Arg
            100                 105
```

<210> SEQ ID NO 14
<211> LENGTH: 11
<212> TYPE: PRT
<213> ORGANISM: Homo sapiens

<400> SEQUENCE: 14

```
Gly Gly Asp Asn Ile Gly Asn Arg Ser Val His
 1               5                  10
```

<210> SEQ ID NO 15
<211> LENGTH: 7
<212> TYPE: PRT
<213> ORGANISM: Homo sapiens

<400> SEQUENCE: 15

```
Tyr Asp Ser Asp Arg Pro Ser
 1               5
```

<210> SEQ ID NO 16
<211> LENGTH: 9
<212> TYPE: PRT
<213> ORGANISM: Homo sapiens

<400> SEQUENCE: 16

```
Gln Val Trp Asp Ser Thr Ser Asp His
 1               5
```

<210> SEQ ID NO 17
<211> LENGTH: 120
<212> TYPE: PRT
<213> ORGANISM: Homo sapiens

<400> SEQUENCE: 17

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Leu Pro Met Val Thr Met Ser Phe Asp Tyr Trp Gly Gln
            100                 105                 110
```

-continued

```
Gly Thr Leu Val Thr Val Ser Arg
        115                 120

<210> SEQ ID NO 18
<211> LENGTH: 7
<212> TYPE: PRT
<213> ORGANISM: Homo sapiens

<400> SEQUENCE: 18

Ser Ser Ser Tyr Tyr Trp Gly
1               5

<210> SEQ ID NO 19
<211> LENGTH: 16
<212> TYPE: PRT
<213> ORGANISM: Homo sapiens

<400> SEQUENCE: 19

Ser Ile Tyr Tyr Ser Gly Ser Thr Tyr Tyr Asn Pro Ser Leu Lys Ser
1               5                   10                  15

<210> SEQ ID NO 20
<211> LENGTH: 10
<212> TYPE: PRT
<213> ORGANISM: Homo sapiens

<400> SEQUENCE: 20

Leu Pro Met Val Thr Met Ser Phe Asp Tyr
1               5                   10

<210> SEQ ID NO 21
<211> LENGTH: 109
<212> TYPE: PRT
<213> ORGANISM: Homo sapiens

<400> SEQUENCE: 21

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 22
<211> LENGTH: 11
<212> TYPE: PRT
<213> ORGANISM: Homo sapiens

<400> SEQUENCE: 22

Gly Gly Asn Asn Ile Gly Ser Lys Ser Val His
1               5                   10

<210> SEQ ID NO 23
```

```
<211> LENGTH: 7
<212> TYPE: PRT
<213> ORGANISM: Homo sapiens

<400> SEQUENCE: 23

Tyr Asp Ser Asp Arg Pro Ser
1               5

<210> SEQ ID NO 24
<211> LENGTH: 9
<212> TYPE: PRT
<213> ORGANISM: Homo sapiens

<400> SEQUENCE: 24

Gln Val Trp Asp Ser Ser Ser Asp His
1               5

<210> SEQ ID NO 25
<211> LENGTH: 121
<212> TYPE: PRT
<213> ORGANISM: Homo sapiens

<400> SEQUENCE: 25

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Thr Leu Ser Tyr Ser Ser Trp Phe Asp Tyr Trp Gly
            100                 105                 110

Gln Gly Thr Leu Val Thr Val Ser Arg
            115                 120

<210> SEQ ID NO 26
<211> LENGTH: 5
<212> TYPE: PRT
<213> ORGANISM: Homo sapiens

<400> SEQUENCE: 26

Ser Tyr Trp Ile Gly
1               5

<210> SEQ ID NO 27
<211> LENGTH: 17
<212> TYPE: PRT
<213> ORGANISM: Homo sapiens

<400> SEQUENCE: 27

Ile Ile Tyr Pro Gly Asp Ser Asp Thr Arg Tyr Ser Pro Ser Phe Gln
1               5                   10                  15

Gly

<210> SEQ ID NO 28
<211> LENGTH: 12
```

```
<212> TYPE: PRT
<213> ORGANISM: Homo sapiens

<400> SEQUENCE: 28

Leu Thr Leu Ser Tyr Ser Ser Ser Trp Phe Asp Tyr
1               5                   10

<210> SEQ ID NO 29
<211> LENGTH: 111
<212> TYPE: PRT
<213> ORGANISM: Homo sapiens

<400> SEQUENCE: 29

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly
            100                 105                 110

<210> SEQ ID NO 30
<211> LENGTH: 14
<212> TYPE: PRT
<213> ORGANISM: Homo sapiens

<400> SEQUENCE: 30

Gly Leu Ser Ser Gly Ser Val Ser Thr Ser Tyr Tyr Pro Ser
1               5                   10

<210> SEQ ID NO 31
<211> LENGTH: 7
<212> TYPE: PRT
<213> ORGANISM: Homo sapiens

<400> SEQUENCE: 31

Ser Thr Asn Thr Arg Ser Ser
1               5

<210> SEQ ID NO 32
<211> LENGTH: 8
<212> TYPE: PRT
<213> ORGANISM: Homo sapiens

<400> SEQUENCE: 32

Val Leu Tyr Met Gly Ser Gly Ile
1               5

<210> SEQ ID NO 33
<211> LENGTH: 118
<212> TYPE: PRT
<213> ORGANISM: Homo sapiens

<400> SEQUENCE: 33

Gln Val Gln Leu Val Gln Ser Gly Ala Glu Val Lys Lys Pro Gly Glu
```

```
                1               5                  10                  15
Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Leu Gly Ile Gly Ala Phe Asp Ile Trp Gly Gln Gly Thr
                100                 105                 110

Thr Val Thr Val Ser Arg
        115
```

<210> SEQ ID NO 34
<211> LENGTH: 5
<212> TYPE: PRT
<213> ORGANISM: Homo sapiens

<400> SEQUENCE: 34

```
Ser Tyr Trp Ile Gly
1               5
```

<210> SEQ ID NO 35
<211> LENGTH: 17
<212> TYPE: PRT
<213> ORGANISM: Homo sapiens

<400> SEQUENCE: 35

```
Ile Ile Tyr Pro Gly Asp Ser Asp Thr Arg Tyr Ser Pro Ser Phe Gln
1               5                   10                  15

Gly
```

<210> SEQ ID NO 36
<211> LENGTH: 9
<212> TYPE: PRT
<213> ORGANISM: Homo sapiens

<400> SEQUENCE: 36

```
Leu Leu Gly Ile Gly Ala Phe Asp Ile
1               5
```

<210> SEQ ID NO 37
<211> LENGTH: 110
<212> TYPE: PRT
<213> ORGANISM: Homo sapiens

<400> SEQUENCE: 37

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
```

```
                65                  70                  75                  80
Asp Glu Ala Asp Tyr Tyr Cys Asn Ser Arg Asp Ser Ser Gly Asn His
                    85                  90                  95

His Tyr Val Phe Gly Thr Gly Thr Lys Val Thr Val Leu Gly
                100                 105                 110
```

<210> SEQ ID NO 38
<211> LENGTH: 11
<212> TYPE: PRT
<213> ORGANISM: Homo sapiens

<400> SEQUENCE: 38

```
Gln Gly Asp Ser Leu Arg Ser Tyr Tyr Ala Ser
1               5                   10
```

<210> SEQ ID NO 39
<211> LENGTH: 7
<212> TYPE: PRT
<213> ORGANISM: Homo sapiens

<400> SEQUENCE: 39

```
Gly Lys Asn Asn Arg Pro Ser
1               5
```

<210> SEQ ID NO 40
<211> LENGTH: 10
<212> TYPE: PRT
<213> ORGANISM: Homo sapiens

<400> SEQUENCE: 40

```
Asn Ser Arg Asp Ser Ser Gly Asn His His
1               5                   10
```

<210> SEQ ID NO 41
<211> LENGTH: 116
<212> TYPE: PRT
<213> ORGANISM: Homo sapiens

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Gly Ile Thr Trp Val Arg Gln Ala Pro Gly Gln Gly Leu Glu Trp Met
            35                  40                  45

Gly Trp Ile Ser Val Tyr Thr Gly Lys Thr Asn Tyr Ala Gln Lys Phe
        50                  55                  60

Gln Gly Arg Val Thr Met Thr Thr Asp Thr Ser Thr Ser Thr Ala Tyr
65                  70                  75                  80

Leu Asp Leu Arg Ser Leu Thr Ser Asp Asp Thr Ala Val Tyr Tyr Cys
                85                  90                  95

Ala Arg Gly Gly Asp His His Glu Tyr Trp Gly Gln Gly Thr Leu Val
                100                 105                 110

Thr Val Ser Arg
        115
```

<210> SEQ ID NO 42
<211> LENGTH: 5
<212> TYPE: PRT
<213> ORGANISM: Homo sapiens

```
<400> SEQUENCE: 42

Ser Tyr Gly Ile Thr
1               5

<210> SEQ ID NO 43
<211> LENGTH: 17
<212> TYPE: PRT
<213> ORGANISM: Homo sapiens

<400> SEQUENCE: 43

Trp Ile Ser Val Tyr Thr Gly Lys Thr Asn Tyr Ala Gln Lys Phe Gln
1               5                   10                  15

Gly

<210> SEQ ID NO 44
<211> LENGTH: 7
<212> TYPE: PRT
<213> ORGANISM: Homo sapiens

<400> SEQUENCE: 44

Gly Gly Asp His His Glu Tyr
1               5

<210> SEQ ID NO 45
<211> LENGTH: 107
<212> TYPE: PRT
<213> ORGANISM: Homo sapiens

<400> SEQUENCE: 45

Asn Phe Met Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Val Val
                85                  90                  95

Phe Gly Gly Gly Thr Lys Leu Thr Val Leu Gly
            100                 105

<210> SEQ ID NO 46
<211> LENGTH: 11
<212> TYPE: PRT
<213> ORGANISM: Homo sapiens

<400> SEQUENCE: 46

Gly Gly Asn Asn Ile Gly Ser Lys Asn Val His
1               5                   10

<210> SEQ ID NO 47
<211> LENGTH: 7
<212> TYPE: PRT
<213> ORGANISM: Homo sapiens

<400> SEQUENCE: 47

Arg Asp Ser Asn Arg Pro Ser
1               5
```

<210> SEQ ID NO 48
<211> LENGTH: 7
<212> TYPE: PRT
<213> ORGANISM: Homo sapiens

<400> SEQUENCE: 48

Gln Val Trp Asp Ser Ser Thr
1               5

<210> SEQ ID NO 49
<211> LENGTH: 128
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Leu Ala Leu Arg Asp Phe Asp Trp Leu Ser Pro Gly
            100                 105                 110

Arg Asp Phe Asp Tyr Trp Gly Gln Gly Thr Leu Val Thr Val Ser Arg
        115                 120                 125

<210> SEQ ID NO 50
<211> LENGTH: 5
<212> TYPE: PRT
<213> ORGANISM: Homo sapiens

<400> SEQUENCE: 50

Ser Tyr Ala Met Ser
1               5

<210> SEQ ID NO 51
<211> LENGTH: 17
<212> TYPE: PRT
<213> ORGANISM: Homo sapiens

<400> SEQUENCE: 51

Gly Ile Ser Gly Ser Gly Gly Arg Thr Tyr Tyr Ala Asp Ser Val Lys
1               5                   10                  15

Gly

<210> SEQ ID NO 52
<211> LENGTH: 19
<212> TYPE: PRT
<213> ORGANISM: Homo sapiens

<400> SEQUENCE: 52

Asp Pro Leu Ala Leu Arg Asp Phe Asp Trp Leu Ser Pro Gly Arg Asp
1               5                   10                  15

Phe Asp Tyr

<210> SEQ ID NO 53
<211> LENGTH: 111
<212> TYPE: PRT
<213> ORGANISM: Homo sapiens

<400> SEQUENCE: 53

Gln Ser Val Leu Thr Gln Pro Pro Ser Val Ala Ala Pro Gly Gln
1               5                   10                  15

Lys Val Thr Ile Ser Cys Ser Gly Ser His Ser Asn Ile Gly Asn Asn
            20                  25                  30

Tyr Val Ser Trp Ser Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Asp Ile Ala Gly Leu Gln
65                  70                  75                  80

Thr Gly Asp Glu Ala Asp Tyr Tyr Cys Gly Ala Trp Asp Thr Ser Leu
                85                  90                  95

Ser Ser Tyr Val Phe Gly Ala Gly Thr Lys Val Thr Val Leu Gly
            100                 105                 110

<210> SEQ ID NO 54
<211> LENGTH: 13
<212> TYPE: PRT
<213> ORGANISM: Homo sapiens

<400> SEQUENCE: 54

Ser Gly Ser His Ser Asn Ile Gly Asn Asn Tyr Val Ser
1               5                   10

<210> SEQ ID NO 55
<211> LENGTH: 7
<212> TYPE: PRT
<213> ORGANISM: Homo sapiens

<400> SEQUENCE: 55

Asp Asn Asn Lys Arg Pro Ser
1               5

<210> SEQ ID NO 56
<211> LENGTH: 9
<212> TYPE: PRT
<213> ORGANISM: Homo sapiens

<400> SEQUENCE: 56

Gly Ala Trp Asp Thr Ser Leu Ser Ser
1               5

<210> SEQ ID NO 57
<211> LENGTH: 120
<212> TYPE: PRT
<213> ORGANISM: Homo sapiens

<400> SEQUENCE: 57

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

```
            35                  40                  45
Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Leu Ser Gly Gly Tyr Gly Met Asp Val Trp Gly Gln
            100                 105                 110

Gly Thr Thr Val Thr Val Ser Ser
            115                 120
```

<210> SEQ ID NO 58
<211> LENGTH: 5
<212> TYPE: PRT
<213> ORGANISM: Homo sapiens

<400> SEQUENCE: 58

```
Ser Tyr Ala Ile Ser
1               5
```

<210> SEQ ID NO 59
<211> LENGTH: 17
<212> TYPE: PRT
<213> ORGANISM: Homo sapiens

<400> SEQUENCE: 59

```
Gly Ile Ile Pro Ile Phe Gly Thr Ala Asn Tyr Ala Gln Lys Phe Gln
1               5                   10                  15

Gly
```

<210> SEQ ID NO 60
<211> LENGTH: 11
<212> TYPE: PRT
<213> ORGANISM: Homo sapiens

<400> SEQUENCE: 60

```
Glu Gly Leu Ser Gly Gly Tyr Gly Met Asp Val
1               5                   10
```

<210> SEQ ID NO 61
<211> LENGTH: 112
<212> TYPE: PRT
<213> ORGANISM: Homo sapiens

<400> SEQUENCE: 61

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
             20                  25                  30

Tyr Asp Val His Trp Tyr Gln Gln Leu Pro Gly Thr Ala Pro Lys Leu
         35                  40                  45

Leu Ile Tyr Arg Asn Asn Asn Arg Pro Ser Gly Val Pro Asp Arg Phe
    50                  55                  60

Ser Gly Ser Asn Ser Gly Thr Ser Ala Ser Leu Ala Ile Thr Gly Leu
 65                  70                  75                  80

Arg Ala Glu Asp Glu Ala Asp Tyr Tyr Cys Gln Ser Tyr Asp Ser Ser
                 85                  90                  95

Leu Ser Ser Tyr Val Phe Gly Thr Gly Thr Lys Val Thr Val Leu Gly
```

<210> SEQ ID NO 62
<211> LENGTH: 14
<212> TYPE: PRT
<213> ORGANISM: Homo sapiens

<400> SEQUENCE: 62

Thr Gly Ser Ser Ser Asn Ile Gly Ala Gly Tyr Asp Val His
1               5                   10

<210> SEQ ID NO 63
<211> LENGTH: 7
<212> TYPE: PRT
<213> ORGANISM: Homo sapiens

<400> SEQUENCE: 63

Arg Asn Asn Asn Arg Pro Ser
1               5

<210> SEQ ID NO 64
<211> LENGTH: 9
<212> TYPE: PRT
<213> ORGANISM: Homo sapiens

<400> SEQUENCE: 64

Gln Ser Tyr Asp Ser Ser Leu Ser Ser
1               5

<210> SEQ ID NO 65
<211> LENGTH: 125
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Asn Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Tyr Asp Ile Leu Thr Gly Tyr Phe Tyr Asn Gly Met
            100                 105                 110

Asp Val Trp Gly Gln Gly Thr Met Val Thr Val Ser Ser
        115                 120                 125

<210> SEQ ID NO 66
<211> LENGTH: 5
<212> TYPE: PRT
<213> ORGANISM: Homo sapiens

<400> SEQUENCE: 66

Ser Tyr Ala Met Ser
1               5

<210> SEQ ID NO 67
<211> LENGTH: 17
<212> TYPE: PRT
<213> ORGANISM: Homo sapiens

<400> SEQUENCE: 67

Ala Ile Ser Gly Ser Gly Gly Ser Thr Tyr Tyr Ala Asp Ser Val Lys
1               5                   10                  15
Gly

<210> SEQ ID NO 68
<211> LENGTH: 16
<212> TYPE: PRT
<213> ORGANISM: Homo sapiens

<400> SEQUENCE: 68

Ala Tyr Tyr Asp Ile Leu Thr Gly Tyr Phe Tyr Asn Gly Met Asp Val
1               5                   10                  15

<210> SEQ ID NO 69
<211> LENGTH: 112
<212> TYPE: PRT
<213> ORGANISM: Homo sapiens

<400> SEQUENCE: 69

Gln Ala Val Leu Thr Gln Pro Ser Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asp Tyr Val Ser Trp Tyr Gln Gln His Pro Gly Lys Ala Pro Lys Leu
        35                  40                  45

Met Ile His Asp Val Arg Asn Arg Pro Ser Gly Val Ser Asn Arg Phe
    50                  55                  60

Ser Gly Ser Lys Phe Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Ser
                85                  90                  95

Ser Thr His Val Leu Phe Gly Gly Gly Thr Lys Leu Thr Val Leu Gly
            100                 105                 110

<210> SEQ ID NO 70
<211> LENGTH: 14
<212> TYPE: PRT
<213> ORGANISM: Homo sapiens

<400> SEQUENCE: 70

Thr Gly Thr Ser Ser Asp Val Gly Gly Tyr Asp Tyr Val Ser
1               5                   10

<210> SEQ ID NO 71
<211> LENGTH: 7
<212> TYPE: PRT
<213> ORGANISM: Homo sapiens

<400> SEQUENCE: 71

Asp Val Arg Asn Arg Pro Ser
1               5

<210> SEQ ID NO 72
<211> LENGTH: 9
<212> TYPE: PRT
<213> ORGANISM: Homo sapiens

<400> SEQUENCE: 72

Ser Ser Tyr Thr Ser Ser Ser Thr His
1               5

<210> SEQ ID NO 73
<211> LENGTH: 123
<212> TYPE: PRT
<213> ORGANISM: Homo sapiens

<400> SEQUENCE: 73

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly His Ser Pro Tyr Ser Ser Gly Trp Ser Asp Phe Asp Tyr
            100                 105                 110

Trp Gly Gln Gly Thr Leu Val Thr Val Ser Ser
        115                 120

<210> SEQ ID NO 74
<211> LENGTH: 5
<212> TYPE: PRT
<213> ORGANISM: Homo sapiens

<400> SEQUENCE: 74

Asp Tyr Ala Met His
1               5

<210> SEQ ID NO 75
<211> LENGTH: 17
<212> TYPE: PRT
<213> ORGANISM: Homo sapiens

<400> SEQUENCE: 75

Gly Ile Ser Trp Asn Ser Gly Ser Ile Gly Tyr Ala Asp Ser Val Lys
1               5                   10                  15

Gly

<210> SEQ ID NO 76
<211> LENGTH: 14
<212> TYPE: PRT
<213> ORGANISM: Homo sapiens

<400> SEQUENCE: 76

Gly His Ser Pro Tyr Ser Ser Gly Trp Ser Asp Phe Asp Tyr
1               5                   10

<210> SEQ ID NO 77
<211> LENGTH: 112
<212> TYPE: PRT
<213> ORGANISM: Homo sapiens -continued

<400> SEQUENCE: 77

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val Gln Trp Tyr Gln Gln Leu Pro Gly Thr Ala Pro Lys Leu
        35                  40                  45

Leu Ile His Ala Asn Lys Asn Arg Pro Ser Gly Val Pro Asp Arg Ile
    50                  55                  60

Ser Gly Ser Lys Ser Gly Thr Thr Ala Ser Leu Ala Ile Thr Gly Phe
65                  70                  75                  80

Gln Ala Glu Asp Glu Ala Asp Tyr Tyr Cys Gln Ser Tyr Asp Ser Ser
                85                  90                  95

Leu Thr Gly Tyr Val Phe Gly Thr Gly Thr Lys Val Thr Val Leu Gly
            100                 105                 110

<210> SEQ ID NO 78
<211> LENGTH: 14
<212> TYPE: PRT
<213> ORGANISM: Homo sapiens

<400> SEQUENCE: 78

Thr Gly Ser Ser Ser Asn Ile Gly Ala Gly Tyr Asp Val Gln
1               5                   10

<210> SEQ ID NO 79
<211> LENGTH: 7
<212> TYPE: PRT
<213> ORGANISM: Homo sapiens

<400> SEQUENCE: 79

Ala Asn Lys Asn Arg Pro Ser
1               5

<210> SEQ ID NO 80
<211> LENGTH: 9
<212> TYPE: PRT
<213> ORGANISM: Homo sapiens

<400> SEQUENCE: 80

Gln Ser Tyr Asp Ser Ser Leu Thr Gly
1               5

<210> SEQ ID NO 81
<211> LENGTH: 125
<212> TYPE: PRT
<213> ORGANISM: Homo sapiens

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ala Asp Tyr
            20                  25                  30

Ala Met His Trp Val Arg Gln Ala Pro Gly Lys Gly Leu Glu Trp Val
        35                  40                  45

Ser Ser Ile Ser Trp Asn Ser Gly Ser Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Leu Tyr Tyr Cys
                85                  90                  95

Ala Lys Ala Ser Ala Ala Gly Thr Glu Tyr Tyr His Tyr Tyr Gly Met
            100                 105                 110

Asp Val Trp Gly Gln Gly Thr Thr Val Thr Val Ser Arg
        115                 120                 125

<210> SEQ ID NO 82
<211> LENGTH: 5
<212> TYPE: PRT
<213> ORGANISM: Homo sapiens

<400> SEQUENCE: 82

Asp Tyr Ala Met His
1               5

<210> SEQ ID NO 83
<211> LENGTH: 17
<212> TYPE: PRT
<213> ORGANISM: Homo sapiens

<400> SEQUENCE: 83

Ser Ile Ser Trp Asn Ser Gly Ser Ile Ala Tyr Ala Asp Ser Val Lys
1               5                   10                  15

Gly

<210> SEQ ID NO 84
<211> LENGTH: 16
<212> TYPE: PRT
<213> ORGANISM: Homo sapiens

<400> SEQUENCE: 84

Ala Ser Ala Ala Gly Thr Glu Tyr Tyr His Tyr Tyr Gly Met Asp Val
1               5                   10                  15

<210> SEQ ID NO 85
<211> LENGTH: 111
<212> TYPE: PRT
<213> ORGANISM: Homo sapiens

<400> SEQUENCE: 85

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Ile Asn Trp Tyr Gln Gln Leu Pro Gly Thr Ala Pro Lys Leu Leu
            35                  40                  45

Ile Tyr Asn Asn His Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Ala Asp Glu Ala Asp Tyr Tyr Cys Gly Ala Trp Asn Asp Ser Leu
                85                  90                  95

Asn Val Tyr Val Phe Gly Thr Gly Thr Lys Val Thr Val Leu Gly
            100                 105                 110

<210> SEQ ID NO 86
<211> LENGTH: 13
<212> TYPE: PRT
<213> ORGANISM: Homo sapiens
```

```
<400> SEQUENCE: 86

Ser Gly Ser Ser Ser Asn Ile Gly Ser Asn Thr Ile Asn
1               5                   10

<210> SEQ ID NO 87
<211> LENGTH: 7
<212> TYPE: PRT
<213> ORGANISM: Homo sapiens

<400> SEQUENCE: 87

Asn Asn His Gln Arg Pro Ser
1               5

<210> SEQ ID NO 88
<211> LENGTH: 9
<212> TYPE: PRT
<213> ORGANISM: Homo sapiens

<400> SEQUENCE: 88

Gly Ala Trp Asn Asp Ser Leu Asn Val
1               5

<210> SEQ ID NO 89
<211> LENGTH: 124
<212> TYPE: PRT
<213> ORGANISM: Homo sapiens

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ala Ala Ser Leu Lys Tyr Tyr Tyr Asp Ser Ser Gly Tyr Tyr
                100                 105                 110

Tyr Trp Gly Gln Gly Thr Leu Val Thr Val Ser Arg
            115                 120

<210> SEQ ID NO 90
<211> LENGTH: 5
<212> TYPE: PRT
<213> ORGANISM: Homo sapiens

<400> SEQUENCE: 90

Ser Tyr Gly Ile Ser
1               5

<210> SEQ ID NO 91
<211> LENGTH: 17
<212> TYPE: PRT
<213> ORGANISM: Homo sapiens

<400> SEQUENCE: 91

Trp Ile Ser Ala Tyr Asn Gly Asn Thr Asn Tyr Ala Gln Lys Leu Gln
```

```
                 1               5                  10                 15
Gly

<210> SEQ ID NO 92
<211> LENGTH: 15
<212> TYPE: PRT
<213> ORGANISM: Homo sapiens

<400> SEQUENCE: 92

Ala Ala Ser Leu Lys Tyr Tyr Tyr Asp Ser Ser Gly Tyr Tyr Tyr
1               5                   10                  15

<210> SEQ ID NO 93
<211> LENGTH: 110
<212> TYPE: PRT
<213> ORGANISM: Homo sapiens

<400> SEQUENCE: 93

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Gly Lys Asn Asn Arg Pro Ser Gly Ile Pro Asp Arg Phe Ser Gly Ser
    50                  55                  60

Ser Ser Gly Asp Thr Ala Ser Leu Thr Ile Thr Gly Ala Gln Ala Glu
65                  70                  75                  80

Asp Glu Ala Asn Tyr Tyr Cys Asn Ser Arg Asp Ser Ser Gly Tyr Pro
                85                  90                  95

Ser Trp Val Phe Gly Gly Gly Thr Lys Leu Thr Val Leu Gly
            100                 105                 110

<210> SEQ ID NO 94
<211> LENGTH: 11
<212> TYPE: PRT
<213> ORGANISM: Homo sapiens

<400> SEQUENCE: 94

Gln Gly Asp Ser Leu Arg Ser Tyr Tyr Ala Ser
1               5                   10

<210> SEQ ID NO 95
<211> LENGTH: 7
<212> TYPE: PRT
<213> ORGANISM: Homo sapiens

<400> SEQUENCE: 95

Gly Lys Asn Asn Arg Pro Ser
1               5

<210> SEQ ID NO 96
<211> LENGTH: 10
<212> TYPE: PRT
<213> ORGANISM: Homo sapiens

<400> SEQUENCE: 96

Asn Ser Arg Asp Ser Ser Gly Tyr Pro Ser
1               5                   10

<210> SEQ ID NO 97
```

```
<211> LENGTH: 130
<212> TYPE: PRT
<213> ORGANISM: Homo sapiens

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Val Phe Asn Ser Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Tyr Thr Asp Tyr Ala Gln Lys Val
    50                  55                  60

Gln Gly Arg Val Thr Met Thr Thr Glu Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Asp Ser Ser Thr Tyr Tyr Ser Ser Asp Tyr Phe
            100                 105                 110

Gln Tyr Tyr Gly Met Asp Val Trp Gly Gln Gly Thr Thr Val Thr Val
        115                 120                 125

Ser Ser
    130

<210> SEQ ID NO 98
<211> LENGTH: 5
<212> TYPE: PRT
<213> ORGANISM: Homo sapiens

<400> SEQUENCE: 98

Ser Tyr Gly Ile Thr
1               5

<210> SEQ ID NO 99
<211> LENGTH: 17
<212> TYPE: PRT
<213> ORGANISM: Homo sapiens

<400> SEQUENCE: 99

Trp Ile Ser Ala Tyr Asn Gly Tyr Thr Asp Tyr Ala Gln Lys Val Gln
1               5                   10                  15

Gly

<210> SEQ ID NO 100
<211> LENGTH: 21
<212> TYPE: PRT
<213> ORGANISM: Homo sapiens

<400> SEQUENCE: 100

Asp Tyr Tyr Asp Ser Ser Thr Tyr Tyr Ser Ser Asp Tyr Phe Gln Tyr
1               5                   10                  15

Tyr Gly Met Asp Val
            20

<210> SEQ ID NO 101
<211> LENGTH: 111
<212> TYPE: PRT
<213> ORGANISM: Homo sapiens

<400> SEQUENCE: 101
```

```
Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Ser Asp Val Ser Arg Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Ser
                85                  90                  95

Asn Thr Val Leu Phe Gly Gly Gly Thr Lys Leu Thr Val Leu Gly
            100                 105                 110
```

<210> SEQ ID NO 102
<211> LENGTH: 14
<212> TYPE: PRT
<213> ORGANISM: Homo sapiens

<400> SEQUENCE: 102

```
Thr Gly Thr Ser Ser Asp Val Gly Ala Tyr Asn Tyr Val Ser
1               5                   10
```

<210> SEQ ID NO 103
<211> LENGTH: 7
<212> TYPE: PRT
<213> ORGANISM: Homo sapiens

<400> SEQUENCE: 103

```
Asp Val Ser Arg Arg Pro Ser
1               5
```

<210> SEQ ID NO 104
<211> LENGTH: 8
<212> TYPE: PRT
<213> ORGANISM: Homo sapiens

<400> SEQUENCE: 104

```
Ser Ser Tyr Thr Ser Ser Asn Thr
1               5
```

<210> SEQ ID NO 105
<211> LENGTH: 122
<212> TYPE: PRT
<213> ORGANISM: Homo sapiens

<400> SEQUENCE: 105

```
Gln Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ala Ala Asp Lys Ser Ile Ser Thr Ala Tyr
65                  70                  75                  80

Leu Gln Trp Ser Ser Leu Met Ala Ser Asp Thr Ala Met Tyr Tyr Cys
                85                  90                  95
```

Ala Arg Arg Gly Ser Arg Ser Ser Gly Glu Asp Ala Phe Glu Val Trp
            100                 105                 110

Gly Gln Gly Thr Thr Val Thr Val Ser Ser
        115                 120

<210> SEQ ID NO 106
<211> LENGTH: 5
<212> TYPE: PRT
<213> ORGANISM: Homo sapiens

<400> SEQUENCE: 106

Asn Tyr Trp Ile Gly
1               5

<210> SEQ ID NO 107
<211> LENGTH: 17
<212> TYPE: PRT
<213> ORGANISM: Homo sapiens

<400> SEQUENCE: 107

Ile Ile Tyr Pro Gly Asp Ser Asp Thr Arg Tyr Ser Pro Ser Phe Gln
1               5                   10                  15

Gly

<210> SEQ ID NO 108
<211> LENGTH: 13
<212> TYPE: PRT
<213> ORGANISM: Homo sapiens

<400> SEQUENCE: 108

Arg Gly Ser Arg Ser Ser Gly Glu Asp Ala Phe Glu Val
1               5                   10

<210> SEQ ID NO 109
<211> LENGTH: 110
<212> TYPE: PRT
<213> ORGANISM: Homo sapiens

<400> SEQUENCE: 109

Ser Tyr Glu Leu Thr Gln Pro Pro Ser Val Ser Val Ala Pro Gly Lys
1               5                   10                  15

Thr Ala Thr Ile Thr Cys Gly Asp Asn Ile Gly Ser Lys Ser Val
            20                  25                  30

His Trp Tyr Gln Gln Arg Pro Gly Gln Ala Pro Val Leu Val Ile Asn
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Glu Asp Arg Arg Gly Gly Tyr
                85                  90                  95

His Val Val Phe Gly Gly Gly Thr Lys Leu Thr Val Leu Gly
            100                 105                 110

<210> SEQ ID NO 110
<211> LENGTH: 11
<212> TYPE: PRT
<213> ORGANISM: Homo sapiens

<400> SEQUENCE: 110

Gly Gly Asp Asn Ile Gly Ser Lys Ser Val His
1               5                  10

<210> SEQ ID NO 111
<211> LENGTH: 7
<212> TYPE: PRT
<213> ORGANISM: Homo sapiens

<400> SEQUENCE: 111

Tyr Asp Ser Asp Arg Pro Ser
1               5

<210> SEQ ID NO 112
<211> LENGTH: 10
<212> TYPE: PRT
<213> ORGANISM: Homo sapiens

<400> SEQUENCE: 112

Gln Val Glu Asp Arg Arg Gly Gly Tyr His
1               5                  10

<210> SEQ ID NO 113
<211> LENGTH: 125
<212> TYPE: PRT
<213> ORGANISM: Homo sapiens

<400> SEQUENCE: 113

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Tyr Cys Ser Gly Gly Ser Cys Tyr Ser Tyr Gly Ala Phe
            100                 105                 110

Asp Ile Trp Gly Gln Gly Thr Thr Val Thr Val Ser Ser
        115                 120                 125

<210> SEQ ID NO 114
<211> LENGTH: 5
<212> TYPE: PRT
<213> ORGANISM: Homo sapiens

<400> SEQUENCE: 114

Ser Asn Tyr Met Ser
1               5

<210> SEQ ID NO 115
<211> LENGTH: 16
<212> TYPE: PRT
<213> ORGANISM: Homo sapiens

<400> SEQUENCE: 115

Val Ile Tyr Ser Gly Gly Ser Thr Tyr Tyr Ala Asp Ser Val Lys Gly
1               5                   10                  15

<210> SEQ ID NO 116
<211> LENGTH: 17
<212> TYPE: PRT
<213> ORGANISM: Homo sapiens

<400> SEQUENCE: 116

Glu Gly Tyr Cys Ser Gly Gly Ser Cys Tyr Ser Tyr Gly Ala Phe Asp
1               5                   10                  15

Ile

<210> SEQ ID NO 117
<211> LENGTH: 108
<212> TYPE: PRT
<213> ORGANISM: Homo sapiens

<400> SEQUENCE: 117

Asp Ile Val Met Thr Gln Ser Pro Ser Ser Val Ser Ala Ser Val Gly
1               5                   10                  15

Asp Arg Val Thr Ile Ser Cys Arg Ala Ser Gln Asn Ile Ala Asn Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Gly Asn Ser Phe Pro Arg
                85                  90                  95

Val Thr Phe Gly Gly Gly Thr Lys Val Glu Ile Lys
            100                 105

<210> SEQ ID NO 118
<211> LENGTH: 11
<212> TYPE: PRT
<213> ORGANISM: Homo sapiens

<400> SEQUENCE: 118

Arg Ala Ser Gln Asn Ile Ala Asn Trp Leu Ala
1               5                   10

<210> SEQ ID NO 119
<211> LENGTH: 7
<212> TYPE: PRT
<213> ORGANISM: Homo sapiens

<400> SEQUENCE: 119

Ala Ala Ser Asn Leu Gln Ser
1               5

<210> SEQ ID NO 120
<211> LENGTH: 8
<212> TYPE: PRT
<213> ORGANISM: Homo sapiens

<400> SEQUENCE: 120

Gln Gln Gly Asn Ser Phe Pro Arg
1               5

<210> SEQ ID NO 121
<211> LENGTH: 130
<212> TYPE: PRT

<213> ORGANISM: Homo sapiens

<400> SEQUENCE: 121

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Val Phe Asn Ser Tyr
            20                  25                  30
Gly Ile Thr Trp Val Arg Gln Ala Pro Gly Gln Gly Leu Glu Trp Met
        35                  40                  45
Gly Trp Ile Ser Ala Tyr Asn Gly Tyr Thr Asp Tyr Ala Gln Lys Val
    50                  55                  60
Gln Gly Arg Val Thr Met Thr Thr Glu Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Tyr Tyr Asp Ser Ser Thr Tyr Tyr Ser Ser Asp Tyr Phe
            100                 105                 110
Lys Tyr Tyr Gly Met Asp Val Trp Gly Gln Gly Thr Thr Val Thr Val
        115                 120                 125
Ser Ser
    130
```

<210> SEQ ID NO 122
<211> LENGTH: 5
<212> TYPE: PRT
<213> ORGANISM: Homo sapiens

<400> SEQUENCE: 122

```
Ser Tyr Gly Ile Thr
1               5
```

<210> SEQ ID NO 123
<211> LENGTH: 17
<212> TYPE: PRT
<213> ORGANISM: Homo sapiens

<400> SEQUENCE: 123

```
Trp Ile Ser Ala Tyr Asn Gly Tyr Thr Asp Tyr Ala Gln Lys Val Gln
1               5                   10                  15
Gly
```

<210> SEQ ID NO 124
<211> LENGTH: 21
<212> TYPE: PRT
<213> ORGANISM: Homo sapiens

<400> SEQUENCE: 124

```
Asp Tyr Tyr Asp Ser Ser Thr Tyr Tyr Ser Asp Tyr Phe Lys Tyr
1               5                   10                  15
Tyr Gly Met Asp Val
            20
```

<210> SEQ ID NO 125
<211> LENGTH: 111
<212> TYPE: PRT
<213> ORGANISM: Homo sapiens

<400> SEQUENCE: 125

```
Gln Ala Val Leu Thr Gln Pro Ser Ser Val Ser Gly Ser Pro Gly Gln
1               5                   10                  15
```

Ser Ile Thr Ile Ser Cys Ser Gly Thr Ser Ser Asp Val Gly Ala Tyr
            20                  25                  30

Asn Tyr Val Ser Trp Tyr Gln Gln His Pro Gly Lys Ala Pro Arg Leu
        35                  40                  45

Leu Thr Phe Asp Val Asn Arg Arg Pro Ser Gly Ser Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asn Ser
                85                  90                  95

Asn Thr Val Val Phe Gly Gly Gly Thr Arg Leu Thr Val Leu Ser
            100                 105                 110

<210> SEQ ID NO 126
<211> LENGTH: 14
<212> TYPE: PRT
<213> ORGANISM: Homo sapiens

<400> SEQUENCE: 126

Ser Gly Thr Ser Ser Asp Val Gly Ala Tyr Asn Tyr Val Ser
1               5                   10

<210> SEQ ID NO 127
<211> LENGTH: 7
<212> TYPE: PRT
<213> ORGANISM: Homo sapiens

<400> SEQUENCE: 127

Asp Val Asn Arg Arg Pro Ser
1               5

<210> SEQ ID NO 128
<211> LENGTH: 8
<212> TYPE: PRT
<213> ORGANISM: Homo sapiens

<400> SEQUENCE: 128

Ser Ser Tyr Thr Asn Ser Asn Thr
1               5

<210> SEQ ID NO 129
<211> LENGTH: 127
<212> TYPE: PRT
<213> ORGANISM: Homo sapiens

<400> SEQUENCE: 129

Gln Val Gln Leu Gln Glu Ser Gly Pro Gly Leu Val Lys Pro Ser Glu
1               5                   10                  15

Thr Leu Ala Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Asp Ile Glu Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Asp Asp Thr Ala Val Tyr Tyr Cys Ala
                85                  90                  95

Arg Asp Ser Arg Val Ile Arg Phe Leu Glu Gly Tyr Ser Tyr Tyr Tyr

```
                100             105             110
Gly Val Asp Val Trp Gly Gln Gly Thr Met Val Thr Val Ser Ser
            115             120             125
```

<210> SEQ ID NO 130
<211> LENGTH: 5
<212> TYPE: PRT
<213> ORGANISM: Homo sapiens

<400> SEQUENCE: 130

```
Asn Tyr Tyr Trp Ser
1               5
```

<210> SEQ ID NO 131
<211> LENGTH: 16
<212> TYPE: PRT
<213> ORGANISM: Homo sapiens

<400> SEQUENCE: 131

```
Tyr Ile Tyr Asp Ile Glu Asn Thr Asn Tyr Asn Pro Ser Leu Lys Ser
1               5                   10                  15
```

<210> SEQ ID NO 132
<211> LENGTH: 19
<212> TYPE: PRT
<213> ORGANISM: Homo sapiens

<400> SEQUENCE: 132

```
Asp Ser Arg Val Ile Arg Phe Leu Glu Gly Tyr Ser Tyr Tyr Tyr Gly
1               5                   10                  15

Val Asp Val
```

<210> SEQ ID NO 133
<211> LENGTH: 111
<212> TYPE: PRT
<213> ORGANISM: Homo sapiens

<400> SEQUENCE: 133

```
Ser Tyr Glu Leu Thr Gln Pro Pro Ser Ala Ser Gly Thr Pro Gly Gln
1               5                   10                  15

Thr Val Ile Ile Ser Cys Ser Gly Ser Arg Ser Asn Ile Gly Gly His
            20                  25                  30

Gly Val Asn Trp His Gln Gln Val Pro Gly Thr Ala Pro Lys Leu Leu
        35                  40                  45

Ile Tyr Arg Asn Asp Arg Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Phe Glu Asp Glu Ala Asp Tyr Tyr Cys Val Ala Trp Glu Asp Ser Leu
                85                  90                  95

Asp Gly Pro Val Phe Gly Gly Gly Thr Lys Leu Thr Val Leu Gly
                100             105             110
```

<210> SEQ ID NO 134
<211> LENGTH: 13
<212> TYPE: PRT
<213> ORGANISM: Homo sapiens

<400> SEQUENCE: 134

```
Ser Gly Ser Arg Ser Asn Ile Gly Gly His Gly Val Asn
1               5                   10
```

<210> SEQ ID NO 135
<211> LENGTH: 7
<212> TYPE: PRT
<213> ORGANISM: Homo sapiens

<400> SEQUENCE: 135

Arg Asn Asp Arg Arg Pro Ser
1               5

<210> SEQ ID NO 136
<211> LENGTH: 9
<212> TYPE: PRT
<213> ORGANISM: Homo sapiens

<400> SEQUENCE: 136

Val Ala Trp Glu Asp Ser Leu Asp Gly
1               5

<210> SEQ ID NO 137
<211> LENGTH: 115
<212> TYPE: PRT
<213> ORGANISM: Homo sapiens

<400> SEQUENCE: 137

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Val Ala Thr Ser Trp Gly Gln Gly Thr Leu Val Thr
            100                 105                 110

Val Ser Arg
        115

<210> SEQ ID NO 138
<211> LENGTH: 5
<212> TYPE: PRT
<213> ORGANISM: Homo sapiens

<400> SEQUENCE: 138

Ser Tyr Ala Met Ser
1               5

<210> SEQ ID NO 139
<211> LENGTH: 17
<212> TYPE: PRT
<213> ORGANISM: Homo sapiens

<400> SEQUENCE: 139

Thr Ile Ser Gly Ser Gly Gly Ser Thr Tyr Tyr Ala Asp Ser Val Lys
1               5                   10                  15

Gly

<210> SEQ ID NO 140
<211> LENGTH: 6
<212> TYPE: PRT
<213> ORGANISM: Homo sapiens

<400> SEQUENCE: 140

Gly Ile Val Ala Thr Ser
1               5

<210> SEQ ID NO 141
<211> LENGTH: 108
<212> TYPE: PRT
<213> ORGANISM: Homo sapiens

<400> SEQUENCE: 141

Ser Tyr Glu Leu Thr Gln Pro Pro Ser Val Ser Val Ala Pro Gly Gln
1               5                   10                  15

Thr Ala Arg Ile Thr Cys Gly Gly Asn Lys Ile Gly Ser Lys Ser Val
            20                  25                  30

His Trp Tyr Gln Gln Lys Gln Gly Gln Ala Pro Val Leu Val Ile Tyr
        35                  40                  45

Leu Asp Arg Asp Arg Pro Ser Gly Ile Pro Glu Arg Phe Ser Gly Ser
    50                  55                  60

Asn Ser Gly Asn Thr Ala Thr Leu Thr Ile Thr Arg Val Glu Ala Glu
65                  70                  75                  80

Asp Glu Ala Asp Tyr Tyr Cys His Leu Trp Asp Ser Gly Ser Asp Gln
                85                  90                  95

Val Phe Gly Gly Gly Thr Lys Leu Thr Val Leu Gly
            100                 105

<210> SEQ ID NO 142
<211> LENGTH: 11
<212> TYPE: PRT
<213> ORGANISM: Homo sapiens

<400> SEQUENCE: 142

Gly Gly Asn Lys Ile Gly Ser Lys Ser Val His
1               5                   10

<210> SEQ ID NO 143
<211> LENGTH: 7
<212> TYPE: PRT
<213> ORGANISM: Homo sapiens

<400> SEQUENCE: 143

Leu Asp Arg Asp Arg Pro Ser
1               5

<210> SEQ ID NO 144
<211> LENGTH: 8
<212> TYPE: PRT
<213> ORGANISM: Homo sapiens

<400> SEQUENCE: 144

His Leu Trp Asp Ser Gly Ser Asp
1               5

<210> SEQ ID NO 145
<211> LENGTH: 114
<212> TYPE: PRT
<213> ORGANISM: Homo sapiens

```
<400> SEQUENCE: 145

Glu Val Gln Leu Val Glu Ser Gly Gly Val Val Gln Pro Gly Gly
1               5                   10                  15

Ser Leu Arg Leu Ser Cys Ala Ala Ser Gly Phe Asn Phe Asp Val Tyr
            20                  25                  30

Gly Met Asn Trp Val Arg Gln Val Pro Gly Lys Gly Leu Glu Trp Val
        35                  40                  45

Ser Leu Ile Asn Gly Asp Gly Gly Leu Arg Tyr Tyr Ala Asp Ser Val
    50                  55                  60

Lys Gly Arg Phe Thr Val Ser Arg Asp Asn Ser Arg Asn Ser Leu Tyr
65                  70                  75                  80

Leu Gln Met Asn Ser Leu Arg Ser Glu Asp Thr Ala Leu Tyr Tyr Cys
                85                  90                  95

Val Lys Gly Asn Phe Gln Gln Trp Gly Gln Gly Thr Leu Val Thr Val
            100                 105                 110

Ser Arg

<210> SEQ ID NO 146
<211> LENGTH: 5
<212> TYPE: PRT
<213> ORGANISM: Homo sapiens

<400> SEQUENCE: 146

Val Tyr Gly Met Asn
1               5

<210> SEQ ID NO 147
<211> LENGTH: 17
<212> TYPE: PRT
<213> ORGANISM: Homo sapiens

<400> SEQUENCE: 147

Leu Ile Asn Gly Asp Gly Gly Leu Arg Tyr Tyr Ala Asp Ser Val Lys
1               5                   10                  15

Gly

<210> SEQ ID NO 148
<211> LENGTH: 5
<212> TYPE: PRT
<213> ORGANISM: Homo sapiens

<400> SEQUENCE: 148

Gly Asn Phe Gln Gln
1               5

<210> SEQ ID NO 149
<211> LENGTH: 109
<212> TYPE: PRT
<213> ORGANISM: Homo sapiens

<400> SEQUENCE: 149

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu Gly
            100                 105
```

<210> SEQ ID NO 150
<211> LENGTH: 11
<212> TYPE: PRT
<213> ORGANISM: Homo sapiens

<400> SEQUENCE: 150

```
Gly Gly Asn Asn Ile Gly Ser Lys Ser Val His
 1               5                  10
```

<210> SEQ ID NO 151
<211> LENGTH: 7
<212> TYPE: PRT
<213> ORGANISM: Homo sapiens

<400> SEQUENCE: 151

```
Tyr Asp Ser Asp Arg Pro Ser
 1               5
```

<210> SEQ ID NO 152
<211> LENGTH: 9
<212> TYPE: PRT
<213> ORGANISM: Homo sapiens

<400> SEQUENCE: 152

```
Gln Val Trp Asp Ser Ser Ser Asp His
 1               5
```

<210> SEQ ID NO 153
<211> LENGTH: 115
<212> TYPE: PRT
<213> ORGANISM: Homo sapiens

<400> SEQUENCE: 153

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Leu Ile Ser Gly Asp Gly Gly Ser Thr Tyr Tyr Ala Asp Ser Val
        50                  55                  60

Lys Asp Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asn Tyr Phe Asp Tyr Trp Gly Gln Gly Thr Leu Val Thr
            100                 105                 110

Val Ser Arg
        115
```

<210> SEQ ID NO 154
<211> LENGTH: 5
<212> TYPE: PRT

```
<213> ORGANISM: Homo sapiens

<400> SEQUENCE: 154

Asp Tyr Ala Met His
1               5

<210> SEQ ID NO 155
<211> LENGTH: 17
<212> TYPE: PRT
<213> ORGANISM: Homo sapiens

<400> SEQUENCE: 155

Leu Ile Ser Gly Asp Gly Gly Ser Thr Tyr Tyr Ala Asp Ser Val Lys
1               5                   10                  15

Asp

<210> SEQ ID NO 156
<211> LENGTH: 6
<212> TYPE: PRT
<213> ORGANISM: Homo sapiens

<400> SEQUENCE: 156

Gly Asn Tyr Phe Asp Tyr
1               5

<210> SEQ ID NO 157
<211> LENGTH: 106
<212> TYPE: PRT
<213> ORGANISM: Homo sapiens

<400> SEQUENCE: 157

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
                20                  25                  30

His Trp Tyr Gln Gln Lys Pro Gly Gln Ala Pro Val Leu Val Ile Tyr
            35                  40                  45

Arg Asp Ser Asn Arg Pro Ser Gly Ile Pro Glu Arg Phe Ser Gly Ser
50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Val Val Phe
                85                  90                  95

Gly Gly Gly Thr Lys Leu Thr Val Leu Gly
                100                 105

<210> SEQ ID NO 158
<211> LENGTH: 11
<212> TYPE: PRT
<213> ORGANISM: Homo sapiens

<400> SEQUENCE: 158

Gly Gly Asn Asn Ile Gly Ser Lys Asn Val His
1               5                   10

<210> SEQ ID NO 159
<211> LENGTH: 7
<212> TYPE: PRT
<213> ORGANISM: Homo sapiens

<400> SEQUENCE: 159
```

Arg Asp Ser Asn Arg Pro Ser
1               5

<210> SEQ ID NO 160
<211> LENGTH: 6
<212> TYPE: PRT
<213> ORGANISM: Homo sapiens

<400> SEQUENCE: 160

Gln Val Trp Asp Ser Ser
1               5

<210> SEQ ID NO 161
<211> LENGTH: 122
<212> TYPE: PRT
<213> ORGANISM: Homo sapiens

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Val Met Pro Ser Tyr Tyr Tyr Tyr Gly Met Asp Val Trp
            100                 105                 110

Gly Gln Gly Thr Thr Val Thr Val Ser Arg
        115                 120

<210> SEQ ID NO 162
<211> LENGTH: 5
<212> TYPE: PRT
<213> ORGANISM: Homo sapiens

<400> SEQUENCE: 162

Ser Tyr Ser Met Asn
1               5

<210> SEQ ID NO 163
<211> LENGTH: 17
<212> TYPE: PRT
<213> ORGANISM: Homo sapiens

<400> SEQUENCE: 163

Tyr Ile Ser Ser Ser Ser Ser Thr Ile Tyr Tyr Ala Asp Ser Val Lys
1               5                   10                  15

Gly

<210> SEQ ID NO 164
<211> LENGTH: 13
<212> TYPE: PRT
<213> ORGANISM: Homo sapiens

<400> SEQUENCE: 164

Val Met Pro Ser Tyr Tyr Tyr Tyr Gly Met Asp Val

<210> SEQ ID NO 165
<211> LENGTH: 111
<212> TYPE: PRT
<213> ORGANISM: Homo sapiens

<400> SEQUENCE: 165

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Arg Pro Gly Ser Ala Pro Thr Thr Val
        35                  40                  45

Ile Tyr Glu Asp Ser Glu Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Gln Asp Glu Ala Asp Tyr Tyr Cys Gln Ser Tyr Asp Gly
                85                  90                  95

Val Asn Trp Val Phe Gly Gly Gly Thr Lys Leu Thr Val Leu Gly
            100                 105                 110

<210> SEQ ID NO 166
<211> LENGTH: 13
<212> TYPE: PRT
<213> ORGANISM: Homo sapiens

<400> SEQUENCE: 166

Thr Gly Ser Ser Gly Ser Ile Ala Ser Asn Tyr Val Gln
1               5                   10

<210> SEQ ID NO 167
<211> LENGTH: 7
<212> TYPE: PRT
<213> ORGANISM: Homo sapiens

<400> SEQUENCE: 167

Glu Asp Ser Glu Arg Pro Ser
1               5

<210> SEQ ID NO 168
<211> LENGTH: 7
<212> TYPE: PRT
<213> ORGANISM: Homo sapiens

<400> SEQUENCE: 168

Gln Ser Tyr Asp Gly Val Asn
1               5

<210> SEQ ID NO 169
<211> LENGTH: 114
<212> TYPE: PRT
<213> ORGANISM: Homo sapiens

<400> SEQUENCE: 169

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val

```
                35                  40                  45
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asp Tyr Gly Met Asp Val Trp Gly Gln Gly Thr Thr Val Thr Val
                100                 105                 110

Ser Arg
```

<210> SEQ ID NO 170
<211> LENGTH: 5
<212> TYPE: PRT
<213> ORGANISM: Homo sapiens

<400> SEQUENCE: 170

```
Ser Tyr Gly Met His
 1               5
```

<210> SEQ ID NO 171
<211> LENGTH: 17
<212> TYPE: PRT
<213> ORGANISM: Homo sapiens

<400> SEQUENCE: 171

```
Val Ile Ser Tyr Asp Gly Ser Asn Lys Tyr Tyr Ala Asp Ser Val Lys
 1               5                  10                  15

Gly
```

<210> SEQ ID NO 172
<211> LENGTH: 5
<212> TYPE: PRT
<213> ORGANISM: Homo sapiens

<400> SEQUENCE: 172

```
Tyr Gly Met Asp Val
 1               5
```

<210> SEQ ID NO 173
<211> LENGTH: 107
<212> TYPE: PRT
<213> ORGANISM: Homo sapiens

<400> SEQUENCE: 173

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Val
                 85                  90                  95

Thr Phe Gly Gln Gly Thr Lys Val Glu Ile Lys
                100                 105
```

<210> SEQ ID NO 174
<211> LENGTH: 11
<212> TYPE: PRT
<213> ORGANISM: Homo sapiens

<400> SEQUENCE: 174

Arg Ala Ser Gln Ser Ile Ser Ser Tyr Leu Asn
1               5                   10

<210> SEQ ID NO 175
<211> LENGTH: 7
<212> TYPE: PRT
<213> ORGANISM: Homo sapiens

<400> SEQUENCE: 175

Ala Ala Ser Ser Leu Gln Ser
1               5

<210> SEQ ID NO 176
<211> LENGTH: 7
<212> TYPE: PRT
<213> ORGANISM: Homo sapiens

<400> SEQUENCE: 176

Gln Gln Ser Tyr Ser Thr Pro
1               5

<210> SEQ ID NO 177
<211> LENGTH: 120
<212> TYPE: PRT
<213> ORGANISM: Homo sapiens

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Gly Thr Gly Asp Ala Phe Asp Ile Trp Gly Gln
            100                 105                 110

Gly Thr Met Val Thr Val Ser Arg
        115                 120

<210> SEQ ID NO 178
<211> LENGTH: 7
<212> TYPE: PRT
<213> ORGANISM: Homo sapiens

<400> SEQUENCE: 178

Ser Gly Gly Tyr Tyr Trp Ser
1               5

<210> SEQ ID NO 179

<211> LENGTH: 16
<212> TYPE: PRT
<213> ORGANISM: Homo sapiens

<400> SEQUENCE: 179

Tyr Ile Tyr Tyr Ser Gly Ser Thr Tyr Tyr Asn Pro Ser Leu Lys Ser
1               5                   10                  15

<210> SEQ ID NO 180
<211> LENGTH: 10
<212> TYPE: PRT
<213> ORGANISM: Homo sapiens

<400> SEQUENCE: 180

Asp Arg Gly Thr Gly Asp Ala Phe Asp Ile
1               5                   10

<210> SEQ ID NO 181
<211> LENGTH: 111
<212> TYPE: PRT
<213> ORGANISM: Homo sapiens

<400> SEQUENCE: 181

Gln Ser Val Leu Thr Gln Pro Pro Ser Val Ser Gly Ala Pro Arg Gln
1               5                   10                  15

Thr Val Thr Ile Ser Cys Ser Gly Ser Ser Ser Asn Ile Gly Gln Asn
            20                  25                  30

Ser Val Thr Trp Tyr Gln Arg Leu Pro Gly Glu Ala Pro Lys Leu Leu
        35                  40                  45

Ile Tyr Tyr Asp Asp Leu Leu His Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ser Trp Asp Ser Ser Leu
                85                  90                  95

Lys Gly Pro Val Phe Gly Gly Gly Thr Lys Leu Thr Val Leu Gly
            100                 105                 110

<210> SEQ ID NO 182
<211> LENGTH: 13
<212> TYPE: PRT
<213> ORGANISM: Homo sapiens

<400> SEQUENCE: 182

Ser Gly Ser Ser Ser Asn Ile Gly Gln Asn Ser Val Thr
1               5                   10

<210> SEQ ID NO 183
<211> LENGTH: 7
<212> TYPE: PRT
<213> ORGANISM: Homo sapiens

<400> SEQUENCE: 183

Tyr Asp Asp Leu Leu His Ser
1               5

<210> SEQ ID NO 184
<211> LENGTH: 9
<212> TYPE: PRT
<213> ORGANISM: Homo sapiens

<400> SEQUENCE: 184

Ala Ser Trp Asp Asp Ser Leu Lys Gly
1               5

<210> SEQ ID NO 185
<211> LENGTH: 360
<212> TYPE: DNA
<213> ORGANISM: Homo sapiens

<400> SEQUENCE: 185
caggtgcagc tgcaggagtc gggcccagga ctggtgaagc cttcacagac cctgtccctc        60
acctgcactg tctctggtgg ctccatcagc agtggtggtt actactggag ctggatccgc       120
cagcacccag ggaagggcct ggagtggatt gggtacatct attacagtgg gagcacctac       180
tacaacccgt ccctcaagag tcgagtcacc atatcagtag acacgtctaa gaaccagttc       240
tccctgaagc tgagctctgt gactgccgcg gacacggccg tgtattactg tgcgaggaca       300
ccgtgggagc tactagcttt tgatatctgg ggccaaggga caatggtcac cgtctcgaga       360

<210> SEQ ID NO 186
<211> LENGTH: 21
<212> TYPE: DNA
<213> ORGANISM: Homo sapiens

<400> SEQUENCE: 186
agtggtggtt actactggag c                                                  21

<210> SEQ ID NO 187
<211> LENGTH: 48
<212> TYPE: DNA
<213> ORGANISM: Homo sapiens

<400> SEQUENCE: 187
tacatctatt acagtgggag cacctactac aacccgtccc tcaagagt                     48

<210> SEQ ID NO 188
<211> LENGTH: 30
<212> TYPE: DNA
<213> ORGANISM: Homo sapiens

<400> SEQUENCE: 188
acaccgtggg agctactagc ttttgatatc                                         30

<210> SEQ ID NO 189
<211> LENGTH: 327
<212> TYPE: DNA
<213> ORGANISM: Homo sapiens

<400> SEQUENCE: 189
tcctatgagc tgactcagcc accctcagtg tcagtggccc caggaaagac gaccaggatt        60
acctgtgggg gaaacaacat tggaagtaaa agtgcgcact ggtaccagca gaagccaggc       120
caggcccctg tgctggtcat ctattatgat agcgaccggc cctcagggat ccctgagcga       180
ttctctggct ccaactctgg gaacacggcc accctgacca tcagcagggt cgaagccggg       240
gatgaggccg actattactg tcaggtgtgg gatagtagta gtgatcattg ggtgttcggc       300
ggagggacca agctgaccgt cctaggt                                           327

<210> SEQ ID NO 190
<211> LENGTH: 33
<212> TYPE: DNA
<213> ORGANISM: Homo sapiens

<400> SEQUENCE: 190
gggggaaaca acattggaag taaaagtgcg cac       33

<210> SEQ ID NO 191
<211> LENGTH: 21
<212> TYPE: DNA
<213> ORGANISM: Homo sapiens

<400> SEQUENCE: 191
tatgatagcg accggccctc a       21

<210> SEQ ID NO 192
<211> LENGTH: 27
<212> TYPE: DNA
<213> ORGANISM: Homo sapiens

<400> SEQUENCE: 192
caggtgtggg atagtagtag tgatcat       27

<210> SEQ ID NO 193
<211> LENGTH: 378
<212> TYPE: DNA
<213> ORGANISM: Homo sapiens

<400> SEQUENCE: 193
caggtgcagc tggtgcagtc tggggctgag gtgaagaaga ctgggtcctc ggtgaaggtc       60
tcctgcaagg cctctggagg ctccttcagc agctctgcaa tcagctgggt gcgacaggcc      120
cctggacacg ggcttgaatg gctgggaggg atcatcccta cctttggtac accaaaccac      180
gcacagaagt tccagggcag agtcacaatt accgcggacg aatcaacggg cacagcctac      240
atggagctga gtggcctgag atctgaggac acggccgtgt attactgtgc gagagcccat      300
tgtggtggtg gtaggtgtta cgactacact gatgcttttc atttctgggg ccaagggaca      360
atggtcaccg tctcgaga      378

<210> SEQ ID NO 194
<211> LENGTH: 15
<212> TYPE: DNA
<213> ORGANISM: Homo sapiens

<400> SEQUENCE: 194
agctctgcaa tcagc       15

<210> SEQ ID NO 195
<211> LENGTH: 51
<212> TYPE: DNA
<213> ORGANISM: Homo sapiens

<400> SEQUENCE: 195
gggatcatcc ctacctttgg tacaccaaac cacgcacaga gttccaggg c       51

<210> SEQ ID NO 196
<211> LENGTH: 51
<212> TYPE: DNA
<213> ORGANISM: Homo sapiens

<400> SEQUENCE: 196
gcccattgtg gtggtggtag gtgttacgac tacactgatg cttttcattt c       51

<210> SEQ ID NO 197
<211> LENGTH: 327

<212> TYPE: DNA
<213> ORGANISM: Homo sapiens

<400> SEQUENCE: 197

```
tcctatgagc tgactcagcc accctcagtg tcagtggccc caggaaagac ggccaggatt    60
acctgtgggg gagacaacat tggaaataga agtgtgcact ggtaccagca gaagccaggc   120
caggcccctg tgctgcttat ctattatgat agcgaccggc cctcagggat ccctaagcga   180
ttctctggct ccaactctgg gaacacggcc accctgacca tcagcagggt cgaagccggg   240
gatgaggccg actattactg tcaggtgtgg gatagtacta gtgatcatgt ggtattcggc   300
ggagggacca agctgaccgt cctacgt                                       327
```

<210> SEQ ID NO 198
<211> LENGTH: 33
<212> TYPE: DNA
<213> ORGANISM: Homo sapiens

<400> SEQUENCE: 198

```
gggggagaca acattggaaa tagaagtgtg cac                                 33
```

<210> SEQ ID NO 199
<211> LENGTH: 21
<212> TYPE: DNA
<213> ORGANISM: Homo sapiens

<400> SEQUENCE: 199

```
tatgatagcg accggccctc a                                              21
```

<210> SEQ ID NO 200
<211> LENGTH: 27
<212> TYPE: DNA
<213> ORGANISM: Homo sapiens

<400> SEQUENCE: 200

```
caggtgtggg atagtactag tgatcat                                        27
```

<210> SEQ ID NO 201
<211> LENGTH: 360
<212> TYPE: DNA
<213> ORGANISM: Homo sapiens

<400> SEQUENCE: 201

```
caggtgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct ggagtggatt gggagtatct attatagtgg gagcacctac   180
tacaacccgt ccctcaagag tcgagtcacc atatccgtag acacgtccaa gaaccagttc   240
tccctgaagc tgagctctgt gaccgccgca gacacggctg tgtattactg tgcgagactt   300
cctatggtta cgatgtcctt tgactactgg ggccagggaa ccctggtcac cgtctcgaga   360
```

<210> SEQ ID NO 202
<211> LENGTH: 21
<212> TYPE: DNA
<213> ORGANISM: Homo sapiens

<400> SEQUENCE: 202

```
agtagtagtt actactgggg c                                              21
```

<210> SEQ ID NO 203

```
<211> LENGTH: 48
<212> TYPE: DNA
<213> ORGANISM: Homo sapiens

<400> SEQUENCE: 203
agtatctatt atagtgggag cacctactac aacccgtccc tcaagagt          48

<210> SEQ ID NO 204
<211> LENGTH: 30
<212> TYPE: DNA
<213> ORGANISM: Homo sapiens

<400> SEQUENCE: 204
cttcctatgg ttacgatgtc ctttgactac                              30

<210> SEQ ID NO 205
<211> LENGTH: 327
<212> TYPE: DNA
<213> ORGANISM: Homo sapiens

<400> SEQUENCE: 205
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca agctgaccgt cctaggt                                      327

<210> SEQ ID NO 206
<211> LENGTH: 33
<212> TYPE: DNA
<213> ORGANISM: Homo sapiens

<400> SEQUENCE: 206
gggggaaaca acattggaag taaaagtgtg cac                          33

<210> SEQ ID NO 207
<211> LENGTH: 21
<212> TYPE: DNA
<213> ORGANISM: Homo sapiens

<400> SEQUENCE: 207
tatgatagcg accggccctc a                                       21

<210> SEQ ID NO 208
<211> LENGTH: 27
<212> TYPE: DNA
<213> ORGANISM: Homo sapiens

<400> SEQUENCE: 208
caggtgtggg atagtagtag tgatcat                                 27

<210> SEQ ID NO 209
<211> LENGTH: 363
<212> TYPE: DNA
<213> ORGANISM: Homo sapiens

<400> SEQUENCE: 209
caggtgcagc tggtgcagtc tggagcagag gtgaaaaagc ccggggagtc tctgaagatc    60
tcctgtaagg gttctggata cagctttacc agctactgga tcggctgggt gcgccagatg   120
```

```
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagacttact    300
ttgtcttata gcagcagctg gtttgactac tggggccagg aaccctggt caccgtctcg    360 aga                                                                  363
```

<210> SEQ ID NO 210
<211> LENGTH: 15
<212> TYPE: DNA
<213> ORGANISM: Homo sapiens

<400> SEQUENCE: 210

```
agctactgga tcggc                                                     15
```

<210> SEQ ID NO 211
<211> LENGTH: 51
<212> TYPE: DNA
<213> ORGANISM: Homo sapiens

<400> SEQUENCE: 211

```
atcatctatc ctggtgactc tgataccaga tacagcccgt ccttccaagg c             51
```

<210> SEQ ID NO 212
<211> LENGTH: 36
<212> TYPE: DNA
<213> ORGANISM: Homo sapiens

<400> SEQUENCE: 212

```
cttactttgt cttatagcag cagctggttt gactac                              36
```

<210> SEQ ID NO 213
<211> LENGTH: 333
<212> TYPE: DNA
<213> ORGANISM: Homo sapiens

<400> SEQUENCE: 213

```
cagactgtgg tgacccagga gccatcgttc tcagtgtccc ctggagggac agtcacactc    60
acttgtggct tgagctctgg ctcagtctct actagttact accccagctg gtaccagcag    120
accccaggcc aggctccacg cacgctcatc tacagcacaa acactcgctc ttctggggtc    180
cctgatcgct tctctggctc catccttggg aacaaagctg ccctcaccat cacgggggcc    240
caggcagatg atgaatctga ttattactgt gtgctgtata tgggtagtgg catttcggtg    300
ttcggcggag ggaccaagct gaccgtccta ggt                                 333
```

<210> SEQ ID NO 214
<211> LENGTH: 42
<212> TYPE: DNA
<213> ORGANISM: Homo sapiens

<400> SEQUENCE: 214

```
ggcttgagct ctggctcagt ctctactagt tactacccca gc                       42
```

<210> SEQ ID NO 215
<211> LENGTH: 21
<212> TYPE: DNA
<213> ORGANISM: Homo sapiens

<400> SEQUENCE: 215
```

```
agcacaaaca ctcgctcttc t                                             21

<210> SEQ ID NO 216
<211> LENGTH: 24
<212> TYPE: DNA
<213> ORGANISM: Homo sapiens

<400> SEQUENCE: 216
gtgctgtata tgggtagtgg catt                                          24

<210> SEQ ID NO 217
<211> LENGTH: 354
<212> TYPE: DNA
<213> ORGANISM: Homo sapiens

<400> SEQUENCE: 217
caggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca gtccatcag caccgcctac   240 ctgcagtgga gcagctgaa ggcctcggac accgccatgt attactgtgc gagacttctg   300
gggataggcg cttttgatat ctggggccaa gggaccacgg tcaccgtctc gaga         354

<210> SEQ ID NO 218
<211> LENGTH: 15
<212> TYPE: DNA
<213> ORGANISM: Homo sapiens

<400> SEQUENCE: 218
agctactgga tcggc                                                    15

<210> SEQ ID NO 219
<211> LENGTH: 51
<212> TYPE: DNA
<213> ORGANISM: Homo sapiens

<400> SEQUENCE: 219
atcatctatc ctggtgactc tgataccaga tacagcccgt ccttccaagg c            51

<210> SEQ ID NO 220
<211> LENGTH: 27
<212> TYPE: DNA
<213> ORGANISM: Homo sapiens

<400> SEQUENCE: 220
cttctgggga taggcgcttt tgatatc                                       27

<210> SEQ ID NO 221
<211> LENGTH: 330
<212> TYPE: DNA
<213> ORGANISM: Homo sapiens

<400> SEQUENCE: 221
tcttctgagc tgactcagga ccctgctgtg tctgtggcct tgggacagac agtcaggatc    60
acatgccaag gagacagcct cagaagctat tatgcaagct ggtaccagca gaagccagga   120
caggcccctg tacttgtcat ctatggtaaa aacaaccggc cctcagggat cccagaccga   180
ttctctggct ccagctcagg aaacacagct tccttgacca tcactgggc tcaggcggaa   240 gatgaggctg actattactg taactcccgg gacagcagtg gtaaccatca ttatgtcttc   300
```

```
ggaactggga ccaaggtcac cgtcctaggt                                       330
```

<210> SEQ ID NO 222
<211> LENGTH: 33
<212> TYPE: DNA
<213> ORGANISM: Homo sapiens

<400> SEQUENCE: 222

```
caaggagaca gcctcagaag ctattatgca agc                                    33
```

<210> SEQ ID NO 223
<211> LENGTH: 21
<212> TYPE: DNA
<213> ORGANISM: Homo sapiens

<400> SEQUENCE: 223

```
ggtaaaaaca accggccctc a                                                 21
```

<210> SEQ ID NO 224
<211> LENGTH: 30
<212> TYPE: DNA
<213> ORGANISM: Homo sapiens

<400> SEQUENCE: 224

```
aactcccggg acagcagtgg taaccatcat                                        30
```

<210> SEQ ID NO 225
<211> LENGTH: 678
<212> TYPE: DNA
<213> ORGANISM: Homo sapiens

<400> SEQUENCE: 225

```
caggtgcagc tggtgcagtc tggagctgag gtgaagaagc ctggggcctc agtgaaggtc       60
tcctgtaagg cttctggtta cacctttaat agctatggta ttacttgggt gcgacaggcc      120
cctggacaag gcttgagtg gatgggatgg atcagcgttt acactggtaa gacaaactat       180
gcacagaagt tccagggcag agtcaccatg accacagaca catccacgag tacagcctac      240
ctggacctga ggagcctgac atctgacgac acggccgttt attactgtgc gagaggaggg      300
gatcaccatg aatattgggg ccagggaacc ctggtcaccg tctcgagatc ttctgagctg      360
actcaggacc ctgctgtgtc tgtggccttg ggacagacag tcaggatcac atgccaagga      420
gacagcctca gaagctatta tgcaagctgg taccagcaga agccaggaca ggcccctgta      480
cttgtcatct atggtaaaaa caaccggccc tcagggatcc cagaccgatt ctctggctcc      540
agctcaggaa acacagcttc cttgaccatc actgggctc aggcggaaga tgaggctgac      600
tattactgta actcccggga cagcagtggt aaccatcatt atgtcttcgg aactgggacc      660
aaggtcaccg tcctaggt                                                    678
```

<210> SEQ ID NO 226
<211> LENGTH: 15
<212> TYPE: DNA
<213> ORGANISM: Homo sapiens

<400> SEQUENCE: 226

```
agctatggta ttact                                                       15
```

<210> SEQ ID NO 227
<211> LENGTH: 51
<212> TYPE: DNA

<213> ORGANISM: Homo sapiens

<400> SEQUENCE: 227
tggatcagcg tttacactgg taagacaaac tatgcacaga agttccaggg c    51

<210> SEQ ID NO 228
<211> LENGTH: 21
<212> TYPE: DNA
<213> ORGANISM: Homo sapiens

<400> SEQUENCE: 228 ggagggatc accatgaata t    21

<210> SEQ ID NO 229
<211> LENGTH: 321
<212> TYPE: DNA
<213> ORGANISM: Homo sapiens

<400> SEQUENCE: 229
aattttatgc tgactcagcc actctcagtg tcagtggccc tgggacagac ggccaggatt    60
acctgtgggg gaaacaacat tggaagtaaa aatgtgcact ggtaccagca gaagccaggc    120
caggcccctg tgctggtcat ctataggat agcaaccggc cctctgggat ccctgagcga    180
ttctctggct ccaactcggg gaacacggcc accctgacca tcagcagagc ccaagccggg    240
gatgaggctg actattactg tcaggtgtgg gacagcagca ctgtggtatt cggcggaggg    300
accaagctga ccgtcctagg t    321

<210> SEQ ID NO 230
<211> LENGTH: 33
<212> TYPE: DNA
<213> ORGANISM: Homo sapiens

<400> SEQUENCE: 230
gggggaaaca acattggaag taaaaatgtg cac    33

<210> SEQ ID NO 231
<211> LENGTH: 21
<212> TYPE: DNA
<213> ORGANISM: Homo sapiens

<400> SEQUENCE: 231
agggatagca accggccctc t    21

<210> SEQ ID NO 232
<211> LENGTH: 21
<212> TYPE: DNA
<213> ORGANISM: Homo sapiens

<400> SEQUENCE: 232
caggtgtggg acagcagcac t    21

<210> SEQ ID NO 233
<211> LENGTH: 384
<212> TYPE: DNA
<213> ORGANISM: Homo sapiens

<400> SEQUENCE: 233
gaggtgcagc tggtggagtc tgggggaggc ttggtacagc cggggggtc cctgagactc    60 tcctgtgcag cctctggatt caccttagc agctatgcca tgagctgggt ccgccaggct    120
ccagggaagg ggctggagtg ggtctcaggt attagtggta gtggtggtag aacatactac    180

```
gcagactccg tgaagggccg gttcaccatc tccagagaca attctaagaa cacgctgtat    240
ctgcaaatga acagcctgag agccgaggac acggccgtat attactgtgc gaaagatccc    300
ctcgcattac gagattttga ctggttatcc cccgggcggg actttgatta ctggggccag    360
ggaaccctgg tcaccgtctc gaga                                          384
```

```
<210> SEQ ID NO 234
<211> LENGTH: 15
<212> TYPE: DNA
<213> ORGANISM: Homo sapiens

<400> SEQUENCE: 234
agctatgcca tgagc                                                     15

<210> SEQ ID NO 235
<211> LENGTH: 51
<212> TYPE: DNA
<213> ORGANISM: Homo sapiens

<400> SEQUENCE: 235
ggtattagtg gtagtggtgg tagaacatac tacgcagact ccgtgaaggg c              51

<210> SEQ ID NO 236
<211> LENGTH: 57
<212> TYPE: DNA
<213> ORGANISM: Homo sapiens

<400> SEQUENCE: 236
gatcccctcg cattacgaga ttttgactgg ttatcccccg ggcgggactt tgattac        57

<210> SEQ ID NO 237
<211> LENGTH: 333
<212> TYPE: DNA
<213> ORGANISM: Homo sapiens

<400> SEQUENCE: 237
cagtctgtgt tgacgcagcc gccctcagtg tctgcggccc cgggacagaa ggtcaccatc     60
tcctgctctg gaagccactc caacattgga ataattatg tatcgtggtc ccagcaactc    120
ccaggaacag cccccaaact cctcatttat gacaataata agcgaccctc agggattcct    180
gaccgattct ctggctccaa gtctggcacg tcagccaccc tggacatcgc cgggctccag    240
actggggacg aggccgatta ttactgcgga gcatgggata ccagcctgag ttcttatgtc    300
ttcggagctg gaccaaggt caccgtccta ggt                                  333

<210> SEQ ID NO 238
<211> LENGTH: 39
<212> TYPE: DNA
<213> ORGANISM: Homo sapiens

<400> SEQUENCE: 238
tctggaagcc actccaacat tggaaataat tatgtatcg                            39

<210> SEQ ID NO 239
<211> LENGTH: 21
<212> TYPE: DNA
<213> ORGANISM: Homo sapiens

<400> SEQUENCE: 239
gacaataata agcgaccctc a                                               21
```

<210> SEQ ID NO 240
<211> LENGTH: 27
<212> TYPE: DNA
<213> ORGANISM: Homo sapiens

<400> SEQUENCE: 240
ggagcatggg ataccagcct gagttct                                           27

<210> SEQ ID NO 241
<211> LENGTH: 360
<212> TYPE: DNA
<213> ORGANISM: Homo sapiens

<400> SEQUENCE: 241
gaggtgcagc tggtggagtc tggggctgag gtgaagaagc ctgggtcctc ggtgaaggtc        60
tcctgcaagg cttctggagg caccttcagc agctatgcta tcagctgggt gcgacaggcc      120
cctggacaag gcttgagtg gatgggaggg atcatccta tctttggtac agcaaactac        180
gcacagaagt tccagggcag agtcacgatt accgcgacg aatccacgag cacagcctac       240
atggagctga gcagcctgag atctgaggac acggccgtgt attactgtgc gagagaaggt      300
ttatcgggtg gtacggtat ggacgtctgg ggccaaggga ccacggtcac cgtctcgagc       360

<210> SEQ ID NO 242
<211> LENGTH: 15
<212> TYPE: DNA
<213> ORGANISM: Homo sapiens

<400> SEQUENCE: 242
agctatgcta tcagc                                                        15

<210> SEQ ID NO 243
<211> LENGTH: 51
<212> TYPE: DNA
<213> ORGANISM: Homo sapiens

<400> SEQUENCE: 243
gggatcatcc ctatctttgg tacagcaaac tacgcacaga gttccaggg c                 51

<210> SEQ ID NO 244
<211> LENGTH: 33
<212> TYPE: DNA
<213> ORGANISM: Homo sapiens

<400> SEQUENCE: 244
gaaggtttat cgggtgggta cggtatggac gtc                                    33

<210> SEQ ID NO 245
<211> LENGTH: 336
<212> TYPE: DNA
<213> ORGANISM: Homo sapiens

<400> SEQUENCE: 245
cagtctgtgt tgacgcagcc gccctcagtg tctggggccc cagggcagag ggtcaccatc        60
tcctgcactg ggagcagctc caacatcggg gcaggttatg atgtacactg gtaccagcag      120
cttccaggaa cagcccccaa actcctcatc tatcgtaaca caatcggcc ctcaggggtc       180 cctgaccgat tctctggctc caactctggc acctcagcct ccctggccat cactgggctc      240
cgggctgaag atgaggctga ttattactgc cagtcctatg acagcagcct gagtagttat      300
gtcttcggaa ctgggaccaa ggtcaccgtc ctaggt                                336

<210> SEQ ID NO 246
<211> LENGTH: 42
<212> TYPE: DNA
<213> ORGANISM: Homo sapiens

<400> SEQUENCE: 246
actgggagca gctccaacat cggggcaggt tatgatgtac ac                          42

<210> SEQ ID NO 247
<211> LENGTH: 21
<212> TYPE: DNA
<213> ORGANISM: Homo sapiens

<400> SEQUENCE: 247
cgtaacaaca atcggccctc a                                                 21

<210> SEQ ID NO 248
<211> LENGTH: 27
<212> TYPE: DNA
<213> ORGANISM: Homo sapiens

<400> SEQUENCE: 248
cagtcctatg acagcagcct gagtagt                                           27

<210> SEQ ID NO 249
<211> LENGTH: 375
<212> TYPE: DNA
<213> ORGANISM: Homo sapiens

<400> SEQUENCE: 249
gaggtgcagc tggtggagtc tgggggaggc ttggtacagc ctgggggtc cctgagactc         60 tcctgtgcag cctctggatt cacctttagc agctatgcca tgagctgggt ccgccaggct       120
ccagggaagg ggctggagtg ggtctcagct attagtggta gtggtggtag cacatactac       180
gcagactccg tgaagggccg gttcaccaac tccagagaca attccaagaa cacgctgtat       240
ctgcaaatga acagcctgag agccgaggac acggccgtat attactgtgc gaaagcgtat       300
tacgatattt tgactggtta tttttacaac ggtatggacg tctggggcca agggacaatg       360
gtcaccgtct cgagc                                                        375

<210> SEQ ID NO 250
<211> LENGTH: 15
<212> TYPE: DNA
<213> ORGANISM: Homo sapiens

<400> SEQUENCE: 250
agctatgcca tgagc                                                        15

<210> SEQ ID NO 251
<211> LENGTH: 51
<212> TYPE: DNA
<213> ORGANISM: Homo sapiens

<400> SEQUENCE: 251
gctattagtg gtagtggtgg tagcacatac tacgcagact ccgtgaaggg c                51

<210> SEQ ID NO 252
<211> LENGTH: 48
<212> TYPE: DNA
<213> ORGANISM: Homo sapiens -continued

<400> SEQUENCE: 252
gcgtattacg atattttgac tggttatttt tacaacggta tggacgtc         48

<210> SEQ ID NO 253
<211> LENGTH: 336
<212> TYPE: DNA
<213> ORGANISM: Homo sapiens

<400> SEQUENCE: 253
caggctgtgc tcactcagcc gtcttccgtg tctgggtctc ctggacagtc gatcaccatc    60
tcctgcactg gaaccagcag tgacgttggt ggttatgact atgtctcctg gtaccaacaa   120
cacccaggca aagcccccaa actcatgatt catgatgtca ggaatcggcc ctcagggggtt  180 tctaatcgct tctctggctc caagtttggc aacacggcct ccctgaccat ctctgggctc   240
cagactgagg acgaggctga ttattactgc agttcatata caagcagcag cactcatgtg   300
ctattcggcg gagggaccaa gctgaccgtc ctaggt                             336

<210> SEQ ID NO 254
<211> LENGTH: 42
<212> TYPE: DNA
<213> ORGANISM: Homo sapiens

<400> SEQUENCE: 254
actggaacca gcagtgacgt tggtggttat gactatgtct cc                       42

<210> SEQ ID NO 255
<211> LENGTH: 21
<212> TYPE: DNA
<213> ORGANISM: Homo sapiens

<400> SEQUENCE: 255
gatgtcagga atcggccctc a                                              21

<210> SEQ ID NO 256
<211> LENGTH: 27
<212> TYPE: DNA
<213> ORGANISM: Homo sapiens

<400> SEQUENCE: 256
agttcatata caagcagcag cactcat                                        27

<210> SEQ ID NO 257
<211> LENGTH: 369
<212> TYPE: DNA
<213> ORGANISM: Homo sapiens

<400> SEQUENCE: 257
caggtgcagc tggtgcagtc tggggggaggc ttggtacagc ctggcaggtc cctgagactc   60
tcctgtgcag cctctggatt cacctttgat gattatgcca tgcactgggt ccggcaagct  120
ccagggaagg gcctggagtg ggtctcaggt attagttgga atagtggtag cataggctat   180
gcggactctg tgaagggccg attcaccatc tccagagaca acgccaagag ctccctgtat   240
ctgcaaatga acagtctgag agctgaggac acggccttgt attactgtgc aaaaggccac   300
tctccgtata gcagtggctg gtctgacttt gactactggg gccagggaac cctggtcacc   360
gtctcgagc                                                            369

<210> SEQ ID NO 258
<211> LENGTH: 15

<212> TYPE: DNA
<213> ORGANISM: Homo sapiens

<400> SEQUENCE: 258
gattatgcca tgcac                                                          15

<210> SEQ ID NO 259
<211> LENGTH: 51
<212> TYPE: DNA
<213> ORGANISM: Homo sapiens

<400> SEQUENCE: 259
ggtattagtt ggaatagtgg tagcataggc tatgcggact ctgtgaaggg c                  51

<210> SEQ ID NO 260
<211> LENGTH: 42
<212> TYPE: DNA
<213> ORGANISM: Homo sapiens

<400> SEQUENCE: 260
ggccactctc cgtatagcag tggctggtct gactttgact ac                            42

<210> SEQ ID NO 261
<211> LENGTH: 336
<212> TYPE: DNA
<213> ORGANISM: Homo sapiens

<400> SEQUENCE: 261
cagtctgtgt tgacgcagcc gccctcagtg tctggggccc cagggcagag ggtcaccatc         60
tcctgcaccg ggagcagctc caacatcggg gcaggttatg atgttcagtg gtaccagcag        120
ctcccaggaa cagcccccaa actcctcatc catgctaaca gaatcggccc tcagggggtc        180
cctgaccgaa tctctggctc caagtctggc accacagcct ccctggccat cactgggttc        240
caggctgagg atgaggctga ttattactgc cagtcctatg acagcagcct gactggttat        300
gtcttcggaa ctgggaccaa ggtcaccgtc ctaggt                                  336

<210> SEQ ID NO 262
<211> LENGTH: 42
<212> TYPE: DNA
<213> ORGANISM: Homo sapiens

<400> SEQUENCE: 262
accgggagca gctccaacat cggggcaggt tatgatgttc ag                            42

<210> SEQ ID NO 263
<211> LENGTH: 21
<212> TYPE: DNA
<213> ORGANISM: Homo sapiens

<400> SEQUENCE: 263
gctaacaaga atcggccctc a                                                   21

<210> SEQ ID NO 264
<211> LENGTH: 27
<212> TYPE: DNA
<213> ORGANISM: Homo sapiens

<400> SEQUENCE: 264
cagtcctatg acagcagcct gactggt                                             27

<210> SEQ ID NO 265

```
<211> LENGTH: 375
<212> TYPE: DNA
<213> ORGANISM: Homo sapiens

<400> SEQUENCE: 265
gaggtgcagc tggtggagtc tgggggaggc ttggtacagc ctggcaggtc cctgagactc      60
tcctgtgcag cctctggatt cacctttgct gattatgcca tgcactgggt ccggcaagct     120
ccagggaagg gcctggagtg ggtctcaagt attagttgga atagtggtag catagcctat     180
gcggactctg tgaagggccg attcaccatc tccagagaca acgccaagaa ctccctgtat     240
ctgcaaatga acagtctgag agctgaggac acggccttgt attactgtgc aaaagcctca     300
gcagctggta ctgaatacta ccactactac ggtatggacg tctggggcca agggaccacg     360
gtcaccgtct cgaga                                                       375

<210> SEQ ID NO 266
<211> LENGTH: 15
<212> TYPE: DNA
<213> ORGANISM: Homo sapiens

<400> SEQUENCE: 266
gattatgcca tgcac                                                        15

<210> SEQ ID NO 267
<211> LENGTH: 51
<212> TYPE: DNA
<213> ORGANISM: Homo sapiens

<400> SEQUENCE: 267
agtattagtt ggaatagtgg tagcatagcc tatgcggact ctgtgaaggg c                51

<210> SEQ ID NO 268
<211> LENGTH: 48
<212> TYPE: DNA
<213> ORGANISM: Homo sapiens

<400> SEQUENCE: 268
gcctcagcag ctggtactga atactaccac tactacggta tggacgtc                    48

<210> SEQ ID NO 269
<211> LENGTH: 333
<212> TYPE: DNA
<213> ORGANISM: Homo sapiens

<400> SEQUENCE: 269
tcctatgtgc tgactcagcc accctcagcg tctgggaccc ccgggcagag ggtcaccatc      60
tcttgttctg gaagcagctc caacatcgga agtaatacta aaactggta ccagcagctc      120 ccaggaacgg cccccaaact cctcatctat aataatcatc agcggccctc agggggtccct    180 gaccgattct ctggctcaaa gtctggcacc tcagcctccc tggccatcag tgggctccag    240
tctgcggatg aggctgatta ttactgtgga gcgtggaatg acagcctgaa tgtctatgtc     300
ttcggaactg ggaccaaggt caccgtccta ggt                                  333

<210> SEQ ID NO 270
<211> LENGTH: 39
<212> TYPE: DNA
<213> ORGANISM: Homo sapiens

<400> SEQUENCE: 270
tctggaagca gctccaacat cggaagtaat actataaac                              39
```

<210> SEQ ID NO 271
<211> LENGTH: 21
<212> TYPE: DNA
<213> ORGANISM: Homo sapiens

<400> SEQUENCE: 271
aataatcatc agcggccctc a                                              21

<210> SEQ ID NO 272
<211> LENGTH: 27
<212> TYPE: DNA
<213> ORGANISM: Homo sapiens

<400> SEQUENCE: 272
ggagcgtgga atgacagcct gaatgtc                                        27

<210> SEQ ID NO 273
<211> LENGTH: 372
<212> TYPE: DNA
<213> ORGANISM: Homo sapiens

<400> SEQUENCE: 273
caggtgcagc tggtgcagtc tggagctgag gtgaagaagc ctggggcctc agtgaaggtc     60
tcctgcaagg cttctggtta cacctttacc agctatggta tcagctgggt gcgacaggcc   120
cctggacaag ggcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gacagcagca   300
agcctaaagt attactatga tagtagtggt tattactact ggggccaggg aaccctggtc   360
accgtctcga ga                                                       372

<210> SEQ ID NO 274
<211> LENGTH: 15
<212> TYPE: DNA
<213> ORGANISM: Homo sapiens

<400> SEQUENCE: 274
agctatggta tcagc                                                     15

<210> SEQ ID NO 275
<211> LENGTH: 51
<212> TYPE: DNA
<213> ORGANISM: Homo sapiens

<400> SEQUENCE: 275
tggatcagcg cttacaatgg taacacaaac tatgcacaga agctccaggg c              51

<210> SEQ ID NO 276
<211> LENGTH: 45
<212> TYPE: DNA
<213> ORGANISM: Homo sapiens

<400> SEQUENCE: 276
gcagcaagcc taaagtatta ctatgatagt agtggttatt actac                     45

<210> SEQ ID NO 277
<211> LENGTH: 330
<212> TYPE: DNA
<213> ORGANISM: Homo sapiens

```
<400> SEQUENCE: 277
tcttctgagc tgactcagga ccctgctgtg tctgtggcct tgggacagac agtcaggatc    60
acatgccaag gagacagcct cagaagctat tatgcaagct ggtaccagca gaagccagga   120
caggcccctg tacttgtcat ctctggtaaa aacaaccggc cctcagggat cccagaccga   180
ttctctggct ccagctcagg agacacagct tccttgacca tcactggggc tcaggcggaa   240
gatgaggcta actattactg taactctcgg gacagcagtg gttacccctc ttgggtgttc   300
ggcggaggga ccaagctgac cgtcctaggc                                    330

<210> SEQ ID NO 278
<211> LENGTH: 33
<212> TYPE: DNA
<213> ORGANISM: Homo sapiens

<400> SEQUENCE: 278
caaggagaca gcctcagaag ctattatgca agc                                33

<210> SEQ ID NO 279
<211> LENGTH: 21
<212> TYPE: DNA
<213> ORGANISM: Homo sapiens

<400> SEQUENCE: 279
ggtaaaaaca accggccctc a                                             21

<210> SEQ ID NO 280
<211> LENGTH: 30
<212> TYPE: DNA
<213> ORGANISM: Homo sapiens

<400> SEQUENCE: 280
aactctcggg acagcagtgg ttacccctct                                    30

<210> SEQ ID NO 281
<211> LENGTH: 390
<212> TYPE: DNA
<213> ORGANISM: Homo sapiens

<400> SEQUENCE: 281
caggtgcagc tggtgcagtc tggggctgag gtgaagaagc ctggggcctc agtgaaggtc    60
tcctgcaagg gttctggtta cgttttttaac agttatggta ttacctgggt gcgacaggcc   120
ccaggacaag gcttgagtg gatgggatgg atcagcgctt acaatggtta cacagactat    180
gcacagaagg tccagggcag agtcaccatg accacagaga catccacgag cacagcctac    240
atggagctga ggagcctgag atctgacgac acggccgttt attattgtgc gagggattac    300
tatgatagta gtacttatta ctccagtgat tacttccagt actacggtat ggacgtctgg    360
ggccaaggga ccacggtcac cgtctcgagc                                    390

<210> SEQ ID NO 282
<211> LENGTH: 15
<212> TYPE: DNA
<213> ORGANISM: Homo sapiens

<400> SEQUENCE: 282
agttatggta ttacc                                                    15

<210> SEQ ID NO 283
<211> LENGTH: 51
```

```
<212> TYPE: DNA
<213> ORGANISM: Homo sapiens

<400> SEQUENCE: 283
tggatcagcg cttacaatgg ttacacagac tatgcacaga aggtccaggg c          51

<210> SEQ ID NO 284
<211> LENGTH: 63
<212> TYPE: DNA
<213> ORGANISM: Homo sapiens

<400> SEQUENCE: 284
gattactatg atagtagtac ttattactcc agtgattact tccagtacta cggtatggac    60
gtc                                                                  63

<210> SEQ ID NO 285
<211> LENGTH: 333
<212> TYPE: DNA
<213> ORGANISM: Homo sapiens

<400> SEQUENCE: 285
caggctgtgc tgactcagcc ggcttccgtg tctgggtctc ctggacagtc gatcaccatc    60
tcctgcactg gaaccagcag tgacgttggt gcttataact atgtctcctg gtaccaacaa   120
cacccaggca aagcccccaa actcatgatt tctgatgtca gtaggcggcc ctcaggggtt   180
tctaatcgct tctctggctc caagtctggc aacacggcct ccctgaccat ctctgggctc   240
cagactgagg acgaggctga ttattactgc agctcatata caagcagcaa cactgtctta   300
ttcggcggag ggaccaagct gaccgtccta ggt                                333

<210> SEQ ID NO 286
<211> LENGTH: 42
<212> TYPE: DNA
<213> ORGANISM: Homo sapiens

<400> SEQUENCE: 286
actggaacca gcagtgacgt tggtgcttat aactatgtct cc                      42

<210> SEQ ID NO 287
<211> LENGTH: 21
<212> TYPE: DNA
<213> ORGANISM: Homo sapiens

<400> SEQUENCE: 287
gatgtcagta ggcggccctc a                                             21

<210> SEQ ID NO 288
<211> LENGTH: 24
<212> TYPE: DNA
<213> ORGANISM: Homo sapiens

<400> SEQUENCE: 288
agctcatata caagcagcaa cact                                          24

<210> SEQ ID NO 289
<211> LENGTH: 333
<212> TYPE: DNA
<213> ORGANISM: Homo sapiens

<400> SEQUENCE: 289
caggctgtgc tgactcagcc ggcttccgtg tctgggtctc ctggacagtc gatcaccatc    60
```

```
tcctgcactg gaaccagcag tgacgttggt gcttataact atgtctcctg gtaccaacaa      120
cacccaggca agcccccaa actcatgatt tctgatgtca gtaggcggcc ctcagggggtt      180 tctaatcgct tctctggctc caagtctggc aacacggcct ccctgaccat ctctgggctc      240
cagactgagg acgaggctga ttattactgc agctcatata caagcagcaa cactgtctta      300
ttcggcggag ggaccaagct gaccgtccta ggt                                   333

<210> SEQ ID NO 290
<211> LENGTH: 15
<212> TYPE: DNA
<213> ORGANISM: Homo sapiens

<400> SEQUENCE: 290
aactactgga tcggc                                                        15

<210> SEQ ID NO 291
<211> LENGTH: 51
<212> TYPE: DNA
<213> ORGANISM: Homo sapiens

<400> SEQUENCE: 291
atcatctatc ctggtgactc tgataccagg tacagtccgt cattccaagg c                51

<210> SEQ ID NO 292
<211> LENGTH: 39
<212> TYPE: DNA
<213> ORGANISM: Homo sapiens

<400> SEQUENCE: 292
cggggctccc gtagtagtgg tgaagatgct tttgaagtc                              39

<210> SEQ ID NO 293
<211> LENGTH: 330
<212> TYPE: DNA
<213> ORGANISM: Homo sapiens

<400> SEQUENCE: 293
tcctatgagc tgactcagcc accctcagtg tcagtggccc caggaaagac ggccacaatt       60
acgtgtgggg gcgacaacat tggaagtaag agtgtgcact ggtaccagca gaggccaggc      120
caggcccctg tgttggtcat caattatgat agtgaccggc cctcagggat ccctgagcga      180
ttctctggct ccaactctgg gaacacggcc accctgacca tcagcagggt cgaagccggg      240
gatgaggccg actattactg tcaggtggaa gatcgccgtg gtggttatca tgtggtattc      300
ggcggaggga ccaagctgac cgtcctaggt                                       330

<210> SEQ ID NO 294
<211> LENGTH: 33
<212> TYPE: DNA
<213> ORGANISM: Homo sapiens

<400> SEQUENCE: 294
gggggcgaca acattggaag taagagtgtg cac                                    33

<210> SEQ ID NO 295
<211> LENGTH: 21
<212> TYPE: DNA
<213> ORGANISM: Homo sapiens

<400> SEQUENCE: 295
tatgatagtg accggcccctc a                                                21
```

```
<210> SEQ ID NO 296
<211> LENGTH: 30
<212> TYPE: DNA
<213> ORGANISM: Homo sapiens

<400> SEQUENCE: 296
caggtggaag atcgccgtgg tggttatcat                                    30

<210> SEQ ID NO 297
<211> LENGTH: 375
<212> TYPE: DNA
<213> ORGANISM: Homo sapiens

<400> SEQUENCE: 297
caggtgcagc tggtgcagtc tggggggaggc ttggtccagc ctggggggtc cctgagactc    60
tcctgtgcag cctctggatt caccgtcagt agcaactaca tgagctgggt ccgccaggct   120
ccagggaagg ggctggagtg ggtctcagtt atttatagcg gtggtagcac atactacgca   180
gactccgtga aggcagatt caccatctcc agagacaatt ccaagaacac gctgtatctt   240
caaatgaaca gcctgagagc cgaggacacg gctgtgtatt actgtgcgag gaaggatat   300 tgtagtggtg gtagctgcta ctcctacggc gcttttgata tctggggcca agggaccacg   360
gtcaccgtct cgagc                                                   375

<210> SEQ ID NO 298
<211> LENGTH: 15
<212> TYPE: DNA
<213> ORGANISM: Homo sapiens

<400> SEQUENCE: 298
agcaactaca tgagc                                                    15

<210> SEQ ID NO 299
<211> LENGTH: 48
<212> TYPE: DNA
<213> ORGANISM: Homo sapiens

<400> SEQUENCE: 299
gttatttata gcggtggtag cacatactac gcagactccg tgaagggc                48

<210> SEQ ID NO 300
<211> LENGTH: 51
<212> TYPE: DNA
<213> ORGANISM: Homo sapiens

<400> SEQUENCE: 300
gaaggatatt gtagtggtgg tagctgctac tcctacggcg cttttgatat c            51

<210> SEQ ID NO 301
<211> LENGTH: 375
<212> TYPE: DNA
<213> ORGANISM: Homo sapiens

<400> SEQUENCE: 301
caggtgcagc tggtgcagtc tggggggaggc ttggtccagc ctggggggtc cctgagactc    60
tcctgtgcag cctctggatt caccgtcagt agcaactaca tgagctgggt ccgccaggct   120
ccagggaagg ggctggagtg ggtctcagtt atttatagcg gtggtagcac atactacgca   180
gactccgtga aggcagatt caccatctcc agagacaatt ccaagaacac gctgtatctt   240
```

```
caaatgaaca gcctgagagc cgaggacacg gctgtgtatt actgtgcgag ggaaggatat    300
tgtagtggtg gtagctgcta ctcctacggc gcttttgata tctggggcca agggaccacg    360
gtcaccgtct cgagc                                                     375
```

<210> SEQ ID NO 302
<211> LENGTH: 33
<212> TYPE: DNA
<213> ORGANISM: Homo sapiens

<400> SEQUENCE: 302

```
cgggcgagtc agaatattgc caactggtta gcc                                  33
```

<210> SEQ ID NO 303
<211> LENGTH: 21
<212> TYPE: DNA
<213> ORGANISM: Homo sapiens

<400> SEQUENCE: 303

```
gctgcatcca atttgcaaag t                                               21
```

<210> SEQ ID NO 304
<211> LENGTH: 24
<212> TYPE: DNA
<213> ORGANISM: Homo sapiens

<400> SEQUENCE: 304

```
caacagggta acagtttccc tcgg                                            24
```

<210> SEQ ID NO 305
<211> LENGTH: 390
<212> TYPE: DNA
<213> ORGANISM: Homo sapiens

<400> SEQUENCE: 305

```
caggtgcagc tggtgcagtc tggagctgag gtgaagaagc ctggggcctc agtgaaggtc     60
tcctgcaagg cttctggtta cgttttaac agttatggta ttacctgggt gcgacaggcc    120
ccaggacaag gcttgagtg gatgggatgg atcagcgctt acaatggtta cacagactat    180
gcacagaagg tccagggcag agtcaccatg accacagaga catccacgag cacagcctac    240
atggagctga ggagcctgag atctgacgac acggccgttt attattgtgc gagggactac    300
tatgatagta gtacttatta ctccagtgat tacttcaagt actacggtat ggacgtctgg    360
ggccaaggga ccacggtcac cgtctcgagc                                    390
```

<210> SEQ ID NO 306
<211> LENGTH: 15
<212> TYPE: DNA
<213> ORGANISM: Homo sapiens

<400> SEQUENCE: 306

```
agttatggta ttacc                                                      15
```

<210> SEQ ID NO 307
<211> LENGTH: 51
<212> TYPE: DNA
<213> ORGANISM: Homo sapiens

<400> SEQUENCE: 307

```
tggatcagcg cttacaatgg ttacacagac tatgcacaga aggtccaggg c              51
```

```
<210> SEQ ID NO 308
<211> LENGTH: 63
<212> TYPE: DNA
<213> ORGANISM: Homo sapiens

<400> SEQUENCE: 308
gactactatg atagtagtac ttattactcc agtgattact tcaagtacta cggtatggac    60
gtc                                                                  63

<210> SEQ ID NO 309
<211> LENGTH: 333
<212> TYPE: DNA
<213> ORGANISM: Homo sapiens

<400> SEQUENCE: 309
caggctgtgc tcactcagcc gtcttccgtg tctgggtctc ctggacagtc gatcaccatc    60
tcctgctctg gaaccagcag tgacgttggt gcttataact atgtctcctg gtaccaacaa   120
cacccaggca aagccccag actcctgact tttgatgtca ataggcgtcc ctcagggtct    180
tctagtcgct tctctggctc caagtctggc aacacggcct ccctgactat ctctgggctc   240
caggctgagg acgaggctga ctattactgc agttcatata caaacagcaa cactgtcgtg   300
ttcggcggag ggaccaggct gaccgtccta agt                                333

<210> SEQ ID NO 310
<211> LENGTH: 42
<212> TYPE: DNA
<213> ORGANISM: Homo sapiens

<400> SEQUENCE: 310
tctggaacca gcagtgacgt tggtgcttat aactatgtct cc                       42

<210> SEQ ID NO 311
<211> LENGTH: 21
<212> TYPE: DNA
<213> ORGANISM: Homo sapiens

<400> SEQUENCE: 311
gatgtcaata ggcgtccctc a                                              21

<210> SEQ ID NO 312
<211> LENGTH: 24
<212> TYPE: DNA
<213> ORGANISM: Homo sapiens

<400> SEQUENCE: 312
agttcatata caaacagcaa cact                                           24

<210> SEQ ID NO 313
<211> LENGTH: 381
<212> TYPE: DNA
<213> ORGANISM: Homo sapiens

<400> SEQUENCE: 313
caggtgcagc tgcaggagtc ggggccagga ctggtgaagc cgtcggagac cctggccctc    60
acctgcactg tctctggtgg ctccatcagt aactactact ggagttggat ccggcagccc   120
ccagggaagg gactggagtg gattgggtat atctatgaca ttgagaatac caactacaac   180
ccctccctca agagtcgagt caccatatca gtggacacgt ccaagaacca gttctccctg   240
aagttgagct ctgtgaccgc tgatgacacg gccgtatatt actgtgcgag agattcaagg   300
```

```
gtcattcgat ttttggaggg gtactcctac tactacggtg tggacgtctg gggccaaggg        360
acaatggtca ccgtctcgag c                                                 381
```

<210> SEQ ID NO 314
<211> LENGTH: 15
<212> TYPE: DNA
<213> ORGANISM: Homo sapiens

<400> SEQUENCE: 314

```
aactactact ggagt                                                         15
```

<210> SEQ ID NO 315
<211> LENGTH: 48
<212> TYPE: DNA
<213> ORGANISM: Homo sapiens

<400> SEQUENCE: 315

```
tatatctatg acattgagaa taccaactac aacccctccc tcaagagt                     48
```

<210> SEQ ID NO 316
<211> LENGTH: 57
<212> TYPE: DNA
<213> ORGANISM: Homo sapiens

<400> SEQUENCE: 316

```
gattcaaggg tcattcgatt tttggagggg tactcctact actacggtgt ggacgtc           57
```

<210> SEQ ID NO 317
<211> LENGTH: 333
<212> TYPE: DNA
<213> ORGANISM: Homo sapiens

<400> SEQUENCE: 317

```
tcctatgagc tgactcagcc accctcagcg tctgggaccc ccgggcagac ggtcatcatc        60
tcttgttctg gaagcaggtc caacatcgga ggtcatggtg taaattggca ccagcaggtt       120
ccaggaacgg cccccaaact cctcatctac cgtaatgatc gccggccctc aggggtcccg       180
gaccgattct ctggctccaa gtctggcact tcagcctccc tggtcatcag tggactgcag       240
tttgaggatg aggctgatta ttactgtgta gcatgggaag acagcctgga tggtccggtg       300
ttcggcggag ggaccaagct gactgtccta ggt                                    333
```

<210> SEQ ID NO 318
<211> LENGTH: 39
<212> TYPE: DNA
<213> ORGANISM: Homo sapiens

<400> SEQUENCE: 318

```
tctggaagca ggtccaacat cggaggtcat ggtgtaaat                               39
```

<210> SEQ ID NO 319
<211> LENGTH: 21
<212> TYPE: DNA
<213> ORGANISM: Homo sapiens

<400> SEQUENCE: 319

```
cgtaatgatc gccggccctc a                                                  21
```

<210> SEQ ID NO 320
<211> LENGTH: 27
<212> TYPE: DNA
<213> ORGANISM: Homo sapiens

<400> SEQUENCE: 320
gtagcatggg aagacagcct ggatggt                                          27

<210> SEQ ID NO 321
<211> LENGTH: 345
<212> TYPE: DNA
<213> ORGANISM: Homo sapiens

<400> SEQUENCE: 321
gaggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcaact attagtggta gtggtggtag tacatactac       180
gcagactccg tgaagggccg attcaccatc tccagagaca attccaagaa cacgctatat     240
cttcaaatga acagcctgag agccgaggac acggccgtct attattgtgc gagaggtata    300
gtggctacta gctggggcca gggaaccctg gtcaccgtct cgaga                   345

<210> SEQ ID NO 322
<211> LENGTH: 15
<212> TYPE: DNA
<213> ORGANISM: Homo sapiens

<400> SEQUENCE: 322
agctatgcca tgagc                                                       15

<210> SEQ ID NO 323
<211> LENGTH: 51
<212> TYPE: DNA
<213> ORGANISM: Homo sapiens

<400> SEQUENCE: 323
actattagtg gtagtggtgg tagtacatac tacgcagact ccgtgaaggg c                51

<210> SEQ ID NO 324
<211> LENGTH: 18
<212> TYPE: DNA
<213> ORGANISM: Homo sapiens

<400> SEQUENCE: 324
ggtatagtgg ctactagc                                                    18

<210> SEQ ID NO 325
<211> LENGTH: 324
<212> TYPE: DNA
<213> ORGANISM: Homo sapiens

<400> SEQUENCE: 325
tcctatgagc tgactcagcc accctcagtg tcagtggccc caggacagac ggccagaatt      60
acctgtgggg gaaacaagat tggaagcaaa agtgtgcact ggtaccagca gaagcaaggc    120
caggcccctg tattggtcat ctatttggat cgcgaccggc cctcagggat ccctgaacga    180
ttctctggct ccaactctgg gaacacggcc accctgacca tcaccagggt cgaagccgag    240
gatgaggccg actattattg tcacctgtgg gatagtggta gtgatcaggt gttcggcgga    300
gggaccaaac tgaccgtcct gggt                                          324

<210> SEQ ID NO 326
<211> LENGTH: 33
<212> TYPE: DNA

<213> ORGANISM: Homo sapiens

<400> SEQUENCE: 326
gggggaaaca agattggaag caaaagtgtg cac    33

<210> SEQ ID NO 327
<211> LENGTH: 21
<212> TYPE: DNA
<213> ORGANISM: Homo sapiens

<400> SEQUENCE: 327
ttggatcgcg accggccctc a    21

<210> SEQ ID NO 328
<211> LENGTH: 24
<212> TYPE: DNA
<213> ORGANISM: Homo sapiens

<400> SEQUENCE: 328
cacctgtggg atagtggtag tgat    24

<210> SEQ ID NO 329
<211> LENGTH: 342
<212> TYPE: DNA
<213> ORGANISM: Homo sapiens

<400> SEQUENCE: 329
gaggtgcagc tggtggagtc tggggggaggc gtagtacagc ctggggggtc cctgagactc    60
tcctgtgcag cctcaggatt caactttgat gtttatggca tgaactgggt ccgtcaagtt   120
ccagggaagg gtctggagtg ggtctctctt atcaacgggg atggcggttt aagatattac   180
gcagactctg tgaagggccg attcaccgtc tccagagaca cagcaggaa ttccctatat   240
ctgcaaatga acagtctcag aagtgaggac accgccctgt attattgtgt aaagggaaac   300
ttccagcagt ggggccaggg aaccctggtc accgtctcga ga    342

<210> SEQ ID NO 330
<211> LENGTH: 15
<212> TYPE: DNA
<213> ORGANISM: Homo sapiens

<400> SEQUENCE: 330
gtttatggca tgaac    15

<210> SEQ ID NO 331
<211> LENGTH: 51
<212> TYPE: DNA
<213> ORGANISM: Homo sapiens

<400> SEQUENCE: 331
cttatcaacg gggatggcgg tttaagatat tacgcagact ctgtgaaggg c    51

<210> SEQ ID NO 332
<211> LENGTH: 15
<212> TYPE: DNA
<213> ORGANISM: Homo sapiens

<400> SEQUENCE: 332
ggaaacttcc agcag    15

<210> SEQ ID NO 333
<211> LENGTH: 327

<212> TYPE: DNA
<213> ORGANISM: Homo sapiens

<400> SEQUENCE: 333

```
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca gctgaccgt cctaggt                                         327
```

<210> SEQ ID NO 334
<211> LENGTH: 33
<212> TYPE: DNA
<213> ORGANISM: Homo sapiens

<400> SEQUENCE: 334

```
gggggaaaca acattggaag taaaagtgtg cac                                  33
```

<210> SEQ ID NO 335
<211> LENGTH: 21
<212> TYPE: DNA
<213> ORGANISM: Homo sapiens

<400> SEQUENCE: 335

```
tatgatagcg accggccctc a                                               21
```

<210> SEQ ID NO 336
<211> LENGTH: 27
<212> TYPE: DNA
<213> ORGANISM: Homo sapiens

<400> SEQUENCE: 336

```
caggtgtggg atagtagtag tgatcat                                         27
```

<210> SEQ ID NO 337
<211> LENGTH: 345
<212> TYPE: DNA
<213> ORGANISM: Homo sapiens

<400> SEQUENCE: 337

```
gaggtgcagc tggtggagtc tggggggaggc ttggtacagc ctggggggtc cctgagactc    60
tcctgtgcag cctctggatt caccttttgat gattatgcca tgcactgggt ccgtcaagct   120
ccagggaagg gtctggagtg ggtctctctt attagtgggg atggtggtag cacatactat   180
gcagactctg tgaaggaccg attcaccatc tccagagaca acagcaaaaa ctccctgtat   240
ctgcaaatga acagcctgag agccgaggac acggccgtgt attactgtgc gaggggaaac   300
tactttgact actgggggcca gggaaccctg gtcaccgtct cgaga                   345
```

<210> SEQ ID NO 338
<211> LENGTH: 15
<212> TYPE: DNA
<213> ORGANISM: Homo sapiens

<400> SEQUENCE: 338

```
gattatgcca tgcac                                                      15
```

<210> SEQ ID NO 339

```
<211> LENGTH: 51
<212> TYPE: DNA
<213> ORGANISM: Homo sapiens

<400> SEQUENCE: 339
cttattagtg gggatggtgg tagcacatac tatgcagact ctgtgaagga c            51

<210> SEQ ID NO 340
<211> LENGTH: 18
<212> TYPE: DNA
<213> ORGANISM: Homo sapiens

<400> SEQUENCE: 340
ggaaactact ttgactac                                                 18

<210> SEQ ID NO 341
<211> LENGTH: 318
<212> TYPE: DNA
<213> ORGANISM: Homo sapiens

<400> SEQUENCE: 341
tcctatgagc tgactcagcc actctcagtg tcagtggccc tgggacagac ggccaggatt   60
acctgtgggg gaaacaacat tggaagtaaa aatgtgcact ggtaccagca gaagccaggc  120
caggcccctg tgctggtcat ctataggggat agcaaccggc cctctgggat ccctgagcga  180
ttctctggct ccaactcggg gaacacggcc accctgacca tcagcagagc ccaagccggg  240
gatgaggctg actattactg tcaggtgtgg acagcagcg tggtattcgg cggagggacc   300
aagctgaccg tcctaggt                                                318

<210> SEQ ID NO 342
<211> LENGTH: 33
<212> TYPE: DNA
<213> ORGANISM: Homo sapiens

<400> SEQUENCE: 342
gggggaaaca acattggaag taaaaatgtg cac                               33

<210> SEQ ID NO 343
<211> LENGTH: 21
<212> TYPE: DNA
<213> ORGANISM: Homo sapiens

<400> SEQUENCE: 343
agggatagca accggccctc t                                            21

<210> SEQ ID NO 344
<211> LENGTH: 18
<212> TYPE: DNA
<213> ORGANISM: Homo sapiens

<400> SEQUENCE: 344
caggtgtggg acagcagc                                                18

<210> SEQ ID NO 345
<211> LENGTH: 366
<212> TYPE: DNA
<213> ORGANISM: Homo sapiens

<400> SEQUENCE: 345
gaggtgcagc tggtggagtc tgggggaggc ttggtacagc ctggggggtc cctgagactc   60
tcctgtgcag cctctggatt caccttcagt agctatagca tgaactgggt ccgccaggct  120
```

```
ccagggaagg ggctggagtg ggtttcatac attagtagta gtagtagtac catatactac    180
gcagactctg tgaagggccg attcaccatc tccagagaca atgccaagaa ctcactgtat    240
ctgcagatga acagcctgag agacgaggac acggctgtgt attactgtgc gagagtgatg    300
ccgagttact actactacta cggtatggac gtctggggcc aagggaccac ggtcaccgtc    360
tcgaga                                                               366
```

<210> SEQ ID NO 346
<211> LENGTH: 15
<212> TYPE: DNA
<213> ORGANISM: Homo sapiens

<400> SEQUENCE: 346

```
agctatagca tgaac                                                     15
```

<210> SEQ ID NO 347
<211> LENGTH: 51
<212> TYPE: DNA
<213> ORGANISM: Homo sapiens

<400> SEQUENCE: 347

```
tacattagta gtagtagtag taccatatac tacgcagact ctgtgaaggg c             51
```

<210> SEQ ID NO 348
<211> LENGTH: 39
<212> TYPE: DNA
<213> ORGANISM: Homo sapiens

<400> SEQUENCE: 348

```
gtgatgccga gttactacta ctactacggt atggacgtc                           39
```

<210> SEQ ID NO 349
<211> LENGTH: 333
<212> TYPE: DNA
<213> ORGANISM: Homo sapiens

<400> SEQUENCE: 349

```
aattttatgc tgactcagcc ccactctgtg tcggagtctc cggggaagac ggtaaccatc    60
tcctgcaccg gcagcagtgg cagcattgcc agcaactatg tgcagtggta ccagcagcgc   120
ccgggcagtg cccccaccac tgtgatctat gaggatagta aaagaccctc tggggtccct   180
gatcggttct ctggctccat cgacagctcc tccaactctg cctccctcac catctctgga   240
ctgaagactc aggacgaggc tgactactac tgtcagtctt atgatggcgt caattgggtg   300
ttcggcggag ggaccaagct gaccgtccta ggt                                333
```

<210> SEQ ID NO 350
<211> LENGTH: 39
<212> TYPE: DNA
<213> ORGANISM: Homo sapiens

<400> SEQUENCE: 350

```
accggcagca gtggcagcat tgccagcaac tatgtgcag                           39
```

<210> SEQ ID NO 351
<211> LENGTH: 21
<212> TYPE: DNA
<213> ORGANISM: Homo sapiens

<400> SEQUENCE: 351
gaggatagtg aaagaccctc t                                            21

<210> SEQ ID NO 352
<211> LENGTH: 21
<212> TYPE: DNA
<213> ORGANISM: Homo sapiens

<400> SEQUENCE: 352
cagtcttatg atggcgtcaa t                                            21

<210> SEQ ID NO 353
<211> LENGTH: 342
<212> TYPE: DNA
<213> ORGANISM: Homo sapiens

<400> SEQUENCE: 353
gaggtgcagc tggtggagtc tgggggaggc gtggtccagc ctggggaggtc cctgagactc    60 tcctgtgcag cctctggatt caccttcagt agctatggca tgcactgggt ccgccaggct   120
ccaggcaagg ggctggagtg ggtggcagtt atatcatatg atggaagtaa taatactat    180 gcagactccg tgaagggccg attcaccatc tccagagaca attccaagaa cacgctgtat   240
ctgcaaatga acagcctgag agctgaggac acggctgtgt attactgtgc ggactacggt   300
atggacgtct ggggccaagg gaccacggtc accgtctcga ga                     342

<210> SEQ ID NO 354
<211> LENGTH: 15
<212> TYPE: DNA
<213> ORGANISM: Homo sapiens

<400> SEQUENCE: 354
agctatggca tgcac                                                   15

<210> SEQ ID NO 355
<211> LENGTH: 51
<212> TYPE: DNA
<213> ORGANISM: Homo sapiens

<400> SEQUENCE: 355
gttatatcat atgatggaag taataaatac tatgcagact ccgtgaaggg c            51

<210> SEQ ID NO 356
<211> LENGTH: 15
<212> TYPE: DNA
<213> ORGANISM: Homo sapiens

<400> SEQUENCE: 356
tacggtatgg acgtc                                                   15

<210> SEQ ID NO 357
<211> LENGTH: 321
<212> TYPE: DNA
<213> ORGANISM: Homo sapiens

<400> SEQUENCE: 357
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggactgat ttcactctca ccatcagcag tctgcaacct   240
gaagattttg caacttacta ctgtcaacag agttacagta ccccgtgac gttcggccaa   300 gggaccaagg tggaaatcaa a                                          321

<210> SEQ ID NO 358
<211> LENGTH: 33
<212> TYPE: DNA
<213> ORGANISM: Homo sapiens

<400> SEQUENCE: 358
cgggcaagtc agagcattag cagctattta aat                              33

<210> SEQ ID NO 359
<211> LENGTH: 21
<212> TYPE: DNA
<213> ORGANISM: Homo sapiens

<400> SEQUENCE: 359
gctgcatcca gtttgcaaag t                                           21

<210> SEQ ID NO 360
<211> LENGTH: 21
<212> TYPE: DNA
<213> ORGANISM: Homo sapiens

<400> SEQUENCE: 360
caacagagtt acagtacccc c                                           21

<210> SEQ ID NO 361
<211> LENGTH: 360
<212> TYPE: DNA
<213> ORGANISM: Homo sapiens

<400> SEQUENCE: 361
caggtgcagc tgcaggagtc gggcccggga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagat   300
cgggggactg gggatgcttt tgatatctgg ggccaaggga caatggtcac cgtctcgaga   360

<210> SEQ ID NO 362
<211> LENGTH: 21
<212> TYPE: DNA
<213> ORGANISM: Homo sapiens

<400> SEQUENCE: 362
agtggtggtt actactggag c                                           21

<210> SEQ ID NO 363
<211> LENGTH: 48
<212> TYPE: DNA
<213> ORGANISM: Homo sapiens

<400> SEQUENCE: 363
tacatctatt acagtgggag cacctactac aacccgtccc tcaagagt               48

<210> SEQ ID NO 364
<211> LENGTH: 30
<212> TYPE: DNA
<213> ORGANISM: Homo sapiens

<400> SEQUENCE: 364
gatcggggga ctggggatgc ttttgatatc        30

<210> SEQ ID NO 365
<211> LENGTH: 333
<212> TYPE: DNA
<213> ORGANISM: Homo sapiens

<400> SEQUENCE: 365
cagtctgtgt tgacgcagcc gccctcggtg tctggggccc cccggcagac ggtcaccatc        60
tcctgctctg ggagcagctc caacatcgga caaaattctg ttacctggta ccagcgcctc       120
ccgggtgagg ctcccaaact cctcatctac tatgatgatc tcttgcactc aggagtctct       180
gaccgattct ctggctccaa gtctggcacc tcagcctcac tggccatcag tggactccag       240
tctgaggatg aggctgagta ctactgtgcg tcatgggatg acagcctgaa aggtccggta       300
ttcggcggag ggaccaaact gaccgtccta ggt                                    333

<210> SEQ ID NO 366
<211> LENGTH: 39
<212> TYPE: DNA
<213> ORGANISM: Homo sapiens

<400> SEQUENCE: 366
tctgggagca gctccaacat cggacaaaat tctgttacc        39

<210> SEQ ID NO 367
<211> LENGTH: 21
<212> TYPE: DNA
<213> ORGANISM: Homo sapiens

<400> SEQUENCE: 367
tatgatgatc tcttgcactc a        21

<210> SEQ ID NO 368
<211> LENGTH: 27
<212> TYPE: DNA
<213> ORGANISM: Homo sapiens

<400> SEQUENCE: 368
gcgtcatggg atgacagcct gaaaggt        27

<210> SEQ ID NO 369
<211> LENGTH: 1200
<212> TYPE: PRT
<213> ORGANISM: Homo sapiens

<400> SEQUENCE: 369

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

```
Glu Arg Ile Pro Leu Glu Asn Leu Gln Ile Ile Arg Gly Asn Met Tyr
                100                 105                 110
Tyr Glu Asn Ser Tyr Ala Leu Ala Gly Leu Lys Glu Leu Pro Met Arg
            115                 120                 125
Asn Leu Gln Glu Ile Leu His Gly Ala Val Arg Phe Ser Asn Asn Pro
        130                 135                 140
Ala Leu Cys Asn Val Glu Ser Ile Gln Trp Arg Asp Ile Val Ser Ser
145                 150                 155                 160
Asp Phe Leu Ser Asn Met Ser Met Asp Phe Gln Asn His Leu Gly Ser
                165                 170                 175
Cys Gln Lys Cys Asp Pro Ser Cys Pro Asn Gly Ser Cys Trp Gly Ala
            180                 185                 190
Gly Glu Glu Asn Cys Gln Lys Leu Thr Lys Ile Ile Cys Ala Gln Gln
        195                 200                 205
Cys Ser Gly Arg Cys Arg Gly Lys Ser Pro Ser Asp Cys Cys His Asn
210                 215                 220
Gln Cys Ala Ala Gly Cys Thr Gly Pro Arg Glu Ser Asp Cys Leu Val
225                 230                 235                 240
Cys Arg Lys Phe Arg Asp Glu Ala Thr Cys Lys Asp Thr Cys Pro Pro
            245                 250                 255
Leu Met Leu Tyr Asn Pro Thr Thr Tyr Gln Met Asp Val Asn Pro Glu
        260                 265                 270
Gly Lys Tyr Ser Phe Gly Ala Thr Cys Val Lys Lys Cys Pro Arg Asn
    275                 280                 285
Tyr Val Val Thr Asp His Gly Ser Cys Val Arg Ala Cys Gly Ala Asp
        290                 295                 300
Ser Tyr Glu Met Glu Glu Asp Gly Val Arg Lys Cys Lys Lys Cys Glu
305                 310                 315                 320
Gly Pro Cys Arg Lys Val Cys Asn Gly Ile Gly Ile Gly Glu Phe Lys
            325                 330                 335
Asp Ser Leu Ser Ile Asn Ala Thr Asn Ile Lys His Phe Lys Asn Cys
            340                 345                 350
Thr Ser Ile Ser Gly Asp Leu His Ile Leu Pro Val Ala Phe Arg Gly
        355                 360                 365
Asp Ser Phe Thr His Thr Pro Pro Leu Asp Pro Gln Glu Leu Asp Ile
    370                 375                 380
Leu Lys Thr Val Lys Glu Ile Thr Gly Phe Leu Leu Ile Gln Ala Trp
385                 390                 395                 400
Pro Glu Asn Arg Thr Asp Leu His Ala Phe Glu Asn Leu Glu Ile Ile
            405                 410                 415
Arg Gly Arg Thr Lys Gln His Gly Gln Phe Ser Leu Ala Val Val Ser
            420                 425                 430
Leu Asn Ile Thr Ser Leu Gly Leu Arg Ser Leu Lys Glu Ile Ser Asp
        435                 440                 445
Gly Asp Val Ile Ile Ser Gly Asn Lys Asn Leu Cys Tyr Ala Asn Thr
    450                 455                 460
Ile Asn Trp Lys Lys Leu Phe Gly Thr Ser Gly Gln Lys Thr Lys Ile
465                 470                 475                 480
Ile Ser Asn Arg Gly Glu Asn Ser Cys Lys Ala Thr Gly Gln Val Cys
            485                 490                 495
His Ala Leu Cys Ser Pro Glu Gly Cys Trp Gly Pro Glu Pro Arg Asp
            500                 505                 510
```

-continued

```
Cys Val Ser Cys Arg Asn Val Ser Arg Gly Arg Glu Cys Val Asp Lys
            515                 520                 525

Cys Asn Leu Leu Glu Gly Glu Pro Arg Glu Phe Val Glu Asn Ser Glu
    530                 535                 540

Cys Ile Gln Cys His Pro Glu Cys Leu Pro Gln Ala Met Asn Ile Thr
545                 550                 555                 560

Cys Thr Gly Arg Gly Pro Asp Asn Cys Ile Gln Cys Ala His Tyr Ile
                565                 570                 575

Asp Gly Pro His Cys Val Lys Thr Cys Pro Ala Gly Val Met Gly Glu
            580                 585                 590

Asn Asn Thr Leu Val Trp Lys Tyr Ala Asp Ala Gly His Val Cys His
            595                 600                 605

Leu Cys His Pro Asn Cys Thr Tyr Gly Cys Thr Gly Pro Gly Leu Glu
    610                 615                 620

Gly Cys Pro Thr Asn Gly Pro Lys Ile Pro Ser Ile Ala Thr Gly Met
625                 630                 635                 640

Val Gly Ala Leu Leu Leu Leu Val Ala Leu Gly Ile Gly Leu
                645                 650                 655

Phe Met Arg Arg Arg His Ile Val Arg Lys Arg Thr Leu Arg Arg Leu
                660                 665                 670

Leu Gln Glu Arg Glu Leu Val Glu Pro Leu Thr Pro Ser Gly Glu Ala
            675                 680                 685

Pro Asn Gln Ala Leu Leu Arg Ile Leu Lys Glu Thr Glu Phe Lys Lys
            690                 695                 700

Ile Lys Val Leu Gly Ser Gly Ala Phe Gly Thr Val Tyr Lys Gly Leu
705                 710                 715                 720

Trp Ile Pro Glu Gly Glu Lys Val Lys Ile Pro Val Ala Ile Lys Glu
                725                 730                 735

Leu Arg Glu Ala Thr Ser Pro Lys Ala Asn Lys Glu Ile Leu Asp Glu
            740                 745                 750

Ala Tyr Val Met Ala Ser Val Asp Asn Pro His Val Cys Arg Leu Leu
            755                 760                 765

Gly Ile Cys Leu Thr Ser Thr Val Gln Leu Ile Thr Gln Leu Met Pro
    770                 775                 780

Phe Gly Cys Leu Leu Asp Tyr Val Arg Glu His Lys Asp Asn Ile Gly
785                 790                 795                 800

Ser Gln Tyr Leu Leu Asn Trp Cys Val Gln Ile Ala Lys Gly Met Asn
                805                 810                 815

Tyr Leu Glu Asp Arg Arg Leu Val His Arg Asp Leu Ala Ala Arg Asn
            820                 825                 830

Val Leu Val Lys Thr Pro Gln His Val Lys Ile Thr Asp Phe Gly Leu
            835                 840                 845

Ala Lys Leu Leu Gly Ala Glu Glu Lys Glu Tyr His Ala Glu Gly Gly
            850                 855                 860

Lys Val Pro Ile Lys Trp Met Ala Leu Glu Ser Ile Leu His Arg Ile
865                 870                 875                 880

Tyr Thr His Gln Ser Asp Val Trp Ser Tyr Gly Val Thr Val Trp Glu
                885                 890                 895

Leu Met Thr Phe Gly Ser Lys Pro Tyr Asp Gly Ile Pro Ala Ser Glu
            900                 905                 910

Ile Ser Ser Ile Leu Glu Lys Gly Glu Arg Leu Pro Gln Pro Pro Ile
            915                 920                 925

Cys Thr Ile Asp Val Tyr Met Ile Met Val Lys Cys Trp Met Ile Asp
```

```
                930             935             940
Ala Asp Ser Arg Pro Lys Phe Arg Glu Leu Ile Ile Glu Phe Ser Lys
945                 950             955                 960

Met Ala Arg Asp Pro Gln Arg Tyr Leu Val Ile Gln Gly Asp Glu Arg
            965             970                 975

Met His Leu Pro Ser Pro Thr Asp Ser Asn Phe Tyr Arg Ala Leu Met
                980             985             990

Asp Glu Glu Asp Met Asp Val Val Asp Ala Asp Glu Tyr Leu Ile
            995             1000            1005

Pro Gln Gln Gly Phe Phe Ser Ser Pro Ser Thr Ser Arg Thr Pro
    1010            1015            1020

Leu Leu Ser Ser Leu Ser Ala Thr Ser Asn Asn Ser Thr Val Ala
    1025            1030            1035

Cys Ile Asp Arg Asn Gly Leu Gln Ser Cys Pro Ile Lys Glu Asp
    1040            1045            1050

Ser Phe Leu Gln Arg Tyr Ser Ser Asp Pro Thr Gly Ala Leu Thr
    1055            1060            1065

Glu Asp Ser Ile Asp Asp Thr Phe Leu Pro Val Pro Glu Tyr Ile
    1070            1075            1080

Asn Gln Ser Val Pro Lys Arg Pro Ala Gly Ser Val Gln Asn Pro
    1085            1090            1095

Val Tyr His Asn Gln Pro Leu Asn Pro Ala Pro Ser Arg Asp Pro
    1100            1105            1110

His Tyr Gln Asp Pro His Ser Thr Ala Val Gly Asn Pro Glu Tyr
    1115            1120            1125

Leu Asn Thr Val Gln Pro Thr Cys Val Asn Ser Thr Phe Asp Ser
    1130            1135            1140

Pro Ala His Trp Ala Gln Lys Gly Ser His Gln Ile Ser Leu Asp
    1145            1150            1155

Asn Pro Asp Tyr Gln Gln Asp Phe Phe Pro Lys Glu Ala Lys Pro
    1160            1165            1170

Asn Gly Ile Phe Lys Gly Ser Thr Ala Glu Asn Ala Glu Tyr Leu
    1175            1180            1185

Arg Val Ala Pro Gln Ser Ser Glu Phe Ile Gly Ala
    1190            1195            1200
```

<210> SEQ ID NO 370
<211> LENGTH: 1255
<212> TYPE: PRT
<213> ORGANISM: Homo sapiens

<400> SEQUENCE: 370

```
Met Glu Leu Ala Ala Leu Cys Arg Trp Gly Leu Leu Ala Leu Leu
1               5               10              15

Pro Pro Gly Ala Ala Ser Thr Gln Val Cys Thr Gly Thr Asp Met Lys
            20              25              30

Leu Arg Leu Pro Ala Ser Pro Glu Thr His Leu Asp Met Leu Arg His
            35              40              45

Leu Tyr Gln Gly Cys Gln Val Val Gln Gly Asn Leu Glu Leu Thr Tyr
    50              55              60

Leu Pro Thr Asn Ala Ser Leu Ser Phe Leu Gln Asp Ile Gln Glu Val
65              70              75              80

Gln Gly Tyr Val Leu Ile Ala His Asn Gln Val Arg Gln Val Pro Leu
                85              90              95
```

-continued

```
Gln Arg Leu Arg Ile Val Arg Gly Thr Gln Leu Phe Glu Asp Asn Tyr
                100                 105                 110
Ala Leu Ala Val Leu Asp Asn Gly Asp Pro Leu Asn Asn Thr Thr Pro
            115                 120                 125
Val Thr Gly Ala Ser Pro Gly Gly Leu Arg Glu Leu Gln Leu Arg Ser
        130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
```

```
            515                 520                 525
Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925

Arg Glu Ile Pro Asp Leu Leu Glu Lys Gly Glu Arg Leu Pro Gln Pro
930                 935                 940
```

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
        980                 985                 990

Asp Leu Gly Pro Ala Ser Pro Leu Asp Ser Thr Phe Tyr Arg Ser Leu
    995                 1000                1005

Leu Glu Asp Asp Asp Met Gly Asp Leu Val Asp Ala Glu Glu Tyr
1010                1015                1020

Leu Val Pro Gln Gln Gly Phe Phe Cys Pro Asp Pro Ala Pro Gly
1025                1030                1035

Ala Gly Gly Met Val His His Arg His Arg Ser Ser Thr Arg
1040                1045                1050

Ser Gly Gly Gly Asp Leu Thr Leu Gly Leu Glu Pro Ser Glu Glu
1055                1060                1065

Glu Ala Pro Arg Ser Pro Leu Ala Pro Ser Glu Gly Ala Gly Ser
1070                1075                1080

Asp Val Phe Asp Gly Asp Leu Gly Met Gly Ala Ala Lys Gly Leu
1085                1090                1095

Gln Ser Leu Pro Thr His Asp Pro Ser Pro Leu Gln Arg Tyr Ser
1100                1105                1110

Glu Asp Pro Thr Val Pro Leu Pro Ser Glu Thr Asp Gly Tyr Val
1115                1120                1125

Ala Pro Leu Thr Cys Ser Pro Gln Pro Glu Tyr Val Asn Gln Pro
1130                1135                1140

Asp Val Arg Pro Gln Pro Pro Ser Pro Arg Glu Gly Pro Leu Pro
1145                1150                1155

Ala Ala Arg Pro Ala Gly Ala Thr Leu Glu Arg Pro Lys Thr Leu
1160                1165                1170

Ser Pro Gly Lys Asn Gly Val Val Lys Asp Val Phe Ala Phe Gly
1175                1180                1185

Gly Ala Val Glu Asn Pro Glu Tyr Leu Thr Pro Gln Gly Gly Ala
1190                1195                1200

Ala Pro Gln Pro His Pro Pro Ala Phe Ser Pro Ala Phe Asp
1205                1210                1215

Asn Leu Tyr Tyr Trp Asp Gln Asp Pro Pro Glu Arg Gly Ala Pro
1220                1225                1230

Pro Ser Thr Phe Lys Gly Thr Pro Thr Ala Glu Asn Pro Glu Tyr
1235                1240                1245

Leu Gly Leu Asp Val Pro Val
1250                1255

<210> SEQ ID NO 371
<211> LENGTH: 392
<212> TYPE: PRT
<213> ORGANISM: Homo sapiens

<400> SEQUENCE: 371

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly 35                  40                  45
Lys Pro Lys Pro Tyr Tyr Glu Ile Gly Glu Arg Val Asp Tyr Lys Cys
 50                  55                  60

Lys Lys Gly Tyr Phe Tyr Ile Pro Pro Leu Ala Thr His Thr Ile Cys
 65                  70                  75                  80

Asp Arg Asn His Thr Trp Leu Pro Val Ser Asp Ala Cys Tyr Arg
                 85                  90                  95

Glu Thr Cys Pro Tyr Ile Arg Asp Pro Leu Asn Gly Gln Ala Val Pro
                100                 105                 110

Ala Asn Gly Thr Tyr Glu Phe Gly Tyr Gln Met His Phe Ile Cys Asn
                115                 120                 125

Glu Gly Tyr Tyr Leu Ile Gly Glu Glu Ile Leu Tyr Cys Glu Leu Lys
                130                 135                 140

Gly Ser Val Ala Ile Trp Ser Gly Lys Pro Pro Ile Cys Glu Lys Val
145                 150                 155                 160

Leu Cys Thr Pro Pro Lys Ile Lys Asn Gly Lys His Thr Phe Ser
                165                 170                 175

Glu Val Glu Val Phe Glu Tyr Leu Asp Ala Val Thr Tyr Ser Cys Asp
                180                 185                 190

Pro Ala Pro Gly Pro Asp Pro Phe Ser Leu Ile Gly Glu Ser Thr Ile
                195                 200                 205

Tyr Cys Gly Asp Asn Ser Val Trp Ser Arg Ala Ala Pro Glu Cys Lys
                210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
                260                 265                 270

Asn Ser Thr Trp Asp Pro Pro Val Pro Lys Cys Leu Lys Val Leu Pro
                275                 280                 285

Pro Ser Ser Thr Lys Pro Pro Ala Leu Ser His Ser Val Ser Thr Ser
                290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
                340                 345                 350

Ala Ile Val Val Gly Val Ala Val Ile Cys Val Val Pro Tyr Arg Tyr
                355                 360                 365

Leu Gln Arg Arg Lys Lys Gly Thr Tyr Leu Thr Asp Glu Thr His
                370                 375                 380

Arg Glu Val Lys Phe Thr Ser Leu
385                 390

<210> SEQ ID NO 372
<211> LENGTH: 1066
<212> TYPE: PRT
<213> ORGANISM: Homo sapiens

<400> SEQUENCE: 372

Met Gly Pro Gly Pro Ser Arg Ala Pro Arg Ala Pro Arg Leu Met Leu
 1               5                   10                  15

```
Cys Ala Leu Ala Leu Met Val Ala Ala Gly Gly Cys Val Val Ser Ala
            20                  25                  30

Phe Asn Leu Asp Thr Arg Phe Leu Val Val Lys Glu Ala Gly Asn Pro
        35                  40                  45

Gly Ser Leu Phe Gly Tyr Ser Val Ala Leu His Arg Gln Thr Glu Arg
 50                  55                  60

Gln Gln Arg Tyr Leu Leu Leu Ala Gly Ala Pro Arg Glu Leu Ala Val
 65                  70                  75                  80

Pro Asp Gly Tyr Thr Asn Arg Thr Gly Ala Val Tyr Leu Cys Pro Leu
                85                  90                  95

Thr Ala His Lys Asp Asp Cys Glu Arg Met Asn Ile Thr Val Lys Asn
            100                 105                 110

Asp Pro Gly His His Ile Ile Glu Asp Met Trp Leu Gly Val Thr Val
        115                 120                 125

Ala Ser Gln Gly Pro Ala Gly Arg Val Leu Val Cys Ala His Arg Tyr
130                 135                 140

Thr Gln Val Leu Trp Ser Gly Ser Glu Asp Gln Arg Arg Met Val Gly
145                 150                 155                 160

Lys Cys Tyr Val Arg Gly Asn Asp Leu Glu Leu Asp Ser Ser Asp Asp
                165                 170                 175

Trp Gln Thr Tyr His Asn Glu Met Cys Asn Ser Asn Thr Asp Tyr Leu
            180                 185                 190

Glu Thr Gly Met Cys Gln Leu Gly Thr Ser Gly Gly Phe Thr Gln Asn
        195                 200                 205

Thr Val Tyr Phe Gly Ala Pro Gly Ala Tyr Asn Trp Lys Gly Asn Ser
210                 215                 220

Tyr Met Ile Gln Arg Lys Glu Trp Asp Leu Ser Glu Tyr Ser Tyr Lys
225                 230                 235                 240

Asp Pro Glu Asp Gln Gly Asn Leu Tyr Ile Gly Tyr Thr Met Gln Val
                245                 250                 255

Gly Ser Phe Ile Leu His Pro Lys Asn Ile Thr Ile Val Thr Gly Ala
            260                 265                 270

Pro Arg His Arg His Met Gly Ala Val Phe Leu Leu Ser Gln Glu Ala
        275                 280                 285

Gly Gly Asp Leu Arg Arg Arg Gln Val Leu Glu Gly Ser Gln Val Gly
290                 295                 300

Ala Tyr Phe Gly Ser Ala Ile Ala Leu Ala Asp Leu Asn Asn Asp Gly
305                 310                 315                 320

Trp Gln Asp Leu Leu Val Gly Ala Pro Tyr Tyr Phe Glu Arg Lys Glu
                325                 330                 335

Glu Val Gly Gly Ala Ile Tyr Val Phe Met Asn Gln Ala Gly Thr Ser
            340                 345                 350

Phe Pro Ala His Pro Ser Leu Leu Leu His Gly Pro Ser Gly Ser Ala
        355                 360                 365

Phe Gly Leu Ser Val Ala Ser Ile Gly Asp Ile Asn Gln Asp Gly Phe
370                 375                 380

Gln Asp Ile Ala Val Gly Ala Pro Phe Glu Gly Leu Gly Lys Val Tyr
385                 390                 395                 400

Ile Tyr His Ser Ser Ser Lys Gly Leu Leu Arg Gln Pro Gln Gln Val
                405                 410                 415

Ile His Gly Glu Lys Leu Gly Leu Pro Gly Leu Ala Thr Phe Gly Tyr
            420                 425                 430

Ser Leu Ser Gly Gln Met Asp Val Asp Glu Asn Phe Tyr Pro Asp Leu
```

```
            435                 440                 445
Leu Val Gly Ser Leu Ser Asp His Ile Val Leu Arg Ala Arg Pro
450                 455                 460
Val Ile Asn Ile Val His Lys Thr Leu Val Pro Arg Pro Ala Val Leu
465                 470                 475                 480
Asp Pro Ala Leu Cys Thr Ala Thr Ser Cys Val Gln Val Glu Leu Cys
                485                 490                 495
Phe Ala Tyr Asn Gln Ser Ala Gly Asn Pro Asn Tyr Arg Arg Asn Ile
                500                 505                 510
Thr Leu Ala Tyr Thr Leu Glu Ala Asp Arg Asp Arg Pro Pro Arg
                515                 520                 525
Leu Arg Phe Ala Gly Ser Glu Ser Ala Val Phe His Gly Phe Phe Ser
530                 535                 540
Met Pro Glu Met Arg Cys Gln Lys Leu Glu Leu Leu Met Asp Asn
545                 550                 555                 560
Leu Arg Asp Lys Leu Arg Pro Ile Ile Ile Ser Met Asn Tyr Ser Leu
                565                 570                 575
Pro Leu Arg Met Pro Asp Arg Pro Arg Leu Gly Leu Arg Ser Leu Asp
                580                 585                 590
Ala Tyr Pro Ile Leu Asn Gln Ala Gln Ala Leu Glu Asn His Thr Glu
                595                 600                 605
Val Gln Phe Gln Lys Glu Cys Gly Pro Asp Asn Lys Cys Glu Ser Asn
                610                 615                 620
Leu Gln Met Arg Ala Ala Phe Val Ser Glu Gln Gln Lys Leu Ser
625                 630                 635                 640
Arg Leu Gln Tyr Ser Arg Asp Val Arg Lys Leu Leu Ser Ile Asn
                645                 650                 655
Val Thr Asn Thr Arg Thr Ser Glu Arg Ser Gly Glu Asp Ala His Glu
                660                 665                 670
Ala Leu Leu Thr Leu Val Val Pro Pro Ala Leu Leu Leu Ser Ser Val
                675                 680                 685
Arg Pro Pro Gly Ala Cys Gln Ala Asn Glu Thr Ile Phe Cys Glu Leu
                690                 695                 700
Gly Asn Pro Phe Lys Arg Asn Gln Arg Met Glu Leu Leu Ile Ala Phe
705                 710                 715                 720
Glu Val Ile Gly Val Thr Leu His Thr Arg Asp Leu Gln Val Gln Leu
                725                 730                 735
Gln Leu Ser Thr Ser Ser His Gln Asp Asn Leu Trp Pro Met Ile Leu
                740                 745                 750
Thr Leu Leu Val Asp Tyr Thr Leu Gln Thr Ser Leu Ser Met Val Asn
                755                 760                 765
His Arg Leu Gln Ser Phe Phe Gly Gly Thr Val Met Gly Glu Ser Gly
                770                 775                 780
Met Lys Thr Val Glu Asp Val Gly Ser Pro Leu Lys Tyr Glu Phe Gln
785                 790                 795                 800
Val Gly Pro Met Gly Glu Gly Leu Val Gly Leu Gly Thr Leu Val Leu
                805                 810                 815
Gly Leu Glu Trp Pro Tyr Glu Val Ser Asn Gly Lys Trp Leu Leu Tyr
                820                 825                 830
Pro Thr Glu Ile Thr Val His Gly Asn Gly Ser Trp Pro Cys Arg Pro
                835                 840                 845
Pro Gly Asp Leu Ile Asn Pro Leu Asn Leu Thr Leu Ser Asp Pro Gly
                850                 855                 860
```

-continued

Asp Arg Pro Ser Ser Pro Gln Arg Arg Arg Gln Leu Asp Pro Gly
865                 870                 875                 880

Gly Gly Gln Gly Pro Pro Val Thr Leu Ala Ala Lys Lys Ala
            885                 890                 895

Lys Ser Glu Thr Val Leu Thr Cys Ala Thr Gly Arg Ala His Cys Val
            900                 905                 910

Trp Leu Glu Cys Pro Ile Pro Asp Ala Pro Val Val Thr Asn Val Thr
            915                 920                 925

Val Lys Ala Arg Val Trp Asn Ser Thr Phe Ile Glu Asp Tyr Arg Asp
930                 935                 940

Phe Asp Arg Val Arg Val Asn Gly Trp Ala Thr Leu Phe Leu Arg Thr
945                 950                 955                 960

Ser Ile Pro Thr Ile Asn Met Glu Asn Lys Thr Thr Trp Phe Ser Val
            965                 970                 975

Asp Ile Asp Ser Glu Leu Val Glu Glu Leu Pro Ala Glu Ile Glu Leu
            980                 985                 990

Trp Leu Val Leu Val Ala Val Gly Ala Gly Leu Leu Leu Leu Gly Leu
            995                 1000                1005

Ile Ile Leu Leu Leu Trp Lys Cys Gly Phe Phe Lys Arg Thr Arg
    1010                1015                1020

Tyr Tyr Gln Ile Met Pro Lys Tyr His Ala Val Arg Ile Arg Glu
    1025                1030                1035

Glu Glu Arg Tyr Pro Pro Gly Ser Thr Leu Pro Thr Lys Lys
    1040                1045                1050

His Trp Val Thr Ser Trp Gln Thr Arg Asp Gln Tyr Tyr
    1055                1060                1065

<210> SEQ ID NO 373
<211> LENGTH: 532
<212> TYPE: PRT
<213> ORGANISM: Homo sapiens

<400> SEQUENCE: 373

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
            35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
            85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
            115                 120                 125

Lys Asn Leu Thr Leu Arg Cys Gln Val Glu Gly Gly Ala Pro Arg Ala
            130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg 165                 170                 175
Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
            195                 200                 205

Leu Gln Thr Phe Val Leu Pro Ala Thr Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
            245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
            275                 280                 285

Thr Cys Ala Val Ile Leu Gly Asn Gln Ser Gln Glu Thr Leu Gln Thr
            290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
            325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
            355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
            405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
            435                 440                 445

Arg Asp Leu Glu Gly Thr Tyr Leu Cys Arg Ala Arg Ser Thr Gln Gly
            450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Val Ile Met Gly Thr Ala
            485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
            515                 520                 525

Ala Thr Pro Pro
    530

<210> SEQ ID NO 374
<211> LENGTH: 583
<212> TYPE: PRT
<213> ORGANISM: Homo sapiens

<400> SEQUENCE: 374

```
Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Pro Cys Arg Leu Asp Val Pro
            35                  40                  45

Gln Asn Leu Met Phe Gly Lys Trp Lys Tyr Glu Lys Pro Asp Gly Ser
50                  55                  60

Pro Val Phe Ile Ala Phe Arg Ser Ser Thr Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
                100                 105                 110

Cys Met Leu Val Thr Glu Asp Asn Val Phe Glu Ala Pro Thr Ile Val
                115                 120                 125

Lys Val Phe Lys Gln Pro Ser Lys Pro Glu Ile Val Ser Lys Ala Leu
                130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Ile Phe Lys Lys Glu Met
                180                 185                 190

Asp Pro Val Thr Gln Leu Tyr Thr Met Thr Ser Thr Leu Glu Tyr Lys
                195                 200                 205

Thr Thr Lys Ala Asp Ile Gln Met Pro Phe Thr Cys Ser Val Thr Tyr
210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
                260                 265                 270

Asn Gly Asn Pro Pro Glu Glu Phe Leu Phe Tyr Leu Pro Gly Gln
                275                 280                 285

Pro Glu Gly Ile Arg Ser Ser Asn Thr Tyr Thr Leu Met Asp Val Arg
                290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
                340                 345                 350

Ser Cys Thr Ile Ser Ala Ser Arg Asn Ala Thr Val Val Trp Met Lys
                355                 360                 365

Asp Asn Ile Arg Leu Arg Ser Ser Pro Ser Phe Ser Ser Leu His Tyr
370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
```

```
                420            425             430
    Ile Ile Cys His Val Glu Gly Phe Pro Lys Pro Ala Ile Gln Trp Thr
                        435                 440                445
    Ile Thr Gly Ser Gly Ser Val Ile Asn Gln Thr Glu Glu Ser Pro Tyr
                450                 455                 460
    Ile Asn Gly Arg Tyr Tyr Ser Lys Ile Ile Ile Ser Pro Glu Glu Asn
    465                 470                 475                 480
    Val Thr Leu Thr Cys Thr Ala Glu Asn Gln Leu Glu Arg Thr Val Asn
                        485                 490                 495
    Ser Leu Asn Val Ser Ala Ile Ser Ile Pro Glu His Asp Glu Ala Asp
                500                 505                 510
    Glu Ile Ser Asp Glu Asn Arg Glu Lys Val Asn Asp Gln Ala Lys Leu
                515                 520                 525
    Ile Val Gly Ile Val Val Gly Leu Leu Leu Ala Ala Leu Val Ala Gly
                530                 535                 540
    Val Val Tyr Trp Leu Tyr Met Lys Lys Ser Lys Thr Ala Ser Lys His
    545                 550                 555                 560
    Val Asn Lys Asp Leu Gly Asn Met Glu Glu Asn Lys Lys Leu Glu Glu
                        565                 570                 575
    Asn Asn His Lys Thr Glu Ala
                580

<210> SEQ ID NO 375
<211> LENGTH: 385
<212> TYPE: PRT
<213> ORGANISM: Homo sapiens

<400> SEQUENCE: 375

Met Ala Ala Ala Leu Phe Val Leu Leu Gly Phe Ala Leu Leu Gly Thr
    1               5                   10                  15
    His Gly Ala Ser Gly Ala Ala Gly Phe Val Gln Ala Pro Leu Ser Gln
                20                  25                  30
    Gln Arg Trp Val Gly Gly Ser Val Glu Leu His Cys Glu Ala Val Gly
                35                  40                  45
    Ser Pro Val Pro Glu Ile Gln Trp Trp Phe Glu Gly Gln Gly Pro Asn
                50                  55                  60
    Asp Thr Cys Ser Gln Leu Trp Asp Gly Ala Arg Leu Asp Arg Val His
    65                  70                  75                  80
    Ile His Ala Thr Tyr His Gln His Ala Ala Ser Thr Ile Ser Ile Asp
                        85                  90                  95
    Thr Leu Val Glu Glu Asp Thr Gly Thr Tyr Glu Cys Arg Ala Ser Asn
                100                 105                 110
    Asp Pro Asp Arg Asn His Leu Thr Arg Ala Pro Arg Val Lys Trp Val
                115                 120                 125
    Arg Ala Gln Ala Val Val Leu Val Leu Glu Pro Gly Thr Val Phe Thr
                130                 135                 140
    Thr Val Glu Asp Leu Gly Ser Lys Ile Leu Leu Thr Cys Ser Leu Asn
    145                 150                 155                 160
    Asp Ser Ala Thr Glu Val Thr Gly His Arg Trp Leu Lys Gly Gly Val
                        165                 170                 175
    Val Leu Lys Glu Asp Ala Leu Pro Gly Gln Lys Thr Glu Phe Lys Val
                180                 185                 190
    Asp Ser Asp Asp Gln Trp Gly Glu Tyr Ser Cys Val Phe Leu Pro Glu
                195                 200                 205
```

```
Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
                260                 265                 270

Arg Phe Phe Val Ser Ser Gln Gly Arg Ser Glu Leu His Ile Glu
                275                 280                 285

Asn Leu Asn Met Glu Ala Asp Pro Gly Gln Tyr Arg Cys Asn Gly Thr
    290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
                340                 345                 350

Asp Val Leu Asp Asp Asp Asp Ala Gly Ser Ala Pro Leu Lys Ser Ser
                355                 360                 365

Gly Gln His Gln Asn Asp Lys Gly Lys Asn Val Arg Gln Arg Asn Ser
    370                 375                 380

Ser
385

<210> SEQ ID NO 376
<211> LENGTH: 442
<212> TYPE: PRT
<213> ORGANISM: Homo sapiens

<400> SEQUENCE: 376

Met Ala Ser Val Val Leu Pro Ser Gly Ser Gln Cys Ala Ala Ala Ala
1               5                   10                  15

Ala Ala Ala Ala Pro Pro Gly Leu Arg Leu Arg Leu Leu Leu Leu Leu
                20                  25                  30

Phe Ser Ala Ala Ala Leu Ile Pro Thr Gly Asp Gly Gln Asn Leu Phe
            35                  40                  45

Thr Lys Asp Val Thr Val Ile Glu Gly Glu Val Ala Thr Ile Ser Cys
    50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
            100                 105                 110

Asn Val Ser Ile Ser Asp Glu Gly Arg Tyr Phe Cys Gln Leu Tyr Thr
        115                 120                 125

Asp Pro Pro Gln Glu Ser Tyr Thr Thr Ile Thr Val Leu Val Pro Pro
    130                 135                 140

Arg Asn Leu Met Ile Asp Ile Gln Arg Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190
```

Glu Glu Trp Ser Asp Met Tyr Thr Val Thr Ser Gln Leu Met Leu Lys
            195                 200                 205

Val His Lys Glu Asp Asp Gly Val Pro Val Ile Cys Gln Val Glu His
210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
            245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
            275                 280                 285

Gln His Ala Val Leu Ser Gly Pro Asn Leu Phe Ile Asn Asn Leu Asn
            290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
            325                 330                 335

Ile Pro Pro Pro Thr Thr Thr Thr Thr Thr Thr Thr Thr Thr Thr Thr
            340                 345                 350

Thr Ile Leu Thr Ile Ile Thr Asp Ser Arg Ala Gly Glu Glu Gly Ser
            355                 360                 365

Ile Arg Ala Val Asp His Ala Val Ile Gly Gly Val Val Ala Val Val
            370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
            405                 410                 415

Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
435                 440

<210> SEQ ID NO 377
<211> LENGTH: 17
<212> TYPE: DNA
<213> ORGANISM: Artificial Sequence
<220> FEATURE:
<223> OTHER INFORMATION: An artificially synthesized primer sequence

<400> SEQUENCE: 377
caggaaacag ctatgac                                                   17

<210> SEQ ID NO 378
<211> LENGTH: 22
<212> TYPE: DNA
<213> ORGANISM: Artificial Sequence
<220> FEATURE:
<223> OTHER INFORMATION: An artificially synthesized primer sequence

<400> SEQUENCE: 378
cggctccaag tcgacgtcgt ca                                             22

<210> SEQ ID NO 379
<211> LENGTH: 83
<212> TYPE: DNA
<213> ORGANISM: Artificial Sequence
<220> FEATURE:

<223> OTHER INFORMATION: An artificially synthesized primer sequence

<400> SEQUENCE: 379
cagctgcagc agtctggggc agagcttgtg aagccagggg cctcagtcaa gttgtcctgc    60
acagcttctg gcttcaacat taa                                            83

<210> SEQ ID NO 380
<211> LENGTH: 81
<212> TYPE: DNA
<213> ORGANISM: Artificial Sequence
<220> FEATURE:
<223> OTHER INFORMATION: An artificially synthesized primer sequence

<400> SEQUENCE: 380
agaccgaagt tgtaatttct gtggatatac gtgacccact tcgtctccgg acttttccca    60
gatctcacct aaccttccta a                                              81

<210> SEQ ID NO 381
<211> LENGTH: 84
<212> TYPE: DNA
<213> ORGANISM: Artificial Sequence
<220> FEATURE:
<223> OTHER INFORMATION: An artificially synthesized primer sequence

<400> SEQUENCE: 381
aagggtctag agtggattgg aaggattgat cctgcgagtg gtaatactaa atatgacccg    60
aaggacaagg ccactataac agca                                           84

<210> SEQ ID NO 382
<211> LENGTH: 66
<212> TYPE: DNA
<213> ORGANISM: Artificial Sequence
<220> FEATURE:
<223> OTHER INFORMATION: An artificially synthesized primer sequence

<400> SEQUENCE: 382
ttcctgttcc ggtgatattg tcgtctgtgt aggaggttgt gtcggatgga tgtcgactta    60
agggac                                                               66

<210> SEQ ID NO 383
<211> LENGTH: 51
<212> TYPE: DNA
<213> ORGANISM: Artificial Sequence
<220> FEATURE:
<223> OTHER INFORMATION: An artificially synthesized primer sequence

<400> SEQUENCE: 383
cagctgaatt ccctgacatc tgaggacact gccgtctatt actgtgctgg t             51

<210> SEQ ID NO 384
<211> LENGTH: 73
<212> TYPE: DNA
<213> ORGANISM: Artificial Sequence
<220> FEATURE:
<223> OTHER INFORMATION: An artificially synthesized primer sequence

<400> SEQUENCE: 384
cagataatga cacgaccaat actaatgccg ttgaaactga tgaccccggt tccgtggtgc    60
cagtggcaca agg                                                       73

<210> SEQ ID NO 385
<211> LENGTH: 54

```
<212> TYPE: DNA
<213> ORGANISM: Artificial Sequence
<220> FEATURE:
<223> OTHER INFORMATION: An artificially synthesized primer sequence

<400> SEQUENCE: 385
ggttctctaa cagtagtggt agtagtggta attattctcg atagggccct cgaa        54

<210> SEQ ID NO 386
<211> LENGTH: 69
<212> TYPE: DNA
<213> ORGANISM: Artificial Sequence
<220> FEATURE:
<223> OTHER INFORMATION: An artificially synthesized primer sequence

<400> SEQUENCE: 386
gacatcgagc tcacccagtc tccagcctcc ctttctgcgt ctgtgggaga aactgtcacc   60
atcacatgt                                                          69

<210> SEQ ID NO 387
<211> LENGTH: 63
<212> TYPE: DNA
<213> ORGANISM: Artificial Sequence
<220> FEATURE:
<223> OTHER INFORMATION: An artificially synthesized primer sequence

<400> SEQUENCE: 387
tgacagtggt agtgtacagc tcgttcaccc ttataagtgt taataaatcg taccatggtc   60
gtc                                                                63

<210> SEQ ID NO 388
<211> LENGTH: 48
<212> TYPE: DNA
<213> ORGANISM: Artificial Sequence
<220> FEATURE:
<223> OTHER INFORMATION: An artificially synthesized primer sequence

<400> SEQUENCE: 388
gcatggtacc agcagaaacc agggaaatct cctcagctcc tggtctat                48

<210> SEQ ID NO 389
<211> LENGTH: 81
<212> TYPE: DNA
<213> ORGANISM: Artificial Sequence
<220> FEATURE:
<223> OTHER INFORMATION: An artificially synthesized primer sequence

<400> SEQUENCE: 389
ggagtcgagg accagatatt acgttttttgg aatcgtctac cacacggtag ttccaagtca  60
ccgtcaccta ggccttgtgt t                                            81

<210> SEQ ID NO 390
<211> LENGTH: 45
<212> TYPE: DNA
<213> ORGANISM: Artificial Sequence
<220> FEATURE:
<223> OTHER INFORMATION: An artificially synthesized primer sequence

<400> SEQUENCE: 390
tcatgaggca cctgcaagcc acctccgtgg ttcgagctct agttt                   45

<210> SEQ ID NO 391
<211> LENGTH: 45
<212> TYPE: DNA
```

```
<213> ORGANISM: Artificial Sequence
<220> FEATURE:
<223> OTHER INFORMATION: An artificially synthesized primer sequence

<400> SEQUENCE: 391
agtactccgt ggacgttcgg tggaggcacc aagctcgaga tcaaa          45

<210> SEQ ID NO 392
<211> LENGTH: 10
<212> TYPE: DNA
<213> ORGANISM: Artificial Sequence
<220> FEATURE:
<223> OTHER INFORMATION: An artificially synthesized primer sequence

<400> SEQUENCE: 392
atcgacagct                                                 10

<210> SEQ ID NO 393
<211> LENGTH: 30
<212> TYPE: DNA
<213> ORGANISM: Artificial Sequence
<220> FEATURE:
<223> OTHER INFORMATION: An artificially synthesized primer sequence

<400> SEQUENCE: 393
aagccacctc catggttcga gctctagttt                           30

<210> SEQ ID NO 394
<211> LENGTH: 44
<212> TYPE: DNA
<213> ORGANISM: Artificial Sequence
<220> FEATURE:
<223> OTHER INFORMATION: An artificially synthesized primer sequence

<400> SEQUENCE: 394
tcgaagttgt ccttactcac aagccgcgcg gtcagctgag gtaa           44

<210> SEQ ID NO 395
<211> LENGTH: 55
<212> TYPE: DNA
<213> ORGANISM: Artificial Sequence
<220> FEATURE:
<223> OTHER INFORMATION: An artificially synthesized primer sequence

<400> SEQUENCE: 395
accctggtca ccgtctcctc agcctccacc aagggcccat cggtcttccc cctgg    55

<210> SEQ ID NO 396
<211> LENGTH: 37
<212> TYPE: DNA
<213> ORGANISM: Artificial Sequence
<220> FEATURE:
<223> OTHER INFORMATION: An artificially synthesized primer sequence

<400> SEQUENCE: 396
gggagtcgtc gcagcactgg cacgggaggt cgtcgaa                   37

<210> SEQ ID NO 397
<211> LENGTH: 36
<212> TYPE: DNA
<213> ORGANISM: Artificial Sequence
<220> FEATURE:
<223> OTHER INFORMATION: An artificially synthesized primer sequence

<400> SEQUENCE: 397
ggactctact ccctcagcag cgtcgtgacc gtgccc                    36
```

<210> SEQ ID NO 398
<211> LENGTH: 63
<212> TYPE: DNA
<213> ORGANISM: Artificial Sequence
<220> FEATURE:
<223> OTHER INFORMATION: An artificially synthesized primer sequence

<400> SEQUENCE: 398
gggtcgttgt ggttccacct gttctttcaa ctcgggttta gaacagtagt ggtagtagtg    60
gta                                                                  63

<210> SEQ ID NO 399
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 399
gggtttagaa cagtagtggt agtagtggta attattctcg atagggccct cgaacg        56

<210> SEQ ID NO 400
<211> LENGTH: 33
<212> TYPE: DNA
<213> ORGANISM: Artificial Sequence
<220> FEATURE:
<223> OTHER INFORMATION: An artificially synthesized primer sequence

<400> SEQUENCE: 400
ggcaccacgg tcaccgtctc gagcgcctcc acc                                 33

<210> SEQ ID NO 401
<211> LENGTH: 1916
<212> TYPE: DNA
<213> ORGANISM: Artificial Sequence
<220> FEATURE:
<223> OTHER INFORMATION: Insert sequence of pscFvCA9-E8VHdVLd

<400> SEQUENCE: 401
aagcttgcat gcaaattcta tttcaaggag acagtcataa tgaaatacct attgcctacg     60
gcagccgctg gattgttatt actcgctgcc caaccagcga tggcccaggt gcagctgcag    120
cagtctgggg cagagcttgt gaagccaggg gcctcagtca agttgtcctg cacagcttct    180
ggcttcaaca ttaaagacac ctatatgcac tgggtgaagc agaggcctga aaagggtcta    240
gaattccctg acatctgagg acactgccgt ctattactgt gctggttatg attacggcaa    300
ctttgactac tggggccaag gcaccacggt caccgtctcg agaggcggtg gcggatcagg    360
tggcggtgga agtggcggtg gtgggtccat ggccgacatc gagctcaccc agtctccagc    420 ctcccttttct gcgtctgtgg gagaaactgt caccatcaca tgtcgagcaa gtgggaatat    480
tcacaattat ttagcatggt accaagctcg agatcaaacg gctgatgct gcaccaactg    540 tatccatctt cccaccatcc agtgagcagt taacatctgg aggtgcctca gtcgtgtgct    600
tcttgaacag cttctacccc aaagacatca atgtcaagtg gaagattgat ggcagtgaac    660
gacaaaatgg cgtcctgaac agttggactg atcaggacag caagacagc acctacagca    720 tgagcagcac cctcacgttg accaaggacg agtatgaacg acataacagc tatacctgtg    780
aggccactca caagacatca acttcaccca ttgtcaagag cttcaacagg aatgagtgtt    840
cggcgcgcca gtcgactcca ttcgtttgtg aatatcaagg ccaatcgtct gacctgcctc    900

-continued

```
aacctcctgt caatgctggc ggcggctctg gtggtggttc tggtggcggc tctgagggtg    960
gtggctctga gggtggcggt tctgagggtg gcggctctga gggaggcggt tccggtggtg   1020
gctctggttc cggtgatttt gattatgaaa agatggcaaa cgctaataag ggggctatga   1080
ccgaaaatgc cgatgaaaac gcgctacagt cagacgctaa aggcaaactt gattctgtcg   1140
ctactgatta cggtgctgct atcgatggtt tcattggtga cgtttccggc cttgctaatg   1200
gtaatggtgc tactggtgat tttgctggct ctaattccca aatggctcaa gtcggtgacg   1260
gtgataattc acctttaatg aataatttcc gtcaatattt accttccctc cctcaatcgg   1320
ttgaatgtcg cccttttgtc tttggcgctg gtaaaccata tgaattttct attgattgtg   1380
acaaaataaa cttattccgt ggtgtctttg cgtttctttt atatgttgcc accttt atgt   1440 atgtattttc tacgtttgct aacatactgc gtaataagga gtcttaatca tgccagttct   1500
tttgggtgct agctgtcgac tgcgcaacac gatgaagccg tagacaacaa attcaacaaa   1560
gaacaacaaa acgcgttcta tgagatctta catttaccta acttaaacga gaacaacga    1620 aacgccttca tccaaagttt aaaagatgac ccaagccaaa gcgctaaccct tttagcagaa   1680 gctaaaaagc taaatgatgc tcaggcgccg aaagtagaca acaaattcaa caagaacaa    1740 caaaacgcgt tctatgagat cttacatttta cctaacttaa acgaagaaca acgaaacgcc   1800
ttcatccaaa gtttaaaaga tgacccaagc caaagcgcta accttttagc agaagctaaa   1860
aagctaaatg atgctcaggc gccgaaagta gacgcgaatt agctgggaat taattc       1916
```

<210> SEQ ID NO 402
<211> LENGTH: 66
<212> TYPE: PRT
<213> ORGANISM: Artificial Sequence
<220> FEATURE:
<223> OTHER INFORMATION: Amino acid sequence encoded by insert sequence of pscFvCA9-E8VHdVLd

<400> SEQUENCE: 402

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Leu Val Lys Pro Gly Ala Ser Val Lys Leu Ser Cys Thr Ala Ser Gly
        35                  40                  45

Phe Asn Ile Lys Asp Thr Tyr Met His Trp Val Lys Gln Arg Pro Glu
    50                  55                  60

Lys Gly
65
```

<210> SEQ ID NO 403
<211> LENGTH: 77
<212> TYPE: DNA
<213> ORGANISM: Artificial Sequence
<220> FEATURE:
<223> OTHER INFORMATION: An artificially synthesized primer sequence

<400> SEQUENCE: 403

```
gtcaccgtct cgagaggcgg tggcggatca ggtggcggtg aagtggcgg tggtgggtcc    60 atggccgaca tcgagct                                                   77
```

<210> SEQ ID NO 404
<211> LENGTH: 68
<212> TYPE: DNA
<213> ORGANISM: Artificial Sequence

```
<220> FEATURE:
<223> OTHER INFORMATION: An artificially synthesized primer sequence

<400> SEQUENCE: 404
cgatgtcggc catggaccca ccaccgccac ttccaccgcc acctgatccg ccaccgcctc    60
tcgagacg                                                             68

<210> SEQ ID NO 405
<211> LENGTH: 1774
<212> TYPE: DNA
<213> ORGANISM: Artificial Sequence
<220> FEATURE:
<223> OTHER INFORMATION: Insert sequence of pscFvCA-E8VHd

<400> SEQUENCE: 405
aagcttgcat gcaaattcta tttcaaggag acagtcataa tgaaatacct attgcctacg    60
gcagccgctg gattgttatt actcgcggcc cagccggcca tggcccaggt gcagctgcag   120
cagtctgggg cagagcttgt gaagccaggg gcctcagtca agttgtcctg cacagcttct   180
ggcttcaaca ttaaagacac ctatatgcac tgggtgaagc agaggcctga aagggtcta    240 gaattccctg acatctgagg acactgccgt ctattactgt gctggttatg attacggcaa   300
ctttgactac tggggccaag gcaccacggt caccgtctcc tcaggcggtg cggatcagg    360 tggcggtgga gtggcggtg tgggtctac tagtgacatc gagctcaccc agtctccagc    420 ctcccttct gcgtctgtgg gagaaactgt caccatcaca tgtcgagcaa gtgggaatat    480
tcacaattat ttagcatggt accagcagaa accagggaaa tctcctcagc tcctggtcta   540
taatgcaaaa accttagcag atggtgtgcc atcaaggttc agtggcagtg gatccggaac   600
acaatattct ctcaagatca acagcctgca gcctgaagat tttgggagtt attactgtca   660
acatttttgg agtactccgt ggacgttcgg tggaggtacc aagctcgagt cgactccatt   720
cgtttgtgaa tatcaaggcc aatcgtctga cctgcctcaa cctcctgtca atgctggcgg   780
cggctctggt ggtggttctg gtggcggctc tgagggtggt ggctctgagg gtggcggttc   840
tgagggtggc ggctctgagg aggcggttc cggtggtggc tctggttccg gtgattttga   900
ttatgaaaag atggcaaacg ctaataaggg ggctatgacc gaaaatgccg atgaaaacgc   960
gctacagtca gacgctaaag gcaaacttga ttctgtcgct actgattacg gtgctgctat  1020
cgatggtttc attggtgacg tttccggcct tgctaatggt aatggtgcta ctggtgattt  1080
tgctggctct aattcccaaa tggctcaagt cggtgacggt gataattcac ctttaatgaa  1140
taatttccgt caatatttac cttccctccc tcaatcggtt gaatgtcgcc cttttgtctt  1200
tggcgctggt aaaccatatg aattttctat tgattgtgac aaaataaact tattccgtgg  1260
tgtctttgcg tttcttttat atgttgccac ctttatgtat gtattttcta cgtttgctaa  1320
catactgcgt aataaggagt cttaatcatg ccagttcttt ggggtgctag ctgtcgactg  1380
cgcaacacga tgaagccgta gacaacaaat tcaacaaaga caacaaaac gcgttctatg  1440 agatcttaca tttacctaac ttaaacgaag aacaacgaaa cgccttcatc caaagtttaa  1500
aagatgaccc aagccaaagc gctaaccttt tagcagaagc taaaaagcta atgatgctc   1560 aggcgccgaa agtagacaac aaattcaaca agaacaacaa aaacgcgttc tatgagatct  1620
tacatttacc taacttaaac gaagaacaac gaaacgcctt catccaaagt ttaaaagatg  1680
acccaagcca aagcgctaac cttttagcag aagctaaaaa gctaaatgat gctcaggcgc  1740
cgaaagtaga cgcgaattag ctgggaatta attc                              1774
```

```
<210> SEQ ID NO 406
<211> LENGTH: 66
<212> TYPE: PRT
<213> ORGANISM: Artificial Sequence
<220> FEATURE:
<223> OTHER INFORMATION: Amino acid sequence encoded by insert sequence
      of pscFvCA-E8VHd

<400> SEQUENCE: 406

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Leu Val Lys Pro Gly Ala Ser Val Lys Leu Ser Cys Thr Ala Ser Gly
        35                  40                  45

Phe Asn Ile Lys Asp Thr Tyr Met His Trp Val Lys Gln Arg Pro Glu
    50                  55                  60

Lys Gly
65

<210> SEQ ID NO 407
<211> LENGTH: 91
<212> TYPE: DNA
<213> ORGANISM: Artificial Sequence
<220> FEATURE:
<223> OTHER INFORMATION: An artificially synthesized primer sequence

<400> SEQUENCE: 407
caccacggtc accgtctcct caggcggtgg cggatcaggt ggcggtggaa gtggcggtgg      60
tgggtctact agtgacatcg agctcaccca g                                    91

<210> SEQ ID NO 408
<211> LENGTH: 91
<212> TYPE: DNA
<213> ORGANISM: Artificial Sequence
<220> FEATURE:
<223> OTHER INFORMATION: An artificially synthesized primer sequence

<400> SEQUENCE: 408
gtggtgccag tggcagagga gtccgccacc gcctagtcca ccgccacctt caccgccacc      60
acccagatga tcactgtagc tcgagtgggt c                                    91

<210> SEQ ID NO 409
<211> LENGTH: 17
<212> TYPE: DNA
<213> ORGANISM: Artificial Sequence
<220> FEATURE:
<223> OTHER INFORMATION: An artificially synthesized primer sequence

<400> SEQUENCE: 409
caggaaacag ctatgac                                                    17

<210> SEQ ID NO 410
<211> LENGTH: 42
<212> TYPE: DNA
<213> ORGANISM: Artificial Sequence
<220> FEATURE:
<223> OTHER INFORMATION: An artificially synthesized primer sequence

<400> SEQUENCE: 410
gacgccgggt cggccggtac cggctccaag tcgacgtcgt ca                        42
```

```
<210> SEQ ID NO 411
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 411
gtcctcgcaa ctgcggccca gccggccatg gccgacatcc agatgaccca gtctcc      56

<210> SEQ ID NO 412
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 412
gtcctcgcaa ctgcggccca gccggccatg gccgatgttg tgatgactca gtctcc      56

<210> SEQ ID NO 413
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 413
gtcctcgcaa ctgcggccca gccggccatg gccgaaattg tgttgacgca gtctcc      56

<210> SEQ ID NO 414
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 414
gtcctcgcaa ctgcggccca gccggccatg gccgacatcg tgatgaccca gtctcc      56

<210> SEQ ID NO 415
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 415
gtcctcgcaa ctgcggccca gccggccatg gccgaaacga cactcacgca gtctcc      56

<210> SEQ ID NO 416
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 416
gtcctcgcaa ctgcggccca gccggccatg gccgaaattg tgctgactca gtctcc      56

<210> SEQ ID NO 417
<211> LENGTH: 56
<212> TYPE: DNA
<213> ORGANISM: Artificial Sequence
<220> FEATURE:
<223> OTHER INFORMATION: An artificially synthesized primer sequence
```

<400> SEQUENCE: 417
gtcctcgcaa ctgcggccca gccggccatg gcccagtctg tgttgacgca gccgcc    56

<210> SEQ ID NO 418
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 418
gtcctcgcaa ctgcggccca gccggccatg gcccagtctg ccctgactca gcctgc    56

<210> SEQ ID NO 419
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 419
gtcctcgcaa ctgcggccca gccggccatg gcctcctatg tgctgactca gccacc    56

<210> SEQ ID NO 420
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 420
gtcctcgcaa ctgcggccca gccggccatg gcctcttctg agctgactca ggaccc    56

<210> SEQ ID NO 421
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 421
gtcctcgcaa ctgcggccca gccggccatg gcccacgtta tactgactca accgcc    56

<210> SEQ ID NO 422
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 422
gtcctcgcaa ctgcggccca gccggccatg gcccaggctg tgctcactca gccgcc    56

<210> SEQ ID NO 423
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 423
gtcctcgcaa ctgcggccca gccggccatg gccaatttta tgctgactca gcccca    56

<210> SEQ ID NO 424
<211> LENGTH: 44

```
<212> TYPE: DNA
<213> ORGANISM: Artificial Sequence
<220> FEATURE:
<223> OTHER INFORMATION: An artificially synthesized primer sequence

<400> SEQUENCE: 424
tcgactggcg cgccgaacac tctcccctgt tgaagctctt tgtg                    44

<210> SEQ ID NO 425
<211> LENGTH: 43
<212> TYPE: DNA
<213> ORGANISM: Artificial Sequence
<220> FEATURE:
<223> OTHER INFORMATION: An artificially synthesized primer sequence

<400> SEQUENCE: 425
tcgactggcg cgccgaacat tctgtagggg ccactgtctt ctc                     43

<210> SEQ ID NO 426
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 426
atggagtcgg gaaggaagtc                                               20

<210> SEQ ID NO 427
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 427
gtcctcgcaa ctgcggccca gccggccatg gcccaggtgc agctggtgca gtctgg       56

<210> SEQ ID NO 428
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 428
gtcctcgcaa ctgcggccca gccggccatg gcccaggtca acttaaggga gtctgg       56

<210> SEQ ID NO 429
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 429
gtcctcgcaa ctgcggccca gccggccatg gccgaggtgc agctggtgga gtctgg       56

<210> SEQ ID NO 430
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 430
```
gtcctcgcaa ctgcggccca gccggccatg gcccaggtgc agctgcagga gtcggg       56

<210> SEQ ID NO 431
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 431
gtcctcgcaa ctgcggccca gccggccatg gcccaggtgc agctgttgca gtctgc       56

<210> SEQ ID NO 432
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 432
gtcctcgcaa ctgcggccca gccggccatg gcccaggtac agctgcagca gtcagg       56

<210> SEQ ID NO 433
<211> LENGTH: 59
<212> TYPE: DNA
<213> ORGANISM: Artificial Sequence
<220> FEATURE:
<223> OTHER INFORMATION: An artificially synthesized primer sequence

<400> SEQUENCE: 433
gtcctcgcaa ctgcggccca gccggccatg gcccagrtca ccttgaagga gtctggtcc    59

<210> SEQ ID NO 434
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 434
gtcctcgcaa ctgcggccca gccggccatg gcccaggtgc agctacagca gtgggg       56

<210> SEQ ID NO 435
<211> LENGTH: 56
<212> TYPE: DNA
<213> ORGANISM: Artificial Sequence
<220> FEATURE:
<223> OTHER INFORMATION: An artificially synthesized primer sequence

<400> SEQUENCE: 435
gtcctcgcaa ctgcggccca gccggccatg gccgaggtgc agctggtgca gtctgg       56

<210> SEQ ID NO 436
<211> LENGTH: 64
<212> TYPE: DNA
<213> ORGANISM: Artificial Sequence
<220> FEATURE:
<223> OTHER INFORMATION: An artificially synthesized primer sequence

<400> SEQUENCE: 436
gtcctcgcaa ctgcggccca gccggccatg gcccaggtgc agctggtgca atctgggtct    60
gagt                                                                 64

<210> SEQ ID NO 437
<211> LENGTH: 32

```
<212> TYPE: DNA
<213> ORGANISM: Artificial Sequence
<220> FEATURE:
<223> OTHER INFORMATION: An artificially synthesized primer sequence

<400> SEQUENCE: 437
ggtggaggca ctcgagacgg tgaccagggt gc                          32

<210> SEQ ID NO 438
<211> LENGTH: 32
<212> TYPE: DNA
<213> ORGANISM: Artificial Sequence
<220> FEATURE:
<223> OTHER INFORMATION: An artificially synthesized primer sequence

<400> SEQUENCE: 438
ggtggaggca ctcgagacgg tgaccattgt cc                          32

<210> SEQ ID NO 439
<211> LENGTH: 32
<212> TYPE: DNA
<213> ORGANISM: Artificial Sequence
<220> FEATURE:
<223> OTHER INFORMATION: An artificially synthesized primer sequence

<400> SEQUENCE: 439
ggtggaggca ctcgagacgg tgaccagggt tc                          32

<210> SEQ ID NO 440
<211> LENGTH: 32
<212> TYPE: DNA
<213> ORGANISM: Artificial Sequence
<220> FEATURE:
<223> OTHER INFORMATION: An artificially synthesized primer sequence

<400> SEQUENCE: 440
ggtggaggca ctcgagacgg tgaccgtggt cc                          32

<210> SEQ ID NO 441
<211> LENGTH: 25
<212> TYPE: RNA
<213> ORGANISM: Artificial Sequence
<220> FEATURE:
<223> OTHER INFORMATION: oligo RNA

<400> SEQUENCE: 441
cagagcuaca cauugagaac cugaa                                  25

<210> SEQ ID NO 442
<211> LENGTH: 25
<212> TYPE: RNA
<213> ORGANISM: Artificial Sequence
<220> FEATURE:
<223> OTHER INFORMATION: oligo RNA

<400> SEQUENCE: 442
uaccuaugug cagaggaauu augau                                  25

<210> SEQ ID NO 443
<211> LENGTH: 25
<212> TYPE: RNA
<213> ORGANISM: Artificial Sequence
<220> FEATURE:
<223> OTHER INFORMATION: oligo RNA

<400> SEQUENCE: 443
```

```
gcaaccaucu aaaccugaaa uugua                                              25
```

<210> SEQ ID NO 444
<211> LENGTH: 25
<212> TYPE: RNA
<213> ORGANISM: Artificial Sequence
<220> FEATURE:
<223> OTHER INFORMATION: oligo RNA

<400> SEQUENCE: 444

```
uaauagaggu ugucgaaggc ugggc                                              25
```

<210> SEQ ID NO 445
<211> LENGTH: 25
<212> TYPE: RNA
<213> ORGANISM: Artificial Sequence
<220> FEATURE:
<223> OTHER INFORMATION: oligo RNA

<400> SEQUENCE: 445

```
cccaacaggc agaccauuua uuuca                                              25
```

<210> SEQ ID NO 446
<211> LENGTH: 652
<212> TYPE: PRT
<213> ORGANISM: Homo sapiens

<400> SEQUENCE: 446

```
Met Ala Thr Ser Met Gly Leu Leu Leu Leu Leu Leu Leu Leu Leu Thr
1               5                   10                  15

Gln Pro Gly Ala Gly Thr Gly Ala Asp Thr Glu Ala Val Val Cys Val
            20                  25                  30

Gly Thr Ala Cys Tyr Thr Ala His Ser Gly Lys Leu Ser Ala Ala Glu
        35                  40                  45

Ala Gln Asn His Cys Asn Gln Asn Gly Gly Asn Leu Ala Thr Val Lys
    50                  55                  60

Ser Lys Glu Glu Ala Gln His Val Gln Arg Val Leu Ala Gln Leu Leu
65                  70                  75                  80

Arg Arg Glu Ala Ala Leu Thr Ala Arg Met Ser Lys Phe Trp Ile Gly
                85                  90                  95

Leu Gln Arg Glu Lys Gly Lys Cys Leu Asp Pro Ser Leu Pro Leu Lys
            100                 105                 110

Gly Phe Ser Trp Val Gly Gly Gly Glu Asp Thr Pro Tyr Ser Asn Trp
        115                 120                 125

His Lys Glu Leu Arg Asn Ser Cys Ile Ser Lys Arg Cys Val Ser Leu
    130                 135                 140

Leu Leu Asp Leu Ser Gln Pro Leu Leu Pro Ser Arg Leu Pro Lys Trp
145                 150                 155                 160

Ser Glu Gly Pro Cys Gly Ser Pro Gly Ser Pro Gly Ser Asn Ile Glu
                165                 170                 175

Gly Phe Val Cys Lys Phe Ser Phe Lys Gly Met Cys Arg Pro Leu Ala
            180                 185                 190

Leu Gly Gly Pro Gly Gln Val Thr Tyr Thr Thr Pro Phe Gln Thr Thr
        195                 200                 205

Ser Ser Ser Leu Glu Ala Val Pro Phe Ala Ser Ala Ala Asn Val Ala
    210                 215                 220

Cys Gly Glu Gly Asp Lys Asp Glu Thr Gln Ser His Tyr Phe Leu Cys
225                 230                 235                 240
```

```
Lys Glu Lys Ala Pro Asp Val Phe Asp Trp Gly Ser Gly Pro Leu
                245                 250                 255
Cys Val Ser Pro Lys Tyr Gly Cys Asn Phe Asn Asn Gly Gly Cys His
            260                 265                 270
Gln Asp Cys Phe Glu Gly Gly Asp Gly Ser Phe Leu Cys Gly Cys Arg
        275                 280                 285
Pro Gly Phe Arg Leu Leu Asp Asp Leu Val Thr Cys Ala Ser Arg Asn
    290                 295                 300
Pro Cys Ser Ser Ser Pro Cys Arg Gly Gly Ala Thr Cys Ala Leu Gly
305                 310                 315                 320
Pro His Gly Lys Asn Tyr Thr Cys Arg Cys Pro Gln Gly Tyr Gln Leu
                325                 330                 335
Asp Ser Ser Gln Leu Asp Cys Val Asp Val Asp Glu Cys Gln Asp Ser
            340                 345                 350
Pro Cys Ala Gln Glu Cys Val Asn Thr Pro Gly Gly Phe Arg Cys Glu
        355                 360                 365
Cys Trp Val Gly Tyr Glu Pro Gly Gly Pro Gly Glu Gly Ala Cys Gln
    370                 375                 380
Asp Val Asp Glu Cys Ala Leu Gly Arg Ser Pro Cys Ala Gln Gly Cys
385                 390                 395                 400
Thr Asn Thr Asp Gly Ser Phe His Cys Ser Cys Glu Glu Gly Tyr Val
                405                 410                 415
Leu Ala Gly Glu Asp Gly Thr Gln Cys Gln Asp Val Asp Glu Cys Val
            420                 425                 430
Gly Pro Gly Gly Pro Leu Cys Asp Ser Leu Cys Phe Asn Thr Gln Gly
        435                 440                 445
Ser Phe His Cys Gly Cys Leu Pro Gly Trp Val Leu Ala Pro Asn Gly
    450                 455                 460
Val Ser Cys Thr Met Gly Pro Val Ser Leu Gly Pro Pro Ser Gly Pro
465                 470                 475                 480
Pro Asp Glu Glu Asp Lys Gly Glu Lys Glu Gly Ser Thr Val Pro Arg
                485                 490                 495
Ala Ala Thr Ala Ser Pro Thr Arg Gly Pro Glu Gly Thr Pro Lys Ala
            500                 505                 510
Thr Pro Thr Thr Ser Arg Pro Ser Leu Ser Ser Asp Ala Pro Ile Thr
        515                 520                 525
Ser Ala Pro Leu Lys Met Leu Ala Pro Ser Gly Ser Ser Gly Val Trp
    530                 535                 540
Arg Glu Pro Ser Ile His His Ala Thr Ala Ala Ser Gly Pro Gln Glu
545                 550                 555                 560
Pro Ala Gly Gly Asp Ser Ser Val Ala Thr Gln Asn Asn Asp Gly Thr
                565                 570                 575
Asp Gly Gln Lys Leu Leu Leu Phe Tyr Ile Leu Gly Thr Val Val Ala
            580                 585                 590
Ile Leu Leu Leu Leu Ala Leu Ala Leu Gly Leu Leu Val Tyr Arg Lys
        595                 600                 605
Arg Arg Ala Lys Arg Glu Glu Lys Lys Glu Lys Lys Pro Gln Asn Ala
    610                 615                 620
Ala Asp Ser Tyr Ser Trp Val Pro Glu Arg Ala Glu Ser Arg Ala Met
625                 630                 635                 640
Glu Asn Gln Tyr Ser Pro Thr Pro Gly Thr Asp Cys
                645                 650
```

-continued

```
<210> SEQ ID NO 447
<211> LENGTH: 719
<212> TYPE: PRT
<213> ORGANISM: Homo sapiens

<400> SEQUENCE: 447

Leu Asn Ile Thr Cys Arg Phe Ala Gly Val Phe His Val Glu Lys Asn
 1               5                  10                  15

Gly Arg Tyr Ser Ile Ser Arg Thr Glu Ala Ala Asp Leu Cys Lys Ala
            20                  25                  30

Phe Asn Ser Thr Leu Pro Thr Met Ala Gln Met Glu Lys Ala Leu Ser
        35                  40                  45

Ile Gly Phe Glu Thr Cys Arg Tyr Gly Phe Ile Glu Gly His Val Val
    50                  55                  60

Ile Pro Arg Ile His Pro Asn Ser Ile Cys Ala Ala Asn Asn Thr Gly
65                  70                  75                  80

Val Tyr Ile Leu Thr Ser Asn Thr Ser Gln Tyr Asp Thr Tyr Cys Phe
                85                  90                  95

Asn Ala Ser Ala Pro Pro Glu Glu Asp Cys Thr Ser Val Thr Asp Leu
            100                 105                 110

Pro Asn Ala Phe Asp Gly Pro Ile Thr Ile Thr Ile Val Asn Arg Asp
        115                 120                 125

Gly Thr Arg Tyr Val Gln Lys Gly Glu Tyr Arg Thr Asn Pro Glu Asp
    130                 135                 140

Ile Tyr Pro Ser Asn Pro Thr Asp Asp Asp Val Ser Ser Gly Ser Ser
145                 150                 155                 160

Ser Glu Arg Ser Ser Thr Ser Gly Gly Tyr Ile Phe Tyr Thr Phe Ser
                165                 170                 175

Thr Val His Pro Ile Pro Asp Glu Asp Ser Pro Trp Ile Thr Asp Ser
            180                 185                 190

Thr Asp Arg Ile Pro Ala Thr Thr Leu Met Ser Thr Ser Ala Thr Ala
        195                 200                 205

Thr Glu Thr Ala Thr Lys Arg Gln Glu Thr Trp Asp Trp Phe Ser Trp
    210                 215                 220

Leu Phe Leu Pro Ser Glu Ser Lys Asn His Leu His Thr Thr Thr Gln
225                 230                 235                 240

Met Ala Gly Thr Ser Ser Asn Thr Ile Ser Ala Gly Trp Glu Pro Asn
                245                 250                 255

Glu Glu Asn Glu Asp Glu Arg Asp Arg His Leu Ser Phe Ser Gly Ser
            260                 265                 270

Gly Ile Asp Asp Asp Glu Asp Phe Ile Ser Ser Thr Ile Ser Thr Thr
        275                 280                 285

Pro Arg Ala Phe Asp His Thr Lys Gln Asn Gln Asp Trp Thr Gln Trp
    290                 295                 300

Asn Pro Ser His Ser Asn Pro Glu Val Leu Leu Gln Thr Thr Thr Arg
305                 310                 315                 320

Met Thr Asp Val Asp Arg Asn Gly Thr Thr Ala Tyr Glu Gly Asn Trp
                325                 330                 335

Asn Pro Glu Ala His Pro Pro Leu Ile His His Glu His His Glu Glu
            340                 345                 350

Glu Glu Thr Pro His Ser Thr Ser Thr Ile Gln Ala Thr Pro Ser Ser
        355                 360                 365

Thr Thr Glu Glu Thr Ala Thr Gln Lys Glu Gln Trp Phe Gly Asn Arg
    370                 375                 380
```

Trp His Glu Gly Tyr Arg Gln Thr Pro Lys Glu Asp Ser His Ser Thr
385                 390                 395                 400

Thr Gly Thr Ala Ala Ser Ala His Thr Ser His Pro Met Gln Gly
            405                 410                 415

Arg Thr Thr Pro Ser Pro Glu Asp Ser Ser Trp Thr Asp Phe Phe Asn
            420                 425                 430

Pro Ile Ser His Pro Met Gly Arg Gly His Gln Ala Gly Arg Arg Met
            435                 440                 445

Asp Met Asp Ser Ser His Ser Ile Thr Leu Gln Pro Thr Ala Asn Pro
            450                 455                 460

Asn Thr Gly Leu Val Glu Asp Leu Asp Arg Thr Gly Pro Leu Ser Met
465                 470                 475                 480

Thr Thr Gln Gln Ser Asn Ser Gln Ser Phe Ser Thr Ser His Glu Gly
            485                 490                 495

Leu Glu Glu Asp Lys Asp His Pro Thr Thr Ser Thr Leu Thr Ser Ser
            500                 505                 510

Asn Arg Asn Asp Val Thr Gly Gly Arg Arg Asp Pro Asn His Ser Glu
            515                 520                 525

Gly Ser Thr Thr Leu Leu Glu Gly Tyr Thr Ser His Tyr Pro His Thr
530                 535                 540

Lys Glu Ser Arg Thr Phe Ile Pro Val Thr Ser Ala Lys Thr Gly Ser
545                 550                 555                 560

Phe Gly Val Thr Ala Val Thr Val Gly Asp Ser Asn Ser Asn Val Asn
            565                 570                 575

Arg Ser Leu Ser Gly Asp Gln Asp Thr Phe His Pro Ser Gly Gly Ser
            580                 585                 590

His Thr Thr His Gly Ser Glu Ser Asp Gly His Ser His Gly Ser Gln
            595                 600                 605

Glu Gly Gly Ala Asn Thr Thr Ser Gly Pro Ile Arg Thr Pro Gln Ile
610                 615                 620

Pro Glu Trp Leu Ile Ile Leu Ala Ser Leu Leu Ala Leu Ala Leu Ile
625                 630                 635                 640

Leu Ala Val Cys Ile Ala Val Asn Ser Arg Arg Arg Cys Gly Gln Lys
            645                 650                 655

Lys Lys Leu Val Ile Asn Ser Gly Asn Gly Ala Val Glu Asp Arg Lys
            660                 665                 670

Pro Ser Gly Leu Asn Gly Glu Ala Ser Lys Ser Gln Glu Met Val His
            675                 680                 685

Leu Val Asn Lys Glu Ser Ser Glu Thr Pro Asp Gln Phe Met Thr Ala
            690                 695                 700

Asp Glu Thr Arg Asn Leu Gln Asn Val Asp Met Lys Ile Gly Val
705                 710                 715

<210> SEQ ID NO 448
<211> LENGTH: 574
<212> TYPE: PRT
<213> ORGANISM: Homo sapiens

<400> SEQUENCE: 448

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
            35                  40                  45

```
Ser Lys Cys Val Asn Ala Ser Arg Cys Met Gly Gly Val Ala Arg Leu
    50                  55                  60
Phe Thr Lys Val Gln Gln Ile Arg Arg Ala Glu Pro Asn Val Leu Leu
65                  70                  75                  80
Leu Asp Ala Gly Asp Gln Tyr Gln Gly Thr Ile Trp Phe Thr Val Tyr
                85                  90                  95
Lys Gly Ala Glu Val Ala His Phe Met Asn Ala Leu Arg Tyr Asp Ala
                100                 105                 110
Met Ala Leu Gly Asn His Glu Phe Asp Asn Gly Val Glu Gly Leu Ile
            115                 120                 125
Glu Pro Leu Leu Lys Glu Ala Lys Phe Pro Ile Leu Ser Ala Asn Ile
    130                 135                 140
Lys Ala Lys Gly Pro Leu Ala Ser Gln Ile Ser Gly Leu Tyr Leu Pro
145                 150                 155                 160
Tyr Lys Val Leu Pro Val Gly Asp Glu Val Val Gly Ile Val Gly Tyr
                165                 170                 175
Thr Ser Lys Glu Thr Pro Phe Leu Ser Asn Pro Gly Thr Asn Leu Val
                180                 185                 190
Phe Glu Asp Glu Ile Thr Ala Leu Gln Pro Glu Val Asp Lys Leu Lys
    195                 200                 205
Thr Leu Asn Val Asn Lys Ile Ile Ala Leu Gly His Ser Gly Phe Glu
    210                 215                 220
Met Asp Lys Leu Ile Ala Gln Lys Val Arg Gly Val Asp Val Val Val
225                 230                 235                 240
Gly Gly His Ser Asn Thr Phe Leu Tyr Thr Gly Asn Pro Pro Ser Lys
                245                 250                 255
Glu Val Pro Ala Gly Lys Tyr Pro Phe Ile Val Thr Ser Asp Asp Gly
                260                 265                 270
Arg Lys Val Pro Val Val Gln Ala Tyr Ala Phe Gly Lys Tyr Leu Gly
    275                 280                 285
Tyr Leu Lys Ile Glu Phe Asp Glu Arg Gly Asn Val Ile Ser Ser His
    290                 295                 300
Gly Asn Pro Ile Leu Leu Asn Ser Ser Ile Pro Glu Asp Pro Ser Ile
305                 310                 315                 320
Lys Ala Asp Ile Asn Lys Trp Arg Ile Lys Leu Asp Asn Tyr Ser Thr
                325                 330                 335
Gln Glu Leu Gly Lys Thr Ile Val Tyr Leu Asp Gly Ser Ser Gln Ser
                340                 345                 350
Cys Arg Phe Arg Glu Cys Asn Met Gly Asn Leu Ile Cys Asp Ala Met
                355                 360                 365
Ile Asn Asn Asn Leu Arg His Thr Asp Glu Met Phe Trp Asn His Val
    370                 375                 380
Ser Met Cys Ile Leu Asn Gly Gly Ile Arg Ser Pro Ile Asp Glu
385                 390                 395                 400
Arg Asn Asn Gly Thr Ile Thr Trp Glu Asn Leu Ala Ala Val Leu Pro
                405                 410                 415
Phe Gly Gly Thr Phe Asp Leu Val Gln Leu Lys Gly Ser Thr Leu Lys
                420                 425                 430
Lys Ala Phe Glu His Ser Val His Arg Tyr Gly Gln Ser Thr Gly Glu
            435                 440                 445
Phe Leu Gln Val Gly Gly Ile His Val Val Tyr Asp Leu Ser Arg Lys
    450                 455                 460
```

```
Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
                515                 520                 525

Ser Thr Tyr Ile Ser Lys Met Lys Val Ile Tyr Pro Ala Val Glu Gly
            530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570
```

<210> SEQ ID NO 449
<211> LENGTH: 314
<212> TYPE: PRT
<213> ORGANISM: Homo sapiens

<400> SEQUENCE: 449

```
Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
            35                  40                  45

Thr Ser Val Gly Ala Gln Asn Thr Val Ile Cys Ser Lys Leu Ala Ala
        50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
                100                 105                 110

Thr Ser Thr Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270
```

```
Val Val Val Val Met Ala Val Ala Gly Ile Val Val Leu Val Ile
            275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 450
<211> LENGTH: 1390
<212> TYPE: PRT
<213> ORGANISM: Homo sapiens

<400> SEQUENCE: 450

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
```

-continued

```
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
            370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
            405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
            450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
            485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
            530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
            565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
            595                 600                 605
Ser Cys Thr Leu Thr Leu Ser Glu Ser Thr Met Asn Thr Leu Lys Cys
            610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
            645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
            690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
            725                 730                 735
Ser Tyr Arg Glu Asp Pro Ile Val Tyr Glu Ile His Pro Thr Lys Ser
            740                 745                 750
```

```
Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
   1010                1015                1020

Val Gln Tyr Pro Leu Thr Asp Met Ser Pro Ile Leu Thr Ser Gly
   1025                1030                1035

Asp Ser Asp Ile Ser Ser Pro Leu Leu Gln Asn Thr Val His Ile
   1040                1045                1050

Asp Leu Ser Ala Leu Asn Pro Glu Leu Val Gln Ala Val Gln His
   1055                1060                1065

Val Val Ile Gly Pro Ser Ser Leu Ile Val His Phe Asn Glu Val
   1070                1075                1080

Ile Gly Arg Gly His Phe Gly Cys Val Tyr His Gly Thr Leu Leu
   1085                1090                1095

Asp Asn Asp Gly Lys Lys Ile His Cys Ala Val Lys Ser Leu Asn
   1100                1105                1110

Arg Ile Thr Asp Ile Gly Glu Val Ser Gln Phe Leu Thr Glu Gly
   1115                1120                1125

Ile Ile Met Lys Asp Phe Ser His Pro Asn Val Leu Ser Leu Leu
   1130                1135                1140

Gly Ile Cys Leu Arg Ser Glu Gly Ser Pro Leu Val Val Leu Pro
   1145                1150                1155
```

```
Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Val Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 451
<211> LENGTH: 121
<212> TYPE: PRT
<213> ORGANISM: Homo sapiens

<400> SEQUENCE: 451

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Ile Leu Thr Gly Tyr Tyr Ala Phe Asp Ile Trp Gly
            100                 105                 110

Gln Gly Thr Met Val Thr Val Ser Arg
        115                 120
```

<210> SEQ ID NO 452
<211> LENGTH: 5
<212> TYPE: PRT
<213> ORGANISM: Homo sapiens

<400> SEQUENCE: 452

Gly Tyr Tyr Met His
1               5

<210> SEQ ID NO 453
<211> LENGTH: 17
<212> TYPE: PRT
<213> ORGANISM: Homo sapiens

<400> SEQUENCE: 453

Trp Ile Asn Pro Asn Ser Gly Gly Thr Asn Tyr Ala Gln Lys Phe Gln
1               5                   10                  15

Gly

<210> SEQ ID NO 454
<211> LENGTH: 12
<212> TYPE: PRT
<213> ORGANISM: Homo sapiens

<400> SEQUENCE: 454

Ser Asp Ile Leu Thr Gly Tyr Tyr Ala Phe Asp Ile
1               5                   10

<210> SEQ ID NO 455
<211> LENGTH: 107
<212> TYPE: PRT
<213> ORGANISM: Homo sapiens

<400> SEQUENCE: 455

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Thr Trp
                85                  90                  95

Thr Phe Gly Gln Gly Thr Lys Val Glu Ile Lys
            100                 105

<210> SEQ ID NO 456
<211> LENGTH: 11
<212> TYPE: PRT
<213> ORGANISM: Homo sapiens

<400> SEQUENCE: 456

Arg Ala Ser Gln Ser Ile Ser Ser Tyr Leu Asn
1               5                   10

<210> SEQ ID NO 457
<211> LENGTH: 7

```
<212> TYPE: PRT
<213> ORGANISM: Homo sapiens

<400> SEQUENCE: 457

Ala Ala Ser Ser Leu Gln Ser
1               5

<210> SEQ ID NO 458
<211> LENGTH: 7
<212> TYPE: PRT
<213> ORGANISM: Homo sapiens

<400> SEQUENCE: 458

Gln Gln Ser Tyr Ser Thr Thr
1               5

<210> SEQ ID NO 459
<211> LENGTH: 129
<212> TYPE: PRT
<213> ORGANISM: Homo sapiens

<400> SEQUENCE: 459

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Trp Tyr Tyr Gly Ser Gly Ser Ser Leu Tyr Tyr
            100                 105                 110

Tyr Tyr Gly Met Asp Val Trp Gly Gln Gly Thr Thr Val Thr Val Ser
        115                 120                 125

Arg

<210> SEQ ID NO 460
<211> LENGTH: 5
<212> TYPE: PRT
<213> ORGANISM: Homo sapiens

<400> SEQUENCE: 460

Gly Tyr Tyr Met His
1               5

<210> SEQ ID NO 461
<211> LENGTH: 17
<212> TYPE: PRT
<213> ORGANISM: Homo sapiens

<400> SEQUENCE: 461

Trp Ile Asn Pro Asn Ser Gly Gly Thr Asn Tyr Ala Gln Lys Phe Gln
1               5                   10                  15

Gly

<210> SEQ ID NO 462
```

<211> LENGTH: 20
<212> TYPE: PRT
<213> ORGANISM: Homo sapiens

<400> SEQUENCE: 462

Asp Leu Trp Tyr Tyr Tyr Gly Ser Gly Ser Ser Leu Tyr Tyr Tyr Tyr
1               5                   10                  15

Gly Met Asp Val
            20

<210> SEQ ID NO 463
<211> LENGTH: 112
<212> TYPE: PRT
<213> ORGANISM: Homo sapiens

<400> SEQUENCE: 463

Gln Ser Val Leu Thr Gln Pro Pro Ser Val Ser Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu Gly
            100                 105                 110

<210> SEQ ID NO 464
<211> LENGTH: 14
<212> TYPE: PRT
<213> ORGANISM: Homo sapiens

<400> SEQUENCE: 464

Thr Gly Ser Ser Ser Asn Ile Gly Ala Gly Tyr Asp Val His
1               5                   10

<210> SEQ ID NO 465
<211> LENGTH: 7
<212> TYPE: PRT
<213> ORGANISM: Homo sapiens

<400> SEQUENCE: 465

Gly Asn Ser Asn Arg Pro Ser
1               5

<210> SEQ ID NO 466
<211> LENGTH: 9
<212> TYPE: PRT
<213> ORGANISM: Homo sapiens

<400> SEQUENCE: 466

Gln Ser Tyr Asp Ser Ser Leu Ser Gly
1               5

<210> SEQ ID NO 467
<211> LENGTH: 122
<212> TYPE: PRT
<213> ORGANISM: Homo sapiens

<400> SEQUENCE: 467

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Ser Gly Ser Tyr Asn Tyr Tyr Tyr Gly Met Asp Val Trp
            100                 105                 110

Gly Gln Gly Thr Thr Val Thr Val Ser Arg
    115                 120

<210> SEQ ID NO 468
<211> LENGTH: 5
<212> TYPE: PRT
<213> ORGANISM: Homo sapiens

<400> SEQUENCE: 468

Asp Tyr Ala Met His
1               5

<210> SEQ ID NO 469
<211> LENGTH: 17
<212> TYPE: PRT
<213> ORGANISM: Homo sapiens

<400> SEQUENCE: 469

Gly Ile Ser Trp Asn Ser Gly Ser Ile Gly Tyr Ala Asp Ser Val Lys
1               5                   10                  15

Gly

<210> SEQ ID NO 470
<211> LENGTH: 13
<212> TYPE: PRT
<213> ORGANISM: Homo sapiens

<400> SEQUENCE: 470

Ser Gly Ser Tyr Asn Tyr Tyr Tyr Gly Met Asp Val
1               5                   10

<210> SEQ ID NO 471
<211> LENGTH: 111
<212> TYPE: PRT
<213> ORGANISM: Homo sapiens

<400> SEQUENCE: 471

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

```
Ile Tyr Ser Asn Asn Gln Arg Pro Ser Gly Val Pro Asp Arg Phe Ser
 50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
             85                  90                  95
Asn Gly Trp Val Phe Gly Gly Gly Thr Lys Leu Thr Val Leu Gly
            100                 105                 110
```

<210> SEQ ID NO 472
<211> LENGTH: 13
<212> TYPE: PRT
<213> ORGANISM: Homo sapiens

<400> SEQUENCE: 472

```
Ser Gly Ser Ser Ser Asn Ile Gly Ser Asn Thr Val Asn
 1               5                  10
```

<210> SEQ ID NO 473
<211> LENGTH: 7
<212> TYPE: PRT
<213> ORGANISM: Homo sapiens

<400> SEQUENCE: 473

```
Ser Asn Asn Gln Arg Pro Ser
 1               5
```

<210> SEQ ID NO 474
<211> LENGTH: 9
<212> TYPE: PRT
<213> ORGANISM: Homo sapiens

<400> SEQUENCE: 474

```
Ala Ala Trp Asp Asp Ser Leu Asn Gly
 1               5
```

<210> SEQ ID NO 475
<211> LENGTH: 123
<212> TYPE: PRT
<213> ORGANISM: Homo sapiens

<400> SEQUENCE: 475

```
Gln Val Gln Leu Gln Glu Ser Gly Gly Gly Leu Val Gln Pro Gly Gly
 1               5                  10                  15
Ser Leu Arg Leu Ser Cys Thr Thr Ser Gly Phe Thr Phe Thr Ser Tyr
             20                  25                  30
Ala Met Ser Trp Val Arg Gln Ala Pro Gly Lys Gly Leu Glu Trp Val
         35                  40                  45
Ser Ser Ile Ser Gly Ser Gly Gly Ile Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
             85                  90                  95
Ala Lys Asp Arg Val Leu Val Pro Ala Ser Ser Ser Tyr Phe Asp Tyr
            100                 105                 110
Trp Gly Gln Gly Thr Leu Val Thr Val Ser Arg
            115                 120
```

<210> SEQ ID NO 476

```
<211> LENGTH: 5
<212> TYPE: PRT
<213> ORGANISM: Homo sapiens

<400> SEQUENCE: 476

Ser Tyr Ala Met Ser
1               5

<210> SEQ ID NO 477
<211> LENGTH: 17
<212> TYPE: PRT
<213> ORGANISM: Homo sapiens

<400> SEQUENCE: 477

Ser Ile Ser Gly Ser Gly Gly Ile Thr Tyr Tyr Ala Asp Ser Val Lys
1               5                   10                  15

Gly

<210> SEQ ID NO 478
<211> LENGTH: 14
<212> TYPE: PRT
<213> ORGANISM: Homo sapiens

<400> SEQUENCE: 478

Asp Arg Val Leu Val Pro Ala Ser Ser Tyr Phe Asp Tyr
1               5                   10

<210> SEQ ID NO 479
<211> LENGTH: 109
<212> TYPE: PRT
<213> ORGANISM: Homo sapiens

<400> SEQUENCE: 479

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly
            100                 105

<210> SEQ ID NO 480
<211> LENGTH: 11
<212> TYPE: PRT
<213> ORGANISM: Homo sapiens

<400> SEQUENCE: 480

Gln Gly Asp Ser Leu Arg Ser Tyr Tyr Ala Ser
1               5                   10

<210> SEQ ID NO 481
<211> LENGTH: 7
<212> TYPE: PRT
<213> ORGANISM: Homo sapiens
```

<400> SEQUENCE: 481

Gly Lys Asn Asn Arg Pro Ser
1               5

<210> SEQ ID NO 482
<211> LENGTH: 9
<212> TYPE: PRT
<213> ORGANISM: Homo sapiens

<400> SEQUENCE: 482

Asn Ser Arg Asp Ser Ser Gly Asn His
1               5

<210> SEQ ID NO 483
<211> LENGTH: 120
<212> TYPE: PRT
<213> ORGANISM: Homo sapiens

<400> SEQUENCE: 483

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Pro Leu Thr Phe Asn Ala Phe Asp Ile Trp Gly Gln
            100                 105                 110

Gly Thr Met Val Thr Val Ser Arg
        115                 120

<210> SEQ ID NO 484
<211> LENGTH: 7
<212> TYPE: PRT
<213> ORGANISM: Homo sapiens

<400> SEQUENCE: 484

Ser Ser Ser Tyr Tyr Trp Gly
1               5

<210> SEQ ID NO 485
<211> LENGTH: 16
<212> TYPE: PRT
<213> ORGANISM: Homo sapiens

<400> SEQUENCE: 485

Ser Ile Tyr Tyr Ser Gly Ser Thr Tyr Tyr Asn Pro Ser Leu Lys Ser
1               5                   10                  15

<210> SEQ ID NO 486
<211> LENGTH: 10
<212> TYPE: PRT
<213> ORGANISM: Homo sapiens

<400> SEQUENCE: 486

Arg Pro Leu Thr Phe Asn Ala Phe Asp Ile

<210> SEQ ID NO 487
<211> LENGTH: 109
<212> TYPE: PRT
<213> ORGANISM: Homo sapiens

<400> SEQUENCE: 487

Ser Tyr Val Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Asp His
                85                  90                  95
Val Val Phe Gly Gly Gly Thr Lys Leu Thr Val Leu Gly
            100                 105

<210> SEQ ID NO 488
<211> LENGTH: 11
<212> TYPE: PRT
<213> ORGANISM: Homo sapiens

<400> SEQUENCE: 488

Gly Gly Asn Asn Ile Gly Ser Lys Ser Val His
1               5                   10

<210> SEQ ID NO 489
<211> LENGTH: 7
<212> TYPE: PRT
<213> ORGANISM: Homo sapiens

<400> SEQUENCE: 489

Tyr Asp Ser Asp Arg Pro Ser
1               5

<210> SEQ ID NO 490
<211> LENGTH: 9
<212> TYPE: PRT
<213> ORGANISM: Homo sapiens

<400> SEQUENCE: 490

Gln Val Trp Asp Ser Ser Ser Asp His
1               5

<210> SEQ ID NO 491
<211> LENGTH: 120
<212> TYPE: PRT
<213> ORGANISM: Homo sapiens

<400> SEQUENCE: 491

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Ser Tyr Tyr Trp Gly Trp Ile Arg Gln Pro Pro Gly Lys Gly Leu Glu

```
              35                  40                  45
Trp Ile Gly Ser Ile Tyr Tyr Ser Gly Ser Thr Tyr Tyr Asn Pro Ser
         50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Ile Pro Met Tyr Ser Ser Val Asp Tyr Trp Gly Gln
            100                 105                 110
Gly Thr Leu Val Thr Val Ser Arg
            115                 120

<210> SEQ ID NO 492
<211> LENGTH: 7
<212> TYPE: PRT
<213> ORGANISM: Homo sapiens

<400> SEQUENCE: 492

Ser Ser Ser Tyr Tyr Trp Gly
1               5

<210> SEQ ID NO 493
<211> LENGTH: 16
<212> TYPE: PRT
<213> ORGANISM: Homo sapiens

<400> SEQUENCE: 493

Ser Ile Tyr Tyr Ser Gly Ser Thr Tyr Tyr Asn Pro Ser Leu Lys Ser
1               5                  10                  15

<210> SEQ ID NO 494
<211> LENGTH: 10
<212> TYPE: PRT
<213> ORGANISM: Homo sapiens

<400> SEQUENCE: 494

Ile Pro Met Tyr Ser Ser Ser Val Asp Tyr
1               5                  10

<210> SEQ ID NO 495
<211> LENGTH: 109
<212> TYPE: PRT
<213> ORGANISM: Homo sapiens

<400> SEQUENCE: 495

Ser Tyr Val Leu Thr Gln Pro Pro Ser Val Ser Val Ala Pro Gly Lys
1               5                  10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Ile Tyr
            35                  40                  45
Tyr Asp Ser Asp Arg Pro Ser Gly Ile Pro Glu Arg Phe Ser Gly Ser
        50                  55                  60
Asn Ser Gly Asn Thr Ala Thr Leu Thr Ile Ser Arg Val Glu Ala Gly
 65                  70                  75                  80
Asp Glu Ala Asp Tyr Tyr Cys Gln Val Trp Asp Ser Ser Ser Asp His
                 85                  90                  95
Val Val Phe Gly Gly Gly Thr Lys Leu Thr Val Leu Gly
            100                 105
```

<210> SEQ ID NO 496
<211> LENGTH: 11
<212> TYPE: PRT
<213> ORGANISM: Homo sapiens

<400> SEQUENCE: 496

Gly Gly Asn Asn Ile Gly Ser Lys Ser Val His
1               5                   10

<210> SEQ ID NO 497
<211> LENGTH: 7
<212> TYPE: PRT
<213> ORGANISM: Homo sapiens

<400> SEQUENCE: 497

Tyr Asp Ser Asp Arg Pro Ser
1               5

<210> SEQ ID NO 498
<211> LENGTH: 9
<212> TYPE: PRT
<213> ORGANISM: Homo sapiens

<400> SEQUENCE: 498

Gln Val Trp Asp Ser Ser Ser Asp His
1               5

<210> SEQ ID NO 499
<211> LENGTH: 120
<212> TYPE: PRT
<213> ORGANISM: Homo sapiens

<400> SEQUENCE: 499

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Pro Leu Thr Phe Asn Ala Phe Asp Ile Trp Gly Gln
            100                 105                 110

Gly Thr Thr Val Thr Val Ser Arg
        115                 120

<210> SEQ ID NO 500
<211> LENGTH: 7
<212> TYPE: PRT
<213> ORGANISM: Homo sapiens

<400> SEQUENCE: 500

Ser Ser Ser Tyr Tyr Trp Gly
1               5

<210> SEQ ID NO 501
<211> LENGTH: 16

```
<212> TYPE: PRT
<213> ORGANISM: Homo sapiens

<400> SEQUENCE: 501

Ser Ile Tyr Tyr Ser Gly Ser Thr Tyr Tyr Asn Pro Ser Leu Lys Ser
1               5                   10                  15

<210> SEQ ID NO 502
<211> LENGTH: 10
<212> TYPE: PRT
<213> ORGANISM: Homo sapiens

<400> SEQUENCE: 502

Arg Pro Leu Thr Phe Asn Ala Phe Asp Ile
1               5                   10

<210> SEQ ID NO 503
<211> LENGTH: 109
<212> TYPE: PRT
<213> ORGANISM: Homo sapiens

<400> SEQUENCE: 503

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 504
<211> LENGTH: 11
<212> TYPE: PRT
<213> ORGANISM: Homo sapiens

<400> SEQUENCE: 504

Gly Gly Asn Asn Ile Gly Ser Lys Ser Val His
1               5                   10

<210> SEQ ID NO 505
<211> LENGTH: 7
<212> TYPE: PRT
<213> ORGANISM: Homo sapiens

<400> SEQUENCE: 505

Tyr Asp Ser Asp Arg Pro Ser
1               5

<210> SEQ ID NO 506
<211> LENGTH: 9
<212> TYPE: PRT
<213> ORGANISM: Homo sapiens

<400> SEQUENCE: 506

Gln Val Trp Asp Ser Ser Ser Asp His
```

```
1               5

<210> SEQ ID NO 507
<211> LENGTH: 122
<212> TYPE: PRT
<213> ORGANISM: Homo sapiens

<400> SEQUENCE: 507

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Trp Phe Gly Glu Leu Asp Tyr Phe Gln His Trp
            100                 105                 110

Gly Gln Gly Thr Leu Val Thr Val Ser Arg
        115                 120

<210> SEQ ID NO 508
<211> LENGTH: 5
<212> TYPE: PRT
<213> ORGANISM: Homo sapiens

<400> SEQUENCE: 508

Ser Tyr Ala Met Ser
1               5

<210> SEQ ID NO 509
<211> LENGTH: 17
<212> TYPE: PRT
<213> ORGANISM: Homo sapiens

<400> SEQUENCE: 509

Ala Ile Ser Gly Ser Gly Gly Ser Thr Tyr Tyr Ala Asp Ser Val Lys
1               5                   10                  15

Gly

<210> SEQ ID NO 510
<211> LENGTH: 13
<212> TYPE: PRT
<213> ORGANISM: Homo sapiens

<400> SEQUENCE: 510

Asp Gly Gly Trp Phe Gly Glu Leu Asp Tyr Phe Gln His
1               5                   10

<210> SEQ ID NO 511
<211> LENGTH: 111
<212> TYPE: PRT
<213> ORGANISM: Homo sapiens

<400> SEQUENCE: 511

Gln Ser Val Leu Thr Gln Pro Pro Ser Val Ser Ala Ala Pro Gly Gln
1               5                   10                  15
```

```
Lys Val Thr Val Ser Cys Thr Gly Ser Asn Ser Asn Ile Glu Lys Asn
             20                  25                  30

Asp Val Ser Trp Tyr Gln Gln Gly Pro Gly Ala Ala Pro Lys Leu Leu
         35                  40                  45

Ile Ser Asp Thr Asp Arg Arg Pro Ser Gly Ile Pro Asp Arg Phe Ser
 50                  55                  60

Gly Ser Lys Ser Gly Thr Ser Ala Thr Leu Ala Ile Ala Gly Leu Gln
 65                  70                  75                  80

Ala Glu Asp Glu Ala Asp Tyr Tyr Cys Gln Ser His Asp Thr Thr Leu
                 85                  90                  95

Ser Gly Pro Ile Phe Gly Gly Gly Thr Gln Leu Thr Val Leu Gly
                100                 105                 110

<210> SEQ ID NO 512
<211> LENGTH: 13
<212> TYPE: PRT
<213> ORGANISM: Homo sapiens

<400> SEQUENCE: 512

Thr Gly Ser Asn Ser Asn Ile Glu Lys Asn Asp Val Ser
1               5                   10

<210> SEQ ID NO 513
<211> LENGTH: 7
<212> TYPE: PRT
<213> ORGANISM: Homo sapiens

<400> SEQUENCE: 513

Asp Thr Asp Arg Arg Pro Ser
1               5

<210> SEQ ID NO 514
<211> LENGTH: 9
<212> TYPE: PRT
<213> ORGANISM: Homo sapiens

<400> SEQUENCE: 514

Gln Ser His Asp Thr Thr Leu Ser Gly
1               5

<210> SEQ ID NO 515
<211> LENGTH: 124
<212> TYPE: PRT
<213> ORGANISM: Homo sapiens

<400> SEQUENCE: 515

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Ser Phe Ser Asp Tyr
             20                  25                  30

Tyr Met Ser Trp Val Arg Gln Ala Pro Gly Lys Gly Leu Glu Trp Ile
         35                  40                  45

Ser Tyr Ile Thr Ser Ser Ser Asp Thr Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Val Gly Tyr Tyr Tyr Asp Tyr Tyr Tyr Tyr Tyr Met Asp
```

```
                100             105             110
Val Trp Gly Lys Gly Thr Thr Val Thr Val Ser Arg
        115                 120

<210> SEQ ID NO 516
<211> LENGTH: 5
<212> TYPE: PRT
<213> ORGANISM: Homo sapiens

<400> SEQUENCE: 516

Asp Tyr Tyr Met Ser
1               5

<210> SEQ ID NO 517
<211> LENGTH: 17
<212> TYPE: PRT
<213> ORGANISM: Homo sapiens

<400> SEQUENCE: 517

Tyr Ile Thr Ser Ser Ser Ser Asp Thr Asp Tyr Ala Asp Ser Val Lys
1               5                   10                  15

Gly

<210> SEQ ID NO 518
<211> LENGTH: 15
<212> TYPE: PRT
<213> ORGANISM: Homo sapiens

<400> SEQUENCE: 518

Val Gly Tyr Tyr Tyr Asp Tyr Tyr Tyr Tyr Met Asp Val
1               5                   10                  15

<210> SEQ ID NO 519
<211> LENGTH: 108
<212> TYPE: PRT
<213> ORGANISM: Homo sapiens

<400> SEQUENCE: 519

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Gly Tyr Tyr Ala
            20                  25                  30

Ser Trp Tyr Gln Gln Lys Pro Gly Gln Ala Pro Val Leu Val Val Tyr
        35                  40                  45

Asp Glu Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Asn Leu Asp Trp
                85                  90                  95

Val Phe Gly Gly Gly Thr Lys Leu Thr Val Leu Gly
            100                 105

<210> SEQ ID NO 520
<211> LENGTH: 11
<212> TYPE: PRT
<213> ORGANISM: Homo sapiens

<400> SEQUENCE: 520

Gln Gly Asp Ser Leu Arg Gly Tyr Tyr Ala Ser
1               5                   10
```

<210> SEQ ID NO 521
<211> LENGTH: 7
<212> TYPE: PRT
<213> ORGANISM: Homo sapiens

<400> SEQUENCE: 521

Asp Glu Asn Asn Arg Pro Ser
1               5

<210> SEQ ID NO 522
<211> LENGTH: 8
<212> TYPE: PRT
<213> ORGANISM: Homo sapiens

<400> SEQUENCE: 522

Asn Ser Arg Asp Ile Asn Leu Asp
1               5

<210> SEQ ID NO 523
<211> LENGTH: 120
<212> TYPE: PRT
<213> ORGANISM: Homo sapiens

<400> SEQUENCE: 523

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Val Ile Val Trp Gly Ser Tyr Asp Tyr Trp Gly Gln
            100                 105                 110

Gly Thr Leu Val Thr Val Ser Arg
        115                 120

<210> SEQ ID NO 524
<211> LENGTH: 7
<212> TYPE: PRT
<213> ORGANISM: Homo sapiens

<400> SEQUENCE: 524

Ser Ser Ser Tyr Tyr Trp Gly
1               5

<210> SEQ ID NO 525
<211> LENGTH: 16
<212> TYPE: PRT
<213> ORGANISM: Homo sapiens

<400> SEQUENCE: 525

Ser Ile Tyr Tyr Ser Gly Ser Thr Tyr Tyr Asn Pro Ser Leu Lys Ser
1               5                   10                  15

<210> SEQ ID NO 526

```
<211> LENGTH: 10
<212> TYPE: PRT
<213> ORGANISM: Homo sapiens

<400> SEQUENCE: 526

Arg Val Ile Val Trp Gly Ser Tyr Asp Tyr
1               5                   10

<210> SEQ ID NO 527
<211> LENGTH: 109
<212> TYPE: PRT
<213> ORGANISM: Homo sapiens

<400> SEQUENCE: 527

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 528
<211> LENGTH: 11
<212> TYPE: PRT
<213> ORGANISM: Homo sapiens

<400> SEQUENCE: 528

Gly Gly Asn Asn Ile Gly Ser Lys Ser Val His
1               5                   10

<210> SEQ ID NO 529
<211> LENGTH: 7
<212> TYPE: PRT
<213> ORGANISM: Homo sapiens

<400> SEQUENCE: 529

Tyr Asp Ser Asp Arg Pro Ser
1               5

<210> SEQ ID NO 530
<211> LENGTH: 9
<212> TYPE: PRT
<213> ORGANISM: Homo sapiens

<400> SEQUENCE: 530

Gln Val Trp Asp Ser Ser Ser Asp His
1               5

<210> SEQ ID NO 531
<211> LENGTH: 120
<212> TYPE: PRT
<213> ORGANISM: Homo sapiens

<400> SEQUENCE: 531
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Met Arg Ala Tyr Gly Ser Gly Ser Tyr Asp Tyr Trp Gly Gln
            100                 105                 110

Gly Thr Leu Val Thr Val Ser Arg
        115                 120

<210> SEQ ID NO 532
<211> LENGTH: 7
<212> TYPE: PRT
<213> ORGANISM: Homo sapiens

<400> SEQUENCE: 532

Ser Ser Ser Tyr Tyr Trp Gly
1               5

<210> SEQ ID NO 533
<211> LENGTH: 16
<212> TYPE: PRT
<213> ORGANISM: Homo sapiens

<400> SEQUENCE: 533

Ser Ile Tyr Tyr Ser Gly Ser Thr Tyr Tyr Asn Pro Ser Leu Lys Ser
1               5                   10                  15

<210> SEQ ID NO 534
<211> LENGTH: 10
<212> TYPE: PRT
<213> ORGANISM: Homo sapiens

<400> SEQUENCE: 534

Arg Ala Tyr Gly Ser Gly Ser Tyr Asp Tyr
1               5                   10

<210> SEQ ID NO 535
<211> LENGTH: 112
<212> TYPE: PRT
<213> ORGANISM: Homo sapiens

<400> SEQUENCE: 535

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 536
<211> LENGTH: 16
<212> TYPE: PRT
<213> ORGANISM: Homo sapiens

<400> SEQUENCE: 536

Arg Ser Ser Gln Ser Leu Leu His Ser Asn Gly Tyr Asn Tyr Leu Asp
1               5                   10                  15

<210> SEQ ID NO 537
<211> LENGTH: 7
<212> TYPE: PRT
<213> ORGANISM: Homo sapiens

<400> SEQUENCE: 537

Leu Gly Ser Asn Arg Ala Ser
1               5

<210> SEQ ID NO 538
<211> LENGTH: 7
<212> TYPE: PRT
<213> ORGANISM: Homo sapiens

<400> SEQUENCE: 538

Met Gln Ala Leu Gln Thr Pro
1               5

<210> SEQ ID NO 539
<211> LENGTH: 121
<212> TYPE: PRT
<213> ORGANISM: Homo sapiens

<400> SEQUENCE: 539

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Gly Leu Arg Tyr Ser Ser Ala Trp Thr Phe Asp Tyr Trp Gly
            100                 105                 110

Gln Gly Thr Leu Val Thr Val Ser Arg
        115                 120

<210> SEQ ID NO 540
<211> LENGTH: 5
<212> TYPE: PRT
<213> ORGANISM: Homo sapiens

<400> SEQUENCE: 540

```
Ser Tyr Ala Met Ser
1               5

<210> SEQ ID NO 541
<211> LENGTH: 17
<212> TYPE: PRT
<213> ORGANISM: Homo sapiens

<400> SEQUENCE: 541

Ala Ile Ser Gly Ser Gly Gly Ser Thr Tyr Tyr Ala Asp Ser Val Lys
1               5                   10                  15

Gly

<210> SEQ ID NO 542
<211> LENGTH: 12
<212> TYPE: PRT
<213> ORGANISM: Homo sapiens

<400> SEQUENCE: 542

Gly Leu Arg Tyr Ser Ser Ala Trp Thr Phe Asp Tyr
1               5                   10

<210> SEQ ID NO 543
<211> LENGTH: 112
<212> TYPE: PRT
<213> ORGANISM: Homo sapiens

<400> SEQUENCE: 543

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Val Val Phe Gly Gly Gly Thr Lys Leu Thr Val Leu Gly
                100                 105                 110

<210> SEQ ID NO 544
<211> LENGTH: 14
<212> TYPE: PRT
<213> ORGANISM: Homo sapiens

<400> SEQUENCE: 544

Thr Gly Thr Ser Ser Asp Val Gly Gly Tyr Asn Tyr Val Ser
1               5                   10

<210> SEQ ID NO 545
<211> LENGTH: 7
<212> TYPE: PRT
<213> ORGANISM: Homo sapiens

<400> SEQUENCE: 545

Asp Val Ser Asn Arg Pro Ser
1               5
```

<210> SEQ ID NO 546
<211> LENGTH: 9
<212> TYPE: PRT
<213> ORGANISM: Homo sapiens

<400> SEQUENCE: 546

Ser Ser Tyr Thr Ser Ser Ser Thr Pro
1               5

<210> SEQ ID NO 547
<211> LENGTH: 119
<212> TYPE: PRT
<213> ORGANISM: Homo sapiens

<400> SEQUENCE: 547

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Arg Tyr
            20                  25                  30

Gly Ile Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Val Val Phe Ser Leu Asp Thr Ser Val Ser Thr Ala Tyr
65                  70                  75                  80

Leu Gln Ile Ser Ser Leu Lys Ala Glu Asp Thr Ala Met Tyr Tyr Cys
                85                  90                  95

Ala Ile Ser Ser Gly Phe Gly Tyr Tyr Phe Asp Tyr Trp Gly Gln Gly
            100                 105                 110

Thr Leu Val Thr Val Ser Arg
        115

<210> SEQ ID NO 548
<211> LENGTH: 5
<212> TYPE: PRT
<213> ORGANISM: Homo sapiens

<400> SEQUENCE: 548

Arg Tyr Gly Ile Asn
1               5

<210> SEQ ID NO 549
<211> LENGTH: 17
<212> TYPE: PRT
<213> ORGANISM: Homo sapiens

<400> SEQUENCE: 549

Trp Ile Asn Thr Asn Thr Gly Asn Pro Thr Tyr Ala Gln Gly Phe Thr
1               5                   10                  15

Gly

<210> SEQ ID NO 550
<211> LENGTH: 10
<212> TYPE: PRT
<213> ORGANISM: Homo sapiens

<400> SEQUENCE: 550

Ser Ser Gly Phe Gly Tyr Tyr Phe Asp Tyr
1               5                   10

```
<210> SEQ ID NO 551
<211> LENGTH: 107
<212> TYPE: PRT
<213> ORGANISM: Homo sapiens

<400> SEQUENCE: 551

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Phe Leu Ile
        35                  40                  45

Tyr Ala Gly Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Val Glu Ile Lys
            100                 105

<210> SEQ ID NO 552
<211> LENGTH: 11
<212> TYPE: PRT
<213> ORGANISM: Homo sapiens

<400> SEQUENCE: 552

Arg Ala Ser Gln Ser Ile Ser Arg Trp Leu Ala
1               5                   10

<210> SEQ ID NO 553
<211> LENGTH: 7
<212> TYPE: PRT
<213> ORGANISM: Homo sapiens

<400> SEQUENCE: 553

Ala Gly Ser Ser Leu Gln Ser
1               5

<210> SEQ ID NO 554
<211> LENGTH: 7
<212> TYPE: PRT
<213> ORGANISM: Homo sapiens

<400> SEQUENCE: 554

Gln Gln Thr Asn Ser Phe Pro
1               5

<210> SEQ ID NO 555
<211> LENGTH: 120
<212> TYPE: PRT
<213> ORGANISM: Homo sapiens

<400> SEQUENCE: 555

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
```

```
            50                  55                  60
Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Ala Phe Arg Asp Trp Gly Ser Leu Arg Asp Tyr Trp Gly Gln
                100                 105                 110

Gly Thr Leu Val Thr Val Ser Arg
            115                 120

<210> SEQ ID NO 556
<211> LENGTH: 5
<212> TYPE: PRT
<213> ORGANISM: Homo sapiens

<400> SEQUENCE: 556

Ser Tyr Gly Ile Ser
1               5

<210> SEQ ID NO 557
<211> LENGTH: 17
<212> TYPE: PRT
<213> ORGANISM: Homo sapiens

<400> SEQUENCE: 557

Trp Ile Ser Ala Tyr Asn Gly Asn Thr Asn Tyr Ala Gln Lys Leu Gln
1               5                  10                  15

Gly

<210> SEQ ID NO 558
<211> LENGTH: 11
<212> TYPE: PRT
<213> ORGANISM: Homo sapiens

<400> SEQUENCE: 558

Ala Phe Arg Asp Trp Gly Ser Leu Arg Asp Tyr
1               5                  10

<210> SEQ ID NO 559
<211> LENGTH: 111
<212> TYPE: PRT
<213> ORGANISM: Homo sapiens

<400> SEQUENCE: 559

Gln Ser Val Leu Thr Gln Pro Pro Ser Val Ala Ala Pro Gly Gln
1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
         50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu Gly
                100                 105                 110
```

<210> SEQ ID NO 560
<211> LENGTH: 13
<212> TYPE: PRT
<213> ORGANISM: Homo sapiens

<400> SEQUENCE: 560

Ser Gly Ser Ser Asn Ile Gly Asn Asn Tyr Val Ser
1               5                   10

<210> SEQ ID NO 561
<211> LENGTH: 7
<212> TYPE: PRT
<213> ORGANISM: Homo sapiens

<400> SEQUENCE: 561

Asp Asn Asn Lys Arg Pro Ser
1               5

<210> SEQ ID NO 562
<211> LENGTH: 9
<212> TYPE: PRT
<213> ORGANISM: Homo sapiens

<400> SEQUENCE: 562

Gly Thr Trp Asp Ser Ser Leu Ser Ala
1               5

<210> SEQ ID NO 563
<211> LENGTH: 121
<212> TYPE: PRT
<213> ORGANISM: Homo sapiens

<400> SEQUENCE: 563

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Ala Val Gly Ala Tyr Gln Tyr Tyr Phe Asp Tyr Trp Gly
            100                 105                 110

Gln Gly Thr Leu Val Thr Val Ser Arg
        115                 120

<210> SEQ ID NO 564
<211> LENGTH: 5
<212> TYPE: PRT
<213> ORGANISM: Homo sapiens

<400> SEQUENCE: 564

Ser Tyr Trp Ile Gly
1               5

<210> SEQ ID NO 565
<211> LENGTH: 17
<212> TYPE: PRT

<213> ORGANISM: Homo sapiens

<400> SEQUENCE: 565

Ile Ile Tyr Pro Gly Asp Ser Asp Thr Arg Tyr Ser Pro Ser Phe Gln
1               5                   10                  15
Gly

<210> SEQ ID NO 566
<211> LENGTH: 12
<212> TYPE: PRT
<213> ORGANISM: Homo sapiens

<400> SEQUENCE: 566

Leu Ala Val Gly Ala Tyr Gln Tyr Tyr Phe Asp Tyr
1               5                   10

<210> SEQ ID NO 567
<211> LENGTH: 111
<212> TYPE: PRT
<213> ORGANISM: Homo sapiens

<400> SEQUENCE: 567

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly
            100                 105                 110

<210> SEQ ID NO 568
<211> LENGTH: 14
<212> TYPE: PRT
<213> ORGANISM: Homo sapiens

<400> SEQUENCE: 568

Gly Leu Ser Ser Gly Ser Val Ser Thr Ser Tyr Tyr Pro Ser
1               5                   10

<210> SEQ ID NO 569
<211> LENGTH: 7
<212> TYPE: PRT
<213> ORGANISM: Homo sapiens

<400> SEQUENCE: 569

Ser Thr Asn Thr Arg Ser Ser
1               5

<210> SEQ ID NO 570
<211> LENGTH: 8
<212> TYPE: PRT
<213> ORGANISM: Homo sapiens

<400> SEQUENCE: 570

```
Val Leu Tyr Met Gly Ser Gly Ile
1               5
```

<210> SEQ ID NO 571
<211> LENGTH: 119
<212> TYPE: PRT
<213> ORGANISM: Homo sapiens

<400> SEQUENCE: 571

```
Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Thr Trp Val Arg Gln Ala Pro Gly Lys Gly Leu Glu Trp Ile
        35                  40                  45

Ser Ser Val Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Trp Pro Gly Trp Tyr Phe Asp Leu Trp Gly Arg Gly
            100                 105                 110

Thr Leu Val Thr Val Ser Arg
        115
```

<210> SEQ ID NO 572
<211> LENGTH: 5
<212> TYPE: PRT
<213> ORGANISM: Homo sapiens

<400> SEQUENCE: 572

```
Arg Tyr Trp Met Thr
1               5
```

<210> SEQ ID NO 573
<211> LENGTH: 17
<212> TYPE: PRT
<213> ORGANISM: Homo sapiens

<400> SEQUENCE: 573

```
Ser Val Ser Ser Ser Gly Ser Thr Ile Tyr Tyr Ala Asp Ser Val Lys
1               5                   10                  15

Gly
```

<210> SEQ ID NO 574
<211> LENGTH: 10
<212> TYPE: PRT
<213> ORGANISM: Homo sapiens

<400> SEQUENCE: 574

```
Asp Tyr Trp Pro Gly Trp Tyr Phe Asp Leu
1               5                   10
```

<210> SEQ ID NO 575
<211> LENGTH: 116
<212> TYPE: PRT
<213> ORGANISM: Homo sapiens

<400> SEQUENCE: 575

```
Gln Ala Val Leu Thr Gln Pro Ser Ser Leu Ser Ala Ser Pro Gly Ala
```

```
                1               5                  10                  15
            Ser Ala Ser Leu Thr Cys Thr Phe Arg Ser Asp Ile Ser Val Gly Ser
                            20                  25                  30

Tyr Arg Ile Tyr Trp Tyr Gln Gln Lys Pro Gly Ser Pro Pro Gln Phe
                            35                  40                  45

Leu Leu Lys Tyr Thr Ser Asp Ser Asp Lys Gln Gln Gly Ser Gly Val
                            50                  55                  60

Pro Ser Arg Phe Ser Gly Ser Lys Asp Val Ser Ala Asn Ala Gly Ile
             65                 70                  75                  80

Leu Leu Ile Ser Gly Leu Gln Ser Glu Asp Glu Ala Asp Tyr Tyr Cys
                            85                  90                  95

Met Thr Trp His Asn Thr Ala Ser Val Phe Gly Gly Gly Thr Lys Leu
                           100                 105                 110

Ala Val Leu Gly
                    115

<210> SEQ ID NO 576
<211> LENGTH: 14
<212> TYPE: PRT
<213> ORGANISM: Homo sapiens

<400> SEQUENCE: 576

Thr Phe Arg Ser Asp Ile Ser Val Gly Ser Tyr Arg Ile Tyr
1               5                   10

<210> SEQ ID NO 577
<211> LENGTH: 11
<212> TYPE: PRT
<213> ORGANISM: Homo sapiens

<400> SEQUENCE: 577

Tyr Thr Ser Asp Ser Asp Lys Gln Gln Gly Ser
1               5                   10

<210> SEQ ID NO 578
<211> LENGTH: 7
<212> TYPE: PRT
<213> ORGANISM: Homo sapiens

<400> SEQUENCE: 578

Met Thr Trp His Asn Thr Ala
1               5

<210> SEQ ID NO 579
<211> LENGTH: 119
<212> TYPE: PRT
<213> ORGANISM: Homo sapiens

<400> SEQUENCE: 579

Glu Val Gln Leu Val Glu Ser Gly Gly Gly Leu Ile Arg Pro Gly Gly
1               5                   10                  15

Ser Leu Arg Leu Ser Cys Thr Ala Ser Gly Phe Thr Phe Ser Ser Tyr
                20                  25                  30

Thr Met Asn Trp Val Arg Gln Ala Pro Gly Lys Gly Leu Glu Trp Leu
                35                  40                  45

Ser Tyr Ile Ser Gly Gly Ser Gly Thr Lys Phe Tyr Ala Asp Ser Val
                50                  55                  60

Lys Gly Arg Phe Thr Val Ser Arg Asp Asn Ala Lys Asn Ser Leu Tyr
 65                 70                  75                  80
```

```
Leu Glu Met Asn Ser Leu Arg Pro Glu Asp Thr Ala Val Tyr Tyr Cys
                 85                  90                  95

Ala Leu Val Ser Tyr Ser Ser Pro Gly Phe Asp Tyr Trp Gly Gln Gly
            100                 105                 110

Thr Leu Val Thr Val Ser Ser
        115

<210> SEQ ID NO 580
<211> LENGTH: 5
<212> TYPE: PRT
<213> ORGANISM: Homo sapiens

<400> SEQUENCE: 580

Ser Tyr Thr Met Asn
1               5

<210> SEQ ID NO 581
<211> LENGTH: 17
<212> TYPE: PRT
<213> ORGANISM: Homo sapiens

<400> SEQUENCE: 581

Tyr Ile Ser Gly Gly Ser Gly Thr Lys Phe Tyr Ala Asp Ser Val Lys
1               5                   10                  15

Gly

<210> SEQ ID NO 582
<211> LENGTH: 10
<212> TYPE: PRT
<213> ORGANISM: Homo sapiens

<400> SEQUENCE: 582

Val Ser Tyr Ser Ser Pro Gly Phe Asp Tyr
1               5                   10

<210> SEQ ID NO 583
<211> LENGTH: 107
<212> TYPE: PRT
<213> ORGANISM: Homo sapiens

<400> SEQUENCE: 583

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Tyr Trp Tyr Gln Gln Lys Pro Gly Gln Ser Pro Ile Leu Leu Ile Phe
        35                  40                  45

Gln Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Ala Ala Val
                85                  90                  95

Phe Gly Gly Gly Thr Lys Leu Thr Val Leu Gly
            100                 105

<210> SEQ ID NO 584
<211> LENGTH: 11
<212> TYPE: PRT
<213> ORGANISM: Homo sapiens
```

-continued

<400> SEQUENCE: 584

Ser Gly Asp Lys Leu Gly Asp Lys Tyr Val Tyr
1               5                   10

<210> SEQ ID NO 585
<211> LENGTH: 7
<212> TYPE: PRT
<213> ORGANISM: Homo sapiens

<400> SEQUENCE: 585

Gln Asp Ser Glu Arg Pro Ser
1               5

<210> SEQ ID NO 586
<211> LENGTH: 7
<212> TYPE: PRT
<213> ORGANISM: Homo sapiens

<400> SEQUENCE: 586

Gln Ala Trp Asp Ser Ser Ala
1               5

<210> SEQ ID NO 587
<211> LENGTH: 115
<212> TYPE: PRT
<213> ORGANISM: Homo sapiens

<400> SEQUENCE: 587

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Ala Phe Asp Ile Trp Gly Gln Gly Thr Thr Val Thr
            100                 105                 110

Val Ser Arg
        115

<210> SEQ ID NO 588
<211> LENGTH: 5
<212> TYPE: PRT
<213> ORGANISM: Homo sapiens

<400> SEQUENCE: 588

Ser Tyr Gly Ile Ser
1               5

<210> SEQ ID NO 589
<211> LENGTH: 17
<212> TYPE: PRT
<213> ORGANISM: Homo sapiens

<400> SEQUENCE: 589

Trp Ile Ser Ala Tyr Asn Gly Asn Thr Asn Tyr Ala Gln Lys Leu Gln

```
1               5                   10                  15

Gly

<210> SEQ ID NO 590
<211> LENGTH: 6
<212> TYPE: PRT
<213> ORGANISM: Homo sapiens

<400> SEQUENCE: 590

Gly Gly Ala Phe Asp Ile
1               5

<210> SEQ ID NO 591
<211> LENGTH: 112
<212> TYPE: PRT
<213> ORGANISM: Homo sapiens

<400> SEQUENCE: 591

Gln Ser Val Leu Thr Gln Pro Pro Ser Val Gly Ala Pro Gly Gln
1               5                   10                  15

Arg Val Thr Ile Ser Cys Thr Gly Ser Ser Ser Asn Ile Gly Ala Gly
            20                  25                  30

Tyr His Val Tyr Trp Tyr Gln Gln Leu Pro Gly Lys Ala Pro Lys Leu
        35                  40                  45

Leu Ile Tyr Val Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Ser
                85                  90                  95

Leu Ser Gly Arg Val Phe Gly Gly Gly Thr Lys Leu Thr Val Leu Gly
            100                 105                 110

<210> SEQ ID NO 592
<211> LENGTH: 14
<212> TYPE: PRT
<213> ORGANISM: Homo sapiens

<400> SEQUENCE: 592

Thr Gly Ser Ser Ser Asn Ile Gly Ala Gly Tyr His Val Tyr
1               5                   10

<210> SEQ ID NO 593
<211> LENGTH: 7
<212> TYPE: PRT
<213> ORGANISM: Homo sapiens

<400> SEQUENCE: 593

Val Asn Ser Asn Arg Pro Ser
1               5

<210> SEQ ID NO 594
<211> LENGTH: 9
<212> TYPE: PRT
<213> ORGANISM: Homo sapiens

<400> SEQUENCE: 594

Gln Ser Tyr Asp Ser Ser Leu Ser Gly
1               5

<210> SEQ ID NO 595
```

```
<211> LENGTH: 119
<212> TYPE: PRT
<213> ORGANISM: Homo sapiens

<400> SEQUENCE: 595

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Trp Met Thr Trp Val Arg Gln Ala Pro Gly Lys Gly Leu Glu Trp Ile
        35                  40                  45

Ser Ser Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Asp Tyr Trp Pro Gly Trp Tyr Phe Asp Leu Trp Gly Arg Gly
            100                 105                 110

Thr Leu Val Thr Val Ser Arg
        115

<210> SEQ ID NO 596
<211> LENGTH: 5
<212> TYPE: PRT
<213> ORGANISM: Homo sapiens

<400> SEQUENCE: 596

Asn Tyr Trp Met Thr
1               5

<210> SEQ ID NO 597
<211> LENGTH: 17
<212> TYPE: PRT
<213> ORGANISM: Homo sapiens

<400> SEQUENCE: 597

Ser Ile Ser Ser Ser Gly Ser Thr Ile Tyr Tyr Ala Asp Ser Val Lys
1               5                   10                  15

Gly

<210> SEQ ID NO 598
<211> LENGTH: 10
<212> TYPE: PRT
<213> ORGANISM: Homo sapiens

<400> SEQUENCE: 598

Asp Tyr Trp Pro Gly Trp Tyr Phe Asp Leu
1               5                   10

<210> SEQ ID NO 599
<211> LENGTH: 116
<212> TYPE: PRT
<213> ORGANISM: Homo sapiens

<400> SEQUENCE: 599

Gln Ala Val Leu Thr Gln Pro Ser Ser Leu Ser Ala Ser Pro Gly Ala
1               5                   10                  15

Ser Ala Ser Leu Thr Cys Thr Phe Arg Ser Asp Ile Ser Val Gly Ser
            20                  25                  30
```

```
Tyr Arg Ile Tyr Trp Tyr Gln Gln Lys Pro Gly Ser Pro Gln Phe
             35                  40                  45

Leu Leu Lys Tyr Thr Ser Asp Ser Asp Lys Gln Gln Gly Ser Gly Val
 50                  55                  60

Pro Ser Arg Phe Ser Gly Ser Lys Asp Val Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Thr Trp His Asn Thr Ala Ser Val Phe Gly Gly Gly Thr Lys Leu
                100                 105                 110

Ala Val Leu Gly
        115
```

<210> SEQ ID NO 600
<211> LENGTH: 14
<212> TYPE: PRT
<213> ORGANISM: Homo sapiens

<400> SEQUENCE: 600

```
Thr Phe Arg Ser Asp Ile Ser Val Gly Ser Tyr Arg Ile Tyr
 1               5                  10
```

<210> SEQ ID NO 601
<211> LENGTH: 11
<212> TYPE: PRT
<213> ORGANISM: Homo sapiens

<400> SEQUENCE: 601

```
Tyr Thr Ser Asp Ser Asp Lys Gln Gln Gly Ser
 1               5                  10
```

<210> SEQ ID NO 602
<211> LENGTH: 7
<212> TYPE: PRT
<213> ORGANISM: Homo sapiens

<400> SEQUENCE: 602

```
Met Thr Trp His Asn Thr Ala
 1               5
```

<210> SEQ ID NO 603
<211> LENGTH: 127
<212> TYPE: PRT
<213> ORGANISM: Homo sapiens

<400> SEQUENCE: 603

```
Gln Val Gln Leu Val Gln Ser Gly Ser Glu Val Lys Lys Pro Gly Ala
 1               5                  10                  15

Ser Val Lys Val Ser Cys Lys Thr Ser Gly Tyr Ile Phe Thr Asp Tyr
                 20                  25                  30

Tyr Met His Trp Val Arg Gln Ala Pro Gly Lys Gly Leu Glu Trp Met
             35                  40                  45

Gly Trp Ile Asn Pro Asn Ser Gly Gly Thr Tyr Tyr Ala Gln Lys Phe
 50                  55                  60

His Gly Arg Val Thr Met Thr Ser Asp Thr Ser Ile Ser Thr Ala Tyr
 65                  70                  75                  80

Met Glu Leu Ser Ser Leu Arg Ser Asp Asp Thr Ala Ile Tyr Tyr Cys
                 85                  90                  95

Ala Arg Glu Asp Tyr Asp Ile Leu Thr Gly Tyr Tyr Pro Ala Ser Gly
                100                 105                 110
```

-continued

His Gly Asp Tyr Trp Gly Gln Gly Thr Leu Val Thr Val Ser Arg
        115                 120                 125

<210> SEQ ID NO 604
<211> LENGTH: 5
<212> TYPE: PRT
<213> ORGANISM: Homo sapiens

<400> SEQUENCE: 604

Asp Tyr Tyr Met His
1               5

<210> SEQ ID NO 605
<211> LENGTH: 17
<212> TYPE: PRT
<213> ORGANISM: Homo sapiens

<400> SEQUENCE: 605

Trp Ile Asn Pro Asn Ser Gly Gly Thr Tyr Tyr Ala Gln Lys Phe His
1               5                   10                  15

Gly

<210> SEQ ID NO 606
<211> LENGTH: 18
<212> TYPE: PRT
<213> ORGANISM: Homo sapiens

<400> SEQUENCE: 606

Glu Asp Tyr Asp Ile Leu Thr Gly Tyr Tyr Pro Ala Ser Gly His Gly
1               5                   10                  15

Asp Tyr

<210> SEQ ID NO 607
<211> LENGTH: 110
<212> TYPE: PRT
<213> ORGANISM: Homo sapiens

<400> SEQUENCE: 607

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Phe Leu Ala Asn Trp Phe Gln Gln Lys Pro Gly Gln Thr Pro Arg Ser
        35                  40                  45

Leu Ile Tyr Lys Thr Ser Asn Lys His Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Asp Tyr Tyr Cys Leu Leu Leu Ser Gly Gly
                85                  90                  95

Ala Trp Val Phe Gly Gly Gly Thr Lys Leu Ser Val Leu Gly
            100                 105                 110

<210> SEQ ID NO 608
<211> LENGTH: 14
<212> TYPE: PRT
<213> ORGANISM: Homo sapiens

<400> SEQUENCE: 608

Ala Ser Ser Thr Gly Ala Val Thr Ser Gly Phe Leu Ala Asn

<210> SEQ ID NO 609
<211> LENGTH: 7
<212> TYPE: PRT
<213> ORGANISM: Homo sapiens

<400> SEQUENCE: 609

Lys Thr Ser Asn Lys His Pro
1               5

<210> SEQ ID NO 610
<211> LENGTH: 7
<212> TYPE: PRT
<213> ORGANISM: Homo sapiens

<400> SEQUENCE: 610

Leu Leu Leu Ser Gly Gly Ala
1               5

<210> SEQ ID NO 611
<211> LENGTH: 122
<212> TYPE: PRT
<213> ORGANISM: Homo sapiens

<400> SEQUENCE: 611

Gln Val Gln Leu Val Gln Ser Gly Ala Glu Val Lys Lys Pro Gly Glu
1               5                   10                  15

Ser Leu Lys Ile Ser Cys Glu Gly Ser Gly Tyr Thr Phe Thr Ser Tyr
            20                  25                  30

Trp Ile Gly Trp Val Arg Gln Met Pro Gly Lys Asp Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Val Val Asp Gly Tyr Asn Thr Gly Met Asp Val Trp
            100                 105                 110

Gly Gln Gly Thr Thr Val Thr Val Ser Arg
        115                 120

<210> SEQ ID NO 612
<211> LENGTH: 5
<212> TYPE: PRT
<213> ORGANISM: Homo sapiens

<400> SEQUENCE: 612

Ser Tyr Trp Ile Gly
1               5

<210> SEQ ID NO 613
<211> LENGTH: 17
<212> TYPE: PRT
<213> ORGANISM: Homo sapiens

<400> SEQUENCE: 613

Ile Ile Tyr Pro Gly Asp Ser Asp Thr Arg Tyr Ser Pro Ser Phe Gln
1               5                   10                  15

Gly

<210> SEQ ID NO 614
<211> LENGTH: 13
<212> TYPE: PRT
<213> ORGANISM: Homo sapiens

<400> SEQUENCE: 614

His Asp Val Val Asp Gly Tyr Asn Thr Gly Met Asp Val
1               5                   10

<210> SEQ ID NO 615
<211> LENGTH: 111
<212> TYPE: PRT
<213> ORGANISM: Homo sapiens

<400> SEQUENCE: 615

Gln Thr Val Val Thr Gln Glu Pro Ser Phe Thr Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Ser Ser Thr Asn Thr Arg Ser Ser Gly Val Pro Asp Arg Phe
    50                  55                  60

Ser Gly Ser Ile Leu Gly Asn Arg Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu Gly
            100                 105                 110

<210> SEQ ID NO 616
<211> LENGTH: 14
<212> TYPE: PRT
<213> ORGANISM: Homo sapiens

<400> SEQUENCE: 616

Gly Leu Ser Ser Gly Ser Val Ser Thr Ser Tyr Tyr Pro Ser
1               5                   10

<210> SEQ ID NO 617
<211> LENGTH: 7
<212> TYPE: PRT
<213> ORGANISM: Homo sapiens

<400> SEQUENCE: 617

Ser Thr Asn Thr Arg Ser Ser
1               5

<210> SEQ ID NO 618
<211> LENGTH: 8
<212> TYPE: PRT
<213> ORGANISM: Homo sapiens

<400> SEQUENCE: 618

Val Leu Tyr Met Gly Ser Gly Ile
1               5

<210> SEQ ID NO 619
<211> LENGTH: 128
<212> TYPE: PRT
<213> ORGANISM: Homo sapiens

<400> SEQUENCE: 619

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Ala Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Thr Gly Ser Ser Tyr Tyr Asp Ser Ser Gly Tyr Ser Ser
            100                 105                 110

Tyr Gly Met Asp Val Trp Gly Gln Gly Thr Thr Val Thr Val Ser Arg
        115                 120                 125

<210> SEQ ID NO 620
<211> LENGTH: 5
<212> TYPE: PRT
<213> ORGANISM: Homo sapiens

<400> SEQUENCE: 620

Ser Tyr Trp Ile Gly
1               5

<210> SEQ ID NO 621
<211> LENGTH: 17
<212> TYPE: PRT
<213> ORGANISM: Homo sapiens

<400> SEQUENCE: 621

Ile Ile Tyr Pro Gly Asp Ser Asp Ala Arg Tyr Ser Pro Ser Phe Gln
1               5                   10                  15

Gly

<210> SEQ ID NO 622
<211> LENGTH: 19
<212> TYPE: PRT
<213> ORGANISM: Homo sapiens

<400> SEQUENCE: 622

Leu Thr Gly Ser Ser Tyr Tyr Asp Ser Ser Gly Tyr Ser Ser Tyr Gly
1               5                   10                  15

Met Asp Val

<210> SEQ ID NO 623
<211> LENGTH: 111
<212> TYPE: PRT
<213> ORGANISM: Homo sapiens

<400> SEQUENCE: 623

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

Tyr Tyr Pro Ser Trp Phe Gln Gln Thr Pro Gly Gln Ala Pro Arg Thr

```
                35                  40                  45
Leu Ile Tyr Ser Thr Asn Thr Arg Ser Ser Gly Val Pro Asp Arg Phe
 50                  55                  60
Ser Gly Ser Ile Leu Gly Asn Lys Ala Ala Leu Thr Ile Thr Gly Ala
 65                  70                  75                  80
Gln Ala Asp Asp Glu Ser Asp Tyr Tyr Cys Val Leu Tyr Met Gly Ser
                 85                  90                  95
Gly Ile Ser Val Phe Gly Gly Thr Gln Leu Thr Val Leu Gly
                100                 105                 110

<210> SEQ ID NO 624
<211> LENGTH: 14
<212> TYPE: PRT
<213> ORGANISM: Homo sapiens

<400> SEQUENCE: 624

Gly Leu Ser Ser Gly Ser Val Ser Thr Ser Tyr Tyr Pro Ser
 1               5                  10

<210> SEQ ID NO 625
<211> LENGTH: 7
<212> TYPE: PRT
<213> ORGANISM: Homo sapiens

<400> SEQUENCE: 625

Ser Thr Asn Thr Arg Ser Ser
 1               5

<210> SEQ ID NO 626
<211> LENGTH: 8
<212> TYPE: PRT
<213> ORGANISM: Homo sapiens

<400> SEQUENCE: 626

Val Leu Tyr Met Gly Ser Gly Ile
 1               5

<210> SEQ ID NO 627
<211> LENGTH: 121
<212> TYPE: PRT
<213> ORGANISM: Homo sapiens

<400> SEQUENCE: 627

Gln Val Gln Leu Val Gln Ser Gly Ala Glu Val Lys Lys Pro Gly Glu
 1               5                  10                  15
Ser Leu Lys Ile Ser Cys Lys Gly Ser Gly Tyr Ser Phe Thr Ser Tyr
                 20                  25                  30
Trp Ile Gly Trp Val Arg Gln Met Pro Gly Lys Gly Leu Glu Trp Met
                 35                  40                  45
Gly Ile Ile Tyr Pro Gly Asp Ser Asp Thr Arg Tyr Ser Pro Ser Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg His Asn Ser Asn Tyr Tyr Tyr Tyr Met Asp Val Trp Gly
                100                 105                 110
Lys Gly Thr Leu Val Thr Val Ser Arg
                115                 120
```

<210> SEQ ID NO 628
<211> LENGTH: 5
<212> TYPE: PRT
<213> ORGANISM: Homo sapiens

<400> SEQUENCE: 628

Ser Tyr Trp Ile Gly
1               5

<210> SEQ ID NO 629
<211> LENGTH: 17
<212> TYPE: PRT
<213> ORGANISM: Homo sapiens

<400> SEQUENCE: 629

Ile Ile Tyr Pro Gly Asp Ser Asp Thr Arg Tyr Ser Pro Ser Phe Gln
1               5                   10                  15

Gly

<210> SEQ ID NO 630
<211> LENGTH: 12
<212> TYPE: PRT
<213> ORGANISM: Homo sapiens

<400> SEQUENCE: 630

His Asn Ser Asn Tyr Tyr Tyr Tyr Tyr Met Asp Val
1               5                   10

<210> SEQ ID NO 631
<211> LENGTH: 111
<212> TYPE: PRT
<213> ORGANISM: Homo sapiens

<400> SEQUENCE: 631

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
            35                  40                  45

Leu Ile Tyr Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser Val Phe Gly Gly Gly Thr Lys Leu Thr Val Leu Gly
            100                 105                 110

<210> SEQ ID NO 632
<211> LENGTH: 14
<212> TYPE: PRT
<213> ORGANISM: Homo sapiens

<400> SEQUENCE: 632

Gly Leu Ser Ser Gly Ser Val Ser Thr Ser Tyr Tyr Pro Ser
1               5                   10

<210> SEQ ID NO 633
<211> LENGTH: 7
<212> TYPE: PRT

<213> ORGANISM: Homo sapiens

<400> SEQUENCE: 633

Ser Thr Asn Thr Arg Ser Ser
1               5

<210> SEQ ID NO 634
<211> LENGTH: 8
<212> TYPE: PRT
<213> ORGANISM: Homo sapiens

<400> SEQUENCE: 634

Val Leu Tyr Met Gly Ser Gly Ile
1               5

<210> SEQ ID NO 635
<211> LENGTH: 127
<212> TYPE: PRT
<213> ORGANISM: Homo sapiens

<400> SEQUENCE: 635

Gln Val Gln Leu Val Gln Ser Gly Ser Glu Val Lys Lys Pro Gly Ala
1               5                   10                  15

Ser Val Lys Val Ser Cys Lys Thr Ser Gly Tyr Ile Phe Thr Asp Tyr
            20                  25                  30

Tyr Met His Trp Val Arg Gln Ala Pro Gly Lys Gly Leu Glu Trp Met
        35                  40                  45

Gly Trp Ile Asn Pro Asn Ser Gly Gly Thr Tyr Tyr Ala Gln Lys Phe
    50                  55                  60

His Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Ile Tyr Tyr Cys
                85                  90                  95

Ala Arg Glu Asp Tyr Asp Ile Leu Thr Gly Phe Tyr Pro Ala Ser Gly
            100                 105                 110

His Gly Asp Tyr Trp Gly Gln Gly Thr Leu Val Thr Val Ser Arg
        115                 120                 125

<210> SEQ ID NO 636
<211> LENGTH: 5
<212> TYPE: PRT
<213> ORGANISM: Homo sapiens

<400> SEQUENCE: 636

Asp Tyr Tyr Met His
1               5

<210> SEQ ID NO 637
<211> LENGTH: 17
<212> TYPE: PRT
<213> ORGANISM: Homo sapiens

<400> SEQUENCE: 637

Trp Ile Asn Pro Asn Ser Gly Gly Thr Tyr Tyr Ala Gln Lys Phe His
1               5                   10                  15

Gly

<210> SEQ ID NO 638
<211> LENGTH: 18
<212> TYPE: PRT
<213> ORGANISM: Homo sapiens

<400> SEQUENCE: 638

Glu Asp Tyr Asp Ile Leu Thr Gly Phe Tyr Pro Ala Ser Gly His Gly
1               5                   10                  15

Asp Tyr

<210> SEQ ID NO 639
<211> LENGTH: 107
<212> TYPE: PRT
<213> ORGANISM: Homo sapiens

<400> SEQUENCE: 639

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 640
<211> LENGTH: 12
<212> TYPE: PRT
<213> ORGANISM: Homo sapiens

<400> SEQUENCE: 640

Arg Ala Ser Gln Ser Val Ser Ser Ser Tyr Leu Ala
1               5                   10

<210> SEQ ID NO 641
<211> LENGTH: 7
<212> TYPE: PRT
<213> ORGANISM: Homo sapiens

<400> SEQUENCE: 641

Gly Ala Ser Ser Arg Ala Thr
1               5

<210> SEQ ID NO 642
<211> LENGTH: 6
<212> TYPE: PRT
<213> ORGANISM: Homo sapiens

<400> SEQUENCE: 642

Gln Gln Tyr Gly Ser Ser
1               5

<210> SEQ ID NO 643
<211> LENGTH: 122
<212> TYPE: PRT
<213> ORGANISM: Homo sapiens

<400> SEQUENCE: 643

Gln Val Gln Leu Val Gln Ser Gly Ala Glu Val Lys Lys Pro Gly Glu

```
                1               5                  10                  15
            Ser Leu Lys Ile Ser Cys Lys Gly Ser Gly Tyr Ser Phe Thr Ser Tyr
                            20                  25                  30

Trp Ile Gly Trp Val Arg Gln Met Pro Gly Lys Gly Leu Glu Trp Met
                        35                  40                  45

Gly Ile Ile Tyr Pro Gly Asp Ser Asp Thr Arg Tyr Ser Pro Ser Phe
                    50                  55                  60

Gln Gly Gln Val Thr Ile Ser Ala Asp Lys Ser Ile Ser Thr Ala Tyr
             65                 70                  75                  80

Leu Gln Trp Ser Ser Leu Lys Ala Ser Asp Thr Ala Met Tyr Tyr Cys
                            85                  90                  95

Ala Arg His Gly Met Thr Ser Gly Tyr Val Ala His Asn Asp Tyr Trp
                       100                 105                 110

Gly Gln Gly Thr Leu Val Thr Val Ser Arg
                       115                 120

<210> SEQ ID NO 644
<211> LENGTH: 5
<212> TYPE: PRT
<213> ORGANISM: Homo sapiens

<400> SEQUENCE: 644

Ser Tyr Trp Ile Gly
1               5

<210> SEQ ID NO 645
<211> LENGTH: 17
<212> TYPE: PRT
<213> ORGANISM: Homo sapiens

<400> SEQUENCE: 645

Ile Ile Tyr Pro Gly Asp Ser Asp Thr Arg Tyr Ser Pro Ser Phe Gln
1               5                   10                  15

Gly

<210> SEQ ID NO 646
<211> LENGTH: 13
<212> TYPE: PRT
<213> ORGANISM: Homo sapiens

<400> SEQUENCE: 646

His Gly Met Thr Ser Gly Tyr Val Ala His Asn Asp Tyr
1               5                   10

<210> SEQ ID NO 647
<211> LENGTH: 111
<212> TYPE: PRT
<213> ORGANISM: Homo sapiens

<400> SEQUENCE: 647

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
                35                  40                  45

Leu Ile Tyr Ser Thr Asn Thr Arg Ser Ser Gly Val Pro Asp Arg Phe
            50                  55                  60

Ser Gly Ser Ile Leu Gly Asn Lys Ala Ala Leu Thr Ile Thr Gly Ala
```

```
                65                  70                  75                  80
Gln Ala Asp Asp Glu Ser Asp Tyr Tyr Cys Val Leu Tyr Met Gly Ser
                    85                  90                  95
Gly Ile Trp Val Phe Gly Gly Gly Thr Lys Leu Thr Val Leu Gly
            100                 105                 110
```

<210> SEQ ID NO 648
<211> LENGTH: 14
<212> TYPE: PRT
<213> ORGANISM: Homo sapiens

<400> SEQUENCE: 648

```
Gly Leu Ser Ser Gly Ser Val Ser Thr Ser Tyr Tyr Pro Ser
1               5                   10
```

<210> SEQ ID NO 649
<211> LENGTH: 7
<212> TYPE: PRT
<213> ORGANISM: Homo sapiens

<400> SEQUENCE: 649

```
Ser Thr Asn Thr Arg Ser Ser
1               5
```

<210> SEQ ID NO 650
<211> LENGTH: 8
<212> TYPE: PRT
<213> ORGANISM: Homo sapiens

<400> SEQUENCE: 650

```
Val Leu Tyr Met Gly Ser Gly Ile
1               5
```

<210> SEQ ID NO 651
<211> LENGTH: 117
<212> TYPE: PRT
<213> ORGANISM: Homo sapiens

<400> SEQUENCE: 651

```
Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Ser
                20                  25                  30
Asn Trp Trp Ser Trp Val Arg Gln Pro Pro Gly Lys Gly Leu Glu Trp
            35                  40                  45
Ile Gly Glu Ile Tyr His Ser Gly Ser Thr Asn Tyr Asn Pro Ser Leu
        50                  55                  60
Lys Ser Arg Val Thr Ile Ser Val Asp Lys Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Gly Ser Tyr Tyr Phe Asp Tyr Trp Gly Gln Gly Thr Leu
            100                 105                 110
Val Thr Val Ser Arg
        115
```

<210> SEQ ID NO 652
<211> LENGTH: 6
<212> TYPE: PRT
<213> ORGANISM: Homo sapiens

```
<400> SEQUENCE: 652

Ser Ser Asn Trp Trp Ser
1               5

<210> SEQ ID NO 653
<211> LENGTH: 16
<212> TYPE: PRT
<213> ORGANISM: Homo sapiens

<400> SEQUENCE: 653

Glu Ile Tyr His Ser Gly Ser Thr Asn Tyr Asn Pro Ser Leu Lys Ser
1               5                   10                  15

<210> SEQ ID NO 654
<211> LENGTH: 8
<212> TYPE: PRT
<213> ORGANISM: Homo sapiens

<400> SEQUENCE: 654

Gly Gly Ser Tyr Tyr Phe Asp Tyr
1               5

<210> SEQ ID NO 655
<211> LENGTH: 112
<212> TYPE: PRT
<213> ORGANISM: Homo sapiens

<400> SEQUENCE: 655

Gln Ser Ala Leu Thr Gln Pro Ala Ser Val Ser Gly Ser Pro Gly Gln
1               5                   10                  15

Ser Ile Thr Ile Ser Cys Thr Gly Thr Ile Ser Asp Val Gly Gly Tyr
            20                  25                  30

Asp Phe Val Ser Trp Tyr Gln His Pro Gly Lys Ala Pro Lys Leu
        35                  40                  45

Leu Ile Tyr Asp Val Asn Asn Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Thr Tyr Tyr Cys Ser Ser Tyr Ser Asn Arg
                85                  90                  95

His Ser Leu Ile Val Phe Gly Gly Thr Gln Val Val Gly Leu Gly
            100                 105                 110

<210> SEQ ID NO 656
<211> LENGTH: 14
<212> TYPE: PRT
<213> ORGANISM: Homo sapiens

<400> SEQUENCE: 656

Thr Gly Thr Ile Ser Asp Val Gly Gly Tyr Asp Phe Val Ser
1               5                   10

<210> SEQ ID NO 657
<211> LENGTH: 7
<212> TYPE: PRT
<213> ORGANISM: Homo sapiens

<400> SEQUENCE: 657

Asp Val Asn Asn Arg Pro Ser
1               5
```

```
<210> SEQ ID NO 658
<211> LENGTH: 9
<212> TYPE: PRT
<213> ORGANISM: Homo sapiens

<400> SEQUENCE: 658

Ser Ser Tyr Ser Asn Arg His Ser Leu
1               5

<210> SEQ ID NO 659
<211> LENGTH: 121
<212> TYPE: PRT
<213> ORGANISM: Homo sapiens

<400> SEQUENCE: 659

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Gly Val Glu Ala Leu Asn Tyr Gly Met Asp Val Trp Gly
            100                 105                 110

Gln Gly Thr Thr Val Thr Val Ser Arg
        115                 120

<210> SEQ ID NO 660
<211> LENGTH: 5
<212> TYPE: PRT
<213> ORGANISM: Homo sapiens

<400> SEQUENCE: 660

Gly Tyr Tyr Trp Ser
1               5

<210> SEQ ID NO 661
<211> LENGTH: 16
<212> TYPE: PRT
<213> ORGANISM: Homo sapiens

<400> SEQUENCE: 661

Glu Ile Asn His Ser Gly Ser Thr Asn Tyr Asn Pro Ser Leu Lys Ser
1               5                   10                  15

<210> SEQ ID NO 662
<211> LENGTH: 13
<212> TYPE: PRT
<213> ORGANISM: Homo sapiens

<400> SEQUENCE: 662

Gly Gly Gly Val Glu Ala Leu Asn Tyr Gly Met Asp Val
1               5                   10

<210> SEQ ID NO 663
<211> LENGTH: 112
<212> TYPE: PRT
```

<213> ORGANISM: Homo sapiens

<400> SEQUENCE: 663

Gln Ser Ala Leu Thr Gln Pro Ala Ser Val Ser Gly Ser Pro Gly Gln
1               5                   10                  15

Thr Ile Thr Ile Ser Cys Thr Gly Thr Ile Ser Asp Val Gly Gly Tyr
            20                  25                  30

Asp Phe Val Ser Trp Tyr Gln His Pro Gly Lys Ala Pro Lys Leu
        35                  40                  45

Leu Ile Tyr Asp Val Asn Asn Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Thr Tyr Tyr Cys Ser Ser Tyr Ser Asn Arg
                85                  90                  95

His Ser Leu Ile Val Phe Gly Ser Gly Thr Gln Val Val Gly Leu Gly
            100                 105                 110

<210> SEQ ID NO 664
<211> LENGTH: 14
<212> TYPE: PRT
<213> ORGANISM: Homo sapiens

<400> SEQUENCE: 664

Thr Gly Thr Ile Ser Asp Val Gly Gly Tyr Asp Phe Val Ser
1               5                   10

<210> SEQ ID NO 665
<211> LENGTH: 7
<212> TYPE: PRT
<213> ORGANISM: Homo sapiens

<400> SEQUENCE: 665

Asp Val Asn Asn Arg Pro Ser
1               5

<210> SEQ ID NO 666
<211> LENGTH: 9
<212> TYPE: PRT
<213> ORGANISM: Homo sapiens

<400> SEQUENCE: 666

Ser Ser Tyr Ser Asn Arg His Ser Leu
1               5

<210> SEQ ID NO 667
<211> LENGTH: 119
<212> TYPE: PRT
<213> ORGANISM: Homo sapiens

<400> SEQUENCE: 667

Gln Val Gln Leu Gln Gln Trp Gly Ala Gly Leu Leu Lys Pro Ser Glu
1               5                   10                  15

Thr Leu Ser Leu Thr Cys Thr Val His Gly Gly Ser Phe Asp Asp Tyr
            20                  25                  30

Tyr Trp Thr Trp Ile Arg Gln Pro Pro Gly Gly Leu Glu Trp Ile
        35                  40                  45

Gly Glu Met Asn Ser Gly Arg Thr Tyr Asn Tyr Asn Pro Phe Leu Glu
    50                  55                  60

Ser Arg Ala Ser Ile Asp Val Asp Thr Phe Lys Lys Gln Phe Ser Leu

```
                65                  70                  75                  80
Ala Leu Arg Ser Val Thr Ala Ala Asp Thr Ala Val Tyr Tyr Cys Ala
                    85                  90                  95

Arg Gly Ala Tyr Val Asn Tyr Tyr Ile Asp Val Trp Gly Asp Gly
                100                 105                 110

Thr Thr Val Thr Val Ser Arg
        115

<210> SEQ ID NO 668
<211> LENGTH: 5
<212> TYPE: PRT
<213> ORGANISM: Homo sapiens

<400> SEQUENCE: 668

Asp Tyr Tyr Trp Thr
1               5

<210> SEQ ID NO 669
<211> LENGTH: 16
<212> TYPE: PRT
<213> ORGANISM: Homo sapiens

<400> SEQUENCE: 669

Glu Met Asn Ser Gly Arg Thr Tyr Asn Tyr Asn Pro Phe Leu Glu Ser
1               5                   10                  15

<210> SEQ ID NO 670
<211> LENGTH: 11
<212> TYPE: PRT
<213> ORGANISM: Homo sapiens

<400> SEQUENCE: 670

Gly Ala Tyr Val Asn Tyr Tyr Ile Asp Val
1               5                   10

<210> SEQ ID NO 671
<211> LENGTH: 112
<212> TYPE: PRT
<213> ORGANISM: Homo sapiens

<400> SEQUENCE: 671

Gln Ser Ala Leu Thr Gln Pro Ala Ser Val Ser Gly Ser Pro Gly Gln
1               5                   10                  15

Thr Ile Thr Ile Ser Cys Thr Gly Thr Ile Ser Asp Val Gly Gly Tyr
                20                  25                  30

Asp Phe Val Ser Trp Tyr Gln His Pro Gly Lys Ala Pro Lys Leu
            35                  40                  45

Leu Ile Tyr Asp Val Asn Asn Arg Pro Ser Gly Val Ser His Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Thr Tyr Tyr Cys Ser Ser Tyr Ser Asn Arg
                85                  90                  95

His Ser Leu Ile Val Phe Gly Ser Gly Thr Gln Val Val Gly Leu Gly
            100                 105                 110

<210> SEQ ID NO 672
<211> LENGTH: 14
<212> TYPE: PRT
<213> ORGANISM: Homo sapiens
```

```
<400> SEQUENCE: 672

Thr Gly Thr Ile Ser Asp Val Gly Gly Tyr Asp Phe Val Ser
1               5                   10

<210> SEQ ID NO 673
<211> LENGTH: 7
<212> TYPE: PRT
<213> ORGANISM: Homo sapiens

<400> SEQUENCE: 673

Asp Val Asn Asn Arg Pro Ser
1               5

<210> SEQ ID NO 674
<211> LENGTH: 9
<212> TYPE: PRT
<213> ORGANISM: Homo sapiens

<400> SEQUENCE: 674

Ser Ser Tyr Ser Asn Arg His Ser Leu
1               5

<210> SEQ ID NO 675
<211> LENGTH: 125
<212> TYPE: PRT
<213> ORGANISM: Homo sapiens

<400> SEQUENCE: 675

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ala Tyr Cys Ser Ser Thr Ser Cys Tyr Arg Asn Ala Phe
            100                 105                 110

Asp Ile Trp Gly Gln Gly Thr Thr Val Thr Val Ser Arg
        115                 120                 125

<210> SEQ ID NO 676
<211> LENGTH: 5
<212> TYPE: PRT
<213> ORGANISM: Homo sapiens

<400> SEQUENCE: 676

Ser Tyr Tyr Trp Ser
1               5

<210> SEQ ID NO 677
<211> LENGTH: 16
<212> TYPE: PRT
<213> ORGANISM: Homo sapiens

<400> SEQUENCE: 677

Arg Ile Tyr Thr Ser Gly Ser Thr Asn Tyr Asn Pro Ser Leu Lys Ser
```

<210> SEQ ID NO 678
<211> LENGTH: 17
<212> TYPE: PRT
<213> ORGANISM: Homo sapiens

<400> SEQUENCE: 678

Glu Arg Ala Tyr Cys Ser Ser Thr Ser Cys Tyr Arg Asn Ala Phe Asp
1               5                   10                  15
Ile

<210> SEQ ID NO 679
<211> LENGTH: 113
<212> TYPE: PRT
<213> ORGANISM: Homo sapiens

<400> SEQUENCE: 679

Gln Ser Val Leu Thr Gln Pro Pro Ser Val Ser Gly Ala Pro Gly Gln
1               5                   10                  15

Arg Val Asn Ile Ser Cys Ala Gly Ser Ser Asn Ile Gly Ala Gly
            20                  25                  30

Tyr Asp Val His Trp Tyr Gln Gln Ile Pro Gly Thr Ala Pro Lys Leu
        35                  40                  45

Leu Met Tyr Gly Asn Ser Asn Arg Pro Ser Gly Val Pro Asp Arg Phe
    50                  55                  60

Ser Gly Ser Lys Ser Gly Ala Ser Ala Ser Leu Ala Ile Thr Arg Leu
65                  70                  75                  80

Gln Ala Glu Asp Glu Ala Asp Tyr Tyr Cys Gln Ser Tyr Asp Ser Ser
                85                  90                  95

Leu Ser Gly Ser Arg Val Phe Gly Thr Gly Thr Lys Val Thr Val Leu
            100                 105                 110

Gly

<210> SEQ ID NO 680
<211> LENGTH: 14
<212> TYPE: PRT
<213> ORGANISM: Homo sapiens

<400> SEQUENCE: 680

Ala Gly Ser Ser Ser Asn Ile Gly Ala Gly Tyr Asp Val His
1               5                   10

<210> SEQ ID NO 681
<211> LENGTH: 7
<212> TYPE: PRT
<213> ORGANISM: Homo sapiens

<400> SEQUENCE: 681

Gly Asn Ser Asn Arg Pro Ser
1               5

<210> SEQ ID NO 682
<211> LENGTH: 10
<212> TYPE: PRT
<213> ORGANISM: Homo sapiens

<400> SEQUENCE: 682

Gln Ser Tyr Asp Ser Ser Leu Ser Gly Ser
1               5                   10

<210> SEQ ID NO 683
<211> LENGTH: 122
<212> TYPE: PRT
<213> ORGANISM: Homo sapiens

<400> SEQUENCE: 683

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Val Ile Ser Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Thr Asn Thr Trp Trp Pro Asp Ala Phe Asp Ile Trp
            100                 105                 110

Gly Gln Gly Thr Thr Val Thr Val Ser Arg
        115                 120

<210> SEQ ID NO 684
<211> LENGTH: 5
<212> TYPE: PRT
<213> ORGANISM: Homo sapiens

<400> SEQUENCE: 684

Ser Tyr Gly Met His
1               5

<210> SEQ ID NO 685
<211> LENGTH: 17
<212> TYPE: PRT
<213> ORGANISM: Homo sapiens

<400> SEQUENCE: 685

Val Ile Ser Phe Asp Gly Ser Asn Lys Tyr Tyr Ala Asp Ser Val Lys
1               5                   10                  15

Gly

<210> SEQ ID NO 686
<211> LENGTH: 13
<212> TYPE: PRT
<213> ORGANISM: Homo sapiens

<400> SEQUENCE: 686

Ala Tyr Thr Asn Thr Trp Trp Pro Asp Ala Phe Asp Ile
1               5                   10

<210> SEQ ID NO 687
<211> LENGTH: 107
<212> TYPE: PRT
<213> ORGANISM: Homo sapiens

<400> SEQUENCE: 687

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr

```
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                 85                  90                  95

Thr Phe Gly Pro Gly Thr Lys Val Asp Ile Lys
             100                 105
```

<210> SEQ ID NO 688
<211> LENGTH: 11
<212> TYPE: PRT
<213> ORGANISM: Homo sapiens

<400> SEQUENCE: 688

```
Gln Ala Ser Gln Asp Ile Ser Asn Tyr Leu Asn
1               5                  10
```

<210> SEQ ID NO 689
<211> LENGTH: 7
<212> TYPE: PRT
<213> ORGANISM: Homo sapiens

<400> SEQUENCE: 689

```
Asp Ala Ser Asn Leu Glu Thr
1               5
```

<210> SEQ ID NO 690
<211> LENGTH: 7
<212> TYPE: PRT
<213> ORGANISM: Homo sapiens

<400> SEQUENCE: 690

```
Gln Gln Tyr Asp Asn Leu Pro
1               5
```

<210> SEQ ID NO 691
<211> LENGTH: 118
<212> TYPE: PRT
<213> ORGANISM: Homo sapiens

<400> SEQUENCE: 691

```
Gln Val Gln Leu Gln Glu Ser Gly Pro Gly Leu Val Lys Pro Ser Glu
1               5                  10                  15

Thr Leu Ser Leu Thr Cys Thr Val Ser Gly Ser Ile Ser Ser Tyr
             20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Asp Leu Tyr Trp Asn Asp Ala Phe Asp Ile Trp Gly Gln Gly Thr
             100                 105                 110
```

Thr Val Thr Val Ser Arg
            115

<210> SEQ ID NO 692
<211> LENGTH: 5
<212> TYPE: PRT
<213> ORGANISM: Homo sapiens

<400> SEQUENCE: 692

Ser Tyr Tyr Trp Ser
1               5

<210> SEQ ID NO 693
<211> LENGTH: 16
<212> TYPE: PRT
<213> ORGANISM: Homo sapiens

<400> SEQUENCE: 693

Tyr Ile Tyr Tyr Ser Gly Ser Thr Asn Tyr Asn Pro Ser Leu Lys Ser
1               5                   10                  15

<210> SEQ ID NO 694
<211> LENGTH: 10
<212> TYPE: PRT
<213> ORGANISM: Homo sapiens

<400> SEQUENCE: 694

Asp Leu Tyr Trp Asn Asp Ala Phe Asp Ile
1               5                   10

<210> SEQ ID NO 695
<211> LENGTH: 111
<212> TYPE: PRT
<213> ORGANISM: Homo sapiens

<400> SEQUENCE: 695

Gln Ser Ala Leu Thr Gln Pro Leu Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 696
<211> LENGTH: 13
<212> TYPE: PRT
<213> ORGANISM: Homo sapiens

<400> SEQUENCE: 696

Ser Gly Ser Ser Ser Asn Ile Gly Ser Asn Thr Val Asn
1               5                   10

<210> SEQ ID NO 697
<211> LENGTH: 7

```
<212> TYPE: PRT
<213> ORGANISM: Homo sapiens

<400> SEQUENCE: 697

Ser Asn Asn Gln Arg Pro Ser
1               5

<210> SEQ ID NO 698
<211> LENGTH: 9
<212> TYPE: PRT
<213> ORGANISM: Homo sapiens

<400> SEQUENCE: 698

Ala Ala Trp Asp Asp Ser Leu Asn Gly
1               5

<210> SEQ ID NO 699
<211> LENGTH: 118
<212> TYPE: PRT
<213> ORGANISM: Homo sapiens

<400> SEQUENCE: 699

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Leu Tyr Trp Asn Asp Ala Phe Asp Ile Trp Gly Gln Gly Thr
            100                 105                 110

Thr Val Thr Val Ser Arg
        115

<210> SEQ ID NO 700
<211> LENGTH: 5
<212> TYPE: PRT
<213> ORGANISM: Homo sapiens

<400> SEQUENCE: 700

Ser Tyr Tyr Trp Ser
1               5

<210> SEQ ID NO 701
<211> LENGTH: 16
<212> TYPE: PRT
<213> ORGANISM: Homo sapiens

<400> SEQUENCE: 701

Tyr Ile Tyr Tyr Ser Gly Ser Thr Asn Tyr Asn Pro Ser Leu Lys Ser
1               5                   10                  15

<210> SEQ ID NO 702
<211> LENGTH: 10
<212> TYPE: PRT
<213> ORGANISM: Homo sapiens
```

```
<400> SEQUENCE: 702

Asp Leu Tyr Trp Asn Asp Ala Phe Asp Ile
1               5                   10

<210> SEQ ID NO 703
<211> LENGTH: 111
<212> TYPE: PRT
<213> ORGANISM: Homo sapiens

<400> SEQUENCE: 703

Gln Ser Val Leu Thr Gln Pro Pro Ser Ala Ser Gly Thr Pro Gly Gln
1               5                   10                  15

Ser Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 704
<211> LENGTH: 13
<212> TYPE: PRT
<213> ORGANISM: Homo sapiens

<400> SEQUENCE: 704

Ser Gly Ser Ser Ser Asn Ile Gly Ser Asn Thr Val Asn
1               5                   10

<210> SEQ ID NO 705
<211> LENGTH: 7
<212> TYPE: PRT
<213> ORGANISM: Homo sapiens

<400> SEQUENCE: 705

Ser Asn Asn Gln Arg Pro Ser
1               5

<210> SEQ ID NO 706
<211> LENGTH: 9
<212> TYPE: PRT
<213> ORGANISM: Homo sapiens

<400> SEQUENCE: 706

Ala Ala Trp Asp Asp Ser Leu Asn Gly
1               5

<210> SEQ ID NO 707
<211> LENGTH: 126
<212> TYPE: PRT
<213> ORGANISM: Homo sapiens

<400> SEQUENCE: 707

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
```

```
                    20                  25                  30
Ser Ala Ala Trp Asn Trp Ile Arg Gln Ser Pro Ser Arg Gly Leu Glu
                35                  40                  45

Trp Leu Gly Arg Thr Tyr Tyr Arg Ser Lys Trp Tyr Asn Asp Tyr Ala
            50                  55                  60

Val Ser Val Lys Ser Arg Ile Thr Ile Asn Pro Asp Thr Ser Lys Asn
 65                 70                  75                  80

Gln Phe Ser Leu Gln Leu Asn Ser Val Thr Pro Glu Asp Thr Ala Val
                85                  90                  95

Tyr Tyr Cys Ala Arg Glu Ser Trp Leu Trp Gly Ile Gly Gly Asp Ala
            100                 105                 110

Phe Asp Ile Trp Gly Gln Gly Thr Thr Val Thr Val Ser Arg
        115                 120                 125

<210> SEQ ID NO 708
<211> LENGTH: 7
<212> TYPE: PRT
<213> ORGANISM: Homo sapiens

<400> SEQUENCE: 708

Ser Asn Ser Ala Ala Trp Asn
1               5

<210> SEQ ID NO 709
<211> LENGTH: 18
<212> TYPE: PRT
<213> ORGANISM: Homo sapiens

<400> SEQUENCE: 709

Arg Thr Tyr Tyr Arg Ser Lys Trp Tyr Asn Asp Tyr Ala Val Ser Val
1               5                   10                  15

Lys Ser

<210> SEQ ID NO 710
<211> LENGTH: 14
<212> TYPE: PRT
<213> ORGANISM: Homo sapiens

<400> SEQUENCE: 710

Glu Ser Trp Leu Trp Gly Ile Gly Gly Asp Ala Phe Asp Ile
1               5                   10

<210> SEQ ID NO 711
<211> LENGTH: 111
<212> TYPE: PRT
<213> ORGANISM: Homo sapiens

<400> SEQUENCE: 711

Gln Ser Val Leu Thr Gln Pro Pro Ser Val Ser Gly Ala Pro Arg Gln
1               5                   10                  15

Thr Val Thr Ile Ser Cys Ser Gly Ser Ser Ser Asn Ile Gly Gln Asn
            20                  25                  30

Ser Val Thr Trp Tyr Gln Arg Leu Pro Gly Glu Ala Pro Lys Leu Leu
        35                  40                  45

Ile Tyr Tyr Asp Asp Leu Leu His Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ser Trp Asp Asp Ser Leu
```

```
                      85                  90                  95

Lys Gly Pro Val Phe Gly Gly Gly Thr Lys Leu Thr Val Leu Gly
            100                 105                 110

<210> SEQ ID NO 712
<211> LENGTH: 13
<212> TYPE: PRT
<213> ORGANISM: Homo sapiens

<400> SEQUENCE: 712

Ser Gly Ser Ser Ser Asn Ile Gly Gln Asn Ser Val Thr
1               5                   10

<210> SEQ ID NO 713
<211> LENGTH: 7
<212> TYPE: PRT
<213> ORGANISM: Homo sapiens

<400> SEQUENCE: 713

Tyr Asp Asp Leu Leu His Ser
1               5

<210> SEQ ID NO 714
<211> LENGTH: 9
<212> TYPE: PRT
<213> ORGANISM: Homo sapiens

<400> SEQUENCE: 714

Ala Ser Trp Asp Asp Ser Leu Lys Gly
1               5

<210> SEQ ID NO 715
<211> LENGTH: 112
<212> TYPE: PRT
<213> ORGANISM: Homo sapiens

<400> SEQUENCE: 715

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Phe Asp Tyr Trp Gly Gln Gly Thr Leu Val Thr Val Ser Arg
            100                 105                 110

<210> SEQ ID NO 716
<211> LENGTH: 5
<212> TYPE: PRT
<213> ORGANISM: Homo sapiens

<400> SEQUENCE: 716

Ser Asn Tyr Met Ser
1               5
```

```
<210> SEQ ID NO 717
<211> LENGTH: 16
<212> TYPE: PRT
<213> ORGANISM: Homo sapiens

<400> SEQUENCE: 717

Val Ile Tyr Ser Gly Gly Ser Thr Tyr Tyr Ala Asp Ser Val Lys Gly
1               5                   10                  15

<210> SEQ ID NO 718
<211> LENGTH: 4
<212> TYPE: PRT
<213> ORGANISM: Homo sapiens

<400> SEQUENCE: 718

Glu Phe Asp Tyr
1

<210> SEQ ID NO 719
<211> LENGTH: 105
<212> TYPE: PRT
<213> ORGANISM: Homo sapiens

<400> SEQUENCE: 719

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Pro Ala Phe
                85                  90                  95

Gly Gly Gly Thr Lys Val Glu Ile Lys
            100                 105

<210> SEQ ID NO 720
<211> LENGTH: 11
<212> TYPE: PRT
<213> ORGANISM: Homo sapiens

<400> SEQUENCE: 720

Gln Ala Ser Gln Asp Ile Ser Asn Tyr Leu Asn
1               5                   10

<210> SEQ ID NO 721
<211> LENGTH: 7
<212> TYPE: PRT
<213> ORGANISM: Homo sapiens

<400> SEQUENCE: 721

Asp Ala Ser Asn Leu Glu Thr
1               5

<210> SEQ ID NO 722
<211> LENGTH: 5
<212> TYPE: PRT
<213> ORGANISM: Homo sapiens

<400> SEQUENCE: 722
```

Gln Gln Tyr Asp Asn
1               5

<210> SEQ ID NO 723
<211> LENGTH: 121
<212> TYPE: PRT
<213> ORGANISM: Homo sapiens

<400> SEQUENCE: 723

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Tyr Tyr Gly Ser Gly Phe Gly Met Asp Val Trp Gly
            100                 105                 110

Gln Gly Thr Met Val Thr Val Ser Arg
        115                 120

<210> SEQ ID NO 724
<211> LENGTH: 5
<212> TYPE: PRT
<213> ORGANISM: Homo sapiens

<400> SEQUENCE: 724

Ser Tyr Gly Ile Ser
1               5

<210> SEQ ID NO 725
<211> LENGTH: 17
<212> TYPE: PRT
<213> ORGANISM: Homo sapiens

<400> SEQUENCE: 725

Trp Ile Ser Ala Tyr Asn Gly Asn Thr Asn Tyr Ala Gln Lys Leu Gln
1               5                   10                  15

Gly

<210> SEQ ID NO 726
<211> LENGTH: 12
<212> TYPE: PRT
<213> ORGANISM: Homo sapiens

<400> SEQUENCE: 726

Asp Arg Tyr Tyr Gly Ser Gly Phe Gly Met Asp Val
1               5                   10

<210> SEQ ID NO 727
<211> LENGTH: 109
<212> TYPE: PRT
<213> ORGANISM: Homo sapiens

<400> SEQUENCE: 727

-continued

```
Ser Ser Glu Leu Thr Gln Asp Pro Ala Met Ser Val Ala Leu Gly Gln
1               5                   10                  15

Thr Val Lys Ile Thr Cys Gln Gly Asp Ser Leu Thr Asn Tyr Tyr Pro
            20                  25                  30

Ser Trp Tyr Gln Gln Lys Pro Gly Gln Ala Pro Val Leu Val Met Tyr
        35                  40                  45

Gly Lys Asp Ser Arg Pro Ser Gly Ile Ser Asp Arg Phe Ser Gly Ser
    50                  55                  60

Ser Ser Gly Ile Ser Ala Ser Leu Thr Ile Thr Gly Ala Gln Ala Glu
65                  70                  75                  80

Asp Glu Ala Asp Tyr Tyr Cys Asn Ser Arg Asp Gly Ser Ala His Arg
                85                  90                  95

Leu Val Phe Gly Gly Gly Thr Lys Leu Thr Val Leu Gly
            100                 105
```

<210> SEQ ID NO 728
<211> LENGTH: 11
<212> TYPE: PRT
<213> ORGANISM: Homo sapiens

<400> SEQUENCE: 728

```
Gln Gly Asp Ser Leu Thr Asn Tyr Tyr Pro Ser
1               5                   10
```

<210> SEQ ID NO 729
<211> LENGTH: 7
<212> TYPE: PRT
<213> ORGANISM: Homo sapiens

<400> SEQUENCE: 729

```
Gly Lys Asp Ser Arg Pro Ser
1               5
```

<210> SEQ ID NO 730
<211> LENGTH: 9
<212> TYPE: PRT
<213> ORGANISM: Homo sapiens

<400> SEQUENCE: 730

```
Asn Ser Arg Asp Gly Ser Ala His Arg
1               5
```

<210> SEQ ID NO 731
<211> LENGTH: 124
<212> TYPE: PRT
<213> ORGANISM: Homo sapiens

<400> SEQUENCE: 731

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Thr Trp Val Arg Gln Ala Pro Gly Gln Gly Leu Glu Trp Met
        35                  40                  45

Gly Trp Ile Ser Thr Tyr Asn Ser Asn Thr Asn Tyr Ala Glu Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Thr Ser Asp Asp Thr Ala Val Tyr Tyr Cys
                85                  90                  95
```

Ala Arg Gly Pro Thr Tyr Ser Phe Asp Ser Ser Gly Tyr Phe Phe Asp
            100                 105                 110

Tyr Trp Gly Gln Gly Thr Leu Val Thr Val Ser Arg
        115                 120

<210> SEQ ID NO 732
<211> LENGTH: 5
<212> TYPE: PRT
<213> ORGANISM: Homo sapiens

<400> SEQUENCE: 732

Asn Tyr Gly Leu Thr
1               5

<210> SEQ ID NO 733
<211> LENGTH: 17
<212> TYPE: PRT
<213> ORGANISM: Homo sapiens

<400> SEQUENCE: 733

Trp Ile Ser Thr Tyr Asn Ser Asn Thr Asn Tyr Ala Glu Lys Leu Gln
1               5                   10                  15

Gly

<210> SEQ ID NO 734
<211> LENGTH: 15
<212> TYPE: PRT
<213> ORGANISM: Homo sapiens

<400> SEQUENCE: 734

Gly Pro Thr Tyr Ser Phe Asp Ser Ser Gly Tyr Phe Phe Asp Tyr
1               5                   10                  15

<210> SEQ ID NO 735
<211> LENGTH: 109
<212> TYPE: PRT
<213> ORGANISM: Homo sapiens

<400> SEQUENCE: 735

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Trp Val Phe Gly Gly Gly Thr Lys Leu Thr Val Leu Gly
            100                 105

<210> SEQ ID NO 736
<211> LENGTH: 11
<212> TYPE: PRT
<213> ORGANISM: Homo sapiens

<400> SEQUENCE: 736

```
Gln Gly Asp Ser Leu Arg Ser Tyr Tyr Ala Ser
1               5                   10
```

<210> SEQ ID NO 737
<211> LENGTH: 7
<212> TYPE: PRT
<213> ORGANISM: Homo sapiens

<400> SEQUENCE: 737

```
Gly Lys Asn Asn Arg Pro Ser
1               5
```

<210> SEQ ID NO 738
<211> LENGTH: 9
<212> TYPE: PRT
<213> ORGANISM: Homo sapiens

<400> SEQUENCE: 738

```
Asn Ser Arg Asp Ser Ser Gly Asn His
1               5
```

<210> SEQ ID NO 739
<211> LENGTH: 120
<212> TYPE: PRT
<213> ORGANISM: Homo sapiens

<400> SEQUENCE: 739

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Tyr Ser Ser Gly Trp Tyr Phe Asp Tyr Trp Gly Gln
            100                 105                 110

Gly Thr Leu Val Thr Val Ser Arg
        115                 120
```

<210> SEQ ID NO 740
<211> LENGTH: 5
<212> TYPE: PRT
<213> ORGANISM: Homo sapiens

<400> SEQUENCE: 740

```
Ser Tyr Gly Ile Ser
1               5
```

<210> SEQ ID NO 741
<211> LENGTH: 17
<212> TYPE: PRT
<213> ORGANISM: Homo sapiens

<400> SEQUENCE: 741

```
Trp Ile Ser Ala Tyr Asn Gly Asn Thr Asn Tyr Ala Gln Lys Leu Gln
1               5                   10                  15
```

Gly

<210> SEQ ID NO 742
<211> LENGTH: 11
<212> TYPE: PRT
<213> ORGANISM: Homo sapiens

<400> SEQUENCE: 742

Asp Thr Tyr Ser Ser Gly Trp Tyr Phe Asp Tyr
1               5                   10

<210> SEQ ID NO 743
<211> LENGTH: 110
<212> TYPE: PRT
<213> ORGANISM: Homo sapiens

<400> SEQUENCE: 743

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Tyr Val Phe Gly Thr Gly Thr Lys Val Thr Val Leu Gly
            100                 105                 110

<210> SEQ ID NO 744
<211> LENGTH: 11
<212> TYPE: PRT
<213> ORGANISM: Homo sapiens

<400> SEQUENCE: 744

Gln Gly Asp Ser Leu Arg Asn Tyr Tyr Ala Ser
1               5                   10

<210> SEQ ID NO 745
<211> LENGTH: 7
<212> TYPE: PRT
<213> ORGANISM: Homo sapiens

<400> SEQUENCE: 745

Gly Lys Asn Asn Arg Pro Ser
1               5

<210> SEQ ID NO 746
<211> LENGTH: 10
<212> TYPE: PRT
<213> ORGANISM: Homo sapiens

<400> SEQUENCE: 746

Asn Ser Arg Asp Ser Ser Gly Asn His Leu
1               5                   10

<210> SEQ ID NO 747
<211> LENGTH: 120
<212> TYPE: PRT

<213> ORGANISM: Homo sapiens

<400> SEQUENCE: 747

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Thr Leu Asn Ile Ser Gly Ser Tyr Tyr Phe Asp Tyr Trp Gly Gln
            100                 105                 110
Gly Thr Leu Val Thr Val Ser Arg
        115                 120
```

<210> SEQ ID NO 748
<211> LENGTH: 5
<212> TYPE: PRT
<213> ORGANISM: Homo sapiens

<400> SEQUENCE: 748

```
Ser Tyr Gly Ile Ser
1               5
```

<210> SEQ ID NO 749
<211> LENGTH: 17
<212> TYPE: PRT
<213> ORGANISM: Homo sapiens

<400> SEQUENCE: 749

```
Trp Ile Ser Ala Tyr Asn Gly Asn Thr Asn Tyr Ala Gln Lys Leu Gln
1               5                   10                  15
Gly
```

<210> SEQ ID NO 750
<211> LENGTH: 11
<212> TYPE: PRT
<213> ORGANISM: Homo sapiens

<400> SEQUENCE: 750

```
Leu Asn Ile Ser Gly Ser Tyr Tyr Phe Asp Tyr
1               5                   10
```

<210> SEQ ID NO 751
<211> LENGTH: 110
<212> TYPE: PRT
<213> ORGANISM: Homo sapiens

<400> SEQUENCE: 751

```
Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
            20                  25                  30
Thr Trp Tyr Gln Gln Lys Pro Gly Gln Ala Pro Val Leu Val Ile Ser
        35                  40                  45
```

```
Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Tyr Pro
                85                  90                  95

Ser Trp Val Phe Gly Gly Gly Thr Lys Leu Thr Val Leu Gly
            100                 105                 110
```

<210> SEQ ID NO 752
<211> LENGTH: 11
<212> TYPE: PRT
<213> ORGANISM: Homo sapiens

<400> SEQUENCE: 752

```
Gln Gly Asp Ser Leu Arg Ser Tyr Tyr Ala Thr
1               5                   10
```

<210> SEQ ID NO 753
<211> LENGTH: 7
<212> TYPE: PRT
<213> ORGANISM: Homo sapiens

<400> SEQUENCE: 753

```
Gly Lys Asn Asn Arg Pro Ser
1               5
```

<210> SEQ ID NO 754
<211> LENGTH: 10
<212> TYPE: PRT
<213> ORGANISM: Homo sapiens

<400> SEQUENCE: 754

```
Asn Ser Arg Asp Ser Ser Gly Tyr Pro Ser
1               5                   10
```

<210> SEQ ID NO 755
<211> LENGTH: 118
<212> TYPE: PRT
<213> ORGANISM: Homo sapiens

<400> SEQUENCE: 755

```
Gln Val Gln Leu Val Gln Ser Glu Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Ile Gly Leu Gly Ala Phe Asp Ile Trp Gly Gln Gly Thr
            100                 105                 110

Thr Val Thr Val Ser Arg
        115
```

```
<210> SEQ ID NO 756
<211> LENGTH: 5
<212> TYPE: PRT
<213> ORGANISM: Homo sapiens

<400> SEQUENCE: 756

Ser Tyr Trp Ile Gly
1               5

<210> SEQ ID NO 757
<211> LENGTH: 17
<212> TYPE: PRT
<213> ORGANISM: Homo sapiens

<400> SEQUENCE: 757

Ile Ile Tyr Pro Gly Asp Ser Asp Thr Arg Tyr Ser Pro Ser Phe Gln
1               5                   10                  15

Gly

<210> SEQ ID NO 758
<211> LENGTH: 9
<212> TYPE: PRT
<213> ORGANISM: Homo sapiens

<400> SEQUENCE: 758

Thr Ile Gly Leu Gly Ala Phe Asp Ile
1               5

<210> SEQ ID NO 759
<211> LENGTH: 110
<212> TYPE: PRT
<213> ORGANISM: Homo sapiens

<400> SEQUENCE: 759

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

His Tyr Val Phe Gly Thr Gly Thr Lys Val Thr Val Leu Gly
            100                 105                 110

<210> SEQ ID NO 760
<211> LENGTH: 11
<212> TYPE: PRT
<213> ORGANISM: Homo sapiens

<400> SEQUENCE: 760

Gln Gly Asp Ser Leu Arg Ser Tyr Tyr Ala Ser
1               5                   10

<210> SEQ ID NO 761
<211> LENGTH: 7
<212> TYPE: PRT
<213> ORGANISM: Homo sapiens
```

```
<400> SEQUENCE: 761

Gly Lys Asn Asn Arg Pro Ser
1               5

<210> SEQ ID NO 762
<211> LENGTH: 10
<212> TYPE: PRT
<213> ORGANISM: Homo sapiens

<400> SEQUENCE: 762

Asn Ser Arg Asp Ser Ser Gly Asn His His
1               5                  10

<210> SEQ ID NO 763
<211> LENGTH: 119
<212> TYPE: PRT
<213> ORGANISM: Homo sapiens

<400> SEQUENCE: 763

Gln Val Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Trp Gly Asn Tyr Ala Phe Asp Ile Trp Gly Gln Gly
            100                 105                 110

Thr Thr Val Thr Val Ser Arg
        115

<210> SEQ ID NO 764
<211> LENGTH: 7
<212> TYPE: PRT
<213> ORGANISM: Homo sapiens

<400> SEQUENCE: 764

Ser Ser Ser Tyr Tyr Trp Gly
1               5

<210> SEQ ID NO 765
<211> LENGTH: 16
<212> TYPE: PRT
<213> ORGANISM: Homo sapiens

<400> SEQUENCE: 765

Ser Ile Tyr Tyr Ser Gly Ser Thr Tyr Tyr Asn Pro Ser Leu Lys Ser
1               5                  10                  15

<210> SEQ ID NO 766
<211> LENGTH: 9
<212> TYPE: PRT
<213> ORGANISM: Homo sapiens

<400> SEQUENCE: 766
```

```
His Trp Gly Asn Tyr Ala Phe Asp Ile
1               5
```

<210> SEQ ID NO 767
<211> LENGTH: 111
<212> TYPE: PRT
<213> ORGANISM: Homo sapiens

<400> SEQUENCE: 767

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Gln Val Phe Gly Gly Gly Thr Gln Leu Thr Val Leu Gly
                100                 105                 110
```

<210> SEQ ID NO 768
<211> LENGTH: 13
<212> TYPE: PRT
<213> ORGANISM: Homo sapiens

<400> SEQUENCE: 768

```
Ser Gly Ser Ser Ser Asn Ile Gly Ser Asn Tyr Val Tyr
1               5                   10
```

<210> SEQ ID NO 769
<211> LENGTH: 7
<212> TYPE: PRT
<213> ORGANISM: Homo sapiens

<400> SEQUENCE: 769

```
Ser Asn Asn Gln Arg Pro Ser
1               5
```

<210> SEQ ID NO 770
<211> LENGTH: 9
<212> TYPE: PRT
<213> ORGANISM: Homo sapiens

<400> SEQUENCE: 770

```
Ala Ala Trp Asp Asp Ser Leu Ser Gly
1               5
```

<210> SEQ ID NO 771
<211> LENGTH: 120
<212> TYPE: PRT
<213> ORGANISM: Homo sapiens

<400> SEQUENCE: 771

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

```
Gly Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Gln Lys Leu
 50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Glu Lys Tyr Ser Ser Gly Trp Tyr Phe Asp Tyr Trp Gly Gln
            100                 105                 110
Gly Thr Leu Val Thr Val Ser Arg
        115                 120

<210> SEQ ID NO 772
<211> LENGTH: 5
<212> TYPE: PRT
<213> ORGANISM: Homo sapiens

<400> SEQUENCE: 772

Ser Tyr Gly Ile Ser
1               5

<210> SEQ ID NO 773
<211> LENGTH: 17
<212> TYPE: PRT
<213> ORGANISM: Homo sapiens

<400> SEQUENCE: 773

Trp Ile Ser Ala Tyr Asn Gly Asn Thr Asn Tyr Ala Gln Lys Leu Gln
1               5                   10                  15
Gly

<210> SEQ ID NO 774
<211> LENGTH: 11
<212> TYPE: PRT
<213> ORGANISM: Homo sapiens

<400> SEQUENCE: 774

Glu Lys Tyr Ser Ser Gly Trp Tyr Phe Asp Tyr
1               5                   10

<210> SEQ ID NO 775
<211> LENGTH: 110
<212> TYPE: PRT
<213> ORGANISM: Homo sapiens

<400> SEQUENCE: 775

Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Pro Ser Gly Ile Pro Asp Arg Phe Ser Gly Ser
 50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Asn His
                85                  90                  95
```

```
His Tyr Val Phe Gly Thr Gly Thr Lys Val Thr Val Leu Gly
            100                 105                 110
```

<210> SEQ ID NO 776
<211> LENGTH: 11
<212> TYPE: PRT
<213> ORGANISM: Homo sapiens

<400> SEQUENCE: 776

```
Gln Gly Asp Ser Leu Arg Ser Tyr Tyr Ala Ser
1               5                   10
```

<210> SEQ ID NO 777
<211> LENGTH: 7
<212> TYPE: PRT
<213> ORGANISM: Homo sapiens

<400> SEQUENCE: 777

```
Gly Lys Asn Asn Arg Pro Ser
1               5
```

<210> SEQ ID NO 778
<211> LENGTH: 10
<212> TYPE: PRT
<213> ORGANISM: Homo sapiens

<400> SEQUENCE: 778

```
Asn Ser Arg Asp Ser Ser Gly Asn His His
1               5                   10
```

<210> SEQ ID NO 779
<211> LENGTH: 115
<212> TYPE: PRT
<213> ORGANISM: Homo sapiens

<400> SEQUENCE: 779

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Lys Gly Ser Ile Ala Ala Asp Trp Gly Gln Gly Thr Leu Val Thr
            100                 105                 110

Val Ser Arg
        115
```

<210> SEQ ID NO 780
<211> LENGTH: 5
<212> TYPE: PRT
<213> ORGANISM: Homo sapiens

<400> SEQUENCE: 780

```
Ser Tyr Ala Met Ser
1               5
```

-continued

<210> SEQ ID NO 781
<211> LENGTH: 17
<212> TYPE: PRT
<213> ORGANISM: Homo sapiens

<400> SEQUENCE: 781

Ala Ile Ser Gly Ser Gly Gly Ser Thr Tyr Tyr Ala Asp Ser Val Lys
1               5                   10                  15
Gly

<210> SEQ ID NO 782
<211> LENGTH: 6
<212> TYPE: PRT
<213> ORGANISM: Homo sapiens

<400> SEQUENCE: 782

Gly Ser Ile Ala Ala Asp
1               5

<210> SEQ ID NO 783
<211> LENGTH: 108
<212> TYPE: PRT
<213> ORGANISM: Homo sapiens

<400> SEQUENCE: 783

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Val
                85                  90                  95

Val Phe Gly Gly Gly Thr Lys Leu Thr Val Leu Gly
            100                 105

<210> SEQ ID NO 784
<211> LENGTH: 11
<212> TYPE: PRT
<213> ORGANISM: Homo sapiens

<400> SEQUENCE: 784

Gln Gly Asp Ser Leu Arg Ser Tyr Tyr Ala Ser
1               5                   10

<210> SEQ ID NO 785
<211> LENGTH: 7
<212> TYPE: PRT
<213> ORGANISM: Homo sapiens

<400> SEQUENCE: 785

Gly Lys Asn Asn Arg Pro Ser
1               5

<210> SEQ ID NO 786
<211> LENGTH: 8
<212> TYPE: PRT

```
<213> ORGANISM: Homo sapiens

<400> SEQUENCE: 786

Asn Ser Arg Asp Ser Ser Gly Asn
1               5

<210> SEQ ID NO 787
<211> LENGTH: 115
<212> TYPE: PRT
<213> ORGANISM: Homo sapiens

<400> SEQUENCE: 787

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Glu Gln Ala Gly Asp Tyr Trp Gly Gln Gly Thr Leu Val Thr
            100                 105                 110

Val Ser Arg
        115

<210> SEQ ID NO 788
<211> LENGTH: 5
<212> TYPE: PRT
<213> ORGANISM: Homo sapiens

<400> SEQUENCE: 788

Ser Tyr Ala Met Ser
1               5

<210> SEQ ID NO 789
<211> LENGTH: 17
<212> TYPE: PRT
<213> ORGANISM: Homo sapiens

<400> SEQUENCE: 789

Ala Ile Ser Gly Ser Gly Gly Ser Thr Tyr Tyr Ala Asp Ser Val Lys
1               5                   10                  15

Gly

<210> SEQ ID NO 790
<211> LENGTH: 6
<212> TYPE: PRT
<213> ORGANISM: Homo sapiens

<400> SEQUENCE: 790

Glu Gln Ala Gly Asp Tyr
1               5

<210> SEQ ID NO 791
<211> LENGTH: 111
<212> TYPE: PRT
<213> ORGANISM: Homo sapiens
```

<400> SEQUENCE: 791

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ala
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly
            100                 105                 110

<210> SEQ ID NO 792
<211> LENGTH: 13
<212> TYPE: PRT
<213> ORGANISM: Homo sapiens

<400> SEQUENCE: 792

Ser Gly Ser Ser Ser Asn Ile Gly Ser Asn Tyr Val Tyr
1               5                   10

<210> SEQ ID NO 793
<211> LENGTH: 7
<212> TYPE: PRT
<213> ORGANISM: Homo sapiens

<400> SEQUENCE: 793

Arg Asn Asn Gln Arg Pro Ser
1               5

<210> SEQ ID NO 794
<211> LENGTH: 9
<212> TYPE: PRT
<213> ORGANISM: Homo sapiens

<400> SEQUENCE: 794

Gly Thr Trp Asp Ser Ser Leu Ser Ala
1               5

<210> SEQ ID NO 795
<211> LENGTH: 119
<212> TYPE: PRT
<213> ORGANISM: Homo sapiens

<400> SEQUENCE: 795

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                 85                  90                  95

Ala Arg Glu Leu Ser Ala Ala Thr Ala Phe Asp Ile Trp Gly Gln Gly
            100                 105                 110

Thr Met Val Thr Val Ser Arg
        115

<210> SEQ ID NO 796
<211> LENGTH: 5
<212> TYPE: PRT
<213> ORGANISM: Homo sapiens

<400> SEQUENCE: 796

Ser Tyr Tyr Met His
1               5

<210> SEQ ID NO 797
<211> LENGTH: 17
<212> TYPE: PRT
<213> ORGANISM: Homo sapiens

<400> SEQUENCE: 797

Ile Ile Asn Pro Ser Gly Gly Ser Thr Ser Tyr Ala Gln Lys Phe Gln
1               5                   10                  15

Gly

<210> SEQ ID NO 798
<211> LENGTH: 10
<212> TYPE: PRT
<213> ORGANISM: Homo sapiens

<400> SEQUENCE: 798

Glu Leu Ser Ala Ala Thr Ala Phe Asp Ile
1               5                   10

<210> SEQ ID NO 799
<211> LENGTH: 107
<212> TYPE: PRT
<213> ORGANISM: Homo sapiens

<400> SEQUENCE: 799

Glu Thr Thr Leu Thr Gln Ser Pro Phe Ser Val Ser Ala Ser Val Gly
1               5                   10                  15

Asp Arg Val Thr Ile Thr Cys Arg Ala Ser Gln Tyr Ile Ser Arg Trp
            20                  25                  30

Leu Ala Trp Tyr Gln Gln Arg Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Val
                85                  90                  95

Thr Phe Gly Gln Gly Thr Arg Leu Glu Ile Lys
            100                 105

<210> SEQ ID NO 800
<211> LENGTH: 11
<212> TYPE: PRT
<213> ORGANISM: Homo sapiens
```

<400> SEQUENCE: 800

Arg Ala Ser Gln Tyr Ile Ser Arg Trp Leu Ala
1               5                   10

<210> SEQ ID NO 801
<211> LENGTH: 7
<212> TYPE: PRT
<213> ORGANISM: Homo sapiens

<400> SEQUENCE: 801

Ala Ala Ala Ser Leu Gln Ser
1               5

<210> SEQ ID NO 802
<211> LENGTH: 7
<212> TYPE: PRT
<213> ORGANISM: Homo sapiens

<400> SEQUENCE: 802

Gln Gln Ala Asn Ser Phe Pro
1               5

<210> SEQ ID NO 803
<211> LENGTH: 120
<212> TYPE: PRT
<213> ORGANISM: Homo sapiens

<400> SEQUENCE: 803

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Tyr Tyr Tyr Tyr Gly Met Asp Val Trp Gly Gln
            100                 105                 110

Gly Thr Thr Val Thr Val Ser Arg
        115                 120

<210> SEQ ID NO 804
<211> LENGTH: 5
<212> TYPE: PRT
<213> ORGANISM: Homo sapiens

<400> SEQUENCE: 804

Ser Tyr Gly Ile Ser
1               5

<210> SEQ ID NO 805
<211> LENGTH: 17
<212> TYPE: PRT
<213> ORGANISM: Homo sapiens

<400> SEQUENCE: 805

Trp Ile Ser Ala Tyr Asn Gly Asn Thr Asn Tyr Ala Gln Lys Leu Gln
1               5                   10                  15

Gly

<210> SEQ ID NO 806
<211> LENGTH: 11
<212> TYPE: PRT
<213> ORGANISM: Homo sapiens

<400> SEQUENCE: 806

Val Gly Tyr Tyr Tyr Tyr Tyr Gly Met Asp Val
1               5                   10

<210> SEQ ID NO 807
<211> LENGTH: 111
<212> TYPE: PRT
<213> ORGANISM: Homo sapiens

<400> SEQUENCE: 807

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu Gly
            100                 105                 110

<210> SEQ ID NO 808
<211> LENGTH: 14
<212> TYPE: PRT
<213> ORGANISM: Homo sapiens

<400> SEQUENCE: 808

Thr Gly Thr Ser Ser Asp Val Gly Ser Tyr Asn Leu Val Ser
1               5                   10

<210> SEQ ID NO 809
<211> LENGTH: 7
<212> TYPE: PRT
<213> ORGANISM: Homo sapiens

<400> SEQUENCE: 809

Glu Gly Ser Lys Arg Pro Ser
1               5

<210> SEQ ID NO 810
<211> LENGTH: 8
<212> TYPE: PRT
<213> ORGANISM: Homo sapiens

<400> SEQUENCE: 810

Ser Ser Tyr Thr Ser Ser Ser Thr
1               5

```
<210> SEQ ID NO 811
<211> LENGTH: 118
<212> TYPE: PRT
<213> ORGANISM: Homo sapiens

<400> SEQUENCE: 811

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Ile Gly Val Phe Asp Tyr Trp Gly Gln Gly Thr
            100                 105                 110

Leu Val Thr Val Ser Arg
        115

<210> SEQ ID NO 812
<211> LENGTH: 5
<212> TYPE: PRT
<213> ORGANISM: Homo sapiens

<400> SEQUENCE: 812

Ser Tyr Ala Ile Ser
1               5

<210> SEQ ID NO 813
<211> LENGTH: 17
<212> TYPE: PRT
<213> ORGANISM: Homo sapiens

<400> SEQUENCE: 813

Trp Met Asn Pro Asn Ser Gly Asn Thr Gly Tyr Ala Gln Lys Phe Gln
1               5                   10                  15

Gly

<210> SEQ ID NO 814
<211> LENGTH: 9
<212> TYPE: PRT
<213> ORGANISM: Homo sapiens

<400> SEQUENCE: 814

Asp Val Gly Ile Gly Val Phe Asp Tyr
1               5

<210> SEQ ID NO 815
<211> LENGTH: 109
<212> TYPE: PRT
<213> ORGANISM: Homo sapiens

<400> SEQUENCE: 815

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30
```

```
His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu Gly
            100                 105

<210> SEQ ID NO 816
<211> LENGTH: 11
<212> TYPE: PRT
<213> ORGANISM: Homo sapiens

<400> SEQUENCE: 816

Gly Gly Asn Asn Ile Gly Ser Lys Ser Val His
 1               5                  10

<210> SEQ ID NO 817
<211> LENGTH: 7
<212> TYPE: PRT
<213> ORGANISM: Homo sapiens

<400> SEQUENCE: 817

Tyr Asp Ser Asp Arg Pro Ser
 1               5

<210> SEQ ID NO 818
<211> LENGTH: 9
<212> TYPE: PRT
<213> ORGANISM: Homo sapiens

<400> SEQUENCE: 818

Gln Val Trp Asp Ser Ser Ser Asp His
 1               5

<210> SEQ ID NO 819
<211> LENGTH: 121
<212> TYPE: PRT
<213> ORGANISM: Homo sapiens

<400> SEQUENCE: 819

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Ala Met Asn Trp Val Arg Gln Ala Pro Gly Lys Gly Leu Glu Trp Val
             35                  40                  45

Ser Ala Thr Ser Gly Ser Gly Ser Thr Phe Tyr Ala Asp Ser Val
         50                  55                  60

Lys Gly Arg Phe Thr Ile Ser Arg Asp Asn Ser Lys Ser Thr Leu Tyr
 65                  70                  75                  80

Leu Gln Met Asn Ser Leu Arg Asp Glu Asp Thr Ala Val Tyr Tyr Cys
                 85                  90                  95

Ala Lys Gly Thr Leu Pro His Tyr Tyr Asp Ser Ser Gly Ile Gly Gly
             100                 105                 110

Gln Gly Thr Leu Val Thr Val Ser Ser
```

```
                     115                 120

<210> SEQ ID NO 820
<211> LENGTH: 5
<212> TYPE: PRT
<213> ORGANISM: Homo sapiens

<400> SEQUENCE: 820

Asp Tyr Ala Met Asn
1               5

<210> SEQ ID NO 821
<211> LENGTH: 17
<212> TYPE: PRT
<213> ORGANISM: Homo sapiens

<400> SEQUENCE: 821

Ala Thr Ser Gly Ser Gly Gly Ser Thr Phe Tyr Ala Asp Ser Val Lys
1               5                   10                  15

Gly

<210> SEQ ID NO 822
<211> LENGTH: 12
<212> TYPE: PRT
<213> ORGANISM: Homo sapiens

<400> SEQUENCE: 822

Gly Thr Leu Pro His Tyr Tyr Asp Ser Ser Gly Ile
1               5                   10

<210> SEQ ID NO 823
<211> LENGTH: 113
<212> TYPE: PRT
<213> ORGANISM: Homo sapiens

<400> SEQUENCE: 823

Gln Ala Val Leu Thr Gln Pro Ser Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Gly Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asn Tyr Tyr Cys Ser Ser Tyr Thr Ser Ser
                85                  90                  95

Ser Thr Trp Phe Val Val Phe Gly Gly Gly Thr Lys Leu Thr Val Leu
            100                 105                 110

Gly

<210> SEQ ID NO 824
<211> LENGTH: 14
<212> TYPE: PRT
<213> ORGANISM: Homo sapiens

<400> SEQUENCE: 824

Thr Gly Thr Ser Ser Asp Val Gly Gly Tyr Asn Tyr Val Ser
1               5                   10
```

<210> SEQ ID NO 825
<211> LENGTH: 7
<212> TYPE: PRT
<213> ORGANISM: Homo sapiens

<400> SEQUENCE: 825

Asp Val Gly Lys Arg Pro Ser
1               5

<210> SEQ ID NO 826
<211> LENGTH: 10
<212> TYPE: PRT
<213> ORGANISM: Homo sapiens

<400> SEQUENCE: 826

Ser Ser Tyr Thr Ser Ser Ser Thr Trp Phe
1               5                   10

<210> SEQ ID NO 827
<211> LENGTH: 121
<212> TYPE: PRT
<213> ORGANISM: Homo sapiens

<400> SEQUENCE: 827

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Glu Asn Thr Asn Tyr Ala Gln Lys Phe
    50                  55                  60

Gln Gly Arg Val Thr Met Thr Arg Asp Thr Ser Thr Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Ile Gly Thr Arg Gly Gly Gly Leu Asp Val Trp Gly
            100                 105                 110

Gln Gly Thr Thr Val Thr Val Ser Arg
        115                 120

<210> SEQ ID NO 828
<211> LENGTH: 5
<212> TYPE: PRT
<213> ORGANISM: Homo sapiens

<400> SEQUENCE: 828

Thr Tyr Tyr Met His
1               5

<210> SEQ ID NO 829
<211> LENGTH: 17
<212> TYPE: PRT
<213> ORGANISM: Homo sapiens

<400> SEQUENCE: 829

Ile Ile Asn Pro Ser Gly Glu Asn Thr Asn Tyr Ala Gln Lys Phe Gln
1               5                   10                  15

Gly

```
<210> SEQ ID NO 830
<211> LENGTH: 12
<212> TYPE: PRT
<213> ORGANISM: Homo sapiens

<400> SEQUENCE: 830

Ser Phe Ile Gly Thr Arg Gly Gly Gly Leu Asp Val
1               5                   10

<210> SEQ ID NO 831
<211> LENGTH: 113
<212> TYPE: PRT
<213> ORGANISM: Homo sapiens

<400> SEQUENCE: 831

Gln Ser Val Leu Thr Gln Pro Pro Ser Val Gly Ala Pro Gly Gln
1               5                   10                  15

Arg Val Asn Ile Ser Cys Ala Gly Ser Ser Asn Ile Gly Ala Gly
                20                  25                  30

Tyr Asp Val His Trp Tyr Gln Gln Ile Pro Gly Thr Ala Pro Lys Leu
                35                  40                  45

Leu Met Tyr Gly Asn Ser Asn Arg Pro Ser Gly Val Pro Asp Arg Phe
50                  55                  60

Ser Gly Ser Lys Ser Gly Ala Ser Ala Ser Leu Ala Ile Thr Arg Leu
65                  70                  75                  80

Gln Ala Glu Asp Glu Ala Asp Tyr Tyr Cys Gln Ser Tyr Asp Ser Ser
                85                  90                  95

Leu Ser Gly Ser Arg Val Phe Gly Thr Gly Thr Lys Val Thr Val Leu
                100                 105                 110

Gly

<210> SEQ ID NO 832
<211> LENGTH: 14
<212> TYPE: PRT
<213> ORGANISM: Homo sapiens

<400> SEQUENCE: 832

Ala Gly Ser Ser Ser Asn Ile Gly Ala Gly Tyr Asp Val His
1               5                   10

<210> SEQ ID NO 833
<211> LENGTH: 7
<212> TYPE: PRT
<213> ORGANISM: Homo sapiens

<400> SEQUENCE: 833

Gly Asn Ser Asn Arg Pro Ser
1               5

<210> SEQ ID NO 834
<211> LENGTH: 10
<212> TYPE: PRT
<213> ORGANISM: Homo sapiens

<400> SEQUENCE: 834

Gln Ser Tyr Asp Ser Ser Leu Ser Gly Ser
1               5                   10

<210> SEQ ID NO 835
<211> LENGTH: 117
<212> TYPE: PRT
<213> ORGANISM: Homo sapiens
```

<400> SEQUENCE: 835

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Glu Glu Trp Trp Arg Phe Asp Leu Trp Gly Arg Gly Thr Leu
            100                 105                 110

Val Thr Val Ser Arg
        115

<210> SEQ ID NO 836
<211> LENGTH: 5
<212> TYPE: PRT
<213> ORGANISM: Homo sapiens

<400> SEQUENCE: 836

Asp Tyr Ala Met His
1               5

<210> SEQ ID NO 837
<211> LENGTH: 17
<212> TYPE: PRT
<213> ORGANISM: Homo sapiens

<400> SEQUENCE: 837

Gly Ile Ser Trp Asn Ser Gly Ser Ile Gly Tyr Ala Asp Ser Val Lys
1               5                   10                  15

Gly

<210> SEQ ID NO 838
<211> LENGTH: 8
<212> TYPE: PRT
<213> ORGANISM: Homo sapiens

<400> SEQUENCE: 838

Glu Glu Trp Trp Arg Phe Asp Leu
1               5

<210> SEQ ID NO 839
<211> LENGTH: 111
<212> TYPE: PRT
<213> ORGANISM: Homo sapiens

<400> SEQUENCE: 839

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Asp Asp Tyr
            20                  25                  30

Asn Tyr Val Ser Trp Tyr Gln Gln His Pro Gly Lys Ala Pro Lys Leu
        35                  40                  45

```
Met Ile Tyr Glu Val Thr Lys Arg Pro Ser Gly Val Pro Asp Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Val Gly Ser
                85                  90                  95
Asp Asn Arg Val Phe Gly Thr Gly Thr Lys Val Thr Val Pro Gly
            100                 105                 110

<210> SEQ ID NO 840
<211> LENGTH: 14
<212> TYPE: PRT
<213> ORGANISM: Homo sapiens

<400> SEQUENCE: 840

Thr Gly Thr Ser Ser Asp Val Asp Asp Tyr Asn Tyr Val Ser
1               5                   10

<210> SEQ ID NO 841
<211> LENGTH: 7
<212> TYPE: PRT
<213> ORGANISM: Homo sapiens

<400> SEQUENCE: 841

Glu Val Thr Lys Arg Pro Ser
1               5

<210> SEQ ID NO 842
<211> LENGTH: 8
<212> TYPE: PRT
<213> ORGANISM: Homo sapiens

<400> SEQUENCE: 842

Ser Ser Tyr Val Gly Ser Asp Asn
1               5

<210> SEQ ID NO 843
<211> LENGTH: 363
<212> TYPE: DNA
<213> ORGANISM: Homo sapiens

<400> SEQUENCE: 843
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaacccta cagtggtgg cacaaactat      180 gcacagaagt tcagggcag ggtcaccatg accagggaca cgtccatcag cacagcctac     240
atggagctga gcaggctgag atctgacgac acggccgtgt attactgtgc gagatccgat     300
attttgactg gttattatgc ttttgatatc tggggccaag gacaatggt caccgtctcg     360 aga                                                                   363

<210> SEQ ID NO 844
<211> LENGTH: 321
<212> TYPE: DNA
<213> ORGANISM: Homo sapiens

<400> SEQUENCE: 844
gacatccaga tgacccagtc tccatcctcc ctgtctgcat ctgtaggaga cagagtcacc      60
atcacttgcc gggcaagtca gagcattagc agctatttaa attggtatca gcagaaacca     120
```

```
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccacgtggac gttcggccaa      300
gggaccaagg tggaaatcaa a                                                321

<210> SEQ ID NO 845
<211> LENGTH: 387
<212> TYPE: DNA
<213> ORGANISM: Homo sapiens

<400> SEQUENCE: 845
gaggtgcagc tggtggagtc tggggctgag gtgaagaagc ctggggcctc agtgaaggtc       60
tcctgcaagg cttctggata caccttcacc ggctactata tgcactgggt gcgacaggcc      120
cctggacaag gcttgagtg gatgggatgg atcaaccctaa cagtggtgg cacaaactat       180 gcacagaagt ttcagggcag ggtcaccatg accaggaca cgtccatcag cacagcctac       240
atggagctga gcaggctgag atctgacgac acggccgtgt attactgtgc gagagattta      300
tggtattact atggttcggg gagttcactg tactactact acggtatgga cgtctggggc      360
caagggacca cggtcaccgt ctcgaga                                          387

<210> SEQ ID NO 846
<211> LENGTH: 336
<212> TYPE: DNA
<213> ORGANISM: Homo sapiens

<400> SEQUENCE: 846
cagtctgtgt tgacgcagcc gccctcagtg tctggggccc cagggcagag ggtcaccatc       60
tcctgcactg ggagcagctc caacatcggg gcaggttatg atgtacactg gtaccagcag      120
cttccaggaa cagcccccaa actcctcatc tatggtaaca gcaatcggcc ctcaggggtc      180
cctgaccgat tctctggctc caagtctggc acctcagcct ccttggccat cactgggctc      240
caggctgagg atgaggctga ttattactgc cagtcctatg acagcagcct gagtggtgtg      300
gtattcggcg agggaccaa gctgaccgtc ctaggt                                 336

<210> SEQ ID NO 847
<211> LENGTH: 366
<212> TYPE: DNA
<213> ORGANISM: Homo sapiens

<400> SEQUENCE: 847
gaggtgcagc tggtggagtc tgggggaggc ttggtacagc ctggcaggtc cctgagactc       60
tcctgtgcag cctctggatt cacctttgat gattatgcca tgcactgggt ccggcaagct      120
ccagggaagg gcctggagtg ggtctcaggt attagttgga atagtggtag cataggctat      180
gcggactctg tgaagggccg attcaccatc tccagagaca acgccaagaa ctccctgtat      240
ctgcaaatga acagtctgag agctgaggac acggccttgt attactgtgt acggagtggg      300
agctacaact actactacta cggtatggac gtctggggcc aagggaccac ggtcaccgtc      360
tcgaga                                                                 366

<210> SEQ ID NO 848
<211> LENGTH: 333
<212> TYPE: DNA
<213> ORGANISM: Homo sapiens

<400> SEQUENCE: 848
```

```
cagtctgtgt tgacgcagcc gccctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggttgggtg     300
ttcggcggag ggaccaagct gaccgtccta ggt                                  333

<210> SEQ ID NO 849
<211> LENGTH: 369
<212> TYPE: DNA
<213> ORGANISM: Homo sapiens

<400> SEQUENCE: 849
caggtgcagc tgcaggagtc gggggggaggc ttggtacagc ctgggggtc cctgagactc      60 tcctgtacaa cctctggatt caccttacc agctatgcca tgagctgggt ccgccaggct     120
ccagggaagg ggctggagtg ggtctcatct attagtggta gtggtggtat cacatactac     180
gcagactccg tgaagggccg gttcaccatc tccagagaca attccaagaa cacactgtat     240
ctgcaaatga acagcctaag agccgaggac acggccgtat attactgtgc gaaagatagg     300
gttctagtcc cagcttcctc ttcgtacttt gactactggg gccagggaac cctggtcacc     360
gtctcgaga                                                            369

<210> SEQ ID NO 850
<211> LENGTH: 327
<212> TYPE: DNA
<213> ORGANISM: Homo sapiens

<400> SEQUENCE: 850
tcttctgagc tgactcagga ccctgctgtg tctgtggcct tgggacagac agtcaggatc      60
acatgccaag agacagcct cagaagctat tatgcaagct ggtaccagca gaagccagga     120
caggcccctg tacttgtcat ctatggtaaa acaaccggc cctcagggat cccagaccga     180
ttctctggct ccagctcagg aaacacagct tccttgacca tcactggggc tcaggcggaa     240
gatgaggctg actattactg taactcccgg gacagcagtg gtaaccatgt ggtattcggc     300
ggagggacca agctgaccgt cctaggt                                        327

<210> SEQ ID NO 851
<211> LENGTH: 360
<212> TYPE: DNA
<213> ORGANISM: Homo sapiens

<400> SEQUENCE: 851
caggtgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagctctgt gaccgccgca gacacggctg tgtattactg tgcgagacgt     300
cccttaacct ttaatgcttt tgatatctgg ggccaaggga caatggtcac cgtctcgaga     360

<210> SEQ ID NO 852
<211> LENGTH: 327
<212> TYPE: DNA
```

<213> ORGANISM: Homo sapiens

<400> SEQUENCE: 852

| tcctatgtgc tgactcagcc accctcagtg tcagtggccc caggaaagac ggccaggatt | 60 |
| acctgtgggg gaaacaacat tggaagtaaa agtgtgcact ggtaccagca gaagccaggc | 120 |
| caggcccctg tgctggtcat ctattatgat agcgaccggc cctcagggat ccctgagcga | 180 |
| ttctctggct ccaactctgg gaacacggcc accctgacca tcagcagggt cgaagccggg | 240 |
| gatgaggccg actattactg tcaggtgtgg gatagtagta gtgatcatgt ggtattcggc | 300 |
| ggagggacca agctgaccgt cctaggt | 327 |

<210> SEQ ID NO 853
<211> LENGTH: 360
<212> TYPE: DNA
<213> ORGANISM: Homo sapiens

<400> SEQUENCE: 853

| caggtgcagc tgcaggagtc gggcccagga ctggtgaagc cttcggagac cctgtccctc | 60 |
| acctgcactg tctctggtgg ctccatcagc agtagtagtt actactgggg ctggatccgc | 120 |
| cagcccccag ggaaggggct ggagtggatt gggagtatct attatagtgg gagcacctac | 180 |
| tacaacccgt ccctcaagag tcgagtcacc atatccgtag acacgtccaa gaaccagttc | 240 |
| tccctgaagc tgagctctgt gaccgccgca gacacggctg tgtattactg tgcgaggatt | 300 |
| cccatgtata gcagctcggt tgactactgg ggccagggaa ccctggtcac cgtctcgaga | 360 |

<210> SEQ ID NO 854
<211> LENGTH: 327
<212> TYPE: DNA
<213> ORGANISM: Homo sapiens

<400> SEQUENCE: 854

| tcctatgtgc tgactcagcc accctcagtg tcagtggccc caggaaagac ggccaggatt | 60 |
| acctgtgggg gaaacaacat tggaagtaaa agtgtgcact ggtaccagca gaagccaggc | 120 |
| caggcccctg tgctggtcat ctattatgat agcgaccggc cctcagggat ccctgagcga | 180 |
| ttctctggct ccaactctgg gaacacggcc accctgacca tcagcagggt cgaagccggg | 240 |
| gatgaggccg actattactg tcaggtgtgg gatagtagta gtgatcatgt ggtattcggc | 300 |
| ggagggacca agctgaccgt cctaggt | 327 |

<210> SEQ ID NO 855
<211> LENGTH: 360
<212> TYPE: DNA
<213> ORGANISM: Homo sapiens

<400> SEQUENCE: 855

| caggtgcagc tgcaggagtc gggcccagga ctggtgaagc cttcggagac cctgtccctc | 60 |
| acctgcactg tctctggtgg ctccatcagc agtagtagtt actactgggg ctggatccgc | 120 |
| cagcccccag ggaaggggct ggagtggatt gggagtatct attatagtgg gagcacctac | 180 |
| tacaacccgt ccctcaagag tcgagtcacc atatccgtag acacgtccaa gaaccagttc | 240 |
| tccctgaagc tgagctctgt gaccgccgca gacacggctg tgtattactg tgcgagacgt | 300 |
| cccttaacct ttaatgcttt tgatatctgg ggccaaggga ccacggtcac cgtctcgaga | 360 |

<210> SEQ ID NO 856
<211> LENGTH: 327

<210> SEQ ID NO 856
<211> LENGTH: (not shown)
<212> TYPE: DNA
<213> ORGANISM: Homo sapiens

<400> SEQUENCE: 856

```
tcctatgtgc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatgt ggtattcggc   300
ggagggacca agctgaccgt cctaggt                                       327
```

<210> SEQ ID NO 857
<211> LENGTH: 366
<212> TYPE: DNA
<213> ORGANISM: Homo sapiens

<400> SEQUENCE: 857

```
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaagatggg   300
ggatggttcg gggagttaga ttacttccag cactggggcc agggcaccct ggtcaccgtc   360
tcgaga                                                              366
```

<210> SEQ ID NO 858
<211> LENGTH: 333
<212> TYPE: DNA
<213> ORGANISM: Homo sapiens

<400> SEQUENCE: 858

```
cagtctgtgt tgacgcagcc gccctcagtg tctgcggccc caggacagaa ggtcaccgtc    60
tcctgcactg gaagcaactc caacattgag aagaatgatg tttcctggta ccagcaggga   120
ccaggagcag cccccaaact cctcatttct gacactgata gcgaccctc agggattcct   180
gaccgattct ctggctccaa gtctggcacg tcagccaccc tggccatcgc tgggctccag   240
gctgaggatg aggctgatta ttactgccag tcccatgaca ccactctgag tggtccgatc   300
ttcggcgggg ggacccagct gaccgtccta ggt                                333
```

<210> SEQ ID NO 859
<211> LENGTH: 372
<212> TYPE: DNA
<213> ORGANISM: Homo sapiens

<400> SEQUENCE: 859

```
caggtgcagc tgcaggagtc gggggaggc ttggtcaagc ctggagggtc cctgagactc    60
tcctgtgcag cctctggatt cagtttcagt gactactaca tgagctgggt ccgccaggct   120
ccagggaagg ggctggagtg gatttcatat attactagta gtagtagtga cacagactac   180
gcagactctg tgaagggccg attcaccatc tccagagaca acgccaagaa ctcactatat   240
ctgcaaatga acagcctgag agccgacgac acggccgtgt attactgtgc gagagtgggc   300
tattattatg attactacta ctactactac atggacgtct ggggcaaagg gaccacggtc   360
```

```
accgtctcga ga                                                        372

<210> SEQ ID NO 860
<211> LENGTH: 324
<212> TYPE: DNA
<213> ORGANISM: Homo sapiens

<400> SEQUENCE: 860
tcttctgagc tgactcagga ccctgctgtg tctgtggcct tgggacagac agtcaggatc     60
acatgccaag agacagcct cagaggctat tatgcaagct ggtaccagca gaagccagga    120
caggcccctg tccttgtcgt ctatgatgaa acaaccggc cctcagggat cccagaccga    180
ttctctggct ccagctcagg aaacacagct tccttgacca tcactggggc tcaggcggaa    240
gatgaggctg actattactg taactcccgg gacattaacc ttgattgggt gttcggcgga    300
gggaccaagt tgaccgtcct aggt                                           324

<210> SEQ ID NO 861
<211> LENGTH: 360
<212> TYPE: DNA
<213> ORGANISM: Homo sapiens

<400> SEQUENCE: 861
caggtgcagc tgcaggattc gggcccagga ctggtgaagc cttcggatac cctgtccctc     60
acctgcactg tctctggtgg ctccatcagc agtattagtt actactgggg ctggatccgc    120
cagcccccag ggaaggggct ggagtgtatt gggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg tgcgagacgg    300
gtcatagtgt gggggagtga tgactactgg ggccagggaa ccctggtcac cgtctcgaga    360

<210> SEQ ID NO 862
<211> LENGTH: 327
<212> TYPE: DNA
<213> ORGANISM: Homo sapiens

<400> SEQUENCE: 862
tcctatgtgc tgactcagcc accctcagtg tcagtggccc caggaaagac ggccaggatt     60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt cctaggt                                        327

<210> SEQ ID NO 863
<211> LENGTH: 360
<212> TYPE: DNA
<213> ORGANISM: Homo sapiens

<400> SEQUENCE: 863
caggtgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag ggaaggggct ggagtgggatt gggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg tgcgatgcgg    300
```

```
gcctatggtt cagggagtta tgactactgg ggccagggaa ccctggtcac cgtctcgaga    360
```

<210> SEQ ID NO 864
<211> LENGTH: 336
<212> TYPE: DNA
<213> ORGANISM: Homo sapiens

<400> SEQUENCE: 864

```
gatgttgtga tgactcagtc tccactctcc ctgcccgtca cccctggaga gccggcctcc     60
atctcctgca ggtctagtca gagcctcctc catagtaatg gatacaacta tttggattgg    120
tacctgcaga agccagggca gtctccgcag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaccccca    300
ttcactttcg gccctgggac caaagtggat atcaaa                              336
```

<210> SEQ ID NO 865
<211> LENGTH: 363
<212> TYPE: DNA
<213> ORGANISM: Homo sapiens

<400> SEQUENCE: 865

```
gaggtgcagc tggtggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagct attagtggta gtggtggtag cacatattac    180
gcagactccg tgaagggccg gttcaccatc tccagagaca attccaagaa cacgctgtat    240
ctgcaaatga acagcctgag agccgaggac acggccgcat attactgtgc gaaaggtctt    300
aggtatagca gtgcctggac gtttgactac tggggccagg aaccctggt caccgtctcg    360 aga                                                                  363
```

<210> SEQ ID NO 866
<211> LENGTH: 336
<212> TYPE: DNA
<213> ORGANISM: Homo sapiens

<400> SEQUENCE: 866

```
cagtctgccc tgactcagcc tgcctccgtg tctgggtctc ctggacagtc gatcaccatc     60
tcctgcactg gaaccagcag tgacgttggt ggttataact atgtctcctg gtaccaacaa    120
cacccaggca aagcccccaa actcatgatt tatgatgtca gtaatcggcc ctcagggtt    180 tctaatcgct tctctggctc caagtctggc aacacggcct ccctgaccat ctctggactc    240
caggctgagg acgaggctga ttattactgc agctcatata caagcagtag cactcctgtg    300
gtattcggcg gagggaccaa gctgaccgtc ctaggt                              336
```

<210> SEQ ID NO 867
<211> LENGTH: 357
<212> TYPE: DNA
<213> ORGANISM: Homo sapiens

<400> SEQUENCE: 867

```
caggtgcagc tggtgcaatc tgggtctgag ttgaagaagc ctggggcctc agtgaaggtt     60
tcctgcaagg cttctggata catcttcact agatatggca taaattgggt gcgacaggcc    120
cctggacaag ggcttgagtg gatgggatgg atcaacacca cactgggaa cccaacgtat    180
```

| | |
|---|---|
| gcccagggct tcacaggccg ggttgtcttc tccttggaca cctctgtcag cacggcatat | 240 |
| ctgcagatca gcagcctaaa ggctgaggac actgccatgt attactgtgc gatcagcagt | 300 |
| ggctttgggt actactttga ctactgggc cagggaaccc tggtcaccgt ctcgaga | 357 |

<210> SEQ ID NO 868
<211> LENGTH: 321
<212> TYPE: DNA
<213> ORGANISM: Homo sapiens

<400> SEQUENCE: 868

| | |
|---|---|
| gacatccaga tgacccagtc tccatcgtcc gtgtctgcat ctgtgggaga cagagtcacc | 60 |
| atcacttgtc gggcgagtca agtattagt aggtggttag cctggtatca gcagaaacca | 120 |
| gggaaagccc ctaagttcct gatctatgct ggatccagtt tgcaaagtgg ggtcccatcg | 180 |
| aggttcagcg gcagtgggtc tgggacagat ttcactctca ccatcagcag cctgcagcct | 240 |
| gaagactttg caacttatta ttgtcaacag actaacagtt ccctctcac cttcggcgga | 300 |
| gggaccaagg tggagatcaa a | 321 |

<210> SEQ ID NO 869
<211> LENGTH: 360
<212> TYPE: DNA
<213> ORGANISM: Homo sapiens

<400> SEQUENCE: 869

| | |
|---|---|
| caggtgcagc tggtgcagtc tggggctgag gtgaagaagc ctggggcctc agtgaaggtc | 60 |
| tcctgcaagg cttctggtta caccttacc agctacggta tcagctgggt gcgacaggcc | 120 |
| cctggacaag gcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgacgac acggccgtgt attactgtgc gagagctttt | 300 |
| agggactggg gatctcttag ggactactgg ggccagggca ccctggtcac cgtctcgaga | 360 |

<210> SEQ ID NO 870
<211> LENGTH: 333
<212> TYPE: DNA
<213> ORGANISM: Homo sapiens

<400> SEQUENCE: 870

| | |
|---|---|
| cagtctgtgt tgacgcagcc gccctcagtg tctgcggccc caggacagaa ggtcaccatc | 60 |
| tcctgctctg gaagcagctc caacattggg aataattatg tatcctggta ccagcagctc | 120 |
| ccaggaacag cccccaaact cctcatttat gacaataata gcgaccctc agggattcct | 180 |
| gaccgattct ctggctccaa gtctggcacg tcagccaccc tgggcatcac cggactccag | 240 |
| actggggacg aggccgatta ttactgcgga acatgggata gcagcctgag tgccgtggta | 300 |
| ttcggcggag ggaccaagct gaccgtccta ggt | 333 |

<210> SEQ ID NO 871
<211> LENGTH: 363
<212> TYPE: DNA
<213> ORGANISM: Homo sapiens

<400> SEQUENCE: 871

| | |
|---|---|
| gaggtgcagc tggtggagtc tggagcagag gtgaaaaagc ccggggagtc tctgaagatc | 60 |
| tcctgtaagg gttctggata cagctttacc agctactgga tcggctgggt gcgccagatg | 120 |
| cccgggaaag gcctggagtg gatggggatc atctatcctg gtgactctga taccagatac | 180 |

```
agcccgtcct tccaaggcca ggtcaccatc tcagccgaca agtccatcag caccgcctac    240
ctgcagtgga gcagcctgaa ggcctcggac accgccatgt attactgtgc gagactggca    300
gtgggagcct accagtacta ctttgactac tggggccagg aaccctggt caccgtctcg    360 aga                                                                   363

<210> SEQ ID NO 872
<211> LENGTH: 333
<212> TYPE: DNA
<213> ORGANISM: Homo sapiens

<400> SEQUENCE: 872
cagactgtgg tgacccagga gccatcgttc tcagtgtccc ctggagggac agtcacactc     60
acttgtggct tgagctctgg ctcagtctct actagttact accccagctg gtaccagcag    120
accccaggcc aggctccacg cacgctcatc tacagcacaa acactcgctc ttctggggtc    180
cctgatcgct tctctggctc catccttggg aacaaagctg ccctcaccat cacggggggcc    240 caggcagatg atgaatctga ttattactgt gtgctgtata tgggtagtgg catttcggtg    300
ttcggcggag ggaccaagct gaccgtccta ggt                                  333

<210> SEQ ID NO 873
<211> LENGTH: 357
<212> TYPE: DNA
<213> ORGANISM: Homo sapiens

<400> SEQUENCE: 873
gaggtgcagc tggtggagtc tggggggaaac ttggtccagc cggggggggtc cctgagactc     60 tcctgtgcag cctctggatt caccttcagt aggtattgga tgacctgggt ccgccaggct    120
ccagggaagg ggctggagtg gatttcatcc gttagtagta gcggcagtac catatactac    180
gcagactctg tgaagggccg attcaccatc tccagagaca acgccaagaa ctcactgtat    240
ctgcaaatga acagcctgag agtcgaggac acggctgttt attactgtgc gcgagactat    300
tggcctggct ggtacttcga tctctggggc cgtggaaccc tggtcaccgt ctcgaga       357

<210> SEQ ID NO 874
<211> LENGTH: 348
<212> TYPE: DNA
<213> ORGANISM: Homo sapiens

<400> SEQUENCE: 874
caggctgtgc tcactcagcc gtcttccctc tctgcatctc ctggagcatc agccagtctc     60
acctgcacct tccgcagtga catcagtgtt ggttcctata ggatatactg gtaccagcag    120
aagccaggga gtcctcccca gtttctcctg aaatatacgt cagactcaga taagcagcag    180
ggctctggag tccccagccg cttctctgga tccaaagatg tttcggccaa tgctggcatt    240
ttactcatct ctgggctcca gtctgaggat gaggctgact attactgtat gacttggcac    300
aacaccgctt cggtattcgg cggagggacc aagctggccg tcctaggt                 348

<210> SEQ ID NO 875
<211> LENGTH: 357
<212> TYPE: DNA
<213> ORGANISM: Homo sapiens

<400> SEQUENCE: 875
gaggtacagc tggtggagtc tggggggaggt ttgataaggc cggggggggtc cctgagactc     60
```

| | |
|---|---|
| tcctgtacag cctctggatt caccttcagt agttatacta tgaattgggt ccgccaggct | 120 |
| ccagggaagg ggctggagtg gctttcatat ataagtggtg gcagtggtac caaattctac | 180 |
| gcagactctg tgaagggccg gttcaccgtc tccagagaca atgccaagaa ttcattgtat | 240 |
| ctggaaatga acagcctgag acccgaggac acggctgtct attactgtgc gctagtgtca | 300 |
| tatagttcgc cgggctttga ctactggggc cagggcaccc tggtcaccgt ctcgagc | 357 |

<210> SEQ ID NO 876
<211> LENGTH: 321
<212> TYPE: DNA
<213> ORGANISM: Homo sapiens

<400> SEQUENCE: 876

| | |
|---|---|
| tcctatgagc tgactcagcc accctcagtg tccgtgtccc caggacagac agccagcatc | 60 |
| acctgctctg gagataaatt gggcgataaa tatgtttact ggtatcaaca gaagccaggc | 120 |
| cagtccccta tattgctcat ctttcaagat agcgagcggc cctcagggat ccctgagcga | 180 |
| ttctctggct ccaactctgg gaacacagcc actctgacca tcagcgggac ccaggctatg | 240 |
| gatgaggctg actattactg tcaggcgtgg gacagcagcg ctgcggtgtt cggcggaggg | 300 |
| accaagctga ccgtcctagg t | 321 |

<210> SEQ ID NO 877
<211> LENGTH: 345
<212> TYPE: DNA
<213> ORGANISM: Homo sapiens

<400> SEQUENCE: 877

| | |
|---|---|
| caggtgcagc tggtgcagtc tggagcagag gtgaaaaagc ctggggcctc agtgaaggtc | 60 |
| tcctgcaagg cttctggtta ccctttacc agctatggta tcagctgggt gcgacaggcc | 120 |
| cctggacaag gcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgacgac acggccgtgt attactgtgc gagaggggt | 300 |
| gcttttgata tctggggcca agggaccacg gtcaccgtct cgaga | 345 |

<210> SEQ ID NO 878
<211> LENGTH: 336
<212> TYPE: DNA
<213> ORGANISM: Homo sapiens

<400> SEQUENCE: 878

| | |
|---|---|
| cagtctgtgt tgacgcagcc gccctcagtg tctggggccc cagggcagag ggtcaccatc | 60 |
| tcctgcactg ggagcagctc caacatcggg gcaggttatc atgtatactg gtaccagcag | 120 |
| cttccaggaa aagccccca actcctcatc tacgttaaca gcaatcggcc ctcaggggtc | 180 |
| cctgaccgat tctctggctc caagtctggc acctcagcct ccctggccat cactgggctc | 240 |
| caggctgacg atgaggctga ttactactgc cagtcctatg acagcagcct gagtggtagg | 300 |
| gttttcggcg gagggaccaa gctgaccgtc ttaggt | 336 |

<210> SEQ ID NO 879
<211> LENGTH: 357
<212> TYPE: DNA
<213> ORGANISM: Homo sapiens

<400> SEQUENCE: 879

| | |
|---|---|
| gaggtgcagc tggtggagtc tgggggcggc ttggtccagc cggggggtc cctgagactc | 60 |

```
tcctgttcag cctctggatt cacctttagt aactattgga tgacctgggt ccgtcaggct    120
ccagggaagg ggctggagtg gatttcatcc attagtagta gcggcagtac catatactac    180
gcagactctg tgaagggccg attcaccatc tccagagaca acgccaagaa ctcactgtat    240
ctgcaaatga acagcctgag agtcgaggac acggctgttt attactgtgc gcgagactat    300
tggcctggct ggtacttcga tctctggggc cgtggcaccc tggtcaccgt ctcgaga       357
```

<210> SEQ ID NO 880
<211> LENGTH: 348
<212> TYPE: DNA
<213> ORGANISM: Homo sapiens

<400> SEQUENCE: 880

```
caggctgtgc tcactcagcc gtcttccctc tctgcatctc ctggagcatc agccagtctc     60
acctgcacct tccgcagtga catcagtgtt ggttcctata ggatatactg gtaccagcag    120
aagccaggga gtcctcccca gtttctcctg aaatatacgt cagactcaga taagcagcag    180
ggctctggag tccccagccg cttctctgga tccaaagatg tttcggccaa tgctggcatt    240
ttactcatct ctgggctcca gtctgaggat gaggctgact attactgtat gacttggcac    300
aacaccgctt cggtattcgg cggagggacc aagctggccg tcctaggt                 348
```

<210> SEQ ID NO 881
<211> LENGTH: 381
<212> TYPE: DNA
<213> ORGANISM: Homo sapiens

<400> SEQUENCE: 881

```
caggtgcagc tggtgcagtc tgggtctgag gtgaagaagc ctggggcctc agtgaaggtc     60
tcctgcaaga cttctggata catcttcacc gactactata tgcactgggt gcgacaggcc    120
cctggaaaag ggcttgagtg gatgggatgg attaacccta acagtggtgg cacatactat    180
gcacagaagt ttcacggcag ggtcaccatg accgtgaca cgtccatcag cacagcctac    240
atggagctga gcagtctgag atctgacgac acggccatat attactgtgc gagagaggat    300
tacgatattt tgactggtta ttatcccgcg tccggccacg gggactactg gggccaggga    360
accctggtca ccgtctcgag a                                              381
```

<210> SEQ ID NO 882
<211> LENGTH: 330
<212> TYPE: DNA
<213> ORGANISM: Homo sapiens

<400> SEQUENCE: 882

```
caggctgtgg tgactcagga gccctcactg actgtgtccc caggagggac agtcactctc     60
acctgtgcat ccagcactgg agcagtcacc agtggtttcc ttgcaaactg gttccagcag    120
aaacctggac aaacacccag gtcactgatt tataaacaa gcaacaaaca tcctggacc     180 cctgcccggt tctcaggctc cctccttggg ggcaaagctg ccctgacact gtcaggtgtg    240
cagcctgagg acgaggctga ctattactgc ctgctcttat ctggtggtgc atgggtgttt    300
ggcggaggga ccaagctgag tgtcctaggt                                     330
```

<210> SEQ ID NO 883
<211> LENGTH: 366
<212> TYPE: DNA
<213> ORGANISM: Homo sapiens

```
<400> SEQUENCE: 883
caggtgcagc tggtgcagtc tggagcagag gtgaaaaagc ccggagagtc tctgaagatc    60
tcgtgtgagg gttctggata cacctttacc agctactgga tcggctgggt gcgccagatg   120
cccgggaaag acctggagtg gatggggatc atctatcctg gtgactctga taccagatac   180
agcccgtcct tccaaggcca ggtcaccatc tcagtcgaca agtctatcag caccgcctac   240
ctgcagtgga gcagcctgaa ggcctcgac accgccatgt attactgtgc gagacacgac   300
gtagttgatg ctacaatac cggtatggac gtctggggcc aagggaccac ggtcaccgtc   360
tcgaga                                                               366

<210> SEQ ID NO 884
<211> LENGTH: 333
<212> TYPE: DNA
<213> ORGANISM: Homo sapiens

<400> SEQUENCE: 884
cagactgtgg tgacccagga gccatcgttc acagtgtccc ctggagggac agtcacactc    60
acttgtggct tgagctctgg ctcagtctct actagttact accccagctg gtaccagcag   120
accccaggcc aggctccacg cacgctcatc tccagcacaa acactcgctc ttctggggtc   180
cctgatcgct tctctggctc catccttggg aacagagctg ccctcaccat cacgggggcc   240
caggcagatg atgagtctga ttattactgt gtgctgtata tgggtagtgg catttgggtg   300
ttcggcggag ggaccaagct gaccgtccta ggt                                 333

<210> SEQ ID NO 885
<211> LENGTH: 384
<212> TYPE: DNA
<213> ORGANISM: Homo sapiens

<400> SEQUENCE: 885
caggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga tgccagatac   180
agcccgtcct tccaaggcca ggtcaccatc tcagccgaca gtccatcag caccgcctac   240 ctgcagtgga gcagcctgaa ggcctcgac accgccatgt attactgtgc gagactcacg   300
ggcagttctt actatgatag tagtggttat tcctcctacg gtatggacgt ctggggccaa   360
gggaccacgg tcaccgtctc gaga                                           384

<210> SEQ ID NO 886
<211> LENGTH: 333
<212> TYPE: DNA
<213> ORGANISM: Homo sapiens

<400> SEQUENCE: 886
cagactgtgg tgacccagga gccatcgttc tcagtgtccc ctggagggac agtcacactc    60
acttgtggct tgagctctgg ctcagtctct actagttact accccagctg gttccagcag   120
accccaggcc aggctccacg cacgctcatc tacagcacaa acactcgctc ttctggggtc   180
cctgatcgct tctctggctc catccttggg aacaaagctg ccctcaccat cacgggggcc   240
caggcagatg atgaatctga ttattactgt gtgctgtata tgggtagtgg catttctgtg   300
ttcggaggag gcacccagct gaccgtcctc ggt                                 333
```

```
<210> SEQ ID NO 887
<211> LENGTH: 363
<212> TYPE: DNA
<213> ORGANISM: Homo sapiens

<400> SEQUENCE: 887
caggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcagc accgcctac      240 ctgcagtgga gcagcctgaa ggcctcggac accgccatgt attactgtgc gagacataac     300
agtaactact actactacta catggacgtc tggggcaaag gaaccctggt caccgtctcg     360
aga                                                                   363

<210> SEQ ID NO 888
<211> LENGTH: 333
<212> TYPE: DNA
<213> ORGANISM: Homo sapiens

<400> SEQUENCE: 888
cagactgtgg tgacccagga gccatcgttc tcagtgtccc ctggagggac agtcacactc      60
acttgtggct tgagctctgg ctcagtctct actagttact accccagctg gtaccagcag     120
accccaggcc aggctccacg cacgctcatc tacagcacaa acactcgctc ttctggggtc     180
cctgatcgct tctctggctc catccttggg aacaaagctg ccctcaccat cacgggggcc     240
caggcagatg atgaatctga ttattactgt gtgctgtata tgggtagtgg catttcggtg     300
ttcggcggag ggaccaagct gaccgtccta ggt                                  333

<210> SEQ ID NO 889
<211> LENGTH: 381
<212> TYPE: DNA
<213> ORGANISM: Homo sapiens

<400> SEQUENCE: 889
caggtgcagc tggtgcagtc tgggtctgag gtgaagaagc ctggggcctc agtgaaggtc      60
tcctgcaaga cttctggata catcttcacc gactactata tgcactgggt gcgacaggcc     120
cctggaaaag gccttgagtg gatgggatgg attaacccta acagtggtgg cacatactat     180
gcacagaagt tcacggcag ggtcaccatg accagtgaca cgtccatcag cacagcctac     240
atggagctga gcagtctgag atctgacgac acggccatat attactgtgc gagagaggat     300
tacgatattt tgactggttt ttatcccgcg tccggccacg gggactactg gggccaggga     360
accctggtca ccgtctcgag a                                               381

<210> SEQ ID NO 890
<211> LENGTH: 321
<212> TYPE: DNA
<213> ORGANISM: Homo sapiens

<400> SEQUENCE: 890
gaaattgtgt tgacgcagtc tccaggcacc ctgtctttgt ctccagggga aagagccacc      60
ctctcctgca gggccagtca gagtgttagc agcagctact agcctggta ccagcagaaa      120 cctggccagg ctcccaggct cctcatctat ggtgcatcca gcagggccac tggcatccca     180
gacaggttca gtggcagtgg gtctgggaca gacttcactc tcaccatcag cagactggag     240
```

```
cctgaagatt ttgcagtgta ttactgtcag cagtatggta gctcactcac tttcggcgga    300
gggaccaagg tggagatcaa a                                              321

<210> SEQ ID NO 891
<211> LENGTH: 366
<212> TYPE: DNA
<213> ORGANISM: Homo sapiens

<400> SEQUENCE: 891
caggtgcagc tggtgcagtc tggagcagag gtgaaaaagc ccggggagtc tctgaagatc    60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac     240 ctgcagtgga gcaccctgaa ggcctcggac accgccatgt attactgtgc gagacatggg   300
atgactagtg gctacgtcgc gcacaatgac tactggggcc agggaaccct ggtcaccgtc    360
tcgaga                                                               366

<210> SEQ ID NO 892
<211> LENGTH: 333
<212> TYPE: DNA
<213> ORGANISM: Homo sapiens

<400> SEQUENCE: 892
cagactgtgg tgacccagga gccatcgttc tcagtgtccc ctggagggac agtcacactc    60
acttgtggct tgagctctgg ctcagtctct actagttact ccccagctg gtaccagcag    120 accccaggcc aggctccacg cacgctcatc tacagcacaa acactcgctc ttctggggtc    180
cctgatcgct tctctggctc catccttggg aacaaagctg ccctcaccat cacgggggcc    240
caggcagatg atgaatctga ttattactgt gtgctgtata gggtagtgg catttgggtg    300 ttcggcggag ggaccaagct gaccgtccta ggt                                 333

<210> SEQ ID NO 893
<211> LENGTH: 351
<212> TYPE: DNA
<213> ORGANISM: Homo sapiens

<400> SEQUENCE: 893
caggtgcagc tgcaggagtc gggcccagga ctggtgaagc cttcggggac cctgtccctc    60
acctgcgctg tctctggtgg ctccatcagc agtagtaact ggtggagttg gtccgccag     120 cccccaggga aggggctgga gtggattggg gaaatctatc atagtgggag caccaactac    180
aacccgtccc tcaagagtcg agtcaccata tcagtagaca gtccaagaa ccagttctcc    240 ctgaagctga gctctgtgac cgccgcggac acggccgtgt attactgtgc gagaggtggg    300
agctactact ttgactactg gggccaggga accctggtca ccgtctcgag a             351

<210> SEQ ID NO 894
<211> LENGTH: 336
<212> TYPE: DNA
<213> ORGANISM: Homo sapiens

<400> SEQUENCE: 894
cagtctgccc tgactcagcc tgcctccgtg tctgggtctc ctggacagtc gatcaccatc    60
tcctgcactg gaaccatcag tgacgttggt ggttatgact ttgtctcctg gtaccaacac    120 cacccccggca aagcccccaa actcctgatt tatgatgtca ataatcggcc ctctggggtt   180
```

```
tctcatcgct tctctggctc caagtctggc aacacggcct ccctgaccat ctctgggctc    240
caggctgagg acgaggctac ttattactgc agttcatatt caaacagaca ttctctcatc    300
gtcttcggat ctgggaccca ggtcgtcggc ctaggt                              336
```

<210> SEQ ID NO 895
<211> LENGTH: 363
<212> TYPE: DNA
<213> ORGANISM: Homo sapiens

<400> SEQUENCE: 895

```
caggtgcagc tacagcagtg gggcgcagga ctgttgaagc cttcggagac cctgtccctc     60
acctgcgctg tctatggtgg gtccttcagt ggttactact ggagctggat ccgccagccc    120
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag aggcggggg     300 gttgaggcgt tgaactacgg tatggacgtc tggggccaag gaccacggt  caccgtctcg    360 aga                                                                  363
```

<210> SEQ ID NO 896
<211> LENGTH: 336
<212> TYPE: DNA
<213> ORGANISM: Homo sapiens

<400> SEQUENCE: 896

```
cagtctgccc tgactcagcc tgcctccgtg tctgggtctc ctggacagac gatcaccatc     60
tcctgcactg gaaccatcag tgacgttggt ggttatgact ttgtctcctg gtaccaacac    120
caccccggca agcccccaa actcctgatt tatgatgtca ataatcggcc ctctggggtt    180
tctcatcgct tctctggctc caagtctggc aacacggcct ccctgaccat ctctgggctc    240
caggctgagg acgaggctac ttattactgc agttcatatt caaacagaca ttctctcatc    300
gtcttcggat ctgggaccca ggtcgtcggc ctaggt                              336
```

<210> SEQ ID NO 897
<211> LENGTH: 357
<212> TYPE: DNA
<213> ORGANISM: Homo sapiens

<400> SEQUENCE: 897

```
caggtgcagc tacagcagtg gggcgcaggg ctgttgaagc cttcggaaac cctgtccctc     60
acctgcactg tccatggtgg gtccttcgat gattactact ggacctggat ccgccagccc    120 cagggggg gctggaatg gattggggaa atgaattccg gtagaactta caactacaac    180
ccgttcctgg agagtcgagc ctccatagat gttgacacgt tcaagaagca gttctccctg    240
gcattgcgtt ctgtgaccgc cgcggacaca gctgtctatt actgtgcgcg gggcgcctat    300
gtcaactact actacataga cgtctggggc gacgggacca cggtcaccgt ctcgaga      357
```

<210> SEQ ID NO 898
<211> LENGTH: 336
<212> TYPE: DNA
<213> ORGANISM: Homo sapiens

<400> SEQUENCE: 898

```
cagtctgccc tgactcagcc tgcctccgtg tctgggtctc ctggacagac gatcaccatc     60
```

```
tcctgcactg gaaccatcag tgacgttggt ggttatgact ttgtctcctg gtaccaacac    120
caccccggca agccccccaa actcctgatt tatgatgtca ataatcggcc ctctggggtt    180
tctcatcgct tctctggctc caagtctggc aacacggcct ccctgaccat ctctgggctc    240
caggctgagg acgaggctac ttattactgc agttcatatt caaacagaca ttctctcatc    300
gtcttcggat ctgggaccca ggtcgtcggc ctaggt                              336

<210> SEQ ID NO 899
<211> LENGTH: 375
<212> TYPE: DNA
<213> ORGANISM: Homo sapiens

<400> SEQUENCE: 899
caggtgcagc tgcaggagtc gggcccagga ctggtgaagc cttcggagac cctgtccctc     60
acctgcactg tctctggtgg ctccatcagt agttactact ggagctggat ccggcagccc    120
gccgggaagg gactggagtg gattggcgt atctatacca gtgggagcac caactacaac    180
ccctccctca agagtcgagt caccatgtca gtagacacgt ccaagaacca gttctccctg    240
aagctgagct ctgtgaccgc cgcggacacg gccgtgtatt actgtgcgag agagagggca    300
tattgtagta gtaccagctg ctatcgaaat gcttttgata tctggggcca agggaccacg    360
gtcaccgtct cgaga                                                    375

<210> SEQ ID NO 900
<211> LENGTH: 357
<212> TYPE: DNA
<213> ORGANISM: Homo sapiens

<400> SEQUENCE: 900
cagtctgtgt tgacgcagcc gccctcagtg tctggggccc agggcagag ggtcaacatc      60 tcctgcgctg ggagcagctc aacatcgggg gcgggttatg atgttcactg gtaccagcag    120
attccaggaa cagccccca actcctcatg tatggtaata gtaatcggcc ctcaggggtc    180
cctgaccgat tctctggctc caagtctggc gcctcagcct ccctggccat cactaggctc    240
caggctgagg atgaggctga ttattactgc cagtcctatg acagcagcct gagtggttcg    300
agggtcttcg gaactgggac caaggtcacc gtcctaggtc agtccaacgt cctaggt       357

<210> SEQ ID NO 901
<211> LENGTH: 366
<212> TYPE: DNA
<213> ORGANISM: Homo sapiens

<400> SEQUENCE: 901
gaggtgcagc tggtggagtc tgggggaggc gtggtccagc ctgggaggtc cctgagactc     60
tcctgtgcag cctctggatt caccttcagt agctatggca tgcactgggt ccgccaggct    120
ccaggcaagg gctggagtg gtgacagtt atatcatttg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagcgtat    300 accaacaccct ggtggcctga tgcttttgat atctggggcc aagggaccac ggtcaccgtc    360
tcgaga                                                             366

<210> SEQ ID NO 902
<211> LENGTH: 321
<212> TYPE: DNA
<213> ORGANISM: Homo sapiens
```

```
<400> SEQUENCE: 902
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaagatattg caacatatta ctgtcaacag tatgataatc tccctcccac tttcggccct     300
gggaccaaag tggatatcaa a                                               321

<210> SEQ ID NO 903
<211> LENGTH: 354
<212> TYPE: DNA
<213> ORGANISM: Homo sapiens

<400> SEQUENCE: 903
caggtgcagc tgcaggagtc gggcccagga ctggtgaagc cttcggagac cctgtccctc      60
acctgcactg tctctggtag ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agatctgtac     300
tggaacgacg cttttgatat ctggggccaa gggaccacgg tcaccgtctc gaga          354

<210> SEQ ID NO 904
<211> LENGTH: 333
<212> TYPE: DNA
<213> ORGANISM: Homo sapiens

<400> SEQUENCE: 904
cagtctgccc tgactcagcc tctctcagcg tctgggaccc ccgggcagag ggtcaccatc      60
tcttgttctg gaagcagctc caacatcgga agtaatactg taaactggta ccagcagctc     120
ccaggaacgg ccccccaaact cctcatctat agtaataatc agcggccctc aggggtccct     180
gaccgattct ctggctccaa gtctggcacc tcagcctccc tggccatcag tgggctccag     240
tctgaggatg aggctgatta ttactgcgca gcatgggatg acagcctgaa tggtccggta     300
ttcggcggag ggaccaagct gaccgtccta ggt                                  333

<210> SEQ ID NO 905
<211> LENGTH: 354
<212> TYPE: DNA
<213> ORGANISM: Homo sapiens

<400> SEQUENCE: 905
caggtgcagc tgcaggagtc gggcccagga ctggtgaagc cttcggagac cctgtccctc      60
acctgcactg tctctggtag ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agatctgtac     300
tggaacgacg cttttgatat ctggggccaa gggaccacgg tcaccgtctc gaga          354

<210> SEQ ID NO 906
<211> LENGTH: 333
<212> TYPE: DNA
```

```
<213> ORGANISM: Homo sapiens

<400> SEQUENCE: 906
cagtctgtgt tgacgcagcc gccctcagcg tctgggaccc ccgggcagag tgtcaccatc    60
tcttgttctg gaagcagctc caacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggtccggtg   300
ttcggcggag ggaccaagct gaccgtccta ggt                                333

<210> SEQ ID NO 907
<211> LENGTH: 378
<212> TYPE: DNA
<213> ORGANISM: Homo sapiens

<400> SEQUENCE: 907
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacta ctacaggtc caagtggtat    180
aatgattatg cagtatctgt gaaaagtcga ataaccatca cccagacac atccaagaac    240
cagttctccc tgcagctgaa ctctgtgact cccgaggaca cggctgtgta ttactgtgca   300
agagaatcat ggctttgggg gattgggggg gatgcttttg atatctgggg ccaagggacc   360
acggtcaccg tctcgaga                                                 378

<210> SEQ ID NO 908
<211> LENGTH: 333
<212> TYPE: DNA
<213> ORGANISM: Homo sapiens

<400> SEQUENCE: 908
cagtctgtgt tgacgcagcc gccctcggtg tctggggccc ccggcagac ggtcaccatc    60
tcctgctctg ggagcagctc caacatcgga caaaattctg ttacctggta ccagcgcctc   120
ccgggtgagg ctcccaaact cctcatctac tatgatgatc tcttgcactc aggagtctct   180
gaccgattct ctggctccaa gtctggcacc tcagcctcac tggccatcag tggactccag   240
tctgaggatg aggctgagta ctactgtgcg tcatgggatg acagcctgaa aggtccggta   300
ttcggcggag ggaccaaact gaccgtccta ggt                                333

<210> SEQ ID NO 909
<211> LENGTH: 336
<212> TYPE: DNA
<213> ORGANISM: Homo sapiens

<400> SEQUENCE: 909
gaggtgcagc tggtggagtc tgggggaggc ttggtccagc ctggggggtc cctgagactc    60
tcctgtgcag cctctggatt caccgtcagt agcaactaca tgagctgggt ccgccaggct   120
ccagggaagg ggctggagtg gtctcagtt atttatagcg gtggtagcac atactacgca   180
gactccgtga aggcagatt caccatctcc agagacaatt ccaagaacac gctgtatctt    240
caaatgaaca gcctgagagc cgaggacacg gctgtgtatt actgtgcgag ggagtttgac   300
tactggggcc agggaaccct ggtcaccgtc tcgaga                             336
```

```
<210> SEQ ID NO 910
<211> LENGTH: 315
<212> TYPE: DNA
<213> ORGANISM: Homo sapiens

<400> SEQUENCE: 910
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaagatatcg caacatatta ctgtcaacag tatgataatc ccgctttcgg cggagggacc     300
aaggtggaga tcaaa                                                      315

<210> SEQ ID NO 911
<211> LENGTH: 363
<212> TYPE: DNA
<213> ORGANISM: Homo sapiens

<400> SEQUENCE: 911
caggtgcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagatcgt     300
tactatggtt cggggttcgg tatggacgtc tggggccaag ggacaatggt caccgtctcg     360
aga                                                                   363

<210> SEQ ID NO 912
<211> LENGTH: 327
<212> TYPE: DNA
<213> ORGANISM: Homo sapiens

<400> SEQUENCE: 912
tcttctgagc tgactcagga ccctgctatg tctgtggcct tgggacagac agtcaaaatc      60
acttgccaag agacagcct cacaaactat tatccaagtt ggtatcagca gaagccagga     120
caggcccctg tccttgtcat gtatggaaaa gacagccggc cctcagggat ctcagaccga     180
ttctctggct ccagctcagg aatctcagct tccttgacca tcactggggc tcaggcggaa     240
gatgaggctg actactactg taactcccga gacggcagtg ctcaccgtct ggttttcggc     300
ggagggacca agttgaccgt cctgggt                                         327

<210> SEQ ID NO 913
<211> LENGTH: 372
<212> TYPE: DNA
<213> ORGANISM: Homo sapiens

<400> SEQUENCE: 913
caggtgcagc tggtgcagtc tggagctgag gtgaagaagc ctggggcctc agtgaaggtc      60
tcctgcaagg cttctggtta cacctttacc aactatggtc tcacctgggt gcgacaggcc     120
cctggacaag gcttgagtg gatgggatgg atcagcactt acaatagtaa cacaaactat     180
gcagagaagc tccagggcag agtcaccatg accacagaca catccacgag cacagcctac     240
atggagttga ggagcctgac atctgacgac acggccgtgt attactgtgc gagaggcccc     300
```

```
acatattcct ttgatagtag tggttatttt tttgactact ggggccaggg aaccctggtc    360
accgtctcga ga                                                        372

<210> SEQ ID NO 914
<211> LENGTH: 327
<212> TYPE: DNA
<213> ORGANISM: Homo sapiens

<400> SEQUENCE: 914
tcttctgagc tgactcagga ccctgctgtg tctgtggcct tgggacagac agtcaggatc     60
acatgccaag gagacagcct cagaagctat tatgcaagct ggtaccagca gaagccagga   120
caggcccctg tacttgtcat ctatggtaaa acaaccggc cctcagggat cccagaccga    180
ttctctggct ccagctcagg aaacacagct tccttgacca tcactggggc tcaggcggaa   240
gatgaggctg actattactg taactcccgg gacagcagtg gtaaccattg ggtgttcggc   300
ggagggacca agctgaccgt cctaggt                                       327

<210> SEQ ID NO 915
<211> LENGTH: 360
<212> TYPE: DNA
<213> ORGANISM: Homo sapiens

<400> SEQUENCE: 915
caggtgcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac   240
atggagctga ggagcctgag atctgacgac acggccgtgt attactgtgc gagagatacg   300
tatagcagtg gctggtactt tgactactgg ggccagggca cctggtcac cgtctcgaga    360

<210> SEQ ID NO 916
<211> LENGTH: 330
<212> TYPE: DNA
<213> ORGANISM: Homo sapiens

<400> SEQUENCE: 916
tcttctgagc tgactcagga ccctgctgtg tctgtggcct tgggacagac agtcaggatc     60
acatgccaag gagacagcct cagaaactat tatgcaagct ggtaccagca gaagccagga   120
caggcccctg tacttgtcat ctatggtaaa acaaccggc cctcagggat cccagaccga    180
ttctctggct ccagctcagg aaacacagct tccttgacca tcactggggc tcaggcggaa   240
gatgaggctg actattactg taactcccga gacagcagtg gtaaccatct ttatgtcttc   300
ggaactggga ccaaggtcac cgtcctaggt                                    330

<210> SEQ ID NO 917
<211> LENGTH: 360
<212> TYPE: DNA
<213> ORGANISM: Homo sapiens

<400> SEQUENCE: 917
caggtgcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac   240
```

```
atggagctga gcagcctgag atctgaggac acggccgtgt attactgtgc aacccttaac    300
attagtggga gctactactt tgactactgg ggccagggaa ccctggtcac cgtctcgaga    360

<210> SEQ ID NO 918
<211> LENGTH: 344
<212> TYPE: DNA
<213> ORGANISM: Homo sapiens

<400> SEQUENCE: 918
tcttctgagc tgactcagga ccctgctgtg tctgtggcct tgggacagac agtcaggatc     60
acatgccaag gagacagcct cagaagctat tatgcaacct ggtaccagca gaagccagga    120
caggcccctg tacttgtcat ctctggtaaa aacaaccggc cctcagggat cccagaccga    180
ttctctggct ccagctcagg aaacacagct tccttgacca tcactggggc tcaggcggaa    240
gatgaggctg actattactg taactcccgg gacagcagtg gttacccctc ttgggtgttc    300
ggcggaggga ccaagctgac cggaccaagc tgaccgtcct aggt                    344

<210> SEQ ID NO 919
<211> LENGTH: 354
<212> TYPE: DNA
<213> ORGANISM: Homo sapiens

<400> SEQUENCE: 919
caggtgcagc tggtgcagtc tgaagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagaacgatc    300
gggcttggtg cttttgatat ctggggccaa gggaccacgg tcaccgtctc gaga         354

<210> SEQ ID NO 920
<211> LENGTH: 330
<212> TYPE: DNA
<213> ORGANISM: Homo sapiens

<400> SEQUENCE: 920
tcttctgagc tgactcagga ccctgctgtg tctgtggcct tgggacagac agtcaggatc     60
acatgccaag gagacagcct cagaagctat tatgcaagct ggtaccagca gaagccagga    120
caggcccctg tacttgtcat ctatggtaaa aacaaccggc cctcagggat cccagaccga    180
ttctctggct ccagctcagg aaacacagct tccttgacca tcactggggc tcaggcggaa    240
gatgaggctg actattactg taactcccgg gacagcagtg gtaaccatca ttatgtcttc    300
ggaactggga ccaaggtcac cgtcctaggt                                    330

<210> SEQ ID NO 921
<211> LENGTH: 357
<212> TYPE: DNA
<213> ORGANISM: Homo sapiens

<400> SEQUENCE: 921
caggtgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag ggaaggggct ggagtggatt gggagtatct attatagtgg gagcacctac    180
```

```
tacaacccgt ccctcaagag tcgagtcacc atatccgtag acacgtccaa gaaccagttc    240
tccctgaagc tgagctctgt gaccgccgca gacacggctg tgtattactg tgcgagacac    300
tggggaaact atgcttttga tatctggggc caagggacca cggtcaccgt ctcgaga       357
```

<210> SEQ ID NO 922
<211> LENGTH: 333
<212> TYPE: DNA
<213> ORGANISM: Homo sapiens

<400> SEQUENCE: 922

```
cagtctgtgt tgacgcagcc gccctcagcg tctgggaccc ccgggcagag ggtcaccatc    60
tcttgttctg gaagcagctc caacatcgga agtaattatg tatactggta ccaacagctc    120
ccaggaacgg cccccaaact cctcatctat agtaataatc agcggccctc agggtccct    180 gaccgattct ctggctccaa gtctggcacc tcagcctccc tggccatcag tgggctccgg    240
tccgaggatg aggctgatta ttactgtgca gcatgggatg acagcctgag tggtcaagtg    300
ttcggaggag gcacccagct gaccgtcctc ggt                                 333
```

<210> SEQ ID NO 923
<211> LENGTH: 360
<212> TYPE: DNA
<213> ORGANISM: Homo sapiens

<400> SEQUENCE: 923

```
gaggtgcagc tggtggagtc tggagctgag gtgaagaagc ctggggcctc agtgaaggtc    60
tcctgcaagg cttctggtta ccctttacc agctatggta tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagagaag    300
tatagcagtg gctggtactt tgactactgg ggccagggca ccctggtcac cgtctcgaga    360
```

<210> SEQ ID NO 924
<211> LENGTH: 330
<212> TYPE: DNA
<213> ORGANISM: Homo sapiens

<400> SEQUENCE: 924

```
tcttctgagc tgactcagga ccctgctgtg tctgtggcct tgggacagac agtcaggatc    60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactgggc tcaggcggaa    240 gatgaggctg actattactg taactcccgg gacagcagtg gtaaccatca ttatgtcttc    300
ggaactggga ccaaggtcac cgtcctaggt                                    330
```

<210> SEQ ID NO 925
<211> LENGTH: 345
<212> TYPE: DNA
<213> ORGANISM: Homo sapiens

<400> SEQUENCE: 925

```
gaggtgcagc tggtggagtc tgggggaggc ttggtacagc ctgggggtc cctgagactc    60 tcctgtgcag cctctggatt cacctttagc agctatgcca tgagctgggt ccgccaggct    120
ccagggaagg ggctggagtg ggtctcagct attagtggta gtggtggtag cacatactac    180
```

```
gcagactccg tgaagggccg gttcaccatc tccagagaca attccaagaa cacgctgtat    240
ctgcaaataa acagcctgag agccgaggac acggccgtat attactgtgc gaaaggttct    300
atagcagcgg actggggcca gggaaccctg gtcaccgtct cgaga                   345
```

```
<210> SEQ ID NO 926
<211> LENGTH: 324
<212> TYPE: DNA
<213> ORGANISM: Homo sapiens

<400> SEQUENCE: 926
tcttctgagc tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct ccttgacca tcactggggc tcaggcggaa    240
gatgaggctg actattactg taactcccgg gacagcagtg gtaacgtggt attcggcgga    300
gggaccaagc tgaccgtcct aggt                                          324
```

```
<210> SEQ ID NO 927
<211> LENGTH: 345
<212> TYPE: DNA
<213> ORGANISM: Homo sapiens

<400> SEQUENCE: 927
gaggtgcagc tggtggagtc tgggggaggc ttggtacagc ctgggggtc cctgagactc      60 tcctgtgcag cctctggatt cacctttagc agctatgcca tgagctgggt ccgccaggct   120
ccagggaagg ggctgagtg gtctcagct attagtggta gtggtggtag cacatactac    180
gcagactccg tgaagggccg gttcaccatc tccagagaca attccaagaa ctcactgtat    240
ctgcaaatga acagcctgag agccgaggac acgctgtgt attactgtgc gagtgagcag    300
gctggggact actggggcca gggaaccctg gtcaccgtct cgaga                   345
```

```
<210> SEQ ID NO 928
<211> LENGTH: 333
<212> TYPE: DNA
<213> ORGANISM: Homo sapiens

<400> SEQUENCE: 928
cagtctgtgt tgacgcagcc gccctcagcg tctgggaccc ccgggcagag ggtcaccatc     60
tcttgttctg gaagcagctc caacatcgga agtaattatg tatactggta ccagcagctc   120
ccaggaacgg cccccaaact cctcatctat aggaataatc agcggccctc agggtccct    180 gaccgattcg ctggctccaa gtctggcacg tcagccaccc tggcatcac cggactccag    240 actggggacg aggccgatta ttactgcgga acatgggata gcagcctgag tgctggggta    300
ttcggcggag ggaccaagct gaccgtccta ggt                                333
```

```
<210> SEQ ID NO 929
<211> LENGTH: 357
<212> TYPE: DNA
<213> ORGANISM: Homo sapiens

<400> SEQUENCE: 929
caggtgcagc tggtgcagtc tggggctgag gtgaagaagc ctggggcctc agtgaaggtt     60
tcctgcaagg catctggata caccttcacc agctactata tgcactgggt gcgacaggcc   120
```

```
cctggacaag ggcttgagtg gatgggaata atcaacccta gtggtggtag cacaagctac      180
gcacagaagt tccagggcag agtcaccatg accagggaca cgtccacgag cacagtctac      240
atggagctga gcagcctgag atctgaggac acggccgtgt attactgtgc gagagaattg      300
tcggctgcta ctgcttttga tatctggggc caagggacaa tggtcaccgt ctcgaga         357
```

<210> SEQ ID NO 930
<211> LENGTH: 321
<212> TYPE: DNA
<213> ORGANISM: Homo sapiens

<400> SEQUENCE: 930

```
gaaacgacac tcacgcagtc tccatttcct gtgtctgcat ctgtaggaga cagagtcacc      60
atcacttgtc gggcgagtca gtatattagc agatggctag cctggtatca gcagagacca     120
gggaaagccc ctaagctcct gatctatgct gcagccagtt tgcaaagtgg ggtcccatca     180
aggttcagcg gcagtggatc tgggacagat ttcactctca ctatcagcag cctgcaacct    240
gaagattttg caacttacta ttgccaacag gctaacagtt tccccgtcac cttcggccaa    300
gggacacgac tggagattaa a                                               321
```

<210> SEQ ID NO 931
<211> LENGTH: 360
<212> TYPE: DNA
<213> ORGANISM: Homo sapiens

<400> SEQUENCE: 931

```
caggtgcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagtaggt    300
tattactact actacggtat ggacgtctgg ggccaaggga ccacggtcac cgtctcgaga    360
```

<210> SEQ ID NO 932
<211> LENGTH: 333
<212> TYPE: DNA
<213> ORGANISM: Homo sapiens

<400> SEQUENCE: 932

```
cagtctgccc tgactcagcc tgcctccgtg tctgggtctc ctggacagtc gatcaccatc      60
tcctgcactg gaaccagcag tgatgttggg agttataacc ttgtctcctg gtaccaacag    120
cacccaggca aagcccccaa actcatgatt tatgagggca gtaagcggcc ctcagggggtt   180 tctaatcgct tctctggctc caagtctggc aacacggcct ccctgaccat ctctgggctc    240
caggctgagg acgaggctga ttattactgc agctcatata caagcagcag cacttgggtg    300
ttcggcggag ggaccaagct gaccgtccta ggt                                  333
```

<210> SEQ ID NO 933
<211> LENGTH: 354
<212> TYPE: DNA
<213> ORGANISM: Homo sapiens

<400> SEQUENCE: 933

```
caggtgcagc tggtgcagtc tggggctgag gtgaagaagc ctgggtcctc ggtgaaggtc      60
tcctgcaagg cttctggagg cacctttcagc agctatgcta tcagctgggt gcgacaggcc   120
```

```
cctggacaag ggcttgagtg gatgggatgg atgaaccota acagtggtaa cacaggctat    180
gcacagaagt tccagggcag agtcaccatg accaggaaca cctccataag cacagcctac    240
atggagctga gcagcctgag atctgaggac acggccgtgt attactgtgc gagagacgtt    300
gggattgggg tctttgacta ctggggccag ggaaccctgg tcaccgtctc gaga           354
```

<210> SEQ ID NO 934
<211> LENGTH: 327
<212> TYPE: DNA
<213> ORGANISM: Homo sapiens

<400> SEQUENCE: 934

```
tcctatgtgc tgactcagcc accctcagtg tcagtggccc caggaaagac ggccaggatt     60
acctgtgggg gaaacaacat tggaagtaaa agtgtgcact ggtaccagca gaagccaggc    120
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt cctaggt                                        327
```

<210> SEQ ID NO 935
<211> LENGTH: 363
<212> TYPE: DNA
<213> ORGANISM: Homo sapiens

<400> SEQUENCE: 935

```
gaggtgcagc tggtggagtc tgggggaggc ttggtacagc ctggggggtc cctgagactc     60
tcctgtgcag cctctggatt cacctttagc gactatgcca tgaactgggt ccgccaggct    120
ccagggaagg ggctggagtg ggtctcagct actagtggta gtggaggcag cacattctac    180
gcagactccg tgaagggccg gttcaccatc tccagagaca attccaagag tacgttgtat    240
ctgcaaatga acagcctgag agacgaggac acggccgtgt attactgtgc gaaagggacc    300
ttaccgcatt actatgatag tagtggtata gggggccagg gcaccctggt caccgtctcg    360
agc                                                                  363
```

<210> SEQ ID NO 936
<211> LENGTH: 339
<212> TYPE: DNA
<213> ORGANISM: Homo sapiens

<400> SEQUENCE: 936

```
caggctgtgc tcactcagcc gtcttccgtg tctgggtctc ctggacagtc gatcaccatc     60
tcctgcactg gaaccagcag tgacgttggt ggttataact atgtctcctg gtaccaacag    120
cacccaggca aagcccccaa actcatgatt tatgatgtcg gtaagcggcc ctcagggatt    180
tctaatcgct tctctggctc caagtctggc aacacggcct ccctgaccat ctctgggctc    240
cgggctgagg acgaggctaa ttattactgc agctcatata caagcagcag cacttggttt    300
gtggtattcg gcggagggac caagctgacc gtcctaggt                           339
```

<210> SEQ ID NO 937
<211> LENGTH: 363
<212> TYPE: DNA
<213> ORGANISM: Homo sapiens

<400> SEQUENCE: 937

```
caggtacagc tgcagcagtc aggggctgag gtgaagaagc ctggggcctc agtgaaggtt      60
tcctgcaagg catctggata caccttcacc acctactata tgcactgggt gcgacaggcc     120
cctggacaag ggcttgagtg gatgggaata atcaatccta gtggtgaaaa tacaaactac     180
gcacagaagt tccagggcag agtcaccatg accaggaca catccacgac cacagtctac     240
atggagctga gcagcctgag atctgaggac acggccgtgt attactgtgc gagatctttc     300
ataggaactc gtggggcgg tttggacgtc tggggccaag ggaccacggt caccgtctcg     360
aga                                                                   363

<210> SEQ ID NO 938
<211> LENGTH: 339
<212> TYPE: DNA
<213> ORGANISM: Homo sapiens

<400> SEQUENCE: 938
cagtctgtgt tgacgcagcc gccctcagtg tctggggccc cagggcagag ggtcaacatc      60
tcctgcgctg ggagcagctc caacatcggg gcgggttatg atgttcactg gtaccagcag     120
attccaggaa cagcccccaa actcctcatg tatggtaata gtaatcggcc ctcaggggtc     180
cctgaccgat tctctggctc caagtctggc gcctcagcct ccctggccat cactaggctc     240
caggctgagg atgaggctga ttattactgc cagtcctatg acagcagcct gagtggttcg     300
agggtcttcg gaactgggac caaggtcacc gtcctaggt                           339

<210> SEQ ID NO 939
<211> LENGTH: 351
<212> TYPE: DNA
<213> ORGANISM: Homo sapiens

<400> SEQUENCE: 939
gaggtgcagc tggtggagtc tgggggaggc gtggtccagc ctgggaggtc cctgagactc      60
tcctgtgcag cctctggatt caccttgat gattatgcca tgcactgggt ccggcaagct     120
ccggggaagg gcctggagtg ggtctcaggt attagttgga atagtggtag cataggctat     180
gcggactctg tgaagggccg attcaccatc tccagagaca cgccaagaa ctccctgtat     240 ctgcaaatga acagtctgag agctgaggac acggctgtgt attactgtgc gacggaagaa     300
tggtggcgct tcgatctctg gggccgtggc accctggtca ccgtctcgag a             351

<210> SEQ ID NO 940
<211> LENGTH: 333
<212> TYPE: DNA
<213> ORGANISM: Homo sapiens

<400> SEQUENCE: 940
cagtctgccc tgactcagcc tccctccgcg tccgggtctc ctggacagtc agtcaccatc      60
tcctgcactg gaaccagcag tgacgttgat gattacaact atgtctcctg gtaccaacag     120
cacccaggca aagcccccaa actcatgatt tatgaggtca ctaagcggcc ctcaggggtc     180
cctgatcgct tctctggctc caagtctggc aacacggcct ccctgaccat ctctgggctc     240
caggctgagg atgaggctga ttattactgc agctcatatg tgggcagcga caatagagtc     300
ttcggaactg ggaccaaggt caccgtccca ggt                                  333

<210> SEQ ID NO 941
<211> LENGTH: 1897
<212> TYPE: PRT
<213> ORGANISM: Homo sapiens
```

<400> SEQUENCE: 941

Met Val Pro Leu Val Pro Ala Leu Val Met Leu Gly Leu Val Ala Gly
1               5                   10                  15

Ala His Gly Asp Ser Lys Pro Val Phe Ile Lys Val Pro Glu Asp Gln
            20                  25                  30

Thr Gly Leu Ser Gly Gly Val Ala Ser Phe Val Cys Gln Ala Thr Gly
        35                  40                  45

Glu Pro Lys Pro Arg Ile Thr Trp Met Lys Lys Gly Lys Lys Val Ser
50                  55                  60

Ser Gln Arg Phe Glu Val Ile Glu Phe Asp Asp Gly Ala Gly Ser Val
65                  70                  75                  80

Leu Arg Ile Gln Pro Leu Arg Val Gln Arg Asp Glu Ala Ile Tyr Glu
                85                  90                  95

Cys Thr Ala Thr Asn Ser Leu Gly Glu Ile Asn Thr Ser Ala Lys Leu
            100                 105                 110

Ser Val Leu Glu Glu Gln Leu Pro Pro Gly Phe Pro Ser Ile Asp
        115                 120                 125

Met Gly Pro Gln Leu Lys Val Val Glu Lys Ala Arg Thr Ala Thr Met
130                 135                 140

Leu Cys Ala Ala Gly Gly Asn Pro Asp Pro Glu Ile Ser Trp Phe Lys
145                 150                 155                 160

Asp Phe Leu Pro Val Asp Pro Ala Thr Ser Asn Gly Arg Ile Lys Gln
                165                 170                 175

Leu Arg Ser Gly Ala Leu Gln Ile Glu Ser Ser Glu Ser Asp Gln
            180                 185                 190

Gly Lys Tyr Glu Cys Val Ala Thr Asn Ser Ala Gly Thr Arg Tyr Ser
        195                 200                 205

Ala Pro Ala Asn Leu Tyr Val Arg Val Arg Arg Val Ala Pro Arg Phe
210                 215                 220

Ser Ile Pro Pro Ser Ser Gln Glu Val Met Pro Gly Gly Ser Val Asn
225                 230                 235                 240

Leu Thr Cys Val Ala Val Gly Ala Pro Met Pro Tyr Val Lys Trp Met
                245                 250                 255

Met Gly Ala Glu Glu Leu Thr Lys Glu Asp Glu Met Pro Val Gly Arg
            260                 265                 270

Asn Val Leu Glu Leu Ser Asn Val Arg Ser Ala Asn Tyr Thr Cys
        275                 280                 285

Val Ala Ile Ser Ser Leu Gly Met Ile Glu Ala Thr Ala Gln Val Thr
290                 295                 300

Val Lys Ala Leu Pro Lys Pro Ile Asp Leu Val Val Thr Glu Thr
305                 310                 315                 320

Thr Ala Thr Ser Val Thr Leu Thr Trp Asp Ser Gly Asn Ser Glu Pro
                325                 330                 335

Val Thr Tyr Tyr Gly Ile Gln Tyr Arg Ala Ala Gly Thr Glu Gly Pro
            340                 345                 350

Phe Gln Glu Val Asp Gly Val Ala Thr Thr Arg Tyr Ser Ile Gly Gly
        355                 360                 365

Leu Ser Pro Phe Ser Glu Tyr Ala Phe Arg Val Leu Ala Val Asn Ser
        370                 375                 380

Ile Gly Arg Gly Pro Pro Ser Glu Ala Val Arg Ala Arg Thr Gly Glu
385                 390                 395                 400

Gln Ala Pro Ser Ser Pro Pro Arg Arg Val Gln Ala Arg Met Leu Ser

```
                  405                 410                 415
Ala Ser Thr Met Leu Val Gln Trp Glu Pro Pro Glu Pro Asn Gly
            420                 425                 430

Leu Val Arg Gly Tyr Arg Val Tyr Tyr Thr Pro Asp Ser Arg Arg Pro
            435                 440                 445

Pro Asn Ala Trp His Lys His Asn Thr Asp Ala Gly Leu Leu Thr Thr
450                 455                 460

Val Gly Ser Leu Leu Pro Gly Ile Thr Tyr Ser Leu Arg Val Leu Ala
465                 470                 475                 480

Phe Thr Ala Val Gly Asp Gly Pro Pro Ser Pro Thr Ile Gln Val Lys
            485                 490                 495

Thr Gln Gln Gly Val Pro Ala Gln Pro Ala Asp Phe Gln Ala Glu Val
            500                 505                 510

Glu Ser Asp Thr Arg Ile Gln Leu Ser Trp Leu Leu Pro Pro Gln Glu
            515                 520                 525

Arg Ile Ile Met Tyr Glu Leu Val Tyr Trp Ala Ala Glu Asp Glu Asp
            530                 535                 540

Gln Gln His Lys Val Thr Phe Asp Pro Thr Ser Ser Tyr Thr Leu Glu
545                 550                 555                 560

Asp Leu Lys Pro Asp Thr Leu Tyr Arg Phe Gln Leu Ala Ala Arg Ser
            565                 570                 575

Asp Met Gly Val Gly Val Phe Thr Pro Thr Ile Glu Ala Arg Thr Ala
            580                 585                 590

Gln Ser Thr Pro Ser Ala Pro Pro Gln Lys Val Met Cys Val Ser Met
            595                 600                 605

Gly Ser Thr Thr Val Arg Val Ser Trp Val Pro Pro Pro Ala Asp Ser
            610                 615                 620

Arg Asn Gly Val Ile Thr Gln Tyr Ser Val Ala His Glu Ala Val Asp
625                 630                 635                 640

Gly Glu Asp Arg Gly Arg His Val Val Asp Gly Ile Ser Arg Glu His
            645                 650                 655

Ser Ser Trp Asp Leu Val Gly Leu Glu Lys Trp Thr Glu Tyr Arg Val
            660                 665                 670

Trp Val Arg Ala His Thr Asp Val Gly Pro Gly Pro Glu Ser Ser Pro
            675                 680                 685

Val Leu Val Arg Thr Asp Glu Asp Val Pro Ser Gly Pro Pro Arg Lys
            690                 695                 700

Val Glu Val Glu Pro Leu Asn Ser Thr Ala Val His Val Tyr Trp Lys
705                 710                 715                 720

Leu Pro Val Pro Ser Lys Gln His Gly Gln Ile Arg Gly Tyr Gln Val
            725                 730                 735

Thr Tyr Val Arg Leu Glu Asn Gly Glu Pro Arg Gly Leu Pro Ile Ile
            740                 745                 750

Gln Asp Val Met Leu Ala Glu Ala Gln Trp Arg Pro Glu Glu Ser Glu
            755                 760                 765

Asp Tyr Glu Thr Thr Ile Ser Gly Leu Thr Pro Glu Thr Thr Tyr Ser
            770                 775                 780

Val Thr Val Ala Ala Tyr Thr Thr Lys Gly Asp Gly Ala Arg Ser Lys
785                 790                 795                 800

Pro Lys Ile Val Thr Thr Thr Gly Ala Val Pro Gly Arg Pro Thr Met
            805                 810                 815

Met Ile Ser Thr Thr Ala Met Asn Thr Ala Leu Leu Gln Trp His Pro
            820                 825                 830
```

-continued

```
Pro Lys Glu Leu Pro Gly Glu Leu Gly Tyr Arg Leu Gln Tyr Cys
        835                 840                 845

Arg Ala Asp Glu Ala Arg Pro Asn Thr Ile Asp Phe Gly Lys Asp Asp
    850                 855                 860

Gln His Phe Thr Val Thr Gly Leu His Lys Gly Thr Thr Tyr Ile Phe
865                 870                 875                 880

Arg Leu Ala Ala Lys Asn Arg Ala Gly Leu Gly Glu Glu Phe Glu Lys
                885                 890                 895

Glu Ile Arg Thr Pro Glu Asp Leu Pro Ser Gly Phe Pro Gln Asn Leu
            900                 905                 910

His Val Thr Gly Leu Thr Thr Ser Thr Thr Glu Leu Ala Trp Asp Pro
        915                 920                 925

Pro Val Leu Ala Glu Arg Asn Gly Arg Ile Ile Ser Tyr Thr Val Val
    930                 935                 940

Phe Arg Asp Ile Asn Ser Gln Gln Glu Leu Gln Asn Ile Thr Thr Asp
945                 950                 955                 960

Thr Arg Phe Thr Leu Thr Gly Leu Lys Pro Asp Thr Thr Tyr Asp Ile
                965                 970                 975

Lys Val Arg Ala Trp Thr Ser Lys Gly Ser Gly Pro Leu Ser Pro Ser
            980                 985                 990

Ile Gln Ser Arg Thr Met Pro Val Glu Gln Val Phe Ala Lys Asn Phe
        995                 1000                1005

Arg Val Ala Ala Ala Met Lys Thr Ser Val Leu Leu Ser Trp Glu
    1010                1015                1020

Val Pro Asp Ser Tyr Lys Ser Ala Val Pro Phe Lys Ile Leu Tyr
    1025                1030                1035

Asn Gly Gln Ser Val Glu Val Asp Gly His Ser Met Arg Lys Leu
    1040                1045                1050

Ile Ala Asp Leu Gln Pro Asn Thr Glu Tyr Ser Phe Val Leu Met
    1055                1060                1065

Asn Arg Gly Ser Ser Ala Gly Gly Leu Gln His Leu Val Ser Ile
    1070                1075                1080

Arg Thr Ala Pro Asp Leu Leu Pro His Lys Pro Leu Pro Ala Ser
    1085                1090                1095

Ala Tyr Ile Glu Asp Gly Arg Phe Asp Leu Ser Met Pro His Val
    1100                1105                1110

Gln Asp Pro Ser Leu Val Arg Trp Phe Tyr Ile Val Val Val Pro
    1115                1120                1125

Ile Asp Arg Val Gly Gly Ser Met Leu Thr Pro Arg Trp Ser Thr
    1130                1135                1140

Pro Glu Glu Leu Glu Leu Asp Glu Leu Leu Glu Ala Ile Glu Gln
    1145                1150                1155

Gly Gly Glu Glu Gln Arg Arg Arg Arg Gln Ala Glu Arg Leu
    1160                1165                1170

Lys Pro Tyr Val Ala Ala Gln Leu Asp Val Leu Pro Glu Thr Phe
    1175                1180                1185

Thr Leu Gly Asp Lys Lys Asn Tyr Arg Gly Phe Tyr Asn Arg Pro
    1190                1195                1200

Leu Ser Pro Asp Leu Ser Tyr Gln Cys Phe Val Leu Ala Ser Leu
    1205                1210                1215

Lys Glu Pro Met Asp Gln Lys Arg Tyr Ala Ser Ser Pro Tyr Ser
    1220                1225                1230
```

```
Asp Glu Ile Val Val Gln Val Thr Pro Ala Gln Gln Gln Glu Glu
    1235                1240                1245

Pro Glu Met Leu Trp Val Thr Gly Pro Val Leu Ala Val Ile Leu
    1250                1255                1260

Ile Ile Leu Ile Val Ile Ala Ile Leu Leu Phe Lys Arg Lys Arg
    1265                1270                1275

Thr His Ser Pro Ser Ser Lys Asp Gln Ser Ile Gly Leu Lys
    1280                1285                1290

Asp Ser Leu Leu Ala His Ser Ser Asp Pro Val Glu Met Arg Arg
    1295                1300                1305

Leu Asn Tyr Gln Thr Pro Gly Met Arg Asp His Pro Pro Ile Pro
    1310                1315                1320

Ile Thr Asp Leu Ala Asp Asn Ile Glu Arg Leu Lys Ala Asn Asp
    1325                1330                1335

Gly Leu Lys Phe Ser Gln Glu Tyr Glu Ser Ile Asp Pro Gly Gln
    1340                1345                1350

Gln Phe Thr Trp Glu Asn Ser Asn Leu Glu Val Asn Lys Pro Lys
    1355                1360                1365

Asn Arg Tyr Ala Asn Val Ile Ala Tyr Asp His Ser Arg Val Ile
    1370                1375                1380

Leu Thr Ser Ile Asp Gly Val Pro Gly Ser Asp Tyr Ile Asn Ala
    1385                1390                1395

Asn Tyr Ile Asp Gly Tyr Arg Lys Gln Asn Ala Tyr Ile Ala Thr
    1400                1405                1410

Gln Gly Pro Leu Pro Glu Thr Met Gly Asp Phe Trp Arg Met Val
    1415                1420                1425

Trp Glu Gln Arg Thr Ala Thr Val Val Met Met Thr Arg Leu Glu
    1430                1435                1440

Glu Lys Ser Arg Val Lys Cys Asp Gln Tyr Trp Pro Ala Arg Gly
    1445                1450                1455

Thr Glu Thr Cys Gly Leu Ile Gln Val Thr Leu Leu Asp Thr Val
    1460                1465                1470

Glu Leu Ala Thr Tyr Thr Val Arg Thr Phe Ala Leu His Lys Ser
    1475                1480                1485

Gly Ser Ser Glu Lys Arg Glu Leu Arg Gln Phe Gln Phe Met Ala
    1490                1495                1500

Trp Pro Asp His Gly Val Pro Glu Tyr Pro Thr Pro Ile Leu Ala
    1505                1510                1515

Phe Leu Arg Arg Val Lys Ala Cys Asn Pro Leu Asp Ala Gly Pro
    1520                1525                1530

Met Val Val His Cys Ser Ala Gly Val Gly Arg Thr Gly Cys Phe
    1535                1540                1545

Ile Val Ile Asp Ala Met Leu Glu Arg Met Lys His Glu Lys Thr
    1550                1555                1560

Val Asp Ile Tyr Gly His Val Thr Cys Met Arg Ser Gln Arg Asn
    1565                1570                1575

Tyr Met Val Gln Thr Glu Asp Gln Tyr Val Phe Ile His Glu Ala
    1580                1585                1590

Leu Leu Glu Ala Ala Thr Cys Gly His Thr Glu Val Pro Ala Arg
    1595                1600                1605

Asn Leu Tyr Ala His Ile Gln Lys Leu Gly Gln Val Pro Pro Gly
    1610                1615                1620

Glu Ser Val Thr Ala Met Glu Leu Glu Phe Lys Leu Leu Ala Ser
```

```
                1625                1630                1635

Ser Lys Ala His Thr Ser Arg Phe Ile Ser Ala Asn Leu Pro Cys
    1640                1645                1650

Asn Lys Phe Lys Asn Arg Leu Val Asn Ile Met Pro Tyr Glu Leu
    1655                1660                1665

Thr Arg Val Cys Leu Gln Pro Ile Arg Gly Val Glu Gly Ser Asp
    1670                1675                1680

Tyr Ile Asn Ala Ser Phe Leu Asp Gly Tyr Arg Gln Gln Lys Ala
    1685                1690                1695

Tyr Ile Ala Thr Gln Gly Pro Leu Ala Glu Ser Thr Glu Asp Phe
    1700                1705                1710

Trp Arg Met Leu Trp Glu His Asn Ser Thr Ile Ile Val Met Leu
    1715                1720                1725

Thr Lys Leu Arg Glu Met Gly Arg Glu Lys Cys His Gln Tyr Trp
    1730                1735                1740

Pro Ala Glu Arg Ser Ala Arg Tyr Gln Tyr Phe Val Val Asp Pro
    1745                1750                1755

Met Ala Glu Tyr Asn Met Pro Gln Tyr Ile Leu Arg Glu Phe Lys
    1760                1765                1770

Val Thr Asp Ala Arg Asp Gly Gln Ser Arg Thr Ile Arg Gln Phe
    1775                1780                1785

Gln Phe Thr Asp Trp Pro Glu Gln Gly Val Pro Lys Thr Gly Glu
    1790                1795                1800

Gly Phe Ile Asp Phe Ile Gly Gln Val His Lys Thr Lys Glu Gln
    1805                1810                1815

Phe Gly Gln Asp Gly Pro Ile Thr Val His Cys Ser Ala Gly Val
    1820                1825                1830

Gly Arg Thr Gly Val Phe Ile Thr Leu Ser Ile Val Leu Glu Arg
    1835                1840                1845

Met Arg Tyr Glu Gly Val Val Asp Met Phe Gln Thr Val Lys Thr
    1850                1855                1860

Leu Arg Thr Gln Arg Pro Ala Met Val Gln Thr Glu Asp Gln Tyr
    1865                1870                1875

Gln Leu Cys Tyr Arg Ala Ala Leu Glu Tyr Leu Gly Ser Phe Asp
    1880                1885                1890

His Tyr Ala Thr
    1895

<210> SEQ ID NO 942
<211> LENGTH: 628
<212> TYPE: PRT
<213> ORGANISM: Homo sapiens

<400> SEQUENCE: 942

Met Glu Pro Pro Asp Ala Pro Ala Gln Ala Arg Gly Ala Pro Arg Leu
1               5                   10                  15

Leu Leu Leu Ala Val Leu Leu Ala Ala His Pro Asp Ala Gln Ala Glu
                20                  25                  30

Val Arg Leu Ser Val Pro Pro Leu Val Glu Val Met Arg Gly Lys Ser
            35                  40                  45

Val Ile Leu Asp Cys Thr Pro Thr Gly Thr His Asp His Tyr Met Leu
        50                  55                  60

Glu Trp Phe Leu Thr Asp Arg Ser Gly Ala Arg Pro Arg Leu Ala Ser
65                  70                  75                  80
```

-continued

```
Ala Glu Met Gln Gly Ser Glu Leu Gln Val Thr Met His Asp Thr Arg
                85                  90                  95
Gly Arg Ser Pro Pro Tyr Gln Leu Asp Ser Gln Gly Arg Leu Val Leu
            100                 105                 110
Ala Glu Ala Gln Val Gly Asp Glu Arg Asp Tyr Val Cys Val Val Arg
        115                 120                 125
Ala Gly Ala Ala Gly Thr Ala Glu Ala Thr Ala Arg Leu Asn Val Phe
    130                 135                 140
Ala Lys Pro Glu Ala Thr Glu Val Ser Pro Asn Lys Gly Thr Leu Ser
145                 150                 155                 160
Val Met Glu Asp Ser Ala Gln Glu Ile Ala Thr Cys Asn Ser Arg Asn
                165                 170                 175
Gly Asn Pro Ala Pro Lys Ile Thr Trp Tyr Arg Asn Gly Gln Arg Leu
            180                 185                 190
Glu Val Pro Val Glu Met Asn Pro Glu Gly Tyr Met Thr Ser Arg Thr
        195                 200                 205
Val Arg Glu Ala Ser Gly Leu Leu Ser Leu Thr Ser Thr Leu Tyr Leu
    210                 215                 220
Arg Leu Arg Lys Asp Asp Arg Asp Ala Ser Phe His Cys Ala Ala His
225                 230                 235                 240
Tyr Ser Leu Pro Glu Gly Arg His Gly Arg Leu Asp Ser Pro Thr Phe
                245                 250                 255
His Leu Thr Leu His Tyr Pro Thr Glu His Val Gln Phe Trp Val Gly
            260                 265                 270
Ser Pro Ser Thr Pro Ala Gly Trp Val Arg Glu Gly Asp Thr Val Gln
        275                 280                 285
Leu Leu Cys Arg Gly Asp Gly Ser Pro Ser Pro Glu Tyr Thr Leu Phe
    290                 295                 300
Arg Leu Gln Asp Glu Gln Glu Val Leu Asn Val Asn Leu Glu Gly
305                 310                 315                 320
Asn Leu Thr Leu Glu Gly Val Thr Arg Gly Gln Ser Gly Thr Tyr Gly
                325                 330                 335
Cys Arg Val Glu Asp Tyr Asp Ala Ala Asp Asp Val Gln Leu Ser Lys
            340                 345                 350
Thr Leu Glu Leu Arg Val Ala Tyr Leu Asp Pro Leu Glu Leu Ser Glu
        355                 360                 365
Gly Lys Val Leu Ser Leu Pro Leu Asn Ser Ser Ala Val Val Asn Cys
    370                 375                 380
Ser Val His Gly Leu Pro Thr Pro Ala Leu Arg Trp Thr Lys Asp Ser
385                 390                 395                 400
Thr Pro Leu Gly Asp Gly Pro Met Leu Ser Leu Ser Ser Ile Thr Phe
                405                 410                 415
Asp Ser Asn Gly Thr Tyr Val Cys Glu Ala Ser Leu Pro Thr Val Pro
            420                 425                 430
Val Leu Ser Arg Thr Gln Asn Phe Thr Leu Leu Val Gln Gly Ser Pro
        435                 440                 445
Glu Leu Lys Thr Ala Glu Ile Glu Pro Lys Ala Asp Gly Ser Trp Arg
    450                 455                 460
Glu Gly Asp Glu Val Thr Leu Ile Cys Ser Ala Arg Gly His Pro Asp
465                 470                 475                 480
Pro Lys Leu Ser Trp Ser Gln Leu Gly Gly Ser Pro Ala Glu Pro Ile
                485                 490                 495
Pro Gly Arg Gln Gly Trp Val Ser Ser Ser Leu Thr Leu Lys Val Thr
```

```
                  500                 505                 510
Ser Ala Leu Ser Arg Asp Gly Ile Ser Cys Glu Ala Ser Asn Pro His
            515                 520                 525

Gly Asn Lys Arg His Val Phe His Phe Gly Thr Val Ser Pro Gln Thr
        530                 535                 540

Ser Gln Ala Gly Val Ala Val Met Ala Val Ala Val Ser Val Gly Leu
545                 550                 555                 560

Leu Leu Leu Val Val Ala Val Phe Tyr Cys Val Arg Arg Lys Gly Gly
                565                 570                 575

Pro Cys Cys Arg Gln Arg Arg Glu Lys Gly Ala Pro Pro Gly Glu
            580                 585                 590

Pro Gly Leu Ser His Ser Gly Ser Glu Gln Pro Glu Gln Thr Gly Leu
        595                 600                 605

Leu Met Gly Gly Ala Ser Gly Gly Ala Arg Gly Gly Ser Gly Gly Phe
    610                 615                 620

Gly Asp Glu Cys
625

<210> SEQ ID NO 943
<211> LENGTH: 621
<212> TYPE: PRT
<213> ORGANISM: Homo sapiens

<400> SEQUENCE: 943

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240
```

```
Pro Pro Leu Met Leu Tyr Asn Pro Thr Thr Tyr Gln Met Asp Val Asn
            245                 250                 255

Pro Glu Gly Lys Tyr Ser Phe Gly Ala Thr Cys Val Lys Lys Cys Pro
        260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
    610                 615                 620

<210> SEQ ID NO 944
<211> LENGTH: 123
<212> TYPE: PRT
<213> ORGANISM: Homo sapiens

<400> SEQUENCE: 944
```

Gln Val Gln Leu Val Gln Ser Gly Ala Glu Val Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Asp Tyr Tyr Gly Ser Gly Ser Tyr Ala Phe Asp Ile
            100                 105                 110

Trp Gly Gln Gly Thr Thr Val Thr Val Ser Arg
        115                 120

<210> SEQ ID NO 945
<211> LENGTH: 111
<212> TYPE: PRT
<213> ORGANISM: Homo sapiens

<400> SEQUENCE: 945

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu Gly
            100                 105                 110

<210> SEQ ID NO 946
<211> LENGTH: 123
<212> TYPE: PRT
<213> ORGANISM: Homo sapiens

<400> SEQUENCE: 946

Gln Val Gln Leu Gln Gln Trp Gly Ala Gly Leu Leu Lys Pro Ser Glu
1               5                   10                  15

Thr Leu Ser Leu Thr Cys Ala Ala Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

```
Arg Thr Tyr Tyr Gly Ser Gly Ser Tyr Gln Tyr Asn Trp Phe Asp Pro
            100                 105                 110

Trp Gly Gln Gly Thr Leu Val Thr Val Ser Arg
        115                 120
```

<210> SEQ ID NO 947
<211> LENGTH: 112
<212> TYPE: PRT
<213> ORGANISM: Homo sapiens

<400> SEQUENCE: 947

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu Gly
            100                 105                 110
```

<210> SEQ ID NO 948
<211> LENGTH: 117
<212> TYPE: PRT
<213> ORGANISM: Homo sapiens

<400> SEQUENCE: 948

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Asn Leu Glu Gly Leu Asp Tyr Trp Gly Gln Gly Thr Leu
            100                 105                 110

Val Thr Val Ser Arg
        115
```

<210> SEQ ID NO 949
<211> LENGTH: 109
<212> TYPE: PRT
<213> ORGANISM: Homo sapiens

<400> SEQUENCE: 949

```
Ser Tyr Val Leu Thr Gln Pro Pro Ser Val Ser Val Ala Pro Gly Lys
1               5                   10                  15
```

```
Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105

<210> SEQ ID NO 950
<211> LENGTH: 120
<212> TYPE: PRT
<213> ORGANISM: Homo sapiens

<400> SEQUENCE: 950

Gln Val Gln Leu Gln Glu Ser Gly Pro Gly Leu Val Lys Pro Ser Gln
 1               5                  10                  15

Thr Leu Ser Leu Thr Cys Thr Val Ser Gly Ser Ile Ser Ser Gly
                20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Gly Thr Gly Asp Leu Glu Trp Phe Asp Pro Trp Gly Gln
            100                 105                 110

Gly Thr Leu Val Thr Val Ser Arg
            115                 120

<210> SEQ ID NO 951
<211> LENGTH: 111
<212> TYPE: PRT
<213> ORGANISM: Homo sapiens

<400> SEQUENCE: 951

Gln Ser Val Leu Thr Gln Pro Pro Ser Val Ser Gly Ala Pro Arg Gln
 1               5                  10                  15

Thr Val Thr Ile Ser Cys Ser Gly Ser Ser Ser Asn Ile Gly Gln Asn
                20                  25                  30

Ser Val Thr Trp Tyr Gln Arg Leu Pro Gly Glu Ala Pro Lys Leu Leu
            35                  40                  45

Ile Tyr Tyr Asp Asp Leu Leu His Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Glu Tyr Tyr Cys Ala Ser Trp Asp Asp Ser Leu
                85                  90                  95

Lys Gly Pro Val Phe Gly Gly Gly Thr Lys Leu Thr Val Leu Gly
            100                 105                 110
```

<210> SEQ ID NO 952
<211> LENGTH: 121
<212> TYPE: PRT
<213> ORGANISM: Homo sapiens

<400> SEQUENCE: 952

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Pro Arg Gly Ser Tyr Tyr Tyr Phe Asp Tyr Trp Gly
            100                 105                 110

Gln Gly Thr Leu Val Thr Val Ser Arg
        115                 120

<210> SEQ ID NO 953
<211> LENGTH: 111
<212> TYPE: PRT
<213> ORGANISM: Homo sapiens

<400> SEQUENCE: 953

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Trp Val Phe Gly Gly Gly Thr Lys Leu Thr Val Leu Gly
            100                 105                 110

<210> SEQ ID NO 954
<211> LENGTH: 119
<212> TYPE: PRT
<213> ORGANISM: Homo sapiens

<400> SEQUENCE: 954

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Lys Arg Arg Gly Ser Ala Phe Asp Ile Trp Gly Gln Gly
            100                 105                 110

Thr Thr Val Thr Val Ser Arg
        115

<210> SEQ ID NO 955
<211> LENGTH: 109
<212> TYPE: PRT
<213> ORGANISM: Homo sapiens

<400> SEQUENCE: 955

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly
            100                 105

<210> SEQ ID NO 956
<211> LENGTH: 369
<212> TYPE: DNA
<213> ORGANISM: Homo sapiens

<400> SEQUENCE: 956
caggtgcagc tggtgcagtc tggagctgag gtgaagaagc ctggggcctc agtgaaggtc    60
tcctgcaagg tttccggata caccctcact gaattatcca tgcactgggt gcgacaggct   120
cctggaaaag ggcttgagtg gatgggaggt tttgatcctg aagatggtga acaatctac    180 gcacagaagt tccagggcag agtcaccatg accgaggaca catctacaga cacagcctac   240
atggagctga gcagcctgag atctgaggac acggccgtgt attactgtgc aacagatctc   300
gattactatg gttcggggag ttatgctttt gatatctggg gccaagggac cacggtcacc   360
gtctcgaga                                                          369

<210> SEQ ID NO 957
<211> LENGTH: 333
<212> TYPE: DNA
<213> ORGANISM: Homo sapiens

<400> SEQUENCE: 957
cagtctgccc tgactcagcc tgcctccgtg tctgggtctc ctggacagtc gatcaccatc    60
tcctgcactg gaaccagcag tgatgttggg agttataacc ttgtctcctg gtaccaacag   120
cacccaggca aagcccccaa actcatgatt tatgagggca gtaagcggcc ctcagggggtt   180

```
tctaatcgct tctctggctc caagtctggc aacacggcct ccctgaccat ctctgggctc        240
caggctgagg acgaggctga ttattactgc agctcatata caagcagcag cacttgggtg        300
ttcggcggag ggaccaagct gaccgtccta ggt                                     333

<210> SEQ ID NO 958
<211> LENGTH: 369
<212> TYPE: DNA
<213> ORGANISM: Homo sapiens

<400> SEQUENCE: 958
caggtgcagc tacagcagtg gggcgcagga ctgttgaagc cttcggagac cctgtccctc         60
acctgcgctg cctatggtgg gtccttcagt ggttactact ggagctggat ccgccagccc        120
ccagggaagg ggctggagtg gattggggaa atcaatcata gtggaagcac caactacaac        180
ccgtccctca agagtcgagt caccatatca gtagacacgt ccaagaacca gttctccctg        240
aagctgagct ctgtgaccgc cgcggacacg gctgtgtatt actgtgcgag gacttactat        300
ggttcgggga gttatcagta caactggttc gaccccctggg gccagggaac cctggtcacc        360
gtctcgaga                                                                369

<210> SEQ ID NO 959
<211> LENGTH: 336
<212> TYPE: DNA
<213> ORGANISM: Homo sapiens

<400> SEQUENCE: 959
cagtctgtgt tgacgcagcc gccctcagtg tctggggccc cagggcagag ggtcaccatc         60
tcctgcactg ggagcagctc caacatcggg gcaggttatg atgtacactg gtaccagcag        120
cttccaggaa cagcccccaa actcctcatc tatggtaaca gcaatcggcc ctcaggggtc        180
cctgaccgat tctctggctc caagtctggc acctcagcct ccttggccat cactgggctc        240
caggctgagg atgaggctga ttattactgc cagtcctatg acagcagcct gagtggtgtg        300
gtattcggcg agggaccaa gctgaccgtc ctaggt                                   336

<210> SEQ ID NO 960
<211> LENGTH: 351
<212> TYPE: DNA
<213> ORGANISM: Homo sapiens

<400> SEQUENCE: 960
gaggtgcagc tggtggagtc tgggggaggc ttggtacagc ctgggggtc cctgagactc          60 tcctgtgcag cctctggatt caccttcagt agctatagca tgaactgggt ccgccaggct        120
ccagggaagg ggctggagtg ggtttcatat attagtagta gtagtagtac catatactac        180
gcagactctg tgaagggccg attcaccatc tccagagaca atgccaagaa ctcactgtat        240
ctgcaaatga acagcctgag agacgaggac acggctgtgt attactgtgc gagagataat        300
cttgaaggcc tggactactg gggccaggga acctggtca ccgtctcgag a                  351

<210> SEQ ID NO 961
<211> LENGTH: 327
<212> TYPE: DNA
<213> ORGANISM: Homo sapiens

<400> SEQUENCE: 961
tcctatgtgc tgactcagcc accctcagtg tcagtggccc caggaaagac ggccaggatt         60
acctgtgggg gaaacaacat tggaagtaaa agtgtgcact ggtaccagca gaagccaggc        120
```

```
caggcccctg tgctggtcat ctattatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcatgt ggtattcggc    300
ggagggacca agctgaccgt cctaggt                                        327
```

<210> SEQ ID NO 962
<211> LENGTH: 360
<212> TYPE: DNA
<213> ORGANISM: Homo sapiens

<400> SEQUENCE: 962

```
caggtgcagc tgcaggagtc gggcccagga ctggtgaagc cttcacagac cctgtccctc     60
acctgcactg tctctggtgg ctccatcagc agtggtgatt actactggag ttggatccgc    120
cagcccccag ggaagggcct ggagtggatt gggtacatct attacagtgg gagcacctac    180
tacaacccgt ccctcaagag tcgagttacc atatcagtag acacgtccaa gaaccagttc    240
tccctgaagc tgagctctgt gactgccgca gacacggccg tgtattactg tccagaggg    300 actggggatc ttgagtggtt cgacccctgg ggccagggca ccctggtcac cgtctcgaga    360
```

<210> SEQ ID NO 963
<211> LENGTH: 333
<212> TYPE: DNA
<213> ORGANISM: Homo sapiens

<400> SEQUENCE: 963

```
cagtctgtgt tgacgcagcc gccctcggtg tctggggccc ccggcagac ggtcaccatc      60 tcctgctctg ggagcagctc aacatcgga caaaattctg ttacctggta ccagcgcctc    120
ccgggtgagg ctcccaaact cctcatctac tatgatgatc tcttgcactc aggagtctct    180
gaccgattct ctggctccaa gtctggcacc tcagcctcac tggccatcag tggactccag    240
tctgaggatg aggctgagta ctactgtgcg tcatgggatg acagcctgaa aggtccggta    300
ttcggcggag ggaccaaact gaccgtccta ggt                                 333
```

<210> SEQ ID NO 964
<211> LENGTH: 363
<212> TYPE: DNA
<213> ORGANISM: Homo sapiens

<400> SEQUENCE: 964

```
gaggtgcagc tggtggagtc tgggggaggc ttggtacagc ctgggggtc cctgagactc     60 tcctgtgcag cctctggatt caccttcagt agctatagca tgaactgggt ccgccaggct    120
ccagggaagg ggctggagtg ggtttcatac attagtagta gtagtagtac catatactac    180
gcagactctg tgaagggccg attcaccatc tccagagaca atgccaagaa ctcactgtat    240
ctgcaaatga acagcctgag agacgaggac acggctgtgt attactgtgc gagagaggggc    300 ccaaggggga gctactacta ctttgactac tggggccagg gaaccctggt caccgtctcg    360
aga                                                                  363
```

<210> SEQ ID NO 965
<211> LENGTH: 333
<212> TYPE: DNA
<213> ORGANISM: Homo sapiens

<400> SEQUENCE: 965

```
aattttatgc tgactcagcc gcactctgtg tcggagtctc cggggaagac ggtaaccatc        60
tcctgcaccc gcagcagtgg cagcattgcc agcaactatg tgcagtggta ccagcagcgc       120
ccgggcagtg cccccaccac tgtgatctat gaggataacc aaagaccctc tggggtccct       180
gatcggttct ctggctccat cgacagctcc tccaactctg cctccctcac catctctgga       240
ctgaagactg aggacgaggc tgactactac tgtcagtctt atgatagcag caattgggtg       300
ttcggcggag ggaccaagct gaccgtccta ggt                                    333
```

<210> SEQ ID NO 966
<211> LENGTH: 357
<212> TYPE: DNA
<213> ORGANISM: Homo sapiens

<400> SEQUENCE: 966

```
caggtgcagc tggtgcagtc tggggctgag gtgaagaagc ctggggcctc agtgaaggtt        60
tcctgcaagg catctggata caccttcacc agctactata tgcactgggt gcgacaggcc       120
cctggacaag gcttgagtg gatgggaata atcaaccta gtggtggtag cacaagctac         180
gcacagaagt tccagggcag agtcaccatg accagggaca cgtccacgag cacagtctac       240
atggagctga gcagcctgag atctgaggac acggccgtgt attactgtgc gagagcgaag       300
agaaggggat ctgcttttga tatctggggc caagggacca cggtcaccgt ctcgaga         357
```

<210> SEQ ID NO 967
<211> LENGTH: 327
<212> TYPE: DNA
<213> ORGANISM: Homo sapiens

<400> SEQUENCE: 967

```
tcttctgagc tgactcagga ccctgctgtg tctgtggcct tgggacagac agtcaggatc        60
acatgccaag agacagcct cagaagctat tatgcaagct ggtaccagca gaagccagga       120
caggcccctg tacttgtcat ctatggtaaa acaaccggc cctcagggat cccagaccga       180
ttctctggct ccagctcagg aaacacagct tccttgacca tcactggggc tcaggcggaa       240
gatgaggctg actattactg taactcccgg gacagcagtg taaccatgt ggtattcggc       300 ggagggacca gctgaccgt cctaggt                                            327
```

<210> SEQ ID NO 968
<211> LENGTH: 124
<212> TYPE: PRT
<213> ORGANISM: Homo sapiens

<400> SEQUENCE: 968

```
Gln Val Gln Leu Val Gln Ser Gly Ala Glu Val Lys Lys Pro Gly Ser
1               5                  10                  15

Ser Val Lys Val Ser Cys Arg Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Gly Asp Ile Ser Arg Gly Ser Ser Trp Tyr Gly Tyr Tyr Phe Asp
            100                 105                 110
Tyr Trp Gly Gln Gly Thr Leu Val Thr Val Ser Arg
        115                 120

<210> SEQ ID NO 969
<211> LENGTH: 106
<212> TYPE: PRT
<213> ORGANISM: Homo sapiens

<400> SEQUENCE: 969

Asp Ile Gln Met Thr Gln Ser Pro Ser Thr Leu Ala Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Ser Tyr Ser Thr
                85                  90                  95
Phe Gly Gln Gly Thr Lys Leu Glu Ile Lys
            100                 105

<210> SEQ ID NO 970
<211> LENGTH: 372
<212> TYPE: DNA
<213> ORGANISM: Homo sapiens

<400> SEQUENCE: 970
caggtgcagc tggtgcagtc tggggctgag gtgaagaagc ctgggtcctc ggtgaaggtc     60
tcctgcaggg cttctggagg caccttcagc agctatgcta tcagctgggt gcgacaggcc    120
cctggacaag gcttgagtg gatgggaggg atcatccta tctttggtac agcaaactac     180
gcacagaagt tccagggcag agtcacgatt accgcggaca atccacgag cacagcctac    240
atggagctga gcagcctgag atctgaggac acggccgtgt attactgtgc gggagatatc    300
agccgaggca gcagctggta cgggtactac tttgactact ggggccaggg aaccctggtc    360
accgtctcga ga                                                       372

<210> SEQ ID NO 971
<211> LENGTH: 318
<212> TYPE: DNA
<213> ORGANISM: Homo sapiens

<400> SEQUENCE: 971
gacatccaga tgacccagtc tccttccacc ctggctgcat ctgtaggaga cagagtcacc     60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attccacttt tggccagggg    300
accaagctgg agatcaaa                                                 318

What is claimed is:

1. An isolated antibody that binds to CD73, comprising:
a heavy chain variable region CDR1, CDR2, and CDR3 defined by SEQ ID No: 468, SEQ ID NO: 469, and SEQ ID NO: 470, respectively, and light chain variable region CDR1, CDR2, and CDR3 defined by SEQ ID No: 472, SEQ ID NO: 473, and SEQ ID NO: 474, respectively; or
a heavy chain variable region SEQ ID NO: 467 and a light chain variable region SEQ ID NO: 471.

2. An isolated nucleic acid molecule, which encodes the heavy chain variable region and/or the light chain variable region of the antibody according to claim 1.

3. A vector including the nucleic acid molecule according to claim 2 in a form capable of being expressed.

4. A transformant into which the nucleic acid molecule according to claim 2 is introduced.

5. A cancer therapeutic agent comprising the antibody according to claim 1 as an effective ingredient.

6. A reagent for examining or studying cancer comprising the antibody according to claim 1.

* * * * *